(12) United States Patent
Alitalo et al.

(10) Patent No.: US 9,896,499 B2
(45) Date of Patent: Feb. 20, 2018

(54) GROWTH FACTOR ANTAGONISTS FOR ORGAN TRANSPLANT ALLOIMMUNITY AND ARTERIOSCLEROSIS

(71) Applicant: VEGENICS PTY LIMITED, South Yarra (AU)

(72) Inventors: Kari Alitalo, Helsinki (FI); Karl B. Lemström, Helsinki (FI); Antti I. Nykänen, Helsinki (FI)

(73) Assignee: VEGENICS PTY LIMITED, South Yarra, Victoria (AU)

( * ) Notice: Subject to any disclaimer, the term of this patent is extended or adjusted under 35 U.S.C. 154(b) by 37 days.

(21) Appl. No.: 14/687,556

(22) Filed: Apr. 15, 2015

(65) Prior Publication Data

US 2015/0218249 A1   Aug. 6, 2015

Related U.S. Application Data

(62) Division of application No. 12/024,454, filed on Feb. 1, 2008, now Pat. No. 9,073,997.

(60) Provisional application No. 60/888,305, filed on Feb. 5, 2007, provisional application No. 60/888,067, filed on Feb. 2, 2007.

(51) Int. Cl.

| C07K 14/71 | (2006.01) |
|---|---|
| C07K 16/28 | (2006.01) |
| C07K 16/22 | (2006.01) |
| A61K 39/395 | (2006.01) |
| A61K 45/06 | (2006.01) |
| C12N 15/113 | (2010.01) |
| A61K 39/00 | (2006.01) |

(52) U.S. Cl.
CPC .......... *C07K 14/71* (2013.01); *A61K 39/3955* (2013.01); *A61K 45/06* (2013.01); *C07K 16/22* (2013.01); *C07K 16/2863* (2013.01); *C12N 15/1136* (2013.01); *C12N 15/1138* (2013.01); *A61K 2039/505* (2013.01); *C07K 2317/24* (2013.01); *C07K 2317/73* (2013.01); *C07K 2317/76* (2013.01); *C07K 2319/30* (2013.01); *C12N 2310/11* (2013.01); *C12N 2320/30* (2013.01)

(58) Field of Classification Search
CPC .............. C07K 14/71; C07K 2319/30; C07K 16/2863; C07K 2317/73; C07K 2317/76; C07K 2317/24; C07K 16/22; A61K 2039/505; C12N 15/1138; C12N 15/1136; C12N 2320/30; C12N 2310/11

See application file for complete search history.

(56) References Cited

U.S. PATENT DOCUMENTS

| 4,284,786 A | 8/1981 | Kammerer et al. |
|---|---|---|
| 5,418,135 A | 5/1995 | Pang |
| 5,468,468 A | 11/1995 | LaRochelle et al. |
| 5,521,184 A | 5/1996 | Zimmermann |
| 5,620,687 A | 4/1997 | Hart et al. |
| 5,776,755 A | 7/1998 | Alitalo et al. |
| 5,840,301 A | 11/1998 | Rockwell et al. |
| 5,874,542 A | 2/1999 | Rockwell et al. |
| 5,932,580 A | 8/1999 | Levitzki et al. |
| 5,952,199 A | 9/1999 | Davis-Smyth et al. |
| 5,955,311 A | 9/1999 | Rockwell et al. |
| 6,100,071 A | 8/2000 | Davis-Smyth et al. |
| 6,107,046 A | 8/2000 | Alitalo et al. |
| 6,331,555 B1 | 12/2001 | Hirth et al. |
| 6,344,339 B1 | 2/2002 | Menrad et al. |
| 6,348,333 B1 | 2/2002 | Niwa et al. |
| 6,358,954 B1 | 3/2002 | Levitzki et al. |
| 6,375,929 B1 | 4/2002 | Thomas, Jr. et al. |
| 6,383,484 B1 | 5/2002 | Achen et al. |
| 6,383,486 B1 | 5/2002 | Davis-Smyth et al. |
| 6,403,088 B1 | 6/2002 | Alitalo et al. |
| 6,610,688 B2 | 8/2003 | Liang et al. |
| 6,642,022 B1 | 11/2003 | Williams et al. |
| 6,730,489 B1 | 5/2004 | Achen et al. |
| 6,734,017 B2 | 5/2004 | Bennett et al. |
| 6,878,720 B2 | 4/2005 | Altmann et al. |
| 6,887,468 B1 | 5/2005 | Thorpe et al. |
| 6,897,294 B2 | 5/2005 | Davis-Smyth et al. |
| 6,921,763 B2 | 7/2005 | Hirst et al. |
| 6,986,890 B1 | 1/2006 | Shitara et al. |
| 7,045,133 B2 | 5/2006 | Achen et al. |
| 7,052,693 B2 | 5/2006 | Shitara et al. |
| 7,056,509 B2 | 6/2006 | Thorpe et al. |
| 7,097,986 B2 | 8/2006 | Achen et al. |
| 7,105,305 B2 | 9/2006 | Williams et al. |

(Continued)

FOREIGN PATENT DOCUMENTS

| EP | 1447095 | 8/2004 |
|---|---|---|
| WO | WO-95/33772 A1 | 12/1995 |

(Continued)

OTHER PUBLICATIONS

Kerjaschki et al., J Am Soc Nephrol 15: 603-612, 2004.*
Achen et al., Monoclonal antibodies to vascular endothelial growth factor-D block its interactions with both VEGF receptor-2 and VEGF receptor-3, Eur. J. Biochem., 267(9):2505-15 (2000).
Borg et al., Biochemical Characterization of Two Isoforms of FLT4, a VEGF Receptor-related Tyrosine Kinase, Oncogene, 10(5):973-84 (1995).
Chen et al., Vascular endothelial growth factor receptor-3 mediates induction of corneal alloimmunity, Nat. Med., 10(8):813-5 (2004).
Cursiefen et al., Lymphatic vessels in vascularized human corneas: immunohistochemical investigation using LYVE-1 and podoplanin, Investigative Ophthalmology & Visual Science, 43: 2127-35 (2002).
Cursiefen et al., Nonvascular VEGR receptor 3 expression by corneal epithelium maintains avascularity and vision, Proc. Natl. Acad. Sci., USA, 103(30), 11405-10 (2006).

(Continued)

*Primary Examiner* — Phuong Huynh
(74) *Attorney, Agent, or Firm* — Marshall, Gerstein & Borun LLP

(57) ABSTRACT

The present invention provides materials and methods for antagonizing the function of vascular endothelial growth factor receptors, platelet derived growth factor receptors and other receptors, to prevent, inhibit, or ameliorate allograft rejection or arteriosclerosis in organisms that receive an organ transplant.

38 Claims, 1 Drawing Sheet

(56) References Cited

U.S. PATENT DOCUMENTS

| | | |
|---|---|---|
| 9,073,997 B2 | 7/2015 | Alitalo et al. |
| 2002/0123481 A1 | 9/2002 | Oliviero |
| 2002/0164667 A1 | 11/2002 | Alitalo et al. |
| 2003/0053989 A1 | 3/2003 | Kovesdi |
| 2003/0064053 A1 | 4/2003 | Liu et al. |
| 2003/0092604 A1 | 5/2003 | Davis-Smyth et al. |
| 2003/0113324 A1 | 6/2003 | Alitalo et al. |
| 2003/0125537 A1 | 7/2003 | Achen et al. |
| 2003/0170287 A1 | 9/2003 | Prescott |
| 2003/0176674 A1 | 9/2003 | Rosen et al. |
| 2003/0180294 A1 | 9/2003 | DeVries |
| 2003/0232437 A1 | 12/2003 | Zhang et al. |
| 2004/0141917 A1 | 7/2004 | Achen et al. |
| 2004/0147726 A1 | 7/2004 | Alitalo et al. |
| 2005/0059117 A1 | 3/2005 | Rosen et al. |
| 2005/0192429 A1 | 9/2005 | Rosen et al. |
| 2005/0222066 A1 | 10/2005 | Richards et al. |
| 2005/0232921 A1 | 10/2005 | Rosen et al. |
| 2005/0282228 A1 | 12/2005 | Mccoll et al. |
| 2005/0282233 A1 | 12/2005 | Eriksson et al. |
| 2006/0024302 A1 | 2/2006 | Achen et al. |
| 2006/0030000 A1 | 2/2006 | Alitalo et al. |
| 2006/0121025 A1 | 6/2006 | Lee et al. |
| 2006/0177428 A1 | 8/2006 | Achen et al. |
| 2006/0177901 A1 | 8/2006 | Alitalo et al. |
| 2006/0269548 A1 | 11/2006 | Alitalo et al. |

FOREIGN PATENT DOCUMENTS

| | | | |
|---|---|---|---|
| WO | WO-97/32604 A1 | | 9/1997 |
| WO | WO-98/07832 A1 | | 2/1998 |
| WO | WO-99/03854 A1 | | 1/1999 |
| WO | WO-99/28304 A2 | | 6/1999 |
| WO | WO-00/09098 A2 | | 2/2000 |
| WO | WO-00/25085 A1 | | 5/2000 |
| WO | WO-00/37025 A2 | | 6/2000 |
| WO | WO-00/42042 A2 | | 7/2000 |
| WO | WO-01/64200 A2 | | 9/2001 |
| WO | WO-02/060950 A2 | | 8/2002 |
| WO | WO-03/029814 A2 | | 4/2003 |
| WO | WO-2004/106378 | | 12/2004 |
| WO | WO-2005/041877 | | 5/2005 |
| WO | WO2005/041877 | * | 5/2005 |
| WO | WO-2005/049021 A1 | | 6/2005 |
| WO | WO-2005/087812 A1 | | 9/2005 |

OTHER PUBLICATIONS

Cursiefen et al., Spontaneous corneal hem- and lymphagiogenesis in mice with destrin-mutation depends on VEGFR3 signaling, Am. J. Pathol., 166: 1367-77 (2005).

Davis-Smyth et al., The Second Immunoglobulin-like Domain of the VEGF Tyrosine Kinase Receptor Flt-1 Determines Ligand Binding and May Initiate a Signal Transduction Cascade, EMBO J., 15(18):4919-27 (1996).

de Azevedo et al., Molecular Cloning and Expression of a Functional Snake Venom Vascular Endothelium Growth Factor (VEGF) from the *Bothrops insularis* Pit Viper. J. Biol. Chem., 276:39836-42 (2001).

De Vries et al., The fms-like Tyrosine Kinase, a Receptor for Vascular Endothelial Growth Factor, Science, 255:989-91 (1992).

Di Cario et al., Quilty effect has the features of lymphoid neogenesis and shares CXCL13-CXCR5 pathway with recurrent acute cardiac rejections, Am. J. Transplant., 7: 201-10 (2007).

Fairbrother et al., Novel Peptides Selected to Bind Vascular Endothelial Growth Factor Target the Receptor-binding Site, Biochem., 37:17754-64 (1998).

Ferrara, Molecular and biological properties of vascular endothelial growth factor, J. Mol. Med., 77:527-43 (1999).

Folkman et al., Long-term Culture of Capillary Endothelial Cells, Proc. Natl. Acad. Sci. (USA), 76:5217-21 (1979).

Fuh et al., Requirements for Binding and Signaling of the Kinase Domain Receptor for Vascular Endothelial Growth Factor, J. Biol. Chem., 273(18):11197-204 (1998).

Gasmi et al., Complete Structure of an Increasing Capillary Permeability Protein (ICPP) Purified from *Vipera lebetina* Venom, J. Biol. Chem., 277(33):29992-8 (2002).

Gasmi et al., Purification and Characterization of a Growth Factorlike Which Increases Capillary Permeability from *Vipera lebetina* Venom, Biochem. Biophys. Res. Commun., 268:69-72 (2002).

Geissler et al., First year changes of myocardial lymphatic endothelial markers in heart transplant recipients, Eur. J. Cardiothorac. Surg., 29(5):767-71 (2006).

Grimmond et al., Cloning and Characterization of a Novel Human Gene Related to Vascular Endothelial Growth Factor,Genome Res., 6:124-31 (1996).

Hauser et al., A Heparin-Binding Form of Placenta Growth Factor (PIGF-2) is Expressed in Human Umbilical Vein Endothelial Cells and in Placenta,Growth Factors, 9:259-68 (1993).

Hu et al., Endothelial replacement and angiogenesis in arteriosclerotic lesions of allografts are contributed by circulating progenitor cells, Circulation, 108(25):3122-7 (2003).

Hughes et al., Alternative Splicing of the Human VEGFR-3/FLT4 Gene as a Consequence of an Integrated Human Endogenous Retrovirus. J. Mot. Evol., 52(2):77-9 (2001).

International Preliminary Report on Patentability, PCT/IB2008/001271, dated Aug. 13, 2009.

International Search Report and Written Opinion, PCT/IB2008/001271, dated Oct. 24, 2008.

Kaplan et al., Characterization of a Soluble Vascular Endothelial Growth Factor Receptor—Immunoglobulin Chimera, *Growth Factors*, 14:243-56 (1997).

Karpanen et al., Vascular Endothelial Growth Factor C Promotes Tumor Lymphangiogensis and Intralymphatic Tumor Growth, *Cancer Res.*, 61:1786-90 (2001).

Kendall et al., Inhibition of Vascular Endothelial Cell Growth Factor Activity by an Endogenously Encoded Soluble Receptor,*PNAS USA*, 90:10705-9 (1993).

Kerjaschki et al., Lymphatic endothelial progenitor cells contribute to de novo lymphangiogenesis in human renal transplants, Nat. Med., 12(2):230-4 (2006).

Kudo et al., Involvement of Vascular Endothelial Growth Factor Receptor-3 in Maintenance of Integrity of Endothelial Cell Lining During Tumor Angiogensis,B/ood, 96(2):546-53 (2000).

Lemström et al., Vascular endothelial growth factor enhances cardiac allograft arteriosclerosis, Circulation, 105(21):2524-30 (2002).

Li et al., Isoform-specific Expression of VEGF-B in Normal Tissues and Tumors, Growth Factor, 19:49-59 (2001).

Li et al., Novel VEGF Family Members: VEGF-B, VEGF-C and VEGF-D, J. Biochem. Cell. Biol., 33(4):421-6 (2001).

Lokker et al., Functional Importance of Platelet-derived Growth Factor (PDGF) Receptor Extracellular Immunoglobulin-like Domains, J. Biol. Chem., 272:33037-40 (1997).

Lu et al., Acquired Antagonistic Activity of a Bispecific Diabody Directed Against Two Different Epitopes on Vascular Endothelial Growth Factor Receptor 2, J. Immunological Methods, 230:159-71 (1999).

Lu et al., Identification of the Residues in the Extracellular Region of KDR Important for Interaction with Vascular Endothelial Growth Factor and Neutralizing Anti-KDR Antibodies, J. Biol. Chem., 275(19):14321-14330 (2000).

Lu et al., Tailoring in Vitro Selection for a Picomolar Affinity Human Antibody Directed Against Vascular Endothelial Growth Factor Receptor 2 for Enhanced Neutralizing Activity, J. Biol. Chem., 278(44):43496-43507 (2003).

Maglione et al., Two Alternative mRNAs Coding for the Angiogenic Factor, Placenta Growth Factor (PIGF), are Transcribed from a Single Gene of Chromosome 14, Oncogene, 8:925-931 (1993).

Matthews et al., A Receptor Tyrosine Kinase cDNA Isolated From a Population of Enriched Primitive Hematopoietic Cells and Exhibiting Close Genetic Linkage to c-kit, Proc. Natl. Acad. Sci. (USA), 88:9026-30 (1991).

Muller et al., The Crystal Structure of Vascular Endothelial Growth Factor (VEGF) Refined to 1.93 A Resolution: Multiple Copy Flexibility and Receptor Binding, Structure, 5:1325-1338 (1997).

(56) References Cited

OTHER PUBLICATIONS

Neufeld et al., Vascular Endothelial Growth Factor (VEGF) and its Receptor, FASEB J., 13:9-22 (1999).
Olofsson et al., Genomic Organization of the Mouse and Human Genes for Vascular Endothelial Growth Factor B (VEGF-B) and Characterization of a Second Splice Isoform, J. Biol. Chem., 271:19310-19317 (1996).
Ortega et al., Signal Relays in the VEGF System, Frontiers in Bioscience, 4:141-52 (1999).
Pajusola et al., Signalling Properties of FLT4, a Proteolyically Processed Receptor Tyrosine Kinase Related to Two VEGF Receptors, *Oncogene*, 9:3545-3555 (1994).
Pajusola et al., Two Human FLT4 Receptor Tyrosine Kinase Isoforms with Distinct Carboxy Terminal Tails are Produced by Alternative Processing of Primary Transcripts, Oncogene, 8(11):2931-7 (1993).
Pertovaara et al., Vascular Endothelial Growth Factor is Induced in Response to Transforming Growth Factor-0 in Fibroblastic and Epithelial Cells, J. Biol. Chem., 269:6271-4 (1994).
Petrova et al., Signaling via Vascular Endothelial Growth Factor Receptors, Exp. Cell. Res., 253:117-130 (1999).
Pietras et al., PDGF Receptors as Cancer Drug Targets, Cancer Cell, 3:439-43 (2003).
Rintala et al., Vascular endothelial growth factor (VEGF) ligand and receptor induction in rat renal allograft rejection. *Transplantation Proceedings*. 38: 3236-8 (2006).
Rosen, Inhibitors of the Vascular Endothelial Growth Factor Receptor, Hematol. Oncol. Clin. N. Am., 16:1173-87 (2002).
Rudikoff et al., Single amino acid substitution altering antigen-binding specificity, Proc. Natl. Acad. Sci. USA, 79(6):1979-83 (1982).
Shinkai et al., Mapping of the Sites Involved in Ligand Association and Dissociation at the Extracellular Domain of the Kinase Insert Domain-containing Receptor for Vascular Endothelial Growth Factor, J. Biol. Chem., 273(47):31283 31288 (1998).
Sho et al., Function of the vascular endothelial growth factor receptor Flt-1 and Flk-1/KDR in the alloimmune response in vivo, Transplantation, 80: 717-22 (2005).
Stacker et al., A mutant form of vascular endothelial growth factor (VEGF) that lacks VEGF receptor-2 activation retains the ability to induce vascular permeability, J. Biol. Chem., 274:34884-92 (1999).
Stacker et al., The Vascular Endothelial Growth Factor Family: Signalling for Vascular Development, Growth Factors, 17:1-11 (1999).
Starovasnik et al., Solution Structure of the VEGF-binding Domain of Flt-1: Comparison of its Free and Bound States, J. Mol. Biol., 293:531-544 (1999).
Terman et al., Identification of the KDR Tyrosine Kinase as a Receptor for Vascular Endothelial Cell Growth Factor, Biochem. Biophys. Res. Comm., 187:1579-86 (1992).
Vaucheret et al., Transgene-induced Gene Silencing in Plants, Plant J., 16:651-9 (1998).
Veikkola et al., Regulation of Angiogensis via Vascular Endothelial Growth Factor Receptors, Cancer Res., 60:203-12 (2000).
Wiesmann et al., Crystal Structure at 1.7 A Resolution of VEGF in Complex with Domain 2 of the Flt-1 Receptor, Cell, 91:695-704 (1997).
Witzenbicheler et al., Vascular endothelial growth factor-C (VEGF-C/VEGF-2) promotes angiogenesis in the setting of tissue ischemia, Am. J. Pathol., 153(2):381-94 (1998).
Wu et al., Humanization of a murine monoclonal antibody by simultaneous optimization of framework and CDR residues, J. Mol. Biol., 294(1):151-62 (1999).
Yu et al., Interaction between bevacizumab and murine VEGF-A: a reassessment, Invest. Ophthalmol. Vis. Sci., 49(2):522-7 (2008).
Zachary, Vascular Endothelial Growth Factor, Intl. J. Biochem. Cell. Bio., 30:1169-1174 (1998).

\* cited by examiner

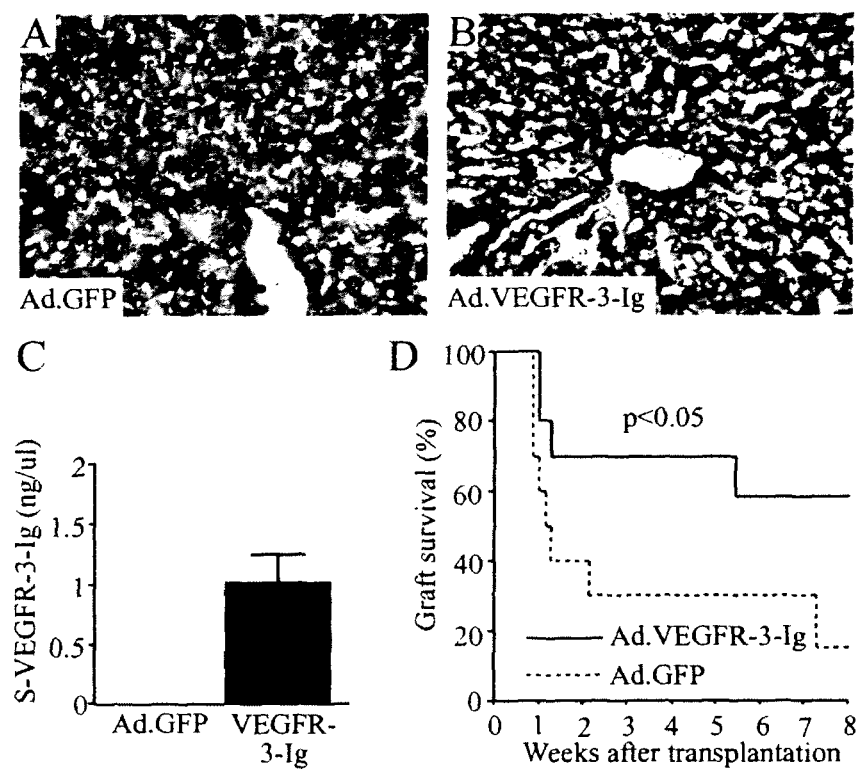

SEQUENCE LISTING

```
<160> NUMBER OF SEQ ID NOS: 144

<210> SEQ ID NO 1
<211> LENGTH: 5777
<212> TYPE: DNA
<213> ORGANISM: Homo sapiens
<220> FEATURE:
<221> NAME/KEY: misc_feature
<223> OTHER INFORMATION: VEGFR-1
<220> FEATURE:
<221> NAME/KEY: CDS
<222> LOCATION: (250)..(4266)

<400> SEQUENCE: 1
gcggacactc ctctcggctc ctccccggca gcggcggcgg ctcggagcgg gctccggggc      60
tcgggtgcag cggccagcgg gcctggcggc gaggattacc cggggaagtg gttgtctcct    120
ggctggagcc gcgagacggg cgctcagggc gcggggccgg cggcggcgaa cgagaggacg    180
gactctggcg gccgggtcgt tggccggggg agcgcgggca ccgggcgagc aggccgcgtc    240 gcgctcacc atg gtc agc tac tgg gac acc ggg gtc ctg ctg tgc gcg ctg   291
           Met Val Ser Tyr Trp Asp Thr Gly Val Leu Leu Cys Ala Leu
             1               5                  10 ctc agc tgt ctg ctt ctc aca gga tct agt tca ggt tca aaa tta aaa    339
Leu Ser Cys Leu Leu Leu Thr Gly Ser Ser Ser Gly Ser Lys Leu Lys
 15                  20                  25                  30 gat cct gaa ctg agt tta aaa ggc acc cag cac atc atg caa gca ggc    387
Asp Pro Glu Leu Ser Leu Lys Gly Thr Gln His Ile Met Gln Ala Gly
                 35                  40                  45 cag aca ctg cat ctc caa tgc agg ggg gaa gca gcc cat aaa tgg tct    435
Gln Thr Leu His Leu Gln Cys Arg Gly Glu Ala Ala His Lys Trp Ser
             50                  55                  60 ttg cct gaa atg gtg agt aag gaa agc gaa agg ctg agc ata act aaa    483
Leu Pro Glu Met Val Ser Lys Glu Ser Glu Arg Leu Ser Ile Thr Lys
 65                  70                  75 tct gcc tgt gga aga aat ggc aaa caa ttc tgc agt act tta acc ttg    531
Ser Ala Cys Gly Arg Asn Gly Lys Gln Phe Cys Ser Thr Leu Thr Leu
             80                  85                  90 aac aca gct caa gca aac cac act ggc ttc tac agc tgc aaa tat cta    579
Asn Thr Ala Gln Ala Asn His Thr Gly Phe Tyr Ser Cys Lys Tyr Leu
 95                 100                 105                 110
```

```
gct gta cct act tca aag aag aag gaa aca gaa tct gca atc tat ata    627
Ala Val Pro Thr Ser Lys Lys Lys Glu Thr Glu Ser Ala Ile Tyr Ile
            115                 120                 125 ttt att agt gat aca ggt aga cct ttc gta gag atg tac agt gaa atc    675
Phe Ile Ser Asp Thr Gly Arg Pro Phe Val Glu Met Tyr Ser Glu Ile
            130                 135                 140 ccc gaa att ata cac atg act gaa gga agg gag ctc gtc att ccc tgc    723
Pro Glu Ile Ile His Met Thr Glu Gly Arg Glu Leu Val Ile Pro Cys
            145                 150                 155 cgg gtt acg tca cct aac atc act gtt act tta aaa aag ttt cca ctt    771
Arg Val Thr Ser Pro Asn Ile Thr Val Thr Leu Lys Lys Phe Pro Leu
            160                 165                 170 gac act ttg atc cct gat gga aaa cgc ata atc tgg gac agt aga aag    819
Asp Thr Leu Ile Pro Asp Gly Lys Arg Ile Ile Trp Asp Ser Arg Lys
175                 180                 185                 190 ggc ttc atc ata tca aat gca acg tac aaa gaa ata ggg ctt ctg acc    867
Gly Phe Ile Ile Ser Asn Ala Thr Tyr Lys Glu Ile Gly Leu Leu Thr
            195                 200                 205 tgt gaa gca aca gtc aat ggg cat ttg tat aag aca aac tat ctc aca    915
Cys Glu Ala Thr Val Asn Gly His Leu Tyr Lys Thr Asn Tyr Leu Thr
            210                 215                 220 cat cga caa acc aat aca atc ata gat gtc caa ata agc aca cca cgc    963
His Arg Gln Thr Asn Thr Ile Ile Asp Val Gln Ile Ser Thr Pro Arg
            225                 230                 235 cca gtc aaa tta ctt aga ggc cat act ctt gtc ctc aat tgt act gct    1011
Pro Val Lys Leu Leu Arg Gly His Thr Leu Val Leu Asn Cys Thr Ala
            240                 245                 250 acc act ccc ttg aac acg aga gtt caa atg acc tgg agt tac cct gat    1059
Thr Thr Pro Leu Asn Thr Arg Val Gln Met Thr Trp Ser Tyr Pro Asp
255                 260                 265                 270 gaa aaa aat aag aga gct tcc gta agg cga cga att gac caa agc aat    1107
Glu Lys Asn Lys Arg Ala Ser Val Arg Arg Ile Asp Gln Ser Asn
            275                 280                 285 tcc cat gcc aac ata ttc tac agt gtt ctt act att gac aaa atg cag    1155
Ser His Ala Asn Ile Phe Tyr Ser Val Leu Thr Ile Asp Lys Met Gln
            290                 295                 300 aac aaa gac aaa gga ctt tat act tgt cgt gta agg agt gga cca tca    1203
Asn Lys Asp Lys Gly Leu Tyr Thr Cys Arg Val Arg Ser Gly Pro Ser
            305                 310                 315 ttc aaa tct gtt aac acc tca gtg cat ata tat gat aaa gca ttc atc    1251
Phe Lys Ser Val Asn Thr Ser Val His Ile Tyr Asp Lys Ala Phe Ile
            320                 325                 330 act gtg aaa cat cga aaa cag cag gtg ctt gaa acc gta gct ggc aag    1299
Thr Val Lys His Arg Lys Gln Gln Val Leu Glu Thr Val Ala Gly Lys
335                 340                 345                 350 cgg tct tac cgg ctc tct atg aaa gtg aag gca ttt ccc tcg ccg gaa    1347
Arg Ser Tyr Arg Leu Ser Met Lys Val Lys Ala Phe Pro Ser Pro Glu
            355                 360                 365 gtt gta tgg tta aaa gat ggg tta cct gcg act gag aaa tct gct cgc    1395
Val Val Trp Leu Lys Asp Gly Leu Pro Ala Thr Glu Lys Ser Ala Arg
            370                 375                 380 tat ttg act cgt ggc tac tcg tta att atc aag gac gta act gaa gag    1443
Tyr Leu Thr Arg Gly Tyr Ser Leu Ile Ile Lys Asp Val Thr Glu Glu
            385                 390                 395 gat gca ggg aat tat aca atc ttg ctg agc ata aaa cag tca aat gtg    1491
Asp Ala Gly Asn Tyr Thr Ile Leu Leu Ser Ile Lys Gln Ser Asn Val
400                 405                 410 ttt aaa aac ctc act gcc act cta att gtc aat gtg aaa ccc cag att    1539
Phe Lys Asn Leu Thr Ala Thr Leu Ile Val Asn Val Lys Pro Gln Ile
```

```
                    415                 420                 425                 430
tac gaa aag gcc gtg tca tcg ttt cca gac ccg gct ctc tac cca ctg        1587
Tyr Glu Lys Ala Val Ser Ser Phe Pro Asp Pro Ala Leu Tyr Pro Leu
                        435                 440                 445 ggc agc aga caa atc ctg act tgt acc gca tat ggt atc cct caa cct        1635
Gly Ser Arg Gln Ile Leu Thr Cys Thr Ala Tyr Gly Ile Pro Gln Pro
            450                 455                 460 aca atc aag tgg ttc tgg cac ccc tgt aac cat aat cat tcc gaa gca        1683
Thr Ile Lys Trp Phe Trp His Pro Cys Asn His Asn His Ser Glu Ala
        465                 470                 475 agg tgt gac ttt tgt tcc aat aat gaa gag tcc ttt atc ctg gat gct        1731
Arg Cys Asp Phe Cys Ser Asn Asn Glu Glu Ser Phe Ile Leu Asp Ala
    480                 485                 490 gac agc aac atg gga aac aga att gag agc atc act cag cgc atg gca        1779
Asp Ser Asn Met Gly Asn Arg Ile Glu Ser Ile Thr Gln Arg Met Ala
495                 500                 505                 510 ata ata gaa gga aag aat aag atg gct agc acc ttg gtt gtg gct gac        1827
Ile Ile Glu Gly Lys Asn Lys Met Ala Ser Thr Leu Val Val Ala Asp
                515                 520                 525 tct aga att tct gga atc tac att tgc ata gct tcc aat aaa gtt ggg        1875
Ser Arg Ile Ser Gly Ile Tyr Ile Cys Ile Ala Ser Asn Lys Val Gly
            530                 535                 540 act gtg gga aga aac ata agc ttt tat atc aca gat gtg cca aat ggg        1923
Thr Val Gly Arg Asn Ile Ser Phe Tyr Ile Thr Asp Val Pro Asn Gly
        545                 550                 555 ttt cat gtt aac ttg gaa aaa atg ccg acg gaa gga gag gac ctg aaa        1971
Phe His Val Asn Leu Glu Lys Met Pro Thr Glu Gly Glu Asp Leu Lys
    560                 565                 570 ctg tct tgc aca gtt aac aag ttc tta tac aga gac gtt act tgg att        2019
Leu Ser Cys Thr Val Asn Lys Phe Leu Tyr Arg Asp Val Thr Trp Ile
575                 580                 585                 590 tta ctg cgg aca gtt aat aac aga aca atg cac tac agt att agc aag        2067
Leu Leu Arg Thr Val Asn Asn Arg Thr Met His Tyr Ser Ile Ser Lys
                595                 600                 605 caa aaa atg gcc atc act aag gag cac tcc atc act ctt aat ctt acc        2115
Gln Lys Met Ala Ile Thr Lys Glu His Ser Ile Thr Leu Asn Leu Thr
            610                 615                 620 atc atg aat gtt tcc ctg caa gat tca ggc acc tat gcc tgc aga gcc        2163
Ile Met Asn Val Ser Leu Gln Asp Ser Gly Thr Tyr Ala Cys Arg Ala
        625                 630                 635 agg aat gta tac aca ggg gaa gaa atc ctc cag aag aaa gaa att aca        2211
Arg Asn Val Tyr Thr Gly Glu Glu Ile Leu Gln Lys Lys Glu Ile Thr
    640                 645                 650 atc aga gat cag gaa gca cca tac ctc ctg cga aac ctc agt gat cac        2259
Ile Arg Asp Gln Glu Ala Pro Tyr Leu Leu Arg Asn Leu Ser Asp His
655                 660                 665                 670 aca gtg gcc atc agc agt tcc acc act tta gac tgt cat gct aat ggt        2307
Thr Val Ala Ile Ser Ser Ser Thr Thr Leu Asp Cys His Ala Asn Gly
                675                 680                 685 gtc ccc gag cct cag atc act tgg ttt aaa aac aac cac aaa ata caa        2355
Val Pro Glu Pro Gln Ile Thr Trp Phe Lys Asn Asn His Lys Ile Gln
            690                 695                 700 caa gag cct gga att att tta gga cca gga agc agc acg ctg ttt att        2403
Gln Glu Pro Gly Ile Ile Leu Gly Pro Gly Ser Ser Thr Leu Phe Ile
        705                 710                 715 gaa aga gtc aca gaa gag gat gaa ggt gtc tat cac tgc aaa gcc acc        2451
Glu Arg Val Thr Glu Glu Asp Glu Gly Val Tyr His Cys Lys Ala Thr
    720                 725                 730 aac cag aag ggc tct gtg gaa agt tca gca tac ctc act gtt caa gga        2499
```

```
                    Asn Gln Lys Gly Ser Val Glu Ser Ser Ala Tyr Leu Thr Val Gln Gly
                    735                 740                 745                 750 acc tcg gac aag tct aat ctg gag ctg atc act cta aca tgc acc tgt                    2547
Thr Ser Asp Lys Ser Asn Leu Glu Leu Ile Thr Leu Thr Cys Thr Cys
                    755                 760                 765 gtg gct gcg act ctc ttc tgg ctc cta tta acc ctc ctt atc cga aaa                    2595
Val Ala Ala Thr Leu Phe Trp Leu Leu Leu Thr Leu Leu Ile Arg Lys
                770                 775                 780 atg aaa agg tct tct tct gaa ata aag act gac tac cta tca att ata                    2643
Met Lys Arg Ser Ser Ser Glu Ile Lys Thr Asp Tyr Leu Ser Ile Ile
            785                 790                 795 atg gac cca gat gaa gtt cct ttg gat gag cag tgt gag cgg ctc cct                    2691
Met Asp Pro Asp Glu Val Pro Leu Asp Glu Gln Cys Glu Arg Leu Pro
        800                 805                 810 tat gat gcc agc aag tgg gag ttt gcc cgg gag aga ctt aaa ctg ggc                    2739
Tyr Asp Ala Ser Lys Trp Glu Phe Ala Arg Glu Arg Leu Lys Leu Gly
815                 820                 825                 830 aaa tca ctt gga aga ggg gct ttt gga aaa gtg gtt caa gca tca gca                    2787
Lys Ser Leu Gly Arg Gly Ala Phe Gly Lys Val Val Gln Ala Ser Ala
                    835                 840                 845 ttt ggc att aag aaa tca cct acg tgc cgg act gtg gct gtg aaa atg                    2835
Phe Gly Ile Lys Lys Ser Pro Thr Cys Arg Thr Val Ala Val Lys Met
                    850                 855                 860 ctg aaa gag ggg gcc acg gcc agc gag tac aaa gct ctg atg act gag                    2883
Leu Lys Glu Gly Ala Thr Ala Ser Glu Tyr Lys Ala Leu Met Thr Glu
                865                 870                 875 cta aaa atc ttg acc cac att ggc cac cat ctg aac gtg gtt aac ctg                    2931
Leu Lys Ile Leu Thr His Ile Gly His His Leu Asn Val Val Asn Leu
            880                 885                 890 ctg gga gcc tgc acc aag caa gga ggg cct ctg atg gtg att gtt gaa                    2979
Leu Gly Ala Cys Thr Lys Gln Gly Gly Pro Leu Met Val Ile Val Glu
895                 900                 905                 910 tac tgc aaa tat gga aat ctc tcc aac tac ctc aag agc aaa cgt gac                    3027
Tyr Cys Lys Tyr Gly Asn Leu Ser Asn Tyr Leu Lys Ser Lys Arg Asp
                    915                 920                 925 tta ttt ttt ctc aac aag gat gca gca cta cac atg gag cct aag aaa                    3075
Leu Phe Phe Leu Asn Lys Asp Ala Ala Leu His Met Glu Pro Lys Lys
                    930                 935                 940 gaa aaa atg gag cca ggc ctg gaa caa ggc aag aaa cca aga cta gat                    3123
Glu Lys Met Glu Pro Gly Leu Glu Gln Gly Lys Lys Pro Arg Leu Asp
                945                 950                 955 agc gtc acc agc agc gaa agc ttt gcg agc tcc ggc ttt cag gaa gat                    3171
Ser Val Thr Ser Ser Glu Ser Phe Ala Ser Ser Gly Phe Gln Glu Asp
            960                 965                 970 aaa agt ctg agt gat gtt gag gaa gag gag gat tct gac ggt ttc tac                    3219
Lys Ser Leu Ser Asp Val Glu Glu Glu Glu Asp Ser Asp Gly Phe Tyr
975                 980                 985                 990 aag gag ccc atc act atg gaa gat ctg att tct tac agt ttt caa gtg                    3267
Lys Glu Pro Ile Thr Met Glu Asp Leu Ile Ser Tyr Ser Phe Gln Val
                    995                 1000                1005 gcc aga ggc atg gag ttc ctg tct tcc aga aag tgc att cat cgg                        3312
Ala Arg Gly Met Glu Phe Leu Ser Ser Arg Lys Cys Ile His Arg
                    1010                1015                1020 gac ctg gca gcg aga aac att ctt tta tct gag aac aac gtg gtg                        3357
Asp Leu Ala Ala Arg Asn Ile Leu Leu Ser Glu Asn Asn Val Val
                    1025                1030                1035 aag att tgt gat ttt ggc ctt gcc cgg gat att tat aag aac ccc                        3402
Lys Ile Cys Asp Phe Gly Leu Ala Arg Asp Ile Tyr Lys Asn Pro
                    1040                1045                1050
```

| | | | | | | | | | | | | |
|---|---|---|---|---|---|---|---|---|---|---|---|---|
| gat | tat | gtg | aga | aaa | gga | gat | act | cga | ctt | cct | ctg | aaa | tgg | atg | 3447 |
| Asp | Tyr | Val | Arg | Lys | Gly | Asp | Thr | Arg | Leu | Pro | Leu | Lys | Trp | Met | |
| | | | 1055 | | | | 1060 | | | | | 1065 | | | |

```
gat tat gtg aga aaa gga gat act cga ctt cct ctg aaa tgg atg     3447
Asp Tyr Val Arg Lys Gly Asp Thr Arg Leu Pro Leu Lys Trp Met
            1055            1060                1065 gct ccc gaa tct atc ttt gac aaa atc tac agc acc aag agc gac     3492
Ala Pro Glu Ser Ile Phe Asp Lys Ile Tyr Ser Thr Lys Ser Asp
            1070            1075                1080 gtg tgg tct tac gga gta ttg ctg tgg gaa atc ttc tcc tta ggt     3537
Val Trp Ser Tyr Gly Val Leu Leu Trp Glu Ile Phe Ser Leu Gly
            1085            1090                1095 ggg tct cca tac cca gga gta caa atg gat gag gac ttt tgc agt     3582
Gly Ser Pro Tyr Pro Gly Val Gln Met Asp Glu Asp Phe Cys Ser
            1100            1105                1110 cgc ctg agg gaa ggc atg agg atg aga gct cct gag tac tct act     3627
Arg Leu Arg Glu Gly Met Arg Met Arg Ala Pro Glu Tyr Ser Thr
            1115            1120                1125 cct gaa atc tat cag atc atg ctg gac tgc tgg cac aga gac cca     3672
Pro Glu Ile Tyr Gln Ile Met Leu Asp Cys Trp His Arg Asp Pro
            1130            1135                1140 aaa gaa agg cca aga ttt gca gaa ctt gtg gaa aaa cta ggt gat     3717
Lys Glu Arg Pro Arg Phe Ala Glu Leu Val Glu Lys Leu Gly Asp
            1145            1150                1155 ttg ctt caa gca aat gta caa cag gat ggt aaa gac tac atc cca     3762
Leu Leu Gln Ala Asn Val Gln Gln Asp Gly Lys Asp Tyr Ile Pro
            1160            1165                1170 atc aat gcc ata ctg aca gga aat agt ggg ttt aca tac tca act     3807
Ile Asn Ala Ile Leu Thr Gly Asn Ser Gly Phe Thr Tyr Ser Thr
            1175            1180                1185 cct gcc ttc tct gag gac ttc ttc aag gaa agt att tca gct ccg     3852
Pro Ala Phe Ser Glu Asp Phe Phe Lys Glu Ser Ile Ser Ala Pro
            1190            1195                1200 aag ttt aat tca gga agc tct gat gat gtc aga tat gta aat gct     3897
Lys Phe Asn Ser Gly Ser Ser Asp Asp Val Arg Tyr Val Asn Ala
            1205            1210                1215 ttc aag ttc atg agc ctg gaa aga atc aaa acc ttt gaa gaa ctt     3942
Phe Lys Phe Met Ser Leu Glu Arg Ile Lys Thr Phe Glu Glu Leu
            1220            1225                1230 tta ccg aat gcc acc tcc atg ttt gat gac tac cag ggc gac agc     3987
Leu Pro Asn Ala Thr Ser Met Phe Asp Asp Tyr Gln Gly Asp Ser
            1235            1240                1245 agc act ctg ttg gcc tct ccc atg ctg aag cgc ttc acc tgg act     4032
Ser Thr Leu Leu Ala Ser Pro Met Leu Lys Arg Phe Thr Trp Thr
            1250            1255                1260 gac agc aaa ccc aag gcc tcg ctc aag att gac ttg aga gta acc     4077
Asp Ser Lys Pro Lys Ala Ser Leu Lys Ile Asp Leu Arg Val Thr
            1265            1270                1275 agt aaa agt aag gag tcg ggg ctg tct gat gtc agc agg ccc agt     4122
Ser Lys Ser Lys Glu Ser Gly Leu Ser Asp Val Ser Arg Pro Ser
            1280            1285                1290 ttc tgc cat tcc agc tgt ggg cac gtc agc gaa ggc aag cgc agg     4167
Phe Cys His Ser Ser Cys Gly His Val Ser Glu Gly Lys Arg Arg
            1295            1300                1305 ttc acc tac gac cac gct gag ctg gaa agg aaa atc gcg tgc tgc     4212
Phe Thr Tyr Asp His Ala Glu Leu Glu Arg Lys Ile Ala Cys Cys
            1310            1315                1320 tcc ccg ccc cca gac tac aac tcg gtg gtc ctg tac tcc acc cca     4257
Ser Pro Pro Pro Asp Tyr Asn Ser Val Val Leu Tyr Ser Thr Pro
            1325            1330                1335 ccc atc tag agtttgacac gaagccttat ttctagaagc acatgtgtat        4306
Pro Ile
```

```
ttataccccc aggaaactag cttttgccag tattatgcat atataagttt acacctttat    4366
ctttccatgg gagccagctg ctttttgtga ttttttttaat agtgctttt ttttttgact    4426 aacaagaatg taactccaga tagagaaata gtgacaagtg aagaacacta ctgctaaatc    4486
ctcatgttac tcagtgttag agaaatcctt cctaaaccca atgacttccc tgctccaacc    4546
cccgccacct cagggcacgc aggaccagtt tgattgagga gctgcactga tcacccaatg    4606
catcacgtac cccactgggc cagccctgca gcccaaaacc cagggcaaca agcccgttag    4666
ccccagggga tcactggctg gcctgagcaa catctcggga gtcctctagc aggcctaaga    4726
catgtgagga ggaaaaggaa aaaagcaaa aagcaaggga gaaagagaaa ccgggagaa     4786 ggcatgagaa agaatttgag acgcaccatg tgggcacgga gggggacggg gctcagcaat    4846
gccatttcag tggcttccca gctctgaccc ttctacattt gagggcccag ccaggagcag    4906
atggacagcg atgaggggac attttctgga ttctgggagg caagaaaagg acaaatatct    4966
tttttggaac taaagcaaat tttagacctt tacctatgga agtggttcta tgtccattct    5026
cattcgtggc atgttttgat ttgtagcact gagggtggca ctcaactctg agcccatact    5086
tttggctcct ctagtaagat gcactgaaaa cttagccaga gttaggttgt ctccaggcca    5146
tgatggcctt acactgaaaa tgtcacattc tattttgggt attaatatat agtccagaca    5206
cttaactcaa tttcttggta ttattctgtt ttgcacagtt agttgtgaaa gaaagctgag    5266
aagaatgaaa atgcagtcct gaggagagtt ttctccatat caaaacgagg gctgatggag    5326
gaaaaaggtc aataaggtca agggaagacc ccgtctctat accaaccaaa ccaattcacc    5386
aacacagttg ggacccaaaa cacaggaagt cagtcacgtt tccttttcat ttaatgggga    5446
ttccactatc tcacactaat ctgaaaggat gtggaagagc attagctggc gcatattaag    5506
cactttaagc tccttgagta aaaggtggt atgtaattta tgcaaggtat ttctccagtt    5566
gggactcagg atattagtta atgagccatc actagaagaa aagcccattt tcaactgctt    5626
tgaaacttgc ctggggtctg agcatgatgg gaatagggag acagggtagg aaagggcgcc    5686
tactcttcag ggtctaaaga tcaagtgggc cttggatcgc taagctggct ctgtttgatg    5746
ctatttatgc aagttagggt ctatgtattt a                                  5777
```

<210> SEQ ID NO 2
<211> LENGTH: 1338
<212> TYPE: PRT
<213> ORGANISM: Homo sapiens

<400> SEQUENCE: 2

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110
```

-continued

```
Pro Thr Ser Lys Lys Glu Thr Glu Ser Ala Ile Tyr Ile Phe Ile
            115                 120                 125
Ser Asp Thr Gly Arg Pro Phe Val Glu Met Tyr Ser Glu Ile Pro Glu
    130                 135                 140
Ile Ile His Met Thr Glu Gly Arg Glu Leu Val Ile Pro Cys Arg Val
145                 150                 155                 160
Thr Ser Pro Asn Ile Thr Val Thr Leu Lys Lys Phe Pro Leu Asp Thr
                165                 170                 175
Leu Ile Pro Asp Gly Lys Arg Ile Ile Trp Asp Ser Arg Lys Gly Phe
                180                 185                 190
Ile Ile Ser Asn Ala Thr Tyr Lys Glu Ile Gly Leu Leu Thr Cys Glu
            195                 200                 205
Ala Thr Val Asn Gly His Leu Tyr Lys Thr Asn Tyr Leu Thr His Arg
    210                 215                 220
Gln Thr Asn Thr Ile Ile Asp Val Gln Ile Ser Thr Pro Arg Pro Val
225                 230                 235                 240
Lys Leu Leu Arg Gly His Thr Leu Val Leu Asn Cys Thr Ala Thr Thr
                245                 250                 255
Pro Leu Asn Thr Arg Val Gln Met Thr Trp Ser Tyr Pro Asp Glu Lys
                260                 265                 270
Asn Lys Arg Ala Ser Val Arg Arg Ile Asp Gln Ser Asn Ser His
            275                 280                 285
Ala Asn Ile Phe Tyr Ser Val Leu Thr Ile Asp Lys Met Gln Asn Lys
    290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Phe Ile Thr Val
                325                 330                 335
Lys His Arg Lys Gln Gln Val Leu Glu Thr Val Ala Gly Lys Arg Ser
                340                 345                 350
Tyr Arg Leu Ser Met Lys Val Lys Ala Phe Pro Ser Pro Glu Val Val
    355                 360                 365
Trp Leu Lys Asp Gly Leu Pro Ala Thr Glu Lys Ser Ala Arg Tyr Leu
370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                405                 410                 415
Asn Leu Thr Ala Thr Leu Ile Val Asn Val Lys Pro Gln Ile Tyr Glu
            420                 425                 430
Lys Ala Val Ser Ser Phe Pro Asp Pro Ala Leu Tyr Pro Leu Gly Ser
    435                 440                 445
Arg Gln Ile Leu Thr Cys Thr Ala Tyr Gly Ile Pro Gln Pro Thr Ile
    450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
                485                 490                 495
Asn Met Gly Asn Arg Ile Glu Ser Ile Thr Gln Arg Met Ala Ile Ile
                500                 505                 510
Glu Gly Lys Asn Lys Met Ala Ser Thr Leu Val Val Ala Asp Ser Arg
            515                 520                 525
Ile Ser Gly Ile Tyr Ile Cys Ile Ala Ser Asn Lys Val Gly Thr Val
```

```
            530             535             540
Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
                580                 585                 590

Arg Thr Val Asn Arg Thr Met His Tyr Ser Ile Ser Lys Gln Lys
                595                 600                 605

Met Ala Ile Thr Lys Glu His Ser Ile Thr Leu Asn Leu Thr Ile Met
610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
                660                 665                 670

Ala Ile Ser Ser Ser Thr Thr Leu Asp Cys His Ala Asn Gly Val Pro
                675                 680                 685

Glu Pro Gln Ile Thr Trp Phe Lys Asn Asn His Lys Ile Gln Gln Glu
690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
                740                 745                 750

Asp Lys Ser Asn Leu Glu Leu Ile Thr Leu Thr Cys Thr Cys Val Ala
                755                 760                 765

Ala Thr Leu Phe Trp Leu Leu Leu Thr Leu Leu Ile Arg Lys Met Lys
                770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
                820                 825                 830

Leu Gly Arg Gly Ala Phe Gly Lys Val Val Gln Ala Ser Ala Phe Gly
                835                 840                 845

Ile Lys Lys Ser Pro Thr Cys Arg Thr Val Ala Val Lys Met Leu Lys
850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
                900                 905                 910

Lys Tyr Gly Asn Leu Ser Asn Tyr Leu Lys Ser Lys Arg Asp Leu Phe
                915                 920                 925

Phe Leu Asn Lys Asp Ala Ala Leu His Met Glu Pro Lys Lys Glu Lys
                930                 935                 940

Met Glu Pro Gly Leu Glu Gln Gly Lys Lys Pro Arg Leu Asp Ser Val
945                 950                 955                 960
```

-continued

```
Thr Ser Ser Glu Ser Phe Ala Ser Ser Gly Phe Gln Glu Asp Lys Ser
            965                 970                 975

Leu Ser Asp Val Glu Glu Glu Asp Ser Asp Gly Phe Tyr Lys Glu
        980                 985                 990

Pro Ile Thr Met Glu Asp Leu Ile Ser Tyr Ser Phe Gln Val Ala Arg
        995                 1000                1005

Gly Met Glu Phe Leu Ser Ser Arg Lys Cys Ile His Arg Asp Leu
    1010                1015                1020

Ala Ala Arg Asn Ile Leu Leu Ser Glu Asn Asn Val Val Lys Ile
    1025                1030                1035

Cys Asp Phe Gly Leu Ala Arg Asp Ile Tyr Lys Asn Pro Asp Tyr
    1040                1045                1050

Val Arg Lys Gly Asp Thr Arg Leu Pro Leu Lys Trp Met Ala Pro
    1055                1060                1065

Glu Ser Ile Phe Asp Lys Ile Tyr Ser Thr Lys Ser Asp Val Trp
    1070                1075                1080

Ser Tyr Gly Val Leu Leu Trp Glu Ile Phe Ser Leu Gly Gly Ser
    1085                1090                1095

Pro Tyr Pro Gly Val Gln Met Asp Glu Asp Phe Cys Ser Arg Leu
    1100                1105                1110

Arg Glu Gly Met Arg Met Arg Ala Pro Glu Tyr Ser Thr Pro Glu
    1115                1120                1125

Ile Tyr Gln Ile Met Leu Asp Cys Trp His Arg Asp Pro Lys Glu
    1130                1135                1140

Arg Pro Arg Phe Ala Glu Leu Val Glu Lys Leu Gly Asp Leu Leu
    1145                1150                1155

Gln Ala Asn Val Gln Gln Asp Gly Lys Asp Tyr Ile Pro Ile Asn
    1160                1165                1170

Ala Ile Leu Thr Gly Asn Ser Gly Phe Thr Tyr Ser Thr Pro Ala
    1175                1180                1185

Phe Ser Glu Asp Phe Phe Lys Glu Ser Ile Ser Ala Pro Lys Phe
    1190                1195                1200

Asn Ser Gly Ser Ser Asp Asp Val Arg Tyr Val Asn Ala Phe Lys
    1205                1210                1215

Phe Met Ser Leu Glu Arg Ile Lys Thr Phe Glu Glu Leu Leu Pro
    1220                1225                1230

Asn Ala Thr Ser Met Phe Asp Asp Tyr Gln Gly Asp Ser Ser Thr
    1235                1240                1245

Leu Leu Ala Ser Pro Met Leu Lys Arg Phe Thr Trp Thr Asp Ser
    1250                1255                1260

Lys Pro Lys Ala Ser Leu Lys Ile Asp Leu Arg Val Thr Ser Lys
    1265                1270                1275

Ser Lys Glu Ser Gly Leu Ser Asp Val Ser Arg Pro Ser Phe Cys
    1280                1285                1290

His Ser Ser Cys Gly His Val Ser Glu Gly Lys Arg Arg Phe Thr
    1295                1300                1305

Tyr Asp His Ala Glu Leu Glu Arg Lys Ile Ala Cys Cys Ser Pro
    1310                1315                1320

Pro Pro Asp Tyr Asn Ser Val Val Leu Tyr Ser Thr Pro Pro Ile
    1325                1330                1335

<210> SEQ ID NO 3
<211> LENGTH: 2292
```

```
<212> TYPE: DNA
<213> ORGANISM: Homo sapiens
<220> FEATURE:
<221> NAME/KEY: CDS
<222> LOCATION: (1)..(2292)

<400> SEQUENCE: 3
```

| | | | | | | | | | | | | | | | | |
|---|---|---|---|---|---|---|---|---|---|---|---|---|---|---|---|---|
| atg | agc | aag | gtg | ctg | ctg | gcc | gtc | gcc | ctg | tgg | ctc | tgc | gtg | gag | | 48 |
| Met | Glu | Ser | Lys | Val | Leu | Leu | Ala | Val | Ala | Leu | Trp | Leu | Cys | Val | Glu | |
| 1 | | | | 5 | | | | | 10 | | | | | 15 | | |
| acc | cgg | gcc | gcc | tct | gtg | ggt | ttg | cct | agt | gtt | tct | ctt | gat | ctg | ccc | 96 |
| Thr | Arg | Ala | Ala | Ser | Val | Gly | Leu | Pro | Ser | Val | Ser | Leu | Asp | Leu | Pro | |
| | | 20 | | | | | 25 | | | | | 30 | | | | |
| agg | ctc | agc | ata | caa | aaa | gac | ata | ctt | aca | att | aag | gct | aat | aca | act | 144 |
| Arg | Leu | Ser | Ile | Gln | Lys | Asp | Ile | Leu | Thr | Ile | Lys | Ala | Asn | Thr | Thr | |
| | | | 35 | | | | | 40 | | | | | 45 | | | |
| ctt | caa | att | act | tgc | agg | gga | cag | agg | gac | ttg | gac | tgg | ctt | tgg | ccc | 192 |
| Leu | Gln | Ile | Thr | Cys | Arg | Gly | Gln | Arg | Asp | Leu | Asp | Trp | Leu | Trp | Pro | |
| | 50 | | | | | 55 | | | | | 60 | | | | | |
| aat | aat | cag | agt | ggc | agt | gag | caa | agg | gtg | gag | gtg | act | gag | tgc | agc | 240 |
| Asn | Asn | Gln | Ser | Gly | Ser | Glu | Gln | Arg | Val | Glu | Val | Thr | Glu | Cys | Ser | |
| 65 | | | | | 70 | | | | | 75 | | | | | 80 | |
| gat | ggc | ctc | ttc | tgt | aag | aca | ctc | aca | att | cca | aaa | gtg | atc | gga | aat | 288 |
| Asp | Gly | Leu | Phe | Cys | Lys | Thr | Leu | Thr | Ile | Pro | Lys | Val | Ile | Gly | Asn | |
| | | | | 85 | | | | | 90 | | | | | 95 | | |
| gac | act | gga | gcc | tac | aag | tgc | ttc | tac | cgg | gaa | act | gac | ttg | gcc | tcg | 336 |
| Asp | Thr | Gly | Ala | Tyr | Lys | Cys | Phe | Tyr | Arg | Glu | Thr | Asp | Leu | Ala | Ser | |
| | | | 100 | | | | | 105 | | | | | 110 | | | |
| gtc | att | tat | gtc | tat | gtt | caa | gat | tac | aga | tct | cca | ttt | att | gct | tct | 384 |
| Val | Ile | Tyr | Val | Tyr | Val | Gln | Asp | Tyr | Arg | Ser | Pro | Phe | Ile | Ala | Ser | |
| | | 115 | | | | | 120 | | | | | 125 | | | | |
| gtt | agt | gac | caa | cat | gga | gtc | gtg | tac | att | act | gag | aac | aaa | aac | aaa | 432 |
| Val | Ser | Asp | Gln | His | Gly | Val | Val | Tyr | Ile | Thr | Glu | Asn | Lys | Asn | Lys | |
| | 130 | | | | | 135 | | | | | 140 | | | | | |
| act | gtg | gtg | att | cca | tgt | ctc | ggg | tcc | att | tca | aat | ctc | aac | gtg | tca | 480 |
| Thr | Val | Val | Ile | Pro | Cys | Leu | Gly | Ser | Ile | Ser | Asn | Leu | Asn | Val | Ser | |
| 145 | | | | | 150 | | | | | 155 | | | | | 160 | |
| ctt | tgt | gca | aga | tac | cca | gaa | aag | aga | ttt | gtt | cct | gat | ggt | aac | aga | 528 |
| Leu | Cys | Ala | Arg | Tyr | Pro | Glu | Lys | Arg | Phe | Val | Pro | Asp | Gly | Asn | Arg | |
| | | | 165 | | | | | 170 | | | | | 175 | | | |
| att | tcc | tgg | gac | agc | aag | aag | ggc | ttt | act | att | ccc | agc | tac | atg | atc | 576 |
| Ile | Ser | Trp | Asp | Ser | Lys | Lys | Gly | Phe | Thr | Ile | Pro | Ser | Tyr | Met | Ile | |
| | | | | 180 | | | | | 185 | | | | | 190 | | |
| agc | tat | gct | ggc | atg | gtc | ttc | tgt | gaa | gca | aaa | att | aat | gat | gaa | agt | 624 |
| Ser | Tyr | Ala | Gly | Met | Val | Phe | Cys | Glu | Ala | Lys | Ile | Asn | Asp | Glu | Ser | |
| | | 195 | | | | | 200 | | | | | 205 | | | | |
| tac | cag | tct | att | atg | tac | ata | gtt | gtc | gtt | gta | ggg | tat | agg | att | tat | 672 |
| Tyr | Gln | Ser | Ile | Met | Tyr | Ile | Val | Val | Val | Val | Gly | Tyr | Arg | Ile | Tyr | |
| | 210 | | | | | 215 | | | | | 220 | | | | | |
| gat | gtg | gtt | ctg | agt | ccg | tct | cat | gga | att | gaa | cta | tct | gtt | gga | gaa | 720 |
| Asp | Val | Val | Leu | Ser | Pro | Ser | His | Gly | Ile | Glu | Leu | Ser | Val | Gly | Glu | |
| 225 | | | | | 230 | | | | | 235 | | | | | 240 | |
| aag | ctt | gtc | tta | aat | tgt | aca | gca | aga | act | gaa | cta | aat | gtg | ggg | att | 768 |
| Lys | Leu | Val | Leu | Asn | Cys | Thr | Ala | Arg | Thr | Glu | Leu | Asn | Val | Gly | Ile | |
| | | | | 245 | | | | | 250 | | | | | 255 | | |
| gac | ttc | aac | tgg | gaa | tac | cct | tct | tcg | aag | cat | cag | cat | aag | aaa | ctt | 816 |
| Asp | Phe | Asn | Trp | Glu | Tyr | Pro | Ser | Ser | Lys | His | Gln | His | Lys | Lys | Leu | |
| | | | 260 | | | | | 265 | | | | | 270 | | | |
| gta | aac | cga | gac | cta | aaa | acc | cag | tct | ggg | agt | gag | atg | aag | aaa | ttt | 864 |
| Val | Asn | Arg | Asp | Leu | Lys | Thr | Gln | Ser | Gly | Ser | Glu | Met | Lys | Lys | Phe | |
| | 275 | | | | | 280 | | | | | 285 | | | | | |

-continued

| | | |
|---|---|---|
| ttg agc acc tta act ata gat ggt gta acc cgg agt gac caa gga ttg<br>Leu Ser Thr Leu Thr Ile Asp Gly Val Thr Arg Ser Asp Gln Gly Leu<br>290                            295                         300 | | 912 |
| tac acc tgt gca gca tcc agt ggg ctg atg acc aag aag aac agc aca<br>Tyr Thr Cys Ala Ala Ser Ser Gly Leu Met Thr Lys Lys Asn Ser Thr<br>305                          310                         315                   320 | | 960 |
| ttt gtc agg gtc cat gaa aaa cct ttt gtt gct ttt gga agt ggc atg<br>Phe Val Arg Val His Glu Lys Pro Phe Val Ala Phe Gly Ser Gly Met<br>                     325                         330                        335 | | 1008 |
| gaa tct ctg gtg gaa gcc acg gtg ggg gag cgt gtc aga atc cct gcg<br>Glu Ser Leu Val Glu Ala Thr Val Gly Glu Arg Val Arg Ile Pro Ala<br>               340                       345                        350 | | 1056 |
| aag tac ctt ggt tac cca ccc cca gaa ata aaa tgg tat aaa aat gga<br>Lys Tyr Leu Gly Tyr Pro Pro Pro Glu Ile Lys Trp Tyr Lys Asn Gly<br>                     355                         360                        365 | | 1104 |
| ata ccc ctt gag tcc aat cac aca att aaa gcg ggg cat gta ctg acg<br>Ile Pro Leu Glu Ser Asn His Thr Ile Lys Ala Gly His Val Leu Thr<br>370                            375                         380 | | 1152 |
| att atg gaa gtg agt gaa aga gac aca gga aat tac act gtc atc ctt<br>Ile Met Glu Val Ser Glu Arg Asp Thr Gly Asn Tyr Thr Val Ile Leu<br>385                            390                         395                   400 | | 1200 |
| acc aat ccc att tca aag gag aag cag agc cat gtg gtc tct ctg gtt<br>Thr Asn Pro Ile Ser Lys Glu Lys Gln Ser His Val Val Ser Leu Val<br>                     405                         410                        415 | | 1248 |
| gtg tat gtc cca ccc cag att ggt gag aaa tct cta atc tct cct gtg<br>Val Tyr Val Pro Pro Gln Ile Gly Glu Lys Ser Leu Ile Ser Pro Val<br>               420                       425                        430 | | 1296 |
| gat tcc tac cag tac ggc acc act caa acg ctg aca tgt acg gtc tat<br>Asp Ser Tyr Gln Tyr Gly Thr Thr Gln Thr Leu Thr Cys Thr Val Tyr<br>                     435                         440                        445 | | 1344 |
| gcc att cct ccc ccg cat cac atc cac tgg tat tgg cag ttg gag gaa<br>Ala Ile Pro Pro Pro His His Ile His Trp Tyr Trp Gln Leu Glu Glu<br>450                            455                         460 | | 1392 |
| gag tgc gcc aac gag ccc agc caa gct gtc tca gtg aca aac cca tac<br>Glu Cys Ala Asn Glu Pro Ser Gln Ala Val Ser Val Thr Asn Pro Tyr<br>465                            470                         475                   480 | | 1440 |
| cct tgt gaa gaa tgg aga agt gtg gag gac ttc cag gga gga aat aaa<br>Pro Cys Glu Glu Trp Arg Ser Val Glu Asp Phe Gln Gly Gly Asn Lys<br>                     485                         490                        495 | | 1488 |
| att gaa gtt aat aaa aat caa ttt gct cta att gaa gga aaa aac aaa<br>Ile Glu Val Asn Lys Asn Gln Phe Ala Leu Ile Glu Gly Lys Asn Lys<br>                     500                         505                        510 | | 1536 |
| act gta agt acc ctt gtt atc caa gcg gca aat gtg tca gct ttg tac<br>Thr Val Ser Thr Leu Val Ile Gln Ala Ala Asn Val Ser Ala Leu Tyr<br>               515                       520                        525 | | 1584 |
| aaa tgt gaa gcg gtc aac aaa gtc ggg aga gga gag agg gtg atc tcc<br>Lys Cys Glu Ala Val Asn Lys Val Gly Arg Gly Glu Arg Val Ile Ser<br>530                            535                         540 | | 1632 |
| ttc cac gtg acc agg ggt cct gaa att act ttg caa cct gac atg cag<br>Phe His Val Thr Arg Gly Pro Glu Ile Thr Leu Gln Pro Asp Met Gln<br>545                            550                         555                   560 | | 1680 |
| ccc act gag cag gag agc gtg tct ttg tgg tgc act gca gac aga tct<br>Pro Thr Glu Gln Glu Ser Val Ser Leu Trp Cys Thr Ala Asp Arg Ser<br>                     565                         570                        575 | | 1728 |
| acg ttt gag aac ctc aca tgg tac aag ctt ggc cca cag cct ctg cca<br>Thr Phe Glu Asn Leu Thr Trp Tyr Lys Leu Gly Pro Gln Pro Leu Pro<br>                     580                         585                        590 | | 1776 |
| atc cat gtg gga gag ttg ccc aca cct gtt tgc aag aac ttg gat act<br>Ile His Val Gly Glu Leu Pro Thr Pro Val Cys Lys Asn Leu Asp Thr | | 1824 |

-continued

```
                 595                 600                 605
ctt tgg aaa ttg aat gcc acc atg ttc tct aat agc aca aat gac att      1872
Leu Trp Lys Leu Asn Ala Thr Met Phe Ser Asn Ser Thr Asn Asp Ile
    610                 615                 620 ttg atc atg gag ctt aag aat gca tcc ttg cag gac caa gga gac tat      1920
Leu Ile Met Glu Leu Lys Asn Ala Ser Leu Gln Asp Gln Gly Asp Tyr
625                 630                 635                 640 gtc tgc ctt gct caa gac agg aag acc aag aaa aga cat tgc gtg gtc      1968
Val Cys Leu Ala Gln Asp Arg Lys Thr Lys Lys Arg His Cys Val Val
                645                 650                 655 agg cag ctc aca gtc cta gag cgt gtg gca ccc acg atc aca gga aac      2016
Arg Gln Leu Thr Val Leu Glu Arg Val Ala Pro Thr Ile Thr Gly Asn
            660                 665                 670 ctg gag aat cag acg aca agt att ggg gaa agc atc gaa gtc tca tgc      2064
Leu Glu Asn Gln Thr Thr Ser Ile Gly Glu Ser Ile Glu Val Ser Cys
        675                 680                 685 acg gca tct ggg aat ccc cct cca cag atc atg tgg ttt aaa gat aat      2112
Thr Ala Ser Gly Asn Pro Pro Pro Gln Ile Met Trp Phe Lys Asp Asn
    690                 695                 700 gag acc ctt gta gaa gac tca ggc att gta ttg aag gat ggg aac cgg      2160
Glu Thr Leu Val Glu Asp Ser Gly Ile Val Leu Lys Asp Gly Asn Arg
705                 710                 715                 720 aac ctc act atc cgc aga gtg agg aag gag gac gaa ggc ctc tac acc      2208
Asn Leu Thr Ile Arg Arg Val Arg Lys Glu Asp Glu Gly Leu Tyr Thr
                725                 730                 735 tgc cag gca tgc agt gtt ctt ggc tgt gca aaa gtg gag gca ttt ttc      2256
Cys Gln Ala Cys Ser Val Leu Gly Cys Ala Lys Val Glu Ala Phe Phe
            740                 745                 750 ata ata gaa ggt gcc cag gaa aag acg aac ttg gaa                      2292
Ile Ile Glu Gly Ala Gln Glu Lys Thr Asn Leu Glu
        755                 760

<210> SEQ ID NO 4
<211> LENGTH: 764
<212> TYPE: PRT
<213> ORGANISM: Homo sapiens

<400> SEQUENCE: 4

Met Glu Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160
```

-continued

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
    450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
            500                 505                 510

Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

```
Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Arg His Cys Val Val
                645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
        675                 680                 685

Thr Ala Ser Gly Asn Pro Pro Pro Gln Ile Met Trp Phe Lys Asp Asn
    690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu
        755                 760

<210> SEQ ID NO 5
<211> LENGTH: 4195
<212> TYPE: DNA
<213> ORGANISM: Homo sapiens
<220> FEATURE:
<221> NAME/KEY: CDS
<222> LOCATION: (20)..(3913)

<400> SEQUENCE: 5
ccacgcgcag cggccggag atg cag cgg ggc gcc gcg ctg tgc ctg cga ctg        52
                    Met Gln Arg Gly Ala Ala Leu Cys Leu Arg Leu
                     1               5                  10 tgg ctc tgc ctg gga ctc ctg gac ggc ctg gtg agt ggc tac tcc atg        100
Trp Leu Cys Leu Gly Leu Leu Asp Gly Leu Val Ser Gly Tyr Ser Met
         15                  20                  25 acc ccc ccg acc ttg aac atc acg gag gag tca cac gtc atc gac acc        148
Thr Pro Pro Thr Leu Asn Ile Thr Glu Glu Ser His Val Ile Asp Thr
     30                  35                  40 ggt gac agc ctg tcc atc tcc tgc agg gga cag cac ccc ctc gag tgg        196
Gly Asp Ser Leu Ser Ile Ser Cys Arg Gly Gln His Pro Leu Glu Trp
 45                  50                  55 gct tgg cca gga gct cag gag gcg cca gcc acc gga gac aag gac agc        244
Ala Trp Pro Gly Ala Gln Glu Ala Pro Ala Thr Gly Asp Lys Asp Ser
 60              65                  70                  75 gag gac acg ggg gtg gtg cga gac tgc gag ggc aca gac gcc agg ccc        292
Glu Asp Thr Gly Val Val Arg Asp Cys Glu Gly Thr Asp Ala Arg Pro
                 80                  85                  90 tac tgc aag gtg ttg ctg ctg cac gag gta cat gcc aac gac aca ggc        340
Tyr Cys Lys Val Leu Leu Leu His Glu Val His Ala Asn Asp Thr Gly
             95                 100                 105 agc tac gtc tgc tac tac aag tac atc aag gca cgc atc gag ggc acc        388
Ser Tyr Val Cys Tyr Tyr Lys Tyr Ile Lys Ala Arg Ile Glu Gly Thr
         110                 115                 120
```

```
acg gcc gcc agc tcc tac gtg ttc gtg aga gac ttt gag cag cca ttc      436
Thr Ala Ala Ser Ser Tyr Val Phe Val Arg Asp Phe Glu Gln Pro Phe
    125                 130                 135 atc aac aag cct gac acg ctc ttg gtc aac agg aag gac gcc atg tgg      484
Ile Asn Lys Pro Asp Thr Leu Leu Val Asn Arg Lys Asp Ala Met Trp
140                 145                 150                 155 gtg ccc tgt ctg gtg tcc atc ccc ggc ctc aat gtc acg ctg cgc tcg      532
Val Pro Cys Leu Val Ser Ile Pro Gly Leu Asn Val Thr Leu Arg Ser
                160                 165                 170 caa agc tcg gtg ctg tgg cca gac ggg cag gag gtg gtg tgg gat gac      580
Gln Ser Ser Val Leu Trp Pro Asp Gly Gln Glu Val Val Trp Asp Asp
            175                 180                 185 cgg cgg ggc atg ctc gtg tcc acg cca ctg ctg cac gat gcc ctg tac      628
Arg Arg Gly Met Leu Val Ser Thr Pro Leu Leu His Asp Ala Leu Tyr
        190                 195                 200 ctg cag tgc gag acc acc tgg gga gac cag gac ttc ctt tcc aac ccc      676
Leu Gln Cys Glu Thr Thr Trp Gly Asp Gln Asp Phe Leu Ser Asn Pro
205                 210                 215 ttc ctg gtg cac atc aca ggc aac gag ctc tat gac atc cag ctg ttg      724
Phe Leu Val His Ile Thr Gly Asn Glu Leu Tyr Asp Ile Gln Leu Leu
220                 225                 230                 235 ccc agg aag tcg ctg gag ctg ctg gta ggg gag aag ctg gtc ctg aac      772
Pro Arg Lys Ser Leu Glu Leu Leu Val Gly Glu Lys Leu Val Leu Asn
                240                 245                 250 tgc acc gtg tgg gct gag ttt aac tca ggt gtc acc ttt gac tgg gac      820
Cys Thr Val Trp Ala Glu Phe Asn Ser Gly Val Thr Phe Asp Trp Asp
            255                 260                 265 tac cca ggg aag cag gca gag cgg ggt aag tgg gtg ccc gag cga cgc      868
Tyr Pro Gly Lys Gln Ala Glu Arg Gly Lys Trp Val Pro Glu Arg Arg
        270                 275                 280 tcc cag cag acc cac aca gaa ctc tcc agc atc ctg acc atc cac aac      916
Ser Gln Gln Thr His Thr Glu Leu Ser Ser Ile Leu Thr Ile His Asn
285                 290                 295 gtc agc cag cac gac ctg ggc tcg tat gtg tgc aag gcc aac aac ggc      964
Val Ser Gln His Asp Leu Gly Ser Tyr Val Cys Lys Ala Asn Asn Gly
300                 305                 310                 315 atc cag cga ttt cgg gag agc acc gag gtc att gtg cat gaa aat ccc     1012
Ile Gln Arg Phe Arg Glu Ser Thr Glu Val Ile Val His Glu Asn Pro
                320                 325                 330 ttc atc agc gtc gag tgg ctc aaa gga ccc atc ctg gag gcc acg gca     1060
Phe Ile Ser Val Glu Trp Leu Lys Gly Pro Ile Leu Glu Ala Thr Ala
            335                 340                 345 gga gac gag ctg gtg aag ctg ccc gtg aag ctg gca gcg tac ccc ccg     1108
Gly Asp Glu Leu Val Lys Leu Pro Val Lys Leu Ala Ala Tyr Pro Pro
        350                 355                 360 ccc gag ttc cag tgg tac aag gat gga aag gca ctg tcc ggg cgc cac     1156
Pro Glu Phe Gln Trp Tyr Lys Asp Gly Lys Ala Leu Ser Gly Arg His
365                 370                 375 agt cca cat gcc ctg gtg ctc aag gag gtg aca gag gcc agc aca ggc     1204
Ser Pro His Ala Leu Val Leu Lys Glu Val Thr Glu Ala Ser Thr Gly
380                 385                 390                 395 acc tac acc ctc gcc ctg tgg aac tcc gct gct ggc ctg agg cgc aac     1252
Thr Tyr Thr Leu Ala Leu Trp Asn Ser Ala Ala Gly Leu Arg Arg Asn
                400                 405                 410 atc agc ctg gag ctg gtg gtg aat gtg ccc ccc cag ata cat gag aag     1300
Ile Ser Leu Glu Leu Val Val Asn Val Pro Pro Gln Ile His Glu Lys
            415                 420                 425 gag gcc tcc tcc ccc agc atc tac tcg cgt cac agc cgc cag gcc ctc     1348
Glu Ala Ser Ser Pro Ser Ile Tyr Ser Arg His Ser Arg Gln Ala Leu
        430                 435                 440
```

```
acc tgc acg gcc tac ggg gtg ccc ctg cct ctc agc atc cag tgg cac      1396
Thr Cys Thr Ala Tyr Gly Val Pro Leu Pro Leu Ser Ile Gln Trp His
    445                 450                 455 tgg cgg ccc tgg aca ccc tgc aag atg ttt gcc cag cgt agt ctc cgg      1444
Trp Arg Pro Trp Thr Pro Cys Lys Met Phe Ala Gln Arg Ser Leu Arg
460                 465                 470                 475 cgg cgg cag cag caa gac ctc atg cca cag tgc cgt gac tgg agg gcg      1492
Arg Arg Gln Gln Gln Asp Leu Met Pro Gln Cys Arg Asp Trp Arg Ala
                    480                 485                 490 gtg acc acg cag gat gcc gtg aac ccc atc gag agc ctg gac acc tgg      1540
Val Thr Thr Gln Asp Ala Val Asn Pro Ile Glu Ser Leu Asp Thr Trp
            495                 500                 505 acc gag ttt gtg gag gga aag aat aag act gtg agc aag ctg gtg atc      1588
Thr Glu Phe Val Glu Gly Lys Asn Lys Thr Val Ser Lys Leu Val Ile
        510                 515                 520 cag aat gcc aac gtg tct gcc atg tac aag tgt gtg gtc tcc aac aag      1636
Gln Asn Ala Asn Val Ser Ala Met Tyr Lys Cys Val Val Ser Asn Lys
    525                 530                 535 gtg ggc cag gat gag cgg ctc atc tac ttc tat gtg acc acc atc ccc      1684
Val Gly Gln Asp Glu Arg Leu Ile Tyr Phe Tyr Val Thr Thr Ile Pro
540                 545                 550                 555 gac ggc ttc acc atc gaa tcc aag cca tcc gag gag cta cta gag ggc      1732
Asp Gly Phe Thr Ile Glu Ser Lys Pro Ser Glu Glu Leu Leu Glu Gly
                    560                 565                 570 cag ccg gtg ctc ctg agc tgc caa gcc gac agc tac aag tac gag cat      1780
Gln Pro Val Leu Leu Ser Cys Gln Ala Asp Ser Tyr Lys Tyr Glu His
            575                 580                 585 ctg cgc tgg tac cgc ctc aac ctg tcc acg ctg cac gat gcg cac ggg      1828
Leu Arg Trp Tyr Arg Leu Asn Leu Ser Thr Leu His Asp Ala His Gly
        590                 595                 600 aac ccg ctt ctg ctc gac tgc aag aac gtg cat ctg ttc gcc acc cct      1876
Asn Pro Leu Leu Leu Asp Cys Lys Asn Val His Leu Phe Ala Thr Pro
    605                 610                 615 ctg gcc gcc agc ctg gag gag gtg gca cct ggg gcg cgc cac gcc acg      1924
Leu Ala Ala Ser Leu Glu Glu Val Ala Pro Gly Ala Arg His Ala Thr
620                 625                 630                 635 ctc agc ctg agt atc ccc cgc gtc gcg ccc gag cac gag ggc cac tat      1972
Leu Ser Leu Ser Ile Pro Arg Val Ala Pro Glu His Glu Gly His Tyr
                    640                 645                 650 gtg tgc gaa gtg caa gac cgg cgc agc cat gac aag cac tgc cac aag      2020
Val Cys Glu Val Gln Asp Arg Arg Ser His Asp Lys His Cys His Lys
            655                 660                 665 aag tac ctg tcg gtg cag gcc ctg gaa gcc cct cgg ctc acg cag aac      2068
Lys Tyr Leu Ser Val Gln Ala Leu Glu Ala Pro Arg Leu Thr Gln Asn
        670                 675                 680 ttg acc gac ctc ctg gtg aac gtg agc gac tcg ctg gag atg cag tgc      2116
Leu Thr Asp Leu Leu Val Asn Val Ser Asp Ser Leu Glu Met Gln Cys
    685                 690                 695 ttg gtg gcc gga gcg cac gcg ccc agc atc gtg tgg tac aaa gac gag      2164
Leu Val Ala Gly Ala His Ala Pro Ser Ile Val Trp Tyr Lys Asp Glu
700                 705                 710                 715 agg ctg ctg gag gaa aag tct gga gtc gac ttg gcg gac tcc aac cag      2212
Arg Leu Leu Glu Glu Lys Ser Gly Val Asp Leu Ala Asp Ser Asn Gln
                    720                 725                 730 aag ctg agc atc cag cgc gtg cgc gag gag gat gcg gga cgc tat ctg      2260
Lys Leu Ser Ile Gln Arg Val Arg Glu Glu Asp Ala Gly Arg Tyr Leu
            735                 740                 745 tgc agc gtg tgc aac gcc aag ggc tgc gtc aac tcc tcc gcc agc gtg      2308
Cys Ser Val Cys Asn Ala Lys Gly Cys Val Asn Ser Ser Ala Ser Val
```

-continued

|   |   |   |   |   |   |   |   |   |   |   |   |   |   |   |   |
|---|---|---|---|---|---|---|---|---|---|---|---|---|---|---|---|
|   | 750 |   |   |   |   | 755 |   |   |   |   | 760 |   |   |   |   |
| gcc | gtg | gaa | ggc | tcc | gag | gat | aag | ggc | agc | atg | gag | atc | gtg | atc | ctt | 2356 |
| Ala | Val | Glu | Gly | Ser | Glu | Asp | Lys | Gly | Ser | Met | Glu | Ile | Val | Ile | Leu |
| 765 |   |   |   |   | 770 |   |   |   |   | 775 |   |   |   |   |   |
| gtc | ggt | acc | ggc | gtc | atc | gct | gtc | ttc | ttc | tgg | gtc | ctc | ctc | ctc | ctc | 2404 |
| Val | Gly | Thr | Gly | Val | Ile | Ala | Val | Phe | Phe | Trp | Val | Leu | Leu | Leu | Leu |
| 780 |   |   |   |   | 785 |   |   |   |   | 790 |   |   |   |   | 795 |
| atc | ttc | tgt | aac | atg | agg | agg | ccg | gcc | cac | gca | gac | atc | aag | acg | ggc | 2452 |
| Ile | Phe | Cys | Asn | Met | Arg | Arg | Pro | Ala | His | Ala | Asp | Ile | Lys | Thr | Gly |
|   |   |   |   | 800 |   |   |   |   | 805 |   |   |   |   | 810 |   |
| tac | ctg | tcc | atc | atc | atg | gac | ccc | ggg | gag | gtg | cct | ctg | gag | gag | caa | 2500 |
| Tyr | Leu | Ser | Ile | Ile | Met | Asp | Pro | Gly | Glu | Val | Pro | Leu | Glu | Glu | Gln |
|   |   |   | 815 |   |   |   |   | 820 |   |   |   |   | 825 |   |   |
| tgc | gaa | tac | ctg | tcc | tac | gat | gcc | agc | cag | tgg | gaa | ttc | ccc | cga | gag | 2548 |
| Cys | Glu | Tyr | Leu | Ser | Tyr | Asp | Ala | Ser | Gln | Trp | Glu | Phe | Pro | Arg | Glu |
|   |   | 830 |   |   |   |   | 835 |   |   |   |   | 840 |   |   |   |
| cgg | ctg | cac | ctg | ggg | aga | gtg | ctc | ggc | tac | ggc | gcc | ttc | ggg | aag | gtg | 2596 |
| Arg | Leu | His | Leu | Gly | Arg | Val | Leu | Gly | Tyr | Gly | Ala | Phe | Gly | Lys | Val |
|   | 845 |   |   |   |   | 850 |   |   |   |   | 855 |   |   |   |   |
| gtg | gaa | gcc | tcc | gct | ttc | ggc | atc | cac | aag | ggc | agc | agc | tgt | gac | acc | 2644 |
| Val | Glu | Ala | Ser | Ala | Phe | Gly | Ile | His | Lys | Gly | Ser | Ser | Cys | Asp | Thr |
| 860 |   |   |   |   | 865 |   |   |   |   | 870 |   |   |   |   | 875 |
| gtg | gcc | gtg | aaa | atg | ctg | aaa | gag | ggc | gcc | acg | gcc | agc | gag | cac | cgc | 2692 |
| Val | Ala | Val | Lys | Met | Leu | Lys | Glu | Gly | Ala | Thr | Ala | Ser | Glu | His | Arg |
|   |   |   |   | 880 |   |   |   |   | 885 |   |   |   |   | 890 |   |
| gcg | ctg | atg | tcg | gag | ctc | aag | atc | ctc | att | cac | atc | ggc | aac | cac | ctc | 2740 |
| Ala | Leu | Met | Ser | Glu | Leu | Lys | Ile | Leu | Ile | His | Ile | Gly | Asn | His | Leu |
|   |   |   | 895 |   |   |   |   | 900 |   |   |   |   | 905 |   |   |
| aac | gtg | gtc | aac | ctc | ctc | ggg | gcg | tgc | acc | aag | ccg | cag | ggc | ccc | ctc | 2788 |
| Asn | Val | Val | Asn | Leu | Leu | Gly | Ala | Cys | Thr | Lys | Pro | Gln | Gly | Pro | Leu |
|   |   | 910 |   |   |   |   | 915 |   |   |   |   | 920 |   |   |   |
| atg | gtg | atc | gtg | gag | ttc | tgc | aag | tac | ggc | aac | ctc | tcc | aac | ttc | ctg | 2836 |
| Met | Val | Ile | Val | Glu | Phe | Cys | Lys | Tyr | Gly | Asn | Leu | Ser | Asn | Phe | Leu |
|   | 925 |   |   |   |   | 930 |   |   |   |   | 935 |   |   |   |   |
| cgc | gcc | aag | cgg | gac | gcc | ttc | agc | ccc | tgc | gcg | gag | aag | tct | ccc | gag | 2884 |
| Arg | Ala | Lys | Arg | Asp | Ala | Phe | Ser | Pro | Cys | Ala | Glu | Lys | Ser | Pro | Glu |
| 940 |   |   |   |   | 945 |   |   |   |   | 950 |   |   |   |   | 955 |
| cag | cgc | gga | cgc | ttc | cgc | gcc | atg | gtg | gag | ctc | gcc | agg | ctg | gat | cgg | 2932 |
| Gln | Arg | Gly | Arg | Phe | Arg | Ala | Met | Val | Glu | Leu | Ala | Arg | Leu | Asp | Arg |
|   |   |   |   | 960 |   |   |   |   | 965 |   |   |   |   | 970 |   |
| agg | cgg | ccg | ggg | agc | agc | gac | agg | gtc | ctc | ttc | gcg | cgg | ttc | tcg | aag | 2980 |
| Arg | Arg | Pro | Gly | Ser | Ser | Asp | Arg | Val | Leu | Phe | Ala | Arg | Phe | Ser | Lys |
|   |   |   | 975 |   |   |   |   | 980 |   |   |   |   | 985 |   |   |
| acc | gag | ggc | gga | gcg | agg | cgg | gct | tct | cca | gac | caa | gaa | gct | gag | gac | 3028 |
| Thr | Glu | Gly | Gly | Ala | Arg | Arg | Ala | Ser | Pro | Asp | Gln | Glu | Ala | Glu | Asp |
|   |   | 990 |   |   |   |   | 995 |   |   |   |   | 1000 |   |   |   |
| ctg | tgg | ctg | agc | ccg | ctg | acc | atg | gaa | gat | ctt | gtc | tgc | tac | agc | | 3073 |
| Leu | Trp | Leu | Ser | Pro | Leu | Thr | Met | Glu | Asp | Leu | Val | Cys | Tyr | Ser |
|   | 1005 |   |   |   |   | 1010 |   |   |   |   | 1015 |   |   |   |   |
| ttc | cag | gtg | gcc | aga | ggg | atg | gag | ttc | ctg | gct | tcc | cga | aag | tgc | | 3118 |
| Phe | Gln | Val | Ala | Arg | Gly | Met | Glu | Phe | Leu | Ala | Ser | Arg | Lys | Cys |
|   |   | 1020 |   |   |   |   | 1025 |   |   |   |   | 1030 |   |   |   |
| atc | cac | aga | gac | ctg | gct | gct | cgg | aac | att | ctg | ctg | tcg | gaa | agc | | 3163 |
| Ile | His | Arg | Asp | Leu | Ala | Ala | Arg | Asn | Ile | Leu | Leu | Ser | Glu | Ser |
|   |   |   | 1035 |   |   |   |   | 1040 |   |   |   |   | 1045 |   |   |
| gac | gtg | gtg | aag | atc | tgt | gac | ttt | ggc | ctt | gcc | cgg | gac | atc | tac | | 3208 |
| Asp | Val | Val | Lys | Ile | Cys | Asp | Phe | Gly | Leu | Ala | Arg | Asp | Ile | Tyr |
|   |   | 1050 |   |   |   |   | 1055 |   |   |   |   | 1060 |   |   |   |
| aaa | gac | cct | gac | tac | gtc | cgc | aag | ggc | agt | gcc | cgg | ctg | ccc | ctg | | 3253 |

```
Lys Asp Pro Asp Tyr Val Arg Lys Gly Ser Ala Arg Leu Pro Leu
    1065                1070                1075 aag tgg atg gcc cct gaa agc atc ttc gac aag gtg tac acc acg      3298
Lys Trp Met Ala Pro Glu Ser Ile Phe Asp Lys Val Tyr Thr Thr
    1080                1085                1090 cag agt gac gtg tgg tcc ttt ggg gtg ctt ctc tgg gag atc ttc      3343
Gln Ser Asp Val Trp Ser Phe Gly Val Leu Leu Trp Glu Ile Phe
    1095                1100                1105 tct ctg ggg gcc tcc ccg tac cct ggg gtg cag atc aat gag gag      3388
Ser Leu Gly Ala Ser Pro Tyr Pro Gly Val Gln Ile Asn Glu Glu
    1110                1115                1120 ttc tgc cag cgg ctg aga gac ggc aca agg atg agg gcc ccg gag      3433
Phe Cys Gln Arg Leu Arg Asp Gly Thr Arg Met Arg Ala Pro Glu
    1125                1130                1135 ctg gcc act ccc gcc ata cgc cgc atc atg ctg aac tgc tgg tcc      3478
Leu Ala Thr Pro Ala Ile Arg Arg Ile Met Leu Asn Cys Trp Ser
    1140                1145                1150 gga gac ccc aag gcg aga cct gca ttc tcg gag ctg gtg gag atc      3523
Gly Asp Pro Lys Ala Arg Pro Ala Phe Ser Glu Leu Val Glu Ile
    1155                1160                1165 ctg ggg gac ctg ctc cag ggc agg ggc ctg caa gag gaa gag gag      3568
Leu Gly Asp Leu Leu Gln Gly Arg Gly Leu Gln Glu Glu Glu Glu
    1170                1175                1180 gtc tgc atg gcc ccg cgc agc tct cag agc tca gaa gag ggc agc      3613
Val Cys Met Ala Pro Arg Ser Ser Gln Ser Ser Glu Glu Gly Ser
    1185                1190                1195 ttc tcg cag gtg tcc acc atg gcc cta cac atc gcc cag gct gac      3658
Phe Ser Gln Val Ser Thr Met Ala Leu His Ile Ala Gln Ala Asp
    1200                1205                1210 gct gag gac agc ccg cca agc ctg cag cgc cac agc ctg gcc gcc      3703
Ala Glu Asp Ser Pro Pro Ser Leu Gln Arg His Ser Leu Ala Ala
    1215                1220                1225 agg tat tac aac tgg gtg tcc ttt ccc ggg tgc ctg gcc aga ggg      3748
Arg Tyr Tyr Asn Trp Val Ser Phe Pro Gly Cys Leu Ala Arg Gly
    1230                1235                1240 gct gag acc cgt ggt tcc tcc agg atg aag aca ttt gag gaa ttc      3793
Ala Glu Thr Arg Gly Ser Ser Arg Met Lys Thr Phe Glu Glu Phe
    1245                1250                1255 ccc atg acc cca acg acc tac aaa ggc tct gtg gac aac cag aca      3838
Pro Met Thr Pro Thr Thr Tyr Lys Gly Ser Val Asp Asn Gln Thr
    1260                1265                1270 gac agt ggg atg gtg ctg gcc tcg gag gag ttt gag cag ata gag      3883
Asp Ser Gly Met Val Leu Ala Ser Glu Glu Phe Glu Gln Ile Glu
    1275                1280                1285 agc agg cat aga caa gaa agc ggc ttc agg tagctgaagc agagagagag    3933
Ser Arg His Arg Gln Glu Ser Gly Phe Arg
    1290                1295 aaggcagcat acgtcagcat tttcttctct gcacttataa gaaagatcaa agactttaag  3993
actttcgcta tttcttctac tgctatctac tacaaacttc aaagaggaac caggaggaca  4053
agaggagcat gaaagtggac aaggagtgtg accactgaag caccacaggg aagggggttag  4113 gcctccggat gactgcgggc aggcctggat aatatccagc ctcccacaag aagctggtgg  4173
agcagagtgt tccctgactc ct                                         4195
```

<210> SEQ ID NO 6
<211> LENGTH: 1298
<212> TYPE: PRT
<213> ORGANISM: Homo sapiens

```
<400> SEQUENCE: 6

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
                35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
    210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
                245                 250                 255

Glu Phe Asn Ser Gly Val Thr Phe Asp Trp Asp Tyr Pro Gly Lys Gln
            260                 265                 270

Ala Glu Arg Gly Lys Trp Val Pro Glu Arg Arg Ser Gln Gln Thr His
        275                 280                 285

Thr Glu Leu Ser Ser Ile Leu Thr Ile His Asn Val Ser Gln His Asp
    290                 295                 300

Leu Gly Ser Tyr Val Cys Lys Ala Asn Asn Gly Ile Gln Arg Phe Arg
305                 310                 315                 320

Glu Ser Thr Glu Val Ile Val His Glu Asn Pro Phe Ile Ser Val Glu
                325                 330                 335

Trp Leu Lys Gly Pro Ile Leu Glu Ala Thr Ala Gly Asp Glu Leu Val
            340                 345                 350

Lys Leu Pro Val Lys Leu Ala Ala Tyr Pro Pro Pro Glu Phe Gln Trp
        355                 360                 365

Tyr Lys Asp Gly Lys Ala Leu Ser Gly Arg His Ser Pro His Ala Leu
    370                 375                 380

Val Leu Lys Glu Val Thr Glu Ala Ser Thr Gly Thr Tyr Thr Leu Ala
385                 390                 395                 400

Leu Trp Asn Ser Ala Ala Gly Leu Arg Arg Asn Ile Ser Leu Glu Leu
                405                 410                 415
```

```
Val Val Asn Val Pro Pro Gln Ile His Glu Lys Ala Ser Ser Pro
            420                 425                 430

Ser Ile Tyr Ser Arg His Ser Arg Gln Ala Leu Thr Cys Thr Ala Tyr
        435                 440                 445

Gly Val Pro Leu Pro Leu Ser Ile Gln Trp His Trp Arg Pro Trp Thr
    450                 455                 460

Pro Cys Lys Met Phe Ala Gln Arg Ser Leu Arg Arg Arg Gln Gln Gln
465                 470                 475                 480

Asp Leu Met Pro Gln Cys Arg Asp Trp Arg Ala Val Thr Thr Gln Asp
            485                 490                 495

Ala Val Asn Pro Ile Glu Ser Leu Asp Thr Trp Thr Glu Phe Val Glu
                500                 505                 510

Gly Lys Asn Lys Thr Val Ser Lys Leu Val Ile Gln Asn Ala Asn Val
        515                 520                 525

Ser Ala Met Tyr Lys Cys Val Val Ser Asn Lys Val Gly Gln Asp Glu
    530                 535                 540

Arg Leu Ile Tyr Phe Tyr Val Thr Thr Ile Pro Asp Gly Phe Thr Ile
545                 550                 555                 560

Glu Ser Lys Pro Ser Glu Glu Leu Leu Glu Gly Gln Pro Val Leu Leu
            565                 570                 575

Ser Cys Gln Ala Asp Ser Tyr Lys Tyr Glu His Leu Arg Trp Tyr Arg
                580                 585                 590

Leu Asn Leu Ser Thr Leu His Asp Ala His Gly Asn Pro Leu Leu Leu
        595                 600                 605

Asp Cys Lys Asn Val His Leu Phe Ala Thr Pro Leu Ala Ala Ser Leu
    610                 615                 620

Glu Glu Val Ala Pro Gly Ala Arg His Ala Thr Leu Ser Leu Ser Ile
625                 630                 635                 640

Pro Arg Val Ala Pro Glu His Glu Gly His Tyr Val Cys Glu Val Gln
            645                 650                 655

Asp Arg Arg Ser His Asp Lys His Cys His Lys Lys Tyr Leu Ser Val
                660                 665                 670

Gln Ala Leu Glu Ala Pro Arg Leu Thr Gln Asn Leu Thr Asp Leu Leu
        675                 680                 685

Val Asn Val Ser Asp Ser Leu Glu Met Gln Cys Leu Val Ala Gly Ala
    690                 695                 700

His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
            725                 730                 735

Arg Val Arg Glu Glu Asp Ala Gly Arg Tyr Leu Cys Ser Val Cys Asn
                740                 745                 750

Ala Lys Gly Cys Val Asn Ser Ser Ala Ser Val Ala Val Glu Gly Ser
        755                 760                 765

Glu Asp Lys Gly Ser Met Glu Ile Val Ile Leu Val Gly Thr Gly Val
    770                 775                 780

Ile Ala Val Phe Phe Trp Val Leu Leu Leu Leu Ile Phe Cys Asn Met
785                 790                 795                 800

Arg Arg Pro Ala His Ala Asp Ile Lys Thr Gly Tyr Leu Ser Ile Ile
            805                 810                 815

Met Asp Pro Gly Glu Val Pro Leu Glu Glu Gln Cys Glu Tyr Leu Ser
                820                 825                 830
```

```
Tyr Asp Ala Ser Gln Trp Glu Phe Pro Arg Glu Arg Leu His Leu Gly
            835                 840                 845

Arg Val Leu Gly Tyr Gly Ala Phe Gly Lys Val Glu Ala Ser Ala
        850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
                885                 890                 895

Leu Lys Ile Leu Ile His Ile Gly Asn His Leu Asn Val Val Asn Leu
                900                 905                 910

Leu Gly Ala Cys Thr Lys Pro Gln Gly Pro Leu Met Val Ile Val Glu
                915                 920                 925

Phe Cys Lys Tyr Gly Asn Leu Ser Asn Phe Leu Arg Ala Lys Arg Asp
930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Pro Gly Ser
                965                 970                 975

Ser Asp Arg Val Leu Phe Ala Arg Phe Ser Lys Thr Glu Gly Gly Ala
                980                 985                 990

Arg Arg Ala Ser Pro Asp Gln Glu  Ala Glu Asp Leu Trp  Leu Ser Pro
            995                 1000                 1005

Leu Thr Met Glu Asp Leu Val  Cys Tyr Ser Phe Gln  Val Ala Arg
        1010                1015                1020

Gly Met Glu Phe Leu Ala Ser  Arg Lys Cys Ile His  Arg Asp Leu
    1025                1030                1035

Ala Ala Arg Asn Ile Leu Leu  Ser Glu Ser Asp Val  Val Lys Ile
    1040                1045                1050

Cys Asp Phe Gly Leu Ala Arg  Asp Ile Tyr Lys Asp  Pro Asp Tyr
    1055                1060                1065

Val Arg Lys Gly Ser Ala Arg  Leu Pro Leu Lys Trp  Met Ala Pro
    1070                1075                1080

Glu Ser Ile Phe Asp Lys Val  Tyr Thr Thr Gln Ser  Asp Val Trp
    1085                1090                1095

Ser Phe Gly Val Leu Leu Trp  Glu Ile Phe Ser Leu  Gly Ala Ser
    1100                1105                1110

Pro Tyr Pro Gly Val Gln Ile  Asn Glu Glu Phe Cys  Gln Arg Leu
    1115                1120                1125

Arg Asp Gly Thr Arg Met Arg  Ala Pro Glu Leu Ala  Thr Pro Ala
    1130                1135                1140

Ile Arg Arg Ile Met Leu Asn  Cys Trp Ser Gly Asp  Pro Lys Ala
    1145                1150                1155

Arg Pro Ala Phe Ser Glu Leu  Val Glu Ile Leu Gly  Asp Leu Leu
    1160                1165                1170

Gln Gly Arg Gly Leu Gln Glu  Glu Glu Glu Val Cys  Met Ala Pro
    1175                1180                1185

Arg Ser Ser Gln Ser Ser Glu  Gly Ser Phe Ser  Gln Val Ser
    1190                1195                1200

Thr Met Ala Leu His Ile Ala  Gln Ala Asp Ala Glu  Asp Ser Pro
    1205                1210                1215

Pro Ser Leu Gln Arg His Ser  Leu Ala Ala Arg Tyr  Tyr Asn Trp
    1220                1225                1230

Val Ser Phe Pro Gly Cys Leu  Ala Arg Gly Ala Glu  Thr Arg Gly
```

```
                    1235                1240                1245
Ser  Ser  Arg  Met  Lys  Thr  Phe  Glu  Glu  Phe  Pro  Met  Thr  Pro  Thr
     1250                1255                1260

Thr  Tyr  Lys  Gly  Ser  Val  Asp  Asn  Gln  Thr  Asp  Ser  Gly  Met  Val
     1265                1270                1275

Leu  Ala  Ser  Glu  Glu  Phe  Glu  Gln  Ile  Glu  Ser  Arg  His  Arg  Gln
     1280                1285                1290

Glu  Ser  Gly  Phe  Arg
     1295

<210> SEQ ID NO 7
<211> LENGTH: 1713
<212> TYPE: DNA
<213> ORGANISM: Artificial sequence
<220> FEATURE:
<223> OTHER INFORMATION: R-2 A
<220> FEATURE:
<221> NAME/KEY: CDS
<222> LOCATION: (1)..(1713)

<400> SEQUENCE: 7 atg  ccg  ctg  ctg  cta  ctg  ctg  ccc  ctg  ctg  tgg  gca  ggg  gcc  ctg  gct      48
Met  Pro  Leu  Leu  Leu  Leu  Leu  Pro  Leu  Leu  Trp  Ala  Gly  Ala  Leu  Ala
1                    5                        10                       15 atg  gat  aag  ctt  gct  agc  gga  tcc  ttg  cct  agt  gtt  tct  ctt  gat  ctg      96
Met  Asp  Lys  Leu  Ala  Ser  Gly  Ser  Leu  Pro  Ser  Val  Ser  Leu  Asp  Leu
             20                       25                       30 ccc  agg  ctc  agc  ata  caa  aaa  gac  ata  ctt  aca  att  aag  gct  aat  aca     144
Pro  Arg  Leu  Ser  Ile  Gln  Lys  Asp  Ile  Leu  Thr  Ile  Lys  Ala  Asn  Thr
                  35                       40                       45 act  ctt  caa  att  act  tgc  agg  gga  cag  agg  gac  ttg  gac  tgg  ctt  tgg     192
Thr  Leu  Gln  Ile  Thr  Cys  Arg  Gly  Gln  Arg  Asp  Leu  Asp  Trp  Leu  Trp
     50                       55                       60 ccc  aat  aat  cag  agt  ggc  agt  gag  caa  agg  gtg  gag  gtg  act  gag  tgc     240
Pro  Asn  Asn  Gln  Ser  Gly  Ser  Glu  Gln  Arg  Val  Glu  Val  Thr  Glu  Cys
65                   70                       75                       80 agc  gat  ggc  ctc  ttc  tgt  aag  aca  ctc  aca  att  cca  aaa  gtg  atc  gga     288
Ser  Asp  Gly  Leu  Phe  Cys  Lys  Thr  Leu  Thr  Ile  Pro  Lys  Val  Ile  Gly
                      85                       90                       95 aat  gac  act  gga  gcc  tac  aag  tgc  ttc  tac  cgg  gaa  act  gac  ttg  gcc     336
Asn  Asp  Thr  Gly  Ala  Tyr  Lys  Cys  Phe  Tyr  Arg  Glu  Thr  Asp  Leu  Ala
                 100                      105                      110 tcg  gtc  att  tat  gtc  tat  gtt  caa  gat  tac  aga  tct  cca  ttt  att  gct     384
Ser  Val  Ile  Tyr  Val  Tyr  Val  Gln  Asp  Tyr  Arg  Ser  Pro  Phe  Ile  Ala
            115                      120                      125 tct  gtt  agt  gac  caa  cat  gga  gtc  gtg  tac  att  act  gag  aac  aaa  aac     432
Ser  Val  Ser  Asp  Gln  His  Gly  Val  Val  Tyr  Ile  Thr  Glu  Asn  Lys  Asn
        130                      135                      140 aaa  act  gtg  gtg  att  cca  tgt  ctc  ggg  tcc  att  tca  aat  ctc  aac  gtg     480
Lys  Thr  Val  Val  Ile  Pro  Cys  Leu  Gly  Ser  Ile  Ser  Asn  Leu  Asn  Val
145                      150                      155                      160 tca  ctt  tgt  gca  aga  tac  cca  gaa  aag  aga  ttt  gtt  cct  gat  ggt  aac     528
Ser  Leu  Cys  Ala  Arg  Tyr  Pro  Glu  Lys  Arg  Phe  Val  Pro  Asp  Gly  Asn
                     165                      170                      175 aga  att  tcc  tgg  gac  agc  aag  aag  ggc  ttt  act  att  ccc  agc  tac  atg     576
Arg  Ile  Ser  Trp  Asp  Ser  Lys  Lys  Gly  Phe  Thr  Ile  Pro  Ser  Tyr  Met
                 180                      185                      190 atc  agc  tat  gct  ggc  atg  gtc  ttc  tgt  gaa  gca  aaa  att  aat  gat  gaa     624
Ile  Ser  Tyr  Ala  Gly  Met  Val  Phe  Cys  Glu  Ala  Lys  Ile  Asn  Asp  Glu
            195                      200                      205
```

|  |  |
|---|---|
| agt tac cag tct att atg tac ata gtt gtc gtt gta ggg tat agg att<br>Ser Tyr Gln Ser Ile Met Tyr Ile Val Val Val Val Gly Tyr Arg Ile<br>210                   215                 220 | 672 |
| tat gat gtg gtt ctg agt ccg tct cat gga att gaa cta tct gtt gga<br>Tyr Asp Val Val Leu Ser Pro Ser His Gly Ile Glu Leu Ser Val Gly<br>225                   230                 235               240 | 720 |
| gaa aag ctt gtc tta aat tgt aca gca aga act gaa cta aat gtg ggg<br>Glu Lys Leu Val Leu Asn Cys Thr Ala Arg Thr Glu Leu Asn Val Gly<br>                   245                 250                 255 | 768 |
| att gac ttc aac tgg gaa tac cct tct tcg aag cat cag cat aag aaa<br>Ile Asp Phe Asn Trp Glu Tyr Pro Ser Ser Lys His Gln His Lys Lys<br>    260                   265                 270 | 816 |
| ctt gta aac cga gac cta aaa acc cag tct ggg agt gag atg aag aaa<br>Leu Val Asn Arg Asp Leu Lys Thr Gln Ser Gly Ser Glu Met Lys Lys<br>            275                 280                 285 | 864 |
| ttt ttg agc acc tta act ata gat ggt gta acc cgg agt gac caa gga<br>Phe Leu Ser Thr Leu Thr Ile Asp Gly Val Thr Arg Ser Asp Gln Gly<br>290                   295                 300 | 912 |
| ttg tac acc tgt gca gca tcc agt ggg ctg atg acc aag aag aac agc<br>Leu Tyr Thr Cys Ala Ala Ser Ser Gly Leu Met Thr Lys Lys Asn Ser<br>305                   310                 315               320 | 960 |
| aca ttt gtc agg gtc cat gaa gat ccc atc gaa ggt cgt ggt ggt ggt<br>Thr Phe Val Arg Val His Glu Asp Pro Ile Glu Gly Arg Gly Gly Gly<br>                  325                 330                 335 | 1008 |
| ggt ggt gat ccc aaa tct tgt gac aaa cct cac aca tgc cca ctg tgc<br>Gly Gly Asp Pro Lys Ser Cys Asp Lys Pro His Thr Cys Pro Leu Cys<br>            340                 345                 350 | 1056 |
| cca gca cct gaa ctc ctg ggg gga ccg tca gtc ttc ctc ttc ccc cca<br>Pro Ala Pro Glu Leu Leu Gly Gly Pro Ser Val Phe Leu Phe Pro Pro<br>                  355                 360                 365 | 1104 |
| aaa ccc aag gac acc ctc atg atc tcc cgg acc cct gag gtc aca tgc<br>Lys Pro Lys Asp Thr Leu Met Ile Ser Arg Thr Pro Glu Val Thr Cys<br>370                   375                 380 | 1152 |
| gtg gtg gtg gac gtg agc cac gaa gac cct gag gtc aag ttc aac tgg<br>Val Val Val Asp Val Ser His Glu Asp Pro Glu Val Lys Phe Asn Trp<br>385                   390                 395               400 | 1200 |
| tac gtg gac ggc gtg gag gtg cat aat gcc aag aca aag ccg cgg gag<br>Tyr Val Asp Gly Val Glu Val His Asn Ala Lys Thr Lys Pro Arg Glu<br>                  405                 410                 415 | 1248 |
| gag cag tac aac agc acg tac cgt gtg gtc agc gtc ctc acc gtc ctg<br>Glu Gln Tyr Asn Ser Thr Tyr Arg Val Val Ser Val Leu Thr Val Leu<br>            420                 425                 430 | 1296 |
| cac cag gac tgg ctg aat ggc aag gag tac aag tgc aag gtc tcc aac<br>His Gln Asp Trp Leu Asn Gly Lys Glu Tyr Lys Cys Lys Val Ser Asn<br>                  435                 440                 445 | 1344 |
| aaa gcc ctc cca gcc ccc atc gag aaa acc atc tcc aaa gcc aaa ggg<br>Lys Ala Leu Pro Ala Pro Ile Glu Lys Thr Ile Ser Lys Ala Lys Gly<br>450                   455                 460 | 1392 |
| cag ccc cga gaa cca cag gtg tac acc ctg ccc cca tcc cgg gat gag<br>Gln Pro Arg Glu Pro Gln Val Tyr Thr Leu Pro Pro Ser Arg Asp Glu<br>465                   470                 475               480 | 1440 |
| ctg acc aag aac cag gtc agc ctg acc tgc cta gtc aaa ggc ttc tat<br>Leu Thr Lys Asn Gln Val Ser Leu Thr Cys Leu Val Lys Gly Phe Tyr<br>                  485                 490                 495 | 1488 |
| ccc agc gac atc gcc gtg gag tgg gag agc aat ggg cag ccg gag aac<br>Pro Ser Asp Ile Ala Val Glu Trp Glu Ser Asn Gly Gln Pro Glu Asn<br>            500                 505                 510 | 1536 |
| aac tac aag gcc acg cct ccc gtg ctg gac tcc gac ggc tcc ttc ttc<br>Asn Tyr Lys Ala Thr Pro Pro Val Leu Asp Ser Asp Gly Ser Phe Phe<br>               515                 520                 525 | 1584 |

```
ctc tac agc aag ctc acc gtg gac aag agc agg tgg cag cag ggg aac    1632
Leu Tyr Ser Lys Leu Thr Val Asp Lys Ser Arg Trp Gln Gln Gly Asn
    530             535                 540 gtc ttc tca tgc tcc gtg atg cat gag gct ctg cac aac cac tac acg    1680
Val Phe Ser Cys Ser Val Met His Glu Ala Leu His Asn His Tyr Thr
545                 550                 555                 560 cag aag agc ctc tcc ctg tct ccg ggt aaa tga                        1713
Gln Lys Ser Leu Ser Leu Ser Pro Gly Lys
                565                 570

<210> SEQ ID NO 8
<211> LENGTH: 570
<212> TYPE: PRT
<213> ORGANISM: Artificial sequence
<220> FEATURE:
<223> OTHER INFORMATION: Synthetic Construct

<400> SEQUENCE: 8

Met Pro Leu Leu Leu Leu Pro Leu Leu Trp Ala Gly Ala Leu Ala
1               5                   10                  15

Met Asp Lys Leu Ala Ser Gly Ser Leu Pro Ser Val Ser Leu Asp Leu
                20                  25                  30

Pro Arg Leu Ser Ile Gln Lys Asp Ile Leu Thr Ile Lys Ala Asn Thr
            35                  40                  45

Thr Leu Gln Ile Thr Cys Arg Gly Gln Arg Asp Leu Asp Trp Leu Trp
    50                  55                  60

Pro Asn Asn Gln Ser Gly Ser Glu Gln Arg Val Glu Val Thr Glu Cys
65                  70                  75                  80

Ser Asp Gly Leu Phe Cys Lys Thr Leu Thr Ile Pro Lys Val Ile Gly
                85                  90                  95

Asn Asp Thr Gly Ala Tyr Lys Cys Phe Tyr Arg Glu Thr Asp Leu Ala
            100                 105                 110

Ser Val Ile Tyr Val Tyr Val Gln Asp Tyr Arg Ser Pro Phe Ile Ala
        115                 120                 125

Ser Val Ser Asp Gln His Gly Val Val Tyr Ile Thr Glu Asn Lys Asn
    130                 135                 140

Lys Thr Val Val Ile Pro Cys Leu Gly Ser Ile Ser Asn Leu Asn Val
145                 150                 155                 160

Ser Leu Cys Ala Arg Tyr Pro Glu Lys Arg Phe Val Pro Asp Gly Asn
                165                 170                 175

Arg Ile Ser Trp Asp Ser Lys Lys Gly Phe Thr Ile Pro Ser Tyr Met
            180                 185                 190

Ile Ser Tyr Ala Gly Met Val Phe Cys Glu Ala Lys Ile Asn Asp Glu
        195                 200                 205

Ser Tyr Gln Ser Ile Met Tyr Ile Val Val Val Gly Tyr Arg Ile
    210                 215                 220

Tyr Asp Val Val Leu Ser Pro Ser His Gly Ile Glu Leu Ser Val Gly
225                 230                 235                 240

Glu Lys Leu Val Leu Asn Cys Thr Ala Arg Thr Glu Leu Asn Val Gly
                245                 250                 255

Ile Asp Phe Asn Trp Glu Tyr Pro Ser Ser Lys His Gln His Lys Lys
            260                 265                 270

Leu Val Asn Arg Asp Leu Lys Thr Gln Ser Gly Ser Glu Met Lys Lys
        275                 280                 285

Phe Leu Ser Thr Leu Thr Ile Asp Gly Val Thr Arg Ser Asp Gln Gly
    290                 295                 300
```

```
Leu Tyr Thr Cys Ala Ala Ser Ser Gly Leu Met Thr Lys Lys Asn Ser
305                 310                 315                 320

Thr Phe Val Arg Val His Glu Asp Pro Ile Glu Gly Arg Gly Gly Gly
            325                 330                 335

Gly Gly Asp Pro Lys Ser Cys Asp Lys Pro His Thr Cys Pro Leu Cys
            340                 345                 350

Pro Ala Pro Glu Leu Leu Gly Gly Pro Ser Val Phe Leu Phe Pro Pro
            355                 360                 365

Lys Pro Lys Asp Thr Leu Met Ile Ser Arg Thr Pro Glu Val Thr Cys
370                 375                 380

Val Val Val Asp Val Ser His Glu Asp Pro Glu Val Lys Phe Asn Trp
385                 390                 395                 400

Tyr Val Asp Gly Val Glu Val His Asn Ala Lys Thr Lys Pro Arg Glu
            405                 410                 415

Glu Gln Tyr Asn Ser Thr Tyr Arg Val Val Ser Val Leu Thr Val Leu
            420                 425                 430

His Gln Asp Trp Leu Asn Gly Lys Glu Tyr Lys Cys Lys Val Ser Asn
            435                 440                 445

Lys Ala Leu Pro Ala Pro Ile Glu Lys Thr Ile Ser Lys Ala Lys Gly
450                 455                 460

Gln Pro Arg Glu Pro Gln Val Tyr Thr Leu Pro Pro Ser Arg Asp Glu
465                 470                 475                 480

Leu Thr Lys Asn Gln Val Ser Leu Thr Cys Leu Val Lys Gly Phe Tyr
            485                 490                 495

Pro Ser Asp Ile Ala Val Glu Trp Glu Ser Asn Gly Gln Pro Glu Asn
            500                 505                 510

Asn Tyr Lys Ala Thr Pro Pro Val Leu Asp Ser Asp Gly Ser Phe Phe
            515                 520                 525

Leu Tyr Ser Lys Leu Thr Val Asp Lys Ser Arg Trp Gln Gln Gly Asn
530                 535                 540

Val Phe Ser Cys Ser Val Met His Glu Ala Leu His Asn His Tyr Thr
545                 550                 555                 560

Gln Lys Ser Leu Ser Leu Ser Pro Gly Lys
            565                 570

<210> SEQ ID NO 9
<211> LENGTH: 1416
<212> TYPE: DNA
<213> ORGANISM: Artificial sequence
<220> FEATURE:
<223> OTHER INFORMATION: R-2 B
<220> FEATURE:
<221> NAME/KEY: CDS
<222> LOCATION: (1)..(1416)

<400> SEQUENCE: 9 atg ccg ctg ctg cta ctg ctg ccc ctg ctg tgg gca ggg gcc ctg gct      48
Met Pro Leu Leu Leu Leu Leu Pro Leu Leu Trp Ala Gly Ala Leu Ala
1               5                   10                  15 atg gat aag ctt gct agc ggt acc ctc gag gat ggc cgc gga tcc ttg      96
Met Asp Lys Leu Ala Ser Gly Thr Leu Glu Asp Gly Arg Gly Ser Leu
            20                  25                  30 cct agt gtt tct ctt gat ctg ccc agg ctc agc ata caa aaa gac ata     144
Pro Ser Val Ser Leu Asp Leu Pro Arg Leu Ser Ile Gln Lys Asp Ile
        35                  40                  45 ctt aca att aag gct aat aca act ctt caa att act tgc agg gga cag     192
Leu Thr Ile Lys Ala Asn Thr Thr Leu Gln Ile Thr Cys Arg Gly Gln
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 50  |     |     |     | 55  |     |     |     | 60  |     |     |     |     |     |     |      |
| agg | gac | ttg | gac | tgg | ctt | tgg | ccc | aat | aat | cag | agt | ggc | agt | gag | caa | 240  |
| Arg | Asp | Leu | Asp | Trp | Leu | Trp | Pro | Asn | Asn | Gln | Ser | Gly | Ser | Glu | Gln |      |
| 65  |     |     |     | 70  |     |     |     |     | 75  |     |     |     |     | 80  |     |      |
| agg | gtg | gag | gtg | act | gag | tgc | agc | gat | ggc | ctc | ttc | tgt | aag | aca | ctc | 288  |
| Arg | Val | Glu | Val | Thr | Glu | Cys | Ser | Asp | Gly | Leu | Phe | Cys | Lys | Thr | Leu |      |
|     |     |     |     |     | 85  |     |     |     |     | 90  |     |     |     |     | 95  |      |
| aca | att | cca | aaa | gtg | atc | gga | aat | gac | act | gga | gcc | tac | aag | tgc | ttc | 336  |
| Thr | Ile | Pro | Lys | Val | Ile | Gly | Asn | Asp | Thr | Gly | Ala | Tyr | Lys | Cys | Phe |      |
|     |     |     | 100 |     |     |     |     | 105 |     |     |     |     | 110 |     |     |      |
| tac | cgg | gaa | act | gac | ttg | gcc | tcg | gtc | att | tat | gtc | tat | gtt | caa | gat | 384  |
| Tyr | Arg | Glu | Thr | Asp | Leu | Ala | Ser | Val | Ile | Tyr | Val | Tyr | Val | Gln | Asp |      |
|     |     | 115 |     |     |     |     | 120 |     |     |     |     | 125 |     |     |     |      |
| tac | aga | tct | cca | ttt | att | gct | tct | gtt | agt | gac | caa | cat | gga | gtc | gtg | 432  |
| Tyr | Arg | Ser | Pro | Phe | Ile | Ala | Ser | Val | Ser | Asp | Gln | His | Gly | Val | Val |      |
| 130 |     |     |     |     | 135 |     |     |     |     | 140 |     |     |     |     |     |      |
| tac | att | act | gag | aac | aaa | aac | aaa | act | gtg | gtg | att | cca | tgt | ctc | ggg | 480  |
| Tyr | Ile | Thr | Glu | Asn | Lys | Asn | Lys | Thr | Val | Val | Ile | Pro | Cys | Leu | Gly |      |
| 145 |     |     |     |     | 150 |     |     |     |     | 155 |     |     |     |     | 160 |      |
| tcc | att | tca | aat | ctc | aac | gtg | tca | ctt | tgt | gca | aga | tac | cca | gaa | aag | 528  |
| Ser | Ile | Ser | Asn | Leu | Asn | Val | Ser | Leu | Cys | Ala | Arg | Tyr | Pro | Glu | Lys |      |
|     |     |     |     | 165 |     |     |     |     | 170 |     |     |     |     | 175 |     |      |
| aga | ttt | gtt | cct | gat | ggt | aac | aga | att | tcc | tgg | gac | agc | aag | aag | ggc | 576  |
| Arg | Phe | Val | Pro | Asp | Gly | Asn | Arg | Ile | Ser | Trp | Asp | Ser | Lys | Lys | Gly |      |
|     |     |     | 180 |     |     |     |     | 185 |     |     |     |     | 190 |     |     |      |
| ttt | act | att | ccc | agc | tac | atg | atc | agc | tat | gct | ggc | atg | gtc | ttc | tgt | 624  |
| Phe | Thr | Ile | Pro | Ser | Tyr | Met | Ile | Ser | Tyr | Ala | Gly | Met | Val | Phe | Cys |      |
|     |     | 195 |     |     |     |     | 200 |     |     |     |     | 205 |     |     |     |      |
| gaa | gca | aaa | att | aat | gat | gaa | agt | tac | cag | tct | att | atg | tac | ata | gtt | 672  |
| Glu | Ala | Lys | Ile | Asn | Asp | Glu | Ser | Tyr | Gln | Ser | Ile | Met | Tyr | Ile | Val |      |
| 210 |     |     |     |     | 215 |     |     |     |     | 220 |     |     |     |     |     |      |
| gtc | gtt | gta | ggg | gat | ccc | atc | gaa | ggt | cgt | ggt | ggt | ggt | ggt | ggt | gat | 720  |
| Val | Val | Val | Gly | Asp | Pro | Ile | Glu | Gly | Arg | Gly | Gly | Gly | Gly | Gly | Asp |      |
| 225 |     |     |     |     | 230 |     |     |     |     | 235 |     |     |     |     | 240 |      |
| ccc | aaa | tct | tgt | gac | aaa | cct | cac | aca | tgc | cca | ctg | tgc | cca | gca | cct | 768  |
| Pro | Lys | Ser | Cys | Asp | Lys | Pro | His | Thr | Cys | Pro | Leu | Cys | Pro | Ala | Pro |      |
|     |     |     |     | 245 |     |     |     |     | 250 |     |     |     |     | 255 |     |      |
| gaa | ctc | ctg | ggg | gga | ccg | tca | gtc | ttc | ctc | ttc | ccc | cca | aaa | ccc | aag | 816  |
| Glu | Leu | Leu | Gly | Gly | Pro | Ser | Val | Phe | Leu | Phe | Pro | Pro | Lys | Pro | Lys |      |
|     |     |     | 260 |     |     |     |     | 265 |     |     |     |     | 270 |     |     |      |
| gac | acc | ctc | atg | atc | tcc | cgg | acc | cct | gag | gtc | aca | tgc | gtg | gtg | gtg | 864  |
| Asp | Thr | Leu | Met | Ile | Ser | Arg | Thr | Pro | Glu | Val | Thr | Cys | Val | Val | Val |      |
|     |     | 275 |     |     |     |     | 280 |     |     |     |     | 285 |     |     |     |      |
| gac | gtg | agc | cac | gaa | gac | cct | gag | gtc | aag | ttc | aac | tgg | tac | gtg | gac | 912  |
| Asp | Val | Ser | His | Glu | Asp | Pro | Glu | Val | Lys | Phe | Asn | Trp | Tyr | Val | Asp |      |
| 290 |     |     |     |     | 295 |     |     |     |     | 300 |     |     |     |     |     |      |
| ggc | gtg | gag | gtg | cat | aat | gcc | aag | aca | aag | ccg | cgg | gag | gag | cag | tac | 960  |
| Gly | Val | Glu | Val | His | Asn | Ala | Lys | Thr | Lys | Pro | Arg | Glu | Glu | Gln | Tyr |      |
| 305 |     |     |     |     | 310 |     |     |     |     | 315 |     |     |     |     | 320 |      |
| aac | agc | acg | tac | cgt | gtg | gtc | agc | gtc | ctc | acc | gtc | ctg | cac | cag | gac | 1008 |
| Asn | Ser | Thr | Tyr | Arg | Val | Val | Ser | Val | Leu | Thr | Val | Leu | His | Gln | Asp |      |
|     |     |     |     | 325 |     |     |     |     | 330 |     |     |     |     | 335 |     |      |
| tgg | ctg | aat | ggc | aag | gag | tac | aag | tgc | aag | gtc | tcc | aac | aaa | gcc | ctc | 1056 |
| Trp | Leu | Asn | Gly | Lys | Glu | Tyr | Lys | Cys | Lys | Val | Ser | Asn | Lys | Ala | Leu |      |
|     |     |     | 340 |     |     |     |     | 345 |     |     |     |     | 350 |     |     |      |
| cca | gcc | ccc | atc | gag | aaa | acc | atc | tcc | aaa | gcc | aaa | ggg | cag | ccc | cga | 1104 |
| Pro | Ala | Pro | Ile | Glu | Lys | Thr | Ile | Ser | Lys | Ala | Lys | Gly | Gln | Pro | Arg |      |
|     |     | 355 |     |     |     |     | 360 |     |     |     |     | 365 |     |     |     |      |
| gaa | cca | cag | gtg | tac | acc | ctg | ccc | cca | tcc | cgg | gat | gag | ctg | acc | aag | 1152 |

```
                                        Glu Pro Gln Val Tyr Thr Leu Pro Pro Ser Arg Asp Glu Leu Thr Lys
                                            370                 375                 380 aac cag gtc agc ctg acc tgc cta gtc aaa ggc ttc tat ccc agc gac                              1200
Asn Gln Val Ser Leu Thr Cys Leu Val Lys Gly Phe Tyr Pro Ser Asp
385                 390                 395                 400 atc gcc gtg gag tgg gag agc aat ggg cag ccg gag aac aac tac aag                              1248
Ile Ala Val Glu Trp Glu Ser Asn Gly Gln Pro Glu Asn Asn Tyr Lys
                405                 410                 415 gcc acg cct ccc gtg ctg gac tcc gac ggc tcc ttc ttc ctc tac agc                              1296
Ala Thr Pro Pro Val Leu Asp Ser Asp Gly Ser Phe Phe Leu Tyr Ser
                420                 425                 430 aag ctc acc gtg gac aag agc agg tgg cag cag ggg aac gtc ttc tca                              1344
Lys Leu Thr Val Asp Lys Ser Arg Trp Gln Gln Gly Asn Val Phe Ser
                435                 440                 445 tgc tcc gtg atg cat gag gct ctg cac aac cac tac acg cag aag agc                              1392
Cys Ser Val Met His Glu Ala Leu His Asn His Tyr Thr Gln Lys Ser
450                 455                 460 ctc tcc ctg tct ccg ggt aaa tga                                                              1416
Leu Ser Leu Ser Pro Gly Lys
465                 470

<210> SEQ ID NO 10
<211> LENGTH: 471
<212> TYPE: PRT
<213> ORGANISM: Artificial sequence
<220> FEATURE:
<223> OTHER INFORMATION: Synthetic Construct

<400> SEQUENCE: 10

Met Pro Leu Leu Leu Leu Leu Pro Leu Leu Trp Ala Gly Ala Leu Ala
1               5                   10                  15

Met Asp Lys Leu Ala Ser Gly Thr Leu Glu Asp Gly Arg Gly Ser Leu
            20                  25                  30

Pro Ser Val Ser Leu Asp Leu Pro Arg Leu Ser Ile Gln Lys Asp Ile
        35                  40                  45

Leu Thr Ile Lys Ala Asn Thr Thr Leu Gln Ile Thr Cys Arg Gly Gln
50                  55                  60

Arg Asp Leu Asp Trp Leu Trp Pro Asn Asn Gln Ser Gly Ser Glu Gln
65                  70                  75                  80

Arg Val Glu Val Thr Glu Cys Ser Asp Gly Leu Phe Cys Lys Thr Leu
                85                  90                  95

Thr Ile Pro Lys Val Ile Gly Asn Asp Thr Gly Ala Tyr Lys Cys Phe
            100                 105                 110

Tyr Arg Glu Thr Asp Leu Ala Ser Val Ile Tyr Val Tyr Val Gln Asp
        115                 120                 125

Tyr Arg Ser Pro Phe Ile Ala Ser Val Ser Asp Gln His Gly Val Val
130                 135                 140

Tyr Ile Thr Glu Asn Lys Asn Lys Thr Val Val Ile Pro Cys Leu Gly
145                 150                 155                 160

Ser Ile Ser Asn Leu Asn Val Ser Leu Cys Ala Arg Tyr Pro Glu Lys
                165                 170                 175

Arg Phe Val Pro Asp Gly Asn Arg Ile Ser Trp Asp Ser Lys Lys Gly
            180                 185                 190

Phe Thr Ile Pro Ser Tyr Met Ile Ser Tyr Ala Gly Met Val Phe Cys
        195                 200                 205

Glu Ala Lys Ile Asn Asp Glu Ser Tyr Gln Ser Ile Met Tyr Ile Val
        210                 215                 220
```

```
Val Val Val Gly Asp Pro Ile Glu Gly Arg Gly Gly Gly Gly Asp
225                 230                 235                 240

Pro Lys Ser Cys Asp Lys Pro His Thr Cys Pro Leu Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Ala Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 11
<211> LENGTH: 1434
<212> TYPE: DNA
<213> ORGANISM: Artificial sequence
<220> FEATURE:
<223> OTHER INFORMATION: R-2 C
<220> FEATURE:
<221> NAME/KEY: CDS
<222> LOCATION: (1)..(1434)

<400> SEQUENCE: 11 atg ccg ctg ctg cta ctg ctg ccc ctg ctg tgg gca ggg gcc ctg gct    48
Met Pro Leu Leu Leu Leu Leu Pro Leu Leu Trp Ala Gly Ala Leu Ala
1               5                   10                  15 atg gat aag ctt gct agc ggt acc ctc gag gat ggc cgc gga tcc ttg    96
Met Asp Lys Leu Ala Ser Gly Thr Leu Glu Asp Gly Arg Gly Ser Leu
            20                  25                  30 cct agt gtt tct ctt gat ctg ccc agg ctc agc ata caa aaa gac ata   144
Pro Ser Val Ser Leu Asp Leu Pro Arg Leu Ser Ile Gln Lys Asp Ile
        35                  40                  45 ctt aca att aag gct aat aca act ctt caa att act tgc agg gga cag   192
Leu Thr Ile Lys Ala Asn Thr Thr Leu Gln Ile Thr Cys Arg Gly Gln
    50                  55                  60 agg gac ttg gac tgg ctt tgg ccc aat aat cag agt ggc agt gag caa   240
Arg Asp Leu Asp Trp Leu Trp Pro Asn Asn Gln Ser Gly Ser Glu Gln
```

|  |  |
|---|---|
| agg gtg gag gtg act gag tgc agc gat ggc ctc ttc tgt aag aca ctc<br>Arg Val Glu Val Thr Glu Cys Ser Asp Gly Leu Phe Cys Lys Thr Leu<br>85 90 95 | 288 |
| aca att cca aaa gtg atc gga aat gac act gga gcc tac aag tgc ttc<br>Thr Ile Pro Lys Val Ile Gly Asn Asp Thr Gly Ala Tyr Lys Cys Phe<br>100 105 110 | 336 |
| tac cgg gaa act gac ttg gcc tcg gtc att tat gtc tat gtt caa gat<br>Tyr Arg Glu Thr Asp Leu Ala Ser Val Ile Tyr Val Tyr Val Gln Asp<br>115 120 125 | 384 |
| tac aga tct cca ttt att gct tct gtt agt gac caa cat gga gtc gtg<br>Tyr Arg Ser Pro Phe Ile Ala Ser Val Ser Asp Gln His Gly Val Val<br>130 135 140 | 432 |
| tac att act gag aac aaa aac aaa act gtg gtg att cca tgt ctc ggg<br>Tyr Ile Thr Glu Asn Lys Asn Lys Thr Val Val Ile Pro Cys Leu Gly<br>145 150 155 160 | 480 |
| tcc att tca aat ctc aac gtg tca ctt tgt gca aga tac cca gaa aag<br>Ser Ile Ser Asn Leu Asn Val Ser Leu Cys Ala Arg Tyr Pro Glu Lys<br>165 170 175 | 528 |
| aga ttt gtt cct gat ggt aac aga att tcc tgg gac agc aag aag ggc<br>Arg Phe Val Pro Asp Gly Asn Arg Ile Ser Trp Asp Ser Lys Lys Gly<br>180 185 190 | 576 |
| ttt act att ccc agc tac atg atc agc tat gct ggc atg gtc ttc tgt<br>Phe Thr Ile Pro Ser Tyr Met Ile Ser Tyr Ala Gly Met Val Phe Cys<br>195 200 205 | 624 |
| gaa gca aaa att aat gat gaa agt tac cag tct att atg tac ata gtt<br>Glu Ala Lys Ile Asn Asp Glu Ser Tyr Gln Ser Ile Met Tyr Ile Val<br>210 215 220 | 672 |
| gtc gtt gta ggg tat agg att tat gat gtg gat ccc atc gaa ggt cgt<br>Val Val Val Gly Tyr Arg Ile Tyr Asp Val Asp Pro Ile Glu Gly Arg<br>225 230 235 240 | 720 |
| ggt ggt ggt ggt ggt gat ccc aaa tct tgt gac aaa cct cac aca tgc<br>Gly Gly Gly Gly Gly Asp Pro Lys Ser Cys Asp Lys Pro His Thr Cys<br>245 250 255 | 768 |
| cca ctg tgc cca gca cct gaa ctc ctg ggg gga ccg tca gtc ttc ctc<br>Pro Leu Cys Pro Ala Pro Glu Leu Leu Gly Gly Pro Ser Val Phe Leu<br>260 265 270 | 816 |
| ttc ccc cca aaa ccc aag gac acc ctc atg atc tcc cgg acc cct gag<br>Phe Pro Pro Lys Pro Lys Asp Thr Leu Met Ile Ser Arg Thr Pro Glu<br>275 280 285 | 864 |
| gtc aca tgc gtg gtg gtg gac gtg agc cac gaa gac cct gag gtc aag<br>Val Thr Cys Val Val Val Asp Val Ser His Glu Asp Pro Glu Val Lys<br>290 295 300 | 912 |
| ttc aac tgg tac gtg gac ggc gtg gag gtg cat aat gcc aag aca aag<br>Phe Asn Trp Tyr Val Asp Gly Val Glu Val His Asn Ala Lys Thr Lys<br>305 310 315 320 | 960 |
| ccg cgg gag gag cag tac aac agc acg tac cgt gtg gtc agc gtc ctc<br>Pro Arg Glu Glu Gln Tyr Asn Ser Thr Tyr Arg Val Val Ser Val Leu<br>325 330 335 | 1008 |
| acc gtc ctg cac cag gac tgg ctg aat ggc aag gag tac aag tgc aag<br>Thr Val Leu His Gln Asp Trp Leu Asn Gly Lys Glu Tyr Lys Cys Lys<br>340 345 350 | 1056 |
| gtc tcc aac aaa gcc ctc cca gcc ccc atc gag aaa acc atc tcc aaa<br>Val Ser Asn Lys Ala Leu Pro Ala Pro Ile Glu Lys Thr Ile Ser Lys<br>355 360 365 | 1104 |
| gcc aaa ggg cag ccc cga gaa cca cag gtg tac acc ctg ccc cca tcc<br>Ala Lys Gly Gln Pro Arg Glu Pro Gln Val Tyr Thr Leu Pro Pro Ser<br>370 375 380 | 1152 |
| cgg gat gag ctg acc aag aac cag gtc agc ctg acc tgc cta gtc aaa<br> | 1200 |

```
Arg Asp Glu Leu Thr Lys Asn Gln Val Ser Leu Thr Cys Leu Val Lys
385                 390                 395                 400 ggc ttc tat ccc agc gac atc gcc gtg gag tgg gag agc aat ggg cag    1248
Gly Phe Tyr Pro Ser Asp Ile Ala Val Glu Trp Glu Ser Asn Gly Gln
            405                 410                 415 ccg gag aac aac tac aag gcc acg cct ccc gtg ctg gac tcc gac ggc    1296
Pro Glu Asn Asn Tyr Lys Ala Thr Pro Pro Val Leu Asp Ser Asp Gly
        420                 425                 430 tcc ttc ttc ctc tac agc aag ctc acc gtg gac aag agc agg tgg cag    1344
Ser Phe Phe Leu Tyr Ser Lys Leu Thr Val Asp Lys Ser Arg Trp Gln
    435                 440                 445 cag ggg aac gtc ttc tca tgc tcc gtg atg cat gag gct ctg cac aac    1392
Gln Gly Asn Val Phe Ser Cys Ser Val Met His Glu Ala Leu His Asn
450                 455                 460 cac tac acg cag aag agc ctc tcc ctg tct ccg ggt aaa tga            1434
His Tyr Thr Gln Lys Ser Leu Ser Leu Ser Pro Gly Lys
465                 470                 475

<210> SEQ ID NO 12
<211> LENGTH: 477
<212> TYPE: PRT
<213> ORGANISM: Artificial sequence
<220> FEATURE:
<223> OTHER INFORMATION: Synthetic Construct

<400> SEQUENCE: 12

Met Pro Leu Leu Leu Leu Leu Pro Leu Leu Trp Ala Gly Ala Leu Ala
1               5                   10                  15

Met Asp Lys Leu Ala Ser Gly Thr Leu Glu Asp Gly Arg Gly Ser Leu
            20                  25                  30

Pro Ser Val Ser Leu Asp Leu Pro Arg Leu Ser Ile Gln Lys Asp Ile
        35                  40                  45

Leu Thr Ile Lys Ala Asn Thr Thr Leu Gln Ile Thr Cys Arg Gly Gln
    50                  55                  60

Arg Asp Leu Asp Trp Leu Trp Pro Asn Asn Gln Ser Gly Ser Glu Gln
65                  70                  75                  80

Arg Val Glu Val Thr Glu Cys Ser Asp Gly Leu Phe Cys Lys Thr Leu
                85                  90                  95

Thr Ile Pro Lys Val Ile Gly Asn Asp Thr Gly Ala Tyr Lys Cys Phe
            100                 105                 110

Tyr Arg Glu Thr Asp Leu Ala Ser Val Ile Tyr Val Tyr Val Gln Asp
        115                 120                 125

Tyr Arg Ser Pro Phe Ile Ala Ser Val Ser Asp Gln His Gly Val Val
    130                 135                 140

Tyr Ile Thr Glu Asn Lys Asn Lys Thr Val Val Ile Pro Cys Leu Gly
145                 150                 155                 160

Ser Ile Ser Asn Leu Asn Val Ser Leu Cys Ala Arg Tyr Pro Glu Lys
                165                 170                 175

Arg Phe Val Pro Asp Gly Asn Arg Ile Ser Trp Asp Ser Lys Lys Gly
            180                 185                 190

Phe Thr Ile Pro Ser Tyr Met Ile Ser Tyr Ala Gly Met Val Phe Cys
        195                 200                 205

Glu Ala Lys Ile Asn Asp Glu Ser Tyr Gln Ser Ile Met Tyr Ile Val
    210                 215                 220

Val Val Val Gly Tyr Arg Ile Tyr Asp Val Asp Pro Ile Glu Gly Arg
225                 230                 235                 240

Gly Gly Gly Gly Gly Asp Pro Lys Ser Cys Asp Lys Pro His Thr Cys
```

```
                      245                 250                 255
Pro Leu Cys Pro Ala Pro Glu Leu Leu Gly Gly Pro Ser Val Phe Leu
            260                 265                 270
Phe Pro Pro Lys Pro Lys Asp Thr Leu Met Ile Ser Arg Thr Pro Glu
        275                 280                 285
Val Thr Cys Val Val Val Asp Val Ser His Glu Asp Pro Glu Val Lys
    290                 295                 300
Phe Asn Trp Tyr Val Asp Gly Val Glu Val His Asn Ala Lys Thr Lys
305                 310                 315                 320
Pro Arg Glu Glu Gln Tyr Asn Ser Thr Tyr Arg Val Val Ser Val Leu
                325                 330                 335
Thr Val Leu His Gln Asp Trp Leu Asn Gly Lys Glu Tyr Lys Cys Lys
            340                 345                 350
Val Ser Asn Lys Ala Leu Pro Ala Pro Ile Glu Lys Thr Ile Ser Lys
        355                 360                 365
Ala Lys Gly Gln Pro Arg Glu Pro Gln Val Tyr Thr Leu Pro Pro Ser
    370                 375                 380
Arg Asp Glu Leu Thr Lys Asn Gln Val Ser Leu Thr Cys Leu Val Lys
385                 390                 395                 400
Gly Phe Tyr Pro Ser Asp Ile Ala Val Glu Trp Glu Ser Asn Gly Gln
                405                 410                 415
Pro Glu Asn Asn Tyr Lys Ala Thr Pro Pro Val Leu Asp Ser Asp Gly
            420                 425                 430
Ser Phe Phe Leu Tyr Ser Lys Leu Thr Val Asp Lys Ser Arg Trp Gln
        435                 440                 445
Gln Gly Asn Val Phe Ser Cys Ser Val Met His Glu Ala Leu His Asn
    450                 455                 460
His Tyr Thr Gln Lys Ser Leu Ser Leu Ser Pro Gly Lys
465                 470                 475

<210> SEQ ID NO 13
<211> LENGTH: 1452
<212> TYPE: DNA
<213> ORGANISM: Artificial sequence
<220> FEATURE:
<223> OTHER INFORMATION: R-2 D
<220> FEATURE:
<221> NAME/KEY: CDS
<222> LOCATION: (1)..(1452)

<400> SEQUENCE: 13 atg ccg ctg ctg cta ctg ctg ccc ctg ctg tgg gca ggg gcc ctg gct      48
Met Pro Leu Leu Leu Leu Pro Leu Leu Trp Ala Gly Ala Leu Ala
1               5                   10                  15 atg gat aag ctt gct agc ggt acc ctc gag gat ggc cgc gga tcc ttg      96
Met Asp Lys Leu Ala Ser Gly Thr Leu Glu Asp Gly Arg Gly Ser Leu
                20                  25                  30 cct agt gtt tct ctt gat ctg ccc agg ctc agc ata caa aaa gac ata     144
Pro Ser Val Ser Leu Asp Leu Pro Arg Leu Ser Ile Gln Lys Asp Ile
            35                  40                  45 ctt aca att aag gct aat aca act ctt caa att act tgc agg gga cag     192
Leu Thr Ile Lys Ala Asn Thr Thr Leu Gln Ile Thr Cys Arg Gly Gln
        50                  55                  60 agg gac ttg gac tgg ctt tgg ccc aat aat cag agt ggc agt gag caa     240
Arg Asp Leu Asp Trp Leu Trp Pro Asn Asn Gln Ser Gly Ser Glu Gln
65                  70                  75                  80 agg gtg gag gtg act gag tgc agc gat ggc ctc ttc tgt aag aca ctc     288
Arg Val Glu Val Thr Glu Cys Ser Asp Gly Leu Phe Cys Lys Thr Leu
```

```
                      85                  90                  95
aca att cca aaa gtg atc gga aat gac act gga gcc tac aag tgc ttc      336
Thr Ile Pro Lys Val Ile Gly Asn Asp Thr Gly Ala Tyr Lys Cys Phe
            100                 105                 110 tac cgg gaa act gac ttg gcc tcg gtc att tat gtc tat gtt caa gat      384
Tyr Arg Glu Thr Asp Leu Ala Ser Val Ile Tyr Val Tyr Val Gln Asp
        115                 120                 125 tac aga tct cca ttt att gct tct gtt agt gac caa cat gga gtc gtg      432
Tyr Arg Ser Pro Phe Ile Ala Ser Val Ser Asp Gln His Gly Val Val
130                 135                 140 tac att act gag aac aaa aac aaa act gtg gtg att cca tgt ctc ggg      480
Tyr Ile Thr Glu Asn Lys Asn Lys Thr Val Val Ile Pro Cys Leu Gly
145                 150                 155                 160 tcc att tca aat ctc aac gtg tca ctt tgt gca aga tac cca gaa aag      528
Ser Ile Ser Asn Leu Asn Val Ser Leu Cys Ala Arg Tyr Pro Glu Lys
            165                 170                 175 aga ttt gtt cct gat ggt aac aga att tcc tgg gac agc aag aag ggc      576
Arg Phe Val Pro Asp Gly Asn Arg Ile Ser Trp Asp Ser Lys Lys Gly
        180                 185                 190 ttt act att ccc agc tac atg atc agc tat gct ggc atg gtc ttc tgt      624
Phe Thr Ile Pro Ser Tyr Met Ile Ser Tyr Ala Gly Met Val Phe Cys
    195                 200                 205 gaa gca aaa att aat gat gaa agt tac cag tct att atg tac ata gtt      672
Glu Ala Lys Ile Asn Asp Glu Ser Tyr Gln Ser Ile Met Tyr Ile Val
210                 215                 220 gtc gtt gta ggg tat agg att tat gat gtg gtt ctg agt ccg tct cat      720
Val Val Val Gly Tyr Arg Ile Tyr Asp Val Val Leu Ser Pro Ser His
225                 230                 235                 240 gat ccc atc gaa ggt cgt ggt ggt ggt ggt gat ccc aaa tct tgt           768
Asp Pro Ile Glu Gly Arg Gly Gly Gly Gly Asp Pro Lys Ser Cys
            245                 250                 255 gac aaa cct cac aca tgc cca ctg tgc cca gca cct gaa ctc ctg ggg      816
Asp Lys Pro His Thr Cys Pro Leu Cys Pro Ala Pro Glu Leu Leu Gly
        260                 265                 270 gga ccg tca gtc ttc ctc ttc ccc cca aaa ccc aag gac acc ctc atg      864
Gly Pro Ser Val Phe Leu Phe Pro Pro Lys Pro Lys Asp Thr Leu Met
    275                 280                 285 atc tcc cgg acc cct gag gtc aca tgc gtg gtg gtg gac gtg agc cac      912
Ile Ser Arg Thr Pro Glu Val Thr Cys Val Val Val Asp Val Ser His
290                 295                 300 gaa gac cct gag gtc aag ttc aac tgg tac gtg gac ggc gtg gag gtg      960
Glu Asp Pro Glu Val Lys Phe Asn Trp Tyr Val Asp Gly Val Glu Val
305                 310                 315                 320 cat aat gcc aag aca aag ccg cgg gag gag cag tac aac agc acg tac     1008
His Asn Ala Lys Thr Lys Pro Arg Glu Glu Gln Tyr Asn Ser Thr Tyr
            325                 330                 335 cgt gtg gtc agc gtc ctc acc gtc ctg cac cag gac tgg ctg aat ggc     1056
Arg Val Val Ser Val Leu Thr Val Leu His Gln Asp Trp Leu Asn Gly
        340                 345                 350 aag gag tac aag tgc aag gtc tcc aac aaa gcc ctc cca gcc ccc atc     1104
Lys Glu Tyr Lys Cys Lys Val Ser Asn Lys Ala Leu Pro Ala Pro Ile
    355                 360                 365 gag aaa acc atc tcc aaa gcc aaa ggg cag ccc cga gaa cca cag gtg     1152
Glu Lys Thr Ile Ser Lys Ala Lys Gly Gln Pro Arg Glu Pro Gln Val
370                 375                 380 tac acc ctg ccc cca tcc cgg gat gag ctg acc aag aac cag gtc agc     1200
Tyr Thr Leu Pro Pro Ser Arg Asp Glu Leu Thr Lys Asn Gln Val Ser
385                 390                 395                 400 ctg acc tgc cta gtc aaa ggc ttc tat ccc agc gac atc gcc gtg gag     1248
```

-continued

```
Leu Thr Cys Leu Val Lys Gly Phe Tyr Pro Ser Asp Ile Ala Val Glu
                405                 410                 415 tgg agc aat ggg cag ccg gag aac aac tac aag gcc acg cct ccc       1296
Trp Glu Ser Asn Gly Gln Pro Glu Asn Asn Tyr Lys Ala Thr Pro Pro
            420                 425                 430 gtg ctg gac tcc gac ggc tcc ttc ttc ctc tac agc aag ctc acc gtg   1344
Val Leu Asp Ser Asp Gly Ser Phe Phe Leu Tyr Ser Lys Leu Thr Val
                435                 440                 445 gac aag agc agg tgg cag cag ggg aac gtc ttc tca tgc tcc gtg atg   1392
Asp Lys Ser Arg Trp Gln Gln Gly Asn Val Phe Ser Cys Ser Val Met
            450                 455                 460 cat gag gct ctg cac aac cac tac acg cag aag agc ctc tcc ctg tct   1440
His Glu Ala Leu His Asn His Tyr Thr Gln Lys Ser Leu Ser Leu Ser
465                 470                 475                 480 ccg ggt aaa tga                                                   1452
Pro Gly Lys <210> SEQ ID NO 14
<211> LENGTH: 483
<212> TYPE: PRT
<213> ORGANISM: Artificial sequence
<220> FEATURE:
<223> OTHER INFORMATION: Synthetic Construct

<400> SEQUENCE: 14

Met Pro Leu Leu Leu Leu Pro Leu Leu Trp Ala Gly Ala Leu Ala
1               5                   10                  15

Met Asp Lys Leu Ala Ser Gly Thr Leu Glu Asp Gly Arg Gly Ser Leu
            20                  25                  30

Pro Ser Val Ser Leu Asp Leu Pro Arg Leu Ser Ile Gln Lys Asp Ile
        35                  40                  45

Leu Thr Ile Lys Ala Asn Thr Thr Leu Gln Ile Thr Cys Arg Gly Gln
    50                  55                  60

Arg Asp Leu Asp Trp Leu Trp Pro Asn Asn Gln Ser Gly Ser Glu Gln
65                  70                  75                  80

Arg Val Glu Val Thr Glu Cys Ser Asp Gly Leu Phe Cys Lys Thr Leu
                85                  90                  95

Thr Ile Pro Lys Val Ile Gly Asn Asp Thr Gly Ala Tyr Lys Cys Phe
            100                 105                 110

Tyr Arg Glu Thr Asp Leu Ala Ser Val Ile Tyr Val Tyr Val Gln Asp
        115                 120                 125

Tyr Arg Ser Pro Phe Ile Ala Ser Val Ser Asp Gln His Gly Val Val
    130                 135                 140

Tyr Ile Thr Glu Asn Lys Asn Lys Thr Val Val Ile Pro Cys Leu Gly
145                 150                 155                 160

Ser Ile Ser Asn Leu Asn Val Ser Leu Cys Ala Arg Tyr Pro Glu Lys
                165                 170                 175

Arg Phe Val Pro Asp Gly Asn Arg Ile Ser Trp Asp Ser Lys Lys Gly
            180                 185                 190

Phe Thr Ile Pro Ser Tyr Met Ile Ser Tyr Ala Gly Met Val Phe Cys
        195                 200                 205

Glu Ala Lys Ile Asn Asp Glu Ser Tyr Gln Ser Ile Met Tyr Ile Val
    210                 215                 220

Val Val Val Gly Tyr Arg Ile Tyr Asp Val Val Leu Ser Pro Ser His
225                 230                 235                 240

Asp Pro Ile Glu Gly Arg Gly Gly Gly Gly Asp Pro Lys Ser Cys
                245                 250                 255
```

```
Asp Lys Pro His Thr Cys Pro Leu Cys Pro Ala Pro Glu Leu Leu Gly
            260                 265                 270

Gly Pro Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
    370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Ala Thr Pro Pro
            420                 425                 430

Val Leu Asp Ser Asp Gly Ser Phe Phe Leu Tyr Ser Lys Leu Thr Val
        435                 440                 445

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Lys

<210> SEQ ID NO 15
<211> LENGTH: 1479
<212> TYPE: DNA
<213> ORGANISM: Artificial sequence
<220> FEATURE:
<223> OTHER INFORMATION: R-2 E
<220> FEATURE:
<221> NAME/KEY: CDS
<222> LOCATION: (1)..(1479)

<400> SEQUENCE: 15 atg ccg ctg ctg cta ctg ctg ccc ctg ctg tgg gca ggg gcc ctg gct      48
Met Pro Leu Leu Leu Leu Leu Pro Leu Leu Trp Ala Gly Ala Leu Ala
1               5                   10                  15 atg gat aag ctt gct agc ggt acc ctc gag gat ggc cgc gga tcc ttg      96
Met Asp Lys Leu Ala Ser Gly Thr Leu Glu Asp Gly Arg Gly Ser Leu
            20                  25                  30 cct agt gtt tct ctt gat ctg ccc agg ctc agc ata caa aaa gac ata     144
Pro Ser Val Ser Leu Asp Leu Pro Arg Leu Ser Ile Gln Lys Asp Ile
        35                  40                  45 ctt aca att aag gct aat aca act ctt caa att act tgc agg gga cag     192
Leu Thr Ile Lys Ala Asn Thr Thr Leu Gln Ile Thr Cys Arg Gly Gln
    50                  55                  60 agg gac ttg gac tgg ctt tgg ccc aat aat cag agt ggc agt gag caa     240
Arg Asp Leu Asp Trp Leu Trp Pro Asn Asn Gln Ser Gly Ser Glu Gln
65                  70                  75                  80 agg gtg gag gtg act gag tgc agc gat ggc ctc ttc tgt aag aca ctc     288
```

-continued

```
Arg Val Glu Val Thr Glu Cys Ser Asp Gly Leu Phe Cys Lys Thr Leu
                85                  90                  95 aca att cca aaa gtg atc gga aat gac act gga gcc tac aag tgc ttc      336
Thr Ile Pro Lys Val Ile Gly Asn Asp Thr Gly Ala Tyr Lys Cys Phe
            100                 105                 110 tac cgg gaa act gac ttg gcc tcg gtc att tat gtc tat gtt caa gat      384
Tyr Arg Glu Thr Asp Leu Ala Ser Val Ile Tyr Val Tyr Val Gln Asp
        115                 120                 125 tac aga tct cca ttt att gct tct gtt agt gac caa cat gga gtc gtg      432
Tyr Arg Ser Pro Phe Ile Ala Ser Val Ser Asp Gln His Gly Val Val
    130                 135                 140 tac att act gag aac aaa aac aaa act gtg gtg att cca tgt ctc ggg      480
Tyr Ile Thr Glu Asn Lys Asn Lys Thr Val Val Ile Pro Cys Leu Gly
145                 150                 155                 160 tcc att tca aat ctc aac gtg tca ctt tgt gca aga tac cca gaa aag      528
Ser Ile Ser Asn Leu Asn Val Ser Leu Cys Ala Arg Tyr Pro Glu Lys
                165                 170                 175 aga ttt gtt cct gat ggt aac aga att tcc tgg gac agc aag aag ggc      576
Arg Phe Val Pro Asp Gly Asn Arg Ile Ser Trp Asp Ser Lys Lys Gly
            180                 185                 190 ttt act att ccc agc tac atg atc agc tat gct ggc atg gtc ttc tgt      624
Phe Thr Ile Pro Ser Tyr Met Ile Ser Tyr Ala Gly Met Val Phe Cys
        195                 200                 205 gaa gca aaa att aat gat gaa agt tac cag tct att atg tac ata gtt      672
Glu Ala Lys Ile Asn Asp Glu Ser Tyr Gln Ser Ile Met Tyr Ile Val
    210                 215                 220 gtc gtt gta ggg tat agg att tat gat gtg gtt ctg agt ccg tct cat      720
Val Val Val Gly Tyr Arg Ile Tyr Asp Val Val Leu Ser Pro Ser His
225                 230                 235                 240 gga att gaa cta tct gtt gga gaa aag gat ccc atc gaa ggt cgt ggt      768
Gly Ile Glu Leu Ser Val Gly Glu Lys Asp Pro Ile Glu Gly Arg Gly
                245                 250                 255 ggt ggt ggt ggt gat ccc aaa tct tgt gac aaa cct cac aca tgc cca      816
Gly Gly Gly Gly Asp Pro Lys Ser Cys Asp Lys Pro His Thr Cys Pro
            260                 265                 270 ctg tgc cca gca cct gaa ctc ctg ggg gga ccg tca gtc ttc ctc ttc      864
Leu Cys Pro Ala Pro Glu Leu Leu Gly Gly Pro Ser Val Phe Leu Phe
        275                 280                 285 ccc cca aaa ccc aag gac acc ctc atg atc tcc cgg acc cct gag gtc      912
Pro Pro Lys Pro Lys Asp Thr Leu Met Ile Ser Arg Thr Pro Glu Val
    290                 295                 300 aca tgc gtg gtg gtg gac gtg agc cac gaa gac cct gag gtc aag ttc      960
Thr Cys Val Val Val Asp Val Ser His Glu Asp Pro Glu Val Lys Phe
305                 310                 315                 320 aac tgg tac gtg gac ggc gtg gag gtg cat aat gcc aag aca aag ccg     1008
Asn Trp Tyr Val Asp Gly Val Glu Val His Asn Ala Lys Thr Lys Pro
                325                 330                 335 cgg gag gag cag tac aac agc acg tac cgt gtg gtc agc gtc ctc acc     1056
Arg Glu Glu Gln Tyr Asn Ser Thr Tyr Arg Val Val Ser Val Leu Thr
            340                 345                 350 gtc ctg cac cag gac tgg ctg aat ggc aag gag tac aag tgc aag gtc     1104
Val Leu His Gln Asp Trp Leu Asn Gly Lys Glu Tyr Lys Cys Lys Val
        355                 360                 365 tcc aac aaa gcc ctc cca gcc ccc atc gag aaa acc atc tcc aaa gcc     1152
Ser Asn Lys Ala Leu Pro Ala Pro Ile Glu Lys Thr Ile Ser Lys Ala
    370                 375                 380 aaa ggg cag ccc cga gaa cca cag gtg tac acc ctg ccc cca tcc cgg     1200
Lys Gly Gln Pro Arg Glu Pro Gln Val Tyr Thr Leu Pro Pro Ser Arg
385                 390                 395                 400
```

```
gat gag ctg acc aag aac cag gtc agc ctg acc tgc cta gtc aaa ggc     1248
Asp Glu Leu Thr Lys Asn Gln Val Ser Leu Thr Cys Leu Val Lys Gly
            405                 410                 415 ttc tat ccc agc gac atc gcc gtg gag tgg gag agc aat ggg cag ccg     1296
Phe Tyr Pro Ser Asp Ile Ala Val Glu Trp Glu Ser Asn Gly Gln Pro
            420                 425                 430 gag aac aac tac aag gcc acg cct ccc gtg ctg gac tcc gac ggc tcc     1344
Glu Asn Asn Tyr Lys Ala Thr Pro Pro Val Leu Asp Ser Asp Gly Ser
            435                 440                 445 ttc ttc ctc tac agc aag ctc acc gtg gac aag agc agg tgg cag cag     1392
Phe Phe Leu Tyr Ser Lys Leu Thr Val Asp Lys Ser Arg Trp Gln Gln
        450                 455                 460 ggg aac gtc ttc tca tgc tcc gtg atg cat gag gct ctg cac aac cac     1440
Gly Asn Val Phe Ser Cys Ser Val Met His Glu Ala Leu His Asn His
465                 470                 475                 480 tac acg cag aag agc ctc tcc ctg tct ccg ggt aaa tga                 1479
Tyr Thr Gln Lys Ser Leu Ser Leu Ser Pro Gly Lys
                485                 490
```

<210> SEQ ID NO 16
<211> LENGTH: 492
<212> TYPE: PRT
<213> ORGANISM: Artificial sequence
<220> FEATURE:
<223> OTHER INFORMATION: Synthetic Construct

<400> SEQUENCE: 16

```
Met Pro Leu Leu Leu Leu Pro Leu Leu Trp Ala Gly Ala Leu Ala
1               5                   10                  15

Met Asp Lys Leu Ala Ser Gly Thr Leu Glu Asp Gly Arg Gly Ser Leu
                20                  25                  30

Pro Ser Val Ser Leu Asp Leu Pro Arg Leu Ser Ile Gln Lys Asp Ile
            35                  40                  45

Leu Thr Ile Lys Ala Asn Thr Thr Leu Gln Ile Thr Cys Arg Gly Gln
        50                  55                  60

Arg Asp Leu Asp Trp Leu Trp Pro Asn Asn Gln Ser Gly Ser Glu Gln
65                  70                  75                  80

Arg Val Glu Val Thr Glu Cys Ser Asp Gly Leu Phe Cys Lys Thr Leu
                85                  90                  95

Thr Ile Pro Lys Val Ile Gly Asn Asp Thr Gly Ala Tyr Lys Cys Phe
            100                 105                 110

Tyr Arg Glu Thr Asp Leu Ala Ser Val Ile Tyr Val Tyr Val Gln Asp
        115                 120                 125

Tyr Arg Ser Pro Phe Ile Ala Ser Val Ser Asp Gln His Gly Val Val
    130                 135                 140

Tyr Ile Thr Glu Asn Lys Asn Lys Thr Val Val Ile Pro Cys Leu Gly
145                 150                 155                 160

Ser Ile Ser Asn Leu Asn Val Ser Leu Cys Ala Arg Tyr Pro Glu Lys
                165                 170                 175

Arg Phe Val Pro Asp Gly Asn Arg Ile Ser Trp Asp Ser Lys Lys Gly
            180                 185                 190

Phe Thr Ile Pro Ser Tyr Met Ile Ser Tyr Ala Gly Met Val Phe Cys
        195                 200                 205

Glu Ala Lys Ile Asn Asp Glu Ser Tyr Gln Ser Ile Met Tyr Ile Val
    210                 215                 220

Val Val Val Gly Tyr Arg Ile Tyr Asp Val Val Leu Ser Pro Ser His
225                 230                 235                 240
```

```
Gly Ile Glu Leu Ser Val Gly Glu Lys Asp Pro Ile Glu Gly Arg Gly
            245                 250                 255

Gly Gly Gly Gly Asp Pro Lys Ser Cys Asp Lys Pro His Thr Cys Pro
        260                 265                 270

Leu Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
        290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
        370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Ala Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490

<210> SEQ ID NO 17
<211> LENGTH: 1113
<212> TYPE: DNA
<213> ORGANISM: Artificial sequence
<220> FEATURE:
<223> OTHER INFORMATION: R-2 F
<220> FEATURE:
<221> NAME/KEY: CDS
<222> LOCATION: (1)..(1113)

<400> SEQUENCE: 17 atg ccg ctg ctg cta ctg ctg ccc ctg ctg tgg gca ggg gcc ctg gct    48
Met Pro Leu Leu Leu Leu Leu Pro Leu Leu Trp Ala Gly Ala Leu Ala
1               5                   10                  15 atg gat aag ctt gct agc ggt acc ctc gag gat ggc cgc gga tcc ttg    96
Met Asp Lys Leu Ala Ser Gly Thr Leu Glu Asp Gly Arg Gly Ser Leu
            20                  25                  30 cct agt gtt tct ctt gat ctg ccc agg ctc agc ata caa aaa gac ata   144
Pro Ser Val Ser Leu Asp Leu Pro Arg Leu Ser Ile Gln Lys Asp Ile
        35                  40                  45 ctt aca att aag gct aat aca act ctt caa att act tgc agg gga cag   192
Leu Thr Ile Lys Ala Asn Thr Thr Leu Gln Ile Thr Cys Arg Gly Gln
    50                  55                  60 agg gac ttg gac tgg ctt tgg ccc aat aat cag agt ggc agt gag caa   240
Arg Asp Leu Asp Trp Leu Trp Pro Asn Asn Gln Ser Gly Ser Glu Gln
```

-continued

```
                65                  70                  75                  80
agg gtg gag gtg act gag tgc agc gat ggc ctc ttc tgt aag aca ctc     288
Arg Val Glu Val Thr Glu Cys Ser Asp Gly Leu Phe Cys Lys Thr Leu
                     85                  90                  95 aca att cca aaa gtg atc gga aat gac act gga gcc tac aag tgc ttc     336
Thr Ile Pro Lys Val Ile Gly Asn Asp Thr Gly Ala Tyr Lys Cys Phe
            100                 105                 110 tac cgg gaa act gac ttg gcc tcg gtc att tat gtc tat gtt caa gat     384
Tyr Arg Glu Thr Asp Leu Ala Ser Val Ile Tyr Val Tyr Val Gln Asp
        115                 120                 125 ccc atc gaa ggt cgt ggt ggt ggt ggt gat ccc aaa tct tgt gac         432
Pro Ile Glu Gly Arg Gly Gly Gly Gly Asp Pro Lys Ser Cys Asp
    130                 135                 140 aaa cct cac aca tgc cca ctg tgc cca gca cct gaa ctc ctg ggg gga     480
Lys Pro His Thr Cys Pro Leu Cys Pro Ala Pro Glu Leu Leu Gly Gly
145                 150                 155                 160 ccg tca gtc ttc ctc ttc ccc cca aaa ccc aag gac acc ctc atg atc     528
Pro Ser Val Phe Leu Phe Pro Pro Lys Pro Lys Asp Thr Leu Met Ile
                    165                 170                 175 tcc cgg acc cct gag gtc aca tgc gtg gtg gtg gac gtg agc cac gaa     576
Ser Arg Thr Pro Glu Val Thr Cys Val Val Val Asp Val Ser His Glu
                180                 185                 190 gac cct gag gtc aag ttc aac tgg tac gtg gac ggc gtg gag gtg cat     624
Asp Pro Glu Val Lys Phe Asn Trp Tyr Val Asp Gly Val Glu Val His
            195                 200                 205 aat gcc aag aca aag ccg cgg gag gag cag tac aac agc acg tac cgt     672
Asn Ala Lys Thr Lys Pro Arg Glu Glu Gln Tyr Asn Ser Thr Tyr Arg
        210                 215                 220 gtg gtc agc gtc ctc acc gtc ctg cac cag gac tgg ctg aat ggc aag     720
Val Val Ser Val Leu Thr Val Leu His Gln Asp Trp Leu Asn Gly Lys
225                 230                 235                 240 gag tac aag tgc aag gtc tcc aac aaa gcc ctc cca gcc ccc atc gag     768
Glu Tyr Lys Cys Lys Val Ser Asn Lys Ala Leu Pro Ala Pro Ile Glu
                    245                 250                 255 aaa acc atc tcc aaa gcc aaa ggg cag ccc cga gaa cca cag gtg tac     816
Lys Thr Ile Ser Lys Ala Lys Gly Gln Pro Arg Glu Pro Gln Val Tyr
                260                 265                 270 acc ctg ccc cca tcc cgg gat gag ctg acc aag aac cag gtc agc ctg     864
Thr Leu Pro Pro Ser Arg Asp Glu Leu Thr Lys Asn Gln Val Ser Leu
            275                 280                 285 acc tgc cta gtc aaa ggc ttc tat ccc agc gac atc gcc gtg gag tgg     912
Thr Cys Leu Val Lys Gly Phe Tyr Pro Ser Asp Ile Ala Val Glu Trp
        290                 295                 300 gag agc aat ggg cag ccg gag aac aac tac aag gcc acg cct ccc gtg     960
Glu Ser Asn Gly Gln Pro Glu Asn Asn Tyr Lys Ala Thr Pro Pro Val
305                 310                 315                 320 ctg gac tcc gac ggc tcc ttc ttc ctc tac agc aag ctc acc gtg gac     1008
Leu Asp Ser Asp Gly Ser Phe Phe Leu Tyr Ser Lys Leu Thr Val Asp
                    325                 330                 335 aag agc agg tgg cag cag ggg aac gtc ttc tca tgc tcc gtg atg cat     1056
Lys Ser Arg Trp Gln Gln Gly Asn Val Phe Ser Cys Ser Val Met His
                340                 345                 350 gag gct ctg cac aac cac tac acg cag aag agc ctc tcc ctg tct ccg     1104
Glu Ala Leu His Asn His Tyr Thr Gln Lys Ser Leu Ser Leu Ser Pro
            355                 360                 365 ggt aaa tga                                                         1113
Gly Lys
    370
```

<210> SEQ ID NO 18
<211> LENGTH: 370
<212> TYPE: PRT
<213> ORGANISM: Artificial sequence
<220> FEATURE:
<223> OTHER INFORMATION: Synthetic Construct

<400> SEQUENCE: 18

```
Met Pro Leu Leu Leu Leu Pro Leu Leu Trp Ala Gly Ala Leu Ala
1               5                   10                  15

Met Asp Lys Leu Ala Ser Gly Thr Leu Glu Asp Gly Arg Gly Ser Leu
            20                  25                  30

Pro Ser Val Ser Leu Asp Leu Pro Arg Leu Ser Ile Gln Lys Asp Ile
        35                  40                  45

Leu Thr Ile Lys Ala Asn Thr Thr Leu Gln Ile Thr Cys Arg Gly Gln
    50                  55                  60

Arg Asp Leu Asp Trp Leu Trp Pro Asn Asn Gln Ser Gly Ser Glu Gln
65                  70                  75                  80

Arg Val Glu Val Thr Glu Cys Ser Asp Gly Leu Phe Cys Lys Thr Leu
                85                  90                  95

Thr Ile Pro Lys Val Ile Gly Asn Asp Thr Gly Ala Tyr Lys Cys Phe
            100                 105                 110

Tyr Arg Glu Thr Asp Leu Ala Ser Val Ile Tyr Val Tyr Val Gln Asp
        115                 120                 125

Pro Ile Glu Gly Arg Gly Gly Gly Gly Asp Pro Lys Ser Cys Asp
    130                 135                 140

Lys Pro His Thr Cys Pro Leu Cys Pro Ala Pro Glu Leu Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser His Glu
            180                 185                 190

Asp Pro Glu Val Lys Phe Asn Trp Tyr Val Asp Gly Val Glu Val His
        195                 200                 205

Asn Ala Lys Thr Lys Pro Arg Glu Glu Gln Tyr Asn Ser Thr Tyr Arg
    210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Ala Leu Pro Ala Pro Ile Glu
                245                 250                 255

Lys Thr Ile Ser Lys Ala Lys Gly Gln Pro Arg Glu Pro Gln Val Tyr
            260                 265                 270

Thr Leu Pro Pro Ser Arg Asp Glu Leu Thr Lys Asn Gln Val Ser Leu
        275                 280                 285

Thr Cys Leu Val Lys Gly Phe Tyr Pro Ser Asp Ile Ala Val Glu Trp
    290                 295                 300

Glu Ser Asn Gly Gln Pro Glu Asn Asn Tyr Lys Ala Thr Pro Pro Val
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
            340                 345                 350

Glu Ala Leu His Asn His Tyr Thr Gln Lys Ser Leu Ser Leu Ser Pro
        355                 360                 365

Gly Lys
```

<210> SEQ ID NO 19
<211> LENGTH: 1425
<212> TYPE: DNA
<213> ORGANISM: Artificial sequence
<220> FEATURE:
<223> OTHER INFORMATION: R-2 G
<220> FEATURE:
<221> NAME/KEY: CDS
<222> LOCATION: (1)..(1425)

<400> SEQUENCE: 19

```
atg ccg ctg ctg cta ctg ctg ccc ctg ctg tgg gca ggg gcc ctg gct      48
Met Pro Leu Leu Leu Leu Leu Pro Leu Leu Trp Ala Gly Ala Leu Ala
1               5                   10                  15 atg gat aag ctt gct agc gtt caa gat tac aga tct cca ttt att gct      96
Met Asp Lys Leu Ala Ser Val Gln Asp Tyr Arg Ser Pro Phe Ile Ala
            20                  25                  30 tct gtt agt gac caa cat gga gtc gtg tac att act gag aac aaa aac     144
Ser Val Ser Asp Gln His Gly Val Val Tyr Ile Thr Glu Asn Lys Asn
        35                  40                  45 aaa act gtg gtg att cca tgt ctc ggg tcc att tca aat ctc aac gtg     192
Lys Thr Val Val Ile Pro Cys Leu Gly Ser Ile Ser Asn Leu Asn Val
50                  55                  60 tca ctt tgt gca aga tac cca gaa aag aga ttt gtt cct gat ggt aac     240
Ser Leu Cys Ala Arg Tyr Pro Glu Lys Arg Phe Val Pro Asp Gly Asn
65                  70                  75                  80 aga att tcc tgg gac agc aag aag ggc ttt act att ccc agc tac atg     288
Arg Ile Ser Trp Asp Ser Lys Lys Gly Phe Thr Ile Pro Ser Tyr Met
                85                  90                  95 atc agc tat gct ggc atg gtc ttc tgt gaa gca aaa att aat gat gaa     336
Ile Ser Tyr Ala Gly Met Val Phe Cys Glu Ala Lys Ile Asn Asp Glu
            100                 105                 110 agt tac cag tct att atg tac ata gtt gtc gtt gta ggg tat agg att     384
Ser Tyr Gln Ser Ile Met Tyr Ile Val Val Val Val Gly Tyr Arg Ile
        115                 120                 125 tat gat gtg gtt ctg agt ccg tct cat gga att gaa cta tct gtt gga     432
Tyr Asp Val Val Leu Ser Pro Ser His Gly Ile Glu Leu Ser Val Gly
130                 135                 140 gaa aag ctt gtc tta aat tgt aca gca aga act gaa cta aat gtg ggg     480
Glu Lys Leu Val Leu Asn Cys Thr Ala Arg Thr Glu Leu Asn Val Gly
145                 150                 155                 160 att gac ttc aac tgg gaa tac cct tct tcg aag cat cag cat aag aaa     528
Ile Asp Phe Asn Trp Glu Tyr Pro Ser Ser Lys His Gln His Lys Lys
                165                 170                 175 ctt gta aac cga gac cta aaa acc cag tct ggg agt gag atg aag aaa     576
Leu Val Asn Arg Asp Leu Lys Thr Gln Ser Gly Ser Glu Met Lys Lys
            180                 185                 190 ttt ttg agc acc tta act ata gat ggt gta acc cgg agt gac caa gga     624
Phe Leu Ser Thr Leu Thr Ile Asp Gly Val Thr Arg Ser Asp Gln Gly
        195                 200                 205 ttg tac acc tgt gca gca tcc agt ggg ctg atg acc aag aag aac agc     672
Leu Tyr Thr Cys Ala Ala Ser Ser Gly Leu Met Thr Lys Lys Asn Ser
210                 215                 220 aca ttt gtc agg gtc cat gaa gat ccc atc gaa ggt cgt ggt ggt ggt     720
Thr Phe Val Arg Val His Glu Asp Pro Ile Glu Gly Arg Gly Gly Gly
225                 230                 235                 240 ggt ggt gat ccc aaa tct tgt gac aaa cct cac aca tgc cca ctg tgc     768
Gly Gly Asp Pro Lys Ser Cys Asp Lys Pro His Thr Cys Pro Leu Cys
                245                 250                 255
```

```
cca gca cct gaa ctc ctg ggg gga ccg tca gtc ttc ctc ttc ccc cca      816
Pro Ala Pro Glu Leu Leu Gly Gly Pro Ser Val Phe Leu Phe Pro Pro
            260                 265                 270 aaa ccc aag gac acc ctc atg atc tcc cgg acc cct gag gtc aca tgc      864
Lys Pro Lys Asp Thr Leu Met Ile Ser Arg Thr Pro Glu Val Thr Cys
        275                 280                 285 gtg gtg gtg gac gtg agc cac gaa gac cct gag gtc aag ttc aac tgg      912
Val Val Val Asp Val Ser His Glu Asp Pro Glu Val Lys Phe Asn Trp
    290                 295                 300 tac gtg gac ggc gtg gag gtg cat aat gcc aag aca aag ccg cgg gag      960
Tyr Val Asp Gly Val Glu Val His Asn Ala Lys Thr Lys Pro Arg Glu
305                 310                 315                 320 gag cag tac aac agc acg tac cgt gtg gtc agc gtc ctc acc gtc ctg     1008
Glu Gln Tyr Asn Ser Thr Tyr Arg Val Val Ser Val Leu Thr Val Leu
                325                 330                 335 cac cag gac tgg ctg aat ggc aag gag tac aag tgc aag gtc tcc aac     1056
His Gln Asp Trp Leu Asn Gly Lys Glu Tyr Lys Cys Lys Val Ser Asn
            340                 345                 350 aaa gcc ctc cca gcc ccc atc gag aaa acc atc tcc aaa gcc aaa ggg     1104
Lys Ala Leu Pro Ala Pro Ile Glu Lys Thr Ile Ser Lys Ala Lys Gly
        355                 360                 365 cag ccc cga gaa cca cag gtg tac acc ctg ccc cca tcc cgg gat gag     1152
Gln Pro Arg Glu Pro Gln Val Tyr Thr Leu Pro Pro Ser Arg Asp Glu
370                 375                 380 ctg acc aag aac cag gtc agc ctg acc tgc cta gtc aaa ggc ttc tat     1200
Leu Thr Lys Asn Gln Val Ser Leu Thr Cys Leu Val Lys Gly Phe Tyr
385                 390                 395                 400 ccc agc gac atc gcc gtg gag tgg gag agc aat ggg cag ccg gag aac     1248
Pro Ser Asp Ile Ala Val Glu Trp Glu Ser Asn Gly Gln Pro Glu Asn
                405                 410                 415 aac tac aag gcc acg cct ccc gtg ctg gac tcc gac ggc tcc ttc ttc     1296
Asn Tyr Lys Ala Thr Pro Pro Val Leu Asp Ser Asp Gly Ser Phe Phe
            420                 425                 430 ctc tac agc aag ctc acc gtg gac aag agc agg tgg cag cag ggg aac     1344
Leu Tyr Ser Lys Leu Thr Val Asp Lys Ser Arg Trp Gln Gln Gly Asn
        435                 440                 445 gtc ttc tca tgc tcc gtg atg cat gag gct ctg cac aac cac tac acg     1392
Val Phe Ser Cys Ser Val Met His Glu Ala Leu His Asn His Tyr Thr
450                 455                 460 cag aag agc ctc tcc ctg tct ccg ggt aaa tga                         1425
Gln Lys Ser Leu Ser Leu Ser Pro Gly Lys
465                 470

<210> SEQ ID NO 20
<211> LENGTH: 474
<212> TYPE: PRT
<213> ORGANISM: Artificial sequence
<220> FEATURE:
<223> OTHER INFORMATION: Synthetic Construct

<400> SEQUENCE: 20

Met Pro Leu Leu Leu Leu Leu Pro Leu Leu Trp Ala Gly Ala Leu Ala
1               5                   10                  15

Met Asp Lys Leu Ala Ser Val Gln Asp Tyr Arg Ser Pro Phe Ile Ala
            20                  25                  30

Ser Val Ser Asp Gln His Gly Val Tyr Ile Thr Glu Asn Lys Asn
            35                  40                  45

Lys Thr Val Val Ile Pro Cys Leu Gly Ser Ile Ser Asn Leu Asn Val
        50                  55                  60

Ser Leu Cys Ala Arg Tyr Pro Glu Lys Arg Phe Val Pro Asp Gly Asn
```

```
              65                  70                  75                  80
        Arg Ile Ser Trp Asp Ser Lys Lys Gly Phe Thr Ile Pro Ser Tyr Met
                            85                  90                  95
        Ile Ser Tyr Ala Gly Met Val Phe Cys Glu Ala Lys Ile Asn Asp Glu
                           100                 105                 110
        Ser Tyr Gln Ser Ile Met Tyr Ile Val Val Val Gly Tyr Arg Ile
                           115                 120                 125
        Tyr Asp Val Val Leu Ser Pro Ser His Gly Ile Glu Leu Ser Val Gly
                      130                 135                 140
        Glu Lys Leu Val Leu Asn Cys Thr Ala Arg Thr Glu Leu Asn Val Gly
        145                 150                 155                 160
        Ile Asp Phe Asn Trp Glu Tyr Pro Ser Ser Lys His Gln His Lys Lys
                           165                 170                 175
        Leu Val Asn Arg Asp Leu Lys Thr Gln Ser Gly Ser Glu Met Lys Lys
                      180                 185                 190
        Phe Leu Ser Thr Leu Thr Ile Asp Gly Val Thr Arg Ser Asp Gln Gly
                      195                 200                 205
        Leu Tyr Thr Cys Ala Ala Ser Ser Gly Leu Met Thr Lys Lys Asn Ser
                      210                 215                 220
        Thr Phe Val Arg Val His Glu Asp Pro Ile Glu Gly Arg Gly Gly Gly
        225                 230                 235                 240
        Gly Gly Asp Pro Lys Ser Cys Asp Lys Pro His Thr Cys Pro Leu Cys
                           245                 250                 255
        Pro Ala Pro Glu Leu Leu Gly Gly Pro Ser Val Phe Leu Phe Pro Pro
                      260                 265                 270
        Lys Pro Lys Asp Thr Leu Met Ile Ser Arg Thr Pro Glu Val Thr Cys
                      275                 280                 285
        Val Val Val Asp Val Ser His Glu Asp Pro Glu Val Lys Phe Asn Trp
                      290                 295                 300
        Tyr Val Asp Gly Val Glu Val His Asn Ala Lys Thr Lys Pro Arg Glu
        305                 310                 315                 320
        Glu Gln Tyr Asn Ser Thr Tyr Arg Val Val Ser Val Leu Thr Val Leu
                           325                 330                 335
        His Gln Asp Trp Leu Asn Gly Lys Glu Tyr Lys Cys Lys Val Ser Asn
                      340                 345                 350
        Lys Ala Leu Pro Ala Pro Ile Glu Lys Thr Ile Ser Lys Ala Lys Gly
                      355                 360                 365
        Gln Pro Arg Glu Pro Gln Val Tyr Thr Leu Pro Pro Ser Arg Asp Glu
                      370                 375                 380
        Leu Thr Lys Asn Gln Val Ser Leu Thr Cys Leu Val Lys Gly Phe Tyr
        385                 390                 395                 400
        Pro Ser Asp Ile Ala Val Glu Trp Glu Ser Asn Gly Gln Pro Glu Asn
                           405                 410                 415
        Asn Tyr Lys Ala Thr Pro Pro Val Leu Asp Ser Asp Gly Ser Phe Phe
                      420                 425                 430
        Leu Tyr Ser Lys Leu Thr Val Asp Lys Ser Arg Trp Gln Gln Gly Asn
                      435                 440                 445
        Val Phe Ser Cys Ser Val Met His Glu Ala Leu His Asn His Tyr Thr
                      450                 455                 460
        Gln Lys Ser Leu Ser Leu Ser Pro Gly Lys
        465                 470

<210> SEQ ID NO 21
```

<211> LENGTH: 1107
<212> TYPE: DNA
<213> ORGANISM: Artificial sequence
<220> FEATURE:
<223> OTHER INFORMATION: R-2 H
<220> FEATURE:
<221> NAME/KEY: CDS
<222> LOCATION: (1)..(1107)

<400> SEQUENCE: 21

| | | | | | | | | | | | | | | | | |
|---|---|---|---|---|---|---|---|---|---|---|---|---|---|---|---|---|
| atg | ccg | ctg | ctg | cta | ctg | ctg | ccc | ctg | ctg | tgg | gca | ggg | gcc | ctg | gct | 48 |
| Met | Pro | Leu | Leu | Leu | Leu | Leu | Pro | Leu | Leu | Trp | Ala | Gly | Ala | Leu | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| atg | gat | aag | ctt | gct | agc | gtt | caa | gat | tac | aga | tct | cca | ttt | att | gct | 96 |
| Met | Asp | Lys | Leu | Ala | Ser | Val | Gln | Asp | Tyr | Arg | Ser | Pro | Phe | Ile | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| tct | gtt | agt | gac | caa | cat | gga | gtc | gtg | tac | att | act | gag | aac | aaa | aac | 144 |
| Ser | Val | Ser | Asp | Gln | His | Gly | Val | Val | Tyr | Ile | Thr | Glu | Asn | Lys | Asn | |
| | | 35 | | | | | 40 | | | | | 45 | | | | |

| | | | | | | | | | | | | | | | | |
|---|---|---|---|---|---|---|---|---|---|---|---|---|---|---|---|---|
| aaa | act | gtg | gtg | att | cca | tgt | ctc | ggg | tcc | att | tca | aat | ctc | aac | gtg | 192 |
| Lys | Thr | Val | Val | Ile | Pro | Cys | Leu | Gly | Ser | Ile | Ser | Asn | Leu | Asn | Val | |
| | 50 | | | | | 55 | | | | | 60 | | | | | |

| | | | | | | | | | | | | | | | | |
|---|---|---|---|---|---|---|---|---|---|---|---|---|---|---|---|---|
| tca | ctt | tgt | gca | aga | tac | cca | gaa | aag | aga | ttt | gtt | cct | gat | ggt | aac | 240 |
| Ser | Leu | Cys | Ala | Arg | Tyr | Pro | Glu | Lys | Arg | Phe | Val | Pro | Asp | Gly | Asn | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aga | att | tcc | tgg | gac | agc | aag | aag | ggc | ttt | act | att | ccc | agc | tac | atg | 288 |
| Arg | Ile | Ser | Trp | Asp | Ser | Lys | Lys | Gly | Phe | Thr | Ile | Pro | Ser | Tyr | Met | |
| | | | | 85 | | | | | 90 | | | | | 95 | | |

| | | | | | | | | | | | | | | | | |
|---|---|---|---|---|---|---|---|---|---|---|---|---|---|---|---|---|
| atc | agc | tat | gct | ggc | atg | gtc | ttc | tgt | gaa | gca | aaa | att | aat | gat | gaa | 336 |
| Ile | Ser | Tyr | Ala | Gly | Met | Val | Phe | Cys | Glu | Ala | Lys | Ile | Asn | Asp | Glu | |
| | | | 100 | | | | | 105 | | | | | 110 | | | |

| | | | | | | | | | | | | | | | | |
|---|---|---|---|---|---|---|---|---|---|---|---|---|---|---|---|---|
| agt | tac | cag | tct | att | atg | tac | ata | gtt | gtc | gtt | gta | ggg | gat | ccc | atc | 384 |
| Ser | Tyr | Gln | Ser | Ile | Met | Tyr | Ile | Val | Val | Val | Val | Gly | Asp | Pro | Ile | |
| | | 115 | | | | | 120 | | | | | 125 | | | | |

| | | | | | | | | | | | | | | | | |
|---|---|---|---|---|---|---|---|---|---|---|---|---|---|---|---|---|
| gaa | ggt | cgt | ggt | ggt | ggt | ggt | ggt | gat | ccc | aaa | tct | tgt | gac | aaa | cct | 432 |
| Glu | Gly | Arg | Gly | Gly | Gly | Gly | Gly | Asp | Pro | Lys | Ser | Cys | Asp | Lys | Pro | |
| | 130 | | | | | 135 | | | | | 140 | | | | | |

| | | | | | | | | | | | | | | | | |
|---|---|---|---|---|---|---|---|---|---|---|---|---|---|---|---|---|
| cac | aca | tgc | cca | ctg | tgc | cca | gca | cct | gaa | ctc | ctg | ggg | gga | ccg | tca | 480 |
| His | Thr | Cys | Pro | Leu | Cys | Pro | Ala | Pro | Glu | Leu | Leu | Gly | Gly | Pro | Ser | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gtc | ttc | ctc | ttc | ccc | cca | aaa | ccc | aag | gac | acc | ctc | atg | atc | tcc | cgg | 528 |
| Val | Phe | Leu | Phe | Pro | Pro | Lys | Pro | Lys | Asp | Thr | Leu | Met | Ile | Ser | Arg | |
| | | | | 165 | | | | | 170 | | | | | 175 | | |

| | | | | | | | | | | | | | | | | |
|---|---|---|---|---|---|---|---|---|---|---|---|---|---|---|---|---|
| acc | cct | gag | gtc | aca | tgc | gtg | gtg | gtg | gac | gtg | agc | cac | gaa | gac | cct | 576 |
| Thr | Pro | Glu | Val | Thr | Cys | Val | Val | Val | Asp | Val | Ser | His | Glu | Asp | Pro | |
| | | | 180 | | | | | 185 | | | | | 190 | | | |

| | | | | | | | | | | | | | | | | |
|---|---|---|---|---|---|---|---|---|---|---|---|---|---|---|---|---|
| gag | gtc | aag | ttc | aac | tgg | tac | gtg | gac | ggc | gtg | gag | gtg | cat | aat | gcc | 624 |
| Glu | Val | Lys | Phe | Asn | Trp | Tyr | Val | Asp | Gly | Val | Glu | Val | His | Asn | Ala | |
| | | 195 | | | | | 200 | | | | | 205 | | | | |

| | | | | | | | | | | | | | | | | |
|---|---|---|---|---|---|---|---|---|---|---|---|---|---|---|---|---|
| aag | aca | aag | ccg | cgg | gag | gag | cag | tac | aac | agc | acg | tac | cgt | gtg | gtc | 672 |
| Lys | Thr | Lys | Pro | Arg | Glu | Glu | Gln | Tyr | Asn | Ser | Thr | Tyr | Arg | Val | Val | |
| | 210 | | | | | 215 | | | | | 220 | | | | | |

| | | | | | | | | | | | | | | | | |
|---|---|---|---|---|---|---|---|---|---|---|---|---|---|---|---|---|
| agc | gtc | ctc | acc | gtc | ctg | cac | cag | gac | tgg | ctg | aat | ggc | aag | gag | tac | 720 |
| Ser | Val | Leu | Thr | Val | Leu | His | Gln | Asp | Trp | Leu | Asn | Gly | Lys | Glu | Tyr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aag | tgc | aag | gtc | tcc | aac | aaa | gcc | ctc | cca | gcc | ccc | atc | gag | aaa | acc | 768 |
| Lys | Cys | Lys | Val | Ser | Asn | Lys | Ala | Leu | Pro | Ala | Pro | Ile | Glu | Lys | Thr | |
| | | | | 245 | | | | | 250 | | | | | 255 | | |

| | | | | | | | | | | | | | | | | |
|---|---|---|---|---|---|---|---|---|---|---|---|---|---|---|---|---|
| atc | tcc | aaa | gcc | aaa | ggg | cag | ccc | cga | gaa | cca | cag | gtg | tac | acc | ctg | 816 |
| Ile | Ser | Lys | Ala | Lys | Gly | Gln | Pro | Arg | Glu | Pro | Gln | Val | Tyr | Thr | Leu | |
| | | | 260 | | | | | 265 | | | | | 270 | | | |

| | | |
|---|---|---|
| ccc cca tcc cgg gat gag ctg acc aag aac cag gtc agc ctg acc tgc<br>Pro Pro Ser Arg Asp Glu Leu Thr Lys Asn Gln Val Ser Leu Thr Cys<br>275 280 285 | | 864 |
| cta gtc aaa ggc ttc tat ccc agc gac atc gcc gtg gag tgg gag agc<br>Leu Val Lys Gly Phe Tyr Pro Ser Asp Ile Ala Val Glu Trp Glu Ser<br>290 295 300 | | 912 |
| aat ggg cag ccg gag aac aac tac aag gcc acg cct ccc gtg ctg gac<br>Asn Gly Gln Pro Glu Asn Asn Tyr Lys Ala Thr Pro Pro Val Leu Asp<br>305 310 315 320 | | 960 |
| tcc gac ggc tcc ttc ttc ctc tac agc aag ctc acc gtg gac aag agc<br>Ser Asp Gly Ser Phe Phe Leu Tyr Ser Lys Leu Thr Val Asp Lys Ser<br>325 330 335 | | 1008 |
| agg tgg cag cag ggg aac gtc ttc tca tgc tcc gtg atg cat gag gct<br>Arg Trp Gln Gln Gly Asn Val Phe Ser Cys Ser Val Met His Glu Ala<br>340 345 350 | | 1056 |
| ctg cac aac cac tac acg cag aag agc ctc tcc ctg tct ccg ggt aaa<br>Leu His Asn His Tyr Thr Gln Lys Ser Leu Ser Leu Ser Pro Gly Lys<br>355 360 365 | | 1104 |
| tga | | 1107 |

<210> SEQ ID NO 22
<211> LENGTH: 368
<212> TYPE: PRT
<213> ORGANISM: Artificial sequence
<220> FEATURE:
<223> OTHER INFORMATION: Synthetic Construct

<400> SEQUENCE: 22

Met Pro Leu Leu Leu Leu Leu Pro Leu Leu Trp Ala Gly Ala Leu Ala
1               5                   10                  15

Met Asp Lys Leu Ala Ser Val Gln Asp Tyr Arg Ser Pro Phe Ile Ala
            20                  25                  30

Ser Val Ser Asp Gln His Gly Val Val Tyr Ile Thr Glu Asn Lys Asn
        35                  40                  45

Lys Thr Val Val Ile Pro Cys Leu Gly Ser Ile Ser Asn Leu Asn Val
    50                  55                  60

Ser Leu Cys Ala Arg Tyr Pro Glu Lys Arg Phe Val Pro Asp Gly Asn
65                  70                  75                  80

Arg Ile Ser Trp Asp Ser Lys Lys Gly Phe Thr Ile Pro Ser Tyr Met
                85                  90                  95

Ile Ser Tyr Ala Gly Met Val Phe Cys Glu Ala Lys Ile Asn Asp Glu
            100                 105                 110

Ser Tyr Gln Ser Ile Met Tyr Ile Val Val Val Gly Asp Pro Ile
        115                 120                 125

Glu Gly Arg Gly Gly Gly Gly Asp Pro Lys Ser Cys Asp Lys Pro
    130                 135                 140

His Thr Cys Pro Leu Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr

```
225                 230                 235                 240
Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
                260                 265                 270

Pro Pro Ser Arg Asp Glu Leu Thr Lys Asn Gln Val Ser Leu Thr Cys
            275                 280                 285

Leu Val Lys Gly Phe Tyr Pro Ser Asp Ile Ala Val Glu Trp Glu Ser
        290                 295                 300

Asn Gly Gln Pro Glu Asn Asn Tyr Lys Ala Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
                340                 345                 350

Leu His Asn His Tyr Thr Gln Lys Ser Leu Ser Leu Ser Pro Gly Lys
            355                 360                 365

<210> SEQ ID NO 23
<211> LENGTH: 1125
<212> TYPE: DNA
<213> ORGANISM: Artificial sequence
<220> FEATURE:
<223> OTHER INFORMATION: R-2 I
<220> FEATURE:
<221> NAME/KEY: CDS
<222> LOCATION: (1)..(1125)

<400> SEQUENCE: 23 atg ccg ctg ctg cta ctg ctg ccc ctg ctg tgg gca ggg gcc ctg gct        48
Met Pro Leu Leu Leu Leu Leu Pro Leu Leu Trp Ala Gly Ala Leu Ala
1               5                   10                  15 atg gat aag ctt gct agc gtt caa gat tac aga tct cca ttt att gct        96
Met Asp Lys Leu Ala Ser Val Gln Asp Tyr Arg Ser Pro Phe Ile Ala
                20                  25                  30 tct gtt agt gac caa cat gga gtc gtg tac att act gag aac aaa aac       144
Ser Val Ser Asp Gln His Gly Val Val Tyr Ile Thr Glu Asn Lys Asn
            35                  40                  45 aaa act gtg gtg att cca tgt ctc ggg tcc att tca aat ctc aac gtg       192
Lys Thr Val Val Ile Pro Cys Leu Gly Ser Ile Ser Asn Leu Asn Val
        50                  55                  60 tca ctt tgt gca aga tac cca gaa aag aga ttt gtt cct gat ggt aac       240
Ser Leu Cys Ala Arg Tyr Pro Glu Lys Arg Phe Val Pro Asp Gly Asn
65                  70                  75                  80 aga att tcc tgg gac agc aag aag ggc ttt act att ccc agc tac atg       288
Arg Ile Ser Trp Asp Ser Lys Lys Gly Phe Thr Ile Pro Ser Tyr Met
                85                  90                  95 atc agc tat gct ggc atg gtc ttc tgt gaa gca aaa att aat gat gaa       336
Ile Ser Tyr Ala Gly Met Val Phe Cys Glu Ala Lys Ile Asn Asp Glu
                100                 105                 110 agt tac cag tct att atg tac ata gtt gtc gtt gta ggg tat agg att       384
Ser Tyr Gln Ser Ile Met Tyr Ile Val Val Val Val Gly Tyr Arg Ile
            115                 120                 125 tat gat gtg gat ccc atc gaa ggt cgt ggt ggt ggt ggt gat ccc            432
Tyr Asp Val Asp Pro Ile Glu Gly Arg Gly Gly Gly Gly Asp Pro
        130                 135                 140 aaa tct tgt gac aaa cct cac aca tgc cca ctg tgc cca gca cct gaa       480
Lys Ser Cys Asp Lys Pro His Thr Cys Pro Leu Cys Pro Ala Pro Glu
145                 150                 155                 160
```

| | | |
|---|---|---|
| ctc ctg ggg gga ccg tca gtc ttc ctc ttc ccc cca aaa ccc aag gac<br>Leu Leu Gly Gly Pro Ser Val Phe Leu Phe Pro Pro Lys Pro Lys Asp<br>165 170 175 | | 528 |
| acc ctc atg atc tcc cgg acc cct gag gtc aca tgc gtg gtg gtg gac<br>Thr Leu Met Ile Ser Arg Thr Pro Glu Val Thr Cys Val Val Val Asp<br>180 185 190 | | 576 |
| gtg agc cac gaa gac cct gag gtc aag ttc aac tgg tac gtg gac ggc<br>Val Ser His Glu Asp Pro Glu Val Lys Phe Asn Trp Tyr Val Asp Gly<br>195 200 205 | | 624 |
| gtg gag gtg cat aat gcc aag aca aag ccg cgg gag gag cag tac aac<br>Val Glu Val His Asn Ala Lys Thr Lys Pro Arg Glu Glu Gln Tyr Asn<br>210 215 220 | | 672 |
| agc acg tac cgt gtg gtc agc gtc ctc acc gtc ctg cac cag gac tgg<br>Ser Thr Tyr Arg Val Val Ser Val Leu Thr Val Leu His Gln Asp Trp<br>225 230 235 240 | | 720 |
| ctg aat ggc aag gag tac aag tgc aag gtc tcc aac aaa gcc ctc cca<br>Leu Asn Gly Lys Glu Tyr Lys Cys Lys Val Ser Asn Lys Ala Leu Pro<br>245 250 255 | | 768 |
| gcc ccc atc gag aaa acc atc tcc aaa gcc aaa ggg cag ccc cga gaa<br>Ala Pro Ile Glu Lys Thr Ile Ser Lys Ala Lys Gly Gln Pro Arg Glu<br>260 265 270 | | 816 |
| cca cag gtg tac acc ctg ccc cca tcc cgg gat gag ctg acc aag aac<br>Pro Gln Val Tyr Thr Leu Pro Pro Ser Arg Asp Glu Leu Thr Lys Asn<br>275 280 285 | | 864 |
| cag gtc agc ctg acc tgc cta gtc aaa ggc ttc tat ccc agc gac atc<br>Gln Val Ser Leu Thr Cys Leu Val Lys Gly Phe Tyr Pro Ser Asp Ile<br>290 295 300 | | 912 |
| gcc gtg gag tgg gag agc aat ggg cag ccg gag aac aac tac aag gcc<br>Ala Val Glu Trp Glu Ser Asn Gly Gln Pro Glu Asn Asn Tyr Lys Ala<br>305 310 315 320 | | 960 |
| acg cct ccc gtg ctg gac tcc gac ggc tcc ttc ttc ctc tac agc aag<br>Thr Pro Pro Val Leu Asp Ser Asp Gly Ser Phe Phe Leu Tyr Ser Lys<br>325 330 335 | | 1008 |
| ctc acc gtg gac aag agc agg tgg cag cag ggg aac gtc ttc tca tgc<br>Leu Thr Val Asp Lys Ser Arg Trp Gln Gln Gly Asn Val Phe Ser Cys<br>340 345 350 | | 1056 |
| tcc gtg atg cat gag gct ctg cac aac cac tac acg cag aag agc ctc<br>Ser Val Met His Glu Ala Leu His Asn His Tyr Thr Gln Lys Ser Leu<br>355 360 365 | | 1104 |
| tcc ctg tct ccg ggt aaa tga<br>Ser Leu Ser Pro Gly Lys<br>370 | | 1125 |

<210> SEQ ID NO 24
<211> LENGTH: 374
<212> TYPE: PRT
<213> ORGANISM: Artificial sequence
<220> FEATURE:
<223> OTHER INFORMATION: Synthetic Construct

<400> SEQUENCE: 24

Met Pro Leu Leu Leu Leu Pro Leu Leu Trp Ala Gly Ala Leu Ala
1               5                   10                  15

Met Asp Lys Leu Ala Ser Val Gln Asp Tyr Arg Ser Pro Phe Ile Ala
            20                  25                  30

Ser Val Ser Asp Gln His Gly Val Tyr Ile Thr Glu Asn Lys Asn
        35                  40                  45

Lys Thr Val Val Ile Pro Cys Leu Gly Ser Ile Ser Asn Leu Asn Val
    50                  55                  60

Ser Leu Cys Ala Arg Tyr Pro Glu Lys Arg Phe Val Pro Asp Gly Asn

```
                    65                  70                  75                  80
Arg Ile Ser Trp Asp Ser Lys Lys Gly Phe Thr Ile Pro Ser Tyr Met
                85                  90                  95

Ile Ser Tyr Ala Gly Met Val Phe Cys Glu Ala Lys Ile Asn Asp Glu
            100                 105                 110

Ser Tyr Gln Ser Ile Met Tyr Ile Val Val Val Gly Tyr Arg Ile
        115                 120                 125

Tyr Asp Val Asp Pro Ile Glu Gly Arg Gly Gly Gly Gly Asp Pro
    130                 135                 140

Lys Ser Cys Asp Lys Pro His Thr Cys Pro Leu Cys Pro Ala Pro Glu
145                 150                 155                 160

Leu Leu Gly Gly Pro Ser Val Phe Leu Phe Pro Pro Lys Pro Lys Asp
                165                 170                 175

Thr Leu Met Ile Ser Arg Thr Pro Glu Val Thr Cys Val Val Val Asp
            180                 185                 190

Val Ser His Glu Asp Pro Glu Val Lys Phe Asn Trp Tyr Val Asp Gly
        195                 200                 205

Val Glu Val His Asn Ala Lys Thr Lys Pro Arg Glu Glu Gln Tyr Asn
    210                 215                 220

Ser Thr Tyr Arg Val Val Ser Val Leu Thr Val Leu His Gln Asp Trp
225                 230                 235                 240

Leu Asn Gly Lys Glu Tyr Lys Cys Lys Val Ser Asn Lys Ala Leu Pro
                245                 250                 255

Ala Pro Ile Glu Lys Thr Ile Ser Lys Ala Lys Gly Gln Pro Arg Glu
            260                 265                 270

Pro Gln Val Tyr Thr Leu Pro Pro Ser Arg Asp Glu Leu Thr Lys Asn
        275                 280                 285

Gln Val Ser Leu Thr Cys Leu Val Lys Gly Phe Tyr Pro Ser Asp Ile
    290                 295                 300

Ala Val Glu Trp Glu Ser Asn Gly Gln Pro Glu Asn Asn Tyr Lys Ala
305                 310                 315                 320

Thr Pro Pro Val Leu Asp Ser Asp Gly Ser Phe Phe Leu Tyr Ser Lys
                325                 330                 335

Leu Thr Val Asp Lys Ser Arg Trp Gln Gln Gly Asn Val Phe Ser Cys
            340                 345                 350

Ser Val Met His Glu Ala Leu His Asn His Tyr Thr Gln Lys Ser Leu
        355                 360                 365

Ser Leu Ser Pro Gly Lys
    370

<210> SEQ ID NO 25
<211> LENGTH: 1143
<212> TYPE: DNA
<213> ORGANISM: Artificial sequence
<220> FEATURE:
<223> OTHER INFORMATION: R-2 J
<220> FEATURE:
<221> NAME/KEY: CDS
<222> LOCATION: (1)..(1143)

<400> SEQUENCE: 25 atg ccg ctg ctg cta ctg ctg ccc ctg ctg tgg gca ggg gcc ctg gct      48
Met Pro Leu Leu Leu Leu Leu Pro Leu Leu Trp Ala Gly Ala Leu Ala
1               5                   10                  15 atg gat aag ctt gct agc gtt caa gat tac aga tct cca ttt att gct      96
Met Asp Lys Leu Ala Ser Val Gln Asp Tyr Arg Ser Pro Phe Ile Ala
            20                  25                  30
```

| | | |
|---|---|---|
| tct gtt agt gac caa cat gga gtc gtg tac att act gag aaa aac<br>Ser Val Ser Asp Gln His Gly Val Val Tyr Ile Thr Glu Asn Lys Asn<br>35　　　　　　　　40　　　　　　　　45 | | 144 |
| aaa act gtg gtg att cca tgt ctc ggg tcc att tca aat ctc aac gtg<br>Lys Thr Val Val Ile Pro Cys Leu Gly Ser Ile Ser Asn Leu Asn Val<br>50　　　　　　　55　　　　　　　　60 | | 192 |
| tca ctt tgt gca aga tac cca gaa aag aga ttt gtt cct gat ggt aac<br>Ser Leu Cys Ala Arg Tyr Pro Glu Lys Arg Phe Val Pro Asp Gly Asn<br>65　　　　　　　　70　　　　　　　75　　　　　　　　80 | | 240 |
| aga att tcc tgg gac agc aag aag ggc ttt act att ccc agc tac atg<br>Arg Ile Ser Trp Asp Ser Lys Lys Gly Phe Thr Ile Pro Ser Tyr Met<br>　　　　　　85　　　　　　　　90　　　　　　　　95 | | 288 |
| atc agc tat gct ggc atg gtc ttc tgt gaa gca aaa att aat gat gaa<br>Ile Ser Tyr Ala Gly Met Val Phe Cys Glu Ala Lys Ile Asn Asp Glu<br>　　　　　100　　　　　　　　105　　　　　　　　110 | | 336 |
| agt tac cag tct att atg tac ata gtt gtc gtt gta ggg tat agg att<br>Ser Tyr Gln Ser Ile Met Tyr Ile Val Val Val Val Gly Tyr Arg Ile<br>115　　　　　　　　120　　　　　　　　125 | | 384 |
| tat gat gtg gtt ctg agt ccg tct cat gat ccc atc gaa ggt cgt ggt<br>Tyr Asp Val Val Leu Ser Pro Ser His Asp Pro Ile Glu Gly Arg Gly<br>130　　　　　　　135　　　　　　　　140 | | 432 |
| ggt ggt ggt ggt gat ccc aaa tct tgt gac aaa cct cac aca tgc cca<br>Gly Gly Gly Gly Asp Pro Lys Ser Cys Asp Lys Pro His Thr Cys Pro<br>145　　　　　　　　150　　　　　　　155　　　　　　　　160 | | 480 |
| ctg tgc cca gca cct gaa ctc ctg ggg gga ccg tca gtc ttc ctc ttc<br>Leu Cys Pro Ala Pro Glu Leu Leu Gly Gly Pro Ser Val Phe Leu Phe<br>　　　　　　165　　　　　　　　170　　　　　　　　175 | | 528 |
| ccc cca aaa ccc aag gac acc ctc atg atc tcc cgg acc cct gag gtc<br>Pro Pro Lys Pro Lys Asp Thr Leu Met Ile Ser Arg Thr Pro Glu Val<br>　　　　　180　　　　　　　　185　　　　　　　　190 | | 576 |
| aca tgc gtg gtg gtg gac gtg agc cac gaa gac cct gag gtc aag ttc<br>Thr Cys Val Val Val Asp Val Ser His Glu Asp Pro Glu Val Lys Phe<br>　　　195　　　　　　　　200　　　　　　　　205 | | 624 |
| aac tgg tac gtg gac ggc gtg gag gtg cat aat gcc aag aca aag ccg<br>Asn Trp Tyr Val Asp Gly Val Glu Val His Asn Ala Lys Thr Lys Pro<br>210　　　　　　　　215　　　　　　　　220 | | 672 |
| cgg gag gag cag tac aac agc acg tac cgt gtg gtc agc gtc ctc acc<br>Arg Glu Glu Gln Tyr Asn Ser Thr Tyr Arg Val Val Ser Val Leu Thr<br>225　　　　　　　　230　　　　　　　　235　　　　　　　　240 | | 720 |
| gtc ctg cac cag gac tgg ctg aat ggc aag gag tac aag tgc aag gtc<br>Val Leu His Gln Asp Trp Leu Asn Gly Lys Glu Tyr Lys Cys Lys Val<br>　　　　　　245　　　　　　　　250　　　　　　　　255 | | 768 |
| tcc aac aaa gcc ctc cca gcc ccc atc gag aaa acc atc tcc aaa gcc<br>Ser Asn Lys Ala Leu Pro Ala Pro Ile Glu Lys Thr Ile Ser Lys Ala<br>　　　　　260　　　　　　　　265　　　　　　　　270 | | 816 |
| aaa ggg cag ccc cga gaa cca cag gtg tac acc ctg ccc cca tcc cgg<br>Lys Gly Gln Pro Arg Glu Pro Gln Val Tyr Thr Leu Pro Pro Ser Arg<br>　　　275　　　　　　　　280　　　　　　　　285 | | 864 |
| gat gag ctg acc aag aac cag gtc agc ctg acc tgc cta gtc aaa ggc<br>Asp Glu Leu Thr Lys Asn Gln Val Ser Leu Thr Cys Leu Val Lys Gly<br>290　　　　　　　　295　　　　　　　　300 | | 912 |
| ttc tat ccc agc gac atc gcc gtg gag tgg gag agc aat ggg cag ccg<br>Phe Tyr Pro Ser Asp Ile Ala Val Glu Trp Glu Ser Asn Gly Gln Pro<br>305　　　　　　　　310　　　　　　　　315　　　　　　　　320 | | 960 |
| gag aac aac tac aag gcc acg cct ccc gtg ctg gac tcc gac ggc tcc<br>Glu Asn Asn Tyr Lys Ala Thr Pro Pro Val Leu Asp Ser Asp Gly Ser<br>　　　　　　325　　　　　　　　330　　　　　　　　335 | | 1008 |
| ttc ttc ctc tac agc aag ctc acc gtg gac aag agc agg tgg cag cag<br>Phe Phe Leu Tyr Ser Lys Leu Thr Val Asp Lys Ser Arg Trp Gln Gln | | 1056 |

```
                    340             345              350
ggg aac gtc ttc tca tgc tcc gtg atg cat gag gct ctg cac aac cac    1104
Gly Asn Val Phe Ser Cys Ser Val Met His Glu Ala Leu His Asn His
        355                 360                 365 tac acg cag aag agc ctc tcc ctg tct ccg ggt aaa tga                1143
Tyr Thr Gln Lys Ser Leu Ser Leu Ser Pro Gly Lys
    370                 375                 380
```

<210> SEQ ID NO 26
<211> LENGTH: 380
<212> TYPE: PRT
<213> ORGANISM: Artificial sequence
<220> FEATURE:
<223> OTHER INFORMATION: Synthetic Construct

<400> SEQUENCE: 26

```
Met Pro Leu Leu Leu Leu Pro Leu Leu Trp Ala Gly Ala Leu Ala
1               5                   10                  15

Met Asp Lys Leu Ala Ser Val Gln Asp Tyr Arg Ser Pro Phe Ile Ala
                20                  25                  30

Ser Val Ser Asp Gln His Gly Val Val Tyr Ile Thr Glu Asn Lys Asn
            35                  40                  45

Lys Thr Val Val Ile Pro Cys Leu Gly Ser Ile Ser Asn Leu Asn Val
    50                  55                  60

Ser Leu Cys Ala Arg Tyr Pro Glu Lys Arg Phe Val Pro Asp Gly Asn
65                  70                  75                  80

Arg Ile Ser Trp Asp Ser Lys Lys Gly Phe Thr Ile Pro Ser Tyr Met
                85                  90                  95

Ile Ser Tyr Ala Gly Met Val Phe Cys Glu Ala Lys Ile Asn Asp Glu
            100                 105                 110

Ser Tyr Gln Ser Ile Met Tyr Ile Val Val Val Gly Tyr Arg Ile
        115                 120                 125

Tyr Asp Val Val Leu Ser Pro Ser His Asp Pro Ile Glu Gly Arg Gly
    130                 135                 140

Gly Gly Gly Gly Asp Pro Lys Ser Cys Asp Lys Pro His Thr Cys Pro
145                 150                 155                 160

Leu Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
    210                 215                 220

Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
        275                 280                 285

Asp Glu Leu Thr Lys Asn Gln Val Ser Leu Thr Cys Leu Val Lys Gly
    290                 295                 300

Phe Tyr Pro Ser Asp Ile Ala Val Glu Trp Ser Asn Gly Gln Pro
305                 310                 315                 320
```

-continued

```
Glu Asn Asn Tyr Lys Ala Thr Pro Pro Val Leu Asp Ser Asp Gly Ser
            325                 330                 335
Phe Phe Leu Tyr Ser Lys Leu Thr Val Asp Lys Ser Arg Trp Gln Gln
            340                 345                 350
Gly Asn Val Phe Ser Cys Ser Val Met His Glu Ala Leu His Asn His
            355                 360                 365
Tyr Thr Gln Lys Ser Leu Ser Leu Ser Pro Gly Lys
            370                 375                 380

<210> SEQ ID NO 27
<211> LENGTH: 1170
<212> TYPE: DNA
<213> ORGANISM: Artificial sequence
<220> FEATURE:
<223> OTHER INFORMATION: R-2 K
<220> FEATURE:
<221> NAME/KEY: CDS
<222> LOCATION: (1)..(1170)

<400> SEQUENCE: 27 atg ccg ctg ctg cta ctg ctc ccc ctg ctg tgg gca ggg gcc ctg gct        48
Met Pro Leu Leu Leu Leu Leu Pro Leu Leu Trp Ala Gly Ala Leu Ala
1               5                   10                  15 atg gat aag ctt gct agc gtt caa gat tac aga tct cca ttt att gct        96
Met Asp Lys Leu Ala Ser Val Gln Asp Tyr Arg Ser Pro Phe Ile Ala
                20                  25                  30 tct gtt agt gac caa cat gga gtc gtg tac att act gag aac aaa aac       144
Ser Val Ser Asp Gln His Gly Val Val Tyr Ile Thr Glu Asn Lys Asn
            35                  40                  45 aaa act gtg gtg att cca tgt ctc ggg tcc att tca aat ctc aac gtg       192
Lys Thr Val Val Ile Pro Cys Leu Gly Ser Ile Ser Asn Leu Asn Val
        50                  55                  60 tca ctt tgt gca aga tac cca gaa aag aga ttt gtt cct gat ggt aac       240
Ser Leu Cys Ala Arg Tyr Pro Glu Lys Arg Phe Val Pro Asp Gly Asn
65                  70                  75                  80 aga att tcc tgg gac agc aag aag ggc ttt act att ccc agc tac atg       288
Arg Ile Ser Trp Asp Ser Lys Lys Gly Phe Thr Ile Pro Ser Tyr Met
                85                  90                  95 atc agc tat gct ggc atg gtc ttc tgt gaa gca aaa att aat gat gaa       336
Ile Ser Tyr Ala Gly Met Val Phe Cys Glu Ala Lys Ile Asn Asp Glu
            100                 105                 110 agt tac cag tct att atg tac ata gtt gtc gtt gta ggg tat agg att       384
Ser Tyr Gln Ser Ile Met Tyr Ile Val Val Val Val Gly Tyr Arg Ile
        115                 120                 125 tat gat gtg gtt ctg agt ccg tct cat gga att gaa cta tct gtt gga       432
Tyr Asp Val Val Leu Ser Pro Ser His Gly Ile Glu Leu Ser Val Gly
    130                 135                 140 gaa aag gat ccc atc gaa ggt cgt ggt ggt ggt ggt gat ccc aaa           480
Glu Lys Asp Pro Ile Glu Gly Arg Gly Gly Gly Gly Asp Pro Lys
145                 150                 155                 160 tct tgt gac aaa cct cac aca tgc cca ctg tgc cca gca cct gaa ctc       528
Ser Cys Asp Lys Pro His Thr Cys Pro Leu Cys Pro Ala Pro Glu Leu
                165                 170                 175 ctg ggg gga ccg tca gtc ttc ctc ttc ccc cca aaa ccc aag gac acc       576
Leu Gly Gly Pro Ser Val Phe Leu Phe Pro Pro Lys Pro Lys Asp Thr
            180                 185                 190 ctc atg atc tcc cgg acc cct gag gtc aca tgc gtg gtg gtg gac gtg       624
Leu Met Ile Ser Arg Thr Pro Glu Val Thr Cys Val Val Val Asp Val
        195                 200                 205 agc cac gaa gac cct gag gtc aag ttc aac tgg tac gtg gac ggc gtg       672
```

```
Ser His Glu Asp Pro Glu Val Lys Phe Asn Trp Tyr Val Asp Gly Val
    210                 215                 220 gag gtg cat aat gcc aag aca aag ccg cgg gag gag cag tac aac agc      720
Glu Val His Asn Ala Lys Thr Lys Pro Arg Glu Glu Gln Tyr Asn Ser
225                 230                 235                 240 acg tac cgt gtg gtc agc gtc ctc acc gtc ctg cac cag gac tgg ctg      768
Thr Tyr Arg Val Val Ser Val Leu Thr Val Leu His Gln Asp Trp Leu
                245                 250                 255 aat ggc aag gag tac aag tgc aag gtc tcc aac aaa gcc ctc cca gcc      816
Asn Gly Lys Glu Tyr Lys Cys Lys Val Ser Asn Lys Ala Leu Pro Ala
            260                 265                 270 ccc atc gag aaa acc atc tcc aaa gcc aaa ggg cag ccc cga gaa cca      864
Pro Ile Glu Lys Thr Ile Ser Lys Ala Lys Gly Gln Pro Arg Glu Pro
        275                 280                 285 cag gtg tac acc ctg ccc cca tcc cgg gat gag ctg acc aag aac cag      912
Gln Val Tyr Thr Leu Pro Pro Ser Arg Asp Glu Leu Thr Lys Asn Gln
    290                 295                 300 gtc agc ctg acc tgc cta gtc aaa ggc ttc tat ccc agc gac atc gcc      960
Val Ser Leu Thr Cys Leu Val Lys Gly Phe Tyr Pro Ser Asp Ile Ala
305                 310                 315                 320 gtg gag tgg gag agc aat ggg cag ccg gag aac aac tac aag gcc acg     1008
Val Glu Trp Glu Ser Asn Gly Gln Pro Glu Asn Asn Tyr Lys Ala Thr
                325                 330                 335 cct ccc gtg ctg gac tcc gac ggc tcc ttc ttc ctc tac agc aag ctc     1056
Pro Pro Val Leu Asp Ser Asp Gly Ser Phe Phe Leu Tyr Ser Lys Leu
            340                 345                 350 acc gtg gac aag agc agg tgg cag cag ggg aac gtc ttc tca tgc tcc     1104
Thr Val Asp Lys Ser Arg Trp Gln Gln Gly Asn Val Phe Ser Cys Ser
        355                 360                 365 gtg atg cat gag gct ctg cac aac cac tac acg cag aag agc ctc tcc     1152
Val Met His Glu Ala Leu His Asn His Tyr Thr Gln Lys Ser Leu Ser
    370                 375                 380 ctg tct ccg ggt aaa tga                                             1170
Leu Ser Pro Gly Lys
385

<210> SEQ ID NO 28
<211> LENGTH: 389
<212> TYPE: PRT
<213> ORGANISM: Artificial sequence
<220> FEATURE:
<223> OTHER INFORMATION: Synthetic Construct

<400> SEQUENCE: 28

Met Pro Leu Leu Leu Leu Leu Pro Leu Leu Trp Ala Gly Ala Leu Ala
1               5                   10                  15

Met Asp Lys Leu Ala Ser Val Gln Asp Tyr Arg Ser Pro Phe Ile Ala
            20                  25                  30

Ser Val Ser Asp Gln His Gly Val Val Tyr Ile Thr Glu Asn Lys Asn
        35                  40                  45

Lys Thr Val Val Ile Pro Cys Leu Gly Ser Ile Ser Asn Leu Asn Val
    50                  55                  60

Ser Leu Cys Ala Arg Tyr Pro Glu Lys Arg Phe Val Pro Asp Gly Asn
65                  70                  75                  80

Arg Ile Ser Trp Asp Ser Lys Lys Gly Phe Thr Ile Pro Ser Tyr Met
                85                  90                  95

Ile Ser Tyr Ala Gly Met Val Phe Cys Glu Ala Lys Ile Asn Asp Glu
            100                 105                 110

Ser Tyr Gln Ser Ile Met Tyr Ile Val Val Val Val Gly Tyr Arg Ile
```

```
            115                 120                 125
Tyr Asp Val Val Leu Ser Pro Ser His Gly Ile Glu Leu Ser Val Gly
    130                 135                 140

Glu Lys Asp Pro Ile Glu Gly Arg Gly Gly Gly Gly Asp Pro Lys
145                 150                 155                 160

Ser Cys Asp Lys Pro His Thr Cys Pro Leu Cys Pro Ala Pro Glu Leu
                165                 170                 175

Leu Gly Gly Pro Ser Val Phe Leu Phe Pro Pro Lys Pro Lys Asp Thr
            180                 185                 190

Leu Met Ile Ser Arg Thr Pro Glu Val Thr Cys Val Val Val Asp Val
        195                 200                 205

Ser His Glu Asp Pro Glu Val Lys Phe Asn Trp Tyr Val Asp Gly Val
    210                 215                 220

Glu Val His Asn Ala Lys Thr Lys Pro Arg Glu Glu Gln Tyr Asn Ser
225                 230                 235                 240

Thr Tyr Arg Val Val Ser Val Leu Thr Val Leu His Gln Asp Trp Leu
                245                 250                 255

Asn Gly Lys Glu Tyr Lys Cys Lys Val Ser Asn Lys Ala Leu Pro Ala
            260                 265                 270

Pro Ile Glu Lys Thr Ile Ser Lys Ala Lys Gly Gln Pro Arg Glu Pro
        275                 280                 285

Gln Val Tyr Thr Leu Pro Pro Ser Arg Asp Glu Leu Thr Lys Asn Gln
    290                 295                 300

Val Ser Leu Thr Cys Leu Val Lys Gly Phe Tyr Pro Ser Asp Ile Ala
305                 310                 315                 320

Val Glu Trp Glu Ser Asn Gly Gln Pro Glu Asn Asn Tyr Lys Ala Thr
                325                 330                 335

Pro Pro Val Leu Asp Ser Asp Gly Ser Phe Phe Leu Tyr Ser Lys Leu
            340                 345                 350

Thr Val Asp Lys Ser Arg Trp Gln Gln Gly Asn Val Phe Ser Cys Ser
        355                 360                 365

Val Met His Glu Ala Leu His Asn His Tyr Thr Gln Lys Ser Leu Ser
    370                 375                 380

Leu Ser Pro Gly Lys
385

<210> SEQ ID NO 29
<211> LENGTH: 1116
<212> TYPE: DNA
<213> ORGANISM: Artificial sequence
<220> FEATURE:
<223> OTHER INFORMATION: R-2 L
<220> FEATURE:
<221> NAME/KEY: CDS
<222> LOCATION: (1)..(1116)

<400> SEQUENCE: 29 atg ccg ctg ctg cta ctg ctg ccc ctg ctg tgg gca ggg gcc ctg gct    48
Met Pro Leu Leu Leu Leu Leu Pro Leu Leu Trp Ala Gly Ala Leu Ala
1               5                   10                  15 atg gat aag ctt gct agc tat agg att tat gat gtg gtt ctg agt ccg    96
Met Asp Lys Leu Ala Ser Tyr Arg Ile Tyr Asp Val Val Leu Ser Pro
            20                  25                  30 tct cat gga att gaa cta tct gtt gga gaa aag ctt gtc tta aat tgt   144
Ser His Gly Ile Glu Leu Ser Val Gly Glu Lys Leu Val Leu Asn Cys
        35                  40                  45 aca gca aga act gaa cta aat gtg ggg att gac ttc aac tgg gaa tac   192
```

```
Thr Ala Arg Thr Glu Leu Asn Val Gly Ile Asp Phe Asn Trp Glu Tyr
        50                  55                  60 cct tct tcg aag cat cag cat aag aaa ctt gta aac cga gac cta aaa      240
Pro Ser Ser Lys His Gln His Lys Lys Leu Val Asn Arg Asp Leu Lys
 65                  70                  75                  80 acc cag tct ggg agt gag atg aag aaa ttt ttg agc acc tta act ata      288
Thr Gln Ser Gly Ser Glu Met Lys Lys Phe Leu Ser Thr Leu Thr Ile
                     85                  90                  95 gat ggt gta acc cgg agt gac caa gga ttg tac acc tgt gca gca tcc      336
Asp Gly Val Thr Arg Ser Asp Gln Gly Leu Tyr Thr Cys Ala Ala Ser
                100                 105                 110 agt ggg ctg atg acc aag aag aac agc aca ttt gtc agg gtc cat gaa      384
Ser Gly Leu Met Thr Lys Lys Asn Ser Thr Phe Val Arg Val His Glu
            115                 120                 125 gat ccc atc gaa ggt cgt ggt ggt ggt ggt gat ccc aaa tct tgt           432
Asp Pro Ile Glu Gly Arg Gly Gly Gly Gly Asp Pro Lys Ser Cys
        130                 135                 140 gac aaa cct cac aca tgc cca ctg tgc cca gca cct gaa ctc ctg ggg      480
Asp Lys Pro His Thr Cys Pro Leu Cys Pro Ala Pro Glu Leu Leu Gly
145                 150                 155                 160 gga ccg tca gtc ttc ctc ttc ccc cca aaa ccc aag gac acc ctc atg      528
Gly Pro Ser Val Phe Leu Phe Pro Pro Lys Pro Lys Asp Thr Leu Met
                165                 170                 175 atc tcc cgg acc cct gag gtc aca tgc gtg gtg gtg gac gtg agc cac      576
Ile Ser Arg Thr Pro Glu Val Thr Cys Val Val Val Asp Val Ser His
            180                 185                 190 gaa gac cct gag gtc aag ttc aac tgg tac gtg gac ggc gtg gag gtg      624
Glu Asp Pro Glu Val Lys Phe Asn Trp Tyr Val Asp Gly Val Glu Val
        195                 200                 205 cat aat gcc aag aca aag ccg cgg gag gag cag tac aac agc acg tac      672
His Asn Ala Lys Thr Lys Pro Arg Glu Glu Gln Tyr Asn Ser Thr Tyr
210                 215                 220 cgt gtg gtc agc gtc ctc acc gtc ctg cac cag gac tgg ctg aat ggc      720
Arg Val Val Ser Val Leu Thr Val Leu His Gln Asp Trp Leu Asn Gly
225                 230                 235                 240 aag gag tac aag tgc aag gtc tcc aac aaa gcc ctc cca gcc ccc atc      768
Lys Glu Tyr Lys Cys Lys Val Ser Asn Lys Ala Leu Pro Ala Pro Ile
                245                 250                 255 gag aaa acc atc tcc aaa gcc aaa ggg cag ccc cga gaa cca cag gtg      816
Glu Lys Thr Ile Ser Lys Ala Lys Gly Gln Pro Arg Glu Pro Gln Val
            260                 265                 270 tac acc ctg ccc cca tcc cgg gat gag ctg acc aag aac cag gtc agc      864
Tyr Thr Leu Pro Pro Ser Arg Asp Glu Leu Thr Lys Asn Gln Val Ser
        275                 280                 285 ctg acc tgc cta gtc aaa ggc ttc tat ccc agc gac atc gcc gtg gag      912
Leu Thr Cys Leu Val Lys Gly Phe Tyr Pro Ser Asp Ile Ala Val Glu
290                 295                 300 tgg gag agc aat ggg cag ccg gag aac aac tac aag gcc acg cct ccc      960
Trp Glu Ser Asn Gly Gln Pro Glu Asn Asn Tyr Lys Ala Thr Pro Pro
305                 310                 315                 320 gtg ctg gac tcc gac ggc tcc ttc ttc ctc tac agc aag ctc acc gtg     1008
Val Leu Asp Ser Asp Gly Ser Phe Phe Leu Tyr Ser Lys Leu Thr Val
                325                 330                 335 gac aag agc agg tgg cag cag ggg aac gtc ttc tca tgc tcc gtg atg     1056
Asp Lys Ser Arg Trp Gln Gln Gly Asn Val Phe Ser Cys Ser Val Met
            340                 345                 350 cat gag gct ctg cac aac cac tac acg cag aag agc ctc tcc ctg tct     1104
His Glu Ala Leu His Asn His Tyr Thr Gln Lys Ser Leu Ser Leu Ser
        355                 360                 365
```

```
ccg ggt aaa tga                                              1116
Pro Gly Lys
    370
```

<210> SEQ ID NO 30
<211> LENGTH: 371
<212> TYPE: PRT
<213> ORGANISM: Artificial sequence
<220> FEATURE:
<223> OTHER INFORMATION: Synthetic Construct

<400> SEQUENCE: 30

```
Met Pro Leu Leu Leu Leu Pro Leu Leu Trp Ala Gly Ala Leu Ala
1               5                   10                  15

Met Asp Lys Leu Ala Ser Tyr Arg Ile Tyr Asp Val Val Leu Ser Pro
                20                  25                  30

Ser His Gly Ile Glu Leu Ser Val Gly Glu Lys Leu Val Leu Asn Cys
            35                  40                  45

Thr Ala Arg Thr Glu Leu Asn Val Gly Ile Asp Phe Asn Trp Glu Tyr
        50                  55                  60

Pro Ser Ser Lys His Gln His Lys Lys Leu Val Asn Arg Asp Leu Lys
65                  70                  75                  80

Thr Gln Ser Gly Ser Glu Met Lys Lys Phe Leu Ser Thr Leu Thr Ile
                85                  90                  95

Asp Gly Val Thr Arg Ser Asp Gln Gly Leu Tyr Thr Cys Ala Ala Ser
            100                 105                 110

Ser Gly Leu Met Thr Lys Lys Asn Ser Thr Phe Val Arg Val His Glu
        115                 120                 125

Asp Pro Ile Glu Gly Arg Gly Gly Gly Gly Asp Pro Lys Ser Cys
    130                 135                 140

Asp Lys Pro His Thr Cys Pro Leu Cys Pro Ala Pro Glu Leu Leu Gly
145                 150                 155                 160

Gly Pro Ser Val Phe Leu Phe Pro Pro Lys Pro Lys Asp Thr Leu Met
                165                 170                 175

Ile Ser Arg Thr Pro Glu Val Thr Cys Val Val Val Asp Val Ser His
            180                 185                 190

Glu Asp Pro Glu Val Lys Phe Asn Trp Tyr Val Asp Gly Val Glu Val
        195                 200                 205

His Asn Ala Lys Thr Lys Pro Arg Glu Glu Gln Tyr Asn Ser Thr Tyr
    210                 215                 220

Arg Val Val Ser Val Leu Thr Val Leu His Gln Asp Trp Leu Asn Gly
225                 230                 235                 240

Lys Glu Tyr Lys Cys Lys Val Ser Asn Lys Ala Leu Pro Ala Pro Ile
                245                 250                 255

Glu Lys Thr Ile Ser Lys Ala Lys Gly Gln Pro Arg Glu Pro Gln Val
            260                 265                 270

Tyr Thr Leu Pro Pro Ser Arg Asp Glu Leu Thr Lys Asn Gln Val Ser
        275                 280                 285

Leu Thr Cys Leu Val Lys Gly Phe Tyr Pro Ser Asp Ile Ala Val Glu
    290                 295                 300

Trp Glu Ser Asn Gly Gln Pro Glu Asn Tyr Lys Ala Thr Pro Pro
305                 310                 315                 320

Val Leu Asp Ser Asp Gly Ser Phe Phe Leu Tyr Ser Lys Leu Thr Val
                325                 330                 335

Asp Lys Ser Arg Trp Gln Gln Gly Asn Val Phe Ser Cys Ser Val Met
            340                 345                 350
```

His Glu Ala Leu His Asn His Tyr Thr Gln Lys Ser Leu Ser Leu Ser
        355                 360                 365

Pro Gly Lys
    370

<210> SEQ ID NO 31
<211> LENGTH: 1368
<212> TYPE: DNA
<213> ORGANISM: Artificial sequence
<220> FEATURE:
<223> OTHER INFORMATION: R-3 A
<220> FEATURE:
<221> NAME/KEY: CDS
<222> LOCATION: (1)..(1368)

<400> SEQUENCE: 31

```
atg ccg ctg ctg cta ctg ctg ccc ctg ctg tgg gca ggg gcc ctg gct      48
Met Pro Leu Leu Leu Leu Leu Pro Leu Leu Trp Ala Gly Ala Leu Ala
1               5                   10                  15 atg gat aag ctt cca ttc atc aac aag cct gac acg ctc ttg gtc aac      96
Met Asp Lys Leu Pro Phe Ile Asn Lys Pro Asp Thr Leu Leu Val Asn
            20                  25                  30 agg aag gac gcc atg tgg gtg ccc tgt ctg gtg tcc atc ccc ggc ctc     144
Arg Lys Asp Ala Met Trp Val Pro Cys Leu Val Ser Ile Pro Gly Leu
        35                  40                  45 aat gtc acg ctg cgc tcg caa agc tcg gtg ctg tgg cca gac ggg cag     192
Asn Val Thr Leu Arg Ser Gln Ser Ser Val Leu Trp Pro Asp Gly Gln
    50                  55                  60 gag gtg gtg tgg gat gac cgg cgg ggc atg ctc gtg tcc acg cca ctg     240
Glu Val Val Trp Asp Asp Arg Arg Gly Met Leu Val Ser Thr Pro Leu
65                  70                  75                  80 ctg cac gat gcc ctg tac ctg cag tgc gag acc acc tgg gga gac cag     288
Leu His Asp Ala Leu Tyr Leu Gln Cys Glu Thr Thr Trp Gly Asp Gln
                85                  90                  95 gac ttc ctt tcc aac ccc ttc ctg gtg cac atc aca ggc aac gag ctc     336
Asp Phe Leu Ser Asn Pro Phe Leu Val His Ile Thr Gly Asn Glu Leu
            100                 105                 110 tat gac atc cag ctg ttg ccc agg aag tcg ctg gag ctg ctg gta ggg     384
Tyr Asp Ile Gln Leu Leu Pro Arg Lys Ser Leu Glu Leu Leu Val Gly
        115                 120                 125 gag aag ctg gtc ctg aac tgc acc gtg tgg gct gag ttt aac tca ggt     432
Glu Lys Leu Val Leu Asn Cys Thr Val Trp Ala Glu Phe Asn Ser Gly
    130                 135                 140 gtc acc ttt gac tgg gac tac cca ggg aag cag gca gag cgg ggt aag     480
Val Thr Phe Asp Trp Asp Tyr Pro Gly Lys Gln Ala Glu Arg Gly Lys
145                 150                 155                 160 tgg gtg ccc gag cga cgc tcc cag cag acc cac aca gaa ctc tcc agc     528
Trp Val Pro Glu Arg Arg Ser Gln Gln Thr His Thr Glu Leu Ser Ser
                165                 170                 175 atc ctg acc atc cac aac gtc agc cag cac gac ctg ggc tcg tat gtg     576
Ile Leu Thr Ile His Asn Val Ser Gln His Asp Leu Gly Ser Tyr Val
            180                 185                 190 tgc aag gcc aac aac ggc atc cag cga ttt cgg gag agc acc gag gtc     624
Cys Lys Ala Asn Asn Gly Ile Gln Arg Phe Arg Glu Ser Thr Glu Val
        195                 200                 205 att gtg cat gag gat ccc atc gaa ggt cgt ggt ggt ggt ggt ggt gat     672
Ile Val His Glu Asp Pro Ile Glu Gly Arg Gly Gly Gly Gly Gly Asp
    210                 215                 220 ccc aaa tct tgt gac aaa cct cac aca tgc cca ctg tgc cca gca cct     720
Pro Lys Ser Cys Asp Lys Pro His Thr Cys Pro Leu Cys Pro Ala Pro
225                 230                 235                 240
```

```
gaa ctc ctg ggg gga ccg tca gtc ttc ctc ttc ccc cca aaa ccc aag      768
Glu Leu Leu Gly Gly Pro Ser Val Phe Leu Phe Pro Pro Lys Pro Lys
            245                 250                 255 gac acc ctc atg atc tcc cgg acc cct gag gtc aca tgc gtg gtg gtg      816
Asp Thr Leu Met Ile Ser Arg Thr Pro Glu Val Thr Cys Val Val Val
        260                 265                 270 gac gtg agc cac gaa gac cct gag gtc aag ttc aac tgg tac gtg gac      864
Asp Val Ser His Glu Asp Pro Glu Val Lys Phe Asn Trp Tyr Val Asp
    275                 280                 285 ggc gtg gag gtg cat aat gcc aag aca aag ccg cgg gag gag cag tac      912
Gly Val Glu Val His Asn Ala Lys Thr Lys Pro Arg Glu Glu Gln Tyr
290                 295                 300 aac agc acg tac cgt gtg gtc agc gtc ctc acc gtc ctg cac cag gac      960
Asn Ser Thr Tyr Arg Val Val Ser Val Leu Thr Val Leu His Gln Asp
305                 310                 315                 320 tgg ctg aat ggc aag gag tac aag tgc aag gtc tcc aac aaa gcc ctc     1008
Trp Leu Asn Gly Lys Glu Tyr Lys Cys Lys Val Ser Asn Lys Ala Leu
                325                 330                 335 cca gcc ccc atc gag aaa acc atc tcc aaa gcc aaa ggg cag ccc cga     1056
Pro Ala Pro Ile Glu Lys Thr Ile Ser Lys Ala Lys Gly Gln Pro Arg
            340                 345                 350 gaa cca cag gtg tac acc ctg ccc cca tcc cgg gat gag ctg acc aag     1104
Glu Pro Gln Val Tyr Thr Leu Pro Pro Ser Arg Asp Glu Leu Thr Lys
        355                 360                 365 aac cag gtc agc ctg acc tgc cta gtc aaa ggc ttc tat ccc agc gac     1152
Asn Gln Val Ser Leu Thr Cys Leu Val Lys Gly Phe Tyr Pro Ser Asp
    370                 375                 380 atc gcc gtg gag tgg gag agc aat ggg cag ccg gag aac aac tac aag     1200
Ile Ala Val Glu Trp Glu Ser Asn Gly Gln Pro Glu Asn Asn Tyr Lys
385                 390                 395                 400 gcc acg cct ccc gtg ctg gac tcc gac ggc tcc ttc ttc ctc tac agc     1248
Ala Thr Pro Pro Val Leu Asp Ser Asp Gly Ser Phe Phe Leu Tyr Ser
                405                 410                 415 aag ctc acc gtg gac aag agc agg tgg cag cag ggg aac gtc ttc tca     1296
Lys Leu Thr Val Asp Lys Ser Arg Trp Gln Gln Gly Asn Val Phe Ser
            420                 425                 430 tgc tcc gtg atg cat gag gct ctg cac aac cac tac acg cag aag agc     1344
Cys Ser Val Met His Glu Ala Leu His Asn His Tyr Thr Gln Lys Ser
        435                 440                 445 ctc tcc ctg tct ccg ggt aaa tga                                      1368
Leu Ser Leu Ser Pro Gly Lys
    450                 455

<210> SEQ ID NO 32
<211> LENGTH: 455
<212> TYPE: PRT
<213> ORGANISM: Artificial sequence
<220> FEATURE:
<223> OTHER INFORMATION: Synthetic Construct

<400> SEQUENCE: 32

Met Pro Leu Leu Leu Leu Leu Pro Leu Leu Trp Ala Gly Ala Leu Ala
1               5                   10                  15

Met Asp Lys Leu Pro Phe Ile Asn Lys Pro Asp Thr Leu Leu Val Asn
            20                  25                  30

Arg Lys Asp Ala Met Trp Val Pro Cys Leu Val Ser Ile Pro Gly Leu
        35                  40                  45

Asn Val Thr Leu Arg Ser Gln Ser Ser Val Leu Trp Pro Asp Gly Gln
    50                  55                  60
```

```
              Glu Val Val Trp Asp Asp Arg Arg Gly Met Leu Val Ser Thr Pro Leu
              65                  70                  75                  80

Leu His Asp Ala Leu Tyr Leu Gln Cys Glu Thr Thr Trp Gly Asp Gln
                              85                  90                  95

Asp Phe Leu Ser Asn Pro Phe Leu Val His Ile Thr Gly Asn Glu Leu
                          100                 105                 110

Tyr Asp Ile Gln Leu Leu Pro Arg Lys Ser Leu Glu Leu Leu Val Gly
                      115                 120                 125

Glu Lys Leu Val Leu Asn Cys Thr Val Trp Ala Glu Phe Asn Ser Gly
                  130                 135                 140

Val Thr Phe Asp Trp Asp Tyr Pro Gly Lys Gln Ala Glu Arg Gly Lys
              145                 150                 155                 160

Trp Val Pro Glu Arg Arg Ser Gln Gln Thr His Thr Glu Leu Ser Ser
                              165                 170                 175

Ile Leu Thr Ile His Asn Val Ser Gln His Asp Leu Gly Ser Tyr Val
                          180                 185                 190

Cys Lys Ala Asn Asn Gly Ile Gln Arg Phe Arg Glu Ser Thr Glu Val
                      195                 200                 205

Ile Val His Glu Asp Pro Ile Glu Gly Arg Gly Gly Gly Gly Gly Asp
                  210                 215                 220

Pro Lys Ser Cys Asp Lys Pro His Thr Cys Pro Leu Cys Pro Ala Pro
              225                 230                 235                 240

Glu Leu Leu Gly Gly Pro Ser Val Phe Leu Phe Pro Pro Lys Pro Lys
                              245                 250                 255

Asp Thr Leu Met Ile Ser Arg Thr Pro Glu Val Thr Cys Val Val Val
                          260                 265                 270

Asp Val Ser His Glu Asp Pro Glu Val Lys Phe Asn Trp Tyr Val Asp
                      275                 280                 285

Gly Val Glu Val His Asn Ala Lys Thr Lys Pro Arg Glu Glu Gln Tyr
                  290                 295                 300

Asn Ser Thr Tyr Arg Val Val Ser Val Leu Thr Val Leu His Gln Asp
              305                 310                 315                 320

Trp Leu Asn Gly Lys Glu Tyr Lys Cys Lys Val Ser Asn Lys Ala Leu
                              325                 330                 335

Pro Ala Pro Ile Glu Lys Thr Ile Ser Lys Ala Lys Gly Gln Pro Arg
                          340                 345                 350

Glu Pro Gln Val Tyr Thr Leu Pro Pro Ser Arg Asp Glu Leu Thr Lys
                      355                 360                 365

Asn Gln Val Ser Leu Thr Cys Leu Val Lys Gly Phe Tyr Pro Ser Asp
                  370                 375                 380

Ile Ala Val Glu Trp Glu Ser Asn Gly Gln Pro Glu Asn Asn Tyr Lys
              385                 390                 395                 400

Ala Thr Pro Pro Val Leu Asp Ser Asp Gly Ser Phe Phe Leu Tyr Ser
                              405                 410                 415

Lys Leu Thr Val Asp Lys Ser Arg Trp Gln Gln Gly Asn Val Phe Ser
                          420                 425                 430

Cys Ser Val Met His Glu Ala Leu His Asn His Tyr Thr Gln Lys Ser
                      435                 440                 445

Leu Ser Leu Ser Pro Gly Lys
                  450                 455

<210> SEQ ID NO 33
              <211> LENGTH: 1059
              <212> TYPE: DNA
```

```
<213> ORGANISM: Artificial sequence
<220> FEATURE:
<223> OTHER INFORMATION: R-3 B
<220> FEATURE:
<221> NAME/KEY: CDS
<222> LOCATION: (1)..(1059)

<400> SEQUENCE: 33 atg ccg ctg ctg cta ctg ctg ccc ctg ctg tgg gca ggg gcc ctg gct    48
Met Pro Leu Leu Leu Leu Leu Pro Leu Leu Trp Ala Gly Ala Leu Ala
1               5                   10                  15 atg gat aag ctt cca ttc atc aac aag cct gac acg ctc ttg gtc aac    96
Met Asp Lys Leu Pro Phe Ile Asn Lys Pro Asp Thr Leu Leu Val Asn
            20                  25                  30 agg aag gac gcc atg tgg gtg ccc tgt ctg gtg tcc atc ccc ggc ctc   144
Arg Lys Asp Ala Met Trp Val Pro Cys Leu Val Ser Ile Pro Gly Leu
        35                  40                  45 aat gtc acg ctg cgc tcg caa agc tcg gtg ctg tgg cca gac ggg cag   192
Asn Val Thr Leu Arg Ser Gln Ser Ser Val Leu Trp Pro Asp Gly Gln
    50                  55                  60 gag gtg gtg tgg gat gac cgg cgg ggc atg ctc gtg tcc acg cca ctg   240
Glu Val Val Trp Asp Asp Arg Arg Gly Met Leu Val Ser Thr Pro Leu
65                  70                  75                  80 ctg cac gat gcc ctg tac ctg cag tgc gag acc acc tgg gga gac cag   288
Leu His Asp Ala Leu Tyr Leu Gln Cys Glu Thr Thr Trp Gly Asp Gln
                85                  90                  95 gac ttc ctt tcc aac ccc ttc ctg gtg cac atc aca ggg gat ccc atc   336
Asp Phe Leu Ser Asn Pro Phe Leu Val His Ile Thr Gly Asp Pro Ile
            100                 105                 110 gaa ggt cgt ggt ggt ggt ggt ggt gat ccc aaa tct tgt gac aaa cct   384
Glu Gly Arg Gly Gly Gly Gly Gly Asp Pro Lys Ser Cys Asp Lys Pro
        115                 120                 125 cac aca tgc cca ctg tgc cca gca cct gaa ctc ctg ggg gga ccg tca   432
His Thr Cys Pro Leu Cys Pro Ala Pro Glu Leu Leu Gly Gly Pro Ser
    130                 135                 140 gtc ttc ctc ttc ccc cca aaa ccc aag gac acc ctc atg atc tcc cgg   480
Val Phe Leu Phe Pro Pro Lys Pro Lys Asp Thr Leu Met Ile Ser Arg
145                 150                 155                 160 acc cct gag gtc aca tgc gtg gtg gtg gac gtg agc cac gaa gac cct   528
Thr Pro Glu Val Thr Cys Val Val Val Asp Val Ser His Glu Asp Pro
                165                 170                 175 gag gtc aag ttc aac tgg tac gtg gac ggc gtg gag gtg cat aat gcc   576
Glu Val Lys Phe Asn Trp Tyr Val Asp Gly Val Glu Val His Asn Ala
            180                 185                 190 aag aca aag ccg cgg gag gag cag tac aac agc acg tac cgt gtg gtc   624
Lys Thr Lys Pro Arg Glu Glu Gln Tyr Asn Ser Thr Tyr Arg Val Val
        195                 200                 205 agc gtc ctc acc gtc ctg cac cag gac tgg ctg aat ggc aag gag tac   672
Ser Val Leu Thr Val Leu His Gln Asp Trp Leu Asn Gly Lys Glu Tyr
    210                 215                 220 aag tgc aag gtc tcc aac aaa gcc ctc cca gcc ccc atc gag aaa acc   720
Lys Cys Lys Val Ser Asn Lys Ala Leu Pro Ala Pro Ile Glu Lys Thr
225                 230                 235                 240 atc tcc aaa gcc aaa ggg cag ccc cga gaa cca cag gtg tac acc ctg   768
Ile Ser Lys Ala Lys Gly Gln Pro Arg Glu Pro Gln Val Tyr Thr Leu
                245                 250                 255 ccc cca tcc cgg gat gag ctg acc aag aac cag gtc agc ctg acc tgc   816
Pro Pro Ser Arg Asp Glu Leu Thr Lys Asn Gln Val Ser Leu Thr Cys
            260                 265                 270 cta gtc aaa ggc ttc tat ccc agc gac atc gcc gtg gag tgg gag agc   864
Leu Val Lys Gly Phe Tyr Pro Ser Asp Ile Ala Val Glu Trp Glu Ser
```

```
                 275                 280                 285
aat ggg cag ccg gag aac aac tac aag gcc acg cct ccc gtg ctg gac      912
Asn Gly Gln Pro Glu Asn Asn Tyr Lys Ala Thr Pro Pro Val Leu Asp
    290                 295                 300 tcc gac ggc tcc ttc ttc ctc tac agc aag ctc acc gtg gac aag agc      960
Ser Asp Gly Ser Phe Phe Leu Tyr Ser Lys Leu Thr Val Asp Lys Ser
305                 310                 315                 320 agg tgg cag cag ggg aac gtc ttc tca tgc tcc gtg atg cat gag gct     1008
Arg Trp Gln Gln Gly Asn Val Phe Ser Cys Ser Val Met His Glu Ala
                325                 330                 335 ctg cac aac cac tac acg cag aag agc ctc tcc ctg tct ccg ggt aaa     1056
Leu His Asn His Tyr Thr Gln Lys Ser Leu Ser Leu Ser Pro Gly Lys
    340                 345                 350 tga                                                                 1059

<210> SEQ ID NO 34
<211> LENGTH: 352
<212> TYPE: PRT
<213> ORGANISM: Artificial sequence
<220> FEATURE:
<223> OTHER INFORMATION: Synthetic Construct

<400> SEQUENCE: 34

Met Pro Leu Leu Leu Leu Pro Leu Leu Trp Ala Gly Ala Leu Ala
1               5                   10                  15

Met Asp Lys Leu Pro Phe Ile Asn Lys Pro Asp Thr Leu Leu Val Asn
                20                  25                  30

Arg Lys Asp Ala Met Trp Val Pro Cys Leu Val Ser Ile Pro Gly Leu
            35                  40                  45

Asn Val Thr Leu Arg Ser Gln Ser Ser Val Leu Trp Pro Asp Gly Gln
        50                  55                  60

Glu Val Val Trp Asp Asp Arg Arg Gly Met Leu Val Ser Thr Pro Leu
65                  70                  75                  80

Leu His Asp Ala Leu Tyr Leu Gln Cys Glu Thr Thr Trp Gly Asp Gln
                85                  90                  95

Asp Phe Leu Ser Asn Pro Phe Leu Val His Ile Thr Gly Asp Pro Ile
            100                 105                 110

Glu Gly Arg Gly Gly Gly Gly Asp Pro Lys Ser Cys Asp Lys Pro
        115                 120                 125

His Thr Cys Pro Leu Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Asp Glu Leu Thr Lys Asn Gln Val Ser Leu Thr Cys
```

```
                    260                 265                 270
Leu Val Lys Gly Phe Tyr Pro Ser Asp Ile Ala Val Glu Trp Glu Ser
            275                 280                 285

Asn Gly Gln Pro Glu Asn Asn Tyr Lys Ala Thr Pro Pro Val Leu Asp
            290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

<210> SEQ ID NO 35
<211> LENGTH: 1422
<212> TYPE: DNA
<213> ORGANISM: Artificial sequence
<220> FEATURE:
<223> OTHER INFORMATION: R-3 C
<220> FEATURE:
<221> NAME/KEY: CDS
<222> LOCATION: (1)..(1422)

<400> SEQUENCE: 35
```

| | | |
|---|---|---|
| atg cag cgg ggc gcc gcg ctg tgc ctg cga ctg tgg ctc tgc ctg gga<br>Met Gln Arg Gly Ala Ala Leu Cys Leu Arg Leu Trp Leu Cys Leu Gly<br>1                 5                    10                 15 | | 48 |
| ctc ctg gac ggc ctg gtg agt ggc tac tcc atg acc ccc ccg acc ttg<br>Leu Leu Asp Gly Leu Val Ser Gly Tyr Ser Met Thr Pro Pro Thr Leu<br>              20                   25                   30 | | 96 |
| aac atc acg gag gag tca cac gtc atc gac acc ggt gac agc ctg tcc<br>Asn Ile Thr Glu Glu Ser His Val Ile Asp Thr Gly Asp Ser Leu Ser<br>                 35                   40                45 | | 144 |
| atc tcc tgc agg gga cag cac ccc ctc gag tgg gct tgg cca gga gct<br>Ile Ser Cys Arg Gly Gln His Pro Leu Glu Trp Ala Trp Pro Gly Ala<br>           50                   55                   60 | | 192 |
| cag gag gcg cca gcc acc gga gac aag gac agc gag gac acg ggg gtg<br>Gln Glu Ala Pro Ala Thr Gly Asp Lys Asp Ser Glu Asp Thr Gly Val<br>65                 70                   75                  80 | | 240 |
| gtg cga gac tgc gag ggc aca gac gcc agg ccc tac tgc aag gtg ttg<br>Val Arg Asp Cys Glu Gly Thr Asp Ala Arg Pro Tyr Cys Lys Val Leu<br>                   85                   90                95 | | 288 |
| ctg ctg cac gag gta cat gcc aac gac aca ggc agc tac gtc tgc tac<br>Leu Leu His Glu Val His Ala Asn Asp Thr Gly Ser Tyr Val Cys Tyr<br>              100                  105                110 | | 336 |
| tac aag tac atc aag gca cgc atc gag ggc acc acg gcc gcc agc tcc<br>Tyr Lys Tyr Ile Lys Ala Arg Ile Glu Gly Thr Thr Ala Ala Ser Ser<br>           115                  120                125 | | 384 |
| tac gtg ttc gtg aga gac ttt gag cag cca ttc atc aac aag cct gac<br>Tyr Val Phe Val Arg Asp Phe Glu Gln Pro Phe Ile Asn Lys Pro Asp<br>     130                  135                140 | | 432 |
| acg ctc ttg gtc aac agg aag gac gcc atg tgg gtg ccc tgt ctg gtg<br>Thr Leu Leu Val Asn Arg Lys Asp Ala Met Trp Val Pro Cys Leu Val<br>145                150                155               160 | | 480 |
| tcc atc ccc ggc ctc aat gtc acg ctg cgc tcg caa agc tcg gtg ctg<br>Ser Ile Pro Gly Leu Asn Val Thr Leu Arg Ser Gln Ser Ser Val Leu<br>                 165                  170                175 | | 528 |
| tgg cca gac ggg cag gag gtg gtg tgg gat gac cgg ggc atg ctc<br>Trp Pro Asp Gly Gln Glu Val Val Trp Asp Asp Arg Arg Gly Met Leu<br>           180                  185                190 | | 576 |
| gtg tcc acg cca ctg ctg cac gat gcc ctg tac ctg cag tgc gag acc | | 624 |

```
Val Ser Thr Pro Leu Leu His Asp Ala Leu Tyr Leu Gln Cys Glu Thr
        195                 200                 205 acc tgg gga gac cag gac ttc ctt tcc aac ccc ttc ctg gtg cac atc      672
Thr Trp Gly Asp Gln Asp Phe Leu Ser Asn Pro Phe Leu Val His Ile
210                 215                 220 aca ggc aac gag ctc gcg gat ccc atc gaa ggt cgt ggt ggt ggt ggt      720
Thr Gly Asn Glu Leu Ala Asp Pro Ile Glu Gly Arg Gly Gly Gly Gly
225                 230                 235                 240 ggt gat ccc aaa tct tgt gac aaa cct cac aca tgc cca ctg tgc cca      768
Gly Asp Pro Lys Ser Cys Asp Lys Pro His Thr Cys Pro Leu Cys Pro
                245                 250                 255 gca cct gaa ctc ctg ggg gga ccg tca gtc ttc ctc ttc ccc cca aaa      816
Ala Pro Glu Leu Leu Gly Gly Pro Ser Val Phe Leu Phe Pro Pro Lys
            260                 265                 270 ccc aag gac acc ctc atg atc tcc cgg acc cct gag gtc aca tgc gtg      864
Pro Lys Asp Thr Leu Met Ile Ser Arg Thr Pro Glu Val Thr Cys Val
        275                 280                 285 gtg gtg gac gtg agc cac gaa gac cct gag gtc aag ttc aac tgg tac      912
Val Val Asp Val Ser His Glu Asp Pro Glu Val Lys Phe Asn Trp Tyr
290                 295                 300 gtg gac ggc gtg gag gtg cat aat gcc aag aca aag ccg cgg gag gag      960
Val Asp Gly Val Glu Val His Asn Ala Lys Thr Lys Pro Arg Glu Glu
305                 310                 315                 320 cag tac aac agc acg tac cgt gtg gtc agc gtc ctc acc gtc ctg cac     1008
Gln Tyr Asn Ser Thr Tyr Arg Val Val Ser Val Leu Thr Val Leu His
                325                 330                 335 cag gac tgg ctg aat ggc aag gag tac aag tgc aag gtc tcc aac aaa     1056
Gln Asp Trp Leu Asn Gly Lys Glu Tyr Lys Cys Lys Val Ser Asn Lys
            340                 345                 350 gcc ctc cca gcc ccc atc gag aaa acc atc tcc aaa gcc aaa ggg cag     1104
Ala Leu Pro Ala Pro Ile Glu Lys Thr Ile Ser Lys Ala Lys Gly Gln
        355                 360                 365 ccc cga gaa cca cag gtg tac acc ctg ccc cca tcc cgg gat gag ctg     1152
Pro Arg Glu Pro Gln Val Tyr Thr Leu Pro Pro Ser Arg Asp Glu Leu
370                 375                 380 acc aag aac cag gtc agc ctg acc tgc cta gtc aaa ggc ttc tat ccc     1200
Thr Lys Asn Gln Val Ser Leu Thr Cys Leu Val Lys Gly Phe Tyr Pro
385                 390                 395                 400 agc gac atc gcc gtg gag tgg gag agc aat ggg cag ccg gag aac aac     1248
Ser Asp Ile Ala Val Glu Trp Glu Ser Asn Gly Gln Pro Glu Asn Asn
                405                 410                 415 tac aag gcc acg cct ccc gtg ctg gac tcc gac ggc tcc ttc ttc ctc     1296
Tyr Lys Ala Thr Pro Pro Val Leu Asp Ser Asp Gly Ser Phe Phe Leu
            420                 425                 430 tac agc aag ctc acc gtg gac aag agc agg tgg cag cag ggg aac gtc     1344
Tyr Ser Lys Leu Thr Val Asp Lys Ser Arg Trp Gln Gln Gly Asn Val
        435                 440                 445 ttc tca tgc tcc gtg atg cat gag gct ctg cac aac cac tac acg cag     1392
Phe Ser Cys Ser Val Met His Glu Ala Leu His Asn His Tyr Thr Gln
450                 455                 460 aag agc ctc tcc ctg tct ccg ggt aaa tga                             1422
Lys Ser Leu Ser Leu Ser Pro Gly Lys
465                 470

<210> SEQ ID NO 36
<211> LENGTH: 473
<212> TYPE: PRT
<213> ORGANISM: Artificial sequence
<220> FEATURE:
<223> OTHER INFORMATION: Synthetic Construct
```

```
<400> SEQUENCE: 36

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
    210                 215                 220

Thr Gly Asn Glu Leu Ala Asp Pro Ile Glu Gly Arg Gly Gly Gly Gly
225                 230                 235                 240

Gly Asp Pro Lys Ser Cys Asp Lys Pro His Thr Cys Pro Leu Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415
```

```
Tyr Lys Ala Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
        450                 455                 460

Lys Ser Leu Ser Leu Ser Pro Gly Lys
465                 470

<210> SEQ ID NO 37
<211> LENGTH: 1410
<212> TYPE: DNA
<213> ORGANISM: Artificial sequence
<220> FEATURE:
<223> OTHER INFORMATION: R-3 D
<220> FEATURE:
<221> NAME/KEY: CDS
<222> LOCATION: (1)..(1410)

<400> SEQUENCE: 37
```

| | | | | | | | | | | | | | | | | |
|---|---|---|---|---|---|---|---|---|---|---|---|---|---|---|---|---|
| atg | cag | cgg | ggc | gcc | gcg | ctg | tgc | ctg | cga | ctg | tgg | ctc | tgc | ctg | gga | 48 |
| Met | Gln | Arg | Gly | Ala | Ala | Leu | Cys | Leu | Arg | Leu | Trp | Leu | Cys | Leu | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ctc | ctg | gac | ggc | ctg | gtg | agt | ggc | tac | tcc | atg | acc | ccc | ccg | acc | ttg | 96 |
| Leu | Leu | Asp | Gly | Leu | Val | Ser | Gly | Tyr | Ser | Met | Thr | Pro | Pro | Thr | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| aac | atc | acg | gag | gag | tca | cac | gtc | atc | gac | acc | ggt | gac | agc | ctg | tcc | 144 |
| Asn | Ile | Thr | Glu | Glu | Ser | His | Val | Ile | Asp | Thr | Gly | Asp | Ser | Leu | Ser | |
| | | | | 35 | | | | | 40 | | | | | 45 | | |

| | | | | | | | | | | | | | | | | |
|---|---|---|---|---|---|---|---|---|---|---|---|---|---|---|---|---|
| atc | tcc | tgc | agg | gga | cag | cac | ccc | ctc | gag | tgg | gct | tgg | cca | gga | gct | 192 |
| Ile | Ser | Cys | Arg | Gly | Gln | His | Pro | Leu | Glu | Trp | Ala | Trp | Pro | Gly | Ala | |
| | 50 | | | | | 55 | | | | | 60 | | | | | |

| | | | | | | | | | | | | | | | | |
|---|---|---|---|---|---|---|---|---|---|---|---|---|---|---|---|---|
| cag | gag | gcg | cca | gcc | acc | gga | gac | aag | gac | agc | gag | gac | acg | ggg | gtg | 240 |
| Gln | Glu | Ala | Pro | Ala | Thr | Gly | Asp | Lys | Asp | Ser | Glu | Asp | Thr | Gly | Val | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gtg | cga | gac | tgc | gag | ggc | aca | gac | gcc | agg | ccc | tac | tgc | aag | gtg | ttg | 288 |
| Val | Arg | Asp | Cys | Glu | Gly | Thr | Asp | Ala | Arg | Pro | Tyr | Cys | Lys | Val | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| ctg | ctg | cac | gag | gta | cat | gcc | aac | gac | aca | ggc | agc | tac | gtc | tgc | tac | 336 |
| Leu | Leu | His | Glu | Val | His | Ala | Asn | Asp | Thr | Gly | Ser | Tyr | Val | Cys | Tyr | |
| | | | 100 | | | | | 105 | | | | | 110 | | | |

| | | | | | | | | | | | | | | | | |
|---|---|---|---|---|---|---|---|---|---|---|---|---|---|---|---|---|
| tac | aag | tac | atc | aag | gca | cgc | atc | gag | ggc | acc | acg | gcc | gcc | agc | tcc | 384 |
| Tyr | Lys | Tyr | Ile | Lys | Ala | Arg | Ile | Glu | Gly | Thr | Thr | Ala | Ala | Ser | Ser | |
| | | | 115 | | | | | 120 | | | | | 125 | | | |

| | | | | | | | | | | | | | | | | |
|---|---|---|---|---|---|---|---|---|---|---|---|---|---|---|---|---|
| tac | gtg | ttc | gtg | aga | gac | ttt | gag | cag | cca | ttc | atc | aac | aag | cct | gac | 432 |
| Tyr | Val | Phe | Val | Arg | Asp | Phe | Glu | Gln | Pro | Phe | Ile | Asn | Lys | Pro | Asp | |
| | | 130 | | | | | 135 | | | | | 140 | | | | |

| | | | | | | | | | | | | | | | | |
|---|---|---|---|---|---|---|---|---|---|---|---|---|---|---|---|---|
| acg | ctc | ttg | gtc | aac | agg | aag | gac | gcc | atg | tgg | gtg | ccc | tgt | ctg | gtg | 480 |
| Thr | Leu | Leu | Val | Asn | Arg | Lys | Asp | Ala | Met | Trp | Val | Pro | Cys | Leu | Val | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tcc | atc | ccc | ggc | ctc | aat | gtc | acg | ctg | cgc | tcg | caa | agc | tcg | gtg | ctg | 528 |
| Ser | Ile | Pro | Gly | Leu | Asn | Val | Thr | Leu | Arg | Ser | Gln | Ser | Ser | Val | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| tgg | cca | gac | ggg | cag | gag | gtg | gtg | tgg | gat | gac | cgg | cgg | ggc | atg | ctc | 576 |
| Trp | Pro | Asp | Gly | Gln | Glu | Val | Val | Trp | Asp | Asp | Arg | Arg | Gly | Met | Leu | |
| | | | 180 | | | | | 185 | | | | | 190 | | | |

| | | | | | | | | | | | | | | | | |
|---|---|---|---|---|---|---|---|---|---|---|---|---|---|---|---|---|
| gtg | tcc | acg | cca | ctg | ctg | cac | gat | gcc | ctg | tac | ctg | cag | tgc | gag | acc | 624 |
| Val | Ser | Thr | Pro | Leu | Leu | His | Asp | Ala | Leu | Tyr | Leu | Gln | Cys | Glu | Thr | |
| | | | | 195 | | | | | 200 | | | | | 205 | | |

| | | | | | | | | | | | | | | |
|---|---|---|---|---|---|---|---|---|---|---|---|---|---|---|
| acc | tgg | gga | gac | cag | gac | ttc | ctt | tcc | aac | ccc | ttc | ctg | gtg | cac | atc | 672 |

| | | | | | | | | | | | | | | | | |
|---|---|---|---|---|---|---|---|---|---|---|---|---|---|---|---|---|
| Thr | Trp | Gly | Asp | Gln | Asp | Phe | Leu | Ser | Asn | Pro | Phe | Leu | Val | His | Ile | |
| | 210 | | | | 215 | | | | | 220 | | | | | | |

```
aca ggg gat ccc atc gaa ggt cgt ggt ggt ggt ggt gat ccc aaa         720
Thr Gly Asp Pro Ile Glu Gly Arg Gly Gly Gly Gly Asp Pro Lys
225             230                 235                 240 tct tgt gac aaa cct cac aca tgc cca ctg tgc cca gca cct gaa ctc     768
Ser Cys Asp Lys Pro His Thr Cys Pro Leu Cys Pro Ala Pro Glu Leu
                245                 250                 255 ctg ggg gga ccg tca gtc ttc ctc ttc ccc cca aaa ccc aag gac acc     816
Leu Gly Gly Pro Ser Val Phe Leu Phe Pro Pro Lys Pro Lys Asp Thr
        260                 265                 270 ctc atg atc tcc cgg acc cct gag gtc aca tgc gtg gtg gtg gac gtg     864
Leu Met Ile Ser Arg Thr Pro Glu Val Thr Cys Val Val Val Asp Val
    275                 280                 285 agc cac gaa gac cct gag gtc aag ttc aac tgg tac gtg gac ggc gtg     912
Ser His Glu Asp Pro Glu Val Lys Phe Asn Trp Tyr Val Asp Gly Val
290                 295                 300 gag gtg cat aat gcc aag aca aag ccg cgg gag gag cag tac aac agc     960
Glu Val His Asn Ala Lys Thr Lys Pro Arg Glu Glu Gln Tyr Asn Ser
305                 310                 315                 320 acg tac cgt gtg gtc agc gtc ctc acc gtc ctg cac cag gac tgg ctg    1008
Thr Tyr Arg Val Val Ser Val Leu Thr Val Leu His Gln Asp Trp Leu
                325                 330                 335 aat ggc aag gag tac aag tgc aag gtc tcc aac aaa gcc ctc cca gcc    1056
Asn Gly Lys Glu Tyr Lys Cys Lys Val Ser Asn Lys Ala Leu Pro Ala
            340                 345                 350 ccc atc gag aaa acc atc tcc aaa gcc aaa ggg cag ccc cga gaa cca    1104
Pro Ile Glu Lys Thr Ile Ser Lys Ala Lys Gly Gln Pro Arg Glu Pro
        355                 360                 365 cag gtg tac acc ctg ccc cca tcc cgg gat gag ctg acc aag aac cag    1152
Gln Val Tyr Thr Leu Pro Pro Ser Arg Asp Glu Leu Thr Lys Asn Gln
370                 375                 380 gtc agc ctg acc tgc cta gtc aaa ggc ttc tat ccc agc gac atc gcc    1200
Val Ser Leu Thr Cys Leu Val Lys Gly Phe Tyr Pro Ser Asp Ile Ala
385                 390                 395                 400 gtg gag tgg gag agc aat ggg cag ccg gag aac aac tac aag gcc acg    1248
Val Glu Trp Glu Ser Asn Gly Gln Pro Glu Asn Asn Tyr Lys Ala Thr
                405                 410                 415 cct ccc gtg ctg gac tcc gac ggc tcc ttc ttc ctc tac agc aag ctc    1296
Pro Pro Val Leu Asp Ser Asp Gly Ser Phe Phe Leu Tyr Ser Lys Leu
            420                 425                 430 acc gtg gac aag agc agg tgg cag cag ggg aac gtc ttc tca tgc tcc    1344
Thr Val Asp Lys Ser Arg Trp Gln Gln Gly Asn Val Phe Ser Cys Ser
        435                 440                 445 gtg atg cat gag gct ctg cac aac cac tac acg cag aag agc ctc tcc    1392
Val Met His Glu Ala Leu His Asn His Tyr Thr Gln Lys Ser Leu Ser
450                 455                 460 ctg tct ccg ggt aaa tga                                            1410
Leu Ser Pro Gly Lys
465
```

<210> SEQ ID NO 38
<211> LENGTH: 469
<212> TYPE: PRT
<213> ORGANISM: Artificial sequence
<220> FEATURE:
<223> OTHER INFORMATION: Synthetic Construct

<400> SEQUENCE: 38

Met Gln Arg Gly Ala Ala Leu Cys Leu Arg Leu Trp Leu Cys Leu Gly
1               5                   10                  15

```
Leu Leu Asp Gly Leu Val Ser Gly Tyr Ser Met Thr Pro Thr Leu
            20                  25              30
Asn Ile Thr Glu Glu Ser His Val Ile Asp Thr Gly Asp Ser Leu Ser
        35                  40                  45
Ile Ser Cys Arg Gly Gln His Pro Leu Glu Trp Ala Trp Pro Gly Ala
    50                  55                  60
Gln Glu Ala Pro Ala Thr Gly Asp Lys Asp Ser Glu Asp Thr Gly Val
65                  70                  75                  80
Val Arg Asp Cys Glu Gly Thr Asp Ala Arg Pro Tyr Cys Lys Val Leu
                85                  90                  95
Leu Leu His Glu Val His Ala Asn Asp Thr Gly Ser Tyr Val Cys Tyr
            100                 105                 110
Tyr Lys Tyr Ile Lys Ala Arg Ile Glu Gly Thr Thr Ala Ala Ser Ser
        115                 120                 125
Tyr Val Phe Val Arg Asp Phe Glu Gln Pro Phe Ile Asn Lys Pro Asp
130                 135                 140
Thr Leu Leu Val Asn Arg Lys Asp Ala Met Trp Val Pro Cys Leu Val
145                 150                 155                 160
Ser Ile Pro Gly Leu Asn Val Thr Leu Arg Ser Gln Ser Ser Val Leu
                165                 170                 175
Trp Pro Asp Gly Gln Glu Val Val Trp Asp Asp Arg Arg Gly Met Leu
            180                 185                 190
Val Ser Thr Pro Leu Leu His Asp Ala Leu Tyr Leu Gln Cys Glu Thr
        195                 200                 205
Thr Trp Gly Asp Gln Asp Phe Leu Ser Asn Pro Phe Leu Val His Ile
210                 215                 220
Thr Gly Asp Pro Ile Glu Gly Arg Gly Gly Gly Gly Asp Pro Lys
225                 230                 235                 240
Ser Cys Asp Lys Pro His Thr Cys Pro Leu Cys Pro Ala Pro Glu Leu
                245                 250                 255
Leu Gly Gly Pro Ser Val Phe Leu Phe Pro Pro Lys Pro Lys Asp Thr
            260                 265                 270
Leu Met Ile Ser Arg Thr Pro Glu Val Thr Cys Val Val Val Asp Val
        275                 280                 285
Ser His Glu Asp Pro Glu Val Lys Phe Asn Trp Tyr Val Asp Gly Val
290                 295                 300
Glu Val His Asn Ala Lys Thr Lys Pro Arg Glu Glu Gln Tyr Asn Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
            340                 345                 350
Pro Ile Glu Lys Thr Ile Ser Lys Ala Lys Gly Gln Pro Arg Glu Pro
        355                 360                 365
Gln Val Tyr Thr Leu Pro Pro Ser Arg Asp Glu Leu Thr Lys Asn Gln
370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Ala Thr
                405                 410                 415
Pro Pro Val Leu Asp Ser Asp Gly Ser Phe Phe Leu Tyr Ser Lys Leu
            420                 425                 430
```

```
Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
    450                 455                 460

Leu Ser Pro Gly Lys
465

<210> SEQ ID NO 39
<211> LENGTH: 1404
<212> TYPE: DNA
<213> ORGANISM: Artificial sequence
<220> FEATURE:
<223> OTHER INFORMATION: R-3 E
<220> FEATURE:
<221> NAME/KEY: CDS
<222> LOCATION: (1)..(1404)

<400> SEQUENCE: 39 atg cag cgg ggc gcc gcg ctg tgc ctg cga ctg tgg ctc tgc ctg gga     48
Met Gln Arg Gly Ala Ala Leu Cys Leu Arg Leu Trp Leu Cys Leu Gly
1               5                   10                  15 ctc ctg gac ggc ctg gtg agt ggc tac tcc atg acc ccg acc ttg          96
Leu Leu Asp Gly Leu Val Ser Gly Tyr Ser Met Thr Pro Thr Leu
            20                  25                  30 aac atc acg gag gag tca cac gtc atc gac acc ggt gac agc ctg tcc    144
Asn Ile Thr Glu Glu Ser His Val Ile Asp Thr Gly Asp Ser Leu Ser
        35                  40                  45 atc tcc tgc agg gga cag cac ccc ctc gag tgg gct tgg cca gga gct    192
Ile Ser Cys Arg Gly Gln His Pro Leu Glu Trp Ala Trp Pro Gly Ala
    50                  55                  60 cag gag gcg cca gcc acc gga gac aag gac agc gag gac acg ggg gtg    240
Gln Glu Ala Pro Ala Thr Gly Asp Lys Asp Ser Glu Asp Thr Gly Val
65                  70                  75                  80 gtg cga gac tgc gag ggc aca gac gcc agg ccc tac tgc aag gtg ttg    288
Val Arg Asp Cys Glu Gly Thr Asp Ala Arg Pro Tyr Cys Lys Val Leu
                85                  90                  95 ctg ctg cac gag gta cat gcc aac gac aca ggc agc tac gtc tgc tac    336
Leu Leu His Glu Val His Ala Asn Asp Thr Gly Ser Tyr Val Cys Tyr
            100                 105                 110 tac aag tac atc aag gca cgc atc gag ggc acc acg gcc gcc agc tcc    384
Tyr Lys Tyr Ile Lys Ala Arg Ile Glu Gly Thr Thr Ala Ala Ser Ser
        115                 120                 125 tac gtg ttc gtg aga gac ttt gag cag cca ttc atc aac aag cct gac    432
Tyr Val Phe Val Arg Asp Phe Glu Gln Pro Phe Ile Asn Lys Pro Asp
    130                 135                 140 acg ctc ttg gtc aac agg aag gac gcc atg tgg gtg ccc tgt ctg gtg    480
Thr Leu Leu Val Asn Arg Lys Asp Ala Met Trp Val Pro Cys Leu Val
145                 150                 155                 160 tcc atc ccc ggc ctc aat gtc acg ctg cgc tcg caa agc tcg gtg ctg    528
Ser Ile Pro Gly Leu Asn Val Thr Leu Arg Ser Gln Ser Ser Val Leu
                165                 170                 175 tgg cca gac ggg cag gag gtg gtg tgg gat gac cgg cgg ggc atg ctc    576
Trp Pro Asp Gly Gln Glu Val Val Trp Asp Asp Arg Arg Gly Met Leu
            180                 185                 190 gtg tcc acg cca ctg ctg cac gat gcc ctg tac ctg cag tgc gag acc    624
Val Ser Thr Pro Leu Leu His Asp Ala Leu Tyr Leu Gln Cys Glu Thr
        195                 200                 205 acc tgg gga gac cag gac ttc ctt tcc aac ccc ttc ctg gtg cac gcg    672
Thr Trp Gly Asp Gln Asp Phe Leu Ser Asn Pro Phe Leu Val His Ala
    210                 215                 220 gat ccc atc gaa ggt cgt ggt ggt ggt ggt ggt gat ccc aaa tct tgt    720
```

```
Asp Pro Ile Glu Gly Arg Gly Gly Gly Asp Pro Lys Ser Cys
225                 230                 235                 240 gac aaa cct cac aca tgc cca ctg tgc cca gca cct gaa ctc ctg ggg    768
Asp Lys Pro His Thr Cys Pro Leu Cys Pro Ala Pro Glu Leu Leu Gly
            245                 250                 255 gga ccg tca gtc ttc ctc ttc ccc cca aaa ccc aag gac acc ctc atg    816
Gly Pro Ser Val Phe Leu Phe Pro Pro Lys Pro Lys Asp Thr Leu Met
        260                 265                 270 atc tcc cgg acc cct gag gtc aca tgc gtg gtg gtg gac gtg agc cac    864
Ile Ser Arg Thr Pro Glu Val Thr Cys Val Val Val Asp Val Ser His
            275                 280                 285 gaa gac cct gag gtc aag ttc aac tgg tac gtg gac ggc gtg gag gtg    912
Glu Asp Pro Glu Val Lys Phe Asn Trp Tyr Val Asp Gly Val Glu Val
        290                 295                 300 cat aat gcc aag aca aag ccg cgg gag gag cag tac aac agc acg tac    960
His Asn Ala Lys Thr Lys Pro Arg Glu Glu Gln Tyr Asn Ser Thr Tyr
305                 310                 315                 320 cgt gtg gtc agc gtc ctc acc gtc ctg cac cag gac tgg ctg aat ggc   1008
Arg Val Val Ser Val Leu Thr Val Leu His Gln Asp Trp Leu Asn Gly
            325                 330                 335 aag gag tac aag tgc aag gtc tcc aac aaa gcc ctc cca gcc ccc atc   1056
Lys Glu Tyr Lys Cys Lys Val Ser Asn Lys Ala Leu Pro Ala Pro Ile
        340                 345                 350 gag aaa acc atc tcc aaa gcc aaa ggg cag ccc cga gaa cca cag gtg   1104
Glu Lys Thr Ile Ser Lys Ala Lys Gly Gln Pro Arg Glu Pro Gln Val
            355                 360                 365 tac acc ctg ccc cca tcc cgg gat gag ctg acc aag aac cag gtc agc   1152
Tyr Thr Leu Pro Pro Ser Arg Asp Glu Leu Thr Lys Asn Gln Val Ser
370                 375                 380 ctg acc tgc cta gtc aaa ggc ttc tat ccc agc gac atc gcc gtg gag   1200
Leu Thr Cys Leu Val Lys Gly Phe Tyr Pro Ser Asp Ile Ala Val Glu
385                 390                 395                 400 tgg gag agc aat ggg cag ccg gag aac aac tac aag gcc acg cct ccc   1248
Trp Glu Ser Asn Gly Gln Pro Glu Asn Asn Tyr Lys Ala Thr Pro Pro
            405                 410                 415 gtg ctg gac tcc gac ggc tcc ttc ttc ctc tac agc aag ctc acc gtg   1296
Val Leu Asp Ser Asp Gly Ser Phe Phe Leu Tyr Ser Lys Leu Thr Val
        420                 425                 430 gac aag agc agg tgg cag cag ggg aac gtc ttc tca tgc tcc gtg atg   1344
Asp Lys Ser Arg Trp Gln Gln Gly Asn Val Phe Ser Cys Ser Val Met
            435                 440                 445 cat gag gct ctg cac aac cac tac acg cag aag agc ctc tcc ctg tct   1392
His Glu Ala Leu His Asn His Tyr Thr Gln Lys Ser Leu Ser Leu Ser
450                 455                 460 ccg ggt aaa tga                                                    1404
Pro Gly Lys
465
```

<210> SEQ ID NO 40
<211> LENGTH: 467
<212> TYPE: PRT
<213> ORGANISM: Artificial sequence
<220> FEATURE:
<223> OTHER INFORMATION: Synthetic Construct

<400> SEQUENCE: 40

```
Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30
```

-continued

Asn Ile Thr Glu Glu Ser His Val Ile Asp Thr Gly Asp Ser Leu Ser
          35                  40                  45

Ile Ser Cys Arg Gly Gln His Pro Leu Glu Trp Ala Trp Pro Gly Ala
 50                  55                  60

Gln Glu Ala Pro Ala Thr Gly Asp Lys Asp Ser Glu Asp Thr Gly Val
 65                  70                  75                  80

Val Arg Asp Cys Glu Gly Thr Asp Ala Arg Pro Tyr Cys Lys Val Leu
              85                  90                  95

Leu Leu His Glu Val His Ala Asn Asp Thr Gly Ser Tyr Val Cys Tyr
             100                 105                 110

Tyr Lys Tyr Ile Lys Ala Arg Ile Glu Gly Thr Thr Ala Ala Ser Ser
         115                 120                 125

Tyr Val Phe Val Arg Asp Phe Glu Gln Pro Phe Ile Asn Lys Pro Asp
 130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
             165                 170                 175

Trp Pro Asp Gly Gln Glu Val Val Trp Asp Asp Arg Arg Gly Met Leu
         180                 185                 190

Val Ser Thr Pro Leu Leu His Asp Ala Leu Tyr Leu Gln Cys Glu Thr
 195                 200                 205

Thr Trp Gly Asp Gln Asp Phe Leu Ser Asn Pro Phe Leu Val His Ala
210                 215                 220

Asp Pro Ile Glu Gly Arg Gly Gly Gly Asp Pro Lys Ser Cys
225                 230                 235                 240

Asp Lys Pro His Thr Cys Pro Leu Cys Pro Ala Pro Glu Leu Leu Gly
             245                 250                 255

Gly Pro Ser Val Phe Leu Phe Pro Pro Lys Pro Lys Asp Thr Leu Met
         260                 265                 270

Ile Ser Arg Thr Pro Glu Val Thr Cys Val Val Val Asp Val Ser His
         275                 280                 285

Glu Asp Pro Glu Val Lys Phe Asn Trp Tyr Val Asp Gly Val Glu Val
 290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
             325                 330                 335

Lys Glu Tyr Lys Cys Lys Val Ser Asn Lys Ala Leu Pro Ala Pro Ile
         340                 345                 350

Glu Lys Thr Ile Ser Lys Ala Lys Gly Gln Pro Arg Glu Pro Gln Val
         355                 360                 365

Tyr Thr Leu Pro Pro Ser Arg Asp Glu Leu Thr Lys Asn Gln Val Ser
 370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Ala Thr Pro Pro
             405                 410                 415

Val Leu Asp Ser Asp Gly Ser Phe Phe Leu Tyr Ser Lys Leu Thr Val
         420                 425                 430

Asp Lys Ser Arg Trp Gln Gln Gly Asn Val Phe Ser Cys Ser Val Met
         435                 440                 445

His Glu Ala Leu His Asn His Tyr Thr Gln Lys Ser Leu Ser Leu Ser

<210> SEQ ID NO 41
<211> LENGTH: 1395
<212> TYPE: DNA
<213> ORGANISM: Artificial sequence
<220> FEATURE:
<223> OTHER INFORMATION: R-3 F
<220> FEATURE:
<221> NAME/KEY: CDS
<222> LOCATION: (1)..(1395)

<400> SEQUENCE: 41

```
atg cag cgg ggc gcc gcg ctg tgc ctg cga ctg tgg ctc tgc ctg gga       48
Met Gln Arg Gly Ala Ala Leu Cys Leu Arg Leu Trp Leu Cys Leu Gly
1               5                   10                  15 ctc ctg gac ggc ctg gtg agt ggc tac tcc atg acc ccc ccg acc ttg       96
Leu Leu Asp Gly Leu Val Ser Gly Tyr Ser Met Thr Pro Pro Thr Leu
            20                  25                  30 aac atc acg gag gag tca cac gtc atc gac acc ggt gac agc ctg tcc      144
Asn Ile Thr Glu Glu Ser His Val Ile Asp Thr Gly Asp Ser Leu Ser
        35                  40                  45 atc tcc tgc agg gga cag cac ccc ctc gag tgg gct tgg cca gga gct      192
Ile Ser Cys Arg Gly Gln His Pro Leu Glu Trp Ala Trp Pro Gly Ala
    50                  55                  60 cag gag gcg cca gcc acc gga gac aag gac agc gag gac acg ggg gtg      240
Gln Glu Ala Pro Ala Thr Gly Asp Lys Asp Ser Glu Asp Thr Gly Val
65                  70                  75                  80 gtg cga gac tgc gag ggc aca gac gcc agg ccc tac tgc aag gtg ttg      288
Val Arg Asp Cys Glu Gly Thr Asp Ala Arg Pro Tyr Cys Lys Val Leu
                85                  90                  95 ctg ctg cac gag gta cat gcc aac gac aca ggc agc tac gtc tgc tac      336
Leu Leu His Glu Val His Ala Asn Asp Thr Gly Ser Tyr Val Cys Tyr
            100                 105                 110 tac aag tac atc aag gca cgc atc gag ggc acc acg gcc gcc agc tcc      384
Tyr Lys Tyr Ile Lys Ala Arg Ile Glu Gly Thr Thr Ala Ala Ser Ser
        115                 120                 125 tac gtg ttc gtg aga gac ttt gag cag cca ttc atc aac aag cct gac      432
Tyr Val Phe Val Arg Asp Phe Glu Gln Pro Phe Ile Asn Lys Pro Asp
    130                 135                 140 acg ctc ttg gtc aac agg aag gac gcc atg tgg gtg ccc tgt ctg gtg      480
Thr Leu Leu Val Asn Arg Lys Asp Ala Met Trp Val Pro Cys Leu Val
145                 150                 155                 160 tcc atc ccc ggc ctc aat gtc acg ctg cgc tcg caa agc tcg gtg ctg      528
Ser Ile Pro Gly Leu Asn Val Thr Leu Arg Ser Gln Ser Ser Val Leu
                165                 170                 175 tgg cca gac ggg cag gag gtg gtg tgg gat gac cgg cgg ggc atg ctc      576
Trp Pro Asp Gly Gln Glu Val Val Trp Asp Asp Arg Arg Gly Met Leu
            180                 185                 190 gtg tcc acg cca ctg ctg cac gat gcc ctg tac ctg cag tgc gag acc      624
Val Ser Thr Pro Leu Leu His Asp Ala Leu Tyr Leu Gln Cys Glu Thr
        195                 200                 205 acc tgg gga gac cag gac ttc ctt tcc aac ccc ttc gcg gat ccc atc      672
Thr Trp Gly Asp Gln Asp Phe Leu Ser Asn Pro Phe Ala Asp Pro Ile
    210                 215                 220 gaa ggt cgt ggt ggt ggt ggt ggt gat ccc aaa tct tgt gac aaa cct      720
Glu Gly Arg Gly Gly Gly Gly Gly Asp Pro Lys Ser Cys Asp Lys Pro
225                 230                 235                 240 cac aca tgc cca ctg tgc cca gca cct gaa ctc ctg ggg gga ccg tca      768
```

```
His Thr Cys Pro Leu Cys Pro Ala Pro Glu Leu Leu Gly Gly Pro Ser
                245                 250                 255 gtc ttc ctc ttc ccc cca aaa ccc aag gac acc ctc atg atc tcc cgg      816
Val Phe Leu Phe Pro Pro Lys Pro Lys Asp Thr Leu Met Ile Ser Arg
            260                 265                 270 acc cct gag gtc aca tgc gtg gtg gtg gac gtg agc cac gaa gac cct      864
Thr Pro Glu Val Thr Cys Val Val Val Asp Val Ser His Glu Asp Pro
        275                 280                 285 gag gtc aag ttc aac tgg tac gtg gac ggc gtg gag gtg cat aat gcc      912
Glu Val Lys Phe Asn Trp Tyr Val Asp Gly Val Glu Val His Asn Ala
    290                 295                 300 aag aca aag ccg cgg gag gag cag tac aac agc acg tac cgt gtg gtc      960
Lys Thr Lys Pro Arg Glu Glu Gln Tyr Asn Ser Thr Tyr Arg Val Val
305                 310                 315                 320 agc gtc ctc acc gtc ctg cac cag gac tgg ctg aat ggc aag gag tac     1008
Ser Val Leu Thr Val Leu His Gln Asp Trp Leu Asn Gly Lys Glu Tyr
                325                 330                 335 aag tgc aag gtc tcc aac aaa gcc ctc cca gcc ccc atc gag aaa acc     1056
Lys Cys Lys Val Ser Asn Lys Ala Leu Pro Ala Pro Ile Glu Lys Thr
            340                 345                 350 atc tcc aaa gcc aaa ggg cag ccc cga gaa cca cag gtg tac acc ctg     1104
Ile Ser Lys Ala Lys Gly Gln Pro Arg Glu Pro Gln Val Tyr Thr Leu
        355                 360                 365 ccc cca tcc cgg gat gag ctg acc aag aac cag gtc agc ctg acc tgc     1152
Pro Pro Ser Arg Asp Glu Leu Thr Lys Asn Gln Val Ser Leu Thr Cys
    370                 375                 380 cta gtc aaa ggc ttc tat ccc agc gac atc gcc gtg gag tgg gag agc     1200
Leu Val Lys Gly Phe Tyr Pro Ser Asp Ile Ala Val Glu Trp Glu Ser
385                 390                 395                 400 aat ggg cag ccg gag aac aac tac aag gcc acg cct ccc gtg ctg gac     1248
Asn Gly Gln Pro Glu Asn Asn Tyr Lys Ala Thr Pro Pro Val Leu Asp
                405                 410                 415 tcc gac ggc tcc ttc ttc ctc tac agc aag ctc acc gtg gac aag agc     1296
Ser Asp Gly Ser Phe Phe Leu Tyr Ser Lys Leu Thr Val Asp Lys Ser
            420                 425                 430 agg tgg cag cag ggg aac gtc ttc tca tgc tcc gtg atg cat gag gct     1344
Arg Trp Gln Gln Gly Asn Val Phe Ser Cys Ser Val Met His Glu Ala
        435                 440                 445 ctg cac aac cac tac acg cag aag agc ctc tcc ctg tct ccg ggt aaa     1392
Leu His Asn His Tyr Thr Gln Lys Ser Leu Ser Leu Ser Pro Gly Lys
    450                 455                 460 tga                                                                  1395

<210> SEQ ID NO 42
<211> LENGTH: 464
<212> TYPE: PRT
<213> ORGANISM: Artificial sequence
<220> FEATURE:
<223> OTHER INFORMATION: Synthetic Construct

<400> SEQUENCE: 42

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
    50                  55                  60
```

```
Gln Glu Ala Pro Ala Thr Gly Asp Lys Asp Ser Glu Asp Thr Gly Val
 65                  70                  75                  80

Val Arg Asp Cys Glu Gly Thr Asp Ala Arg Pro Tyr Cys Lys Val Leu
                 85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Ala Asp Pro Ile
    210                 215                 220

Glu Gly Arg Gly Gly Gly Gly Asp Pro Lys Ser Cys Asp Lys Pro
225                 230                 235                 240

His Thr Cys Pro Leu Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Ala Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 43
<211> LENGTH: 1719
<212> TYPE: DNA
```

<213> ORGANISM: Artificial sequence
<220> FEATURE:
<223> OTHER INFORMATION: R-3 G
<220> FEATURE:
<221> NAME/KEY: CDS
<222> LOCATION: (1)..(1719)

<400> SEQUENCE: 43

```
atg cag cgg ggc gcc gcg ctg tgc ctg cga ctg tgg ctc tgc ctg gga      48
Met Gln Arg Gly Ala Ala Leu Cys Leu Arg Leu Trp Leu Cys Leu Gly
1               5                   10                  15 ctc ctg gac ggc ctg gtg agt ggc tac tcc atg acc ccg acc ttg          96
Leu Leu Asp Gly Leu Val Ser Gly Tyr Ser Met Thr Pro Thr Leu
            20                  25                  30 aac atc acg gag gag tca cac gtc atc gac acc ggt gac agc ctg tcc     144
Asn Ile Thr Glu Glu Ser His Val Ile Asp Thr Gly Asp Ser Leu Ser
        35                  40                  45 atc tcc tgc agg gga cag cac ccc ctc gag tgg gct tgg cca gga gct     192
Ile Ser Cys Arg Gly Gln His Pro Leu Glu Trp Ala Trp Pro Gly Ala
    50                  55                  60 cag gag gcg cca gcc acc gga gac aag gac agc gag gac acg ggg gtg     240
Gln Glu Ala Pro Ala Thr Gly Asp Lys Asp Ser Glu Asp Thr Gly Val
65                  70                  75                  80 gtg cga gac tgc gag ggc aca gac gcc agg ccc tac tgc aag gtg ttg     288
Val Arg Asp Cys Glu Gly Thr Asp Ala Arg Pro Tyr Cys Lys Val Leu
                85                  90                  95 ctg ctg cac gag gta cat gcc aac gac aca ggc agc tac gtc tgc tac     336
Leu Leu His Glu Val His Ala Asn Asp Thr Gly Ser Tyr Val Cys Tyr
            100                 105                 110 tac aag tac atc aag gca cgc atc gag ggc acc acg gcc gcc agc tcc     384
Tyr Lys Tyr Ile Lys Ala Arg Ile Glu Gly Thr Thr Ala Ala Ser Ser
        115                 120                 125 tac gtg ttc gtg aga gac ttt gag cag cca ttc atc aac aag cct gac     432
Tyr Val Phe Val Arg Asp Phe Glu Gln Pro Phe Ile Asn Lys Pro Asp
    130                 135                 140 acg ctc ttg gtc aac agg aag gac gcc atg tgg gtg ccc tgt ctg gtg     480
Thr Leu Leu Val Asn Arg Lys Asp Ala Met Trp Val Pro Cys Leu Val
145                 150                 155                 160 tcc atc ccc ggc ctc aat gtc acg ctg cgc tcg caa agc tcg gtg ctg     528
Ser Ile Pro Gly Leu Asn Val Thr Leu Arg Ser Gln Ser Ser Val Leu
                165                 170                 175 tgg cca gac ggg cag gag gtg gtg tgg gat gac cgg cgg ggc atg ctc     576
Trp Pro Asp Gly Gln Glu Val Val Trp Asp Asp Arg Arg Gly Met Leu
            180                 185                 190 gtg tcc acg cca ctg ctg cac gat gcc ctg tac ctg cag tgc gag acc     624
Val Ser Thr Pro Leu Leu His Asp Ala Leu Tyr Leu Gln Cys Glu Thr
        195                 200                 205 acc tgg gga gac cag gac ttc ctt tcc aac ccc ttc ctg gtg cac atc     672
Thr Trp Gly Asp Gln Asp Phe Leu Ser Asn Pro Phe Leu Val His Ile
    210                 215                 220 aca ggc aac gag ctc tat gac atc cag ctg ttg ccc agg aag tcg ctg     720
Thr Gly Asn Glu Leu Tyr Asp Ile Gln Leu Leu Pro Arg Lys Ser Leu
225                 230                 235                 240 gag ctg ctg gta ggg gag aag ctg gtc ctg aac tgc acc gtg tgg gct     768
Glu Leu Leu Val Gly Glu Lys Leu Val Leu Asn Cys Thr Val Trp Ala
                245                 250                 255 gag ttt aac tca ggt gtc acc ttt gac tgg gac tac cca ggg aag cag     816
Glu Phe Asn Ser Gly Val Thr Phe Asp Trp Asp Tyr Pro Gly Lys Gln
            260                 265                 270 gca gag cgg ggt aag tgg gtg ccc gag cga cgc tcc cag cag acc cac     864
Ala Glu Arg Gly Lys Trp Val Pro Glu Arg Arg Ser Gln Gln Thr His
```

```
                275                 280                 285
aca gaa ctc tcc agc atc ctg acc atc cac aac gtc agc cag cac gac        912
Thr Glu Leu Ser Ser Ile Leu Thr Ile His Asn Val Ser Gln His Asp
    290                 295                 300 ctg ggc tcg tat gtg tgc aag gcc aac aac ggc atc cag cga ttt cgg        960
Leu Gly Ser Tyr Val Cys Lys Ala Asn Asn Gly Ile Gln Arg Phe Arg
305                 310                 315                 320 gag agc acc gag gtc att gtg cat gag gat ccc atc gaa ggt cgt ggt       1008
Glu Ser Thr Glu Val Ile Val His Glu Asp Pro Ile Glu Gly Arg Gly
                325                 330                 335 ggt ggt ggt ggt gat ccc aaa tct tgt gac aaa cct cac aca tgc cca       1056
Gly Gly Gly Gly Asp Pro Lys Ser Cys Asp Lys Pro His Thr Cys Pro
            340                 345                 350 ctg tgc cca gca cct gaa ctc ctg ggg gga ccg tca gtc ttc ctc ttc       1104
Leu Cys Pro Ala Pro Glu Leu Leu Gly Gly Pro Ser Val Phe Leu Phe
        355                 360                 365 ccc cca aaa ccc aag gac acc ctc atg atc tcc cgg acc cct gag gtc       1152
Pro Pro Lys Pro Lys Asp Thr Leu Met Ile Ser Arg Thr Pro Glu Val
370                 375                 380 aca tgc gtg gtg gtg gac gtg agc cac gaa gac cct gag gtc aag ttc       1200
Thr Cys Val Val Val Asp Val Ser His Glu Asp Pro Glu Val Lys Phe
385                 390                 395                 400 aac tgg tac gtg gac ggc gtg gag gtg cat aat gcc aag aca aag ccg       1248
Asn Trp Tyr Val Asp Gly Val Glu Val His Asn Ala Lys Thr Lys Pro
                405                 410                 415 cgg gag gag cag tac aac agc acg tac cgt gtg gtc agc gtc ctc acc       1296
Arg Glu Glu Gln Tyr Asn Ser Thr Tyr Arg Val Val Ser Val Leu Thr
            420                 425                 430 gtc ctg cac cag gac tgg ctg aat ggc aag gag tac aag tgc aag gtc       1344
Val Leu His Gln Asp Trp Leu Asn Gly Lys Glu Tyr Lys Cys Lys Val
        435                 440                 445 tcc aac aaa gcc ctc cca gcc ccc atc gag aaa acc atc tcc aaa gcc       1392
Ser Asn Lys Ala Leu Pro Ala Pro Ile Glu Lys Thr Ile Ser Lys Ala
450                 455                 460 aaa ggg cag ccc cga gaa cca cag gtg tac acc ctg ccc cca tcc cgg       1440
Lys Gly Gln Pro Arg Glu Pro Gln Val Tyr Thr Leu Pro Pro Ser Arg
465                 470                 475                 480 gat gag ctg acc aag aac cag gtc agc ctg acc tgc cta gtc aaa ggc       1488
Asp Glu Leu Thr Lys Asn Gln Val Ser Leu Thr Cys Leu Val Lys Gly
                485                 490                 495 ttc tat ccc agc gac atc gcc gtg gag tgg gag agc aat ggg cag ccg       1536
Phe Tyr Pro Ser Asp Ile Ala Val Glu Trp Glu Ser Asn Gly Gln Pro
            500                 505                 510 gag aac aac tac aag gcc acg cct ccc gtg ctg gac tcc gac ggc tcc       1584
Glu Asn Asn Tyr Lys Ala Thr Pro Pro Val Leu Asp Ser Asp Gly Ser
        515                 520                 525 ttc ttc ctc tac agc aag ctc acc gtg gac aag agc agg tgg cag cag       1632
Phe Phe Leu Tyr Ser Lys Leu Thr Val Asp Lys Ser Arg Trp Gln Gln
530                 535                 540 ggg aac gtc ttc tca tgc tcc gtg atg cat gag gct ctg cac aac cac       1680
Gly Asn Val Phe Ser Cys Ser Val Met His Glu Ala Leu His Asn His
545                 550                 555                 560 tac acg cag aag agc ctc tcc ctg tct ccg ggt aaa tga                   1719
Tyr Thr Gln Lys Ser Leu Ser Leu Ser Pro Gly Lys
                565                 570

<210> SEQ ID NO 44
<211> LENGTH: 572
<212> TYPE: PRT
<213> ORGANISM: Artificial sequence
```

```
<220> FEATURE:
<223> OTHER INFORMATION: Synthetic Construct

<400> SEQUENCE: 44

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
    210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
                245                 250                 255

Glu Phe Asn Ser Gly Val Thr Phe Asp Trp Asp Tyr Pro Gly Lys Gln
            260                 265                 270

Ala Glu Arg Gly Lys Trp Val Pro Glu Arg Arg Ser Gln Gln Thr His
        275                 280                 285

Thr Glu Leu Ser Ser Ile Leu Thr Ile His Asn Val Ser Gln His Asp
    290                 295                 300

Leu Gly Ser Tyr Val Cys Lys Ala Asn Asn Gly Ile Gln Arg Phe Arg
305                 310                 315                 320

Glu Ser Thr Glu Val Ile Val His Glu Asp Pro Ile Glu Gly Arg Gly
                325                 330                 335

Gly Gly Gly Gly Asp Pro Lys Ser Cys Asp Lys Pro His Thr Cys Pro
            340                 345                 350

Leu Cys Pro Ala Pro Glu Leu Leu Gly Gly Pro Ser Val Phe Leu Phe
        355                 360                 365

Pro Pro Lys Pro Lys Asp Thr Leu Met Ile Ser Arg Thr Pro Glu Val
    370                 375                 380

Thr Cys Val Val Val Asp Val Ser His Glu Asp Pro Glu Val Lys Phe
385                 390                 395                 400
```

```
Asn Trp Tyr Val Asp Gly Val Glu Val His Asn Ala Lys Thr Lys Pro
                405                 410                 415
Arg Glu Glu Gln Tyr Asn Ser Thr Tyr Arg Val Val Ser Val Leu Thr
            420                 425                 430
Val Leu His Gln Asp Trp Leu Asn Gly Lys Glu Tyr Lys Cys Lys Val
        435                 440                 445
Ser Asn Lys Ala Leu Pro Ala Pro Ile Glu Lys Thr Ile Ser Lys Ala
    450                 455                 460
Lys Gly Gln Pro Arg Glu Pro Gln Val Tyr Thr Leu Pro Pro Ser Arg
465                 470                 475                 480
Asp Glu Leu Thr Lys Asn Gln Val Ser Leu Thr Cys Leu Val Lys Gly
                485                 490                 495
Phe Tyr Pro Ser Asp Ile Ala Val Glu Trp Glu Ser Asn Gly Gln Pro
            500                 505                 510
Glu Asn Asn Tyr Lys Ala Thr Pro Pro Val Leu Asp Ser Asp Gly Ser
        515                 520                 525
Phe Phe Leu Tyr Ser Lys Leu Thr Val Asp Lys Ser Arg Trp Gln Gln
    530                 535                 540
Gly Asn Val Phe Ser Cys Ser Val Met His Glu Ala Leu His Asn His
545                 550                 555                 560
Tyr Thr Gln Lys Ser Leu Ser Leu Ser Pro Gly Lys
                565                 570

<210> SEQ ID NO 45
<211> LENGTH: 1131
<212> TYPE: DNA
<213> ORGANISM: Artificial sequence
<220> FEATURE:
<223> OTHER INFORMATION: R-3 H
<220> FEATURE:
<221> NAME/KEY: CDS
<222> LOCATION: (1)..(1131)

<400> SEQUENCE: 45 atg cag cgg ggc gcc gcg ctg tgc ctg cga ctg tgg ctc tgc ctg gga    48
Met Gln Arg Gly Ala Ala Leu Cys Leu Arg Leu Trp Leu Cys Leu Gly
1               5                   10                  15 ctc ctg gac ggc ctg gtg agt ggc tac tcc atg acc ccc ccg acc ttg    96
Leu Leu Asp Gly Leu Val Ser Gly Tyr Ser Met Thr Pro Pro Thr Leu
            20                  25                  30 aac atc acg gag gag tca cac gtc atc gac acc ggt gac agc ctg tcc   144
Asn Ile Thr Glu Glu Ser His Val Ile Asp Thr Gly Asp Ser Leu Ser
        35                  40                  45 atc tcc tgc agg gga cag cac ccc ctc gag tgg gct tgg cca gga gct   192
Ile Ser Cys Arg Gly Gln His Pro Leu Glu Trp Ala Trp Pro Gly Ala
    50                  55                  60 cag gag gcg cca gcc acc gga gac aag gac agc gag gac acg ggg gtg   240
Gln Glu Ala Pro Ala Thr Gly Asp Lys Asp Ser Glu Asp Thr Gly Val
65                  70                  75                  80 gtg cga gac tgc gag ggc aca gac gcc agg ccc tac tgc aag gtg ttg   288
Val Arg Asp Cys Glu Gly Thr Asp Ala Arg Pro Tyr Cys Lys Val Leu
                85                  90                  95 ctg ctg cac gag gta cat gcc aac gac aca ggc agc tac gtc tgc tac   336
Leu Leu His Glu Val His Ala Asn Asp Thr Gly Ser Tyr Val Cys Tyr
            100                 105                 110 tac aag tac atc aag gca cgc atc gag ggc acc acg gcc gcc agc tcc   384
Tyr Lys Tyr Ile Lys Ala Arg Ile Glu Gly Thr Thr Ala Ala Ser Ser
        115                 120                 125
```

```
tac gtg ttc gtg agg gat ccc atc gaa ggt cgt ggt ggt ggt ggt ggt        432
Tyr Val Phe Val Arg Asp Pro Ile Glu Gly Arg Gly Gly Gly Gly Gly
130                 135                 140 gat ccc aaa tct tgt gac aaa cct cac aca tgc cca ctg tgc cca gca        480
Asp Pro Lys Ser Cys Asp Lys Pro His Thr Cys Pro Leu Cys Pro Ala
145                 150                 155                 160 cct gaa ctc ctg ggg gga ccg tca gtc ttc ctc ttc ccc cca aaa ccc        528
Pro Glu Leu Leu Gly Gly Pro Ser Val Phe Leu Phe Pro Pro Lys Pro
                165                 170                 175 aag gac acc ctc atg atc tcc cgg acc cct gag gtc aca tgc gtg gtg        576
Lys Asp Thr Leu Met Ile Ser Arg Thr Pro Glu Val Thr Cys Val Val
            180                 185                 190 gtg gac gtg agc cac gaa gac cct gag gtc aag ttc aac tgg tac gtg        624
Val Asp Val Ser His Glu Asp Pro Glu Val Lys Phe Asn Trp Tyr Val
        195                 200                 205 gac ggc gtg gag gtg cat aat gcc aag aca aag ccg cgg gag gag cag        672
Asp Gly Val Glu Val His Asn Ala Lys Thr Lys Pro Arg Glu Glu Gln
210                 215                 220 tac aac agc acg tac cgt gtg gtc agc gtc ctc acc gtc ctg cac cag        720
Tyr Asn Ser Thr Tyr Arg Val Val Ser Val Leu Thr Val Leu His Gln
225                 230                 235                 240 gac tgg ctg aat ggc aag gag tac aag tgc aag gtc tcc aac aaa gcc        768
Asp Trp Leu Asn Gly Lys Glu Tyr Lys Cys Lys Val Ser Asn Lys Ala
                245                 250                 255 ctc cca gcc ccc atc gag aaa acc atc tcc aaa gcc aaa ggg cag ccc        816
Leu Pro Ala Pro Ile Glu Lys Thr Ile Ser Lys Ala Lys Gly Gln Pro
            260                 265                 270 cga gaa cca cag gtg tac acc ctg ccc cca tcc cgg gat gag ctg acc        864
Arg Glu Pro Gln Val Tyr Thr Leu Pro Pro Ser Arg Asp Glu Leu Thr
        275                 280                 285 aag aac cag gtc agc ctg acc tgc cta gtc aaa ggc ttc tat ccc agc        912
Lys Asn Gln Val Ser Leu Thr Cys Leu Val Lys Gly Phe Tyr Pro Ser
290                 295                 300 gac atc gcc gtg gag tgg gag agc aat ggg cag ccg gag aac aac tac        960
Asp Ile Ala Val Glu Trp Glu Ser Asn Gly Gln Pro Glu Asn Asn Tyr
305                 310                 315                 320 aag gcc acg cct ccc gtg ctg gac tcc gac ggc tcc ttc ttc ctc tac       1008
Lys Ala Thr Pro Pro Val Leu Asp Ser Asp Gly Ser Phe Phe Leu Tyr
                325                 330                 335 agc aag ctc acc gtg gac aag agc agg tgg cag cag ggg aac gtc ttc       1056
Ser Lys Leu Thr Val Asp Lys Ser Arg Trp Gln Gln Gly Asn Val Phe
            340                 345                 350 tca tgc tcc gtg atg cat gag gct ctg cac aac cac tac acg cag aag       1104
Ser Cys Ser Val Met His Glu Ala Leu His Asn His Tyr Thr Gln Lys
        355                 360                 365 agc ctc tcc ctg tct ccg ggt aaa tga                                   1131
Ser Leu Ser Leu Ser Pro Gly Lys
    370                 375
```

<210> SEQ ID NO 46
<211> LENGTH: 376
<212> TYPE: PRT
<213> ORGANISM: Artificial sequence
<220> FEATURE:
<223> OTHER INFORMATION: Synthetic Construct

<400> SEQUENCE: 46

```
Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30
```

Asn Ile Thr Glu Glu Ser His Val Ile Asp Thr Gly Asp Ser Leu Ser
    35                  40                  45

Ile Ser Cys Arg Gly Gln His Pro Leu Glu Trp Ala Trp Pro Gly Ala
50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Pro Ile Glu Gly Arg Gly Gly Gly Gly Gly
    130                 135                 140

Asp Pro Lys Ser Cys Asp Lys Pro His Thr Cys Pro Leu Cys Pro Ala
145                 150                 155                 160

Pro Glu Leu Leu Gly Gly Pro Ser Val Phe Leu Phe Pro Pro Lys Pro
                165                 170                 175

Lys Asp Thr Leu Met Ile Ser Arg Thr Pro Glu Val Thr Cys Val Val
            180                 185                 190

Val Asp Val Ser His Glu Asp Pro Glu Val Lys Phe Asn Trp Tyr Val
        195                 200                 205

Asp Gly Val Glu Val His Asn Ala Lys Thr Lys Pro Arg Glu Glu Gln
    210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Pro Ala Pro Ile Glu Lys Thr Ile Ser Lys Ala Lys Gly Gln Pro
            260                 265                 270

Arg Glu Pro Gln Val Tyr Thr Leu Pro Pro Ser Arg Asp Glu Leu Thr
        275                 280                 285

Lys Asn Gln Val Ser Leu Thr Cys Leu Val Lys Gly Phe Tyr Pro Ser
    290                 295                 300

Asp Ile Ala Val Glu Trp Glu Ser Asn Gly Gln Pro Glu Asn Asn Tyr
305                 310                 315                 320

Lys Ala Thr Pro Pro Val Leu Asp Ser Asp Gly Ser Phe Phe Leu Tyr
                325                 330                 335

Ser Lys Leu Thr Val Asp Lys Ser Arg Trp Gln Gln Gly Asn Val Phe
            340                 345                 350

Ser Cys Ser Val Met His Glu Ala Leu His Asn His Tyr Thr Gln Lys
        355                 360                 365

Ser Leu Ser Leu Ser Pro Gly Lys
    370                 375

<210> SEQ ID NO 47
<211> LENGTH: 1443
<212> TYPE: DNA
<213> ORGANISM: Artificial sequence
<220> FEATURE:
<223> OTHER INFORMATION: R-3 I
<220> FEATURE:
<221> NAME/KEY: CDS
<222> LOCATION: (1)..(1443)

<400> SEQUENCE: 47

```
atg cag cgg ggc gcc gcg ctg tgc ctg cga ctg tgg ctc tgc ctg gga        48
Met Gln Arg Gly Ala Ala Leu Cys Leu Arg Leu Trp Leu Cys Leu Gly
1               5                   10                  15 ctc ctg gac ggc ctg gtg agt ggc tac tcc atg acc ccc ccg acc ttg        96
Leu Leu Asp Gly Leu Val Ser Gly Tyr Ser Met Thr Pro Pro Thr Leu
            20                  25                  30 aac atc acg gag gag tca cac gtc aga gac ttt gag cag cca ttc atc       144
Asn Ile Thr Glu Glu Ser His Val Arg Asp Phe Glu Gln Pro Phe Ile
        35                  40                  45 aac aag cct gac acg ctc ttg gtc aac agg aag gac gcc atg tgg gtg       192
Asn Lys Pro Asp Thr Leu Leu Val Asn Arg Lys Asp Ala Met Trp Val
    50                  55                  60 ccc tgt ctg gtg tcc atc ccc ggc ctc aat gtc acg ctg cgc tcg caa       240
Pro Cys Leu Val Ser Ile Pro Gly Leu Asn Val Thr Leu Arg Ser Gln
65                  70                  75                  80 agc tcg gtg ctg tgg cca gac ggg cag gag gtg gtg tgg gat gac cgg       288
Ser Ser Val Leu Trp Pro Asp Gly Gln Glu Val Val Trp Asp Asp Arg
                85                  90                  95 cgg ggc atg ctc gtg tcc acg cca ctg ctg cac gat gcc ctg tac ctg       336
Arg Gly Met Leu Val Ser Thr Pro Leu Leu His Asp Ala Leu Tyr Leu
            100                 105                 110 cag tgc gag acc acc tgg gga gac cag gac ttc ctt tcc aac ccc ttc       384
Gln Cys Glu Thr Thr Trp Gly Asp Gln Asp Phe Leu Ser Asn Pro Phe
        115                 120                 125 ctg gtg cac atc aca ggc aac gag ctc tat gac atc cag ctg ttg ccc       432
Leu Val His Ile Thr Gly Asn Glu Leu Tyr Asp Ile Gln Leu Leu Pro
    130                 135                 140 agg aag tcg ctg gag ctg ctg gta ggg gag aag ctg gtc ctg aac tgc       480
Arg Lys Ser Leu Glu Leu Leu Val Gly Glu Lys Leu Val Leu Asn Cys
145                 150                 155                 160 acc gtg tgg gct gag ttt aac tca ggt gtc acc ttt gac tgg gac tac       528
Thr Val Trp Ala Glu Phe Asn Ser Gly Val Thr Phe Asp Trp Asp Tyr
                165                 170                 175 cca ggg aag cag gca gag cgg ggt aag tgg gtg ccc gag cga cgc tcc       576
Pro Gly Lys Gln Ala Glu Arg Gly Lys Trp Val Pro Glu Arg Arg Ser
            180                 185                 190 cag cag acc cac aca gaa ctc tcc agc atc ctg acc atc cac aac gtc       624
Gln Gln Thr His Thr Glu Leu Ser Ser Ile Leu Thr Ile His Asn Val
        195                 200                 205 agc cag cac gac ctg ggc tcg tat gtg tgc aag gcc aac aac ggc atc       672
Ser Gln His Asp Leu Gly Ser Tyr Val Cys Lys Ala Asn Asn Gly Ile
    210                 215                 220 cag cga ttt cgg gag agc acc gag gtc att gtg cat gag gat ccc atc       720
Gln Arg Phe Arg Glu Ser Thr Glu Val Ile Val His Glu Asp Pro Ile
225                 230                 235                 240 gaa ggt cgt ggt ggt ggt ggt ggt gat ccc aaa tct tgt gac aaa cct       768
Glu Gly Arg Gly Gly Gly Gly Gly Asp Pro Lys Ser Cys Asp Lys Pro
                245                 250                 255 cac aca tgc cca ctg tgc cca gca cct gaa ctc ctg ggg gga ccg tca       816
His Thr Cys Pro Leu Cys Pro Ala Pro Glu Leu Leu Gly Gly Pro Ser
            260                 265                 270 gtc ttc ctc ttc ccc cca aaa ccc aag gac acc ctc atg atc tcc cgg       864
Val Phe Leu Phe Pro Pro Lys Pro Lys Asp Thr Leu Met Ile Ser Arg
        275                 280                 285 acc cct gag gtc aca tgc gtg gtg gtg gac gtg agc cac gaa gac cct       912
Thr Pro Glu Val Thr Cys Val Val Val Asp Val Ser His Glu Asp Pro
    290                 295                 300 gag gtc aag ttc aac tgg tac gtg gac ggc gtg gag gtg cat aat gcc       960
Glu Val Lys Phe Asn Trp Tyr Val Asp Gly Val Glu Val His Asn Ala
```

```
                        305                 310                 315                 320
aag aca aag ccg cgg gag gag cag tac aac agc acg tac cgt gtg gtc        1008
Lys Thr Lys Pro Arg Glu Glu Gln Tyr Asn Ser Thr Tyr Arg Val Val
                325                 330                 335 agc gtc ctc acc gtc ctg cac cag gac tgg ctg aat ggc aag gag tac        1056
Ser Val Leu Thr Val Leu His Gln Asp Trp Leu Asn Gly Lys Glu Tyr
            340                 345                 350 aag tgc aag gtc tcc aac aaa gcc ctc cca gcc ccc atc gag aaa acc        1104
Lys Cys Lys Val Ser Asn Lys Ala Leu Pro Ala Pro Ile Glu Lys Thr
        355                 360                 365 atc tcc aaa gcc aaa ggg cag ccc cga gaa cca cag gtg tac acc ctg        1152
Ile Ser Lys Ala Lys Gly Gln Pro Arg Glu Pro Gln Val Tyr Thr Leu
    370                 375                 380 ccc cca tcc cgg gat gag ctg acc aag aac cag gtc agc ctg acc tgc        1200
Pro Pro Ser Arg Asp Glu Leu Thr Lys Asn Gln Val Ser Leu Thr Cys
385                 390                 395                 400 cta gtc aaa ggc ttc tat ccc agc gac atc gcc gtg gag tgg gag agc        1248
Leu Val Lys Gly Phe Tyr Pro Ser Asp Ile Ala Val Glu Trp Glu Ser
                405                 410                 415 aat ggg cag ccg gag aac aac tac aag gcc acg cct ccc gtg ctg gac        1296
Asn Gly Gln Pro Glu Asn Asn Tyr Lys Ala Thr Pro Pro Val Leu Asp
            420                 425                 430 tcc gac ggc tcc ttc ttc ctc tac agc aag ctc acc gtg gac aag agc        1344
Ser Asp Gly Ser Phe Phe Leu Tyr Ser Lys Leu Thr Val Asp Lys Ser
        435                 440                 445 agg tgg cag cag ggg aac gtc ttc tca tgc tcc gtg atg cat gag gct        1392
Arg Trp Gln Gln Gly Asn Val Phe Ser Cys Ser Val Met His Glu Ala
    450                 455                 460 ctg cac aac cac tac acg cag aag agc ctc tcc ctg tct ccg ggt aaa        1440
Leu His Asn His Tyr Thr Gln Lys Ser Leu Ser Leu Ser Pro Gly Lys
465                 470                 475                 480 tga                                                                    1443

<210> SEQ ID NO 48
<211> LENGTH: 480
<212> TYPE: PRT
<213> ORGANISM: Artificial sequence
<220> FEATURE:
<223> OTHER INFORMATION: Synthetic Construct

<400> SEQUENCE: 48

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Arg Asp Phe Glu Gln Pro Phe Ile
        35                  40                  45

Asn Lys Pro Asp Thr Leu Leu Val Asn Arg Lys Asp Ala Met Trp Val
    50                  55                  60

Pro Cys Leu Val Ser Ile Pro Gly Leu Asn Val Thr Leu Arg Ser Gln
65                  70                  75                  80

Ser Ser Val Leu Trp Pro Asp Gly Gln Glu Val Val Trp Asp Asp Arg
                85                  90                  95

Arg Gly Met Leu Val Ser Thr Pro Leu Leu His Asp Ala Leu Tyr Leu
            100                 105                 110

Gln Cys Glu Thr Thr Trp Gly Asp Gln Asp Phe Leu Ser Asn Pro Phe
        115                 120                 125

Leu Val His Ile Thr Gly Asn Glu Leu Tyr Asp Ile Gln Leu Leu Pro
```

```
                130                 135                 140
Arg Lys Ser Leu Glu Leu Leu Val Gly Glu Lys Leu Val Leu Asn Cys
145                 150                 155                 160

Thr Val Trp Ala Glu Phe Asn Ser Gly Val Thr Phe Asp Trp Asp Tyr
                165                 170                 175

Pro Gly Lys Gln Ala Glu Arg Gly Lys Trp Val Pro Glu Arg Arg Ser
                180                 185                 190

Gln Gln Thr His Thr Glu Leu Ser Ser Ile Leu Thr Ile His Asn Val
                195                 200                 205

Ser Gln His Asp Leu Gly Ser Tyr Val Cys Lys Ala Asn Asn Gly Ile
                210                 215                 220

Gln Arg Phe Arg Glu Ser Thr Glu Val Ile Val His Glu Asp Pro Ile
225                 230                 235                 240

Glu Gly Arg Gly Gly Gly Gly Asp Pro Lys Ser Cys Asp Lys Pro
                    245                 250                 255

His Thr Cys Pro Leu Cys Pro Ala Pro Glu Leu Leu Gly Gly Pro Ser
                260                 265                 270

Val Phe Leu Phe Pro Pro Lys Pro Lys Asp Thr Leu Met Ile Ser Arg
                275                 280                 285

Thr Pro Glu Val Thr Cys Val Val Asp Val Ser His Glu Asp Pro
290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Glu Tyr
                340                 345                 350

Lys Cys Lys Val Ser Asn Lys Ala Leu Pro Ala Pro Ile Glu Lys Thr
                355                 360                 365

Ile Ser Lys Ala Lys Gly Gln Pro Arg Glu Pro Gln Val Tyr Thr Leu
                370                 375                 380

Pro Pro Ser Arg Asp Glu Leu Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Ala Thr Pro Pro Val Leu Asp
                420                 425                 430

Ser Asp Gly Ser Phe Phe Leu Tyr Ser Lys Leu Thr Val Asp Lys Ser
                435                 440                 445

Arg Trp Gln Gln Gly Asn Val Phe Ser Cys Ser Val Met His Glu Ala
                450                 455                 460

Leu His Asn His Tyr Thr Gln Lys Ser Leu Ser Leu Ser Pro Gly Lys
465                 470                 475                 480

<210> SEQ ID NO 49
<211> LENGTH: 1197
<212> TYPE: DNA
<213> ORGANISM: Artificial sequence
<220> FEATURE:
<223> OTHER INFORMATION: R-3 J
<220> FEATURE:
<221> NAME/KEY: CDS
<222> LOCATION: (1)..(1197)

<400> SEQUENCE: 49 atg cag cgg ggc gcc gcg ctg tgc ctg cga ctg tgg ctc tgc ctg gga      48
```

```
Met Gln Arg Gly Ala Ala Leu Cys Leu Arg Leu Trp Leu Cys Leu Gly
1               5                   10                  15 ctc ctg gac ggc ctg gtg agt ggc tac tcc atg acc ccc ccg acc ttg         96
Leu Leu Asp Gly Leu Val Ser Gly Tyr Ser Met Thr Pro Pro Thr Leu
            20                  25                  30 aac atc acg gag gag tca cac gtc aga gac ttt gag cag cca ttc atc        144
Asn Ile Thr Glu Glu Ser His Val Arg Asp Phe Glu Gln Pro Phe Ile
            35                  40              45 aac aag cct gac acg ctc ttg gtc aac agg aag gac gcc atg tgg gtg        192
Asn Lys Pro Asp Thr Leu Leu Val Asn Arg Lys Asp Ala Met Trp Val
50                  55                  60 ccc tgt ctg gtg tcc atc ccc ggc ctc aat gtc acg ctg cgc tcg caa        240
Pro Cys Leu Val Ser Ile Pro Gly Leu Asn Val Thr Leu Arg Ser Gln
65                  70                  75                  80 agc tcg gtg ctg tgg cca gac ggg cag gag gtg gtg tgg gat gac cgg        288
Ser Ser Val Leu Trp Pro Asp Gly Gln Glu Val Val Trp Asp Asp Arg
                85                  90                  95 cgg ggc atg ctc gtg tcc acg cca ctg ctg cac gat gcc ctg tac ctg        336
Arg Gly Met Leu Val Ser Thr Pro Leu Leu His Asp Ala Leu Tyr Leu
            100                 105                 110 cag tgc gag acc acc tgg gga gac cag gac ttc ctt tcc aac ccc ttc        384
Gln Cys Glu Thr Thr Trp Gly Asp Gln Asp Phe Leu Ser Asn Pro Phe
            115                 120                 125 ctg gtg cac atc aca ggc aac gag ctc tat gac atc cag ctg ttg ccc        432
Leu Val His Ile Thr Gly Asn Glu Leu Tyr Asp Ile Gln Leu Leu Pro
130                 135                 140 agg aag tcg ctg gag ctg ctg gta ggg gag aag gat ccc atc gaa ggt        480
Arg Lys Ser Leu Glu Leu Leu Val Gly Glu Lys Asp Pro Ile Glu Gly
145                 150                 155                 160 cgt ggt ggt ggt ggt gat ccc aaa tct tgt gac aaa cct cac aca            528
Arg Gly Gly Gly Gly Asp Pro Lys Ser Cys Asp Lys Pro His Thr
                165                 170                 175 tgc cca ctg tgc cca gca cct gaa ctc ctg ggg gga ccg tca gtc ttc        576
Cys Pro Leu Cys Pro Ala Pro Glu Leu Leu Gly Gly Pro Ser Val Phe
            180                 185                 190 ctc ttc ccc cca aaa ccc aag gac acc ctc atg atc tcc cgg acc cct        624
Leu Phe Pro Pro Lys Pro Lys Asp Thr Leu Met Ile Ser Arg Thr Pro
        195                 200                 205 gag gtc aca tgc gtg gtg gtg gac gtg agc cac gaa gac cct gag gtc        672
Glu Val Thr Cys Val Val Val Asp Val Ser His Glu Asp Pro Glu Val
210                 215                 220 aag ttc aac tgg tac gtg gac ggc gtg gag gtg cat aat gcc aag aca        720
Lys Phe Asn Trp Tyr Val Asp Gly Val Glu Val His Asn Ala Lys Thr
225                 230                 235                 240 aag ccg cgg gag gag cag tac aac agc acg tac cgt gtg gtc agc gtc        768
Lys Pro Arg Glu Glu Gln Tyr Asn Ser Thr Tyr Arg Val Val Ser Val
            245                 250                 255 ctc acc gtc ctg cac cag gac tgg ctg aat ggc aag gag tac aag tgc        816
Leu Thr Val Leu His Gln Asp Trp Leu Asn Gly Lys Glu Tyr Lys Cys
            260                 265                 270 aag gtc tcc aac aaa gcc ctc cca gcc ccc atc gag aaa acc atc tcc        864
Lys Val Ser Asn Lys Ala Leu Pro Ala Pro Ile Glu Lys Thr Ile Ser
            275                 280                 285 aaa gcc aaa ggg cag ccc cga gaa cca cag gtg tac acc ctg ccc cca        912
Lys Ala Lys Gly Gln Pro Arg Glu Pro Gln Val Tyr Thr Leu Pro Pro
290                 295                 300 tcc cgg gat gag ctg acc aag aac cag gtc agc ctg acc tgc cta gtc        960
Ser Arg Asp Glu Leu Thr Lys Asn Gln Val Ser Leu Thr Cys Leu Val
305                 310                 315                 320
```

```
aaa ggc ttc tat ccc agc gac atc gcc gtg gag tgg gag agc aat ggg    1008
Lys Gly Phe Tyr Pro Ser Asp Ile Ala Val Glu Trp Glu Ser Asn Gly
            325                 330                 335 cag ccg gag aac aac tac aag gcc acg cct ccc gtg ctg gac tcc gac    1056
Gln Pro Glu Asn Asn Tyr Lys Ala Thr Pro Pro Val Leu Asp Ser Asp
            340                 345                 350 ggc tcc ttc ttc ctc tac agc aag ctc acc gtg gac aag agc agg tgg    1104
Gly Ser Phe Phe Leu Tyr Ser Lys Leu Thr Val Asp Lys Ser Arg Trp
            355                 360                 365 cag cag ggg aac gtc ttc tca tgc tcc gtg atg cat gag gct ctg cac    1152
Gln Gln Gly Asn Val Phe Ser Cys Ser Val Met His Glu Ala Leu His
        370                 375                 380 aac cac tac acg cag aag agc ctc tcc ctg tct ccg ggt aaa tga        1197
Asn His Tyr Thr Gln Lys Ser Leu Ser Leu Ser Pro Gly Lys
385                 390                 395
```

<210> SEQ ID NO 50
<211> LENGTH: 398
<212> TYPE: PRT
<213> ORGANISM: Artificial sequence
<220> FEATURE:
<223> OTHER INFORMATION: Synthetic Construct

<400> SEQUENCE: 50

```
Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Arg Asp Phe Glu Gln Pro Phe Ile
        35                  40                  45

Asn Lys Pro Asp Thr Leu Leu Val Asn Arg Lys Asp Ala Met Trp Val
    50                  55                  60

Pro Cys Leu Val Ser Ile Pro Gly Leu Asn Val Thr Leu Arg Ser Gln
65                  70                  75                  80

Ser Ser Val Leu Trp Pro Asp Gly Gln Glu Val Val Trp Asp Asp Arg
                85                  90                  95

Arg Gly Met Leu Val Ser Thr Pro Leu Leu His Asp Ala Leu Tyr Leu
            100                 105                 110

Gln Cys Glu Thr Thr Trp Gly Asp Gln Asp Phe Leu Ser Asn Pro Phe
        115                 120                 125

Leu Val His Ile Thr Gly Asn Glu Leu Tyr Asp Ile Gln Leu Leu Pro
    130                 135                 140

Arg Lys Ser Leu Glu Leu Leu Val Gly Glu Lys Asp Pro Ile Glu Gly
145                 150                 155                 160

Arg Gly Gly Gly Gly Asp Pro Lys Ser Cys Asp Lys Pro His Thr
                165                 170                 175

Cys Pro Leu Cys Pro Ala Pro Glu Leu Leu Gly Gly Pro Ser Val Phe
            180                 185                 190

Leu Phe Pro Pro Lys Pro Lys Asp Thr Leu Met Ile Ser Arg Thr Pro
        195                 200                 205

Glu Val Thr Cys Val Val Val Asp Val Ser His Glu Asp Pro Glu Val
    210                 215                 220

Lys Phe Asn Trp Tyr Val Asp Gly Val Glu Val His Asn Ala Lys Thr
225                 230                 235                 240

Lys Pro Arg Glu Glu Gln Tyr Asn Ser Thr Tyr Arg Val Val Ser Val
                245                 250                 255

Leu Thr Val Leu His Gln Asp Trp Leu Asn Gly Lys Glu Tyr Lys Cys
```

```
                    260                 265                 270
Lys Val Ser Asn Lys Ala Leu Pro Ala Pro Ile Glu Lys Thr Ile Ser
            275                 280                 285

Lys Ala Lys Gly Gln Pro Arg Glu Pro Gln Val Tyr Thr Leu Pro Pro
        290                 295                 300

Ser Arg Asp Glu Leu Thr Lys Asn Gln Val Ser Leu Thr Cys Leu Val
305                 310                 315                 320

Lys Gly Phe Tyr Pro Ser Asp Ile Ala Val Glu Trp Glu Ser Asn Gly
                325                 330                 335

Gln Pro Glu Asn Asn Tyr Lys Ala Thr Pro Pro Val Leu Asp Ser Asp
            340                 345                 350

Gly Ser Phe Phe Leu Tyr Ser Lys Leu Thr Val Asp Lys Ser Arg Trp
        355                 360                 365

Gln Gln Gly Asn Val Phe Ser Cys Ser Val Met His Glu Ala Leu His
    370                 375                 380

Asn His Tyr Thr Gln Lys Ser Leu Ser Leu Ser Pro Gly Lys
385                 390                 395
```

<210> SEQ ID NO 51
<211> LENGTH: 1146
<212> TYPE: DNA
<213> ORGANISM: Artificial sequence
<220> FEATURE:
<223> OTHER INFORMATION: R-3 K
<220> FEATURE:
<221> NAME/KEY: CDS
<222> LOCATION: (1)..(1146)

<400> SEQUENCE: 51

```
atg cag cgg ggc gcc gcg ctg tgc ctg cga ctg tgg ctc tgc ctg gga      48
Met Gln Arg Gly Ala Ala Leu Cys Leu Arg Leu Trp Leu Cys Leu Gly
1               5                   10                  15 ctc ctg gac ggc ctg gtg agt ggc tac tcc atg acc ccc ccg acc ttg      96
Leu Leu Asp Gly Leu Val Ser Gly Tyr Ser Met Thr Pro Pro Thr Leu
            20                  25                  30 aac atc acg gag gag tca cac gtc aga gac ttt gag cag cca ttc atc     144
Asn Ile Thr Glu Glu Ser His Val Arg Asp Phe Glu Gln Pro Phe Ile
        35                  40                  45 aac aag cct gac acg ctc ttg gtc aac agg aag gac gcc atg tgg gtg     192
Asn Lys Pro Asp Thr Leu Leu Val Asn Arg Lys Asp Ala Met Trp Val
    50                  55                  60 ccc tgt ctg gtg tcc atc ccc ggc ctc aat gtc acg ctg cgc tcg caa     240
Pro Cys Leu Val Ser Ile Pro Gly Leu Asn Val Thr Leu Arg Ser Gln
65                  70                  75                  80 agc tcg gtg ctg tgg cca gac ggg cag gag gtg gtg tgg gat gac cgg     288
Ser Ser Val Leu Trp Pro Asp Gly Gln Glu Val Val Trp Asp Asp Arg
                85                  90                  95 cgg ggc atg ctc gtg tcc acg cca ctg ctg cac gat gcc ctg tac ctg     336
Arg Gly Met Leu Val Ser Thr Pro Leu Leu His Asp Ala Leu Tyr Leu
            100                 105                 110 cag tgc gag acc acc tgg gga gac cag gac ttc ctt tcc aac ccc ttc     384
Gln Cys Glu Thr Thr Trp Gly Asp Gln Asp Phe Leu Ser Asn Pro Phe
        115                 120                 125 ctg gtg cac atc aca ggc aac gag ctc gcg gat ccc atc gaa ggt cgt     432
Leu Val His Ile Thr Gly Asn Glu Leu Ala Asp Pro Ile Glu Gly Arg
    130                 135                 140 ggt ggt ggt ggt gat ccc aaa tct tgt gac aaa cct cac aca tgc         480
Gly Gly Gly Gly Asp Pro Lys Ser Cys Asp Lys Pro His Thr Cys
145                 150                 155                 160
```

-continued

| | | |
|---|---|---|
| cca ctg tgc cca gca cct gaa ctc ctg ggg gga ccg tca gtc ttc ctc<br>Pro Leu Cys Pro Ala Pro Glu Leu Leu Gly Gly Pro Ser Val Phe Leu<br>165                        170                      175 | | 528 |
| ttc ccc cca aaa ccc aag gac acc ctc atg atc tcc cgg acc cct gag<br>Phe Pro Pro Lys Pro Lys Asp Thr Leu Met Ile Ser Arg Thr Pro Glu<br>         180                      185                      190 | | 576 |
| gtc aca tgc gtg gtg gtg gac gtg agc cac gaa gac cct gag gtc aag<br>Val Thr Cys Val Val Val Asp Val Ser His Glu Asp Pro Glu Val Lys<br>195                        200                      205 | | 624 |
| ttc aac tgg tac gtg gac ggc gtg gag gtg cat aat gcc aag aca aag<br>Phe Asn Trp Tyr Val Asp Gly Val Glu Val His Asn Ala Lys Thr Lys<br>    210                      215                      220 | | 672 |
| ccg cgg gag gag cag tac aac agc acg tac cgt gtg gtc agc gtc ctc<br>Pro Arg Glu Glu Gln Tyr Asn Ser Thr Tyr Arg Val Val Ser Val Leu<br>225                        230                      235                      240 | | 720 |
| acc gtc ctg cac cag gac tgg ctg aat ggc aag gag tac aag tgc aag<br>Thr Val Leu His Gln Asp Trp Leu Asn Gly Lys Glu Tyr Lys Cys Lys<br>                      245                      250                      255 | | 768 |
| gtc tcc aac aaa gcc ctc cca gcc ccc atc gag aaa acc atc tcc aaa<br>Val Ser Asn Lys Ala Leu Pro Ala Pro Ile Glu Lys Thr Ile Ser Lys<br>260                        265                      270 | | 816 |
| gcc aaa ggg cag ccc cga gaa cca cag gtg tac acc ctg ccc cca tcc<br>Ala Lys Gly Gln Pro Arg Glu Pro Gln Val Tyr Thr Leu Pro Pro Ser<br>    275                      280                      285 | | 864 |
| cgg gat gag ctg acc aag aac cag gtc agc ctg acc tgc cta gtc aaa<br>Arg Asp Glu Leu Thr Lys Asn Gln Val Ser Leu Thr Cys Leu Val Lys<br>290                        295                      300 | | 912 |
| ggc ttc tat ccc agc gac atc gcc gtg gag tgg gag agc aat ggg cag<br>Gly Phe Tyr Pro Ser Asp Ile Ala Val Glu Trp Glu Ser Asn Gly Gln<br>305                        310                      315                      320 | | 960 |
| ccg gag aac aac tac aag gcc acg cct ccc gtg ctg gac tcc gac ggc<br>Pro Glu Asn Asn Tyr Lys Ala Thr Pro Pro Val Leu Asp Ser Asp Gly<br>                      325                      330                      335 | | 1008 |
| tcc ttc ttc ctc tac agc aag ctc acc gtg gac aag agc agg tgg cag<br>Ser Phe Phe Leu Tyr Ser Lys Leu Thr Val Asp Lys Ser Arg Trp Gln<br>                  340                      345                      350 | | 1056 |
| cag ggg aac gtc ttc tca tgc tcc gtg atg cat gag gct ctg cac aac<br>Gln Gly Asn Val Phe Ser Cys Ser Val Met His Glu Ala Leu His Asn<br>355                        360                      365 | | 1104 |
| cac tac acg cag aag agc ctc tcc ctg tct ccg ggt aaa tga<br>His Tyr Thr Gln Lys Ser Leu Ser Leu Ser Pro Gly Lys<br>370                        375                      380 | | 1146 |

<210> SEQ ID NO 52
<211> LENGTH: 381
<212> TYPE: PRT
<213> ORGANISM: Artificial sequence
<220> FEATURE:
<223> OTHER INFORMATION: Synthetic Construct

<400> SEQUENCE: 52

Met Gln Arg Gly Ala Ala Leu Cys Leu Arg Leu Trp Leu Cys Leu Gly
1                  5                      10                      15

Leu Leu Asp Gly Leu Val Ser Gly Tyr Ser Met Thr Pro Pro Thr Leu
                20                      25                      30

Asn Ile Thr Glu Glu Ser His Val Arg Asp Phe Glu Gln Pro Phe Ile
                35                      40                      45

Asn Lys Pro Asp Thr Leu Leu Val Asn Arg Lys Asp Ala Met Trp Val
    50                      55                      60

Pro Cys Leu Val Ser Ile Pro Gly Leu Asn Val Thr Leu Arg Ser Gln

```
                65                  70                  75                  80
            Ser Ser Val Leu Trp Pro Asp Gly Gln Glu Val Val Trp Asp Asp Arg
                            85                  90                  95

Arg Gly Met Leu Val Ser Thr Pro Leu Leu His Asp Ala Leu Tyr Leu
                        100                 105                 110

Gln Cys Glu Thr Thr Trp Gly Asp Gln Asp Phe Leu Ser Asn Pro Phe
                    115                 120                 125

Leu Val His Ile Thr Gly Asn Glu Leu Ala Asp Pro Ile Glu Gly Arg
                130                 135                 140

Gly Gly Gly Gly Gly Asp Pro Lys Ser Cys Asp Lys Pro His Thr Cys
            145                 150                 155                 160

Pro Leu Cys Pro Ala Pro Glu Leu Leu Gly Gly Pro Ser Val Phe Leu
                            165                 170                 175

Phe Pro Pro Lys Pro Lys Asp Thr Leu Met Ile Ser Arg Thr Pro Glu
                        180                 185                 190

Val Thr Cys Val Val Val Asp Val Ser His Glu Asp Pro Glu Val Lys
                    195                 200                 205

Phe Asn Trp Tyr Val Asp Gly Val Glu Val His Asn Ala Lys Thr Lys
                210                 215                 220

Pro Arg Glu Glu Gln Tyr Asn Ser Thr Tyr Arg Val Val Ser Val Leu
            225                 230                 235                 240

Thr Val Leu His Gln Asp Trp Leu Asn Gly Lys Glu Tyr Lys Cys Lys
                            245                 250                 255

Val Ser Asn Lys Ala Leu Pro Ala Pro Ile Glu Lys Thr Ile Ser Lys
                        260                 265                 270

Ala Lys Gly Gln Pro Arg Glu Pro Gln Val Tyr Thr Leu Pro Pro Ser
                    275                 280                 285

Arg Asp Glu Leu Thr Lys Asn Gln Val Ser Leu Thr Cys Leu Val Lys
                290                 295                 300

Gly Phe Tyr Pro Ser Asp Ile Ala Val Glu Trp Glu Ser Asn Gly Gln
            305                 310                 315                 320

Pro Glu Asn Asn Tyr Lys Ala Thr Pro Pro Val Leu Asp Ser Asp Gly
                            325                 330                 335

Ser Phe Phe Leu Tyr Ser Lys Leu Thr Val Asp Lys Ser Arg Trp Gln
                        340                 345                 350

Gln Gly Asn Val Phe Ser Cys Ser Val Met His Glu Ala Leu His Asn
                    355                 360                 365

His Tyr Thr Gln Lys Ser Leu Ser Leu Ser Pro Gly Lys
                370                 375                 380

<210> SEQ ID NO 53
<211> LENGTH: 1128
<212> TYPE: DNA
<213> ORGANISM: Artificial sequence
<220> FEATURE:
<223> OTHER INFORMATION: R-3 L
<220> FEATURE:
<221> NAME/KEY: CDS
<222> LOCATION: (1)..(1128)

<400> SEQUENCE: 53 atg cag cgg ggc gcc gcg ctg tgc ctg cga ctg tgg ctc tgc ctg gga     48
Met Gln Arg Gly Ala Ala Leu Cys Leu Arg Leu Trp Leu Cys Leu Gly
1               5                   10                  15 ctc ctg gac ggc ctg gtg agt ggc tac tcc atg acc ccc ccg acc ttg     96
Leu Leu Asp Gly Leu Val Ser Gly Tyr Ser Met Thr Pro Pro Thr Leu
            20                  25                  30
```

-continued

```
aac atc acg gag gag tca cac gtc aga gac ttt gag cag cca ttc atc      144
Asn Ile Thr Glu Glu Ser His Val Arg Asp Phe Glu Gln Pro Phe Ile
        35                  40                  45 aac aag cct gac acg ctc ttg gtc aac agg aag gac gcc atg tgg gtg      192
Asn Lys Pro Asp Thr Leu Leu Val Asn Arg Lys Asp Ala Met Trp Val
 50                  55                  60 ccc tgt ctg gtg tcc atc ccc ggc ctc aat gtc acg ctg cgc tcg caa      240
Pro Cys Leu Val Ser Ile Pro Gly Leu Asn Val Thr Leu Arg Ser Gln
 65                  70                  75                  80 agc tcg gtg ctg tgg cca gac ggg cag gag gtg gtg tgg gat gac cgg      288
Ser Ser Val Leu Trp Pro Asp Gly Gln Glu Val Val Trp Asp Asp Arg
                 85                  90                  95 cgg ggc atg ctc gtg tcc acg cca ctg ctg cac gat gcc ctg tac ctg      336
Arg Gly Met Leu Val Ser Thr Pro Leu Leu His Asp Ala Leu Tyr Leu
            100                 105                 110 cag tgc gag acc acc tgg gga gac cag gac ttc ctt tcc aac ccc ttc      384
Gln Cys Glu Thr Thr Trp Gly Asp Gln Asp Phe Leu Ser Asn Pro Phe
            115                 120                 125 ctg gtg cac gcg gat ccc atc gaa ggt cgt ggt ggt ggt ggt gat          432
Leu Val His Ala Asp Pro Ile Glu Gly Arg Gly Gly Gly Gly Asp
        130                 135                 140 ccc aaa tct tgt gac aaa cct cac aca tgc cca ctg tgc cca gca cct      480
Pro Lys Ser Cys Asp Lys Pro His Thr Cys Pro Leu Cys Pro Ala Pro
145                 150                 155                 160 gaa ctc ctg ggg gga ccg tca gtc ttc ctc ttc ccc cca aaa ccc aag      528
Glu Leu Leu Gly Gly Pro Ser Val Phe Leu Phe Pro Pro Lys Pro Lys
                165                 170                 175 gac acc ctc atg atc tcc cgg acc cct gag gtc aca tgc gtg gtg gtg      576
Asp Thr Leu Met Ile Ser Arg Thr Pro Glu Val Thr Cys Val Val Val
            180                 185                 190 gac gtg agc cac gaa gac cct gag gtc aag ttc aac tgg tac gtg gac      624
Asp Val Ser His Glu Asp Pro Glu Val Lys Phe Asn Trp Tyr Val Asp
            195                 200                 205 ggc gtg gag gtg cat aat gcc aag aca aag ccg cgg gag gag cag tac      672
Gly Val Glu Val His Asn Ala Lys Thr Lys Pro Arg Glu Glu Gln Tyr
        210                 215                 220 aac agc acg tac cgt gtg gtc agc gtc ctc acc gtc ctg cac cag gac      720
Asn Ser Thr Tyr Arg Val Val Ser Val Leu Thr Val Leu His Gln Asp
225                 230                 235                 240 tgg ctg aat ggc aag gag tac aag tgc aag gtc tcc aac aaa gcc ctc      768
Trp Leu Asn Gly Lys Glu Tyr Lys Cys Lys Val Ser Asn Lys Ala Leu
                245                 250                 255 cca gcc ccc atc gag aaa acc atc tcc aaa gcc aaa ggg cag ccc cga      816
Pro Ala Pro Ile Glu Lys Thr Ile Ser Lys Ala Lys Gly Gln Pro Arg
            260                 265                 270 gaa cca cag gtg tac acc ctg ccc cca tcc cgg gat gag ctg acc aag      864
Glu Pro Gln Val Tyr Thr Leu Pro Pro Ser Arg Asp Glu Leu Thr Lys
        275                 280                 285 aac cag gtc agc ctg acc tgc cta gtc aaa ggc ttc tat ccc agc gac      912
Asn Gln Val Ser Leu Thr Cys Leu Val Lys Gly Phe Tyr Pro Ser Asp
        290                 295                 300 atc gcc gtg gag tgg gag agc aat ggg cag ccg gag aac aac tac aag      960
Ile Ala Val Glu Trp Glu Ser Asn Gly Gln Pro Glu Asn Asn Tyr Lys
305                 310                 315                 320 gcc acg cct ccc gtg ctg gac tcc gac ggc tcc ttc ttc ctc tac agc     1008
Ala Thr Pro Pro Val Leu Asp Ser Asp Gly Ser Phe Phe Leu Tyr Ser
                325                 330                 335 aag ctc acc gtg gac aag agc agg tgg cag cag ggg aac gtc ttc tca     1056
Lys Leu Thr Val Asp Lys Ser Arg Trp Gln Gln Gly Asn Val Phe Ser
```

```
                    340                 345                 350
tgc tcc gtg atg cat gag gct ctg cac aac cac tac acg cag aag agc      1104
Cys Ser Val Met His Glu Ala Leu His Asn His Tyr Thr Gln Lys Ser
            355                 360                 365 ctc tcc ctg tct ccg ggt aaa tga                                      1128
Leu Ser Leu Ser Pro Gly Lys
        370                 375

<210> SEQ ID NO 54
<211> LENGTH: 375
<212> TYPE: PRT
<213> ORGANISM: Artificial sequence
<220> FEATURE:
<223> OTHER INFORMATION: Synthetic Construct

<400> SEQUENCE: 54

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Arg Asp Phe Glu Gln Pro Phe Ile
        35                  40                  45

Asn Lys Pro Asp Thr Leu Leu Val Asn Arg Lys Asp Ala Met Trp Val
    50                  55                  60

Pro Cys Leu Val Ser Ile Pro Gly Leu Asn Val Thr Leu Arg Ser Gln
65                  70                  75                  80

Ser Ser Val Leu Trp Pro Asp Gly Gln Glu Val Val Trp Asp Arg
            85                  90                  95

Arg Gly Met Leu Val Ser Thr Pro Leu Leu His Asp Ala Leu Tyr Leu
            100                 105                 110

Gln Cys Glu Thr Thr Trp Gly Asp Gln Asp Phe Leu Ser Asn Pro Phe
        115                 120                 125

Leu Val His Ala Asp Pro Ile Glu Gly Arg Gly Gly Gly Gly Asp
    130                 135                 140

Pro Lys Ser Cys Asp Lys Pro His Thr Cys Pro Leu Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Asp Glu Leu Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320
```

```
Ala Thr Pro Pro Val Leu Asp Ser Asp Gly Ser Phe Phe Leu Tyr Ser
            325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
            355                 360                 365

Leu Ser Leu Ser Pro Gly Lys
            370         375

<210> SEQ ID NO 55
<211> LENGTH: 1119
<212> TYPE: DNA
<213> ORGANISM: Artificial sequence
<220> FEATURE:
<223> OTHER INFORMATION: R-3 M
<220> FEATURE:
<221> NAME/KEY: CDS
<222> LOCATION: (1)..(1119)

<400> SEQUENCE: 55 atg cag cgg ggc gcc gcg ctg tgc ctg cga ctg tgg ctc tgc ctg gga     48
Met Gln Arg Gly Ala Ala Leu Cys Leu Arg Leu Trp Leu Cys Leu Gly
1               5                   10                  15 ctc ctg gac ggc ctg gtg agt ggc tac tcc atg acc ccc ccg acc ttg     96
Leu Leu Asp Gly Leu Val Ser Gly Tyr Ser Met Thr Pro Pro Thr Leu
                20                  25                  30 aac atc acg gag gag tca cac gtc aga gac ttt gag cag cca ttc atc    144
Asn Ile Thr Glu Glu Ser His Val Arg Asp Phe Glu Gln Pro Phe Ile
            35                  40                  45 aac aag cct gac acg ctc ttg gtc aac agg aag gac gcc atg tgg gtg    192
Asn Lys Pro Asp Thr Leu Leu Val Asn Arg Lys Asp Ala Met Trp Val
        50                  55                  60 ccc tgt ctg gtg tcc atc ccc ggc ctc aat gtc acg ctg cgc tcg caa    240
Pro Cys Leu Val Ser Ile Pro Gly Leu Asn Val Thr Leu Arg Ser Gln
65                  70                  75                  80 agc tcg gtg ctg tgg cca gac ggg cag gag gtg gtg tgg gat gac cgg    288
Ser Ser Val Leu Trp Pro Asp Gly Gln Glu Val Val Trp Asp Asp Arg
                85                  90                  95 cgg ggc atg ctc gtg tcc acg cca ctg ctg cac gat gcc ctg tac ctg    336
Arg Gly Met Leu Val Ser Thr Pro Leu Leu His Asp Ala Leu Tyr Leu
            100                 105                 110 cag tgc gag acc acc tgg gga gac cag gac ttc ctt tcc aac ccc ttc    384
Gln Cys Glu Thr Thr Trp Gly Asp Gln Asp Phe Leu Ser Asn Pro Phe
        115                 120                 125 gcg gat ccc atc gaa ggt cgt ggt ggt ggt ggt gat ccc aaa tct        432
Ala Asp Pro Ile Glu Gly Arg Gly Gly Gly Gly Asp Pro Lys Ser
    130                 135                 140 tgt gac aaa cct cac aca tgc cca ctg tgc cca gca cct gaa ctc ctg    480
Cys Asp Lys Pro His Thr Cys Pro Leu Cys Pro Ala Pro Glu Leu Leu
145                 150                 155                 160 ggg gga ccg tca gtc ttc ctc ttc ccc cca aaa ccc aag gac acc ctc    528
Gly Gly Pro Ser Val Phe Leu Phe Pro Pro Lys Pro Lys Asp Thr Leu
                165                 170                 175 atg atc tcc cgg acc cct gag gtc aca tgc gtg gtg gtg gac gtg agc    576
Met Ile Ser Arg Thr Pro Glu Val Thr Cys Val Val Val Asp Val Ser
            180                 185                 190 cac gaa gac cct gag gtc aag ttc aac tgg tac gtg gac ggc gtg gag    624
His Glu Asp Pro Glu Val Lys Phe Asn Trp Tyr Val Asp Gly Val Glu
        195                 200                 205 gtg cat aat gcc aag aca aag ccg cgg gag gag cag tac aac agc acg    672
```

```
Val His Asn Ala Lys Thr Lys Pro Arg Glu Glu Gln Tyr Asn Ser Thr
    210                 215                 220 tac cgt gtg gtc agc gtc ctc acc gtc ctg cac cag gac tgg ctg aat      720
Tyr Arg Val Val Ser Val Leu Thr Val Leu His Gln Asp Trp Leu Asn
225                 230                 235                 240 ggc aag gag tac aag tgc aag gtc tcc aac aaa gcc ctc cca gcc ccc      768
Gly Lys Glu Tyr Lys Cys Lys Val Ser Asn Lys Ala Leu Pro Ala Pro
                245                 250                 255 atc gag aaa acc atc tcc aaa gcc aaa ggg cag ccc cga gaa cca cag      816
Ile Glu Lys Thr Ile Ser Lys Ala Lys Gly Gln Pro Arg Glu Pro Gln
            260                 265                 270 gtg tac acc ctg ccc cca tcc cgg gat gag ctg acc aag aac cag gtc      864
Val Tyr Thr Leu Pro Pro Ser Arg Asp Glu Leu Thr Lys Asn Gln Val
        275                 280                 285 agc ctg acc tgc cta gtc aaa ggc ttc tat ccc agc gac atc gcc gtg      912
Ser Leu Thr Cys Leu Val Lys Gly Phe Tyr Pro Ser Asp Ile Ala Val
    290                 295                 300 gag tgg gag agc aat ggg cag ccg gag aac aac tac aag gcc acg cct      960
Glu Trp Glu Ser Asn Gly Gln Pro Glu Asn Asn Tyr Lys Ala Thr Pro
305                 310                 315                 320 ccc gtg ctg gac tcc gac ggc tcc ttc ttc ctc tac agc aag ctc acc     1008
Pro Val Leu Asp Ser Asp Gly Ser Phe Phe Leu Tyr Ser Lys Leu Thr
                325                 330                 335 gtg gac aag agc agg tgg cag cag ggg aac gtc ttc tca tgc tcc gtg     1056
Val Asp Lys Ser Arg Trp Gln Gln Gly Asn Val Phe Ser Cys Ser Val
            340                 345                 350 atg cat gag gct ctg cac aac cac tac acg cag aag agc ctc tcc ctg     1104
Met His Glu Ala Leu His Asn His Tyr Thr Gln Lys Ser Leu Ser Leu
        355                 360                 365 tct ccg ggt aaa tga                                                 1119
Ser Pro Gly Lys
    370

<210> SEQ ID NO 56
<211> LENGTH: 372
<212> TYPE: PRT
<213> ORGANISM: Artificial sequence
<220> FEATURE:
<223> OTHER INFORMATION: Synthetic Construct

<400> SEQUENCE: 56

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Arg Asp Phe Glu Gln Pro Phe Ile
        35                  40                  45

Asn Lys Pro Asp Thr Leu Leu Val Asn Arg Lys Asp Ala Met Trp Val
    50                  55                  60

Pro Cys Leu Val Ser Ile Pro Gly Leu Asn Val Thr Leu Arg Ser Gln
65                  70                  75                  80

Ser Ser Val Leu Trp Pro Asp Gly Gln Glu Val Val Trp Asp Asp Arg
                85                  90                  95

Arg Gly Met Leu Val Ser Thr Pro Leu Leu His Asp Ala Leu Tyr Leu
            100                 105                 110

Gln Cys Glu Thr Thr Trp Gly Asp Gln Asp Phe Leu Ser Asn Pro Phe
        115                 120                 125

Ala Asp Pro Ile Glu Gly Arg Gly Gly Gly Gly Asp Pro Lys Ser
    130                 135                 140
```

```
Cys Asp Lys Pro His Thr Cys Pro Leu Cys Pro Ala Pro Glu Leu Leu
145                 150                 155                 160

Gly Gly Pro Ser Val Phe Leu Phe Pro Pro Lys Pro Lys Asp Thr Leu
            165                 170                 175

Met Ile Ser Arg Thr Pro Glu Val Thr Cys Val Val Val Asp Val Ser
        180                 185                 190

His Glu Asp Pro Glu Val Lys Phe Asn Trp Tyr Val Asp Gly Val Glu
    195                 200                 205

Val His Asn Ala Lys Thr Lys Pro Arg Glu Glu Gln Tyr Asn Ser Thr
210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Asp Glu Leu Thr Lys Asn Gln Val
        275                 280                 285

Ser Leu Thr Cys Leu Val Lys Gly Phe Tyr Pro Ser Asp Ile Ala Val
    290                 295                 300

Glu Trp Glu Ser Asn Gly Gln Pro Glu Asn Asn Tyr Lys Ala Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
        355                 360                 365

Ser Pro Gly Lys
    370

<210> SEQ ID NO 57
<211> LENGTH: 1161
<212> TYPE: DNA
<213> ORGANISM: Artificial sequence
<220> FEATURE:
<223> OTHER INFORMATION: R-3 N
<220> FEATURE:
<221> NAME/KEY: CDS
<222> LOCATION: (1)..(1161)

<400> SEQUENCE: 57 atg cag cgg ggc gcc gcg ctg tgc ctg cga ctg tgg ctc tgc ctg gga     48
Met Gln Arg Gly Ala Ala Leu Cys Leu Arg Leu Trp Leu Cys Leu Gly
1               5                   10                  15 ctc ctg gac ggc ctg gtg agt ggc tac tcc atg acc ccc ccg acc ttg     96
Leu Leu Asp Gly Leu Val Ser Gly Tyr Ser Met Thr Pro Pro Thr Leu
            20                  25                  30 aac atc acg gag gag tca cac gtc aac gag ctc tat gac atc cag ctg    144
Asn Ile Thr Glu Glu Ser His Val Asn Glu Leu Tyr Asp Ile Gln Leu
        35                  40                  45 ttg ccc agg aag tcg ctg gag ctg ctg gta ggg gag aag ctg gtc ctg    192
Leu Pro Arg Lys Ser Leu Glu Leu Leu Val Gly Glu Lys Leu Val Leu
    50                  55                  60 aac tgc acc gtg tgg gct gag ttt aac tca ggt gtc acc ttt gac tgg    240
Asn Cys Thr Val Trp Ala Glu Phe Asn Ser Gly Val Thr Phe Asp Trp
65                  70                  75                  80
```

```
gac tac cca ggg aag cag gca gag cgg ggt aag tgg gtg ccc gag cga    288
Asp Tyr Pro Gly Lys Gln Ala Glu Arg Gly Lys Trp Val Pro Glu Arg
                85                  90                  95 cgc tcc cag cag acc cac aca gaa ctc tcc agc atc ctg acc atc cac    336
Arg Ser Gln Gln Thr His Thr Glu Leu Ser Ser Ile Leu Thr Ile His
            100                 105                 110 aac gtc agc cag cac gac ctg ggc tcg tat gtg tgc aag gcc aac aac    384
Asn Val Ser Gln His Asp Leu Gly Ser Tyr Val Cys Lys Ala Asn Asn
        115                 120                 125 ggc atc cag cga ttt cgg gag agc acc gag gtc att gtg cat gag gat    432
Gly Ile Gln Arg Phe Arg Glu Ser Thr Glu Val Ile Val His Glu Asp
    130                 135                 140 ccc atc gaa ggt cgt ggt ggt ggt ggt gat ccc aaa tct tgt gac        480
Pro Ile Glu Gly Arg Gly Gly Gly Gly Asp Pro Lys Ser Cys Asp
145                 150                 155                 160 aaa cct cac aca tgc cca ctg tgc cca gca cct gaa ctc ctg ggg gga    528
Lys Pro His Thr Cys Pro Leu Cys Pro Ala Pro Glu Leu Leu Gly Gly
                165                 170                 175 ccg tca gtc ttc ctc ttc ccc cca aaa ccc aag gac acc ctc atg atc    576
Pro Ser Val Phe Leu Phe Pro Pro Lys Pro Lys Asp Thr Leu Met Ile
            180                 185                 190 tcc cgg acc cct gag gtc aca tgc gtg gtg gtg gac gtg agc cac gaa    624
Ser Arg Thr Pro Glu Val Thr Cys Val Val Val Asp Val Ser His Glu
        195                 200                 205 gac cct gag gtc aag ttc aac tgg tac gtg gac ggc gtg gag gtg cat    672
Asp Pro Glu Val Lys Phe Asn Trp Tyr Val Asp Gly Val Glu Val His
    210                 215                 220 aat gcc aag aca aag ccg cgg gag gag cag tac aac agc acg tac cgt    720
Asn Ala Lys Thr Lys Pro Arg Glu Glu Gln Tyr Asn Ser Thr Tyr Arg
225                 230                 235                 240 gtg gtc agc gtc ctc acc gtc ctg cac cag gac tgg ctg aat ggc aag    768
Val Val Ser Val Leu Thr Val Leu His Gln Asp Trp Leu Asn Gly Lys
                245                 250                 255 gag tac aag tgc aag gtc tcc aac aaa gcc ctc cca gcc ccc atc gag    816
Glu Tyr Lys Cys Lys Val Ser Asn Lys Ala Leu Pro Ala Pro Ile Glu
            260                 265                 270 aaa acc atc tcc aaa gcc aaa ggg cag ccc cga gaa cca cag gtg tac    864
Lys Thr Ile Ser Lys Ala Lys Gly Gln Pro Arg Glu Pro Gln Val Tyr
        275                 280                 285 acc ctg ccc cca tcc cgg gat gag ctg acc aag aac cag gtc agc ctg    912
Thr Leu Pro Pro Ser Arg Asp Glu Leu Thr Lys Asn Gln Val Ser Leu
    290                 295                 300 acc tgc cta gtc aaa ggc ttc tat ccc agc gac atc gcc gtg gag tgg    960
Thr Cys Leu Val Lys Gly Phe Tyr Pro Ser Asp Ile Ala Val Glu Trp
305                 310                 315                 320 gag agc aat ggg cag ccg gag aac aac tac aag gcc acg cct ccc gtg   1008
Glu Ser Asn Gly Gln Pro Glu Asn Asn Tyr Lys Ala Thr Pro Pro Val
                325                 330                 335 ctg gac tcc gac ggc tcc ttc ttc ctc tac agc aag ctc acc gtg gac   1056
Leu Asp Ser Asp Gly Ser Phe Phe Leu Tyr Ser Lys Leu Thr Val Asp
            340                 345                 350 aag agc agg tgg cag cag ggg aac gtc ttc tca tgc tcc gtg atg cat   1104
Lys Ser Arg Trp Gln Gln Gly Asn Val Phe Ser Cys Ser Val Met His
        355                 360                 365 gag gct ctg cac aac cac tac acg cag aag agc ctc tcc ctg tct ccg   1152
Glu Ala Leu His Asn His Tyr Thr Gln Lys Ser Leu Ser Leu Ser Pro
    370                 375                 380 ggt aaa tga                                                       1161
Gly Lys
385
```

<210> SEQ ID NO 58
<211> LENGTH: 386
<212> TYPE: PRT
<213> ORGANISM: Artificial sequence
<220> FEATURE:
<223> OTHER INFORMATION: Synthetic Construct

<400> SEQUENCE: 58

```
Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Asn Glu Leu Tyr Asp Ile Gln Leu
        35                  40                  45

Leu Pro Arg Lys Ser Leu Glu Leu Leu Val Gly Glu Lys Leu Val Leu
    50                  55                  60

Asn Cys Thr Val Trp Ala Glu Phe Asn Ser Gly Val Thr Phe Asp Trp
65                  70                  75                  80

Asp Tyr Pro Gly Lys Gln Ala Glu Arg Gly Lys Trp Val Pro Glu Arg
                85                  90                  95

Arg Ser Gln Gln Thr His Thr Glu Leu Ser Ser Ile Leu Thr Ile His
            100                 105                 110

Asn Val Ser Gln His Asp Leu Gly Ser Tyr Val Cys Lys Ala Asn Asn
        115                 120                 125

Gly Ile Gln Arg Phe Arg Glu Ser Thr Glu Val Ile Val His Glu Asp
    130                 135                 140

Pro Ile Glu Gly Arg Gly Gly Gly Gly Asp Pro Lys Ser Cys Asp
145                 150                 155                 160

Lys Pro His Thr Cys Pro Leu Cys Pro Ala Pro Glu Leu Leu Gly Gly
                165                 170                 175

Pro Ser Val Phe Leu Phe Pro Pro Lys Pro Lys Asp Thr Leu Met Ile
            180                 185                 190

Ser Arg Thr Pro Glu Val Thr Cys Val Val Val Asp Val Ser His Glu
        195                 200                 205

Asp Pro Glu Val Lys Phe Asn Trp Tyr Val Asp Gly Val Glu Val His
    210                 215                 220

Asn Ala Lys Thr Lys Pro Arg Glu Glu Gln Tyr Asn Ser Thr Tyr Arg
225                 230                 235                 240

Val Val Ser Val Leu Thr Val Leu His Gln Asp Trp Leu Asn Gly Lys
                245                 250                 255

Glu Tyr Lys Cys Lys Val Ser Asn Lys Ala Leu Pro Ala Pro Ile Glu
            260                 265                 270

Lys Thr Ile Ser Lys Ala Lys Gly Gln Pro Arg Glu Pro Gln Val Tyr
        275                 280                 285

Thr Leu Pro Pro Ser Arg Asp Glu Leu Thr Lys Asn Gln Val Ser Leu
    290                 295                 300

Thr Cys Leu Val Lys Gly Phe Tyr Pro Ser Asp Ile Ala Val Glu Trp
305                 310                 315                 320

Glu Ser Asn Gly Gln Pro Glu Asn Asn Tyr Lys Ala Thr Pro Pro Val
                325                 330                 335

Leu Asp Ser Asp Gly Ser Phe Phe Leu Tyr Ser Lys Leu Thr Val Asp
            340                 345                 350

Lys Ser Arg Trp Gln Gln Gly Asn Val Phe Ser Cys Ser Val Met His
        355                 360                 365
```

Glu Ala Leu His Asn His Tyr Thr Gln Lys Ser Leu Ser Leu Ser Pro
        370                 375                 380
Gly Lys
385

<210> SEQ ID NO 59
<211> LENGTH: 27
<212> TYPE: DNA
<213> ORGANISM: Artificial sequence
<220> FEATURE:
<223> OTHER INFORMATION: VEGFR-2 D1 reverse primer

<400> SEQUENCE: 59
gctggatctt gaacatagac ataaatg                                        27

<210> SEQ ID NO 60
<211> LENGTH: 27
<212> TYPE: DNA
<213> ORGANISM: Artificial sequence
<220> FEATURE:
<223> OTHER INFORMATION: VEGFR-2 D1-2 reverse primer #1

<400> SEQUENCE: 60
ctaggatccc ctacaacgac aactatg                                        27

<210> SEQ ID NO 61
<211> LENGTH: 27
<212> TYPE: DNA
<213> ORGANISM: Artificial sequence
<220> FEATURE:
<223> OTHER INFORMATION: VEGFR-2 D1-2 reverse primer #2

<400> SEQUENCE: 61
ctaggatcca catcataaat cctatac                                        27

<210> SEQ ID NO 62
<211> LENGTH: 36
<212> TYPE: DNA
<213> ORGANISM: Artificial sequence
<220> FEATURE:
<223> OTHER INFORMATION: VEGFR-2 D1-2 reverse primer #3

<400> SEQUENCE: 62
gcatggtctc ggatcatgag aagacggact cagaac                              36

<210> SEQ ID NO 63
<211> LENGTH: 26
<212> TYPE: DNA
<213> ORGANISM: Artificial sequence
<220> FEATURE:
<223> OTHER INFORMATION: VEGFR-2 D1-2 reverse primer #4

<400> SEQUENCE: 63
ctaggatcct tttctccaac agatag                                         26

<210> SEQ ID NO 64
<211> LENGTH: 29
<212> TYPE: DNA
<213> ORGANISM: Artificial sequence
<220> FEATURE:
<223> OTHER INFORMATION: VEGFR-2 D2 forward primer

<400> SEQUENCE: 64
agcgctagcg ttcaagatta cagatctcc                                      29

<210> SEQ ID NO 65
<211> LENGTH: 21
<212> TYPE: DNA
<213> ORGANISM: Artificial sequence
<220> FEATURE:
<223> OTHER INFORMATION: VEGFR--2 D2-3 reverse primer

<400> SEQUENCE: 65
atgtgtgagg ttttgcacaa g                                                   21

<210> SEQ ID NO 66
<211> LENGTH: 27
<212> TYPE: DNA
<213> ORGANISM: Artificial sequence
<220> FEATURE:
<223> OTHER INFORMATION: VEGFR-2 D2 reverse primer #1

<400> SEQUENCE: 66
ctaggatccc ctacaacgac aactatg                                             27

<210> SEQ ID NO 67
<211> LENGTH: 27
<212> TYPE: DNA
<213> ORGANISM: Artificial sequence
<220> FEATURE:
<223> OTHER INFORMATION: VEGFR-2 D2 reverse primer #2

<400> SEQUENCE: 67
ctaggatcca catcataaat cctatac                                             27

<210> SEQ ID NO 68
<211> LENGTH: 36
<212> TYPE: DNA
<213> ORGANISM: Artificial sequence
<220> FEATURE:
<223> OTHER INFORMATION: VEGFR-2 D2 reverse primer #3

<400> SEQUENCE: 68
gcatggtctc ggatcatgag aagacggact cagaac                                   36

<210> SEQ ID NO 69
<211> LENGTH: 26
<212> TYPE: DNA
<213> ORGANISM: Artificial sequence
<220> FEATURE:
<223> OTHER INFORMATION: VEGFR-2 D2 reverse primer #4

<400> SEQUENCE: 69
ctaggatcct tttctccaac agatag                                              26

<210> SEQ ID NO 70
<211> LENGTH: 27
<212> TYPE: DNA
<213> ORGANISM: Artificial sequence
<220> FEATURE:
<223> OTHER INFORMATION: VEGFR-2 D3 forward primer

<400> SEQUENCE: 70
agcgctagct ataggattta tgatgtg                                             27

<210> SEQ ID NO 71
<211> LENGTH: 21
<212> TYPE: DNA
<213> ORGANISM: Artificial sequence
<220> FEATURE:
<223> OTHER INFORMATION: VEGFR-2 D3 reverse primer

<400> SEQUENCE: 71
atgtgtgagg ttttgcacaa g                                           21

<210> SEQ ID NO 72
<211> LENGTH: 30
<212> TYPE: DNA
<213> ORGANISM: Artificial sequence
<220> FEATURE:
<223> OTHER INFORMATION: VEGFR-2 D1-3 primer 1

<400> SEQUENCE: 72
gcggatcctt gcctagtgtt tctcttgatc                                  30

<210> SEQ ID NO 73
<211> LENGTH: 40
<212> TYPE: DNA
<213> ORGANISM: Artificial sequence
<220> FEATURE:
<223> OTHER INFORMATION: VEGFR-2 D1-3 primer 2

<400> SEQUENCE: 73
ccagtcacct gctccggatc ttcatggacc ctgacaaatg                       40

<210> SEQ ID NO 74
<211> LENGTH: 25
<212> TYPE: DNA
<213> ORGANISM: Artificial sequence
<220> FEATURE:
<223> OTHER INFORMATION: VEGFR-3 D1-2 reverse primer 1

<400> SEQUENCE: 74
tcaggatccg cgagctcgtt gcctg                                       25

<210> SEQ ID NO 75
<211> LENGTH: 27
<212> TYPE: DNA
<213> ORGANISM: Artificial sequence
<220> FEATURE:
<223> OTHER INFORMATION: VEGFR-3 D1-2 reverse primer 2

<400> SEQUENCE: 75
tacaggatcc cctgtgatgt gcaccag                                     27

<210> SEQ ID NO 76
<211> LENGTH: 25
<212> TYPE: DNA
<213> ORGANISM: Artificial sequence
<220> FEATURE:
<223> OTHER INFORMATION: VEGFR-3 D1-2 reverse primer 3

<400> SEQUENCE: 76
tcaggatccg cgtgcaccag gaagg                                       25

<210> SEQ ID NO 77
<211> LENGTH: 26
<212> TYPE: DNA
<213> ORGANISM: Artificial sequence
<220> FEATURE:
<223> OTHER INFORMATION: VEGFR-3 D1-2 reverse primer 4

<400> SEQUENCE: 77
tcaggatccg cgaaggggtt ggaaag                                      26

<210> SEQ ID NO 78

```
<211> LENGTH: 60
<212> TYPE: DNA
<213> ORGANISM: Artificial sequence
<220> FEATURE:
<223> OTHER INFORMATION: VEGFR-3 Delta D1 primer 1

<400> SEQUENCE: 78
ccttgaacat cacggaggag tcacacgtca gagactttga gcagccattc atcaacaagc    60

<210> SEQ ID NO 79
<211> LENGTH: 42
<212> TYPE: DNA
<213> ORGANISM: Artificial sequence
<220> FEATURE:
<223> OTHER INFORMATION: VEGFR-3 Delta D1 primer 2

<400> SEQUENCE: 79
agctgctggt aggggagaag gatcctgaac tgcaccgtgt gg                       42

<210> SEQ ID NO 80
<211> LENGTH: 990
<212> TYPE: DNA
<213> ORGANISM: Homo sapiens
<220> FEATURE:
<221> NAME/KEY: misc_feature
<223> OTHER INFORMATION: VEGF-A
<220> FEATURE:
<221> NAME/KEY: CDS
<222> LOCATION: (57)..(629)

<400> SEQUENCE: 80
cagtgtgctg gcggcccggc gcgagccggc ccggccccgg tcgggcctcc gaaacc atg    59
                                                              Met
                                                              1 aac ttt ctg ctg tct tgg gtg cat tgg agc ctc gcc ttg ctg ctc tac    107
Asn Phe Leu Leu Ser Trp Val His Trp Ser Leu Ala Leu Leu Leu Tyr
        5                   10                  15 ctc cac cat gcc aag tgg tcc cag gct gca ccc atg gca gaa gga gga    155
Leu His His Ala Lys Trp Ser Gln Ala Ala Pro Met Ala Glu Gly Gly
            20                  25                  30 ggg cag aat cat cac gaa gtg gtg aag ttc atg gat gtc tat cag cgc    203
Gly Gln Asn His His Glu Val Val Lys Phe Met Asp Val Tyr Gln Arg
 35                  40                  45 agc tac tgc cat cca atc gag acc ctg gtg gac atc ttc cag gag tac    251
Ser Tyr Cys His Pro Ile Glu Thr Leu Val Asp Ile Phe Gln Glu Tyr
 50                  55                  60                  65 cct gat gag atc gag tac atc ttc aag cca tcc tgt gtg ccc ctg atg    299
Pro Asp Glu Ile Glu Tyr Ile Phe Lys Pro Ser Cys Val Pro Leu Met
                 70                  75                  80 cga tgc ggg ggc tgc tgc aat gac gag ggc ctg gag tgt gtg ccc act    347
Arg Cys Gly Gly Cys Cys Asn Asp Glu Gly Leu Glu Cys Val Pro Thr
             85                  90                  95 gag gag tcc aac atc acc atg cag att atg cgg atc aaa cct cac caa    395
Glu Glu Ser Asn Ile Thr Met Gln Ile Met Arg Ile Lys Pro His Gln
        100                 105                 110 ggc cag cac ata gga gag atg agc ttc cta cag cac aac aaa tgt gaa    443
Gly Gln His Ile Gly Glu Met Ser Phe Leu Gln His Asn Lys Cys Glu
    115                 120                 125 tgc aga cca aag aaa gat aga gca aga caa gaa aat ccc tgt ggg cct    491
Cys Arg Pro Lys Lys Asp Arg Ala Arg Gln Glu Asn Pro Cys Gly Pro
130                 135                 140                 145 tgc tca gag cgg aga aag cat ttg ttt gta caa gat ccg cag acg tgt    539
Cys Ser Glu Arg Arg Lys His Leu Phe Val Gln Asp Pro Gln Thr Cys
                150                 155                 160
```

```
aaa tgt tcc tgc aaa aac aca gac tcg cgt tgc aag gcg agg cag ctt    587
Lys Cys Ser Cys Lys Asn Thr Asp Ser Arg Cys Lys Ala Arg Gln Leu
            165                 170                 175 gag tta aac gaa cgt act tgc aga tgt gac aag ccg agg cgg            629
Glu Leu Asn Glu Arg Thr Cys Arg Cys Asp Lys Pro Arg Arg
        180                 185                 190 tgagccgggc aggaggaagg agcctccctc agggtttcgg gaaccagatc tctcaccagg  689
aaagactgat acagaacgat cgatacagaa accacgctgc cgccaccaca ccatcaccat  749
cgacagaaca gtccttaatc agaaacctg aaatgaagga agaggagact ctgcgcagag   809
cactttgggt ccggagggcg agactccggc ggaagcattc ccgggcgggt gacccagcac  869
ggtccctctt ggaattggat tcgccatttt attttcttg ctgctaaatc accgagcccg   929
gaagattaga gagttttatt tctgggattc ctgtagacac accgcggccg ccagcacact  989
g                                                                 990
```

```
<210> SEQ ID NO 81
<211> LENGTH: 191
<212> TYPE: PRT
<213> ORGANISM: Homo sapiens

<400> SEQUENCE: 81
```

```
Met Asn Phe Leu Leu Ser Trp Val His Trp Ser Leu Ala Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
                35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Asn Pro Cys Gly
        130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190
```

```
<210> SEQ ID NO 82
<211> LENGTH: 1997
<212> TYPE: DNA
<213> ORGANISM: Homo sapiens
<220> FEATURE:
<221> NAME/KEY: misc_feature
<223> OTHER INFORMATION: VEGF-C
<220> FEATURE:
<221> NAME/KEY: CDS
<222> LOCATION: (352)..(1608)
```

<400> SEQUENCE: 82

```
cccgccccgc ctctccaaaa agctacaccg acgcggaccg cggcggcgtc ctccctcgcc      60
ctcgcttcac ctcgcgggct ccgaatgcgg ggagctcgga tgtccggttt cctgtgaggc     120
ttttacctga cacccgccgc ctttcccgg cactggctgg gagggcgccc tgcaaagttg      180
ggaacgcgga gccccggacc cgctcccgcc gcctccggct cgcccagggg gggtcgccgg     240
gaggagcccg ggggagaggg accaggaggg gcccgcggcc tcgcagggggc gcccgcgccc    300 ccaccccctgc ccccgccagc ggaccggtcc cccaccccccg gtccttccac c atg cac    357
                                                            Met His
                                                             1
```

| | | | | | | | | | | | | | | | | |
|---|---|---|---|---|---|---|---|---|---|---|---|---|---|---|---|---|
| ttg | ctg | ggc | ttc | ttc | tct | gtg | gcg | tgt | tct | ctg | ctc | gcc | gct | gcg | ctg | 405 |
| Leu | Leu | Gly | Phe | Phe | Ser | Val | Ala | Cys | Ser | Leu | Leu | Ala | Ala | Ala | Leu | |
| | | 5 | | | | 10 | | | | | 15 | | | | | |
| ctc | ccg | ggt | cct | cgc | gag | gcg | ccc | gcc | gcc | gcc | gcc | ttc | gag | tcc | | 453 |
| Leu | Pro | Gly | Pro | Arg | Glu | Ala | Pro | Ala | Ala | Ala | Ala | Phe | Glu | Ser | | |
| | 20 | | | | | 25 | | | | | 30 | | | | | |
| gga | ctc | gac | ctc | tcg | gac | gcg | gag | ccc | gac | gcg | ggc | gag | gcc | acg | gct | 501 |
| Gly | Leu | Asp | Leu | Ser | Asp | Ala | Glu | Pro | Asp | Ala | Gly | Glu | Ala | Thr | Ala | |
| 35 | | | | | 40 | | | | | 45 | | | | | 50 | |
| tat | gca | agc | aaa | gat | ctg | gag | gag | cag | tta | cgg | tct | gtg | tcc | agt | gta | 549 |
| Tyr | Ala | Ser | Lys | Asp | Leu | Glu | Glu | Gln | Leu | Arg | Ser | Val | Ser | Ser | Val | |
| | | | | 55 | | | | | 60 | | | | | 65 | | |
| gat | gaa | ctc | atg | act | gta | ctc | tac | cca | gaa | tat | tgg | aaa | atg | tac | aag | 597 |
| Asp | Glu | Leu | Met | Thr | Val | Leu | Tyr | Pro | Glu | Tyr | Trp | Lys | Met | Tyr | Lys | |
| | | | 70 | | | | | 75 | | | | | 80 | | | |
| tgt | cag | cta | agg | aaa | gga | ggc | tgg | caa | cat | aac | aga | gaa | cag | gcc | aac | 645 |
| Cys | Gln | Leu | Arg | Lys | Gly | Gly | Trp | Gln | His | Asn | Arg | Glu | Gln | Ala | Asn | |
| | 85 | | | | | 90 | | | | | 95 | | | | | |
| ctc | aac | tca | agg | aca | gaa | gag | act | ata | aaa | ttt | gct | gca | gca | cat | tat | 693 |
| Leu | Asn | Ser | Arg | Thr | Glu | Glu | Thr | Ile | Lys | Phe | Ala | Ala | Ala | His | Tyr | |
| 100 | | | | | 105 | | | | | 110 | | | | | | |
| aat | aca | gag | atc | ttg | aaa | agt | att | gat | aat | gag | tgg | aga | aag | act | caa | 741 |
| Asn | Thr | Glu | Ile | Leu | Lys | Ser | Ile | Asp | Asn | Glu | Trp | Arg | Lys | Thr | Gln | |
| 115 | | | | 120 | | | | | 125 | | | | | 130 | | |
| tgc | atg | cca | cgg | gag | gtg | tgt | ata | gat | gtg | ggg | aag | gag | ttt | gga | gtc | 789 |
| Cys | Met | Pro | Arg | Glu | Val | Cys | Ile | Asp | Val | Gly | Lys | Glu | Phe | Gly | Val | |
| | | | 135 | | | | | 140 | | | | | 145 | | | |
| gcg | aca | aac | acc | ttc | ttt | aaa | cct | cca | tgt | gtg | tcc | gtc | tac | aga | tgt | 837 |
| Ala | Thr | Asn | Thr | Phe | Phe | Lys | Pro | Pro | Cys | Val | Ser | Val | Tyr | Arg | Cys | |
| | | 150 | | | | | 155 | | | | | 160 | | | | |
| ggg | ggt | tgc | tgc | aat | agt | gag | ggg | ctg | cag | tgc | atg | aac | acc | agc | acg | 885 |
| Gly | Gly | Cys | Cys | Asn | Ser | Glu | Gly | Leu | Gln | Cys | Met | Asn | Thr | Ser | Thr | |
| | 165 | | | | | 170 | | | | | 175 | | | | | |
| agc | tac | ctc | agc | aag | acg | tta | ttt | gaa | att | aca | gtg | cct | ctc | tct | caa | 933 |
| Ser | Tyr | Leu | Ser | Lys | Thr | Leu | Phe | Glu | Ile | Thr | Val | Pro | Leu | Ser | Gln | |
| 180 | | | | | 185 | | | | | 190 | | | | | | |
| ggc | ccc | aaa | cca | gta | aca | atc | agt | ttt | gcc | aat | cac | act | tcc | tgc | cga | 981 |
| Gly | Pro | Lys | Pro | Val | Thr | Ile | Ser | Phe | Ala | Asn | His | Thr | Ser | Cys | Arg | |
| 195 | | | | 200 | | | | | 205 | | | | | 210 | | |
| tgc | atg | tct | aaa | ctg | gat | gtt | tac | aga | caa | gtt | cat | tcc | att | att | aga | 1029 |
| Cys | Met | Ser | Lys | Leu | Asp | Val | Tyr | Arg | Gln | Val | His | Ser | Ile | Ile | Arg | |
| | | | 215 | | | | | 220 | | | | | 225 | | | |
| cgt | tcc | ctg | cca | gca | aca | cta | cca | cag | tgt | cag | gca | gcg | aac | aag | acc | 1077 |
| Arg | Ser | Leu | Pro | Ala | Thr | Leu | Pro | Gln | Cys | Gln | Ala | Ala | Asn | Lys | Thr | |
| | | 230 | | | | | 235 | | | | | 240 | | | | |
| tgc | ccc | acc | aat | tac | atg | tgg | aat | aat | cac | atc | tgc | aga | tgc | ctg | gct | 1125 |
| Cys | Pro | Thr | Asn | Tyr | Met | Trp | Asn | Asn | His | Ile | Cys | Arg | Cys | Leu | Ala | |
| | 245 | | | | | 250 | | | | | 255 | | | | | |

```
cag gaa gat ttt atg ttt tcc tcg gat gct gga gat gac tca aca gat    1173
Gln Glu Asp Phe Met Phe Ser Ser Asp Ala Gly Asp Asp Ser Thr Asp
    260                 265                 270 gga ttc cat gac atc tgt gga cca aac aag gag ctg gat gaa gag acc    1221
Gly Phe His Asp Ile Cys Gly Pro Asn Lys Glu Leu Asp Glu Glu Thr
275                 280                 285                 290 tgt cag tgt gtc tgc aga gcg ggg ctt cgg cct gcc agc tgt gga ccc    1269
Cys Gln Cys Val Cys Arg Ala Gly Leu Arg Pro Ala Ser Cys Gly Pro
                295                 300                 305 cac aaa gaa cta gac aga aac tca tgc cag tgt gtc tgt aaa aac aaa    1317
His Lys Glu Leu Asp Arg Asn Ser Cys Gln Cys Val Cys Lys Asn Lys
            310                 315                 320 ctc ttc ccc agc caa tgt ggg gcc aac cga gaa ttt gat gaa aac aca    1365
Leu Phe Pro Ser Gln Cys Gly Ala Asn Arg Glu Phe Asp Glu Asn Thr
        325                 330                 335 tgc cag tgt gta tgt aaa aga acc tgc ccc aga aat caa ccc cta aat    1413
Cys Gln Cys Val Cys Lys Arg Thr Cys Pro Arg Asn Gln Pro Leu Asn
    340                 345                 350 cct gga aaa tgt gcc tgt gaa tgt aca gaa agt cca cag aaa tgc ttg    1461
Pro Gly Lys Cys Ala Cys Glu Cys Thr Glu Ser Pro Gln Lys Cys Leu
355                 360                 365                 370 tta aaa gga aag aag ttc cac cac caa aca tgc agc tgt tac aga cgg    1509
Leu Lys Gly Lys Lys Phe His His Gln Thr Cys Ser Cys Tyr Arg Arg
                375                 380                 385 cca tgt acg aac cgc cag aag gct tgt gag cca gga ttt tca tat agt    1557
Pro Cys Thr Asn Arg Gln Lys Ala Cys Glu Pro Gly Phe Ser Tyr Ser
                390                 395                 400 gaa gaa gtg tgt cgt tgt gtc cct tca tat tgg aaa aga cca caa atg    1605
Glu Glu Val Cys Arg Cys Val Pro Ser Tyr Trp Lys Arg Pro Gln Met
            405                 410                 415 agc taagattgta ctgttttcca gttcatcgat tttctattat ggaaaactgt          1658
Ser gttgccacag tagaactgtc tgtgaacaga gagacccttg tgggtccatg ctaacaaaga   1718
caaaagtctg tctttcctga accatgtgga taactttaca gaaatggact ggagctcatc   1778
tgcaaaaggc ctcttgtaaa gactggtttt ctgccaatga ccaaacagcc aagatttttcc  1838 tcttgtgatt tctttaaaag aatgactata aatttatttt ccactaaaaa tattgtttct   1898
gcattcattt ttatagcaac aacaattggt aaaactcact gtgatcaata tttttatatc   1958
atgcaaaata tgtttaaaat aaaatgaaaa ttgtattat                          1997

<210> SEQ ID NO 83
<211> LENGTH: 419
<212> TYPE: PRT
<213> ORGANISM: Homo sapiens

<400> SEQUENCE: 83

Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
            20                  25                  30

Glu Ser Gly Leu Asp Leu Ser Asp Ala Glu Pro Asp Ala Gly Glu Ala
        35                  40                  45

Thr Ala Tyr Ala Ser Lys Asp Leu Glu Glu Gln Leu Arg Ser Val Ser
    50                  55                  60

Ser Val Asp Glu Leu Met Thr Val Leu Tyr Pro Glu Tyr Trp Lys Met
65                  70                  75                  80
```

Tyr Lys Cys Gln Leu Arg Lys Gly Gly Trp Gln His Asn Arg Glu Gln
            85                  90                  95

Ala Asn Leu Asn Ser Arg Thr Glu Glu Thr Ile Lys Phe Ala Ala Ala
        100                 105                 110

His Tyr Asn Thr Glu Ile Leu Lys Ser Ile Asp Asn Glu Trp Arg Lys
        115                 120                 125

Thr Gln Cys Met Pro Arg Glu Val Cys Ile Asp Val Gly Lys Glu Phe
    130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
        195                 200                 205

Cys Arg Cys Met Ser Lys Leu Asp Val Tyr Arg Gln Val His Ser Ile
    210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
        275                 280                 285

Glu Thr Cys Gln Cys Val Cys Arg Ala Gly Leu Arg Pro Ala Ser Cys
    290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
            340                 345                 350

Leu Asn Pro Gly Lys Cys Ala Cys Glu Cys Thr Glu Ser Pro Gln Lys
        355                 360                 365

Cys Leu Leu Lys Gly Lys Lys Phe His His Gln Thr Cys Ser Cys Tyr
    370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                405                 410                 415

Gln Met Ser

<210> SEQ ID NO 84
<211> LENGTH: 1645
<212> TYPE: DNA
<213> ORGANISM: Homo sapiens
<220> FEATURE:
<221> NAME/KEY: misc_feature
<223> OTHER INFORMATION: PIGF
<220> FEATURE:
<221> NAME/KEY: CDS
<222> LOCATION: (322)..(768)

<400> SEQUENCE: 84

```
gggattcggg ccgcccagct acgggaggac ctggagtggc actgggcgcc cgacggacca      60
tccccgggac ccgcctgccc ctcggcgccc cgccccgccg ggccgctccc cgtcgggttc     120
cccagccaca gccttaccta cgggctcctg actccgcaag gcttccagaa gatgctcgaa     180
ccaccggccg gggcctcggg gcagcagtga gggaggcgtc cagcccccca ctcagctctt     240
ctcctcctgt gccaggggct ccccggggga tgagcatggt ggttttccct cggagccccc     300
tggctcggga cgtctgagaa g atg ccg gtc atg agg ctg ttc cct tgc ttc      351
                        Met Pro Val Met Arg Leu Phe Pro Cys Phe
                          1               5                  10 ctg cag ctc ctg gcc ggg ctg gcg ctg cct gct gtg ccc ccc cag cag      399
Leu Gln Leu Leu Ala Gly Leu Ala Leu Pro Ala Val Pro Pro Gln Gln
                 15                  20                  25 tgg gcc ttg tct gct ggg aac ggc tcg tca gag gtg gaa gtg gta ccc      447
Trp Ala Leu Ser Ala Gly Asn Gly Ser Ser Glu Val Glu Val Val Pro
             30                  35                  40 ttc cag gaa gtg tgg ggc cgc agc tac tgc cgg gcg ctg gag agg ctg      495
Phe Gln Glu Val Trp Gly Arg Ser Tyr Cys Arg Ala Leu Glu Arg Leu
         45                  50                  55 gtg gac gtc gtg tcc gag tac ccc agc gag gtg gag cac atg ttc agc      543
Val Asp Val Val Ser Glu Tyr Pro Ser Glu Val Glu His Met Phe Ser
     60                  65                  70 cca tcc tgt gtc tcc ctg ctg cgc tgc acc ggc tgc tgc ggc gat gag      591
Pro Ser Cys Val Ser Leu Leu Arg Cys Thr Gly Cys Cys Gly Asp Glu
 75                  80                  85                  90 aat ctg cac tgt gtg ccg gtg gag acg gcc aat gtc acc atg cag ctc      639
Asn Leu His Cys Val Pro Val Glu Thr Ala Asn Val Thr Met Gln Leu
                 95                 100                 105 cta aag atc cgt tct ggg gac cgg ccc tcc tac gtg gag ctg acg ttc      687
Leu Lys Ile Arg Ser Gly Asp Arg Pro Ser Tyr Val Glu Leu Thr Phe
             110                 115                 120 tct cag cac gtt cgc tgc gaa tgc cgg cct ctg cgg gag aag atg aag      735
Ser Gln His Val Arg Cys Glu Cys Arg Pro Leu Arg Glu Lys Met Lys
         125                 130                 135 ccg gaa agg tgc ggc gat gct gtt ccc cgg agg taacccaccc cttggaggag     788
Pro Glu Arg Cys Gly Asp Ala Val Pro Arg Arg
    140                 145 agagacccccg caccccggctc gtgtatttat taccgtcaca ctcttcagtg actcctgctg     848
gtacctgccc tctatttatt agccaactgt ttccctgctg aatgcctcgc tcccttcaag     908
acgaggggca gggaaggaca ggaccctcag gaattcagtg ccttcaacaa cgtgagagaa     968
agagagaagc cagccacaga cccctgggag cttccgcttt gaaagaagca agacacgtgg    1028
cctcgtgagg ggcaagctag gccccagagg ccctggaggt ctccaggggc ctgcagaagg    1088
aaagaagggg gccctgctac ctgttcttgg gcctcaggct ctgcacagac aagcagccct    1148
tgctttcgga gctcctgtcc aaagtaggga tgcggattct gctggggccg ccacggcctg    1208
gtggtgggaa ggccggcagc gggcggaggg gattcagcca cttcccccctc ttcttctgaa    1268 gatcagaaca ttcagctctg gagaacagtg gttgcctggg ggcttttgcc actccttgtc    1328
ccccgtgatc tcccctcaca ctttgccatt tgcttgtact gggacattgt tctttccggc    1388
cgaggtgcca ccaccctgcc cccactaaga gacacataca gagtgggccc cgggctggag    1448
aaagagctgc ctggatgaga aacagctcag ccagtgggga tgaggtcacc aggggaggag    1508
cctgtgcgtc ccagctgaag gcagtggcag gggagcaggt tccccaaggg ccctggcacc    1568
cccacaagct gtccctgcag ggccatctga ctgccaagcc agattctctt gaataaagta    1628
ttctagtgtg gaaacgc                                                    1645
```

<210> SEQ ID NO 85
<211> LENGTH: 149
<212> TYPE: PRT
<213> ORGANISM: Homo sapiens

<400> SEQUENCE: 85

```
Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
            20                  25                  30

Asn Gly Ser Ser Glu Val Glu Val Pro Phe Gln Glu Val Trp Gly
        35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
        115                 120                 125

Glu Cys Arg Pro Leu Arg Glu Lys Met Lys Pro Glu Arg Cys Gly Asp
    130                 135                 140

Ala Val Pro Arg Arg
145
```

<210> SEQ ID NO 86
<211> LENGTH: 2029
<212> TYPE: DNA
<213> ORGANISM: Homo sapiens
<220> FEATURE:
<221> NAME/KEY: misc_feature
<223> OTHER INFORMATION: VEGF-D
<220> FEATURE:
<221> NAME/KEY: CDS
<222> LOCATION: (411)..(1472)

<400> SEQUENCE: 86

```
gttgggttcc agctttctgt agctgtaagc attggtggcc acaccacctc cttacaaagc      60
aactagaacc tgcggcatac attggagaga ttttttttaat tttctggaca tgaagtaaat    120
ttagagtgct ttctaatttc aggtagaaga catgtccacc ttctgattat ttttggagaa    180
cattttgatt tttttcatct ctctctcccc accctaaga ttgtgcaaaa aaagcgtacc    240
ttgcctaatt gaaataattt cattggattt tgatcagaac tgattattg gttttctgtg     300 tgaagttttg aggtttcaaa ctttccttct ggagaatgcc ttttgaaaca attttctcta    360
gctgcctgat gtcaactgct tagtaatcag tggatattga atattcaaa atg tac        416
                                                     Met Tyr
                                                       1 aga gag tgg gta gtg gtg aat gtt ttc atg atg ttg tac gtc cag ctg      464
Arg Glu Trp Val Val Val Asn Val Phe Met Met Leu Tyr Val Gln Leu
        5                   10                  15 gtg cag ggc tcc agt aat gaa cat gga cca gtg aag cga tca tct cag      512
Val Gln Gly Ser Ser Asn Glu His Gly Pro Val Lys Arg Ser Ser Gln
    20                  25                  30 tcc aca ttg gaa cga tct gaa cag cag atc agg gct gct tct agt ttg      560
Ser Thr Leu Glu Arg Ser Glu Gln Gln Ile Arg Ala Ala Ser Ser Leu
```

-continued

```
            35                  40                  45                  50
gag gaa cta ctt cga att act cac tct gag gac tgg aag ctg tgg aga           608
Glu Glu Leu Leu Arg Ile Thr His Ser Glu Asp Trp Lys Leu Trp Arg
                55                  60                  65 tgc agg ctg agg ctc aaa agt ttt acc agt atg gac tct cgc tca gca           656
Cys Arg Leu Arg Leu Lys Ser Phe Thr Ser Met Asp Ser Arg Ser Ala
            70                  75                  80 tcc cat cgg tcc act agg ttt gcg gca act ttc tat gac att gaa aca           704
Ser His Arg Ser Thr Arg Phe Ala Ala Thr Phe Tyr Asp Ile Glu Thr
        85                  90                  95 cta aaa gtt ata gat gaa gaa tgg caa aga act cag tgc agc cct aga           752
Leu Lys Val Ile Asp Glu Glu Trp Gln Arg Thr Gln Cys Ser Pro Arg
    100                 105                 110 gaa acg tgc gtg gag gtg gcc agt gag ctg ggg aag agt acc aac aca           800
Glu Thr Cys Val Glu Val Ala Ser Glu Leu Gly Lys Ser Thr Asn Thr
115                 120                 125                 130 ttc ttc aag ccc cct tgt gtg aac gtg ttc cga tgt ggt ggc tgt tgc           848
Phe Phe Lys Pro Pro Cys Val Asn Val Phe Arg Cys Gly Gly Cys Cys
                135                 140                 145 aat gaa gag agc ctt atc tgt atg aac acc agc acc tcg tac att tcc           896
Asn Glu Glu Ser Leu Ile Cys Met Asn Thr Ser Thr Ser Tyr Ile Ser
            150                 155                 160 aaa cag ctc ttt gag ata tca gtg cct ttg aca tca gta cct gaa tta           944
Lys Gln Leu Phe Glu Ile Ser Val Pro Leu Thr Ser Val Pro Glu Leu
        165                 170                 175 gtg cct gtt aaa gtt gcc aat cat aca ggt tgt aag tgc ttg cca aca           992
Val Pro Val Lys Val Ala Asn His Thr Gly Cys Lys Cys Leu Pro Thr
    180                 185                 190 gcc ccc cgc cat cca tac tca att atc aga aga tcc atc cag atc cct          1040
Ala Pro Arg His Pro Tyr Ser Ile Ile Arg Arg Ser Ile Gln Ile Pro
195                 200                 205                 210 gaa gaa gat cgc tgt tcc cat tcc aag aaa ctc tgt cct att gac atg          1088
Glu Glu Asp Arg Cys Ser His Ser Lys Lys Leu Cys Pro Ile Asp Met
                215                 220                 225 cta tgg gat agc aac aaa tgt aaa tgt gtt ttg cag gag gaa aat cca          1136
Leu Trp Asp Ser Asn Lys Cys Lys Cys Val Leu Gln Glu Glu Asn Pro
            230                 235                 240 ctt gct gga aca gaa gac cac tct cat ctc cag gaa cca gct ctc tgt          1184
Leu Ala Gly Thr Glu Asp His Ser His Leu Gln Glu Pro Ala Leu Cys
        245                 250                 255 ggg cca cac atg atg ttt gac gaa gat cgt tgc gag tgt gtc tgt aaa          1232
Gly Pro His Met Met Phe Asp Glu Asp Arg Cys Glu Cys Val Cys Lys
    260                 265                 270 aca cca tgt ccc aaa gat cta atc cag cac ccc aaa aac tgc agt tgc          1280
Thr Pro Cys Pro Lys Asp Leu Ile Gln His Pro Lys Asn Cys Ser Cys
275                 280                 285                 290 ttt gag tgc aaa gaa agt ctg gag acc tgc tgc cag aag cac aag cta          1328
Phe Glu Cys Lys Glu Ser Leu Glu Thr Cys Cys Gln Lys His Lys Leu
                295                 300                 305 ttt cac cca gac acc tgc agc tgt gag gac aga tgc ccc ttt cat acc          1376
Phe His Pro Asp Thr Cys Ser Cys Glu Asp Arg Cys Pro Phe His Thr
            310                 315                 320 aga cca tgt gca agt ggc aaa aca gca tgt gca aag cat tgc cgc ttt          1424
Arg Pro Cys Ala Ser Gly Lys Thr Ala Cys Ala Lys His Cys Arg Phe
        325                 330                 335 cca aag gag aaa agg gct gcc cag ggg ccc cac agc cga aag aat cct          1472
Pro Lys Glu Lys Arg Ala Ala Gln Gly Pro His Ser Arg Lys Asn Pro
    340                 345                 350 tgattcagcg ttccaagttc cccatccctg tcattttaa cagcatgctg ctttgccaag          1532
```

```
ttgctgtcac tgttttttc ccaggtgtta aaaaaaaat ccattttaca cagcaccaca    1592
gtgaatccag accaaccttc cattcacacc agctaaggag tccctggttc attgatggat    1652
gtcttctagc tgcagatgcc tctgcgcacc aaggaatgga gaggagggga cccatgtaat    1712
ccttttgttt agttttgttt ttgttttttg gtgaatgaga aaggtgtgct ggtcatggaa    1772
tggcaggtgt catatgactg attactcaga gcagatgagg aaaactgtag tctctgagtc    1832
ctttgctaat cgcaactctt gtgaattatt ctgattcttt tttatgcaga atttgattcg    1892
tatgatcagt actgactttc tgattactgt ccagcttata gtcttccagt ttaatgaact    1952
accatctgat gtttcatatt taagtgtatt taaagaaaat aaacaccatt attcaagcca    2012
aaaaaaaaaa aaaaaaa                                                   2029
```

<210> SEQ ID NO 87
<211> LENGTH: 354
<212> TYPE: PRT
<213> ORGANISM: Homo sapiens

<400> SEQUENCE: 87

```
Met Tyr Arg Glu Trp Val Val Asn Val Phe Met Met Leu Tyr Val
1               5                   10                  15

Gln Leu Val Gln Gly Ser Ser Asn Glu His Gly Pro Val Lys Arg Ser
            20                  25                  30

Ser Gln Ser Thr Leu Glu Arg Ser Glu Gln Gln Ile Arg Ala Ala Ser
        35                  40                  45

Ser Leu Glu Glu Leu Leu Arg Ile Thr His Ser Glu Asp Trp Lys Leu
    50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Pro Cys Val Asn Val Phe Arg Cys Gly Gly
    130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
        195                 200                 205

Ile Pro Glu Glu Asp Arg Cys Ser His Ser Lys Lys Leu Cys Pro Ile
    210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
```

```
                275                 280                 285
Ser Cys Phe Glu Cys Lys Glu Ser Leu Glu Thr Cys Cys Gln Lys His
            290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
            340                 345                 350

Asn Pro

<210> SEQ ID NO 88
<211> LENGTH: 1830
<212> TYPE: DNA
<213> ORGANISM: ORF Virus
<220> FEATURE:
<221> NAME/KEY: misc_feature
<223> OTHER INFORMATION: VEGF-E
<220> FEATURE:
<221> NAME/KEY: CDS
<222> LOCATION: (312)..(755)

<400> SEQUENCE: 88
cggccacgcg gccgcgaact gcgcgctcgc gcgcgtggcg accgcgctga cgcgccgcgt       60
gcccgcgagc cggcacggcc tcgcggaggg cggcacgccg ccgtggacgc tgctgctggc      120
ggtggccgcg gtggcggtgc tcggcgtggt ggcaatttcg ctgctgcgcc gcgcgctaag      180
aatacggttt agatactcaa agtctatcca gacacttaga gtgtaacttt gagtaaaaaa      240
tgtaaatact aacgccaaaa tttcgatagt tgttaagcaa tatataacat ttttaaaacg      300
tcatcaccag c atg aag tta aca gct acg tta caa gtt gtt gtt gca ttg      350
            Met Lys Leu Thr Ala Thr Leu Gln Val Val Val Ala Leu
              1               5                  10 tta ata tgt atg tat aat ttg cca gaa tgc gtg tct cag agt aat gat      398
Leu Ile Cys Met Tyr Asn Leu Pro Glu Cys Val Ser Gln Ser Asn Asp
 15                  20                  25 tca cct cct tca acc aat gac tgg atg cgt aca cta gac aaa agt ggt      446
Ser Pro Pro Ser Thr Asn Asp Trp Met Arg Thr Leu Asp Lys Ser Gly
30                  35                  40                  45 tgt aaa cct aga gat act gtt gtt tat ttg gga gaa gaa tat cca gaa      494
Cys Lys Pro Arg Asp Thr Val Val Tyr Leu Gly Glu Glu Tyr Pro Glu
                50                  55                  60 agc act aac cta caa tat aat ccc cgg tgc gta act gtt aaa cga tgc      542
Ser Thr Asn Leu Gln Tyr Asn Pro Arg Cys Val Thr Val Lys Arg Cys
             65                  70                  75 agt ggt tgc tgt aac ggt gac ggt caa ata tgt aca gcg gtt gaa aca      590
Ser Gly Cys Cys Asn Gly Asp Gly Gln Ile Cys Thr Ala Val Glu Thr
         80                  85                  90 aga aat aca act gta aca gtt tca gta acc ggc gtg tct agt tcg tct      638
Arg Asn Thr Thr Val Thr Val Ser Val Thr Gly Val Ser Ser Ser Ser
     95                 100                 105 ggt act aat agt ggt gta tct act aac ctt caa aga ata agt gtt aca      686
Gly Thr Asn Ser Gly Val Ser Thr Asn Leu Gln Arg Ile Ser Val Thr
110                 115                 120                 125 gaa cac aca aag tgc gat tgt att ggt aga aca acg aca aca cct acg      734
Glu His Thr Lys Cys Asp Cys Ile Gly Arg Thr Thr Thr Thr Pro Thr
                130                 135                 140 acc act agg gaa cct aga cga taactaataa caaaaaatgt ttatttttgt        785
Thr Thr Arg Glu Pro Arg Arg
                145
```

```
aaatacttaa ttattacaca ctttacaata atctcaaaaa taaattgcgt gcccggacgg    845
ctgcagctgg tgacgctgct gtgtcacaca ctgcgtattc gattcaagtt cactaacgcc    905
actaaactag ttgtgcgtgt ccgagtgtta accgtacgtc aaactaacat cttacctgtc    965
cgtgacaaga actaaaactt gaaccacata tttttaaagt atatttaaca aaatcactca   1025
cactcacaca atcataaaca ccacaaccac aaccaaacac gcatgagaat taatattctt   1085
acttatccgt aacactctat gctgtacatc aacgcatcag agcagtctga gtctgactaa   1145
tggcggcaaa cgggaacgca ggcgcgacat aatcactgag aatctccgca gcaaccgctc   1205
aaggacatct ctagcgctaa cggctgtttg tcattccccc gtgtgttcat ctcacacgac   1265
attgtgaccg tcgcaaagca cacattcaaa gtgccgcatg tggaagaatt caccgtcgag   1325
acacacacca taattaaaca agatcagtgc ataagagaga ttagcattct acagcacacc   1385
acgtgcgaat acggacctcg taattgttta gactagaaca cctctggtct aaacaacatg   1445
tccgatctta gaacagagtt tatgacgcat atgtaactgt gttctttatg tagaagttat   1505
cttttatgtc actcccttgt cttagatgag ttatacatga catgatgtat gtgtcgcccg   1565
cggcggcgcg gggcgctcgg cggcggggct gctgcgcgcg gcgggcccgc ggtggcggcg   1625
gctggcgcgg cgctgcggcc gcgggcgcgc ggcggggtag cggcccgccc gcccgggcgc   1685
ccgccgcagc ccttgccccg gaccaggcgc acggagcaa agtgaaaaag gaccgcctag    1745
cagtcgagac cctcccgccg cagccgcgac accccacacc cgccttccac ccgccagacg   1805
ccaacaccac agccaacaag catgc                                         1830
```

<210> SEQ ID NO 89
<211> LENGTH: 148
<212> TYPE: PRT
<213> ORGANISM: ORF Virus

<400> SEQUENCE: 89

Met Lys Leu Thr Ala Thr Leu Gln Val Val Ala Leu Leu Ile Cys
1               5                   10                  15

Met Tyr Asn Leu Pro Glu Cys Val Ser Gln Ser Asn Asp Ser Pro Pro
            20                  25                  30

Ser Thr Asn Asp Trp Met Arg Thr Leu Asp Lys Ser Gly Cys Lys Pro
        35                  40                  45

Arg Asp Thr Val Val Tyr Leu Gly Glu Glu Tyr Pro Glu Ser Thr Asn
    50                  55                  60

Leu Gln Tyr Asn Pro Arg Cys Val Thr Lys Arg Cys Ser Gly Cys
65                  70                  75                  80

Cys Asn Gly Asp Gly Gln Ile Cys Thr Ala Val Glu Thr Arg Asn Thr
                85                  90                  95

Thr Val Thr Val Ser Val Thr Gly Val Ser Ser Ser Gly Thr Asn
            100                 105                 110

Ser Gly Val Ser Thr Asn Leu Gln Arg Ile Ser Val Thr Glu His Thr
        115                 120                 125

Lys Cys Asp Cys Ile Gly Arg Thr Thr Thr Thr Pro Thr Thr Thr Arg
    130                 135                 140

Glu Pro Arg Arg
145

<210> SEQ ID NO 90
<211> LENGTH: 815
<212> TYPE: DNA

<213> ORGANISM: Homo sapiens
<220> FEATURE:
<221> NAME/KEY: misc_feature
<223> OTHER INFORMATION: 232 amino acid isoform of VEGF-A
<220> FEATURE:
<221> NAME/KEY: CDS
<222> LOCATION: (69)..(767)

<400> SEQUENCE: 90

```
gaattcgaat tccagtgtgc tggcggccgc gcgcgagccg cgccggcccc ggtcgggcct      60 ccgaaacc atg aac ttt ctg ctg tct tgg gtg cat tgg agc ctc gcc ttg     110
         Met Asn Phe Leu Leu Ser Trp Val His Trp Ser Leu Ala Leu
         1               5                   10 ctg ctc tac ctc cac cat gcc aag tgg tcc cag gct gca ccc atg gca      158
Leu Leu Tyr Leu His His Ala Lys Trp Ser Gln Ala Ala Pro Met Ala
15                  20                  25                  30 gaa gga gga ggg cag aat cat cac gaa gtg gtg aag ttc atg gat gtc      206
Glu Gly Gly Gly Gln Asn His His Glu Val Val Lys Phe Met Asp Val
                35                  40                  45 tat cag cgc agc tac tgc cat cca atc gag acc ctg gtg gac atc ttc      254
Tyr Gln Arg Ser Tyr Cys His Pro Ile Glu Thr Leu Val Asp Ile Phe
        50                  55                  60 cag gag tac cct gat gag atc gag tac atc ttc aag cca tcc tgt gtg      302
Gln Glu Tyr Pro Asp Glu Ile Glu Tyr Ile Phe Lys Pro Ser Cys Val
    65                  70                  75 ccc ctg atg cga tgc ggg ggc tgc tgc aat gac gag ggc ctg gag tgt      350
Pro Leu Met Arg Cys Gly Gly Cys Cys Asn Asp Glu Gly Leu Glu Cys
80                  85                  90 gtg ccc act gag gag tcc aac atc acc atg cag att atg cgg atc aaa      398
Val Pro Thr Glu Glu Ser Asn Ile Thr Met Gln Ile Met Arg Ile Lys
95                  100                 105                 110 cct cac caa ggc cag cac ata gga gag atg agc ttc cta cag cac aac      446
Pro His Gln Gly Gln His Ile Gly Glu Met Ser Phe Leu Gln His Asn
                115                 120                 125 aaa tgt gaa tgc aga cca aag aaa gat aga gca aga caa gaa aaa aaa      494
Lys Cys Glu Cys Arg Pro Lys Lys Asp Arg Ala Arg Gln Glu Lys Lys
            130                 135                 140 tca gtt cga gga aag gga aag ggg caa aaa cga aag cgc aag aaa tcc      542
Ser Val Arg Gly Lys Gly Lys Gly Gln Lys Arg Lys Arg Lys Lys Ser
        145                 150                 155 cgg tat aag tcc tgg agc gtg tac gtt ggt gcc cgc tgc tgt cta atg      590
Arg Tyr Lys Ser Trp Ser Val Tyr Val Gly Ala Arg Cys Cys Leu Met
    160                 165                 170 ccc tgg agc ctc cct ggc ccc cat ccc tgt ggg cct tgc tca gag cgg      638
Pro Trp Ser Leu Pro Gly Pro His Pro Cys Gly Pro Cys Ser Glu Arg
175                 180                 185                 190 aga aag cat ttg ttt gta caa gat ccg cag acg tgt aaa tgt tcc tgc      686
Arg Lys His Leu Phe Val Gln Asp Pro Gln Thr Cys Lys Cys Ser Cys
                195                 200                 205 aaa aac aca gac tcg cgt tgc aag gcg agg cag ctt gag tta aac gaa      734
Lys Asn Thr Asp Ser Arg Cys Lys Ala Arg Gln Leu Glu Leu Asn Glu
            210                 215                 220 cgt act tgc aga tgt gac aag ccg agg cgg tga gccgggctgg aggaaggagc    787
Arg Thr Cys Arg Cys Asp Lys Pro Arg Arg
        225                 230 ctccctcagg gtttcgggaa ccagatcc                                       815
```

<210> SEQ ID NO 91
<211> LENGTH: 232
<212> TYPE: PRT
<213> ORGANISM: Homo sapiens

<400> SEQUENCE: 91

| Met | Asn | Phe | Leu | Leu | Ser | Trp | Val | His | Trp | Ser | Leu | Ala | Leu | Leu |
| 1 | | | | 5 | | | | | 10 | | | | | 15 |

| Tyr | Leu | His | His | Ala | Lys | Trp | Ser | Gln | Ala | Ala | Pro | Met | Ala | Glu | Gly |
| | | | 20 | | | | | 25 | | | | | 30 | | |

| Gly | Gly | Gln | Asn | His | His | Glu | Val | Val | Lys | Phe | Met | Asp | Val | Tyr | Gln |
| | | 35 | | | | | 40 | | | | | 45 | | | |

| Arg | Ser | Tyr | Cys | His | Pro | Ile | Glu | Thr | Leu | Val | Asp | Ile | Phe | Gln | Glu |
| | 50 | | | | | 55 | | | | | 60 | | | | |

| Tyr | Pro | Asp | Glu | Ile | Glu | Tyr | Ile | Phe | Lys | Pro | Ser | Cys | Val | Pro | Leu |
| 65 | | | | | 70 | | | | | 75 | | | | | 80 |

| Met | Arg | Cys | Gly | Gly | Cys | Cys | Asn | Asp | Glu | Gly | Leu | Glu | Cys | Val | Pro |
| | | | | 85 | | | | | 90 | | | | | 95 | |

| Thr | Glu | Glu | Ser | Asn | Ile | Thr | Met | Gln | Ile | Met | Arg | Ile | Lys | Pro | His |
| | | | | 100 | | | | | 105 | | | | | 110 | |

| Gln | Gly | Gln | His | Ile | Gly | Glu | Met | Ser | Phe | Leu | Gln | His | Asn | Lys | Cys |
| | | | 115 | | | | | 120 | | | | | 125 | | |

| Glu | Cys | Arg | Pro | Lys | Lys | Asp | Arg | Ala | Arg | Gln | Glu | Lys | Lys | Ser | Val |
| | 130 | | | | | 135 | | | | | 140 | | | | |

| Arg | Gly | Lys | Gly | Lys | Gly | Gln | Lys | Arg | Lys | Arg | Lys | Lys | Ser | Arg | Tyr |
| 145 | | | | | 150 | | | | | 155 | | | | | 160 |

| Lys | Ser | Trp | Ser | Val | Tyr | Val | Gly | Ala | Arg | Cys | Cys | Leu | Met | Pro | Trp |
| | | | | 165 | | | | | 170 | | | | | 175 | |

| Ser | Leu | Pro | Gly | Pro | His | Pro | Cys | Gly | Pro | Cys | Ser | Glu | Arg | Arg | Lys |
| | | | 180 | | | | | 185 | | | | | 190 | | |

| His | Leu | Phe | Val | Gln | Asp | Pro | Gln | Thr | Cys | Lys | Cys | Ser | Cys | Lys | Asn |
| | | | 195 | | | | | 200 | | | | | 205 | | |

| Thr | Asp | Ser | Arg | Cys | Lys | Ala | Arg | Gln | Leu | Glu | Leu | Asn | Glu | Arg | Thr |
| | 210 | | | | | 215 | | | | | 220 | | | | |

| Cys | Arg | Cys | Asp | Lys | Pro | Arg | Arg |
| 225 | | | | | 230 | | |

<210> SEQ ID NO 92
<211> LENGTH: 399
<212> TYPE: DNA
<213> ORGANISM: ORF virus
<220> FEATURE:
<221> NAME/KEY: misc_feature
<223> OTHER INFORMATION: D1701 VEGF
<220> FEATURE:
<221> NAME/KEY: CDS
<222> LOCATION: (1)..(399)

<400> SEQUENCE: 92

| atg | aag | ttt | ctc | gtc | ggc | ata | ctg | gta | gct | gtg | tgc | ttg | cac | cag | tat | 48 |
| Met | Lys | Phe | Leu | Val | Gly | Ile | Leu | Val | Ala | Val | Cys | Leu | His | Gln | Tyr | |
| 1 | | | | 5 | | | | | 10 | | | | | 15 | | |

| ctg | ctg | aac | gcg | gac | agc | acg | aaa | aca | tgg | tcc | gaa | gtg | ttt | gaa | aac | 96 |
| Leu | Leu | Asn | Ala | Asp | Ser | Thr | Lys | Thr | Trp | Ser | Glu | Val | Phe | Glu | Asn | |
| | | | | 20 | | | | | 25 | | | | | 30 | | |

| agc | ggg | tgc | aag | cca | agg | ccg | atg | gtc | ttt | cga | gta | cac | gac | gag | cac | 144 |
| Ser | Gly | Cys | Lys | Pro | Arg | Pro | Met | Val | Phe | Arg | Val | His | Asp | Glu | His | |
| | | | 35 | | | | | 40 | | | | | 45 | | | |

| ccg | gag | cta | act | tct | cag | cgg | ttc | aac | ccg | ccg | tgt | gtc | acg | ttg | atg | 192 |
| Pro | Glu | Leu | Thr | Ser | Gln | Arg | Phe | Asn | Pro | Pro | Cys | Val | Thr | Leu | Met | |
| | 50 | | | | | 55 | | | | | 60 | | | | | |

| cga | tgc | ggc | ggg | tgc | tgc | aac | gac | gag | agc | tta | gaa | tgc | gtc | ccc | acg | 240 |

```
                Arg Cys Gly Gly Cys Cys Asn Asp Glu Ser Leu Glu Cys Val Pro Thr
                65                  70                  75                  80 gaa gag gca aac gta acg atg caa ctc atg gga gcg tcg gtc tcc ggt              288
Glu Glu Ala Asn Val Thr Met Gln Leu Met Gly Ala Ser Val Ser Gly
                85                  90                  95 ggt aac ggg atg caa cat ctg agc ttc gta gag cat aag aaa tgc gat              336
Gly Asn Gly Met Gln His Leu Ser Phe Val Glu His Lys Lys Cys Asp
            100                 105                 110 tgt aaa cca cca ctc acg acc acg cca ccg acg acc aca agg ccg ccc              384
Cys Lys Pro Pro Leu Thr Thr Thr Pro Pro Thr Thr Thr Arg Pro Pro
            115                 120                 125 aga aga cgc cgc tag                                                          399
Arg Arg Arg Arg
        130

<210> SEQ ID NO 93
<211> LENGTH: 132
<212> TYPE: PRT
<213> ORGANISM: ORF virus

<400> SEQUENCE: 93

Met Lys Phe Leu Val Gly Ile Leu Val Ala Val Cys Leu His Gln Tyr
1               5                   10                  15

Leu Leu Asn Ala Asp Ser Thr Lys Thr Trp Ser Glu Val Phe Glu Asn
            20                  25                  30

Ser Gly Cys Lys Pro Arg Pro Met Val Phe Arg Val His Asp Glu His
        35                  40                  45

Pro Glu Leu Thr Ser Gln Arg Phe Asn Pro Pro Cys Val Thr Leu Met
    50                  55                  60

Arg Cys Gly Gly Cys Cys Asn Asp Glu Ser Leu Glu Cys Val Pro Thr
65                  70                  75                  80

Glu Glu Ala Asn Val Thr Met Gln Leu Met Gly Ala Ser Val Ser Gly
                85                  90                  95

Gly Asn Gly Met Gln His Leu Ser Phe Val Glu His Lys Lys Cys Asp
            100                 105                 110

Cys Lys Pro Pro Leu Thr Thr Thr Pro Pro Thr Thr Thr Arg Pro Pro
        115                 120                 125

Arg Arg Arg Arg
        130

<210> SEQ ID NO 94
<211> LENGTH: 570
<212> TYPE: DNA
<213> ORGANISM: Homo sapiens
<220> FEATURE:
<221> NAME/KEY: misc_feature
<223> OTHER INFORMATION: VEGF-B Isoform 1

<400> SEQUENCE: 94
accatgagcc ctctgctccg ccgcctgctg ctcgccgcac tcctgcagct ggccccgcc        60 caggcccctg tctcccagcc tgatgcccct ggccaccaga ggaaagtggt gtcatggata      120
gatgtgtata ctcgcgctac ctgccagccc cgggaggtgg tggtgcccct gactgtggag      180
ctcatgggca ccgtggccaa acagctggtg cccagctgcg tgactgtgca gcgctgtggt      240
ggctgctgcc ctgacgatgg cctggagtgt gtgcccactg gcagcacca  agtccggatg      300 cagatcctca tgatccggta cccgagcagt cagctggggg agatgtccct ggaagaacac      360
agccagtgtg aatgcagacc taaaaaaaag acagtgctg tgaagccaga cagccccagg      420
```

```
cccctctgcc cacgctgcac ccagcaccac cagcgccctg accccggac ctgccgctgc    480 cgctgccgac gccgcagctt cctccgttgc caagggcggg gcttagagct caacccagac    540
acctgcaggt gccggaagct gcgaaggtga                                     570
```

```
<210> SEQ ID NO 95
<211> LENGTH: 188
<212> TYPE: PRT
<213> ORGANISM: Homo sapiens
<220> FEATURE:
<221> NAME/KEY: MISC_FEATURE
<223> OTHER INFORMATION: VEGF-B Isoform 1
<220> FEATURE:
<221> NAME/KEY: mat_peptide
<222> LOCATION: (22)..(188)

<400> SEQUENCE: 95
```

```
Met Ser Pro Leu Leu Arg Arg Leu Leu Ala Ala Leu Leu Gln Leu
    -20             -15                 -10

Ala Pro Ala Gln Ala Pro Val Ser Gln Pro Asp Ala Pro Gly His Gln
 -5          -1   1               5                   10

Arg Lys Val Val Ser Trp Ile Asp Val Tyr Thr Arg Ala Thr Cys Gln
             15              20              25

Pro Arg Glu Val Val Val Pro Leu Thr Val Glu Leu Met Gly Thr Val
         30              35              40

Ala Lys Gln Leu Val Pro Ser Cys Val Thr Val Gln Arg Cys Gly Gly
 45              50              55

Cys Cys Pro Asp Asp Gly Leu Glu Cys Val Pro Thr Gly Gln His Gln
 60          65              70              75

Val Arg Met Gln Ile Leu Met Ile Arg Tyr Pro Ser Ser Gln Leu Gly
             80              85              90

Glu Met Ser Leu Glu Glu His Ser Gln Cys Glu Cys Arg Pro Lys Lys
         95              100             105

Lys Asp Ser Ala Val Lys Pro Asp Ser Pro Arg Pro Leu Cys Pro Arg
     110             115             120

Cys Thr Gln His His Gln Arg Pro Asp Pro Arg Thr Cys Arg Cys Arg
 125             130             135

Cys Arg Arg Arg Ser Phe Leu Arg Cys Gln Gly Arg Gly Leu Glu Leu
 140             145             150             155

Asn Pro Asp Thr Cys Arg Cys Arg Lys Leu Arg Arg
                 160             165
```

```
<210> SEQ ID NO 96
<211> LENGTH: 624
<212> TYPE: DNA
<213> ORGANISM: Homo sapiens
<220> FEATURE:
<221> NAME/KEY: misc_feature
<223> OTHER INFORMATION: VEGF-B Isoform 2

<400> SEQUENCE: 96
atgagccctc tgctccgccg cctgctgctc gccgcactcc tgcagctggc ccccgcccag    60
gcccctgtct cccagcctga tgcccctggc accagagga aagtggtgtc atggatagat    120
gtgtatactc gcgctacctg ccagcccgg gaggtggtgg tgcccttgac tgtggagctc    180
atgggcaccg tggccaaaca gctggtgccc agctgcgtga ctgtgcagcg ctgtggtggc    240
tgctgccctg acgatggcct ggagtgtgtg cccactgggc agcaccaagt ccggatgcag    300
atcctcatga tccggtaccc gagcagtcag ctgggggaga tgtccctgga agaacacagc    360
```

-continued

```
cagtgtgaat gcagacctaa aaaaaaggac agtgctgtga agccagacag ggctgccact    420
ccccaccacc gtccccagcc ccgttctgtt ccgggctggg actctgcccc cggagcaccc    480
tccccagctg acatcaccca tcccactcca gccccaggcc cctctgccca cgctgcaccc    540
agcaccacca gcgccctgac ccccggacct gccgccgccg ctgccgacgc cgcagcttcc    600
tccgttgcca agggcggggc ttag                                           624
```

<210> SEQ ID NO 97
<211> LENGTH: 207
<212> TYPE: PRT
<213> ORGANISM: Homo sapiens
<220> FEATURE:
<221> NAME/KEY: MISC_FEATURE
<223> OTHER INFORMATION: VEGF-B Isoform 2
<220> FEATURE:
<221> NAME/KEY: mat_peptide
<222> LOCATION: (22)..(207)

<400> SEQUENCE: 97

```
Met Ser Pro Leu Leu Arg Arg Leu Leu Leu Ala Ala Leu Leu Gln Leu
    -20             -15                 -10

Ala Pro Ala Gln Ala Pro Val Ser Gln Pro Asp Ala Pro Gly His Gln
 -5              -1  1               5                   10

Arg Lys Val Val Ser Trp Ile Asp Val Tyr Thr Arg Ala Thr Cys Gln
                15                  20                  25

Pro Arg Glu Val Val Val Pro Leu Thr Val Glu Leu Met Gly Thr Val
            30                  35                  40

Ala Lys Gln Leu Val Pro Ser Cys Val Thr Val Gln Arg Cys Gly Gly
        45                  50                  55

Cys Cys Pro Asp Asp Gly Leu Glu Cys Val Pro Thr Gly Gln His Gln
60                  65                  70                  75

Val Arg Met Gln Ile Leu Met Ile Arg Tyr Pro Ser Ser Gln Leu Gly
                80                  85                  90

Glu Met Ser Leu Glu Glu His Ser Gln Cys Glu Cys Arg Pro Lys Lys
                95                  100                 105

Lys Asp Ser Ala Val Lys Pro Asp Arg Ala Ala Thr Pro His His Arg
            110                 115                 120

Pro Gln Pro Arg Ser Val Pro Gly Trp Asp Ser Ala Pro Gly Ala Pro
        125                 130                 135

Ser Pro Ala Asp Ile Thr His Pro Thr Pro Ala Pro Gly Pro Ser Ala
140                 145                 150                 155

His Ala Ala Pro Ser Thr Thr Ser Ala Leu Thr Pro Gly Pro Ala Ala
                160                 165                 170

Ala Ala Ala Asp Ala Ala Ala Ser Ser Val Ala Lys Gly Gly Ala
            175                 180                 185
```

<210> SEQ ID NO 98
<211> LENGTH: 2305
<212> TYPE: DNA
<213> ORGANISM: Homo sapiens
<220> FEATURE:
<221> NAME/KEY: misc_feature
<223> OTHER INFORMATION: PDGF-A
<220> FEATURE:
<221> NAME/KEY: CDS
<222> LOCATION: (404)..(991)
<223> OTHER INFORMATION: PDGF-A

<400> SEQUENCE: 98

```
ttcttggggc tgatgtccgc aaatatgcag aattaccggc cgggtcgctc ctgaagccag    60
```

```
cgcggggagc gagcgcggcg gcggccagca ccgggaacgc accgaggaag aagcccagcc    120
cccgccctcc gccccttccg tccccacccc ctacccggcg gcccaggagg ctccccggct    180
gcggcgcgca ctccctgttt ctcctcctcc tggctggcgc tgcctgcctc tccgcactca    240
ctgctcgccg ggcgccgtcc gccagctccg tgctccccgc gccaccctcc tccgggccgc    300
gctccctaag ggatggtact gaatttcgcc gccacaggag accggctgga gcgcccgccc    360
cgcgcctcgc ctctcctccg agcagccagc gcctcggac gcg atg agg acc ttg       415
                                              Met Arg Thr Leu
                                              1
```

| | | | | | | | | | | | | | | | | |
|---|---|---|---|---|---|---|---|---|---|---|---|---|---|---|---|---|
| gct | tgc | ctg | ctg | ctc | ctc | ggc | tgc | gga | tac | ctc | gcc | cat | gtt | ctg | gcc | 463 |
| Ala | Cys | Leu | Leu | Leu | Leu | Gly | Cys | Gly | Tyr | Leu | Ala | His | Val | Leu | Ala | |
| 5 | | | | 10 | | | | | 15 | | | | | 20 | | |

| | | | | | | | | | | | | | | | | |
|---|---|---|---|---|---|---|---|---|---|---|---|---|---|---|---|---|
| gag | gaa | gcc | gag | atc | ccc | cgc | gag | gtg | atc | gag | agg | ctg | gcc | cgc | agt | 511 |
| Glu | Glu | Ala | Glu | Ile | Pro | Arg | Glu | Val | Ile | Glu | Arg | Leu | Ala | Arg | Ser | |
| | | | | 25 | | | | | 30 | | | | | 35 | | |

| | | | | | | | | | | | | | | | | |
|---|---|---|---|---|---|---|---|---|---|---|---|---|---|---|---|---|
| cag | atc | cac | agc | atc | cgg | gac | ctc | cag | cga | ctc | ctg | gag | ata | gac | tcc | 559 |
| Gln | Ile | His | Ser | Ile | Arg | Asp | Leu | Gln | Arg | Leu | Leu | Glu | Ile | Asp | Ser | |
| | | | 40 | | | | | 45 | | | | | 50 | | | |

| | | | | | | | | | | | | | | | | |
|---|---|---|---|---|---|---|---|---|---|---|---|---|---|---|---|---|
| gta | ggg | agt | gag | gat | tct | ttg | gac | acc | agc | ctg | aga | gct | cac | ggg | gtc | 607 |
| Val | Gly | Ser | Glu | Asp | Ser | Leu | Asp | Thr | Ser | Leu | Arg | Ala | His | Gly | Val | |
| | | 55 | | | | | 60 | | | | | 65 | | | | |

| | | | | | | | | | | | | | | | | |
|---|---|---|---|---|---|---|---|---|---|---|---|---|---|---|---|---|
| cac | gcc | act | aag | cat | gtg | ccc | gag | aag | cgg | ccc | ctg | ccc | att | cgg | agg | 655 |
| His | Ala | Thr | Lys | His | Val | Pro | Glu | Lys | Arg | Pro | Leu | Pro | Ile | Arg | Arg | |
| 70 | | | | | 75 | | | | | 80 | | | | | | |

| | | | | | | | | | | | | | | | | |
|---|---|---|---|---|---|---|---|---|---|---|---|---|---|---|---|---|
| aag | aga | agc | atc | gag | gaa | gct | gtc | ccc | gct | gtc | tgc | aag | acc | agg | acg | 703 |
| Lys | Arg | Ser | Ile | Glu | Glu | Ala | Val | Pro | Ala | Val | Cys | Lys | Thr | Arg | Thr | |
| 85 | | | | | 90 | | | | | 95 | | | | | 100 | |

| | | | | | | | | | | | | | | | | |
|---|---|---|---|---|---|---|---|---|---|---|---|---|---|---|---|---|
| gtc | att | tac | gag | att | cct | cgg | agt | cag | gtc | gac | ccc | acg | tcc | gcc | aac | 751 |
| Val | Ile | Tyr | Glu | Ile | Pro | Arg | Ser | Gln | Val | Asp | Pro | Thr | Ser | Ala | Asn | |
| | | | | 105 | | | | | 110 | | | | | 115 | | |

| | | | | | | | | | | | | | | | | |
|---|---|---|---|---|---|---|---|---|---|---|---|---|---|---|---|---|
| ttc | ctg | atc | tgg | ccc | ccg | tgc | gtg | gag | gtg | aaa | cgc | tgc | acc | ggc | tgc | 799 |
| Phe | Leu | Ile | Trp | Pro | Pro | Cys | Val | Glu | Val | Lys | Arg | Cys | Thr | Gly | Cys | |
| | | | 120 | | | | | 125 | | | | | 130 | | | |

| | | | | | | | | | | | | | | | | |
|---|---|---|---|---|---|---|---|---|---|---|---|---|---|---|---|---|
| tgc | aac | acg | agc | agt | gtc | aag | tgc | cag | ccc | tcc | cgc | gtc | cac | cac | cgc | 847 |
| Cys | Asn | Thr | Ser | Ser | Val | Lys | Cys | Gln | Pro | Ser | Arg | Val | His | His | Arg | |
| | | 135 | | | | | 140 | | | | | 145 | | | | |

| | | | | | | | | | | | | | | | | |
|---|---|---|---|---|---|---|---|---|---|---|---|---|---|---|---|---|
| agc | gtc | aag | gtg | gcc | aag | gtg | gaa | tac | gtc | agg | aag | aag | cca | aaa | tta | 895 |
| Ser | Val | Lys | Val | Ala | Lys | Val | Glu | Tyr | Val | Arg | Lys | Lys | Pro | Lys | Leu | |
| | 150 | | | | | 155 | | | | | 160 | | | | | |

| | | | | | | | | | | | | | | | | |
|---|---|---|---|---|---|---|---|---|---|---|---|---|---|---|---|---|
| aaa | gaa | gtc | cag | gtg | agg | tta | gag | gag | cat | ttg | gag | tgc | gcc | tgc | gcg | 943 |
| Lys | Glu | Val | Gln | Val | Arg | Leu | Glu | Glu | His | Leu | Glu | Cys | Ala | Cys | Ala | |
| 165 | | | | 170 | | | | | 175 | | | | | 180 | | |

| | | | | | | | | | | | | | | | | |
|---|---|---|---|---|---|---|---|---|---|---|---|---|---|---|---|---|
| acc | aca | agc | ctg | aat | ccg | gat | tat | cgg | gaa | gag | gac | acg | gat | gtg | agg | 991 |
| Thr | Thr | Ser | Leu | Asn | Pro | Asp | Tyr | Arg | Glu | Glu | Asp | Thr | Asp | Val | Arg | |
| | | | | 185 | | | | | 190 | | | | | 195 | | |

```
tgaggatgag ccgcagccct ttcctgggac atggatgtac atggcgtgtt acattcctga   1051
acctactatg tacggtgctt tattgccagt gtgcggtctt tgttctcctc cgtgaaaaac   1111
tgtgtccgag aacactcggg agaacaaaga gacagtgcac atttgtttaa tgtgacatca   1171
aagcaagtat tgtagcactc ggtgaagcag taagaagctt ccttgtcaaa agagagaga   1231 gagagagaga gagagaaaac aaaaccacaa atgacaaaaa caaaacggac tcacaaaaat   1291
atctaaactc gatgagatgg agggtcgccc cgtgggatgg aagtgcagag gtctcagcag   1351
actggatttc tgtccgggtg gtcacaggtg cttttttgcc gaggatgcag agcctgcttt   1411
gggaacgact ccagagggggt gctggtgggc tctgcagggc ccgcaggaag caggaatgtc   1471
```

```
ttggaaaccg ccacgcgaac tttagaaacc acacctcctc gctgtagtat ttaagcccat    1531
acagaaacct tcctgagagc cttaagtggt tttttttttt gttttttgttt tgttttttttt   1591 tttttttgttt tttttttttt tttttttttt tacaccataa agtgattatt aagcttcctt    1651
ttactctttg gctagctttt tttttttttt tttttttttt ttttttttaat tatctcttgg    1711 atgacattta caccgataac acacaggctg ctgtaactgt caggacagtg cgacggtatt    1771
tttcctagca agatgcaaac taatgagatg tattaaaata aacatggtat acctacctat    1831
gcatcatttc ctaaatgttt ctggctttgt gtttctccct taccctgctt tatttgttaa    1891
tttaagccat tttgaaagaa ctatgcgtca accaatcgta cgccgtccct gcggcacctg    1951
ccccagagcc cgtttgtggc tgagtgacaa cttgttcccc gcagtgcaca cctagaatgc    2011
tgtgttccca cgcggcacgt gagatgcatt gccgcttctg tctgtgttgt tggtgtgccc    2071
tggtgccgtg gtggcggtca ctccctctgc tgccagtgtt tggacagaac ccaaattctt    2131 tattttggt aagatattgt gctttacctg tattaacaga aatgtgtgtg tgtggtttgt     2191 tttttgtaa aggtgaagtt tgtatgttta cctaatatta cctgttttgt atacctgaga     2251
gcctgctatg ttcttctttt gttgatccaa aattaaaaaa aaaataccac caac          2305
```

<210> SEQ ID NO 99
<211> LENGTH: 196
<212> TYPE: PRT
<213> ORGANISM: Homo sapiens

<400> SEQUENCE: 99

```
Met Arg Thr Leu Ala Cys Leu Leu Leu Gly Cys Gly Tyr Leu Ala
1               5                   10                  15

His Val Leu Ala Glu Glu Ala Glu Ile Pro Arg Glu Val Ile Glu Arg
            20                  25                  30

Leu Ala Arg Ser Gln Ile His Ser Ile Arg Asp Leu Gln Arg Leu Leu
        35                  40                  45

Glu Ile Asp Ser Val Gly Ser Glu Asp Ser Leu Asp Thr Ser Leu Arg
    50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
        115                 120                 125

Cys Thr Gly Cys Cys Asn Thr Ser Ser Val Lys Cys Gln Pro Ser Arg
    130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Asp Val Arg
        195
```

<210> SEQ ID NO 100
<211> LENGTH: 2137
<212> TYPE: DNA

```
<213> ORGANISM: Homo sapiens
<220> FEATURE:
<221> NAME/KEY: misc_feature
<223> OTHER INFORMATION: PDGF-B
<220> FEATURE:
<221> NAME/KEY: CDS
<222> LOCATION: (983)..(1705)

<400> SEQUENCE: 100
ccctgcctgc ctccctgcgc acccgcagcc tcccccgctg cctccctagg gctcccctcc      60
ggccgccagc gcccattttt cattccctag atagagatac tttgcgcgca cacacataca     120
tacgcgcgca aaaggaaaa aaaaaaaaaa aagcccaccc tccagcctcg ctgcaaagag      180
aaaaccggag cagccgcagc tcgcagctcg cagcccgcag cccgcagagg acgcccagag     240
cggcgagcgg gcgggcagac ggaccgacgg actcgcgccg cgtccacctg tcggccgggc     300
ccagccgagc gcgcagcggg cacgccgcgc gcgcggagca gccgtgcccg ccgcccgggc     360
ccgccgccag ggcgcacacg ctcccgcccc cctacccggc ccgggcggga gtttgcacct     420
ctccctgccc gggtgctcga gctgccgttg caaagccaac tttggaaaaa gttttttggg     480
ggagacttgg gccttgaggt gcccagctcc gcgctttccg attttggggg cctttccaga     540
aaatgttgca aaaagctaa gccggcgggc agaggaaaac gcctgtagcc ggcgagtgaa      600
gacgaaccat cgactgccgt gttccttttc ctcttggagg ttggagtccc ctgggcgccc     660
ccacacggct agacgcctcg gctggttcgc gacgcagccc cccggccgtg gatgctgcac     720
tcgggctcgg gatccgccca ggtagcggcc tcggacccag gtcctgcgcc caggtcctcc     780
cctgcccccc agcgacggag ccggggccgg ggcggcggc gccgggggca tgcgggtgag      840
ccgcggctgc agaggcctga gcgcctgatc gccgcggacc cgagccgagc ccaccccccct    900 ccccagcccc ccaccctggc cgcggggggcg gcgcgctcga tctacgcgtt cggggcccccg   960 cggggccggg cccggagtcg gc atg aat cgc tgc tgg gcg ctc ttc ctg tct     1012
                          Met Asn Arg Cys Trp Ala Leu Phe Leu Ser
                            1               5                  10 ctc tgc tgc tac ctg cgt ctg gtc agc gcc gag ggg gac ccc att ccc      1060
Leu Cys Cys Tyr Leu Arg Leu Val Ser Ala Glu Gly Asp Pro Ile Pro
             15                  20                  25 gag gag ctt tat gag atg ctg agt gac cac tcg atc cgc tcc ttt gat      1108
Glu Glu Leu Tyr Glu Met Leu Ser Asp His Ser Ile Arg Ser Phe Asp
         30                  35                  40 gat ctc caa cgc ctg ctg cac gga gac ccc gga gag gaa gat ggg gcc      1156
Asp Leu Gln Arg Leu Leu His Gly Asp Pro Gly Glu Glu Asp Gly Ala
     45                  50                  55 gag ttg gac ctg aac atg acc cgc tcc cac tct gga ggc gag ctg gag      1204
Glu Leu Asp Leu Asn Met Thr Arg Ser His Ser Gly Gly Glu Leu Glu
 60                  65                  70 agc ttg gct cgt gga aga agg agc ctg ggt tcc ctg acc att gct gag      1252
Ser Leu Ala Arg Gly Arg Arg Ser Leu Gly Ser Leu Thr Ile Ala Glu
 75                  80                  85                  90 ccg gcc atg atc gcc gag tgc aag acg cgc acc gag gtg ttc gag atc      1300
Pro Ala Met Ile Ala Glu Cys Lys Thr Arg Thr Glu Val Phe Glu Ile
                 95                 100                 105 tcc cgg cgc ctc ata gac cgc acc aac gcc aac ttc ctg gtg tgg ccg      1348
Ser Arg Arg Leu Ile Asp Arg Thr Asn Ala Asn Phe Leu Val Trp Pro
             110                 115                 120 ccc tgt gtg gag gtg cag cgc tgc tcc ggc tgc tgc aac aac cgc aac      1396
Pro Cys Val Glu Val Gln Arg Cys Ser Gly Cys Cys Asn Asn Arg Asn
         125                 130                 135 gtg cag tgc cgc ccc acc cag gtg cag ctg cga cct gtc cag gtg aga      1444
```

```
                Val Gln Cys Arg Pro Thr Gln Val Gln Leu Arg Pro Val Gln Val Arg
                    140                 145                 150 aag atc gag att gtg cgg aag aag cca atc ttt aag aag gcc acg gtg         1492
Lys Ile Glu Ile Val Arg Lys Lys Pro Ile Phe Lys Lys Ala Thr Val
155                 160                 165                 170 acg ctg gaa gac cac ctg gca tgc aag tgt gag aca gtg gca gct gca         1540
Thr Leu Glu Asp His Leu Ala Cys Lys Cys Glu Thr Val Ala Ala Ala
                175                 180                 185 cgg cct gtg acc cga agc ccg ggg ggt tcc cag gag cag cga gcc aaa         1588
Arg Pro Val Thr Arg Ser Pro Gly Gly Ser Gln Glu Gln Arg Ala Lys
            190                 195                 200 acg ccc caa act cgg gtg acc att cgg acg gtg cga gtc cgc cgg ccc         1636
Thr Pro Gln Thr Arg Val Thr Ile Arg Thr Val Arg Val Arg Arg Pro
        205                 210                 215 ccc aag ggc aag cac cgg aaa ttc aag cac acg cat gac aag acg gca         1684
Pro Lys Gly Lys His Arg Lys Phe Lys His Thr His Asp Lys Thr Ala
    220                 225                 230 ctg aag gag acc ctt gga gcc tagggcatc ggcaggagag tgtgtgggca             1735
Leu Lys Glu Thr Leu Gly Ala
235                 240 gggttattta atatggtatt tgctgtattg cccccatggg gccttggagt agataatatt       1795
gtttccctcg tccgtctgtc tcgatgcctg attcggacgg ccaatggtgc ctcccccacc       1855
cctccacgtg tccgtccacc cttccatcag cgggtctcct cccagcggcc tccggctctt       1915
gcccagcagc tcaagaagaa aaagaaggac tgaactccat cgccatcttc ttcccttaac       1975
tccaagaact tgggataaga gtgtgagaga gactgatggg gtcgctcttt ggggaaacg        2035 ggttccttcc cctgcacctg gcctgggcca cacctgagcg ctgtggactg tcctgaggag       2095
ccctgaggac ctctcagcat agcctgcctg atccctgaac cc                         2137

<210> SEQ ID NO 101
<211> LENGTH: 241
<212> TYPE: PRT
<213> ORGANISM: Homo sapiens

<400> SEQUENCE: 101

Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
                20                  25                  30

Leu Ser Asp His Ser Ile Arg Ser Phe Asp Asp Leu Gln Arg Leu Leu
            35                  40                  45

His Gly Asp Pro Gly Glu Glu Asp Gly Ala Glu Leu Asp Leu Asn Met
        50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
                100                 105                 110

Arg Thr Asn Ala Asn Phe Leu Val Trp Pro Pro Cys Val Glu Val Gln
            115                 120                 125

Arg Cys Ser Gly Cys Cys Asn Asn Arg Asn Val Gln Cys Arg Pro Thr
        130                 135                 140

Gln Val Gln Leu Arg Pro Val Gln Val Arg Lys Ile Glu Ile Val Arg
145                 150                 155                 160
```

```
Lys Lys Pro Ile Phe Lys Lys Ala Thr Val Thr Leu Glu Asp His Leu
            165                 170                 175

Ala Cys Lys Cys Glu Thr Val Ala Ala Ala Arg Pro Val Thr Arg Ser
        180                 185                 190

Pro Gly Gly Ser Gln Glu Gln Arg Ala Lys Thr Pro Gln Thr Arg Val
            195                 200                 205

Thr Ile Arg Thr Val Arg Val Arg Arg Pro Pro Lys Gly Lys His Arg
        210                 215                 220

Lys Phe Lys His Thr His Asp Lys Thr Ala Leu Lys Glu Thr Leu Gly
225                 230                 235                 240

Ala

<210> SEQ ID NO 102
<211> LENGTH: 2108
<212> TYPE: DNA
<213> ORGANISM: Homo sapiens
<220> FEATURE:
<221> NAME/KEY: misc_feature
<223> OTHER INFORMATION: PDGF-C
<220> FEATURE:
<221> NAME/KEY: misc_feature
<222> LOCATION: (2002)..(2002)
<223> OTHER INFORMATION: n = a, c, g, or t
<220> FEATURE:
<221> NAME/KEY: misc_feature
<222> LOCATION: (2065)..(2065)
<223> OTHER INFORMATION: n = a, c, g, or t
<220> FEATURE:
<221> NAME/KEY: misc_feature
<222> LOCATION: (2070)..(2070)
<223> OTHER INFORMATION: n = a, c, g, or t
<220> FEATURE:
<221> NAME/KEY: misc_feature
<222> LOCATION: (2089)..(2089)
<223> OTHER INFORMATION: n = a, c, g, or t

<400> SEQUENCE: 102
ccccgccgtg agtgagctct caccccagtc agccaaatga gcctcttcgg gcttctcctg      60
gtgacatctg ccctggccgg ccagagacga gggactcagg cggaatccaa cctgagtagt     120
aaattccagt tttccagcaa caaggaacag aacggagtac aagatcctca gcatgagaga     180
attattactg tgtctactaa tggaagtatt cacagcccaa ggtttcctca tacttatcca     240
agaaatacgg tcttggtatg gagattagta gcagtagagg aaaatgtatg gatacaactt     300
acgtttgatg aaagatttgg gcttgaagac ccagaagatg acatatgcaa gtatgatttt     360
gtagaagttg aggaacccag tgatggaact atattagggc gctggtgtgg ttctggtact     420
gtaccaggaa aacagatttc taaggaaat caaattagga taagatttgt atctgatgaa     480
tattttcctt ctgaaccagg gttctgcatc cactacaaca ttgtcatgcc acaattcaca     540
gaagctgtga gtccttcagt gctaccccct tcagctttgc cactggacct gcttaataat     600
gctataactg cctttagtac cttggaagac cttattcgat atcttgaacc agagagatgg     660
cagttggact agaagatct atataggcca acttggcaac ttcttggcaa ggcttttgtt     720
tttggaagaa atccagagt ggtggatctg aaccttctaa cagaggaggt aagattatac     780
agctgcacac ctcgtaactt ctcagtgtcc ataaggaag aactaaagag aaccgatacc     840
attttctggc caggttgtct cctggttaaa cgctgtggtg ggaactgtgc ctgttgtctc     900
cacaattgca atgaatgtca atgtgtccca agcaaagtta ctaaaaaata ccacgaggtc     960
cttcagttga gaccaaagac cggtgtcagg ggattgcaca atcactcac cgacgtggcc    1020 ctggagcacc atgaggagtg tgactgtgtg tgcagaggga gcacaggagg atagccgcat   1080
```

```
caccaccagc agctcttgcc cagagctgtg cagtgcagtg gctgattcta ttagagaacg    1140
tatgcgttat ctccatcctt aatctcagtt gtttgcttca aggacctttc atcttcagga    1200
tttacagtgc attctgaaag aggagacatc aaacagaatt aggagttgtg caacagctct    1260
tttgagagga ggcctaaagg acaggagaaa aggtcttcaa tcgtggaaag aaaattaaat    1320
gttgtattaa atagatcacc agctagtttc agagttacca tgtacgtatt ccactagctg    1380
ggttctgtat ttcagttctt tcgatacggc ttagggtaat gtcagtacag gaaaaaaact    1440
gtgcaagtga gcacctgatt ccgttgcctt gcttaactct aaagctccat gtcctgggcc    1500
taaaatcgta taaaatctgg attttttttt tttttttgc tcatattcac atatgtaaac    1560
cagaacattc tatgtactac aaacctggtt tttaaaaagg aactatgttg ctatgaatta    1620
aacttgtgtc rtgctgatag acagactgg attttcata tttcttatta aaatttctgc    1680
catttagaag aagagaacta cattcatggt ttggaagaga taaacctgaa agaagagtg    1740 gccttatctt cactttatcg ataagtcagt ttatttgttt cattgtgtac attttttatt    1800
tctccttttg acattataac tgttggcttt tctaatcttg ttaaatatat ctatttttac    1860
caaaggtatt taatattctt ttttatgaca acttagatca actattttta gcttggtaaa    1920
tttttctaaa cacaattgtt atagccagag gaacaaagat ggatataaaa atattgttgc    1980
cctggacaaa aatacatgta tntccatccc ggaatggtgc tagagttgga ttaaacctgc    2040
attttaaaaa acctgaattg ggaanggaan ttggtaaggt tggccaaanc tttttttgaaa    2100 ataattaa                                                             2108
```

<210> SEQ ID NO 103
<211> LENGTH: 345
<212> TYPE: PRT
<213> ORGANISM: Homo sapiens
<220> FEATURE:
<221> NAME/KEY: MISC_FEATURE
<223> OTHER INFORMATION: PDGF-C

<400> SEQUENCE: 103

```
Met Ser Leu Phe Gly Leu Leu Leu Val Thr Ser Ala Leu Ala Gly Gln
1               5                   10                  15

Arg Arg Gly Thr Gln Ala Glu Ser Asn Leu Ser Ser Lys Phe Gln Phe
            20                  25                  30

Ser Ser Asn Lys Glu Gln Asn Gly Val Gln Asp Pro Gln His Glu Arg
        35                  40                  45

Ile Ile Thr Val Ser Thr Asn Gly Ser Ile His Ser Pro Arg Phe Pro
    50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
        115                 120                 125

Val Pro Gly Lys Gln Ile Ser Lys Gly Asn Gln Ile Arg Ile Arg Phe
    130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
```

|     |     |     | 165 |     |     |     | 170 |     |     |     | 175 |     |     |
| --- | --- | --- | --- | --- | --- | --- | --- | --- | --- | --- | --- | --- | --- |
| Pro | Pro | Ser | Ala | Leu | Pro | Leu | Asp | Leu | Leu | Asn | Asn | Ala | Ile | Thr | Ala |
|     |     |     | 180 |     |     |     | 185 |     |     |     | 190 |     |     |

Phe Ser Thr Leu Glu Asp Leu Ile Arg Tyr Leu Glu Pro Glu Arg Trp
          195                 200                 205

Gln Leu Asp Leu Glu Asp Leu Tyr Arg Pro Thr Trp Gln Leu Leu Gly
    210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
        275                 280                 285

His Asn Cys Asn Glu Cys Gln Cys Val Pro Ser Lys Val Thr Lys Lys
    290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
            340                 345

<210> SEQ ID NO 104
<211> LENGTH: 2253
<212> TYPE: DNA
<213> ORGANISM: Homo sapiens
<220> FEATURE:
<221> NAME/KEY: misc_feature
<223> OTHER INFORMATION: PDGF-D

<400> SEQUENCE: 104

```
cgctcggaaa gttcagcatg caggaagttt ggggagagct cggcgattag cacagcgacc     60
cgggccagcg cagggcgagc gcaggcggcg agagcgcagg gcggcgcggc gtcggtcccg    120
ggagcagaac ccggcttttt cttggagcga cgctgtctct agtcgctgat cccaaatgca    180
ccggctcatc tttgtctaca ctctaatctg cgcaaacttt tgcagctgtc gggacacttc    240
tgcaaccccg cagagcgcat ccatcaaagc tttgcgcaac gccaacctca ggcgagatga    300
gagcaatcac ctcacagact gtaccgaaga gatgagacc atccaggtga aaggaaacgg    360
ctacgtgcag agtcctagat tcccgaacag ctaccccagg aacctgctcc tgacatggcg    420
gcttcactct caggagaata cacgatacag ctagtgtttt gacaatcagt ttggattaga    480
ggaagcagaa aatgatatct gtaggtatga ttttgtggaa gttgaagata tatccgaaac    540
cagtaccatt attagaggac gatggtgtgg cacacaagga agttcctcca aggataaaatc    600
aagaacgaac caaattaaaa tcacattcaa gtccgatgac tactttgtgg ctaaacctgg    660
attcaagatt tattattctt tgctggaaga tttccaaccc gcagcagctt cagagaccaa    720
ctgggaatct gtcacaagct ctatttcagg ggtatcctat aactctccat cagtaacgga    780
tcccactctg attgcggatg ctctggacaa aaaaattgca gaatttgata cagtggaaga    840
tctgctcaag tacttcaatc cagagtcatg gcaagaagat cttgagaata tgtatctgga    900
cacccctcgg tatcgaggca ggtcatacca tgaccggaag tcaaaagttg acctggatag    960
gctcaatgat gatgccaagc gttacagttg cactcccagg aattactcgg tcaatataag   1020
```

```
agaagagctg aagttggcca atgtggtctt ctttccacgt tgcctcctcg tgcagcgctg    1080
tggaggaaat tgtggctgtg gaactgtcaa ctggaggtcc tgcacatgca attcagggaa    1140
aaccgtgaaa aagtatcatg aggtattaca gtttgagcct ggccacatca agaggagggg    1200
tagagctaag accatggctc tagttgacat ccagttggat caccatgaac gatgcgattg    1260
tatctgcagc tcaagaccac ctcgataaga gaatgtgcac atccttacat taagcctgaa    1320
agaaccttta gtttaaggag ggtgagataa gagacccttt tcctaccagc aaccaaactt    1380
actactagcc tgcaatgcaa tgaacacaag tggttgctga gtctcagcct tgctttgtta    1440
atgccatggc aagtagaaag gtatatcatc aacttctata cctaagaata taggattgca    1500
tttaataata gtgtttgagg ttatatatgc acaaacacac acagaaatat attcatgtct    1560
atgtgtatat agatcaaatg ttttttttgg tatatataac caggtacacc agagcttaca    1620
tatgtttgag ttagactctt aaaatccttt gccaaaataa gggatggtca aatatatgaa    1680
acatgtcttt agaaaattta ggagataaat ttatttttaa attttgaaac acaaaacaat    1740
tttgaatctt gctctcttaa agaaagcatc ttgtatatta aaaatcaaaa gatgaggctt    1800
tcttacatat acatcttagt tgattattaa aaaggaaaa aggtttccag agaaaaggcc    1860
aatacctaag cattttttcc atgagaagca ctgcatactt acctatgtgg actgtaataa    1920
cctgtctcca aaaccatgcc ataataatat aagtgcttta gaaattaaat cattgtgttt    1980
tttatgcatt ttgctgaggc atccttattc atttaacacc tatctcaaaa acttacttag    2040 aaggttttt attatagtcc tacaaaagac aatgtataag ctgtaacaga attttgaatt    2100
gttttctttt gcaaaacccc tccacaaaag caaatccttt caagaatggc atgggcattc    2160
tgtatgaacc tttccagatg gtgttcagtg aaagatgtgg gtagttgaga acttaaaaag    2220
tgaacattga aacatcgacg taactggaaa ccg                                 2253
```

<210> SEQ ID NO 105
<211> LENGTH: 116
<212> TYPE: PRT
<213> ORGANISM: Homo sapiens
<220> FEATURE:
<221> NAME/KEY: MISC_FEATURE
<223> OTHER INFORMATION: PDGF-D

<400> SEQUENCE: 105

```
Gly Arg Lys Ser Arg Val Val Asp Leu Asn Leu Leu Thr Glu Glu Val
1               5                   10                  15

Arg Leu Tyr Ser Cys Thr Pro Arg Asn Phe Ser Val Ser Ile Arg Glu
            20                  25                  30

Glu Leu Lys Arg Thr Asp Thr Ile Phe Trp Pro Gly Cys Leu Leu Val
        35                  40                  45

Lys Arg Cys Gly Gly Asn Cys Ala Cys Cys Leu His Asn Cys Asn Glu
    50                  55                  60

Cys Gln Cys Val Pro Ser Lys Val Thr Lys Lys Tyr His Glu Val Leu
65                  70                  75                  80

Gln Leu Arg Pro Lys Thr Gly Val Arg Gly Leu His Lys Ser Leu Thr
                85                  90                  95

Asp Val Ala Leu Glu His His Glu Glu Cys Asp Cys Val Cys Arg Gly
            100                 105                 110

Ser Thr Gly Gly
        115
```

<210> SEQ ID NO 106
<211> LENGTH: 456
<212> TYPE: DNA
<213> ORGANISM: Artificial sequence
<220> FEATURE:
<223> OTHER INFORMATION: hVEGFA109

<400> SEQUENCE: 106

```
atggagacag acacactcct gctatgggta ctgctgctct gggttccagg ttccactggt    60
gacgcggccc aggatcctgg gcagaatcat cacgaagtgg tgaaattcat ggatgtctat   120
cagcgcagct actgccatcc gatcgagaca ctggtggaca tcttccagga ataccctgat   180
gagatcgagt acatcttcaa gccatcctgc gtgcccctga tgagatgtgg gggttgctgc   240
aatgacgaag gctggagtg cgttcccacc gaggagtcca acatcaccat gcagattatg   300
agaattaaac ctcaccaagg gcagcacatc ggagagatga gctttctcca gcataacaaa   360
tgtgaatgta gaccaaagaa agatttggtc ttcgaacaaa aactcatctc agaagaggat   420
ctgaatagcg ccgtcgacca tcatcatcat catcat                             456
```

<210> SEQ ID NO 107
<211> LENGTH: 152
<212> TYPE: PRT
<213> ORGANISM: Artificial sequence
<220> FEATURE:
<223> OTHER INFORMATION: hVEGFA109

<400> SEQUENCE: 107

```
Met Glu Thr Asp Thr Leu Leu Trp Val Leu Leu Trp Val Pro
1               5                   10                  15

Gly Ser Thr Gly Asp Ala Ala Gln Asp Pro Gly Gln Asn His His Glu
            20                  25                  30

Val Val Lys Phe Met Asp Val Tyr Gln Arg Ser Tyr Cys His Pro Ile
        35                  40                  45

Glu Thr Leu Val Asp Ile Phe Gln Glu Tyr Pro Asp Glu Ile Glu Tyr
    50                  55                  60

Ile Phe Lys Pro Ser Cys Val Pro Leu Met Arg Cys Gly Gly Cys Cys
65                  70                  75                  80

Asn Asp Glu Gly Leu Glu Cys Val Pro Thr Glu Glu Ser Asn Ile Thr
                85                  90                  95

Met Gln Ile Met Arg Ile Lys Pro His Gln Gly Gln His Ile Gly Glu
            100                 105                 110

Met Ser Phe Leu Gln His Asn Lys Cys Glu Cys Arg Pro Lys Lys Asp
        115                 120                 125

Leu Val Phe Glu Gln Lys Leu Ile Ser Glu Glu Asp Leu Asn Ser Ala
    130                 135                 140

Val Asp His His His His His His
145                 150
```

<210> SEQ ID NO 108
<211> LENGTH: 504
<212> TYPE: DNA
<213> ORGANISM: Artificial sequence
<220> FEATURE:
<223> OTHER INFORMATION: hVEGFC109

<400> SEQUENCE: 108

```
atggagacag acacactcct gctatgggta ctgctgctct gggttccagg ttccactggt    60
gacgcggccc agccggccag gcgcgccgta cgaagcttgg taccgagctc ggatccagca   120
```

```
cattataata cagagatctt gaaaagtatt gataatgagt ggagaaagac tcaatgcatg    180
ccacgggagg tgtgtataga tgtggggaag gagtttggag tcgcgacaaa caccttcttt    240
aaacctccat gtgtgtccgt ctacagatgt gggggttgct gcaatagtga ggggctgcag    300
tgcatgaaca ccagcacgag ctacctcagc aagacgttat ttgaaattac agtgcctctc    360
tctcaaggcc ccaaaccagt aacaatcagt tttgccaatc acacttcctg ccgatgcatg    420
tctaagctgg atttggtctt cgaacaaaaa ctcatctcag aagaggatct gaatagcgcc    480
gtcgaccatc atcatcatca tcat                                            504
```

<210> SEQ ID NO 109
<211> LENGTH: 168
<212> TYPE: PRT
<213> ORGANISM: Artificial sequence
<220> FEATURE:
<223> OTHER INFORMATION: hVEGFC109

<400> SEQUENCE: 109

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Val Arg Ser
            20                  25                  30

Leu Val Pro Ser Ser Asp Pro Ala His Tyr Asn Thr Glu Ile Leu Lys
        35                  40                  45

Ser Ile Asp Asn Glu Trp Arg Lys Thr Gln Cys Met Pro Arg Glu Val
    50                  55                  60

Cys Ile Asp Val Gly Lys Glu Phe Gly Val Ala Thr Asn Thr Phe Phe
65                  70                  75                  80

Lys Pro Pro Cys Val Ser Val Tyr Arg Cys Gly Gly Cys Cys Asn Ser
                85                  90                  95

Glu Gly Leu Gln Cys Met Asn Thr Ser Thr Ser Tyr Leu Ser Lys Thr
            100                 105                 110

Leu Phe Glu Ile Thr Val Pro Leu Ser Gln Gly Pro Lys Pro Val Thr
        115                 120                 125

Ile Ser Phe Ala Asn His Thr Ser Cys Arg Cys Met Ser Lys Leu Asp
    130                 135                 140

Leu Val Phe Glu Gln Lys Leu Ile Ser Glu Glu Asp Leu Asn Ser Ala
145                 150                 155                 160

Val Asp His His His His His His
                165
```

<210> SEQ ID NO 110
<211> LENGTH: 87
<212> TYPE: PRT
<213> ORGANISM: Artificial sequence
<220> FEATURE:
<223> OTHER INFORMATION: VHD motif
<220> FEATURE:
<221> NAME/KEY: misc_feature
<222> LOCATION: (2)..(23)
<223> OTHER INFORMATION: Xaa = any or unknown amino acid
<220> FEATURE:
<221> NAME/KEY: misc_feature
<222> LOCATION: (24)..(25)
<223> OTHER INFORMATION: Xaa = any amino acid or unknown amino acid or nothing
<220> FEATURE:
<221> NAME/KEY: misc_feature
<222> LOCATION: (27)..(27)
<223> OTHER INFORMATION: Xaa = Proline, Serine or Arginine
<220> FEATURE:
<221> NAME/KEY: misc_feature

```
<222> LOCATION: (30)..(32)
<223> OTHER INFORMATION: Xaa = any or unknown amino acid
<220> FEATURE:
<221> NAME/KEY: misc_feature
<222> LOCATION: (35)..(35)
<223> OTHER INFORMATION: Xaa = Guanine, Serine, Threonine or Alanine
<220> FEATURE:
<221> NAME/KEY: misc_feature
<222> LOCATION: (39)..(44)
<223> OTHER INFORMATION: Xaa = any or unknown amino acid
<220> FEATURE:
<221> NAME/KEY: misc_feature
<222> LOCATION: (46)..(77)
<223> OTHER INFORMATION: Xaa = any or unknown amino acid
<220> FEATURE:
<221> NAME/KEY: misc_feature
<222> LOCATION: (78)..(86)
<223> OTHER INFORMATION: Xaa = any amino acid or unknown amino acid or
      nothing

<400> SEQUENCE: 110

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Pro Xaa Cys Val Xaa Xaa Xaa
            20                  25                  30

Arg Cys Xaa Gly Cys Cys Xaa Xaa Xaa Xaa Xaa Cys Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Cys
                85

<210> SEQ ID NO 111
<211> LENGTH: 13
<212> TYPE: PRT
<213> ORGANISM: Artificial sequence
<220> FEATURE:
<223> OTHER INFORMATION: PDGF motif
<220> FEATURE:
<221> NAME/KEY: misc_feature
<222> LOCATION: (2)..(2)
<223> OTHER INFORMATION: Xaa = Proline or Serine
<220> FEATURE:
<221> NAME/KEY: misc_feature
<222> LOCATION: (5)..(7)
<223> OTHER INFORMATION: Xaa = any or unknown amino acid
<220> FEATURE:
<221> NAME/KEY: misc_feature
<222> LOCATION: (10)..(10)
<223> OTHER INFORMATION: Xaa = Arginine, Serine, Threonine or Alanine

<400> SEQUENCE: 111

Pro Xaa Cys Val Xaa Xaa Xaa Arg Cys Xaa Gly Cys Cys
1               5                   10

<210> SEQ ID NO 112
<211> LENGTH: 2772
<212> TYPE: DNA
<213> ORGANISM: Homo sapiens
<220> FEATURE:
<221> NAME/KEY: CDS
<222> LOCATION: (1)..(2772)

<400> SEQUENCE: 112 atg gag agg ggg ctg ccg ctc ctc tgc gcc gtg ctc gcc ctc gtc ctc      48
Met Glu Arg Gly Leu Pro Leu Leu Cys Ala Val Leu Ala Leu Val Leu
1               5                   10                  15
```

| | | |
|---|---|---|
| gcc ccg gcc ggc gct ttt cgc aac gat gaa tgt ggc gat act ata aaa<br>Ala Pro Ala Gly Ala Phe Arg Asn Asp Glu Cys Gly Asp Thr Ile Lys<br>             20                        25                       30 | 96 |
| att gaa agc ccc ggg tac ctt aca tct cct ggt tat cct cat tct tat<br>Ile Glu Ser Pro Gly Tyr Leu Thr Ser Pro Gly Tyr Pro His Ser Tyr<br>        35                    40                       45 | 144 |
| cac cca agt gaa aaa tgc gaa tgg ctg att cag gct ccg gac cca tac<br>His Pro Ser Glu Lys Cys Glu Trp Leu Ile Gln Ala Pro Asp Pro Tyr<br>50                         55                       60 | 192 |
| cag aga att atg atc aac ttc aac cct cac ttc gat ttg gag gac aga<br>Gln Arg Ile Met Ile Asn Phe Asn Pro His Phe Asp Leu Glu Asp Arg<br>65                     70                       75                 80 | 240 |
| gac tgc aag tat gac tac gtg gaa gtc ttc gat gga gaa aat gaa aat<br>Asp Cys Lys Tyr Asp Tyr Val Glu Val Phe Asp Gly Glu Asn Glu Asn<br>                       85                    90                     95 | 288 |
| gga cat ttt agg gga aag ttc tgt gga aag ata gcc cct cct cct gtt<br>Gly His Phe Arg Gly Lys Phe Cys Gly Lys Ile Ala Pro Pro Pro Val<br>               100                   105                 110 | 336 |
| gtg tct tca ggg cca ttt ctt ttt atc aaa ttt gtc tct gac tac gaa<br>Val Ser Ser Gly Pro Phe Leu Phe Ile Lys Phe Val Ser Asp Tyr Glu<br>             115                   120                 125 | 384 |
| aca cat ggt gca gga ttt tcc ata cgt tat gaa att ttc aag aga ggt<br>Thr His Gly Ala Gly Phe Ser Ile Arg Tyr Glu Ile Phe Lys Arg Gly<br>     130                   135                   140 | 432 |
| cct gaa tgt tcc cag aac tac aca aca cct agt gga gtg ata aag tcc<br>Pro Glu Cys Ser Gln Asn Tyr Thr Thr Pro Ser Gly Val Ile Lys Ser<br>145                 150                   155               160 | 480 |
| ccc gga ttc cct gaa aaa tat ccc aac agc ctt gaa tgc act tat att<br>Pro Gly Phe Pro Glu Lys Tyr Pro Asn Ser Leu Glu Cys Thr Tyr Ile<br>                 165                 170                 175 | 528 |
| gtc ttt gcg cca aag atg tca gag att atc ctg gaa ttt gaa agc ttt<br>Val Phe Ala Pro Lys Met Ser Glu Ile Ile Leu Glu Phe Glu Ser Phe<br>               180                   185                 190 | 576 |
| gac ctg gag cct gac tca aat cct cca ggg ggg atg ttc tgt cgc tac<br>Asp Leu Glu Pro Asp Ser Asn Pro Pro Gly Gly Met Phe Cys Arg Tyr<br>             195                   200                 205 | 624 |
| gac cgg cta gaa atc tgg gat gga ttc cct gat gtt ggc cct cac att<br>Asp Arg Leu Glu Ile Trp Asp Gly Phe Pro Asp Val Gly Pro His Ile<br>210                 215                   220 | 672 |
| ggg cgt tac tgt gga cag aaa aca cca ggt cga atc cga tcc tca tcg<br>Gly Arg Tyr Cys Gly Gln Lys Thr Pro Gly Arg Ile Arg Ser Ser Ser<br>225                 230                   235               240 | 720 |
| ggc att ctc tcc atg gtt ttt tac acc gac agc gcg ata gca aaa gaa<br>Gly Ile Leu Ser Met Val Phe Tyr Thr Asp Ser Ala Ile Ala Lys Glu<br>               245                   250                 255 | 768 |
| ggt ttc tca gca aac tac agt gtc ttg cag agc agt gtc tca gaa gat<br>Gly Phe Ser Ala Asn Tyr Ser Val Leu Gln Ser Ser Val Ser Glu Asp<br>             260                   265                 270 | 816 |
| ttc aaa tgt atg gaa gct ctg ggc atg gaa tca gga gaa att cat tct<br>Phe Lys Cys Met Glu Ala Leu Gly Met Glu Ser Gly Glu Ile His Ser<br>     275                   280                   285 | 864 |
| gac cag atc aca gct tct tcc cag tat agc acc aac tgg tct gca gag<br>Asp Gln Ile Thr Ala Ser Ser Gln Tyr Ser Thr Asn Trp Ser Ala Glu<br>290                 295                   300 | 912 |
| cgc tcc cgc ctg aac tac cct gag aat ggg tgg act ccc gga gag gat<br>Arg Ser Arg Leu Asn Tyr Pro Glu Asn Gly Trp Thr Pro Gly Glu Asp<br>305                 310                   315               320 | 960 |
| tcc tac cga gag tgg ata cag gta gac ttg ggc ctt ctg cgc ttt gtc<br>Ser Tyr Arg Glu Trp Ile Gln Val Asp Leu Gly Leu Leu Arg Phe Val | 1008 |

-continued

|  |  |  |  |  |  |  |  |  |  |  |  |  |  |  |  |
|---|---|---|---|---|---|---|---|---|---|---|---|---|---|---|---|
|  |  |  | 325 |  |  |  | 330 |  |  |  | 335 |  |  |  |  |
| acg | gct | gtc | ggg | aca | cag | ggc | gcc | att | tca | aaa | gaa | acc | aag | aag | aaa | 1056 |
| Thr | Ala | Val | Gly | Thr | Gln | Gly | Ala | Ile | Ser | Lys | Glu | Thr | Lys | Lys | Lys |  |
|  |  |  | 340 |  |  |  | 345 |  |  |  | 350 |  |  |  |  |
| tat | tat | gtc | aag | act | tac | aag | atc | gac | gtt | agc | tcc | aac | ggg | gaa | gac | 1104 |
| Tyr | Tyr | Val | Lys | Thr | Tyr | Lys | Ile | Asp | Val | Ser | Ser | Asn | Gly | Glu | Asp |  |
|  |  |  |  | 355 |  |  |  | 360 |  |  |  | 365 |  |  |  |
| tgg | atc | acc | ata | aaa | gaa | gga | aac | aaa | cct | gtt | ctc | ttt | cag | gga | aac | 1152 |
| Trp | Ile | Thr | Ile | Lys | Glu | Gly | Asn | Lys | Pro | Val | Leu | Phe | Gln | Gly | Asn |  |
|  | 370 |  |  |  |  | 375 |  |  |  |  | 380 |  |  |  |  |
| acc | aac | ccc | aca | gat | gtt | gtg | gtt | gca | gta | ttc | ccc | aaa | cca | ctg | ata | 1200 |
| Thr | Asn | Pro | Thr | Asp | Val | Val | Val | Ala | Val | Phe | Pro | Lys | Pro | Leu | Ile |  |
| 385 |  |  |  |  | 390 |  |  |  |  | 395 |  |  |  |  | 400 |
| act | cga | ttt | gtc | cga | atc | aag | cct | gca | act | tgg | gaa | act | ggc | ata | tct | 1248 |
| Thr | Arg | Phe | Val | Arg | Ile | Lys | Pro | Ala | Thr | Trp | Glu | Thr | Gly | Ile | Ser |  |
|  |  |  |  | 405 |  |  |  | 410 |  |  |  | 415 |  |  |  |
| atg | aga | ttt | gaa | gta | tac | ggt | tgc | aag | ata | aca | gat | tat | cct | tgc | tct | 1296 |
| Met | Arg | Phe | Glu | Val | Tyr | Gly | Cys | Lys | Ile | Thr | Asp | Tyr | Pro | Cys | Ser |  |
|  |  |  | 420 |  |  |  | 425 |  |  |  | 430 |  |  |  |  |
| gga | atg | ttg | ggt | atg | gtg | tct | gga | ctt | att | tct | gac | tcc | cag | atc | aca | 1344 |
| Gly | Met | Leu | Gly | Met | Val | Ser | Gly | Leu | Ile | Ser | Asp | Ser | Gln | Ile | Thr |  |
|  |  | 435 |  |  |  |  | 440 |  |  |  |  | 445 |  |  |  |
| tca | tcc | aac | caa | gga | gac | aga | aac | tgg | atg | cct | gaa | aac | atc | cgc | ctg | 1392 |
| Ser | Ser | Asn | Gln | Gly | Asp | Arg | Asn | Trp | Met | Pro | Glu | Asn | Ile | Arg | Leu |  |
| 450 |  |  |  |  | 455 |  |  |  |  | 460 |  |  |  |  |  |
| gta | acc | agt | cgc | tct | ggc | tgg | gca | ctt | cca | ccc | gca | cct | cat | tcc | tac | 1440 |
| Val | Thr | Ser | Arg | Ser | Gly | Trp | Ala | Leu | Pro | Pro | Ala | Pro | His | Ser | Tyr |  |
| 465 |  |  |  |  | 470 |  |  |  |  | 475 |  |  |  |  | 480 |
| atc | aat | gag | tgg | ctc | caa | ata | gac | ctg | ggg | gag | gag | aag | atc | gtg | agg | 1488 |
| Ile | Asn | Glu | Trp | Leu | Gln | Ile | Asp | Leu | Gly | Glu | Glu | Lys | Ile | Val | Arg |  |
|  |  |  |  | 485 |  |  |  | 490 |  |  |  | 495 |  |  |  |
| ggc | atc | atc | att | cag | ggt | ggg | aag | cac | cga | gag | aac | aag | gtg | ttc | atg | 1536 |
| Gly | Ile | Ile | Ile | Gln | Gly | Gly | Lys | His | Arg | Glu | Asn | Lys | Val | Phe | Met |  |
|  |  |  | 500 |  |  |  | 505 |  |  |  | 510 |  |  |  |  |
| agg | aag | ttc | aag | atc | ggg | tac | agc | aac | aac | ggc | tcg | gac | tgg | aag | atg | 1584 |
| Arg | Lys | Phe | Lys | Ile | Gly | Tyr | Ser | Asn | Asn | Gly | Ser | Asp | Trp | Lys | Met |  |
|  | 515 |  |  |  |  | 520 |  |  |  |  | 525 |  |  |  |  |
| atc | atg | gat | gac | agc | aaa | cgc | aag | gcg | aag | tct | ttt | gag | ggc | aac | aac | 1632 |
| Ile | Met | Asp | Asp | Ser | Lys | Arg | Lys | Ala | Lys | Ser | Phe | Glu | Gly | Asn | Asn |  |
| 530 |  |  |  |  | 535 |  |  |  |  | 540 |  |  |  |  |  |
| aac | tat | gat | aca | cct | gag | ctg | cgg | act | ttt | cca | gct | ctc | tcc | acg | cga | 1680 |
| Asn | Tyr | Asp | Thr | Pro | Glu | Leu | Arg | Thr | Phe | Pro | Ala | Leu | Ser | Thr | Arg |  |
| 545 |  |  |  |  | 550 |  |  |  |  | 555 |  |  |  |  | 560 |
| ttc | atc | agg | atc | tac | ccc | gag | aga | gcc | act | cat | ggc | gga | ctg | ggg | ctc | 1728 |
| Phe | Ile | Arg | Ile | Tyr | Pro | Glu | Arg | Ala | Thr | His | Gly | Gly | Leu | Gly | Leu |  |
|  |  |  |  | 565 |  |  |  | 570 |  |  |  | 575 |  |  |  |
| aga | atg | gag | ctg | ctg | ggc | tgt | gaa | gtg | gaa | gcc | cct | aca | gct | gga | ccg | 1776 |
| Arg | Met | Glu | Leu | Leu | Gly | Cys | Glu | Val | Glu | Ala | Pro | Thr | Ala | Gly | Pro |  |
|  |  |  | 580 |  |  |  | 585 |  |  |  | 590 |  |  |  |  |
| acc | act | ccc | aac | ggg | aac | ttg | gtg | gat | gaa | tgt | gat | gac | gac | cag | gcc | 1824 |
| Thr | Thr | Pro | Asn | Gly | Asn | Leu | Val | Asp | Glu | Cys | Asp | Asp | Asp | Gln | Ala |  |
|  |  | 595 |  |  |  |  | 600 |  |  |  |  | 605 |  |  |  |
| aac | tgc | cac | agt | gga | aca | ggt | gat | gac | ttc | cag | ctc | aca | ggt | ggc | acc | 1872 |
| Asn | Cys | His | Ser | Gly | Thr | Gly | Asp | Asp | Phe | Gln | Leu | Thr | Gly | Gly | Thr |  |
| 610 |  |  |  |  | 615 |  |  |  |  | 620 |  |  |  |  |  |
| act | gtg | ctg | gcc | aca | gaa | aag | ccc | acg | gtc | ata | gac | agc | acc | ata | caa | 1920 |
| Thr | Val | Leu | Ala | Thr | Glu | Lys | Pro | Thr | Val | Ile | Asp | Ser | Thr | Ile | Gln |  |
| 625 |  |  |  |  | 630 |  |  |  |  | 635 |  |  |  |  | 640 |
| tca | gag | ttt | cca | aca | tat | ggt | ttt | aac | tgt | gaa | ttt | ggc | tgg | ggc | tct | 1968 |

| | | | | | | | | | | | | | | |
|---|---|---|---|---|---|---|---|---|---|---|---|---|---|---|
| Ser | Glu | Phe | Pro | Thr | Tyr | Gly | Phe | Asn | Cys | Glu | Phe | Gly | Trp | Gly | Ser |
| | | | | 645 | | | | 650 | | | | | 655 | | | cac aag acc ttc tgc cac tgg gaa cat gac aat cac gtg cag ctc aag 2016
His Lys Thr Phe Cys His Trp Glu His Asp Asn His Val Gln Leu Lys
            660                 665                 670 tgg agt gtg ttg acc agc aag acg gga ccc att cag gat cac aca gga 2064
Trp Ser Val Leu Thr Ser Lys Thr Gly Pro Ile Gln Asp His Thr Gly
        675                 680                 685 gat ggc aac ttc atc tat tcc caa gct gac gaa aat cag aag ggc aaa 2112
Asp Gly Asn Phe Ile Tyr Ser Gln Ala Asp Glu Asn Gln Lys Gly Lys
    690                 695                 700 gtg gct cgc ctg gtg agc cct gtg gtt tat tcc cag aac tct gcc cac 2160
Val Ala Arg Leu Val Ser Pro Val Val Tyr Ser Gln Asn Ser Ala His
705                 710                 715                 720 tgc atg acc ttc tgg tat cac atg tct ggg tcc cac gtc ggc aca ctc 2208
Cys Met Thr Phe Trp Tyr His Met Ser Gly Ser His Val Gly Thr Leu
                725                 730                 735 agg gtc aaa ctg cgc tac cag aag cca gag gag tac gat cag ctg gtc 2256
Arg Val Lys Leu Arg Tyr Gln Lys Pro Glu Glu Tyr Asp Gln Leu Val
            740                 745                 750 tgg atg gcc att gga cac caa ggt gac cac tgg aag gaa ggg cgt gtc 2304
Trp Met Ala Ile Gly His Gln Gly Asp His Trp Lys Glu Gly Arg Val
        755                 760                 765 ttg ctc cac aag tct ctg aaa ctt tat cag gtg att ttc gag ggc gaa 2352
Leu Leu His Lys Ser Leu Lys Leu Tyr Gln Val Ile Phe Glu Gly Glu
    770                 775                 780 atc gga aaa gga aac ctt ggt ggg att gct gtg gat gac att agt att 2400
Ile Gly Lys Gly Asn Leu Gly Gly Ile Ala Val Asp Asp Ile Ser Ile
785                 790                 795                 800 aat aac cac att tca caa gaa gat tgt gca aaa cca gca gac ctg gat 2448
Asn Asn His Ile Ser Gln Glu Asp Cys Ala Lys Pro Ala Asp Leu Asp
                805                 810                 815 aaa aag aac cca gaa att aaa att gat gaa aca ggg agc acg cca gga 2496
Lys Lys Asn Pro Glu Ile Lys Ile Asp Glu Thr Gly Ser Thr Pro Gly
            820                 825                 830 tac gaa ggt gaa gga gaa ggt gac aag aac atc tcc agg aag cca ggc 2544
Tyr Glu Gly Glu Gly Glu Gly Asp Lys Asn Ile Ser Arg Lys Pro Gly
        835                 840                 845 aat gtg ttg aag acc tta gaa ccc atc ctc atc acc atc ata gcc atg 2592
Asn Val Leu Lys Thr Leu Glu Pro Ile Leu Ile Thr Ile Ile Ala Met
    850                 855                 860 agc gcc ctg ggg gtc ctc ctg ggg gct gtc tgt ggg gtc gtg ctg tac 2640
Ser Ala Leu Gly Val Leu Leu Gly Ala Val Cys Gly Val Val Leu Tyr
865                 870                 875                 880 tgt gcc tgt tgg cat aat ggg atg tca gaa aga aac ttg tct gcc ctg 2688
Cys Ala Cys Trp His Asn Gly Met Ser Glu Arg Asn Leu Ser Ala Leu
                885                 890                 895 gag aac tat aac ttt gaa ctt gtg gat ggt gtg aag ttg aaa aaa gac 2736
Glu Asn Tyr Asn Phe Glu Leu Val Asp Gly Val Lys Leu Lys Lys Asp
            900                 905                 910 aaa ctg aat aca cag agt act tat tcg gag gca tga 2772
Lys Leu Asn Thr Gln Ser Thr Tyr Ser Glu Ala
    915                 920

<210> SEQ ID NO 113
<211> LENGTH: 923
<212> TYPE: PRT
<213> ORGANISM: Homo sapiens

<400> SEQUENCE: 113

-continued

```
Met Glu Arg Gly Leu Pro Leu Leu Cys Ala Val Leu Ala Leu Val Leu
1               5                   10                  15

Ala Pro Ala Gly Ala Phe Arg Asn Asp Glu Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
                100                 105                 110

Val Ser Ser Gly Pro Phe Leu Phe Ile Lys Phe Val Ser Asp Tyr Glu
            115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
    370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
```

```
                420             425             430
Gly Met Leu Gly Met Val Ser Gly Leu Ile Ser Asp Ser Gln Ile Thr
            435                 440                 445
Ser Ser Asn Gln Gly Asp Arg Asn Trp Met Pro Glu Asn Ile Arg Leu
450                 455                 460
Val Thr Ser Arg Ser Gly Trp Ala Leu Pro Pro Ala Pro His Ser Tyr
465                 470                 475                 480
Ile Asn Glu Trp Leu Gln Ile Asp Leu Gly Glu Glu Lys Ile Val Arg
                485                 490                 495
Gly Ile Ile Ile Gln Gly Gly Lys His Arg Glu Asn Lys Val Phe Met
            500                 505                 510
Arg Lys Phe Lys Ile Gly Tyr Ser Asn Asn Gly Ser Asp Trp Lys Met
            515                 520                 525
Ile Met Asp Asp Ser Lys Arg Lys Ala Lys Ser Phe Glu Gly Asn Asn
            530                 535                 540
Asn Tyr Asp Thr Pro Glu Leu Arg Thr Phe Pro Ala Leu Ser Thr Arg
545                 550                 555                 560
Phe Ile Arg Ile Tyr Pro Glu Arg Ala Thr His Gly Gly Leu Gly Leu
                565                 570                 575
Arg Met Glu Leu Leu Gly Cys Glu Val Glu Ala Pro Thr Ala Gly Pro
            580                 585                 590
Thr Thr Pro Asn Gly Asn Leu Val Asp Glu Cys Asp Asp Gln Ala
            595                 600                 605
Asn Cys His Ser Gly Thr Gly Asp Asp Phe Gln Leu Thr Gly Gly Thr
            610                 615                 620
Thr Val Leu Ala Thr Glu Lys Pro Thr Val Ile Asp Ser Thr Ile Gln
625                 630                 635                 640
Ser Glu Phe Pro Thr Tyr Gly Phe Asn Cys Glu Phe Gly Trp Gly Ser
                645                 650                 655
His Lys Thr Phe Cys His Trp Glu His Asp Asn His Val Gln Leu Lys
            660                 665                 670
Trp Ser Val Leu Thr Ser Lys Thr Gly Pro Ile Gln Asp His Thr Gly
            675                 680                 685
Asp Gly Asn Phe Ile Tyr Ser Gln Ala Asp Glu Asn Gln Lys Gly Lys
            690                 695                 700
Val Ala Arg Leu Val Ser Pro Val Val Tyr Ser Gln Asn Ser Ala His
705                 710                 715                 720
Cys Met Thr Phe Trp Tyr His Met Ser Gly Ser His Val Gly Thr Leu
                725                 730                 735
Arg Val Lys Leu Arg Tyr Gln Lys Pro Glu Glu Tyr Asp Gln Leu Val
            740                 745                 750
Trp Met Ala Ile Gly His Gln Gly Asp His Trp Lys Glu Gly Arg Val
            755                 760                 765
Leu Leu His Lys Ser Leu Lys Leu Tyr Gln Val Ile Phe Glu Gly Glu
            770                 775                 780
Ile Gly Lys Gly Asn Leu Gly Gly Ile Ala Val Asp Asp Ile Ser Ile
785                 790                 795                 800
Asn Asn His Ile Ser Gln Glu Asp Cys Ala Lys Pro Ala Asp Leu Asp
                805                 810                 815
Lys Lys Asn Pro Glu Ile Lys Ile Asp Glu Thr Gly Ser Thr Pro Gly
            820                 825                 830
Tyr Glu Gly Glu Gly Glu Gly Asp Lys Asn Ile Ser Arg Lys Pro Gly
            835                 840                 845
```

```
Asn Val Leu Lys Thr Leu Glu Pro Ile Leu Ile Thr Ile Ile Ala Met
        850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
                885                 890                 895

Glu Asn Tyr Asn Phe Glu Leu Val Asp Gly Val Lys Leu Lys Lys Asp
            900                 905                 910

Lys Leu Asn Thr Gln Ser Thr Tyr Ser Glu Ala
            915                 920

<210> SEQ ID NO 114
<211> LENGTH: 2781
<212> TYPE: DNA
<213> ORGANISM: Homo sapiens
<220> FEATURE:
<221> NAME/KEY: CDS
<222> LOCATION: (1)..(2781)

<400> SEQUENCE: 114 atg atg ttt cct ctc acc tgg gtt ttc tta gcc ctc tac ttt tca         48
Met Asp Met Phe Pro Leu Thr Trp Val Phe Leu Ala Leu Tyr Phe Ser
1               5                   10                  15 aga cac caa gtg aga ggc caa cca gac cca ccg tgc gga ggt cgt ttg     96
Arg His Gln Val Arg Gly Gln Pro Asp Pro Pro Cys Gly Gly Arg Leu
                20                  25                  30 aat tcc aaa gat gct ggc tat atc acc tct ccc ggt tac ccc cag gac    144
Asn Ser Lys Asp Ala Gly Tyr Ile Thr Ser Pro Gly Tyr Pro Gln Asp
            35                  40                  45 tac ccc tcc cac cag aac tgc gag tgg att gtt tac gcc ccc gaa ccc    192
Tyr Pro Ser His Gln Asn Cys Glu Trp Ile Val Tyr Ala Pro Glu Pro
        50                  55                  60 aac cag aag att gtc ctc aac ttc aac cct cac ttt gaa atc gag aag    240
Asn Gln Lys Ile Val Leu Asn Phe Asn Pro His Phe Glu Ile Glu Lys
65                  70                  75                  80 cac gac tgc aag tat gac ttt atc gag att cgg gat ggg gac agt gaa    288
His Asp Cys Lys Tyr Asp Phe Ile Glu Ile Arg Asp Gly Asp Ser Glu
                85                  90                  95 tcc gca gac ctc ctg ggc aaa cac tgt ggg aac atc gcc ccg ccc acc    336
Ser Ala Asp Leu Leu Gly Lys His Cys Gly Asn Ile Ala Pro Pro Thr
                100                 105                 110 atc atc tcc tcg ggc tcc atg ctc tac atc aag ttc acc tcc gac tac    384
Ile Ile Ser Ser Gly Ser Met Leu Tyr Ile Lys Phe Thr Ser Asp Tyr
            115                 120                 125 gcc cgg cag ggg gca ggc ttc tct ctg cgc tac gag atc ttc aag aca    432
Ala Arg Gln Gly Ala Gly Phe Ser Leu Arg Tyr Glu Ile Phe Lys Thr
        130                 135                 140 ggc tct gaa gat tgc tca aaa aac ttc aca agc ccc aac ggg acc atc    480
Gly Ser Glu Asp Cys Ser Lys Asn Phe Thr Ser Pro Asn Gly Thr Ile
145                 150                 155                 160 gaa tct cct ggg ttt cct gag aag tat cca cac aac ttg gac tgc acc    528
Glu Ser Pro Gly Phe Pro Glu Lys Tyr Pro His Asn Leu Asp Cys Thr
                165                 170                 175 ttt acc atc ctg gcc aaa ccc aag atg gag atc atc ctg cag ttc ctg    576
Phe Thr Ile Leu Ala Lys Pro Lys Met Glu Ile Ile Leu Gln Phe Leu
                180                 185                 190 atc ttt gac ctg gag cat gac cct ttg cag gtg gga gag ggg gac tgc    624
Ile Phe Asp Leu Glu His Asp Pro Leu Gln Val Gly Glu Gly Asp Cys
            195                 200                 205
```

| | |
|---|---|
| aag tac gat tgg ctg gac atc tgg gat ggc att cca cat gtt ggc ccc<br>Lys Tyr Asp Trp Leu Asp Ile Trp Asp Gly Ile Pro His Val Gly Pro<br>210                 215                 220 | 672 |
| ctg att ggc aag tac tgt ggg acc aaa aca ccc tct gaa ctt cgt tca<br>Leu Ile Gly Lys Tyr Cys Gly Thr Lys Thr Pro Ser Glu Leu Arg Ser<br>225                 230                 235                 240 | 720 |
| tcg acg ggg atc ctc tcc ctg acc ttt cac acg gac atg gcg gtg gcc<br>Ser Thr Gly Ile Leu Ser Leu Thr Phe His Thr Asp Met Ala Val Ala<br>                 245                 250                 255 | 768 |
| aag gat ggc ttc tct gcg cgt tac tac ctg gtc cac caa gag cca cta<br>Lys Asp Gly Phe Ser Ala Arg Tyr Tyr Leu Val His Gln Glu Pro Leu<br>                 260                 265                 270 | 816 |
| gag aac ttt cag tgc aat gtt cct ctg ggc atg gag tct ggc cgg att<br>Glu Asn Phe Gln Cys Asn Val Pro Leu Gly Met Glu Ser Gly Arg Ile<br>275                 280                 285 | 864 |
| gct aat gaa cag atc agt gcc tca tct acc tac tct gat ggg agg tgg<br>Ala Asn Glu Gln Ile Ser Ala Ser Ser Thr Tyr Ser Asp Gly Arg Trp<br>290                 295                 300 | 912 |
| acc cct caa caa agc cgg ctc cat ggt gat gac aat ggc tgg acc ccc<br>Thr Pro Gln Gln Ser Arg Leu His Gly Asp Asp Asn Gly Trp Thr Pro<br>305                 310                 315                 320 | 960 |
| aac ttg gat tcc aac aag gag tat ctc cag gtg gac ctg cgc ttt tta<br>Asn Leu Asp Ser Asn Lys Glu Tyr Leu Gln Val Asp Leu Arg Phe Leu<br>                 325                 330                 335 | 1008 |
| acc atg ctc acg gcc atc gca aca cag gga gcg att tcc agg gaa aca<br>Thr Met Leu Thr Ala Ile Ala Thr Gln Gly Ala Ile Ser Arg Glu Thr<br>                 340                 345                 350 | 1056 |
| cag aat ggc tac tac gtc aaa tcc tac aag ctg gaa gtc agc act aat<br>Gln Asn Gly Tyr Tyr Val Lys Ser Tyr Lys Leu Glu Val Ser Thr Asn<br>355                 360                 365 | 1104 |
| gga gag gac tgg atg gtg tac cgg cat ggc aaa aac cac aag gta ttt<br>Gly Glu Asp Trp Met Val Tyr Arg His Gly Lys Asn His Lys Val Phe<br>370                 375                 380 | 1152 |
| caa gcc aac aac gat gca act gag gtg gtt ctg aac aag ctc cac gct<br>Gln Ala Asn Asn Asp Ala Thr Glu Val Val Leu Asn Lys Leu His Ala<br>385                 390                 395                 400 | 1200 |
| cca ctg ctg aca agg ttt gtt aga atc cgc cct cag acc tgg cac tca<br>Pro Leu Leu Thr Arg Phe Val Arg Ile Arg Pro Gln Thr Trp His Ser<br>                 405                 410                 415 | 1248 |
| ggt atc gcc ctc cgg ctg gag ctc ttc ggc tgc cgg gtc aca gat gct<br>Gly Ile Ala Leu Arg Leu Glu Leu Phe Gly Cys Arg Val Thr Asp Ala<br>                 420                 425                 430 | 1296 |
| ccc tgc tcc aac atg ctg ggg atg ctc tca ggc ctc att gca gac tcc<br>Pro Cys Ser Asn Met Leu Gly Met Leu Ser Gly Leu Ile Ala Asp Ser<br>                 435                 440                 445 | 1344 |
| cag atc tcc gcc tct tcc acc cag gaa tac ctc tgg agc ccc agt gca<br>Gln Ile Ser Ala Ser Ser Thr Gln Glu Tyr Leu Trp Ser Pro Ser Ala<br>450                 455                 460 | 1392 |
| gcc cgc ctg gtc agc agc cgc tcg ggc tgg ttc cct cga atc cct cag<br>Ala Arg Leu Val Ser Ser Arg Ser Gly Trp Phe Pro Arg Ile Pro Gln<br>465                 470                 475                 480 | 1440 |
| gcc cag ccc ggt gag gag tgg ctt cag gta gat ctg gga aca ccc aag<br>Ala Gln Pro Gly Glu Glu Trp Leu Gln Val Asp Leu Gly Thr Pro Lys<br>                 485                 490                 495 | 1488 |
| aca gtg aaa ggt gtc atc atc cag gga gcc cgc gga gga gac agt atc<br>Thr Val Lys Gly Val Ile Ile Gln Gly Ala Arg Gly Gly Asp Ser Ile<br>                 500                 505                 510 | 1536 |
| act gct gtg gaa gcc aga gca ttt gtg cgc aag ttc aaa gtc tcc tac<br>Thr Ala Val Glu Ala Arg Ala Phe Val Arg Lys Phe Lys Val Ser Tyr<br>515                 520                 525 | 1584 |

| | |
|---|---|
| agc cta aac ggc aag gac tgg gaa tac att cag gac ccc agg acc cag<br>Ser Leu Asn Gly Lys Asp Trp Glu Tyr Ile Gln Asp Pro Arg Thr Gln<br>530                             535                     540 | 1632 |
| cag cca aag ctg ttc gaa ggg aac atg cac tat gac acc cct gac atc<br>Gln Pro Lys Leu Phe Glu Gly Asn Met His Tyr Asp Thr Pro Asp Ile<br>545                        550                        555                        560 | 1680 |
| cga agg ttt gac ccc att ccg gca cag tat gtg cgg gta tac ccg gag<br>Arg Arg Phe Asp Pro Ile Pro Ala Gln Tyr Val Arg Val Tyr Pro Glu<br>                              565                        570                        575 | 1728 |
| agg tgg tcg ccg gcg ggg att ggg atg cgg ctg gag gtg ctg ggc tgt<br>Arg Trp Ser Pro Ala Gly Ile Gly Met Arg Leu Glu Val Leu Gly Cys<br>                    580                        585                        590 | 1776 |
| gac tgg aca gac tcc aag ccc acg gta aaa acg ctg gga ccc act gtg<br>Asp Trp Thr Asp Ser Lys Pro Thr Val Lys Thr Leu Gly Pro Thr Val<br>595                        600                        605 | 1824 |
| aag agc gaa gag aca acc acc ccc tac ccc acc gaa gag gag gcc aca<br>Lys Ser Glu Glu Thr Thr Thr Pro Tyr Pro Thr Glu Glu Glu Ala Thr<br>              610                        615                        620 | 1872 |
| gag tgt ggg gag aac tgc agc ttt gag gat gac aaa gat ttg cag ctc<br>Glu Cys Gly Glu Asn Cys Ser Phe Glu Asp Asp Lys Asp Leu Gln Leu<br>625                        630                        635                        640 | 1920 |
| cct tcg gga ttc aat tgc aac ttc gat ttc ctc gag gag ccc tgt ggt<br>Pro Ser Gly Phe Asn Cys Asn Phe Asp Phe Leu Glu Glu Pro Cys Gly<br>                              645                        650                        655 | 1968 |
| tgg atg tat gac cat gcc aag tgg ctc cgg acc acc tgg gcc agc agc<br>Trp Met Tyr Asp His Ala Lys Trp Leu Arg Thr Thr Trp Ala Ser Ser<br>                    660                        665                        670 | 2016 |
| tcc agc cca aac gac cgg acg ttt cca gat gac agg aat ttc ttg cgg<br>Ser Ser Pro Asn Asp Arg Thr Phe Pro Asp Asp Arg Asn Phe Leu Arg<br>              675                        680                        685 | 2064 |
| ctg cag agt gac agc cag aga gag ggc cag tat gcc cgg ctc atc agc<br>Leu Gln Ser Asp Ser Gln Arg Glu Gly Gln Tyr Ala Arg Leu Ile Ser<br>                    690                        695                        700 | 2112 |
| ccc cct gtc cac ctg ccc cga agc ccg gtg tgc atg gag ttc cag tac<br>Pro Pro Val His Leu Pro Arg Ser Pro Val Cys Met Glu Phe Gln Tyr<br>705                        710                        715                        720 | 2160 |
| cag gcc acg ggc ggc cgc ggg gtg gcg ctg cag gtg gtg cgg gaa gcc<br>Gln Ala Thr Gly Gly Arg Gly Val Ala Leu Gln Val Val Arg Glu Ala<br>                              725                        730                        735 | 2208 |
| agc cag gag agc aag ttg ctg tgg gtc atc cgt gag gac cag ggc ggc<br>Ser Gln Glu Ser Lys Leu Leu Trp Val Ile Arg Glu Asp Gln Gly Gly<br>                    740                        745                        750 | 2256 |
| gag tgg aag cac ggg cgg atc atc ctg ccc agc tac gac atg gag tac<br>Glu Trp Lys His Gly Arg Ile Ile Leu Pro Ser Tyr Asp Met Glu Tyr<br>              755                        760                        765 | 2304 |
| cag att gtg ttc gag gga gtg ata ggg aaa gga cgt tcc gga gag att<br>Gln Ile Val Phe Glu Gly Val Ile Gly Lys Gly Arg Ser Gly Glu Ile<br>770                        775                        780 | 2352 |
| gcc att gat gac att cgg ata agc act gat gtc cca ctg gag aac tgc<br>Ala Ile Asp Asp Ile Arg Ile Ser Thr Asp Val Pro Leu Glu Asn Cys<br>785                        790                        795                        800 | 2400 |
| atg gaa ccc atc tcg gct ttt gca gtg gac atc cca gaa ata cat gag<br>Met Glu Pro Ile Ser Ala Phe Ala Val Asp Ile Pro Glu Ile His Glu<br>                              805                        810                        815 | 2448 |
| aga gaa gga tat gaa gat gaa att gat gat gaa tac gag gtg gac tgg<br>Arg Glu Gly Tyr Glu Asp Glu Ile Asp Asp Glu Tyr Glu Val Asp Trp<br>                    820                        825                        830 | 2496 |
| agc aat tct tct tct gca acc tca ggg tct ggc gcc ccc tcg acc gac<br>Ser Asn Ser Ser Ser Ala Thr Ser Gly Ser Gly Ala Pro Ser Thr Asp | 2544 |

|   |   |   |   |   |   |   |   |   |   |   |   |   |   |   |   |      |
|---|---|---|---|---|---|---|---|---|---|---|---|---|---|---|---|------|
|   | 835 |   |   |   |   | 840 |   |   |   |   | 845 |   |   |   |   |      |
| aaa | gaa | aag | agc | tgg | ctg | tac | acc | ctg | gat | ccc | atc | ctc | atc | acc | atc | 2592 |
| Lys | Glu | Lys | Ser | Trp | Leu | Tyr | Thr | Leu | Asp | Pro | Ile | Leu | Ile | Thr | Ile |      |
| 850 |   |   |   |   | 855 |   |   |   |   | 860 |   |   |   |   |   |      |
| atc | gcc | atg | agc | tca | ctg | ggc | gtc | ctc | ctg | ggg | gcc | acc | tgt | gca | ggc | 2640 |
| Ile | Ala | Met | Ser | Ser | Leu | Gly | Val | Leu | Leu | Gly | Ala | Thr | Cys | Ala | Gly |      |
| 865 |   |   |   | 870 |   |   |   |   | 875 |   |   |   |   | 880 |   |      |
| ctc | ctg | ctc | tac | tgc | acc | tgt | tcc | tac | tcg | ggc | ctg | agc | tcc | cga | agc | 2688 |
| Leu | Leu | Leu | Tyr | Cys | Thr | Cys | Ser | Tyr | Ser | Gly | Leu | Ser | Ser | Arg | Ser |      |
|   |   |   |   | 885 |   |   |   |   | 890 |   |   |   |   | 895 |   |      |
| tgc | acc | aca | ctg | gag | aac | tac | aac | ttc | gag | ctc | tac | gat | ggc | ctt | aag | 2736 |
| Cys | Thr | Thr | Leu | Glu | Asn | Tyr | Asn | Phe | Glu | Leu | Tyr | Asp | Gly | Leu | Lys |      |
|   |   |   | 900 |   |   |   |   | 905 |   |   |   |   | 910 |   |   |      |
| cac | aag | gtc | aag | atg | aac | cac | caa | aag | tgc | tgc | tcc | gag | gca | tga |   | 2781 |
| His | Lys | Val | Lys | Met | Asn | His | Gln | Lys | Cys | Cys | Ser | Glu | Ala |   |   |      |
|   |   | 915 |   |   |   |   | 920 |   |   |   |   | 925 |   |   |   |      |

<210> SEQ ID NO 115
<211> LENGTH: 926
<212> TYPE: PRT
<213> ORGANISM: Homo sapiens

<400> SEQUENCE: 115

Met Asp Met Phe Pro Leu Thr Trp Val Phe Leu Ala Leu Tyr Phe Ser
1               5                   10                  15

Arg His Gln Val Arg Gly Gln Pro Asp Pro Pro Cys Gly Gly Arg Leu
                20                  25                  30

Asn Ser Lys Asp Ala Gly Tyr Ile Thr Ser Pro Gly Tyr Pro Gln Asp
            35                  40                  45

Tyr Pro Ser His Gln Asn Cys Glu Trp Ile Val Tyr Ala Pro Glu Pro
        50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Met Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Lys Met Glu Ile Ile Leu Gln Phe Leu
            180                 185                 190

Ile Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Glu Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Val His Gln Glu Pro Leu

```
                 260                 265                 270
Glu Asn Phe Gln Cys Asn Val Pro Leu Gly Met Glu Ser Gly Arg Ile
            275                 280                 285

Ala Asn Glu Gln Ile Ser Ala Ser Ser Thr Tyr Ser Asp Gly Arg Trp
        290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350

Gln Asn Gly Tyr Tyr Val Lys Ser Tyr Lys Leu Glu Val Ser Thr Asn
        355                 360                 365

Gly Glu Asp Trp Met Val Tyr Arg His Gly Lys Asn His Lys Val Phe
    370                 375                 380

Gln Ala Asn Asn Asp Ala Thr Glu Val Val Leu Asn Lys Leu His Ala
385                 390                 395                 400

Pro Leu Leu Thr Arg Phe Val Arg Ile Arg Pro Gln Thr Trp His Ser
                405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Ser
        435                 440                 445

Gln Ile Ser Ala Ser Ser Thr Gln Glu Tyr Leu Trp Ser Pro Ser Ala
    450                 455                 460

Ala Arg Leu Val Ser Ser Arg Ser Gly Trp Phe Pro Arg Ile Pro Gln
465                 470                 475                 480

Ala Gln Pro Gly Glu Glu Trp Leu Gln Val Asp Leu Gly Thr Pro Lys
                485                 490                 495

Thr Val Lys Gly Val Ile Ile Gln Gly Ala Arg Gly Gly Asp Ser Ile
            500                 505                 510

Thr Ala Val Glu Ala Arg Ala Phe Val Arg Lys Phe Lys Val Ser Tyr
        515                 520                 525

Ser Leu Asn Gly Lys Asp Trp Glu Tyr Ile Gln Asp Pro Arg Thr Gln
    530                 535                 540

Gln Pro Lys Leu Phe Glu Gly Asn Met His Tyr Asp Thr Pro Asp Ile
545                 550                 555                 560

Arg Arg Phe Asp Pro Ile Pro Ala Gln Tyr Val Arg Val Tyr Pro Glu
                565                 570                 575

Arg Trp Ser Pro Ala Gly Ile Gly Met Arg Leu Glu Val Leu Gly Cys
            580                 585                 590

Asp Trp Thr Asp Ser Lys Pro Thr Val Lys Thr Leu Gly Pro Thr Val
        595                 600                 605

Lys Ser Glu Glu Thr Thr Thr Pro Tyr Pro Thr Glu Glu Ala Thr
    610                 615                 620

Glu Cys Gly Glu Asn Cys Ser Phe Glu Asp Asp Lys Asp Leu Gln Leu
625                 630                 635                 640

Pro Ser Gly Phe Asn Cys Asn Phe Asp Phe Leu Glu Glu Pro Cys Gly
                645                 650                 655

Trp Met Tyr Asp His Ala Lys Trp Leu Arg Thr Thr Trp Ala Ser Ser
            660                 665                 670

Ser Ser Pro Asn Asp Arg Thr Phe Pro Asp Asp Arg Asn Phe Leu Arg
        675                 680                 685
```

```
Leu Gln Ser Asp Ser Gln Arg Glu Gly Gln Tyr Ala Arg Leu Ile Ser
        690                 695                 700

Pro Pro Val His Leu Pro Arg Ser Pro Val Cys Met Glu Phe Gln Tyr
705                 710                 715                 720

Gln Ala Thr Gly Gly Arg Gly Val Ala Leu Gln Val Val Arg Glu Ala
                725                 730                 735

Ser Gln Glu Ser Lys Leu Leu Trp Val Ile Arg Glu Asp Gln Gly Gly
            740                 745                 750

Glu Trp Lys His Gly Arg Ile Ile Leu Pro Ser Tyr Asp Met Glu Tyr
        755                 760                 765

Gln Ile Val Phe Glu Gly Val Ile Gly Lys Gly Arg Ser Gly Glu Ile
770                 775                 780

Ala Ile Asp Asp Ile Arg Ile Ser Thr Asp Val Pro Leu Glu Asn Cys
785                 790                 795                 800

Met Glu Pro Ile Ser Ala Phe Ala Val Asp Ile Pro Glu Ile His Glu
                805                 810                 815

Arg Glu Gly Tyr Glu Asp Glu Ile Asp Asp Glu Tyr Glu Val Asp Trp
            820                 825                 830

Ser Asn Ser Ser Ala Thr Ser Gly Ser Gly Ala Pro Ser Thr Asp
        835                 840                 845

Lys Glu Lys Ser Trp Leu Tyr Thr Leu Asp Pro Ile Leu Ile Thr Ile
850                 855                 860

Ile Ala Met Ser Ser Leu Gly Val Leu Leu Gly Ala Thr Cys Ala Gly
865                 870                 875                 880

Leu Leu Leu Tyr Cys Thr Cys Ser Tyr Ser Gly Leu Ser Ser Arg Ser
                885                 890                 895

Cys Thr Thr Leu Glu Asn Tyr Asn Phe Glu Leu Tyr Asp Gly Leu Lys
            900                 905                 910

His Lys Val Lys Met Asn His Gln Lys Cys Cys Ser Glu Ala
        915                 920                 925

<210> SEQ ID NO 116
<211> LENGTH: 6375
<212> TYPE: DNA
<213> ORGANISM: Homo sapiens
<220> FEATURE:
<221> NAME/KEY: CDS
<222> LOCATION: (129)..(3398)
<220> FEATURE:
<221> NAME/KEY: misc_feature
<222> LOCATION: (4476)..(4476)
<223> OTHER INFORMATION: n is a, c, g, or t
<220> FEATURE:
<221> NAME/KEY: misc_feature
<222> LOCATION: (4499)..(4499)
<223> OTHER INFORMATION: n is a, c, g, or t

<400> SEQUENCE: 116
ttggagctac agggagagaa acagaggagg agactgcaag agatcattgg aggccgtggg    60
cacgctcttt actccatgtg tgggacattc attgcggaat acatcggag gagaagtttc   120 ccagagct atg ggg act tcc cat ccg gcg ttc ctg gtc tta ggc tgt ctt   170
         Met Gly Thr Ser His Pro Ala Phe Leu Val Leu Gly Cys Leu
         1               5                   10 ctc aca ggg ctg agc cta atc ctc tgc cag ctt tca tta ccc tct atc   218
Leu Thr Gly Leu Ser Leu Ile Leu Cys Gln Leu Ser Leu Pro Ser Ile
 15                  20                  25                  30 ctt cca aat gaa aat gaa aag gtt gtg cag ctg aat tca tcc ttt tct   266
Leu Pro Asn Glu Asn Glu Lys Val Val Gln Leu Asn Ser Ser Phe Ser
```

```
                    35                  40                  45
ctg aga tgc ttt ggg gag agt gaa gtg agc tgg cag tac ccc atg tct      314
Leu Arg Cys Phe Gly Glu Ser Glu Val Ser Trp Gln Tyr Pro Met Ser
         50                  55                  60 gaa gaa gag agc tcc gat gtg gaa atc aga aat gaa gaa aac aac agc      362
Glu Glu Glu Ser Ser Asp Val Glu Ile Arg Asn Glu Glu Asn Asn Ser
     65                  70                  75 ggc ctt ttt gtg acg gtc ttg gaa gtg agc agt gcc tcg gcg gcc cac      410
Gly Leu Phe Val Thr Val Leu Glu Val Ser Ser Ala Ser Ala Ala His
 80                  85                  90 aca ggg ttg tac act tgc tat tac aac cac act cag aca gaa gag aat      458
Thr Gly Leu Tyr Thr Cys Tyr Tyr Asn His Thr Gln Thr Glu Glu Asn
 95                 100                 105                 110 gag ctt gaa ggc agg cac att tac atc tat gtg cca gac cca gat gta      506
Glu Leu Glu Gly Arg His Ile Tyr Ile Tyr Val Pro Asp Pro Asp Val
                115                 120                 125 gcc ttt gta cct cta gga atg acg gat tat tta gtc atc gtg gag gat      554
Ala Phe Val Pro Leu Gly Met Thr Asp Tyr Leu Val Ile Val Glu Asp
            130                 135                 140 gat gat tct gcc att ata cct tgt cgc aca act gat ccc gag act cct      602
Asp Asp Ser Ala Ile Ile Pro Cys Arg Thr Thr Asp Pro Glu Thr Pro
        145                 150                 155 gta acc tta cac aac agt gag ggg gtg gta cct gcc tcc tac gac agc      650
Val Thr Leu His Asn Ser Glu Gly Val Val Pro Ala Ser Tyr Asp Ser
    160                 165                 170 aga cag ggc ttt aat ggg acc ttc act gta ggg ccc tat atc tgt gag      698
Arg Gln Gly Phe Asn Gly Thr Phe Thr Val Gly Pro Tyr Ile Cys Glu
175                 180                 185                 190 gcc acc gtc aaa gga aag aag ttc cag acc atc cca ttt aat gtt tat      746
Ala Thr Val Lys Gly Lys Lys Phe Gln Thr Ile Pro Phe Asn Val Tyr
                195                 200                 205 gct tta aaa gca aca tca gag ctg gat cta gaa atg gaa gct ctt aaa      794
Ala Leu Lys Ala Thr Ser Glu Leu Asp Leu Glu Met Glu Ala Leu Lys
            210                 215                 220 acc gtg tat aag tca ggg gaa acg att gtg gtc acc tgt gct gtt ttt      842
Thr Val Tyr Lys Ser Gly Glu Thr Ile Val Val Thr Cys Ala Val Phe
        225                 230                 235 aac aat gag gtg gtt gac ctt caa tgg act tac cct gga gaa gtg aaa      890
Asn Asn Glu Val Val Asp Leu Gln Trp Thr Tyr Pro Gly Glu Val Lys
    240                 245                 250 ggc aaa ggc atc aca atg ctg gaa gaa atc aaa gtc cca tcc atc aaa      938
Gly Lys Gly Ile Thr Met Leu Glu Glu Ile Lys Val Pro Ser Ile Lys
255                 260                 265                 270 ttg gtg tac act ttg acg gtc ccc gag gcc acg gtg aaa gac agt gga      986
Leu Val Tyr Thr Leu Thr Val Pro Glu Ala Thr Val Lys Asp Ser Gly
                275                 280                 285 gat tac gaa tgt gct gcc cgc cag gct acc agg gag gtc aaa gaa atg     1034
Asp Tyr Glu Cys Ala Ala Arg Gln Ala Thr Arg Glu Val Lys Glu Met
            290                 295                 300 aag aaa gtc act att tct gtc cat gag aaa ggt ttc att gaa atc aaa     1082
Lys Lys Val Thr Ile Ser Val His Glu Lys Gly Phe Ile Glu Ile Lys
        305                 310                 315 ccc acc ttc agc cag ttg gaa gct gtc aac ctg cat gaa gtc aaa cat     1130
Pro Thr Phe Ser Gln Leu Glu Ala Val Asn Leu His Glu Val Lys His
    320                 325                 330 ttt gtt gta gag gtg cgg gcc tac cca cct ccc agg ata tcc tgg ctg     1178
Phe Val Val Glu Val Arg Ala Tyr Pro Pro Pro Arg Ile Ser Trp Leu
335                 340                 345                 350 aaa aac aat ctg act ctg att gaa aat ctc act gag atc acc act gat     1226
```

```
                Lys Asn Asn Leu Thr Leu Ile Glu Asn Leu Thr Glu Ile Thr Thr Asp
                                355                 360                 365 gtg aaa aag att cag gaa ata agg tat cga agc aaa tta aag ctg atc            1274
Val Glu Lys Ile Gln Glu Ile Arg Tyr Arg Ser Lys Leu Lys Leu Ile
            370                 375                 380 cgt gct aag gaa gaa gac agt ggc cat tat act att gta gct caa aat            1322
Arg Ala Lys Glu Glu Asp Ser Gly His Tyr Thr Ile Val Ala Gln Asn
                385                 390                 395 gaa gat gct gtg aag agc tat act ttt gaa ctg tta act caa gtt cct            1370
Glu Asp Ala Val Lys Ser Tyr Thr Phe Glu Leu Leu Thr Gln Val Pro
400                 405                 410 tca tcc att ctg gac ttg gtc gat gat cac cat ggc tca act ggg gga            1418
Ser Ser Ile Leu Asp Leu Val Asp Asp His His Gly Ser Thr Gly Gly
415                 420                 425                 430 cag acg gtg agg tgc aca gct gaa ggc acg ccg ctt cct gat att gag            1466
Gln Thr Val Arg Cys Thr Ala Glu Gly Thr Pro Leu Pro Asp Ile Glu
                435                 440                 445 tgg atg ata tgc aaa gat att aag aaa tgt aat aat gaa act tcc tgg            1514
Trp Met Ile Cys Lys Asp Ile Lys Lys Cys Asn Asn Glu Thr Ser Trp
                450                 455                 460 act att ttg gcc aac aat gtc tca aac atc atc acg gag atc cac tcc            1562
Thr Ile Leu Ala Asn Asn Val Ser Asn Ile Ile Thr Glu Ile His Ser
            465                 470                 475 cga gac agg agt acc gtg gag ggc cgt gtg act ttc gcc aaa gtg gag            1610
Arg Asp Arg Ser Thr Val Glu Gly Arg Val Thr Phe Ala Lys Val Glu
480                 485                 490 gag acc atc gcc gtg cga tgc ctg gct aag aat ctc ctt gga gct gag            1658
Glu Thr Ile Ala Val Arg Cys Leu Ala Lys Asn Leu Leu Gly Ala Glu
495                 500                 505                 510 aac cga gag ctg aag ctg gtg gct ccc acc ctg cgt tct gaa ctc acg            1706
Asn Arg Glu Leu Lys Leu Val Ala Pro Thr Leu Arg Ser Glu Leu Thr
                515                 520                 525 gtg gct gct gca gtc ctg gtg ctg ttg gtg att gtg atc atc tca ctt            1754
Val Ala Ala Ala Val Leu Val Leu Leu Val Ile Val Ile Ile Ser Leu
            530                 535                 540 att gtc ctg gtt gtc att tgg aaa cag aaa ccg agg tat gaa att cgc            1802
Ile Val Leu Val Val Ile Trp Lys Gln Lys Pro Arg Tyr Glu Ile Arg
            545                 550                 555 tgg agg gtc att gaa tca atc agc cca gat gga cat gaa tat att tat            1850
Trp Arg Val Ile Glu Ser Ile Ser Pro Asp Gly His Glu Tyr Ile Tyr
            560                 565                 570 gtg gac ccg atg cag ctg cct tat gac tca aga tgg gag ttt cca aga            1898
Val Asp Pro Met Gln Leu Pro Tyr Asp Ser Arg Trp Glu Phe Pro Arg
575                 580                 585                 590 gat gga cta gtg ctt ggt cgg gtc ttg ggg tct gga gcg ttt ggg aag            1946
Asp Gly Leu Val Leu Gly Arg Val Leu Gly Ser Gly Ala Phe Gly Lys
                595                 600                 605 gtg gtt gaa gga aca gcc tat gga tta agc cgg tcc caa cct gtc atg            1994
Val Val Glu Gly Thr Ala Tyr Gly Leu Ser Arg Ser Gln Pro Val Met
            610                 615                 620 aaa gtt gca gtg aag atg cta aaa ccc acg gcc aga tcc agt gaa aaa            2042
Lys Val Ala Val Lys Met Leu Lys Pro Thr Ala Arg Ser Ser Glu Lys
                625                 630                 635 caa gct ctc atg tct gaa ctg aag ata atg act cac ctg ggg cca cat            2090
Gln Ala Leu Met Ser Glu Leu Lys Ile Met Thr His Leu Gly Pro His
            640                 645                 650 ttg aac att gta aac ttg ctg gga gcc tgc acc aag tca ggc ccc att            2138
Leu Asn Ile Val Asn Leu Leu Gly Ala Cys Thr Lys Ser Gly Pro Ile
655                 660                 665                 670
```

-continued

| | | |
|---|---|---|
| tac atc atc aca gag tat tgc ttc tat gga gat ttg gtc aac tat ttg<br>Tyr Ile Ile Thr Glu Tyr Cys Phe Tyr Gly Asp Leu Val Asn Tyr Leu<br>675 680 685 | | 2186 |
| cat aag aat agg gat agc ttc ctg agc cac cca gag aag cca aag<br>His Lys Asn Arg Asp Ser Phe Leu Ser His His Pro Glu Lys Pro Lys<br>690 695 700 | | 2234 |
| aaa gag ctg gat atc ttt gga ttg aac cct gct gat gaa agc aca cgg<br>Lys Glu Leu Asp Ile Phe Gly Leu Asn Pro Ala Asp Glu Ser Thr Arg<br>705 710 715 | | 2282 |
| agc tat gtt att tta tct ttt gaa aac aat ggt gac tac atg gac atg<br>Ser Tyr Val Ile Leu Ser Phe Glu Asn Asn Gly Asp Tyr Met Asp Met<br>720 725 730 | | 2330 |
| aag cag gct gat act aca cag tat gtc ccc atg cta gaa agg aaa gag<br>Lys Gln Ala Asp Thr Thr Gln Tyr Val Pro Met Leu Glu Arg Lys Glu<br>735 740 745 750 | | 2378 |
| gtt tct aaa tat tcc gac atc cag aga tca ctc tat gat cgt cca gcc<br>Val Ser Lys Tyr Ser Asp Ile Gln Arg Ser Leu Tyr Asp Arg Pro Ala<br>755 760 765 | | 2426 |
| tca tat aag aag aaa tct atg tta gac tca gaa gtc aaa aac ctc ctt<br>Ser Tyr Lys Lys Lys Ser Met Leu Asp Ser Glu Val Lys Asn Leu Leu<br>770 775 780 | | 2474 |
| tca gat gat aac tca gaa ggc ctt act tta ttg gat ttg ttg agc ttc<br>Ser Asp Asp Asn Ser Glu Gly Leu Thr Leu Leu Asp Leu Leu Ser Phe<br>785 790 795 | | 2522 |
| acc tat caa gtt gcc cga gga atg gag ttt ttg gct tca aaa aat tgt<br>Thr Tyr Gln Val Ala Arg Gly Met Glu Phe Leu Ala Ser Lys Asn Cys<br>800 805 810 | | 2570 |
| gtc cac cgt gat ctg gct gct cgc aac gtt ctc ctg gca caa gga aaa<br>Val His Arg Asp Leu Ala Ala Arg Asn Val Leu Leu Ala Gln Gly Lys<br>815 820 825 830 | | 2618 |
| att gtg aag atc tgt gac ttt ggc ctg gcc aga gac atc atg cat gat<br>Ile Val Lys Ile Cys Asp Phe Gly Leu Ala Arg Asp Ile Met His Asp<br>835 840 845 | | 2666 |
| tcg aac tat gtg tcg aaa ggc agt acc ttt ctg ccc gtg aag tgg atg<br>Ser Asn Tyr Val Ser Lys Gly Ser Thr Phe Leu Pro Val Lys Trp Met<br>850 855 860 | | 2714 |
| gct cct gag agc atc ttt gac aac ctc tac acc aca ctg agt gat gtc<br>Ala Pro Glu Ser Ile Phe Asp Asn Leu Tyr Thr Thr Leu Ser Asp Val<br>865 870 875 | | 2762 |
| tgg tct tat ggc att ctg ctc tgg gag atc ttt tcc ctt ggt ggc acc<br>Trp Ser Tyr Gly Ile Leu Leu Trp Glu Ile Phe Ser Leu Gly Gly Thr<br>880 885 890 | | 2810 |
| cct tac ccc ggc atg atg gtg gat tct act ttc tac aat aag atc aag<br>Pro Tyr Pro Gly Met Met Val Asp Ser Thr Phe Tyr Asn Lys Ile Lys<br>895 900 905 910 | | 2858 |
| agt ggg tac cgg atg gcc aag cct gac cac gct acc agt gaa gtc tac<br>Ser Gly Tyr Arg Met Ala Lys Pro Asp His Ala Thr Ser Glu Val Tyr<br>915 920 925 | | 2906 |
| gag atc atg gtg aaa tgc tgg aac agt gag ccg gag aag aga ccc tcc<br>Glu Ile Met Val Lys Cys Trp Asn Ser Glu Pro Glu Lys Arg Pro Ser<br>930 935 940 | | 2954 |
| ttt tac cac ctg agt gag att gtg gag aat ctg ctg cct gga caa tat<br>Phe Tyr His Leu Ser Glu Ile Val Glu Asn Leu Leu Pro Gly Gln Tyr<br>945 950 955 | | 3002 |
| aaa aag agt tat gaa aaa att cac ctg gac ttc ctg aag agt gac cat<br>Lys Lys Ser Tyr Glu Lys Ile His Leu Asp Phe Leu Lys Ser Asp His<br>960 965 970 | | 3050 |
| cct gct gtg gca cgc atg cgt gtg gac tca gac aat gca tac att ggt<br>Pro Ala Val Ala Arg Met Arg Val Asp Ser Asp Asn Ala Tyr Ile Gly<br>975 980 985 990 | | 3098 |

```
gtc acc tac aaa aac gag gaa gac aag ctg  aag gac tgg gag ggt  ggt      3146
Val Thr Tyr Lys Asn Glu Glu Asp Lys Leu  Lys Asp Trp Glu Gly  Gly
                995                 1000                1005 ctg gat gag cag  aga ctg agc gct gac  agt ggc tac atc att  cct          3191
Leu Asp Glu Gln  Arg Leu Ser Ala Asp  Ser Gly Tyr Ile Ile  Pro
        1010                  1015                  1020 ctg cct gac att  gac cct gtc cct gag  gag gag gac ctg ggc  aag          3236
Leu Pro Asp Ile  Asp Pro Val Pro Glu  Glu Glu Asp Leu Gly  Lys
        1025                  1030                  1035 agg aac aga cac  agc tcg cag acc tct  gaa gag agt gcc att  gag          3281
Arg Asn Arg His  Ser Ser Gln Thr Ser  Glu Glu Ser Ala Ile  Glu
        1040                  1045                  1050 acg ggt tcc agc  agt tcc acc ttc atc  aag aga gag gac gag  acc          3326
Thr Gly Ser Ser  Ser Ser Thr Phe Ile  Lys Arg Glu Asp Glu  Thr
        1055                  1060                  1065 att gaa gac atc  gac atg atg gac gac  atc ggc ata gac tct  tca          3371
Ile Glu Asp Ile  Asp Met Met Asp Asp  Ile Gly Ile Asp Ser  Ser
        1070                  1075                  1080 gac ctg gtg gaa  gac agc ttc ctg taa ctggcggatt cgaggggttc              3418
Asp Leu Val Glu  Asp Ser Phe Leu
        1085 cttccacttc tggggccacc tctggatccc gttcagaaaa ccactttatt gcaatgcgga       3478 ggttgagagg aggacttggt tgatgtttaa agagaagttc ccagccaagg gcctcgggga       3538 gcctttctaa atatgaatga atgggatatt ttgaaatgaa ctttgtcagt gttgcctctt       3598 gcaatgcctc agtagcatct cagtggtgtg tgaagtttgg agatagatgg ataagggaat       3658 aataggccac agaaggtgaa ctttctgctt caaggacatt ggtgagagtc caacagacac       3718 aatttatact gcgacagaac ttcagcattg taattatgta ataaactcta accacggctg       3778 tgtttagatt gtattaacta tcttctttgg acttctgaag agaccactca atccatccat       3838 gtacttccct cttgaaacct gatgtcagct gctgttgaac ttttttaaaga agtgcatgaa      3898 aaaccatttt tgaccttaaa aggtactggt actatagcat tttgctatct tttttagtgt       3958 taaagagata aagaataata attaaccaac cttgtttaat agatttgggt catttagaag       4018 cctgacaact cattttcata ttgtaatcta tgtttataat actactactg ttatcagtaa       4078 tgctaaatgt gtaataatgt aacatgattt ccctccacac aaagcacaat ttaaaaacaa       4138 tccttactaa gtaggtgatg agtttgacag ttttgacat ttatattaaa taacatgttt        4198 ctctataaag tatggtaata gctttagtga attaaattta gttgagcata gagaacaaag       4258 taaaagtagt gttgtccagg aagtcagaat ttttaactgt actgaatagg ttccccaatc       4318 catcgtatta aaaacaatt aactgccctc tgaaataatg ggattagaaa caaacaaaac        4378 tcttaagtcc taaagttct caatgtagag gcataaacct gtgctgaaca taacttctca       4438 tgtatattac ccaatggaaa atataatgat cagcgcanaa agactggatt tgcagaagtt       4498 ntttttttt tttcttcttg cctgatgaaa gctttggcga ccccaatata tgtattttt        4558 gaatctatga acctgaaaag ggtcacaaag gatgcccaga catcagcctc cttctttcac       4618 cccttacccc aaagagaaag agtttgaaac tcgagaccat aaagatattc tttagtggag       4678 gctggaagtg cattagcctg atcctcagtt ctcaaatgtg tgtggcagcc aggtagacta       4738 gtacctgggt ttccatcctt gagattctga agtatgaagt ctgagggaaa ccagagtctg       4798 tattttccta aactccctgg ctgttctgat cggccaggtt tcggaaacac tgacttaggt       4858 ttcaggaagt tgccatggga aacaaataat ttgaactttg gaacagggtt cttaagttgg       4918
```

```
tgcgtccttc ggatgataaa tttaggaacc gaagtccaat cactgtaaat tacggtagat    4978
cgatcgttaa cgctggaatt aaattgaaag gtcagaatcg actccgactc tttcgatttc    5038
aaaccaaaac tgtccaaaag gttttcattt ctacgatgaa gggtgacata cccctctaa     5098
cttgaaaggg gcagagggca gaagagcgga gggtgaggta tggggcggtt cctttccgta    5158
catgtttta atacgttaag tcacaaggtt cagagacaca ttggtcgagt cacaaaacca    5218
ccttttttgt aaaattcaaa atgactatta aactccaatc taccctccta cttaacagtg    5278
tagataggtg tgacagtttg tccaaccaca cccaagtaac cgtaagaaac gttatgacga    5338
attaacgact atggtatact tactttgtac ccgacactaa tgacgttagt gacacgatag    5398
ccgtctacta cgaaaccttc tacgtcttcg ttattatttc atgaactgat ggatgaccac    5458
attagagtta cgttcgtggt tgaaagaata ggttgaaaaa gtatcattca cgcttctgac    5518
tcggtctaac cggttaattt ttcttttgga ctgatccaag acatctcggt taatctgaac    5578
tttatgcaaa cacaaagatc ttagtgtcga gttcgtaaga caaatagcga gtgagaggga    5638
acatgtcgga ataaaacaac cacgaaacgt aaaactataa cgacactcgg aacgtactgt    5698
agtactccgg cctactttga agagtcaggt cgtcaaaggt caggattgtt tacgagggtg    5758
gacttaaaca tatactgacg taaacaccca cacacacaca aaagtcgttt aaggtctaaa    5818
caaaggaaaa ccggaggacg tttcagaggt cttcttttaa acggttagaa aggatgaaag    5878
ataaaaatac tactgttagt ttcggccgga ctctttgtga taaacactga aaaatttgct    5938
aatcactaca ggaattttac accagacggt tagacatgtt ttaccaggat aaaaacactt    5998
ctccctgtat tctatttac tacaatatgt agttatacat atatacataa agatatatct     6058
gaacctctta tgacggtttt gtaaatactg ttcgacatag tgacggaagc aaatataaaa    6118
aaattgacac tattagggt gtccgtgtaa ttgacaacgt gaaaacttac aggttttaaa     6178
tataaaatct ttattatttt tctttctatg aatgtacaag ggttttgtta ccacaccact    6238
tacacactct ttttgattga actatcccag atggttatgt tttacataat gcttacgggg    6298
acaagtacaa aaacaaaatt ttgcacattt acttctagaa atataaagtt atttactata    6358
tattaaattt ccttaag                                                    6375
```

<210> SEQ ID NO 117
<211> LENGTH: 1089
<212> TYPE: PRT
<213> ORGANISM: Homo sapiens

<400> SEQUENCE: 117

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

-continued

Glu Gly Arg His Ile Tyr Ile Tyr Val Pro Asp Pro Asp Val Ala Phe
            115                 120                 125

Val Pro Leu Gly Met Thr Asp Tyr Leu Val Ile Val Glu Asp Asp
130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Pro Arg Ile Ser Trp Leu Lys Asn
            340                 345                 350

Asn Leu Thr Leu Ile Glu Asn Leu Thr Glu Ile Thr Thr Asp Val Glu
        355                 360                 365

Lys Ile Gln Glu Ile Arg Tyr Arg Ser Lys Leu Lys Leu Ile Arg Ala
370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
        515                 520                 525

Ala Ala Val Leu Val Leu Leu Val Ile Val Ile Ile Ser Leu Ile Val

```
                530             535             540
Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
        595                 600                 605

Glu Gly Thr Ala Tyr Gly Leu Ser Arg Ser Gln Pro Val Met Lys Val
    610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
                660                 665                 670

Ile Thr Glu Tyr Cys Phe Tyr Gly Asp Leu Val Asn Tyr Leu His Lys
            675                 680                 685

Asn Arg Asp Ser Phe Leu Ser His His Pro Glu Lys Pro Lys Lys Glu
        690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ile Met His Asp Ser Asn
        835                 840                 845

Tyr Val Ser Lys Gly Ser Thr Phe Leu Pro Val Lys Trp Met Ala Pro
850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
            930                 935                 940

His Leu Ser Glu Ile Val Glu Asn Leu Leu Pro Gly Gln Tyr Lys Lys
945                 950                 955                 960
```

```
Ser Tyr Glu Lys Ile His Leu Asp Phe Leu Lys Ser Asp His Pro Ala
            965                 970                 975

Val Ala Arg Met Arg Val Asp Ser Asp Asn Ala Tyr Ile Gly Val Thr
        980                 985                 990

Tyr Lys Asn Glu Glu Asp Lys Leu  Lys Asp Trp Glu Gly  Gly Leu Asp
        995                 1000                 1005

Glu Gln  Arg Leu Ser Ala Asp  Ser Gly Tyr Ile Ile  Pro Leu Pro
    1010                 1015                 1020

Asp Ile  Asp Pro Val Pro Glu  Glu Glu Asp Leu Gly  Lys Arg Asn
    1025                 1030                 1035

Arg His  Ser Ser Gln Thr Ser  Glu Glu Ser Ala Ile  Glu Thr Gly
    1040                 1045                 1050

Ser Ser  Ser Ser Thr Phe Ile  Lys Arg Glu Asp Glu  Thr Ile Glu
    1055                 1060                 1065

Asp Ile  Asp Met Met Asp Asp  Ile Gly Ile Asp Ser  Ser Asp Leu
    1070                 1075                 1080

Val Glu  Asp Ser Phe Leu
    1085

<210> SEQ ID NO 118
<211> LENGTH: 5427
<212> TYPE: DNA
<213> ORGANISM: Homo sapiens
<220> FEATURE:
<221> NAME/KEY: CDS
<222> LOCATION: (187)..(3507)

<400> SEQUENCE: 118
tgttctcctg agccttcagg agcctgcacc agtcctgcct gtccttctac tcagctgtta      60
cccactctgg gaccagcagt ctttctgata actgggagag ggcagtaagg aggacttcct     120 ggaggggggtg actgtccaga gcctggaact gtgcccacac cagaagccat cagcagcaag    180 gacacc atg cgg ctt ccg ggt gcg atg cca gct ctg gcc ctc aaa ggc       228
       Met Arg Leu Pro Gly Ala Met Pro Ala Leu Ala Leu Lys Gly
       1               5                  10 gag ctg ctg ttg ctg tct ctc ctg tta ctt ctg gaa cca cag atc tct       276
Glu Leu Leu Leu Leu Ser Leu Leu Leu Leu Leu Glu Pro Gln Ile Ser
15                  20                  25                  30 cag ggc ctg gtc gtc aca ccc ccg ggg cca gag ctt gtc ctc aat gtc       324
Gln Gly Leu Val Val Thr Pro Pro Gly Pro Glu Leu Val Leu Asn Val
                35                  40                  45 tcc agc acc ttc gtt ctg acc tgc tcg ggt tca gct ccg gtg gtg tgg       372
Ser Ser Thr Phe Val Leu Thr Cys Ser Gly Ser Ala Pro Val Val Trp
            50                  55                  60 gaa cgg atg tcc cag gag ccc cca cag gaa atg gcc aag gcc cag gat       420
Glu Arg Met Ser Gln Glu Pro Pro Gln Glu Met Ala Lys Ala Gln Asp
        65                  70                  75 ggc acc ttc tcc agc gtg ctc aca ctg acc aac ctc act ggg cta gac       468
Gly Thr Phe Ser Ser Val Leu Thr Leu Thr Asn Leu Thr Gly Leu Asp
    80                  85                  90 acg gga gaa tac ttt tgc acc cac aat gac tcc cgt gga ctg gag acc       516
Thr Gly Glu Tyr Phe Cys Thr His Asn Asp Ser Arg Gly Leu Glu Thr
95                 100                 105                 110 gat gag cgg aaa cgg ctc tac atc ttt gtg cca gat ccc acc gtg ggc       564
Asp Glu Arg Lys Arg Leu Tyr Ile Phe Val Pro Asp Pro Thr Val Gly
                115                 120                 125 ttc ctc cct aat gat gcc gag gaa cta ttc atc ttt ctc acg gaa ata       612
Phe Leu Pro Asn Asp Ala Glu Glu Leu Phe Ile Phe Leu Thr Glu Ile
```

```
                    130                 135                 140
act gag atc acc att cca tgc cga gta aca gac cca cag ctg gtg gtg      660
Thr Glu Ile Thr Ile Pro Cys Arg Val Thr Asp Pro Gln Leu Val Val
            145                 150                 155 aca ctg cac gag aag aaa ggg gac gtt gca ctg cct gtc ccc tat gat      708
Thr Leu His Glu Lys Lys Gly Asp Val Ala Leu Pro Val Pro Tyr Asp
    160                 165                 170 cac caa cgt ggc ttt tct ggt atc ttt gag gac aga agc tac atc tgc      756
His Gln Arg Gly Phe Ser Gly Ile Phe Glu Asp Arg Ser Tyr Ile Cys
175                 180                 185                 190 aaa acc acc att ggg gac agg gag gtg gat tct gat gcc tac tat gtc      804
Lys Thr Thr Ile Gly Asp Arg Glu Val Asp Ser Asp Ala Tyr Tyr Val
                195                 200                 205 tac aga ctc cag gtg tca tcc atc aac gtc tct gtg aac gca gtg cag      852
Tyr Arg Leu Gln Val Ser Ser Ile Asn Val Ser Val Asn Ala Val Gln
            210                 215                 220 act gtg gtc cgc cag ggt gag aac atc acc ctc atg tgc att gtg atc      900
Thr Val Val Arg Gln Gly Glu Asn Ile Thr Leu Met Cys Ile Val Ile
    225                 230                 235 ggg aat gat gtg gtc aac ttc gag tgg aca tac ccc cgc aaa gaa agt      948
Gly Asn Asp Val Val Asn Phe Glu Trp Thr Tyr Pro Arg Lys Glu Ser
240                 245                 250 ggg cgg ctg gtg gag ccg gtg act gac ttc ctc ttg gat atg cct tac      996
Gly Arg Leu Val Glu Pro Val Thr Asp Phe Leu Leu Asp Met Pro Tyr
255                 260                 265                 270 cac atc cgc tcc atc ctg cac atc ccc agt gcc gag tta gaa gac tcg     1044
His Ile Arg Ser Ile Leu His Ile Pro Ser Ala Glu Leu Glu Asp Ser
                275                 280                 285 ggg acc tac acc tgc aat gtg acg gag agt gtg aat gac cat cag gat     1092
Gly Thr Tyr Thr Cys Asn Val Thr Glu Ser Val Asn Asp His Gln Asp
            290                 295                 300 gaa aag gcc atc aac atc acc gtg gtt gag agc ggc tac gtg cgg ctc     1140
Glu Lys Ala Ile Asn Ile Thr Val Val Glu Ser Gly Tyr Val Arg Leu
    305                 310                 315 ctg gga gag gtg ggc aca cta caa ttt gct gag ctg cat cgg agc cgg     1188
Leu Gly Glu Val Gly Thr Leu Gln Phe Ala Glu Leu His Arg Ser Arg
320                 325                 330 aca ctg cag gta gtg ttc gag gcc tac cca ccg ccc act gtc ctg tgg     1236
Thr Leu Gln Val Val Phe Glu Ala Tyr Pro Pro Pro Thr Val Leu Trp
335                 340                 345                 350 ttc aaa gac aac cgc acc ctg ggc gac tcc agc gct ggc gaa atc gcc     1284
Phe Lys Asp Asn Arg Thr Leu Gly Asp Ser Ser Ala Gly Glu Ile Ala
            355                 360                 365 ctg tcc acg cgc aac gtg tcg gag acc cgg tat gtg tca gag ctg aca     1332
Leu Ser Thr Arg Asn Val Ser Glu Thr Arg Tyr Val Ser Glu Leu Thr
    370                 375                 380 ctg gtt cgc gtg aag gtg gca gag gct ggc cac tac acc atg cgg gcc     1380
Leu Val Arg Val Lys Val Ala Glu Ala Gly His Tyr Thr Met Arg Ala
385                 390                 395 ttc cat gag gat gct gag gtc cag ctc tcc ttc cag cta cag atc aat     1428
Phe His Glu Asp Ala Glu Val Gln Leu Ser Phe Gln Leu Gln Ile Asn
            400                 405                 410 gtc cct gtc cga gtg ctg gag cta agt gag agc cac cct gac agt ggg     1476
Val Pro Val Arg Val Leu Glu Leu Ser Glu Ser His Pro Asp Ser Gly
415                 420                 425                 430 gaa cag aca gtc cgc tgt cgt ggc cgg ggc atg ccg cag ccg aac atc     1524
Glu Gln Thr Val Arg Cys Arg Gly Arg Gly Met Pro Gln Pro Asn Ile
                435                 440                 445 atc tgg tct gcc tgc aga gac ctc aaa agg tgt cca cgt gag ctg ccg     1572
```

```
        Ile Trp Ser Ala Cys Arg Asp Leu Lys Arg Cys Pro Arg Glu Leu Pro
                    450                 455                 460 ccc acg ctg ctg ggg aac agt tcc gaa gag gag agc cag ctg gag act        1620
Pro Thr Leu Leu Gly Asn Ser Ser Glu Glu Glu Ser Gln Leu Glu Thr
                465                 470                 475 aac gtg acg tac tgg gag gag gag cag gag ttt gag gtg gtg agc aca        1668
Asn Val Thr Tyr Trp Glu Glu Glu Gln Glu Phe Glu Val Val Ser Thr
        480                 485                 490 ctg cgt ctg cag cac gtg gat cgg cca ctg tcg gtg cgc tgc acg ctg        1716
Leu Arg Leu Gln His Val Asp Arg Pro Leu Ser Val Arg Cys Thr Leu
495                 500                 505                 510 cgc aac gct gtg ggc cag gac acg cag gag gtc atc gtg gtg cca cac        1764
Arg Asn Ala Val Gly Gln Asp Thr Gln Glu Val Ile Val Val Pro His
                515                 520                 525 tcc ttg ccc ttt aag gtg gtg gtg atc tca gcc atc ctg gcc ctg gtg        1812
Ser Leu Pro Phe Lys Val Val Val Ile Ser Ala Ile Leu Ala Leu Val
                530                 535                 540 gtg ctc acc atc atc tcc ctt atc atc ctc atc atg ctt tgg cag aag        1860
Val Leu Thr Ile Ile Ser Leu Ile Ile Leu Ile Met Leu Trp Gln Lys
                545                 550                 555 aag cca cgt tac gag atc cga tgg aag gtg att gag tct gtg agc tct        1908
Lys Pro Arg Tyr Glu Ile Arg Trp Lys Val Ile Glu Ser Val Ser Ser
                560                 565                 570 gac ggc cat gag tac atc tac gtg gac ccc atg cag ctg ccc tat gac        1956
Asp Gly His Glu Tyr Ile Tyr Val Asp Pro Met Gln Leu Pro Tyr Asp
575                 580                 585                 590 tcc acg tgg gag ctg ccg cgg gac cag ctt gtg ctg gga cgc acc ctc        2004
Ser Thr Trp Glu Leu Pro Arg Asp Gln Leu Val Leu Gly Arg Thr Leu
                595                 600                 605 ggc tct ggg gcc ttt ggg cag gtg gtg gag gcc aca gct cat ggt ctg        2052
Gly Ser Gly Ala Phe Gly Gln Val Val Glu Ala Thr Ala His Gly Leu
                610                 615                 620 agc cat tct cag gcc acg atg aaa gtg gcc gtc aag atg ctt aaa tcc        2100
Ser His Ser Gln Ala Thr Met Lys Val Ala Val Lys Met Leu Lys Ser
                625                 630                 635 aca gcc cgc agc agt gag aag caa gcc ctt atg tcg gag ctg aag atc        2148
Thr Ala Arg Ser Ser Glu Lys Gln Ala Leu Met Ser Glu Leu Lys Ile
            640                 645                 650 atg agt cac ctt ggg ccc cac ctg aac gtg gtc aac ctg ttg ggg gcc        2196
Met Ser His Leu Gly Pro His Leu Asn Val Val Asn Leu Leu Gly Ala
655                 660                 665                 670 tgc acc aaa gga gga ccc atc tat atc atc act gag tac tgc cgc tac        2244
Cys Thr Lys Gly Gly Pro Ile Tyr Ile Ile Thr Glu Tyr Cys Arg Tyr
                675                 680                 685 gga gac ctg gtg gac tac ctg cac cgc aac aaa cac acc ttc ctg cag        2292
Gly Asp Leu Val Asp Tyr Leu His Arg Asn Lys His Thr Phe Leu Gln
                690                 695                 700 cac cac tcc gac aag cgc cgc ccg ccc agc gcg gag ctc tac agc aat        2340
His His Ser Asp Lys Arg Arg Pro Pro Ser Ala Glu Leu Tyr Ser Asn
                705                 710                 715 gct ctg ccc gtt ggg ctc ccc ctg ccc agc cat gtg tcc ttg acc ggg        2388
Ala Leu Pro Val Gly Leu Pro Leu Pro Ser His Val Ser Leu Thr Gly
            720                 725                 730 gag agc gac ggt ggc tac atg gac atg agc aag gac gag tcg gtg gac        2436
Glu Ser Asp Gly Gly Tyr Met Asp Met Ser Lys Asp Glu Ser Val Asp
735                 740                 745                 750 tat gtg ccc atg ctg gac atg aaa gga gac gtc aaa tat gca gac atc        2484
Tyr Val Pro Met Leu Asp Met Lys Gly Asp Val Lys Tyr Ala Asp Ile
                755                 760                 765
```

```
gag tcc tcc aac tac atg gcc cct tac gat aac tac gtt ccc tct gcc       2532
Glu Ser Ser Asn Tyr Met Ala Pro Tyr Asp Asn Tyr Val Pro Ser Ala
            770                 775                 780 cct gag agg acc tgc cga gca act ttg atc aac gag tct cca gtg cta       2580
Pro Glu Arg Thr Cys Arg Ala Thr Leu Ile Asn Glu Ser Pro Val Leu
            785                 790                 795 agc tac atg gac ctc gtg ggc ttc agc tac cag gtg gcc aat ggc atg       2628
Ser Tyr Met Asp Leu Val Gly Phe Ser Tyr Gln Val Ala Asn Gly Met
            800                 805                 810 gag ttt ctg gcc tcc aag aac tgc gtc cac aga gac ctg gcg gct agg       2676
Glu Phe Leu Ala Ser Lys Asn Cys Val His Arg Asp Leu Ala Ala Arg
815                 820                 825                 830 aac gtg ctc atc tgt gaa ggc aag ctg gtc aag atc tgt gac ttt ggc       2724
Asn Val Leu Ile Cys Glu Gly Lys Leu Val Lys Ile Cys Asp Phe Gly
                835                 840                 845 ctg gct cga gac atc atg cgg gac tcg aat tac atc tcc aaa ggc agc       2772
Leu Ala Arg Asp Ile Met Arg Asp Ser Asn Tyr Ile Ser Lys Gly Ser
            850                 855                 860 acc ttt ttg cct tta aag tgg atg gct ccg gag agc atc ttc aac agc       2820
Thr Phe Leu Pro Leu Lys Trp Met Ala Pro Glu Ser Ile Phe Asn Ser
            865                 870                 875 ctc tac acc acc ctg agc gac gtg tgg tcc ttc ggg atc ctg ctc tgg       2868
Leu Tyr Thr Thr Leu Ser Asp Val Trp Ser Phe Gly Ile Leu Leu Trp
            880                 885                 890 gag atc ttc acc ttg ggt ggc acc cct tac cca gag ctg ccc atg aac       2916
Glu Ile Phe Thr Leu Gly Gly Thr Pro Tyr Pro Glu Leu Pro Met Asn
895                 900                 905                 910 gag cag ttc tac aat gcc atc aaa cgg ggt tac cgc atg gcc cag cct       2964
Glu Gln Phe Tyr Asn Ala Ile Lys Arg Gly Tyr Arg Met Ala Gln Pro
                915                 920                 925 gcc cat gcc tcc gac gag atc tat gag atc atg cag aag tgc tgg gaa       3012
Ala His Ala Ser Asp Glu Ile Tyr Glu Ile Met Gln Lys Cys Trp Glu
            930                 935                 940 gag aag ttt gag att cgg ccc ccc ttc tcc cag ctg gtg ctc ttc ctc       3060
Glu Lys Phe Glu Ile Arg Pro Pro Phe Ser Gln Leu Val Leu Leu Leu
            945                 950                 955 gag aga ctg ttg ggc gaa ggt tac aaa aag aag tac cag cag gtg gat       3108
Glu Arg Leu Leu Gly Glu Gly Tyr Lys Lys Lys Tyr Gln Gln Val Asp
960                 965                 970 gag gag ttt ctg agg agt gac cac cca gcc atc ctt cgg tcc cag gcc       3156
Glu Glu Phe Leu Arg Ser Asp His Pro Ala Ile Leu Arg Ser Gln Ala
975                 980                 985                 990 cgc ttg cct ggg ttc cat ggc ctc cga tct ccc ctg gac acc agc tcc       3204
Arg Leu Pro Gly Phe His Gly Leu Arg Ser Pro Leu Asp Thr Ser Ser
                995                1000                1005 gtc ctc tat act gcc gtg cag ccc aat gag ggt gac aac gac tat           3249
Val Leu Tyr Thr Ala Val Gln Pro Asn Glu Gly Asp Asn Asp Tyr
            1010                1015                1020 atc atc ccc ctg cct gac ccc aaa cct gag gtt gct gac gag ggc           3294
Ile Ile Pro Leu Pro Asp Pro Lys Pro Glu Val Ala Asp Glu Gly
            1025                1030                1035 cca ctg gag ggt tcc ccc agc cta gcc agc tcc acc ctg aat gaa           3339
Pro Leu Glu Gly Ser Pro Ser Leu Ala Ser Ser Thr Leu Asn Glu
            1040                1045                1050 gtc aac acc tcc tca acc atc tcc tgt gac agc ccc ctg gag ccc           3384
Val Asn Thr Ser Ser Thr Ile Ser Cys Asp Ser Pro Leu Glu Pro
            1055                1060                1065 cag gac gaa cca gag cca gag ccc cag ctt gag ctc cag gtg gag           3429
Gln Asp Glu Pro Glu Pro Glu Pro Gln Leu Glu Leu Gln Val Glu
            1070                1075                1080
```

| ccg gag ccg gag ctg gaa cag ttg ccg gat tcg ggg tgc cct gcg | 3474 |
| Pro Glu Pro Glu Leu Glu Gln Leu Pro Asp Ser Gly Cys Pro Ala | |
|             1085                     1090                  1095 | |

| cct cgg gcg gaa gca gag gat agc ttc ctg tag ggggctggcc | 3517 |
| Pro Arg Ala Glu Ala Glu Asp Ser Phe Leu | |
|             1100                     1105 | |

```
cctaccctgc cctgcctgaa gctccccgc tgccagcacc cagcatctcc tggcctggcc      3577
tggccgggct tcctgtcagc caggctgccc ttatcagctg tcccttctg gaagctttct      3637 gctcctgacg tgttgtgccc aaaccctgg ggctggctta ggaggcaaga aaactgcagg      3697
ggccgtgacc agccctctgc ctccagggag gccaactgac tctgagccag gttccccca      3757 gggaactcag ttttcccata tgtaagatgg gaaagttagg cttgatgacc agaatctag     3817 gattctctcc ctggctgaca ggtggggaga ccgaatccct ccctgggaag attcttggag    3877
ttactgaggt ggtaaattaa cttttttctg ttcagccagc taccctcaa ggaatcatag    3937 ctctctcctc gcacttttat ccacccagga gctaggaag agaccctagc ctccctggct    3997
gctggctgag ctagggccta gccttgagca gtgttgcctc atccagaaga agccagtct    4057 cctcctatg atgccagtcc ctgcgttccc tggcccgagc tggtctgggg ccattaggca    4117
gcctaattaa tgctggaggc tgagccaagt acaggacacc cccagcctgc agcccttgcc   4177
cagggcactt ggagcacacg cagccatagc aagtgcctgt gtccctgtcc ttcaggccca   4237
tcagtcctgg ggcttttct ttatcaccct cagtcttaat ccatccacca gagtctagaa    4297
ggccagacgg gccccgcatc tgtgatgaga atgtaaatgt gccagtgtgg agtggccacg    4357
tgtgtgtgcc agatatggcc ctggctctgc attggacctg ctatgaggct ttggaggaat    4417
ccctcaccct ctctgggcct cagtttcccc ttcaaaaaat gaataagtcg gacttattaa    4477
ctctgagtgc cttgccagca ctaacattct agagtatcca ggtggttgca catttgtcca    4537
gatgaagcaa ggccatatac cctaaacttc catcctgggg gtcagctggg ctcctgggag    4597
attccagatc acacatcaca ctctggggac tcaggaacca tgccccttcc ccaggccccc    4657
agcaagtctc aagaacacag ctgcacaggc cttgacttag agtgacagcc ggtgtcctgg    4717
aaagccccca gcagctgccc cagggacatg ggaagaccac gggacctctt tcactaccca    4777
cgatgacctc cgggggtatc ctgggcaaaa gggacaaaga gggcaaatga gatcacctcc    4837
tgcagcccac cactccagca cctgtgccga ggtctgcgtc gaagacagaa tggacagtga    4897
ggacagttat gtcttgtaaa agacaagaag cttcagatgg gtaccccaag aaggatgtga    4957
gaggtgggcg cttggaggt ttgccctca cccaccagct gccccatccc tgaggcagcg      5017
ctccatgggg gtatggtttt gtcactgccc agacctagca gtgacatctc attgtcccca    5077
gcccagtggg cattggaggt gccaggggag tcagggttgt agccaagacg ccccgcacg     5137 gggagggttg gaaggggt gcaggaagct caacccctct gggcaccaac cctgcattgc     5197
aggttggcac cttacttccc tgggatccca gagttggtcc aaggagggag agtgggttct    5257
caatacggta ccaaagatat aatcacctag gtttacaaat attttttagga ctcacgttaa   5317 ctcacattta tacagcagaa atgctatttt gtatgctgtt aagttttct atctgtgtac     5377 ttttttttaa gggaaagatt ttaatattaa acctggtgct tctcactcac                5427
```

<210> SEQ ID NO 119
<211> LENGTH: 1106
<212> TYPE: PRT
<213> ORGANISM: Homo sapiens

<400> SEQUENCE: 119

```
Met Arg Leu Pro Gly Ala Met Pro Ala Leu Ala Leu Lys Gly Glu Leu
1               5                   10                  15
Leu Leu Leu Ser Leu Leu Leu Leu Glu Pro Gln Ile Ser Gln Gly
            20                  25                  30
Leu Val Val Thr Pro Pro Gly Pro Glu Leu Val Leu Asn Val Ser Ser
            35                  40                  45
Thr Phe Val Leu Thr Cys Ser Gly Ser Ala Pro Val Val Trp Glu Arg
50                  55                  60
Met Ser Gln Glu Pro Pro Gln Glu Met Ala Lys Ala Gln Asp Gly Thr
65                  70                  75                  80
Phe Ser Ser Val Leu Thr Leu Thr Asn Leu Thr Gly Leu Asp Thr Gly
                85                  90                  95
Glu Tyr Phe Cys Thr His Asn Asp Ser Arg Gly Leu Glu Thr Asp Glu
            100                 105                 110
Arg Lys Arg Leu Tyr Ile Phe Val Pro Asp Pro Thr Val Gly Phe Leu
            115                 120                 125
Pro Asn Asp Ala Glu Glu Leu Phe Ile Phe Leu Thr Glu Ile Thr Glu
        130                 135                 140
Ile Thr Ile Pro Cys Arg Val Thr Asp Pro Gln Leu Val Val Thr Leu
145                 150                 155                 160
His Glu Lys Lys Gly Asp Val Ala Leu Pro Val Pro Tyr Asp His Gln
                165                 170                 175
Arg Gly Phe Ser Gly Ile Phe Glu Asp Arg Ser Tyr Ile Cys Lys Thr
            180                 185                 190
Thr Ile Gly Asp Arg Glu Val Asp Ser Asp Ala Tyr Tyr Val Tyr Arg
        195                 200                 205
Leu Gln Val Ser Ser Ile Asn Val Ser Val Asn Ala Val Gln Thr Val
    210                 215                 220
Val Arg Gln Gly Glu Asn Ile Thr Leu Met Cys Ile Val Ile Gly Asn
225                 230                 235                 240
Asp Val Val Asn Phe Glu Trp Thr Tyr Pro Arg Lys Glu Ser Gly Arg
                245                 250                 255
Leu Val Glu Pro Val Thr Asp Phe Leu Leu Asp Met Pro Tyr His Ile
            260                 265                 270
Arg Ser Ile Leu His Ile Pro Ser Ala Glu Leu Glu Asp Ser Gly Thr
        275                 280                 285
Tyr Thr Cys Asn Val Thr Glu Ser Val Asn Asp His Gln Asp Glu Lys
290                 295                 300
Ala Ile Asn Ile Thr Val Val Glu Ser Gly Tyr Val Arg Leu Leu Gly
305                 310                 315                 320
Glu Val Gly Thr Leu Gln Phe Ala Glu Leu His Arg Ser Arg Thr Leu
                325                 330                 335
Gln Val Val Phe Glu Ala Tyr Pro Pro Pro Thr Val Leu Trp Phe Lys
            340                 345                 350
Asp Asn Arg Thr Leu Gly Asp Ser Ser Ala Gly Glu Ile Ala Leu Ser
        355                 360                 365
Thr Arg Asn Val Ser Glu Thr Arg Tyr Val Ser Glu Leu Thr Leu Val
    370                 375                 380
Arg Val Lys Val Ala Glu Ala Gly His Tyr Thr Met Arg Ala Phe His
385                 390                 395                 400
Glu Asp Ala Glu Val Gln Leu Ser Phe Gln Leu Gln Ile Asn Val Pro
                405                 410                 415
```

Val Arg Val Leu Glu Leu Ser Glu Ser His Pro Asp Ser Gly Glu Gln
            420                 425                 430

Thr Val Arg Cys Arg Gly Arg Gly Met Pro Gln Pro Asn Ile Ile Trp
            435                 440                 445

Ser Ala Cys Arg Asp Leu Lys Arg Cys Pro Arg Glu Leu Pro Pro Thr
450                 455                 460

Leu Leu Gly Asn Ser Ser Glu Glu Ser Gln Leu Glu Thr Asn Val
465                 470                 475                 480

Thr Tyr Trp Glu Glu Gln Glu Phe Glu Val Val Ser Thr Leu Arg
            485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Val Pro His Ser Leu
            515                 520                 525

Pro Phe Lys Val Val Ile Ser Ala Ile Leu Ala Leu Val Val Leu
            530                 535                 540

Thr Ile Ile Ser Leu Ile Ile Leu Ile Met Leu Trp Gln Lys Lys Pro
545                 550                 555                 560

Arg Tyr Glu Ile Arg Trp Lys Val Ile Glu Ser Val Ser Ser Asp Gly
            565                 570                 575

His Glu Tyr Ile Tyr Val Asp Pro Met Gln Leu Pro Tyr Asp Ser Thr
            580                 585                 590

Trp Glu Leu Pro Arg Asp Gln Leu Val Leu Gly Arg Thr Leu Gly Ser
            595                 600                 605

Gly Ala Phe Gly Gln Val Val Glu Ala Thr Ala His Gly Leu Ser His
            610                 615                 620

Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser
            645                 650                 655

His Leu Gly Pro His Leu Asn Val Val Asn Leu Leu Gly Ala Cys Thr
            660                 665                 670

Lys Gly Gly Pro Ile Tyr Ile Ile Thr Glu Tyr Cys Arg Tyr Gly Asp
            675                 680                 685

Leu Val Asp Tyr Leu His Arg Asn Lys His Thr Phe Leu Gln His His
            690                 695                 700

Ser Asp Lys Arg Arg Pro Pro Ser Ala Glu Leu Tyr Ser Asn Ala Leu
705                 710                 715                 720

Pro Val Gly Leu Pro Leu Pro Ser His Val Ser Leu Thr Gly Glu Ser
            725                 730                 735

Asp Gly Gly Tyr Met Asp Met Ser Lys Asp Glu Ser Val Asp Tyr Val
            740                 745                 750

Pro Met Leu Asp Met Lys Gly Asp Val Lys Tyr Ala Asp Ile Glu Ser
            755                 760                 765

Ser Asn Tyr Met Ala Pro Tyr Asp Asn Tyr Val Pro Ser Ala Pro Glu
            770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
            805                 810                 815

Leu Ala Ser Lys Asn Cys Val His Arg Asp Leu Ala Ala Arg Asn Val
            820                 825                 830

| | | | | | | | | | | | | |
|---|---|---|---|---|---|---|---|---|---|---|---|---|
|Leu|Ile|Cys|Glu|Gly|Lys|Leu|Lys|Ile|Cys|Asp|Phe|Gly|Leu|Ala|
| | |835| | | |840| | | |845| | | |

Arg Asp Ile Met Arg Asp Ser Asn Tyr Ile Ser Lys Gly Ser Thr Phe
850 855 860

Leu Pro Leu Lys Trp Met Ala Pro Glu Ser Ile Phe Asn Ser Leu Tyr
865 870 875 880

Thr Thr Leu Ser Asp Val Trp Ser Phe Gly Ile Leu Leu Trp Glu Ile
885 890 895

Phe Thr Leu Gly Gly Thr Pro Tyr Pro Glu Leu Pro Met Asn Glu Gln
900 905 910

Phe Tyr Asn Ala Ile Lys Arg Gly Tyr Arg Met Ala Gln Pro Ala His
915 920 925

Ala Ser Asp Glu Ile Tyr Glu Ile Met Gln Lys Cys Trp Glu Glu Lys
930 935 940

Phe Glu Ile Arg Pro Pro Phe Ser Gln Leu Val Leu Leu Leu Glu Arg
945 950 955 960

Leu Leu Gly Glu Gly Tyr Lys Lys Lys Tyr Gln Gln Val Asp Glu Glu
965 970 975

Phe Leu Arg Ser Asp His Pro Ala Ile Leu Arg Ser Gln Ala Arg Leu
980 985 990

Pro Gly Phe His Gly Leu Arg Ser Pro Leu Asp Thr Ser Ser Val Leu
995 1000 1005

Tyr Thr Ala Val Gln Pro Asn Glu Gly Asp Asn Asp Tyr Ile Ile
1010 1015 1020

Pro Leu Pro Asp Pro Lys Pro Glu Val Ala Asp Glu Gly Pro Leu
1025 1030 1035

Glu Gly Ser Pro Ser Leu Ala Ser Ser Thr Leu Asn Glu Val Asn
1040 1045 1050

Thr Ser Ser Thr Ile Ser Cys Asp Ser Pro Leu Glu Pro Gln Asp
1055 1060 1065

Glu Pro Glu Pro Glu Pro Gln Leu Glu Leu Gln Val Glu Pro Glu
1070 1075 1080

Pro Glu Leu Glu Gln Leu Pro Asp Ser Gly Cys Pro Ala Pro Arg
1085 1090 1095

Ala Glu Ala Glu Asp Ser Phe Leu
1100 1105

<210> SEQ ID NO 120
<211> LENGTH: 4795
<212> TYPE: DNA
<213> ORGANISM: Homo sapiens
<220> FEATURE:
<221> NAME/KEY: CDS
<222> LOCATION: (20)..(4111)

<400> SEQUENCE: 120

```
ccacgcgcag cggccggag atg cag cgg ggc gcc gcg ctg tgc ctg cga ctg      52
                    Met Gln Arg Gly Ala Ala Leu Cys Leu Arg Leu
                     1               5                  10 tgg ctc tgc ctg gga ctc ctg gac ggc ctg gtg agt ggc tac tcc atg      100
Trp Leu Cys Leu Gly Leu Leu Asp Gly Leu Val Ser Gly Tyr Ser Met
            15                  20                  25 acc ccc ccg acc ttg aac atc acg gag gag tca cac gtc atc gac acc      148
Thr Pro Pro Thr Leu Asn Ile Thr Glu Glu Ser His Val Ile Asp Thr
        30                  35                  40 ggt gac agc ctg tcc atc tcc tgc agg gga cag cac ccc ctc gag tgg      196
Gly Asp Ser Leu Ser Ile Ser Cys Arg Gly Gln His Pro Leu Glu Trp
```

-continued

```
            45                  50                  55
gct tgg cca gga gct cag gag gcg cca gcc acc gga gac aag gac agc       244
Ala Trp Pro Gly Ala Gln Glu Ala Pro Ala Thr Gly Asp Lys Asp Ser
60                  65                  70                  75 gag gac acg ggg gtg gtg cga gac tgc gag ggc aca gac gcc agg ccc       292
Glu Asp Thr Gly Val Val Arg Asp Cys Glu Gly Thr Asp Ala Arg Pro
                80                  85                  90 tac tgc aag gtg ttg ctg ctg cac gag gta cat gcc aac gac aca ggc       340
Tyr Cys Lys Val Leu Leu Leu His Glu Val His Ala Asn Asp Thr Gly
            95                  100                 105 agc tac gtc tgc tac tac aag tac atc aag gca cgc atc gag ggc acc       388
Ser Tyr Val Cys Tyr Tyr Lys Tyr Ile Lys Ala Arg Ile Glu Gly Thr
        110                 115                 120 acg gcc gcc agc tcc tac gtg ttc gtg aga gac ttt gag cag cca ttc       436
Thr Ala Ala Ser Ser Tyr Val Phe Val Arg Asp Phe Glu Gln Pro Phe
    125                 130                 135 atc aac aag cct gac acg ctc ttg gtc aac agg aag gac gcc atg tgg       484
Ile Asn Lys Pro Asp Thr Leu Leu Val Asn Arg Lys Asp Ala Met Trp
140                 145                 150                 155 gtg ccc tgt ctg gtg tcc atc ccc ggc ctc aat gtc acg ctg cgc tcg       532
Val Pro Cys Leu Val Ser Ile Pro Gly Leu Asn Val Thr Leu Arg Ser
                160                 165                 170 caa agc tcg gtg ctg tgg cca gac ggg cag gag gtg gtg tgg gat gac       580
Gln Ser Ser Val Leu Trp Pro Asp Gly Gln Glu Val Val Trp Asp Asp
            175                 180                 185 cgg cgg ggc atg ctc gtg tcc acg cca ctg ctg cac gat gcc ctg tac       628
Arg Arg Gly Met Leu Val Ser Thr Pro Leu Leu His Asp Ala Leu Tyr
        190                 195                 200 ctg cag tgc gag acc acc tgg gga gac cag gac ttc ctt tcc aac ccc       676
Leu Gln Cys Glu Thr Thr Trp Gly Asp Gln Asp Phe Leu Ser Asn Pro
    205                 210                 215 ttc ctg gtg cac atc aca ggc aac gag ctc tat gac atc cag ctg ttg       724
Phe Leu Val His Ile Thr Gly Asn Glu Leu Tyr Asp Ile Gln Leu Leu
220                 225                 230                 235 ccc agg aag tcg ctg gag ctg ctg gta ggg gag aag ctg gtc ctg aac       772
Pro Arg Lys Ser Leu Glu Leu Leu Val Gly Glu Lys Leu Val Leu Asn
                240                 245                 250 tgc acc gtg tgg gct gag ttt aac tca ggt gtc acc ttt gac tgg gac       820
Cys Thr Val Trp Ala Glu Phe Asn Ser Gly Val Thr Phe Asp Trp Asp
            255                 260                 265 tac cca ggg aag cag gca gag cgg ggt aag tgg gtg ccc gag cga cgc       868
Tyr Pro Gly Lys Gln Ala Glu Arg Gly Lys Trp Val Pro Glu Arg Arg
        270                 275                 280 tcc cag cag acc cac aca gaa ctc tcc agc atc ctg acc atc cac aac       916
Ser Gln Gln Thr His Thr Glu Leu Ser Ser Ile Leu Thr Ile His Asn
    285                 290                 295 gtc agc cag cac gac ctg ggc tcg tat gtg tgc aag gcc aac aac ggc       964
Val Ser Gln His Asp Leu Gly Ser Tyr Val Cys Lys Ala Asn Asn Gly
300                 305                 310                 315 atc cag cga ttt cgg gag agc acc gag gtc att gtg cat gaa aat ccc      1012
Ile Gln Arg Phe Arg Glu Ser Thr Glu Val Ile Val His Glu Asn Pro
                320                 325                 330 ttc atc agc gtc gag tgg ctc aaa gga ccc atc ctg gag gcc acg gca      1060
Phe Ile Ser Val Glu Trp Leu Lys Gly Pro Ile Leu Glu Ala Thr Ala
            335                 340                 345 gga gac gag ctg gtg aag ctg ccc gtg aag ctg gcg gcg tac ccc ccg      1108
Gly Asp Glu Leu Val Lys Leu Pro Val Lys Leu Ala Ala Tyr Pro Pro
        350                 355                 360 ccc gag ttc cag tgg tac aag gat gga aag gca ctg tcc ggg cgc cac      1156
```

-continued

```
Pro Glu Phe Gln Trp Tyr Lys Asp Gly Lys Ala Leu Ser Gly Arg His
    365                 370                 375 agt cca cat gcc ctg gtg ctc aag gag gtg aca gag gcc agc aca ggc   1204
Ser Pro His Ala Leu Val Leu Lys Glu Val Thr Glu Ala Ser Thr Gly
380                 385                 390                 395 acc tac acc ctc gcc ctg tgg aac tcc gct gct ggc ctg agg cgc aac   1252
Thr Tyr Thr Leu Ala Leu Trp Asn Ser Ala Ala Gly Leu Arg Arg Asn
                400                 405                 410 atc agc ctg gag ctg gtg gtg aat gtg ccc ccc cag ata cat gag aag   1300
Ile Ser Leu Glu Leu Val Val Asn Val Pro Pro Gln Ile His Glu Lys
            415                 420                 425 gag gcc tcc tcc ccc agc atc tac tcg cgt cac agc cgc cag gcc ctc   1348
Glu Ala Ser Ser Pro Ser Ile Tyr Ser Arg His Ser Arg Gln Ala Leu
        430                 435                 440 acc tgc acg gcc tac ggg gtg ccc ctg cct ctc agc atc cag tgg cac   1396
Thr Cys Thr Ala Tyr Gly Val Pro Leu Pro Leu Ser Ile Gln Trp His
    445                 450                 455 tgg cgg ccc tgg aca ccc tgc aag atg ttt gcc cag cgt agt ctc cgg   1444
Trp Arg Pro Trp Thr Pro Cys Lys Met Phe Ala Gln Arg Ser Leu Arg
460                 465                 470                 475 cgg cgg cag cag caa gac ctc atg cca cag tgc cgt gac tgg agg gcg   1492
Arg Arg Gln Gln Gln Asp Leu Met Pro Gln Cys Arg Asp Trp Arg Ala
                480                 485                 490 gtg acc acg cag gat gcc gtg aac ccc atc gag agc ctg gac acc tgg   1540
Val Thr Thr Gln Asp Ala Val Asn Pro Ile Glu Ser Leu Asp Thr Trp
            495                 500                 505 acc gag ttt gtg gag gga aag aat aag act gtg agc aag ctg gtg atc   1588
Thr Glu Phe Val Glu Gly Lys Asn Lys Thr Val Ser Lys Leu Val Ile
        510                 515                 520 cag aat gcc aac gtg tct gcc atg tac aag tgt gtg gtc tcc aac aag   1636
Gln Asn Ala Asn Val Ser Ala Met Tyr Lys Cys Val Val Ser Asn Lys
    525                 530                 535 gtg ggc cag gat gag cgg ctc atc tac ttc tat gtg acc acc atc ccc   1684
Val Gly Gln Asp Glu Arg Leu Ile Tyr Phe Tyr Val Thr Thr Ile Pro
540                 545                 550                 555 gac ggc ttc acc atc gaa tcc aag cca tcc gag gag cta cta gag ggc   1732
Asp Gly Phe Thr Ile Glu Ser Lys Pro Ser Glu Glu Leu Leu Glu Gly
                560                 565                 570 cag ccg gtg ctc ctg agc tgc caa gcc gac agc tac aag tac gag cat   1780
Gln Pro Val Leu Leu Ser Cys Gln Ala Asp Ser Tyr Lys Tyr Glu His
            575                 580                 585 ctg cgc tgg tac cgc ctc aac ctg tcc acg ctg cac gat gcg cac ggg   1828
Leu Arg Trp Tyr Arg Leu Asn Leu Ser Thr Leu His Asp Ala His Gly
        590                 595                 600 aac ccg ctt ctc ctc gac tgc aag aac gtg cat ctg ttc gcc acc cct   1876
Asn Pro Leu Leu Leu Asp Cys Lys Asn Val His Leu Phe Ala Thr Pro
    605                 610                 615 ctg gcc gcc agc ctg gag gag gtg gca cct ggg gcg cgc cac gcc acg   1924
Leu Ala Ala Ser Leu Glu Glu Val Ala Pro Gly Ala Arg His Ala Thr
620                 625                 630                 635 ctc agc ctg agt atc ccc cgc gtc gcg ccc gag cac gag ggc cac tat   1972
Leu Ser Leu Ser Ile Pro Arg Val Ala Pro Glu His Glu Gly His Tyr
                640                 645                 650 gtg tgc gaa gtg caa gac cgg cgc agc cat gac aag cac tgc cac aag   2020
Val Cys Glu Val Gln Asp Arg Arg Ser His Asp Lys His Cys His Lys
            655                 660                 665 aag tac ctg tcg gtg cag gcc ctg gaa gcc cct cgg ctc acg cag aac   2068
Lys Tyr Leu Ser Val Gln Ala Leu Glu Ala Pro Arg Leu Thr Gln Asn
        670                 675                 680
```

```
ttg acc gac ctc ctg gtg aac gtg agc gac tcg ctg gag atg cag tgc    2116
Leu Thr Asp Leu Leu Val Asn Val Ser Asp Ser Leu Glu Met Gln Cys
    685             690             695 ttg gtg gcc gga gcg cac gcg ccc agc atc gtg tgg tac aaa gac gag    2164
Leu Val Ala Gly Ala His Ala Pro Ser Ile Val Trp Tyr Lys Asp Glu
700             705             710             715 agg ctg ctg gag gaa aag tct gga gtc gac ttg gcg gac tcc aac cag    2212
Arg Leu Leu Glu Glu Lys Ser Gly Val Asp Leu Ala Asp Ser Asn Gln
            720             725             730 aag ctg agc atc cag cgc gtg cgc gag gag gat gcg gga cgc tat ctg    2260
Lys Leu Ser Ile Gln Arg Val Arg Glu Glu Asp Ala Gly Arg Tyr Leu
        735             740             745 tgc agc gtg tgc aac gcc aag ggc tgc gtc aac tcc tcc gcc agc gtg    2308
Cys Ser Val Cys Asn Ala Lys Gly Cys Val Asn Ser Ser Ala Ser Val
        750             755             760 gcc gtg gaa ggc tcc gag gat aag ggc agc atg gag atc gtg atc ctt    2356
Ala Val Glu Gly Ser Glu Asp Lys Gly Ser Met Glu Ile Val Ile Leu
765             770             775 gtc ggt acc ggc gtc atc gct gtc ttc ttc tgg gtc ctc ctc ctc ctc    2404
Val Gly Thr Gly Val Ile Ala Val Phe Phe Trp Val Leu Leu Leu Leu
780             785             790             795 atc ttc tgt aac atg agg agg ccg gcc cac gca gac atc aag acg ggc    2452
Ile Phe Cys Asn Met Arg Arg Pro Ala His Ala Asp Ile Lys Thr Gly
            800             805             810 tac ctg tcc atc atc atg gac ccc ggg gag gtg cct ctg gag gag caa    2500
Tyr Leu Ser Ile Ile Met Asp Pro Gly Glu Val Pro Leu Glu Glu Gln
        815             820             825 tgc gaa tac ctg tcc tac gat gcc agc cag tgg gaa ttc ccc cga gag    2548
Cys Glu Tyr Leu Ser Tyr Asp Ala Ser Gln Trp Glu Phe Pro Arg Glu
        830             835             840 cgg ctg cac ctg ggg aga gtg ctc ggc tac ggc gcc ttc ggg aag gtg    2596
Arg Leu His Leu Gly Arg Val Leu Gly Tyr Gly Ala Phe Gly Lys Val
    845             850             855 gtg gaa gcc tcc gct ttc ggc atc cac aag ggc agc agc tgt gac acc    2644
Val Glu Ala Ser Ala Phe Gly Ile His Lys Gly Ser Ser Cys Asp Thr
860             865             870             875 gtg gcc gtg aaa atg ctg aaa gag ggc gcc acg gcc agc gag cac cgc    2692
Val Ala Val Lys Met Leu Lys Glu Gly Ala Thr Ala Ser Glu His Arg
            880             885             890 gcg ctg atg tcg gag ctc aag atc ctc att cac atc ggc aac cac ctc    2740
Ala Leu Met Ser Glu Leu Lys Ile Leu Ile His Ile Gly Asn His Leu
        895             900             905 aac gtg gtc aac ctc ctc ggg gcg tgc acc aag ccg cag ggc ccc ctc    2788
Asn Val Val Asn Leu Leu Gly Ala Cys Thr Lys Pro Gln Gly Pro Leu
        910             915             920 atg gtg atc gtg gag ttc tgc aag tac ggc aac ctc tcc aac ttc ctg    2836
Met Val Ile Val Glu Phe Cys Lys Tyr Gly Asn Leu Ser Asn Phe Leu
925             930             935 cgc gcc aag cgg gac gcc ttc agc ccc tgc gcg gag aag tct ccc gag    2884
Arg Ala Lys Arg Asp Ala Phe Ser Pro Cys Ala Glu Lys Ser Pro Glu
940             945             950             955 cag cgc gga cgc ttc cgc gcc atg gtg gag ctc gcc agg ctg gat cgg    2932
Gln Arg Gly Arg Phe Arg Ala Met Val Glu Leu Ala Arg Leu Asp Arg
            960             965             970 agg cgg ccg ggg agc agc gac agg gtc ctc ttc gcg cgg ttc tcg aag    2980
Arg Arg Pro Gly Ser Ser Asp Arg Val Leu Phe Ala Arg Phe Ser Lys
        975             980             985 acc gag ggc gga gcg agg cgg gct tct cca gac caa gaa gct gag gac    3028
Thr Glu Gly Gly Ala Arg Arg Ala Ser Pro Asp Gln Glu Ala Glu Asp
        990             995             1000
```

-continued

| | | | | | | | | | | |
|---|---|---|---|---|---|---|---|---|---|---|
| ctg | tgg | ctg | agc | ccg | ctg | acc | atg | gaa | gat | ctt | gtc | tgc | tac | agc | 3073 |
| Leu | Trp | Leu | Ser | Pro | Leu | Thr | Met | Glu | Asp | Leu | Val | Cys | Tyr | Ser | |
| | 1005 | | | | 1010 | | | | | 1015 | | | | | | ttc cag gtg gcc aga ggg atg gag ttc ctg gct tcc cga aag tgc    3118
Phe Gln Val Ala Arg Gly Met Glu Phe Leu Ala Ser Arg Lys Cys
    1020                1025                1030 atc cac aga gac ctg gct gct cgg aac att ctg ctg tcg gaa agc    3163
Ile His Arg Asp Leu Ala Ala Arg Asn Ile Leu Leu Ser Glu Ser
1035                1040                1045 gac gtg gtg aag atc tgt gac ttt ggc ctt gcc cgg gac atc tac    3208
Asp Val Val Lys Ile Cys Asp Phe Gly Leu Ala Arg Asp Ile Tyr
    1050                1055                1060 aaa gac cct gac tac gtc cgc aag ggc agt gcc cgg ctg ccc ctg    3253
Lys Asp Pro Asp Tyr Val Arg Lys Gly Ser Ala Arg Leu Pro Leu
1065                1070                1075 aag tgg atg gcc cct gaa agc atc ttc gac aag gtg tac acc acg    3298
Lys Trp Met Ala Pro Glu Ser Ile Phe Asp Lys Val Tyr Thr Thr
    1080                1085                1090 cag agt gac gtg tgg tcc ttt ggg gtg ctt ctc tgg gag atc ttc    3343
Gln Ser Asp Val Trp Ser Phe Gly Val Leu Leu Trp Glu Ile Phe
1095                1100                1105 tct ctg ggg gcc tcc ccg tac cct ggg gtg cag atc aat gag gag    3388
Ser Leu Gly Ala Ser Pro Tyr Pro Gly Val Gln Ile Asn Glu Glu
    1110                1115                1120 ttc tgc cag cgg ctg aga gac ggc aca agg atg agg gcc ccg gag    3433
Phe Cys Gln Arg Leu Arg Asp Gly Thr Arg Met Arg Ala Pro Glu
1125                1130                1135 ctg gcc act ccc gcc ata cgc cgc atc atg ctg aac tgc tgg tcc    3478
Leu Ala Thr Pro Ala Ile Arg Arg Ile Met Leu Asn Cys Trp Ser
    1140                1145                1150 gga gac ccc aag gcg aga cct gca ttc tcg gag ctg gtg gag atc    3523
Gly Asp Pro Lys Ala Arg Pro Ala Phe Ser Glu Leu Val Glu Ile
1155                1160                1165 ctg ggg gac ctg ctc cag ggc agg ggc ctg caa gag gaa gag gag    3568
Leu Gly Asp Leu Leu Gln Gly Arg Gly Leu Gln Glu Glu Glu Glu
    1170                1175                1180 gtc tgc atg gcc ccg cgc agc tct cag agc tca gaa gag ggc agc    3613
Val Cys Met Ala Pro Arg Ser Ser Gln Ser Ser Glu Glu Gly Ser
1185                1190                1195 ttc tcg cag gtg tcc acc atg gcc cta cac atc gcc cag gct gac    3658
Phe Ser Gln Val Ser Thr Met Ala Leu His Ile Ala Gln Ala Asp
    1200                1205                1210 gct gag gac agc ccg cca agc ctg cag cgc cac agc ctg gcc gcc    3703
Ala Glu Asp Ser Pro Pro Ser Leu Gln Arg His Ser Leu Ala Ala
1215                1220                1225 agg tat tac aac tgg gtg tcc ttt ccc ggg tgc ctg gcc aga ggg    3748
Arg Tyr Tyr Asn Trp Val Ser Phe Pro Gly Cys Leu Ala Arg Gly
    1230                1235                1240 gct gag acc cgt ggt tcc tcc agg atg aag aca ttt gag gaa ttc    3793
Ala Glu Thr Arg Gly Ser Ser Arg Met Lys Thr Phe Glu Glu Phe
1245                1250                1255 ccc atg acc cca acg acc tac aaa ggc tct gtg gac aac cag aca    3838
Pro Met Thr Pro Thr Thr Tyr Lys Gly Ser Val Asp Asn Gln Thr
    1260                1265                1270 gac agt ggg atg gtg ctg gcc tcg gag gag ttt gag cag ata gag    3883
Asp Ser Gly Met Val Leu Ala Ser Glu Glu Phe Glu Gln Ile Glu
1275                1280                1285 agc agg cat aga caa gaa agc ggc ttc agc tgt aaa gga cct ggc    3928
Ser Arg His Arg Gln Glu Ser Gly Phe Ser Cys Lys Gly Pro Gly

```
                  1290                1295                1300
cag aat gtg gct gtg acc agg gca cac cct gac tcc caa ggg agg      3973
Gln Asn Val Ala Val Thr Arg Ala His Pro Asp Ser Gln Gly Arg
    1305                1310                1315 cgg cgg cgg cct gag cgg ggg gcc cga gga ggc cag gtg ttt tac      4018
Arg Arg Arg Pro Glu Arg Gly Ala Arg Gly Gly Gln Val Phe Tyr
1320                1325                1330 aac agc gag tat ggg gag ctg tcg gag cca agc gag gag gac cac      4063
Asn Ser Glu Tyr Gly Glu Leu Ser Glu Pro Ser Glu Glu Asp His
    1335                1340                1345 tgc tcc ccg tct gcc cgc gtg act ttc ttc aca gac aac agc tac      4108
Cys Ser Pro Ser Ala Arg Val Thr Phe Phe Thr Asp Asn Ser Tyr
        1350                1355                1360 taa gcagcatcgg acaagacccc cagcacttgg gggttcaggc ccggcagggc       4161
gggcagaggg ctggaggccc aggctgggaa ctcatctggt tgaactctgg tggcacagga    4221
gtgtcctctt ccctctctgc agacttccca gctaggaaga gcaggactcc aggcccaagg    4281
ctcccggaat tccgtcacca cgactggcca gggcacgctc cagctgcccc ggcccctccc    4341
cctgagattc agatgtcatt tagttcagca tccgcaggtg ctggtccgg ggccagcact     4401 tccatgggaa tgtctctttg cgacctcct ttcatcacac tgggtggtgg cctggtccct     4461
gttttcccac gaggaatctg tgggtctggg agtcacacag tgttggaggt taaggcatac    4521
gagagcagag gtctcccaaa cgcccttccc tcctcaggca cacagctact ctccccacga    4581
gggctggctg gcctcaccca cccctgcaca gttgaaggga ggggctgtgt tccatctca    4641 aagaaggcat ttgcagggtc ctcttctggg cctgaccaaa cagccaacta gcccctgggg    4701
tggccaccag tatgacagta ttatacgctg gcaacacaga ggcagcccgc acacctgcgc    4761
ctgggtgttg agagccatcc tgcaagtctt tttc                               4795

<210> SEQ ID NO 121
<211> LENGTH: 1363
<212> TYPE: PRT
<213> ORGANISM: Homo sapiens

<400> SEQUENCE: 121

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160
```

-continued

```
Ser Ile Pro Gly Leu Asn Val Thr Leu Arg Ser Gln Ser Val Leu
            165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
            195                 200                 205

Thr Trp Gly Asp Gln Asp Phe Leu Ser Asn Pro Phe Leu Val His Ile
            210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
                    245                 250                 255

Glu Phe Asn Ser Gly Val Thr Phe Asp Trp Asp Tyr Pro Gly Lys Gln
            260                 265                 270

Ala Glu Arg Gly Lys Trp Val Pro Glu Arg Arg Ser Gln Gln Thr His
            275                 280                 285

Thr Glu Leu Ser Ser Ile Leu Thr Ile His Asn Val Ser Gln His Asp
            290                 295                 300

Leu Gly Ser Tyr Val Cys Lys Ala Asn Asn Gly Ile Gln Arg Phe Arg
305                 310                 315                 320

Glu Ser Thr Glu Val Ile Val His Glu Asn Pro Phe Ile Ser Val Glu
                    325                 330                 335

Trp Leu Lys Gly Pro Ile Leu Glu Ala Thr Ala Gly Asp Glu Leu Val
            340                 345                 350

Lys Leu Pro Val Lys Leu Ala Ala Tyr Pro Pro Pro Glu Phe Gln Trp
            355                 360                 365

Tyr Lys Asp Gly Lys Ala Leu Ser Gly Arg His Ser Pro His Ala Leu
            370                 375                 380

Val Leu Lys Glu Val Thr Glu Ala Ser Thr Gly Thr Tyr Thr Leu Ala
385                 390                 395                 400

Leu Trp Asn Ser Ala Ala Gly Leu Arg Arg Asn Ile Ser Leu Glu Leu
                    405                 410                 415

Val Val Asn Val Pro Pro Gln Ile His Glu Lys Glu Ala Ser Ser Pro
            420                 425                 430

Ser Ile Tyr Ser Arg His Ser Arg Gln Ala Leu Thr Cys Thr Ala Tyr
            435                 440                 445

Gly Val Pro Leu Pro Leu Ser Ile Gln Trp His Trp Arg Pro Trp Thr
            450                 455                 460

Pro Cys Lys Met Phe Ala Gln Arg Ser Leu Arg Arg Arg Gln Gln Gln
465                 470                 475                 480

Asp Leu Met Pro Gln Cys Arg Asp Trp Arg Ala Val Thr Thr Gln Asp
                    485                 490                 495

Ala Val Asn Pro Ile Glu Ser Leu Asp Thr Trp Thr Glu Phe Val Glu
            500                 505                 510

Gly Lys Asn Lys Thr Val Ser Lys Leu Val Ile Gln Asn Ala Asn Val
            515                 520                 525

Ser Ala Met Tyr Lys Cys Val Val Ser Asn Lys Val Gly Gln Asp Glu
            530                 535                 540

Arg Leu Ile Tyr Phe Tyr Val Thr Thr Ile Pro Asp Gly Phe Thr Ile
545                 550                 555                 560

Glu Ser Lys Pro Ser Glu Glu Leu Leu Glu Gly Gln Pro Val Leu Leu
                    565                 570                 575
```

```
Ser Cys Gln Ala Asp Ser Tyr Lys Tyr Glu His Leu Arg Trp Tyr Arg
            580                 585                 590

Leu Asn Leu Ser Thr Leu His Asp Ala His Gly Asn Pro Leu Leu Leu
            595                 600                 605

Asp Cys Lys Asn Val His Leu Phe Ala Thr Pro Leu Ala Ala Ser Leu
            610                 615                 620

Glu Glu Val Ala Pro Gly Ala Arg His Ala Thr Leu Ser Leu Ser Ile
625                 630                 635                 640

Pro Arg Val Ala Pro Glu His Glu Gly His Tyr Val Cys Glu Val Gln
            645                 650                 655

Asp Arg Arg Ser His Asp Lys His Cys His Lys Lys Tyr Leu Ser Val
            660                 665                 670

Gln Ala Leu Glu Ala Pro Arg Leu Thr Gln Asn Leu Thr Asp Leu Leu
            675                 680                 685

Val Asn Val Ser Asp Ser Leu Glu Met Gln Cys Leu Ala Gly Ala
            690                 695                 700

His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
            725                 730                 735

Arg Val Arg Glu Glu Asp Ala Gly Arg Tyr Leu Cys Ser Val Cys Asn
            740                 745                 750

Ala Lys Gly Cys Val Asn Ser Ala Ser Val Ala Val Glu Gly Ser
            755                 760                 765

Glu Asp Lys Gly Ser Met Glu Ile Val Ile Leu Val Gly Thr Gly Val
770                 775                 780

Ile Ala Val Phe Phe Trp Val Leu Leu Leu Leu Ile Phe Cys Asn Met
785                 790                 795                 800

Arg Arg Pro Ala His Ala Asp Ile Lys Thr Gly Tyr Leu Ser Ile Ile
            805                 810                 815

Met Asp Pro Gly Glu Val Pro Leu Glu Glu Gln Cys Glu Tyr Leu Ser
            820                 825                 830

Tyr Asp Ala Ser Gln Trp Glu Phe Pro Arg Glu Arg Leu His Leu Gly
            835                 840                 845

Arg Val Leu Gly Tyr Gly Ala Phe Gly Lys Val Val Glu Ala Ser Ala
850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
            885                 890                 895

Leu Lys Ile Leu Ile His Ile Gly Asn His Leu Asn Val Val Asn Leu
            900                 905                 910

Leu Gly Ala Cys Thr Lys Pro Gln Gly Pro Leu Met Val Ile Val Glu
            915                 920                 925

Phe Cys Lys Tyr Gly Asn Leu Ser Asn Phe Leu Arg Ala Lys Arg Asp
            930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Pro Gly Ser
            965                 970                 975

Ser Asp Arg Val Leu Phe Ala Arg Phe Ser Lys Thr Glu Gly Gly Ala
            980                 985                 990

Arg Arg Ala Ser Pro Asp Gln Glu  Ala Glu Asp Leu Trp  Leu Ser Pro
```

```
              995                 1000                1005
Leu Thr Met Glu Asp Leu Val Cys Tyr Ser Phe Gln Val Ala Arg
    1010                1015                1020

Gly Met Glu Phe Leu Ala Ser Arg Lys Cys Ile His Arg Asp Leu
    1025                1030                1035

Ala Ala Arg Asn Ile Leu Leu Ser Glu Ser Asp Val Val Lys Ile
    1040                1045                1050

Cys Asp Phe Gly Leu Ala Arg Asp Ile Tyr Lys Asp Pro Asp Tyr
    1055                1060                1065

Val Arg Lys Gly Ser Ala Arg Leu Pro Leu Lys Trp Met Ala Pro
    1070                1075                1080

Glu Ser Ile Phe Asp Lys Val Tyr Thr Thr Gln Ser Asp Val Trp
    1085                1090                1095

Ser Phe Gly Val Leu Leu Trp Glu Ile Phe Ser Leu Gly Ala Ser
    1100                1105                1110

Pro Tyr Pro Gly Val Gln Ile Asn Glu Glu Phe Cys Gln Arg Leu
    1115                1120                1125

Arg Asp Gly Thr Arg Met Arg Ala Pro Glu Leu Ala Thr Pro Ala
    1130                1135                1140

Ile Arg Arg Ile Met Leu Asn Cys Trp Ser Gly Asp Pro Lys Ala
    1145                1150                1155

Arg Pro Ala Phe Ser Glu Leu Val Glu Ile Leu Gly Asp Leu Leu
    1160                1165                1170

Gln Gly Arg Gly Leu Gln Glu Glu Glu Val Cys Met Ala Pro
    1175                1180                1185

Arg Ser Ser Gln Ser Ser Glu Glu Gly Ser Phe Ser Gln Val Ser
    1190                1195                1200

Thr Met Ala Leu His Ile Ala Gln Ala Asp Ala Glu Asp Ser Pro
    1205                1210                1215

Pro Ser Leu Gln Arg His Ser Leu Ala Ala Arg Tyr Tyr Asn Trp
    1220                1225                1230

Val Ser Phe Pro Gly Cys Leu Ala Arg Gly Ala Glu Thr Arg Gly
    1235                1240                1245

Ser Ser Arg Met Lys Thr Phe Glu Glu Phe Pro Met Thr Pro Thr
    1250                1255                1260

Thr Tyr Lys Gly Ser Val Asp Asn Gln Thr Asp Ser Gly Met Val
    1265                1270                1275

Leu Ala Ser Glu Glu Phe Glu Gln Ile Glu Ser Arg His Arg Gln
    1280                1285                1290

Glu Ser Gly Phe Ser Cys Lys Gly Pro Gly Gln Asn Val Ala Val
    1295                1300                1305

Thr Arg Ala His Pro Asp Ser Gln Gly Arg Arg Arg Pro Glu
    1310                1315                1320

Arg Gly Ala Arg Gly Gly Gln Val Phe Tyr Asn Ser Glu Tyr Gly
    1325                1330                1335

Glu Leu Ser Glu Pro Ser Glu Glu Asp His Cys Ser Pro Ser Ala
    1340                1345                1350

Arg Val Thr Phe Phe Thr Asp Asn Ser Tyr
    1355                1360

<210> SEQ ID NO 122
<211> LENGTH: 33
<212> TYPE: DNA
<213> ORGANISM: Artificial sequence
```

```
<220> FEATURE:
<223> OTHER INFORMATION: Synthetic primer

<400> SEQUENCE: 122
tacttggcag tacatctacg tattagtcat cgc                                      33

<210> SEQ ID NO 123
<211> LENGTH: 39
<212> TYPE: DNA
<213> ORGANISM: Artificial sequence
<220> FEATURE:
<223> OTHER INFORMATION: Synthetic primer

<400> SEQUENCE: 123
cggagatctg tagtcttgca cgtacacgta ggagctggc                                39

<210> SEQ ID NO 124
<211> LENGTH: 1752
<212> TYPE: DNA
<213> ORGANISM: Homo sapiens

<400> SEQUENCE: 124
atgcagcggg gcgccgcgct gtgcctgcga ctgtggctct gcctgggact cctggacggc          60
ctggtgagtg gctactccat gaccccccg accttgaaca tcacggagga gtcacacgtc         120
atcgacaccg gtgacagcct gtccatctcc tgcaggggac agcacccct cgagtgggct         180 tggccaggag ctcaggaggc gccagccacc ggagacaagg acagcgagga cacggggctg        240
gtgcgagact gcgagggcac agacgccagg ccctactgca aggtgttgct gctgcacgag        300
gtacatgcca acgacacagg cagctacgtc tgctactaca gtacatcaa ggcacgcatc        360 gagggcacca cggccgccag ctcctacgtg tacgtgcaag actacagatc tccatttatt        420
gcttctgtta gtgaccaaca tggagtcgtg tacattactg agaacaaaaa caaaactgtg        480
gtgattccat gtctcgggtc catttcaaat ctcaacgtgt cactttgtgc aagataccca        540
gaaaagagat ttgttcctga tggtaacaga atttcctggg acagcaagaa gggctttact        600
attcccagct acatgatcag ctatgctggc atggtcttct gtgaagcaaa aattaatgat        660
gaaagttacc agtctattat gtacatagtt gtcgttgtag ggtataggat ttatgatgtg        720
gttctgagtc cgtctcatgg aattgaacta tctgttggag aaaagcttgt cttaaattgt        780
acagcaagaa ctgaactaaa tgtggggatt gacttcaact gggaatacc ttcttcgaag         840 catcagcata gaaacttgt aaaccgagac ctaaaaaccc agtctgggag tgagatgaag         900 aaattttga gcaccttaac tatagatggt gtaaccccgga gtgaccaagg attgtacacc        960
tgtgcagcat ccagtgggct gatgaccaag aagaacagca catttgtcag ggtccatgaa       1020
gatcccatcg aaggtcgtgg tggtggtggt ggtgatccca atcttgtga caaacctcac       1080 acatgcccac tgtgcccagc acctgaactc ctgggggac cgtcagtctt cctcttcccc       1140
ccaaaaccca aggacaccct catgatctcc cggaccctg aggtcacatg cgtggtggtg       1200
gacgtgagcc acgaagaccc tgaggtcaag ttcaactggt acgtggacgg cgtggaggtg       1260
cataatgcca agacaaagcc gcgggaggag cagtacaaca gcacgtaccg tgtggtcagc       1320
gtcctcaccg tcctgcacca ggactggctg aatggcaagg agtacaagtg caaggtctcc       1380
aacaaagccc tcccagcccc catcgagaaa accatctcca aagccaaagg gcagccccga       1440
gaaccacagg tgtacaccct gcccccatcc cgggatgagc tgaccaagaa ccaggtcagc       1500
ctgacctgcc tagtcaaagg cttctatccc agcgacatcg ccgtggagtg ggagagcaat       1560
```

```
gggcagccgg agaacaacta caaggccacg cctcccgtgc tggactccga cggctccttc    1620
ttcctctaca gcaagctcac cgtggacaag agcaggtggc agcaggggaa cgtcttctca    1680
tgctccgtga tgcatgaggc tctgcacaac cactacacgc agaagagcct ctccctgtct    1740
ccgggtaaat ga                                                        1752

<210> SEQ ID NO 125
<211> LENGTH: 583
<212> TYPE: PRT
<213> ORGANISM: Homo sapiens

<400> SEQUENCE: 125

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Tyr Val Gln Asp Tyr Arg Ser Pro Phe Ile Ala Ser Val Ser
    130                 135                 140

Asp Gln His Gly Val Val Tyr Ile Thr Glu Asn Lys Asn Lys Thr Val
145                 150                 155                 160

Val Ile Pro Cys Leu Gly Ser Ile Ser Asn Leu Asn Val Ser Leu Cys
                165                 170                 175

Ala Arg Tyr Pro Glu Lys Arg Phe Val Pro Asp Gly Asn Arg Ile Ser
            180                 185                 190

Trp Asp Ser Lys Lys Gly Phe Thr Ile Pro Ser Tyr Met Ile Ser Tyr
        195                 200                 205

Ala Gly Met Val Phe Cys Glu Ala Lys Ile Asn Asp Glu Ser Tyr Gln
    210                 215                 220

Ser Ile Met Tyr Ile Val Val Val Gly Tyr Arg Ile Tyr Asp Val
225                 230                 235                 240

Val Leu Ser Pro Ser His Gly Ile Glu Leu Ser Val Gly Glu Lys Leu
                245                 250                 255

Val Leu Asn Cys Thr Ala Arg Thr Glu Leu Asn Val Gly Ile Asp Phe
            260                 265                 270

Asn Trp Glu Tyr Pro Ser Ser Lys His Gln His Lys Lys Leu Val Asn
        275                 280                 285

Arg Asp Leu Lys Thr Gln Ser Gly Ser Glu Met Lys Lys Phe Leu Ser
    290                 295                 300

Thr Leu Thr Ile Asp Gly Val Thr Arg Ser Asp Gln Gly Leu Tyr Thr
305                 310                 315                 320

Cys Ala Ala Ser Ser Gly Leu Met Thr Lys Lys Asn Ser Thr Phe Val
                325                 330                 335
```

```
Arg Val His Glu Asp Pro Ile Glu Gly Arg Gly Gly Gly Asp
            340                 345                 350
Pro Lys Ser Cys Asp Lys Pro His Thr Cys Pro Leu Cys Pro Ala Pro
        355                 360                 365
Glu Leu Leu Gly Gly Pro Ser Val Phe Leu Phe Pro Pro Lys Pro Lys
    370                 375                 380
Asp Thr Leu Met Ile Ser Arg Thr Pro Glu Val Thr Cys Val Val Val
385                 390                 395                 400
Asp Val Ser His Glu Asp Pro Glu Val Lys Phe Asn Trp Tyr Val Asp
                405                 410                 415
Gly Val Glu Val His Asn Ala Lys Thr Lys Pro Arg Glu Glu Gln Tyr
            420                 425                 430
Asn Ser Thr Tyr Arg Val Val Ser Val Leu Thr Val Leu His Gln Asp
        435                 440                 445
Trp Leu Asn Gly Lys Glu Tyr Lys Cys Lys Val Ser Asn Lys Ala Leu
    450                 455                 460
Pro Ala Pro Ile Glu Lys Thr Ile Ser Lys Ala Lys Gly Gln Pro Arg
465                 470                 475                 480
Glu Pro Gln Val Tyr Thr Leu Pro Pro Ser Arg Asp Glu Leu Thr Lys
                485                 490                 495
Asn Gln Val Ser Leu Thr Cys Leu Val Lys Gly Phe Tyr Pro Ser Asp
            500                 505                 510
Ile Ala Val Glu Trp Glu Ser Asn Gly Gln Pro Glu Asn Asn Tyr Lys
        515                 520                 525
Ala Thr Pro Pro Val Leu Asp Ser Asp Gly Ser Phe Phe Leu Tyr Ser
    530                 535                 540
Lys Leu Thr Val Asp Lys Ser Arg Trp Gln Gln Gly Asn Val Phe Ser
545                 550                 555                 560
Cys Ser Val Met His Glu Ala Leu His Asn His Tyr Thr Gln Lys Ser
                565                 570                 575
Leu Ser Leu Ser Pro Gly Lys
            580

<210> SEQ ID NO 126
<211> LENGTH: 81
<212> TYPE: DNA
<213> ORGANISM: Homo sapiens

<400> SEQUENCE: 126
tacaattgag acaagcgta tgtccacgaa gtagtttaac tggacgaggc gtgcttattt      60
gcacatcata aatcctatac c                                              81

<210> SEQ ID NO 127
<211> LENGTH: 1752
<212> TYPE: DNA
<213> ORGANISM: Homo sapiens

<400> SEQUENCE: 127
atgcagcggg gcgccgcgct gtgcctgcga ctgtggctct gcctgggact cctggacggc      60
ctggtgagtg ctactccat gaccccccg accttgaaca tcacggagga gtcacacgtc     120
atcgacaccg gtgacagcct gtccatctcc tgcagggac agcacccct cgagtgggct     180 tggccaggag ctcaggaggc gccagccacc ggagacaagg acagcgagga cacgggggtg     240
gtgcgagact gcgagggcac agacgccagg ccctactgca aggtgttgct gctgcacgag     300
gtacatgcca acgacacagg cagctacgtc tgctactaca gtacatcaa ggcacgcatc     360
```

-continued

```
gagggcacca cggccgccag ctcctacgtg tacgtgcaag actacagatc tccatttatt    420
gcttctgtta gtgaccaaca tggagtcgtg tacattactg agaacaaaaa caaaactgtg    480
gtgattccat gtctcgggtc catttcaaat ctcaacgtgt cactttgtgc aagatacccca   540 gaaaagagat ttgttcctga tggtaacaga atttcctggg acagcaagaa gggctttact    600
attcccagct acatgatcag ctatgctggc atggtcttct gtgaagcaaa aattaatgat    660
gaaagttacc agtctattat gtacatagtt gtcgttgtag ggtataggat ttatgatgtg    720
gttctgagtc cgtctcatgg aattgaacta tctgttggag aaaagcttgt cttaaattgt    780
acagcaagaa ctgaactaaa tgtggggatt gacttcaact gggaataccc ttcttcgaag    840
catcagcata gaaacttgt aaaccgagac ctaaaaaccc agtctgggag tgagatgaag    900 aaattttga gcaccttaac tatagatggt gtaacccgga gtgaccaagg attgtacacc    960
tgtgcagcat ccagtgggct gatgaccaag aagaacagca catttgtcag ggtccatgaa   1020
gatcccatcg aaggtcgtgg tggtggtggt ggtgatccca atcttgtga caaacctcac   1080 acatgcccac tgtgcccagc acctgaactc ctggggggac cgtcagtctt cctcttcccc   1140
ccaaaaccca aggacaccct catgatctcc cggacccctg aggtcacatg cgtggtggtg   1200
gacgtgagcc acgaagaccc tgaggtcaag ttcaactggt acgtggacgg cgtggaggtg   1260
cataatgcca agacaaagcc gcgggaggag cagtacaaca gcacgtaccg tgtggtcagc   1320
gtcctcaccg tcctgcacca ggactggctg aatggcaagg agtacaagtg caaggtctcc   1380
aacaaagccc tcccagcccc catcgagaaa accatctcca aagccaaagg gcagccccga   1440
gaaccacagg tgtacaccct gcccccatcc cgggatgagc tgaccaagaa ccaggtcagc   1500
ctgacctgcc tagtcaaagg cttctatccc agcgacatcg ccgtggagtg ggagagcaat   1560
gggcagccgg agaacaacta caaggccacg cctcccgtgc tggactccga cggctccttc   1620
ttcctctaca gcaagctcac cgtggacaag agcaggtggc agcaggggaa cgtcttctca   1680
tgctccgtga tgcatgaggc tctgcacaac cactacacgc agaagagcct ctccctgtct   1740
ccgggtaaat ga                                                       1752
```

<210> SEQ ID NO 128
<211> LENGTH: 583
<212> TYPE: PRT
<213> ORGANISM: Homo sapiens

<400> SEQUENCE: 128

```
Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
```

```
                115                 120                 125
Tyr Val Tyr Val Gln Asp Tyr Arg Ser Pro Phe Ile Ala Ser Val Ser
            130                 135                 140

Asp Gln His Gly Val Val Tyr Ile Thr Glu Asn Lys Asn Lys Thr Val
145                 150                 155                 160

Val Ile Pro Cys Leu Gly Ser Ile Ser Asn Leu Asn Val Ser Leu Cys
                165                 170                 175

Ala Arg Tyr Pro Glu Lys Arg Phe Val Pro Asp Gly Asn Arg Ile Ser
                180                 185                 190

Trp Asp Ser Lys Lys Gly Phe Thr Ile Pro Ser Tyr Met Ile Ser Tyr
                195                 200                 205

Ala Gly Met Val Phe Cys Glu Ala Lys Ile Asn Asp Glu Ser Tyr Gln
                210                 215                 220

Ser Ile Met Tyr Ile Val Val Val Gly Tyr Arg Ile Tyr Asp Val
225                 230                 235                 240

Val Leu Ser Pro Ser His Gly Ile Glu Leu Ser Val Gly Glu Lys Leu
                245                 250                 255

Val Leu Asn Cys Thr Ala Arg Thr Glu Leu Asn Val Gly Ile Asp Phe
                260                 265                 270

Asn Trp Glu Tyr Pro Ser Ser Lys His Gln His Lys Lys Leu Val Asn
                275                 280                 285

Arg Asp Leu Lys Thr Gln Ser Gly Ser Glu Met Lys Lys Phe Leu Ser
290                 295                 300

Thr Leu Thr Ile Asp Gly Val Thr Arg Ser Asp Gln Gly Leu Tyr Thr
305                 310                 315                 320

Cys Ala Ala Ser Ser Gly Leu Met Thr Lys Lys Asn Ser Thr Phe Val
                325                 330                 335

Arg Val His Glu Asp Pro Ile Glu Gly Arg Gly Gly Gly Gly Asp
                340                 345                 350

Pro Lys Ser Cys Asp Lys Pro His Thr Cys Pro Leu Cys Pro Ala Pro
                355                 360                 365

Glu Leu Leu Gly Gly Pro Ser Val Phe Leu Phe Pro Pro Lys Pro Lys
370                 375                 380

Asp Thr Leu Met Ile Ser Arg Thr Pro Glu Val Thr Cys Val Val Val
385                 390                 395                 400

Asp Val Ser His Glu Asp Pro Gln Val Lys Phe Asn Trp Tyr Val Asp
                405                 410                 415

Gly Val Glu Val His Asn Ala Lys Thr Lys Pro Arg Glu Glu Gln Tyr
                420                 425                 430

Asn Ser Thr Tyr Arg Val Val Ser Val Leu Thr Val Leu His Gln Asp
                435                 440                 445

Trp Leu Asn Gly Lys Glu Tyr Lys Cys Lys Val Ser Asn Lys Ala Leu
                450                 455                 460

Pro Ala Pro Ile Glu Lys Thr Ile Ser Lys Ala Lys Gly Gln Pro Arg
465                 470                 475                 480

Glu Pro Gln Val Tyr Thr Leu Pro Pro Ser Arg Asp Glu Leu Thr Lys
                485                 490                 495

Asn Gln Val Ser Leu Thr Cys Leu Val Lys Gly Phe Tyr Pro Ser Asp
                500                 505                 510

Ile Ala Val Glu Trp Glu Ser Asn Gly Gln Pro Glu Asn Asn Tyr Lys
                515                 520                 525

Ala Thr Pro Pro Val Leu Asp Ser Asp Gly Ser Phe Phe Leu Tyr Ser
530                 535                 540
```

Lys Leu Thr Val Asp Lys Ser Arg Trp Gln Gln Gly Asn Val Phe Ser
545                 550                 555                 560

Cys Ser Val Met His Glu Ala Leu His Asn His Tyr Thr Gln Lys Ser
                565                 570                 575

Leu Ser Leu Ser Pro Gly Lys
            580

<210> SEQ ID NO 129
<211> LENGTH: 25
<212> TYPE: DNA
<213> ORGANISM: Artificial sequence
<220> FEATURE:
<223> OTHER INFORMATION: Synthetic primer

<400> SEQUENCE: 129
ctgagaggga tcgataatta caaga                                           25

<210> SEQ ID NO 130
<211> LENGTH: 24
<212> TYPE: DNA
<213> ORGANISM: Artificial sequence
<220> FEATURE:
<223> OTHER INFORMATION: Synthetic primer

<400> SEQUENCE: 130
attggcactc aaatttgttt tcag                                            24

<210> SEQ ID NO 131
<211> LENGTH: 24
<212> TYPE: DNA
<213> ORGANISM: Artificial sequence
<220> FEATURE:
<223> OTHER INFORMATION: Synthetic primer

<400> SEQUENCE: 131
atgtttgtac cagacgtcct tacg                                            24

<210> SEQ ID NO 132
<211> LENGTH: 17
<212> TYPE: DNA
<213> ORGANISM: Artificial sequence
<220> FEATURE:
<223> OTHER INFORMATION: Synthetic primer

<400> SEQUENCE: 132
tgcgaagcac cctggaa                                                    17

<210> SEQ ID NO 133
<211> LENGTH: 25
<212> TYPE: DNA
<213> ORGANISM: Artificial sequence
<220> FEATURE:
<223> OTHER INFORMATION: Synthetic primer

<400> SEQUENCE: 133
cccaacttcc aatgctctcc taatg                                           25

<210> SEQ ID NO 134
<211> LENGTH: 25
<212> TYPE: DNA
<213> ORGANISM: Artificial sequence
<220> FEATURE:
<223> OTHER INFORMATION: Synthetic primer

<400> SEQUENCE: 134
gcacactagg tttgccgagt agacc            25

<210> SEQ ID NO 135
<211> LENGTH: 20
<212> TYPE: DNA
<213> ORGANISM: Artificial sequence
<220> FEATURE:
<223> OTHER INFORMATION: Synthetic primer

<400> SEQUENCE: 135
taagggttac ttgggttgcc                  20

<210> SEQ ID NO 136
<211> LENGTH: 19
<212> TYPE: DNA
<213> ORGANISM: Artificial sequence
<220> FEATURE:
<223> OTHER INFORMATION: Synthetic primer

<400> SEQUENCE: 136
tatccagagg gtcttcagc                   19

<210> SEQ ID NO 137
<211> LENGTH: 24
<212> TYPE: DNA
<213> ORGANISM: Artificial sequence
<220> FEATURE:
<223> OTHER INFORMATION: Synthetic primer

<400> SEQUENCE: 137
ctgtgcctca gcctcttctc attc             24

<210> SEQ ID NO 138
<211> LENGTH: 24
<212> TYPE: DNA
<213> ORGANISM: Artificial sequence
<220> FEATURE:
<223> OTHER INFORMATION: Synthetic primer

<400> SEQUENCE: 138
ttgggaactt ctcctccttg ttgg             24

<210> SEQ ID NO 139
<211> LENGTH: 19
<212> TYPE: DNA
<213> ORGANISM: Artificial sequence
<220> FEATURE:
<223> OTHER INFORMATION: Synthetic primer

<400> SEQUENCE: 139
gaggtgaaca acccacaga                   19

<210> SEQ ID NO 140
<211> LENGTH: 20
<212> TYPE: DNA
<213> ORGANISM: Artificial sequence
<220> FEATURE:
<223> OTHER INFORMATION: Synthetic primer

<400> SEQUENCE: 140
tattggcaca ctctctaccc                  20

<210> SEQ ID NO 141
<211> LENGTH: 18
<212> TYPE: DNA

```
<213> ORGANISM: Artificial sequence
<220> FEATURE:
<223> OTHER INFORMATION: Synthetic primer

<400> SEQUENCE: 141
ccctggaccc aaggcagt                                                     18

<210> SEQ ID NO 142
<211> LENGTH: 20
<212> TYPE: DNA
<213> ORGANISM: Artificial sequence
<220> FEATURE:
<223> OTHER INFORMATION: Synthetic primer

<400> SEQUENCE: 142
aggcttagag tgcttccggg                                                   20

<210> SEQ ID NO 143
<211> LENGTH: 21
<212> TYPE: DNA
<213> ORGANISM: Artificial sequence
<220> FEATURE:
<223> OTHER INFORMATION: Synthetic primer

<400> SEQUENCE: 143
gcttgtttgc tgtgcggaga c                                                 21

<210> SEQ ID NO 144
<211> LENGTH: 21
<212> TYPE: DNA
<213> ORGANISM: Artificial sequence
<220> FEATURE:
<223> OTHER INFORMATION: Synthetic primer

<400> SEQUENCE: 144
gtttctgaag taggcgaaca t                                                 21
```

GROWTH FACTOR ANTAGONISTS FOR ORGAN TRANSPLANT ALLOIMMUNITY AND ARTERIOSCLEROSIS

CROSS-REFERENCE TO RELATED APPLICATIONS

The present application claims the benefit of priority of U.S. Provisional Application No. 60/888,067, filed Feb. 2, 2007, and U.S. Provisional Application No. 60/888,305, filed Feb. 5, 2007. The disclosure of each priority application is incorporated herein by reference in its entirety.

BACKGROUND

Interaction of innate and adaptive immunity leads to alloimmune responses that may be detrimental to cardiac allografts and heart transplant recipients. Antigen-presenting cells (APC) initiate allorecognition by processing foreign peptides, migrating to secondary lymphoid tissue, and presenting these peptides to recipient lymphocytes. After recognition, alloreactive T lymphocytes proliferate and migrate to their target tissue. Although the current immunosuppressive regiments effectively inhibit the proliferation of alloreactive T lymphocytes, they have several metabolic, infectious, renal and malignant side-effects. In addition, the long-term survival of heart transplant patients is decreased by gradual concentric intimal thickening of large and small allograft coronary arteries—cardiac allograft arteriosclerosis—despite the use of modern immunosuppression.

The lymphatic network forms a conduit system that transfers interstitial fluids and inflammatory cells from the target tissue to secondary LN, and is essential in the activation of adaptive immunity. Vascular endothelial growth factor C (VEGF-C) and its receptor VEGFR-3 are the key regulators for lymphatic growth. VEGF-C is essential in the development and maintenance of the lymphatic system, and improper lymphangiogenesis is related to many pathological conditions. Lymphatic vascular insufficiency leads to lymphedema, whereas extensive lymphangiogenesis is often seen in tumor metastasis and inflammatory situations. During inflammation, macrophages are a rich source for VEGF-C, and pro-inflammatory cytokines such as TNF-α, IL-1α and -β☐(15) as well as TGF-β (16)☐ induce VEGF-C expression. Dendritic cells (DC) may express VEGFR-3 during inflammation (Hamrah et al., (2003), Am J Pathol., 163: 57-6817) which renders them responsive for VEGF-C-induced migration (Chen et al., (2004), Nat. Med., 10: 813-81518). Also, lymphatic endothelial cells (EC)—in contrast to vascular EC—secrete CCL21 chemokine that mediates CCR7+ inflammatory cell traffic to lymphoid organs and peripheral effector sites. (See Kriehuber et al., (2001), J. Exp. Med., 194: 797-808; Saeki et al., (1999), J. Immunol. 162: 2472-2475; Campbell et al., (1998), J. Cell. Biol. 141: 1053-1059; and Lo et al., (2003), J. Clin. Invest. 112: 1495-1505.

Corneal transplant is currently the most successful tissue transplantation procedures in humans, with a first year survival rate as high as 90%, even in the absence of routine HLA tying and with minimal immunosuppressive therapy. The healthy cornea is generally a non-vascular tissue. DeVries, U.S. Patent Publication No. 2003/0180294 purports to describe use of a VEGFR-3 inhibitor to reduce lymhangiogenesis in a transplanted cornea to extend its survival. Chen et al., (2004), Nat. Med., 10: 813-81518, purport to describe that blockade of VEGFR-3 in corneal transplants suppresses corneal antigen presenting dendritic cells, delaying rejection of corneal transplants. The same research group previously reported that dendritic cells in the cornea were VEGFR-3+, whereas similar dendritic cells were absent in the skin, even though the cornea shares embryological origins with the skin.

A need exists for all transplanted tissues and organs, especially vascularized tissues and organs, for new materials and methods for slowing, reducing, or eliminating rejection and also for slowing, reducing, or eliminating graft arteriosclerosis.

SUMMARY OF THE INVENTION

The present invention provides materials and methods to improve the outcomes of transplant recipients, e.g., by postponing or inhibiting or reducing or ameliorating an immune reaction against the transplant (rejection), and/or by postponing or inhibiting or reducing or ameliorating arteriosclerosis or other deleterious side effects often associated with transplants.

Thus, in one embodiment, the invention is a method for inducing tolerance or inhibiting rejection of a cell, tissue, or organ transplant, or for inhibiting arteriosclerosis in a transplant recipient. For example, one such method comprises administering to a mammalian transplant recipient a composition that comprises a growth factor inhibitor, such as an endothelial growth factor inhibitor, in an amount effective to induce tolerance for the transplant by the recipient, or inhibit rejection, or inhibit arteriosclerosis. "Transplant recipient" refers to the mammalian subject or patient that receives the transplanted cells, tissue, or organ, from a donor. Preferred mammalian donors and recipients are human donors and recipients. The method also may be practiced with pets (dogs, cats), racing animals (dogs, horses); agriculturally important animals (cows, pigs); non-human primates (chimps, gorillas, etc.); and important lab animals (e.g., rodents). The method may be practiced with xenografts of from one donor species to a different recipient species.

In a related embodiment, the invention is a method for inducing tolerance or inhibiting rejection of a cell, tissue, or organ transplant, or for inhibiting arteriosclerosis in a transplant recipient, comprising: administering to a mammalian transplant recipient a composition that comprises an nucleic acid that comprises a nucleotide sequence that encodes a growth factor inhibitor, such as an endothelial growth factor inhibitor, wherein the nucleic acid is expressible in cells of the recipient or expressible in the transplanted cell, tissue, or organ to produce an amount of the endothelial growth factor inhibitor effective to induce tolerance for the transplant by the recipient, or inhibit rejection, or inhibit arteriosclerosis. To facilitate expression of the encoded inhibitor, the nucleic acid preferably comprises at least one expression control sequence operatively connected to the sequence that encodes the endothelial growth factor inhibitor. Exemplary expression control sequences include promoters and enhancers, for example. In some preferred variations, the method comprises administering an expression vector that comprises the nucleic acid to the transplant recipient. For example, the vector comprises a replication deficient viral vector; such as a retrovirus, an adenovirus, an adeno-associated virus, a vaccinia virus or a herpesvirus vector. In some variations, the vector is inducible by administration of an exogenous pharmaceutical agent. In other variations, expression of the vector is induced by an endogenous stress in the organ transplant recipient, such as an elevation of a biological marker correlated with rejection. In still other variations, the vector is constitutively expressed.

In still related embodiments, the method is directed to a method for reducing a transplant recipients dependence or need for immunosuppressive drugs, by administering such inhibitors to the recipient, in an amount effective to reduce the dose or doing of one or more immunosuppressant drugs administered to the transplant recipient.

For all embodiments of the invention, whether the therapeutic agent is a polypeptide, an antibody, a polynucleotide, a small molecule, or some combination thereof, the administered composition preferably further includes a pharmaceutically acceptable carrier. The composition may include one inhibitor or may include a combination of inhibitors, or may include one inhibitor that targets multiple growth factor or growth factor receptor targets described herein.

Methods of the invention can be practiced with respect to all variations of transplanted cells or tissue. For example, in some variations, the transplant is a xenograft, and the method induces tolerance for the xenograft or inhibits xenograft rejection, or reduces xenograft-related arteriosclerosis. In other preferred variations, the transplant is an allograft transplant, and the composition is administered in an amount effective to induce tolerance for the allograft or inhibit alloimmunity, or reduce graft related arteriosclerosis.

In some variations, the transplant may be limited to specified cell types or to a tissue transplant. For example, the cell or tissue comprises embryonic stem cells, pluripotent stem cells, hematopoietic precursor cells, neuronal precursor cells, or endothelial precursor cells. In some variations, the cell or tissue comprises a member selected from the group consisting of pancreatic islet cells, cardiac myocytes, bone marrow cells, endothelial cells, and skin cells.

In some variations of the invention, treatment of corneal transplant patients is specifically excluded from the invention.

In many preferred embodiments, the transplant is an organ or organ fragment capable of performing functions of the organ or capable of regenerating into the organ. For example, the method is practiced on a recipient of at least one transplanted organ, or fragment thereof, selected from the group consisting of a heart, a kidney, a lung, a liver, an intestine, a pancreas, skin, and bone. In some highly preferred variations, the method is practiced on the recipient of at least one transplanted organ selected from the group consisting of heart, lung, liver, and kidney. Treatment of cardiac (heart) transplant recipients is highly preferred.

All variety of formulations and routes of administration are contemplated. For example, in some variations, the composition is administered locally to the transplanted cell, tissue, or organ in the recipient. In some variations, the composition is administered systemically to the recipient. In some variations of the method, the composition is administered intravenously, intramuscularly, or intraperitoneally, or perorally.

To provide just a few exemplary variations, pharmacological agents may preferably be administered systemically. Monoclonal antibodies may be administered intravenously, intramuscularly, or intraperitoneally. Receptor tyrosine kinase inhibitors may be administered perorally or intravenously. Nucleic acid or vectors preferably would be administered intravascularly or intraparenchymally to the transplanted organ, optionally during the organ procurement.

All variations of timing of administration also are contemplated.

For example, in some variations, the method further comprises administering the composition to the organ or the organ donor before the transplant. (In other variations, the inhibitor composition administered at this stage contains a different inhibitor from the composition administered to the recipient.) As described below in detail, donor cells are implicated in graft rejection, and administering the inhibitors to the donor organ or donor prior to the transplant is contemplated to have beneficial effects during the critical perioperative period.

In some variations, the method further comprises repeated administration of the composition to the recipient.

The composition may be administered to the recipient perioperatively, relative to the transplant operation. The composition may be administered for varying lengths of time after the transplant operation for prophylaxis, e.g., 1, 2, 3, 4, 5, 6, 7, 10, 14, 21, 28, 30, 31, 45, 56, 60, 90, 120, 180 days post-transplant. All durations from one day to fifty years post-transplant are specifically contemplated.

In other variations, the method is practiced at discrete times to ameliorate acute rejection events. For example, in some variations, the method is practiced upon detection of symptoms of rejection, and the inhibitor is administered in an amount effective to alleviate the symptoms. In some variations, the method comprises a step of screening the organ transplant recipient for symptoms of an acute rejection reaction; where the composition that contains the inhibitor is administered to the recipient upon detection of symptoms of acute rejection, in an amount effective to inhibit the rejection.

A wide variety of growth factor (including endothelial growth factor) inhibitors are described below in detail for practice of the invention. Some of the inhibitors bind to a growth factor or to a receptor, and may be described below as binding constructs. Other inhibitors may act indirectly, e.g., at the level of effecting gene or protein expression, or inhibiting downstream signaling by an activated receptor.

In some variations, the endothelial growth factor inhibitor comprises a compound that inhibits stimulation of at least one receptor selected from the group consisting of VEGFR-1, VEGFR-2, VEGFR-3, PDGFR-alpha, and PDGFR-beta by a growth factor ligand of said at least one receptor. In some highly preferred variations, the endothelial growth factor inhibitor comprises a compound that inhibits stimulation of VEGFR-3 by VEGF-C or inhibits stimulation of VEGFR-3 by VEGF-D.

For example, in some embodiments, the compound comprises an antibody substance selected from the group consisting of antibody substances that immunoreact with VEGFR-3, antibody substances that immunoreact with VEGF-C, and antibody substances that immunoreact with VEGF-D. The term antibody substance is intended to refer to traditional antibodies and also to the wide variety of engineered antibody fragments and variants that are engineered for therapeutic purposes. For example, exemplary preferred antibody substances include a humanized antibody, a human antibody, a monoclonal antibody, a fragment of an antibody that retains antigen binding characteristics, and a polypeptide that comprises an antigen binding fragment of an antibody. A preferred antibody substance is a monoclonal antibody (preferably humanized or fully human) that binds VEGFR-3 or VEGF-C or VEGF-D and inhibits binding between VEGFR-3 and VEGF-C or -D.

Yet another preferred class of inhibitor substances are soluble receptor constructs that are capable of binding circulating endothelial cell growth factor molecules and preventing them from binding and stimulating receptors expressed on endothelial or other cell surfaces. Thus, in some embodiments, the endothelial growth factor inhibitor comprises a soluble receptor that binds to at least one endothelial cell growth factor. In a preferred variation, the endothelial growth factor inhibitor comprises a soluble VEGFR-3 polypeptide that binds to VEGF-C or VEGF-D. For example, the soluble VEGFR-3 polypeptide comprises the VEGFR-3 extracellular domain, or a fragment thereof sufficient to bind VEGF-C or VEGF-D. Exemplary fragments include the first and second immunoglobulin-like domains of the VEGFR-3; or include the first, second, and third immunoglobulin-like domains of the VEGFR-3. In some preferred variations, the soluble receptor is fused to an immunoglobulin constant domain to increase serum half life. Such constructs can be expressed recombinantly, as fusion proteins.

In still another variation, the inhibitor comprises an antisense nucleic acid or an interfering RNA nucleic acid that inhibits expression of an endothelial cell growth factor or endothelial cell growth factor receptor. Preferred examples include a short interfering RNA that inhibits expression of a protein selected from the group consisting of VEGFR-3, VEGF-C, and VEGF-D; and an antisense nucleic acid that inhibits expression of a protein selected from the group consisting of VEGFR-3, VEGF-C, and VEGF-D.

In still other variations of the invention, the inhibitor compound comprises bevacizumab (Avastin®) or Ranibizumab (Lucentis®), both marketed by Genentech.

In some variations of the invention, a composition that comprises two different inhibitors is administered; or a two or more inhibitor compositions are administered. Combinations that include an inhibitor of VEGFR-3 (or VEGF-C or VEGF-D) in combination with an inhibitor of one or more of the following growth factor receptors (or their ligands) are particularly preferred: VEGFR-1, VEGFR-2, PDGFR-alpha, and PDGFR-beta.

In still other variations of the invention, the compound is a multivalent inhibitor of two or more receptors selected from the group consisting of VEGFR-1, VEGFR-2, VEGFR-3, PDGFR-alpha, and PDGFR-beta. For example, in some variations, the method of the invention comprises administering to the transplant recipient a composition that inhibits ligand binding to VEGFR-2 and inhibits ligand binding to VEGFR-3.

It is contemplated that the inhibitors of the invention protect the transplant recipient by different mechanisms than traditional or existing immunosuppressive regimens. In some variations of the invention, the inhibitors of the invention are co-administered with immunosuppressive therapy. The combination is expected to provide at least additive, and preferably synergistic, effects compared to either type of agent alone. The synergistic effects can be in the form of increased efficacy for survival of the transplant; and also for reduced side effects, possibly due to the need for reduced dosing of the immunosuppressive agents.

Thus, in some variations, the method of the invention further comprises administering an immunosuppressive agent to the organ transplant recipient. Exemplary classes of immunosuppressive agents include corticosteriods, calcineurine inhibitors, antiproliferative agents, monoclonal antilymphocyte antibodies, and polyclonal antilymphocyte antibodies. Exemplary immunosuppressive agents include Tacrolimus, Mycophenolic acid, Prednisone, Ciclosporin, Azathioprine, Basiliximab, Daclizumab, Muromonab-CD3, Mycophenolate Mofetil, Sirolimus, Methylprednisolone, Thymoglobulin, OKT3, Rapamycin, Azathioprine, Cyclosporine, and Interleukin-2 Receptor Antagonist. These agents can be administered singly or in combination.

In yet another variation, the method of the invention further comprising administering an antibiotic or antifungal agent to the recipient, to protect the recipient from infections.

In still further variations of the invention, the transplant recipient is helped by pre-treating the donor (or the tissue or organ to be transplanted), with the inhibitory agent. Thus, in some embodiments, the method of the invention further comprises administering to a donor organism a composition that comprises an endothelial growth factor inhibitor, prior to harvesting a cell, tissue, or organ for transplantation into the recipient. In other embodiments, the method further comprises contacting a cell, tissue, or organ with a composition that comprises an endothelial growth factor inhibitor, prior to transplanting the cell, tissue, or organ into the mammalian organ transplant recipient. In still other embodiments, the method further comprises administering to a donor organism, prior to harvesting cells, tissue, or an organ for transplantation, a composition that comprises an nucleic acid that comprises a nucleotide sequence that encodes an endothelial growth factor inhibitor, wherein the nucleic acid is expressible in cells of the tissue or organ to be transplanted. In still further variations, the method further comprises contacting a cell, tissue, or organ with a composition that comprises an nucleic acid that comprises a nucleotide sequence that encodes an endothelial growth factor inhibitor, prior to transplanting the cell, tissue, or organ into the recipient.

Other embodiments of the invention do not require administration of a growth factor inhibitor to the recipient at all. For example, one embodiment of the invention is a method of preparing a donor cell, tissue, or organ for allograft or xenograft transplantation comprising contacting the cell, tissue, or organ with a composition that comprises a growth factor inhibitor, such as an endothelial growth factor inhibitor, prior to transplanting the cell, tissue, or organ into a mammalian organ transplant recipient. A related embodiment is a method of preparing a donor cell, tissue, or organ for allograft or xenograft transplantation comprising contacting the cell, tissue, or organ with a composition that comprises an nucleic acid that comprises a nucleotide sequence that encodes a growth factor inhibitor, such as an endothelial growth factor inhibitor, prior to transplanting the cell, tissue, or organ into a mammalian organ transplant recipient.

Other variations of the invention are directed to material, useful for practicing methods of the invention. For example, in one embodiment, the invention is a composition that comprises an endothelial growth factor inhibitor, an immunosuppressant, and a pharmaceutically acceptable carrier. Preferably, the inhibitor and the immunosuppressant are present in the composition in synergistically effective amounts.

In a related variation, the invention is a kit or unit dose in which the inhibitor and the immunosuppressant are packaged together, but not in admixture.

The present invention relates to compositions and methods of use thereof for the inhibition of graft (e.g., allograft) rejection and graft-related arteriosclerosis, and inhibition of other effects of members of the PDGF/VEGF family of growth factors: VEGF-A, VEGF-B, VEGF-C, VEGF-D, VEGF-E, PlGF, PDGF-A, PDGF-B, PDGF-C, and PDGF-D, each of which is able to bind at least one growth factor receptor tyrosine kinase and stimulate phosphorylation of the same. The compositions of the invention include binding constructs that bind one or more PDGF/VEGF molecules.

The binding constructs include one or more binding units. Likewise, many of the inhibitors for use in practicing the invention are described herein as binding units or binding constructs.

In some embodiments, the binding unit comprises a polypeptide, e.g., a fragment of a growth factor receptor tyrosine kinase extracellular domain. The invention also provides nucleic acids encoding such binding constructs, and uses thereof. Binding units are not limited to receptor fragments, nor are they limited to polypeptides, but rather comprise any species that binds a growth factor or binds a receptor, and thereby inhibits the circulating growth factor from binding or stimulating the receptor naturally expressed on the surface of cells. Administration of the compositions of the invention to patients inhibits growth factor stimulation of VEGF receptors and/or PDGF receptors (e.g., inhibits phosphorylation of the receptors) and thereby inhibits biological responses mediated through the receptors including, but not limited to, PDGFR- and/or VEGFR-mediated angiogenesis and lymphangiogenesis.

Each member of the growth factor genus described above binds with high affinity to, and stimulation phosphorylation of, at least one PDGF receptor or VEGF receptor (or receptor heterodimer) selected from VEGFR-1, VEGFR-2, VEGFR-3, PDGFR-alpha, and PDGFR-beta. This statement refers to well known properties of the growth factors toward their cognate receptors, and is not meant as a limiting feature per se of the binding constructs of the invention. (For example, VEGF-A has been shown to bind to VEGFR-1 and VEGFR-2 and induce tyrosine phosphorylation of both receptors and initiate downstream receptor signaling.) However, preferred binding units of the invention do more than simply bind their target growth factors: a preferred binding construct also inhibits the growth factor(s) to which it binds from stimulating phosphorylation of at least one (and preferably all) of the receptor tyrosine kinases to which the growth factor(s) bind. Stimulation of tyrosine phosphorylation is readily measured using in vitro cell-based assays and anti-phosphotyrosine antibodies. Because phosphorylation of the receptor tyrosine kinases is an initial step in a signaling cascade, it is a convenient indicator of whether the binding construct is capable of inhibiting growth factor-mediated signal transduction that leads to cell migration, cell growth, and other responses. A number of other cell based and in vivo assays can be used to confirm the growth factor neutralizing properties of binding constructs of the invention.

As described herein, binding constructs can be chemically modified (e.g., heterologous peptide fusions, glycosylation, pegylation, etc.) to impart desired characteristics, while maintaining their specific growth factor binding properties. An exemplary peptide fusion comprises a immunoglobulin constant domain fragment. Exemplary desired characteristics imparted by chemical modifications include increased serum half life, increased solubility in an aqueous medium, and the ability to target a specific cell population, e.g., cancer cells.

Binding constructs and units that are "specific" for a particular growth factor are binding constructs and units that specifically recognize a circulating, active form of the growth factor. Preferably, the binding constructs specifically bind other forms of the growth factors as well. By way of example, VEGF-A exists in multiple isoforms, some of which circulate and others of which associate with heparin sulfate proteoglycans on cell surfaces. Binding constructs that are specific for VEGF-A bind to at least a circulating isoform, preferably all circulating isoforms, and more preferably, bind other major isoforms as well. By way of another example, VEGF-C is translated as a prepro-molecule with extensive amino-terminal and carboxy-terminal propeptides that are cleaved to yield a "fully processed" form of VEGF-C that binds and stimulates VEGFR-2 and VEGFR-3. Binding constructs specific for VEGF-C bind to at least the fully processed form of VEGF-C, and preferably also bind to partly processed forms and unprocessed forms.

Additional description is used herein when a more specialized meaning is intended. For example, VEGF-B167 is heparin bound whereas VEGF-B186 is freely secreted. An binding construct of the invention that minimally binds the circulating isoform is said to be specific for VEGF-B, and such a binding construct preferably also binds the heparin bound form. A binding construct of the invention that is "specific for heparin-bound VEGF-B" or "specific for VEGF-B167" is a binding construct that differentially recognizes the heparin bound isoform, compared to the freely circulating isoform. A binding construct of the invention that is "specific for VEGF-B186" is a binding construct that differentially recognizes the circulating form, compared to the heparin bound form. Binding constructs specific for each isoform of a growth factor are contemplated as components of some embodiments of the binding constructs of the invention.

The designations "first" and "second" and "third" in respect to the binding units of the binding constructs is for ease and clarity in description only, and is not meant to signify a particular order, e.g., order in the amino acid sequence of a polypeptide binding construct.

A binding construct comprising two or more binding units may further comprise a linker connecting adjacent binding units. The linker may take on a number of different forms. Preferably, the linker comprises a peptide which allows adjacent binding units to be linked to form a single polypeptide.

The invention also includes compositions comprising a polypeptide, binding construct, or nucleic acid encoding the same, together with a pharmaceutically acceptable carrier. Such compositions may further comprise a pharmaceutically acceptable diluent, adjuvant, or carrier medium.

Nucleic acids (polynucleotides) of the invention include nucleic acids that constitute binding units, e.g., aptamers, and also nucleic acids that encode polypeptide binding units and constructs, which may be used for such applications as gene therapy and recombinant in vitro expression of polypeptide binding constructs. In some embodiments, nucleic acids are purified or isolated. In some embodiments, polynucleotides further comprise a promoter sequence operatively connected to a nucleotide sequence encoding a polypeptide, wherein the promoter sequence promotes transcription of the sequence that encodes the polypeptide in a host cell. Polynucleotides may also comprise a polyadenylation sequence. Other nucleic acids of the invention (e.g., antisense nucleic acids, interfering RNA nucleic acids) operate to inhibit transcription or translation of growth factor genes or receptor genes.

Vectors comprising polynucleotides are also aspects of the invention. Such vectors may comprise an expression control sequence operatively connected to the sequence that encodes the polypeptide, and the vector may be selected from the group consisting of a lentivirus vector, an adeno-associated viral vector, an adenoviral vector, a liposomal vector, and combinations thereof. In some embodiments, the vector comprises a replication-deficient adenovirus, said adenovirus comprising the polynucleotide operatively connected to a promoter and flanked by adenoviral polynucleotide sequences. Host cells comprising the polynucleotides, vectors and other nucleic acids, and methods for using the same to express and isolate the binding constructs and units are also aspects of the invention.

For binding units of a binding construct that comprises an aptamer, the aptamer may be generated by preparing a library of nucleic acids; contacting the library of nucleic acids with a growth factor, wherein nucleic acids having greater binding affinity for the growth factor (relative to other library nucleic acids) are selected and amplified to yield a mixture of nucleic acids enriched for nucleic acids with relatively higher affinity and specificity for binding to the growth factor. The processes may be repeated, and the selected nucleic acids mutated and rescreened, whereby a growth factor aptamer is be identified. Nucleic acids may be screened to select for molecules that bind to more than growth factor.

In one aspect of the invention, the binding construct comprises a purified polypeptide comprising an amino acid sequence at least 95% identical to a vascular endothelial growth factor receptor 3 (VEGFR-3) fragment, wherein the VEGFR-3 fragment comprises an amino acid sequence consisting of a portion of SEQ ID NO: 6, wherein the carboxy-terminal residue of the fragment is selected from the group consisting of positions 211 to 247 of SEQ ID NO: 6. The fragment, and the polypeptide comprising the same, specifically bind to at least one growth factor selected from the group consisting of human vascular endothelial growth factor-C (VEGF-C), and human vascular endothelial growth factor-D (VEGF-D). In some embodiments the VEGFR-3 fragments has an amino terminal amino acid selected from the group consisting of positions 1 to 47 of SEQ ID NO: 6. In some embodiments, the polypeptide comprises an amino acid sequence selected from the group consisting of SEQ ID NOS: 36 and 38. In some embodiments, the fragment has an amino acid sequence selected from the group consisting of positions 1-226 and 1-229 of SEQ ID NO: 6. In some embodiments, the polypeptide is part of a binding construct, and the polypeptide is operatively connected with a second polypeptide that binds at least one growth factor selected from the group consisting of VEGF-A, VEGF-B, VEGF-C, VEGF-D, VEGF-E, PlGF, PDGF-A, PDGF-B, PDGF-C, and PDGF-D. In some embodiments, the second polypeptide is selected from the group consisting of a polypeptide comprising a vascular endothelial growth factor receptor extracellular domain fragment, a platelet derived growth factor receptor extracellular domain fragment, and a polypeptide comprising an antigen binding fragment of an antibody that immunoreacts with the at least one of said growth factors. In some embodiments, at least one of the polypeptides is encoded by a polynucleotide comprising a nucleotide sequence selected from the group consisting of SEQ ID NOS: 35 and 37.

In another aspect of the invention, a binding construct comprises a purified polypeptide comprising an amino acid sequence at least 95% identical to a VEGFR-2 fragment, wherein the VEGFR-2 fragment comprises an amino acid sequence consisting of a portion of SEQ ID NO: 4, wherein the amino terminal amino acid of the VEGFR-2 fragment is selected from the group consisting of positions 106-145 of SEQ ID NO: 4, wherein the carboxy terminal amino acid of the VEGFR-2 fragment is selected from the group consisting of positions 203 to 240 of SEQ ID NO: 4, and wherein the VEGFR-2 fragment and the polypeptide bind VEGF-C or VEGF-D. In some embodiments, the polypeptide comprises an amino acid sequence selected from the group consisting of SEQ ID NO: 22, 24, and 26. In some embodiments, the fragment consists of an amino acid sequence selected from the group consisting of residues 118-220, 118-226, and 118-232 of SEQ ID NO: 4. In some embodiments, the polypeptide is part of a binding construct, and the polypeptide is operatively connected with a second polypeptide that binds at least one growth factor selected from the group consisting of VEGF-A, VEGF-B, VEGF-C, VEGF-D, VEGF-E, PlGF, PDGF-A, PDGF-B, PDGF-C, and PDGF-D. In some embodiments, the second polypeptide is selected from the group consisting of a polypeptide comprising a vascular endothelial growth factor receptor extracellular domain fragment, a platelet derived growth factor receptor extracellular domain fragment, and a polypeptide comprising an antigen binding fragment of an antibody that immunoreacts with the at least one of said growth factors. In some embodiments, at least one of the polypeptides is encoded by a polynucleotide comprising a nucleotide sequence selected from the group consisting of SEQ ID NOS: 21, 23, and 25.

In still another aspect, the invention provides a binding construct comprising a first polypeptide operatively connected to a second polypeptide. The first and second polypeptides each binds at least one growth factor selected from the group consisting of VEGF-A, VEGF-B, VEGF-C, VEGF-D, VEGF-E, PlGF, PDGF-A, PDGF-B, PDGF-C, and PDGF-D polypeptides. The amino acid sequence of the first polypeptide differs from the amino acid sequence of the second polypeptide. The first and second polypeptides comprise members independently selected from the group consisting of:

(a) a polypeptide comprising an amino acid sequence at least 90% identical to the VEGFR-1 extracellular domain amino acid sequence comprising positions 27-758 of SEQ ID NO: 2;

(b) a fragment of (a) that binds VEGF-A, VEGF-B, or PlGF;

(c) a polypeptide comprising an amino acid sequence at least 90% identical to the VEGFR-2 extracellular domain amino acid sequence comprising positions 20-764 of SEQ ID NO: 4;

(d) a fragment of (c) that binds VEGF-A, VEGF-C, VEGF-E or VEGF-D;

(e) a polypeptide comprising an amino acid sequence at least 90% identical to the VEGFR-3 extracellular domain amino acid sequence comprising residues 24-775 of SEQ ID NO: 6;

(f) a fragment of (e) that binds VEGF-C or VEGF-D;

(g) a polypeptide comprising an amino acid sequence at least 90% identical to the neuropilin-1 extracellular domain amino acid sequence comprising residues 22-856 of SEQ ID NO: 113;

(h) a fragment of (g) that binds VEGF-A, VEGF-B, VEGF-C, VEGF-E, or PlGF;

(i) a polypeptide comprising an amino acid sequence at least 90% identical to the neuropilin-2 extracellular domain amino acid sequence comprising residues 21-864 of SEQ ID NO: 115;

(j) a fragment of (i) that binds VEGF-A, VEGF-C, or PlGF;

(k) a polypeptide comprising an amino acid sequence at least 90% identical to the platelet derived growth factor receptor alpha extracellular domain amino acid sequence comprising residues 24-524 of SEQ ID NO: 117;

(l) a fragment of (k) that binds PDGF-A, PDGF-B, or PDGF-C;

(m) a polypeptide comprising an amino acid sequence at least 90% identical to the platelet derived growth factor beta extracellular domain amino acid sequence comprising residues 33 to 531 of SEQ ID NO: 119;

(n) a fragment of (m) that binds PDGF-B or PDGF-D; and (o) a polypeptide comprising an antigen binding fragment of an antibody that binds to at least one growth factor selected from the group consisting of VEGF-A, VEGF-B, VEGF-C, VEGF-D, VEGF-E, PlGF, PDGF-A, PDGF-B, PDGF-C, and PDGF-D.

Still further examples of polypeptides that comprise binding units of the invention are antibodies and antibody fragments that immunoreact with one or more receptors selected from VEGFR-1, VEGFR-2, VEGFR-3, PDGFR-alpha, and PDGFR-beta.

In one embodiment, the binding construct of the invention comprises a first polypeptide comprising a fragment of a polypeptide comprising an amino acid sequence at least 90% identical to the VEGFR-2 extracellular domain amino acid sequence comprising positions 20-764 of SEQ ID NO: 4, wherein the fragment binds VEGF-A, VEGF-C, VEGF-E or VEGF-D. Optionally, the binding construct further comprises a second polypeptide comprising a fragment of a polypeptide comprising an amino acid sequence at least 90% identical to the VEGFR-1 extracellular domain amino acid sequence comprising positions 27-758 of SEQ ID NO: 2; wherein the fragment binds VEGF-A, VEGF-B, or PlGF. Additionally, the binding construct optionally further comprises a third polypeptide operatively connected to the first or second polypeptide, wherein the third polypeptide comprises a fragment of a polypeptide comprising an amino acid sequence at least 90% identical to the VEGFR-3 extracellular domain amino acid sequence comprising residues 24-775 of SEQ ID NO: 6, wherein the fragment binds VEGF-C or VEGF-D.

As described herein in greater detail, the extracellular domain of VEGFR or PDGFR have immunoglobulin-like domain structure. In a related embodiment, the binding construct of the invention comprises a first, second and third polypeptide as described above, wherein: (a) the first polypeptide comprises an amino acid sequence at least 90% identical to a fragment of the VEGFR-2 extracellular domain, wherein the fragment comprises immunoglobulin-like domain 2 amino acid sequence; (b) the second polypeptide comprises an amino acid sequence at least 90% identical to a fragment of the VEGFR-1 extracellular domain, wherein the fragment comprises immunoglobulin-like domain 3 amino acid sequence; and (c) the third polypeptide comprises an amino acid sequence at least 90% identical to a fragment of the VEGFR-3 extracellular domain, wherein said fragment comprises VEGFR-3 immunoglobulin-like domain 1 amino acid sequence.

In another aspect, the invention involves use of a binding construct comprising: a) a first amino acid sequence at least 90% identical to a fragment of the VEGFR-3 extracellular domain, wherein said fragment comprises VEGFR-3 immunoglobulin-like domain 1 amino acid sequence; (b) a second amino acid sequence at least 90% identical to a fragment of the VEGFR-2 extracellular domain, wherein the fragment comprises immunoglobulin-like domain 2 amino acid sequence; and, (c) a third amino acid sequence at least 90% identical to a fragment of the VEGFR-1 extracellular domain, wherein the fragment comprises immunoglobulin-like domain 3 amino acid sequence; wherein the first, second, and third amino acid sequences are operatively connected, and wherein the binding construct binds to at least VEGF-A and VEGF-C. In one embodiment, the binding construct comprises an amino acid sequence at least 95% identical to the amino acid sequence set out in SEQ ID NO: 128. In a related embodiment, the binding construct comprises the amino acid sequence of SEQ ID NO: 128.

In some embodiments, the binding construct of the invention comprises a first polypeptide comprising a fragment of a polypeptide comprising an amino acid sequence at least 90% identical to the VEGFR-3 extracellular domain amino acid sequence comprising residues 24-775 of SEQ ID NO: 6, wherein the fragment binds VEGF-C or VEGF-D. It is contemplated that the binding construct of the invention comprises a second polypeptide comprising a fragment of a polypeptide comprising an amino acid sequence at least 90% identical to the VEGFR-2 extracellular domain amino acid sequence comprising positions 20-764 of SEQ ID NO: 4, wherein the fragment binds VEGF-A, VEGF-C, VEGF-E or VEGF-D.

In a related embodiment, the binding construct of the invention comprises a first and second polypeptide as described above, wherein: (a) the first polypeptide comprises an amino acid sequence at least 90% identical to a fragment of the VEGFR-3 extracellular domain, wherein said fragment comprises VEGFR-3 immunoglobulin-like domain 1 amino acid sequence; and, (b) the second polypeptide comprises an amino acid sequence at least 90% identical to a fragment of the VEGFR-2 extracellular domain, wherein the fragment comprises immunoglobulin-like domains 2 and 3 amino acid sequence.

In another aspect, the invention provides a binding construct comprising: a) a first amino acid sequence at least 90% identical to a fragment of the VEGFR-3 extracellular domain, wherein said fragment comprises VEGFR-3 immunoglobulin-like domain 1 amino acid sequence; and, (b) a second amino acid sequence at least 90% identical to a fragment of the VEGFR-2 extracellular domain, wherein the fragment comprises immunoglobulin-like domain 2 amino acid sequence; and an immunoglobulin-like domain 3 amino acid sequence; wherein the first, second, and third amino acid sequences are operatively connected, and wherein the binding construct binds to at least VEGF-A and VEGF-C. It is further contemplated that the construct binds VEGF-D. In one embodiment, the binding construct comprises an amino acid sequence at least 95% identical to the amino acid sequence set out in SEQ ID NO: 125. In a related embodiment, the binding construct comprises the amino acid sequence of SEQ ID NO: 125.

In some variations, the binding unit or units of a binding comprise antibodies or antibody antigen binding fragments. In some embodiments, the binding construct comprises at least one non-antigen binding fragment binding unit. In some embodiments, the binding units all comprise antigen binding fragments of antibodies. Exemplary Bispecific antibodies are provided in U.S. patent application Ser. No. 11/075,400, published as U.S. Patent Publication No. 2005/0282233, and related, co-filed International Patent Application No. PCT/US2005/007742, published as WO 2005/087812, both applications incorporated herein by reference it their entirety. Antibodies that target the growth factors identified herein, and antibodies that target the receptors identified herein, all are useful for practicing the invention. Monoclonal antibody therapeutics are preferred. Humanized and fully human antibodies are highly preferred, as are fragments of such antibodies.

One aspect of the invention is a method for inhibiting allograft rejection or graft-related arteriosclerosis comprising administering to a mammalian subject in need of said inhibition a binding construct according to the invention, in an amount effective to inhibit the allograft rejection or the arteriosclerosis.

The method may also comprise the step of screening an organ transplant recipient mammal to identify elevated levels of at least one growth factor selected from the group consisting of VEGF-A, VEGF-B, VEGF-C, VEGF-D, VEGF-E, PlGF, PDGF-A, PDGF-B, PDGF-C, and PDGF-D polypeptides. In some embodiments, the screening step comprises obtaining a serum sample, a fluid sample, or a tissue sample from the transplanted organ and detecting elevated levels of at least one growth factor selected from the group consisting of VEGF-A, VEGF-B, VEGF-C, VEGF-D, VEGF-E, PlGF, PDGF-A, PDGF-B, PDGF-C, and PDGF-D polypeptides, or elevated levels of at least one receptor capable of binding the same.

The methods of the invention may also be carried out with another therapeutic. For example, other therapeutics that may be used alone, or in combination with the binding constructs of the invention, include anti-sense RNA, RNA interference, bispecific antibodies, other antibody types, and small molecules, e.g., chemotherapeutic agents, which target growth factors and/or their receptors. Combination therapies are preferably synergistic, but they need not be, and additive therapies are also considered aspects of the invention.

In addition to their use in methods, the binding constructs may be combined or packaged with other therapeutics in kits or as unit doses.

This summary of the invention is not intended to be limiting or comprehensive, and additional embodiments are described in the drawings and detailed description, including the examples. All such embodiments are aspects of the invention. Moreover, for the sake of brevity, various details that are applicable to multiple embodiments have not been repeated for every embodiment. Variations reflecting combinations and rearrangements of the embodiments described herein are intended as aspects of the invention. In addition to the foregoing, the invention includes, as an additional aspect, all embodiments of the invention narrower in scope in any way than the variations specifically mentioned above. For example, for aspects described as a genus or range, every subgenus, subrange or species is specifically contemplated as an embodiment of the invention.

BRIEF DESCRIPTION OF THE DRAWINGS

FIG. 1 shows that VEGFR-3 inhibit on markedly improves long-term survival of rat cardiac allografts in suboptimally-immunosuppressed recipients.

DETAILED DESCRIPTION

The present invention provides binding constructs, compositions, and materials and methods for making and using the same. The binding constructs bind growth factors that have been shown or are hypothesized to contribute to allograft rejection or arteriosclerosis in allograft recipients in vivo, and are useful for inhibiting those effects.

I. Binding Constructs

For the purposes of this invention, a "binding construct" comprises one or more binding units associated with each other by covalent or other forms of attachment. A "binding unit" binds a growth factor receptor or a growth factor ligand, i.e., binds to one or more growth factor polypeptides or growth factor receptor polypeptides, and preferably does so with high affinity. A binding unit preferably comprises at least one peptide or polypeptide, but other embodiments are possible as well, including organic small molecules, aptamers, and combinations of the same. While a binding unit preferably comprises a single polypeptide, it may comprise multiple polypeptides if a single polypeptide is not sufficient for binding a particular growth factor. When more than one binding unit or polypeptide segment is in a given binding construct, the binding units may be joined directly (i.e., through a covalent bond, e.g., a peptide, ester, or sulfhydryl bond, or non-covalently, e.g., hydrophobically) together via a linker. A binding construct may further include a heterologous peptide or other chemical moieties. Such additions are can modify binding construct properties such as stability, solubility, toxicity, serum half-life, immunogenicity, detectability, or other properties.

The term "high affinity" is used in a physiological context pertaining to the relative affinity of the binding construct for the growth factor ligand(s) or receptor(s) in vivo in a mammal, such as a laboratory test animal, a domesticated farm or pet animal, or a human. The targeted growth factors of the invention, e.g., the VEGF/PDGF family members, have characteristic affinities for their receptors in vivo, typically measured in terms of sub-nanomolar dissociation constants ($K_d$). For the purposes of this invention, a binding construct can bind to its target growth factor(s) or receptor(s) with a $K_d$ less than or equal to 1000 times the $K_d$ of the natural growth factor-receptor pair, while retaining the specificity of the natural pair. A binding unit that binds a growth factor with a $K_d$ less than or equal to 10 times the $K_d$ of the natural growth factor-receptor pair, while retaining the specificity of the natural pair, is considered high affinity. While high affinity is preferred, it is not a requirement. In a preferred embodiment, the affinity of the binding unit for the growth factor or receptor equals or exceeds the affinity of the natural receptor for the growth factor (or vice versa). Such affinities may be readily determined using conventional techniques, such as by using a BIAcore instrument or by radioimmunoassay using radiolabeled target antigen. Affinity data may be analyzed, for example, by the method of Scatchard et al., Ann N.Y. Acad. Sci., 51:660 (1949).

By binding activity is meant the ability to bind to a ligand, receptor, or binding construct, and does not require the retention of biological activity in so far as enzymatic activity or signaling is concerned. Binding may include either binding to a monomer or a dimer, homodimers or heterodimers, whether of receptors or ligands. Polypeptides for use according to the present invention can be used in the form of a protein dimer, particularly a disulfide-linked dimer. Mechanistic descriptions of binding constructs, e.g., as ligand traps, are not meant to be limiting. For example, a binding construct comprising a receptor extracellular domain fragment may function by forming inactive dimers with an endogenous receptor monomer.

In some embodiments, a binding construct comprises a first binding unit (e.g., a polypeptide) operatively associated with a second binding unit (e.g., a polypeptide), wherein each binding unit binds a growth factor selected from the group consisting of VEGF-A, VEGF-B, VEGF-C, VEGF-D, VEGF-E, PlGF, PDGF-A, PDGF-B, PDGF-C, PDGF-D, D1701 VEGF, NZ2 VEGF, NZ7 VEGF, and fallotein. In some embodiments the first and second binding units act together to bind a single ligand molecule (wherein the ligand may comprise a monomer or dimer). In some embodiments, the binding units act independently, i.e., each polypeptide binds a separate ligand molecule. In some embodiments, the first and second binding units are capable of either acting together or acting independently to bind one or more ligand polypeptides. In some embodiments, a binding unit of a first binding construct is able to interact with a binding unit on a second binding construct, e.g., to form dimers between binding units.

In some embodiments, a binding construct comprises a first binding unit operatively associated with a second binding unit, wherein each binding unit binds to a growth factor receptor selected from the group consisting of VEGFR-1, VEGFR-2, VEGFR-3, PDGFR-alpha, PDGFR-beta, and the neuropilins.

In some embodiments, the binding construct comprises a first polypeptide operatively connected to a second polypeptide, wherein the first and second polypeptides each binds at least one growth factor selected from the group consisting of VEGF-A, VEGF-B, VEGF-C, VEGF-D, VEGF-E, and PlGF polypeptides; or bind at least one growth factor receptor selected from VEGFR-1, VEGFR-2, VEGFR-3, PDGFR-alpha, PDGFR-beta, and the neuropilins, wherein the amino acid sequence of the first polypeptide differs from the amino acid sequence of the second polypeptide; and wherein the first and second polypeptides comprise members independently selected from the group consisting of:

(a) a polypeptide comprising an amino acid sequence at least 35% identical to the VEGFR-1 extracellular domain amino acid sequence comprising positions 27-758 of SEQ ID NO: 2;

(b) a fragment of (a) that binds VEGF-A, VEGF-B, or PlGF;

(c) a polypeptide comprising an amino acid sequence at least 35% identical to the VEGFR-2 extracellular domain amino acid sequence comprising positions 20-764 of SEQ ID NO: 4;

(d) a fragment of (c) that binds VEGF-A, VEGF-C, VEGF-E or VEGF-D;

(e) a polypeptide comprising an amino acid sequence at least 35% identical to the VEGFR-3 extracellular domain amino acid sequence comprising residues 24-775 of SEQ ID NO: 6;

(f) a fragment of (e) that binds VEGF-C or VEGF-D;

(g) a polypeptide comprising an amino acid sequence at least 35% identical to the neuropilin-1 extracellular domain amino acid sequence comprising residues 22-856 of SEQ ID NO: 113;

(h) a fragment of (g) that binds VEGF-A, VEGF-B, VEGF-C, VEGF-E, or PlGF;

(i) a polypeptide comprising an amino acid sequence at least 35% identical to the neuropilin-2 extracellular domain amino acid sequence comprising residues 21-864 of SEQ ID NO: 115;

(j) a fragment of (i) that binds VEGF-A, VEGF-C, or PlGF;

(k) a polypeptide comprising an amino acid sequence at least 35% identical to the platelet derived growth factor receptor alpha extracellular domain amino acid sequence comprising residues 24-524 of SEQ ID NO: 117;

(l) a fragment of (k) that binds PDGF-A, PDGF-B, or PDGF-C;

(m) a polypeptide comprising an amino acid sequence at least 35% identical to the platelet derived growth factor beta extracellular domain amino acid sequence comprising residues 33 to 531 of SEQ ID NO: 119;

(n) a fragment of (m) that binds PDGF-B or PDGF-D;

(o) an antibody that binds to at least one growth factor or receptor selected from the group consisting of VEGF-A, VEGF-B, VEGF-C, VEGF-D, VEGF-E, PlGF, PDGF-A, PDGF-B, PDGF-C, PDGF-D; VEGFR-1, VEGFR-2, VEGFR-3, PDGFR-alpha, and PDGFR-beta;

(p) a polypeptide comprising an antigen binding fragment of an antibody that binds to at least one growth factor selected from the group consisting of VEGF-A, VEGF-B, VEGF-C, VEGF-D, VEGF-E, PlGF, PDGF-A, PDGF-B, PDGF-C, and PDGF-D; or of an antibody that binds to at least one growth factor receptor selected from the group consisting of VEGFR-1, VEGFR-2, VEGFR-3, PDGFR-alpha, and PDGFR-beta;

(q) a polypeptide that binds at least one growth factor selected from the group consisting of VEGF-A, VEGF-B, VEGF-C, VEGF-D, VEGF-E, PlGF, PDGF-A, PDGF-B, PDGF-C, and PDGF-D polypeptides, wherein the polypeptide is generated using phage display;

(r) compounds that comprises peptide fragments of one or more of VEGF-A, VEGF-B, VEGF-C, VEGF-D, VEGF-E, PlGF, PDGF-A, PDGF-B, PDGF-C, and PDGF-D, and that inhibit the binding between such growth factors and their receptors; and (s) an organic molecule that mimics the binding properties of (a)-(r).

In some embodiments, the binding units all comprise antigen binding fragments. Exemplary bispecific antibodies are provided in U.S. patent application Ser. No. 11/075,400, published as U.S. Patent Publication No. 2005/0282233, and related International Patent Application No. PCT/US2005/007742, published as WO 2005/087812, both applications incorporated herein by reference it their entirety.

In some embodiments, one or more of the polypeptides of a binding construct is replaced with another type of molecule, e.g., a nucleic acid, that mimics the binding properties of any of the polypeptides described above in (a) through (p). Such nucleic acids include, for example, aptamers.

A. Binding Units

The growth factors that are the targets of the binding constructs of the invention exert their physiological effects in vivo by binding to the extracellular domains of growth factor receptors. Accordingly, growth factor receptors and fragments thereof constitute examples of binding units. Exemplary human nucleotide and amino acid sequences, for relevant ligands and receptors are set forth in the sequence listing as summarized below:

TABLE 1A

| RECEPTOR SEQUENCES | |
| --- | --- |
| RECEPTOR | SEQ ID NOS: |
| VEGFR-1 | 1 and 2 |
| VEGFR-2 | 3 and 4 |
| VEGFR-3 short | 5 and 6 |
| VEGFR-3 long | 120 and 121 |
| PDGFR-α | 116 and 117 |
| PDGFR-β | 118 and 119 |
| Neuropilin-1 | 112 and 113 |
| Neuropilin-2 | 114 and 115 |

TABLE 1B

| LIGAND SEQUENCES | |
| --- | --- |
| LIGAND | SEQ ID NOS: |
| VEGF-A | 80 and 81 |
| VEGF-A 232 isoform | 90 and 91 |
| VEGF-B isoform 1 | 94 and 95 |
| VEGF-B isoform 2 | 96 and 97 |
| VEGF-C | 82 and 83 |
| VEGF-D | 86 and 87 |
| VEGF-E (NZ7) | 88 and 89 |
| PlGF | 84 and 85 |
| D1701 VEGF | 92 and 93 |
| PDGF-A | 98 and 99 |
| PDGF-B | 100 and 101 |

TABLE 1B-continued

LIGAND SEQUENCES

| LIGAND | SEQ ID NOS: |
|---|---|
| PDGF-C | 102 and 103 |
| PDGF-D | 104 and 105 |

Other VEGF growth factors members include snake venom VEGFs (e.g., EMBL. AY033151, AY033152, and AY42981), various VEGF-E (orf virus VEGF homologs, some of which are presented in Table 1B) molecules including VEGF-E NZ2 [S67520], VEGF-E NZ7, VEGF-E D1701, VEGF-E Orf-11, and VEGF-E OV-IA82. [See generally, WO 00/25085.]

Members of the PDGF/VEGF family are characterized by a number of structural motifs including a conserved PDGF motif defined by the sequence: P-[PS]-C-V-X(3)-R-C-[GSTA]-G-C-C(SEQ ID NO: 111), where the brackets indicate a variable position that can be any one of the amino acids within the brackets. The number contained within the parentheses indicates the number of amino acids that separate the "V" and "R" residues. This conserved motif falls within a large domain of 70-150 amino acids defined in part by eight highly conserved cysteine residues that form inter- and intramolecular disulfide bonds. This domain forms a cysteine knot motif composed of two disulfide bonds which form a covalently linked ring structure between two adjacent β strands, and a third disulfide bond that penetrates the ring [see for example, FIG. 1 in Muller et al., Structure 5:1325-1338 (1997)], similar to that found in other cysteine knot growth factors, e.g., transforming growth factor-β (TGF-β). The amino acid sequence of all known PDGF/VEGF proteins, with the exception of VEGF-E, contains the PDGF domain. The PDGF/VEGF family proteins are predominantly secreted glycoproteins that form either disulfide-linked or non-covalently bound homo- or heterodimers whose subunits are arranged in an anti-parallel manner [Stacker and Achen, *Growth Factors* 17:1-11 (1999); Muller et al., Structure 5:1325-1338 (1997)]. Binding constructs of the invention include those that bind VEGF/PDGF growth factor monomers, homodimers, and heterodimers.

The VEGF subfamily is composed of members that share a VEGF homology domain (VHD) characterized by the sequence: C-X(22-24)-P-[PSR]-C-V-X(3)-R-C-[GSTA]-G-C-C-X(6)-C-X(32-41)-C. (SEQ ID: 110) The VHD domain, determined through analysis of the VEGF subfamily members, comprises the PDGF motif but is more specific. The VEGF subfamily of growth factors and receptors regulate the development and growth of the vascular endothelial system. VEGF family members include, but are not limited to VEGF-A, VEGF-B, VEGF-C, VEGF-D and PlGF [Li, X. and U. Eriksson, "Novel VEGF Family Members: VEGF-B, VEGF-C and VEGF-D," *Int. J. Biochem. Cell. Biol.*, 33(4): 421-6 (2001))] Other VEGFs are bacterial or viral, the "VEGF-Es." Other VEGFs are derived from snake venom, the "NZ" series. [See e.g., Komori, et al. Biochemistry, 38(36):11796-803 (1999); Gasmi, et al., Biochem Biophys Res Commun, 268(1):69-72 (2002); Gasmi, et al., J Biol Chem; 277(33):29992-8 (2002); de Azevedo, et al., J. Biol. Chem., 276: 39836-39842 (2001)].

At least seven cell surface receptors that interact with PDGF/VEGF family members have been identified. These include PDGFR-α [See e.g., GenBank Acc. No. NM006206; Swiss Prot No. P16234], PDGFR-β [See e.g., GenBank Acc. No. NM002609; Swiss Prot. No. P09619], VEGFR-1/Flt-1 (fms-like tyrosine kinase-1; hereinafter "R-1") [GenBank Acc. No. X51602; De Vries, et al., *Science* 255:989-991 (1992)]; VEGFR-2/KDR/Flk-1 (kinase insert domain containing receptor/fetal liver kinase-1, hereinafter "R-2") [GenBank Acc. Nos. X59397 (Flk-1) and L04947 (KDR); Terman, et al., *Biochem. Biophys. Res. Comm.* 187:1579-1586 (1992); Matthews, et al., *Proc. Natl. Acad. Sci. USA* 88:9026-9030 (1991)]; VEGFR-3/Flt4 (fms-like tyrosine kinase 4; hereinafter "R-3") [U.S. Pat. No. 5,776,755 and GenBank Acc. No. X68203 and S66407; Pajusola et al., *Oncogene* 9:3545-3555 (1994); Hughes, et al., *J. Mol. Evol.* 52(2):77-79 (2001); Pajusola, et al., *Oncogene* 8(11):2931-37) (1993); Borg, et al., *Oncogene* 10(5):973-984 (1995), neuropilin-1 [Gen Bank Acc. No. NM003873], and neuropilin-2 [Gen Bank Acc. No. NM003872; SwissProt O60462]. The two PDGF receptors mediate signaling of PDGFs. Non-human VEGF and PDGF receptors may also be employed as part of the invention, e.g., chicken VEGFR-1 may be used alone or in hybrid form with human R-1 for improved expression.

VEGF121, VEGF165, VEGF-B, PlGF-1 and PlGF-2 bind VEGF-R1; VEGF121, VEGF145, VEGF165, (fully processed mature) VEGF-C, (fully processed mature) VEGF-D, VEGF-E, and NZ2 VEGF bind VEGF-R2; VEGF-C and VEGF-D bind VEGFR-3; VEGF165, VEGF-C, PlGF-2, and NZ2 VEGF bind neuropilin-1; and VEGF165 and VEGF-C binds neuropilin-2. [Neufeld, et al., *FASEB. J.* 13:9-22 (1999); Stacker and Achen, *Growth Factors* 17:1-11 (1999); Ortega, et al., *Fron. Biosci.* 4:141-152 (1999); Zachary, *Intl. J. Biochem. Cell. Bio.* 30:1169-1174 (1998); Petrova, et al., *Exp. Cell. Res.* 253:117-130 (1999); U.S. Pat. Appl. Pub. No. 20030113324]. PDGF-A, PDGF-B, and PDGF-C bind PDGFR-α. PDGF-B and PDGF-D bind PDGF-β.

Both the ligands and the receptors generally exist as dimers, including both homodimers and heterodimers. Such dimers can influence binding. For example, for the PDGFs, PDGF-AA binds PDGFR-α/α. PDGF-AB and PDGF-CC bind PDGFR-α/α and PDGFR-α/β. PDGFR-BB binds both of the homodimers and the heterodimeric PDGF receptor. PDGF-DD binds PDGF receptor heterodimers and beta receptor homodimers. [See, e.g., Pietras, et al., Cancer Cell, 3:439-443 (2003).] VEGF-A can heterodimerize with VEGF-B and PlGF. The VEGFs, PDGFs, and PlGFs, may exist as two or more isoforms, e.g., splice variants, and not all isoforms of a particular growth factor will share the same binding profile, or ability to dimerize with particular molecules. Certain isoforms of the same growth factor may also dimerize with each other. For example the 167 and 186 isoforms of VEGF-B can heterodimerize with each other.

Growth factor receptor tyrosine kinases generally comprise three principal domains: an extracellular domain, a transmembrane domain, and an intracellular domain. The extracellular domain binds ligands, the transmembrane domain anchors the receptor to a cell membrane, and the intracellular domain possesses one or more tyrosine kinase enzymatic domains and interacts with downstream signal transduction molecules. The vascular endothelial growth factor receptors (VEGFRs) and platelet derived growth factor receptors (PDGFRs) bind their ligand through their extracellular domains (ECDs), which are comprised of multiple immunoglobulin-like domains (Ig-domains). Ig-domains are identified herein using the designation "D#." For example "D1" refers to the first Ig-domain of a particular receptor ECD. "D1-3" refers to a construct containing at least the first three Ig-domains, and intervening sequence between domains 1 and 2 and 2 and 3, of a particular construct. Table 2 defines the boundaries of the Ig-domains for VEGFR-1, VEGFR-2, and VEGFR-3 of the invention. These boundaries are significant as the boundaries chosen can be used to form constructs, and so can influence the binding properties of the resulting constructs. This relationship is discussed in Example 1.

The complete ECD of PDGFRs and VEGFRs is not required for ligand (growth factor) binding. The ECD of VEGFR-1 (R-1) and VEGFR-2 (R-2) consists of seven Ig-like domains and the ECD of VEGFR-3 (R-3) has six intact Ig-like domains—D5 of R-3 is cleaved post-translationally into disulfide linked subunits leaving VEGFR-3. Veikkola, T., et al., *Cancer Res.* 60:203-212 (2000). In general, receptor fragments of at least the first three Ig-domains for this family are sufficient to bind ligand. The PDGFRs have five Ig-domains.

Olofsson, et al., J. Biol. Chem., 271:19310-19317 (1996).] Three isoforms of PlGF produced by alternative mRNA splicing have been described [Hauser, et al., Growth Factors 9:259-268 (1993); Maglione, et al., Oncogene 8:925-931 (1993)]. PDGF-A and PDGF-B can homodimerize or heterodimerize to produce three different isoforms: PDGF-AA, PDGF-AB, or PDGF-BB.

The term "identity", as known in the art, refers to a relationship between the sequences of two or more polypeptide molecules or two or more nucleic acid molecules, as determined by comparing the sequences. In the art, "identity" also means the degree of sequence relatedness nucleic acid molecules or polypeptides sequences, as the case may be, as determined by the match between strings of two or more nucleotide or two or more amino acid sequences.

TABLE 2

IMMUNOGLOBULIN-LIKE DOMAINS FOR VEGFR-1, VEGFR-2 AND VEGFR-3

| | R-1 SEQ ID NO: 1 positions | R-1 SEQ ID NO: 2 positions | R-2 SEQ ID NO: 3 positions | R-2 SEQ ID NO: 4 positions | R-3 SEQ ID NO: 5 positions | R-3 SEQ ID NO: 6 positions |
|---|---|---|---|---|---|---|
| D1 | 394-580 | 49-111 | 145-316 | 48-105 | 158-364 | 47-115 |
| D2 | 709-880 | 154-211 | 436-610 | 145-203 | 479-649 | 154-210 |
| D3 | 990-1192 | 248-315 | 724-931 | 241-310 | 761-961 | 248-314 |
| D4 | 1303-1474 | 352-409 | 1039-1204 | 346-401 | 1070-1228 | 351-403 |
| D5 | 1957-1864 | 450-539 | 1321-1600 | 440-533 | 1340-1633 | 441-538 |
| D6 | 1966-2167 | 573-640 | 1699-1936 | 566-645 | 1739-1990 | 574-657 |
| D7 | 2281-2452 | 678-735 | 2050-2221 | 683-740 | 2102-2275 | 695-752 |

In some embodiments, a binding unit of a binding construct comprises the ECD of a growth factor receptor. A binding unit may comprise at least one Ig-domain of a VEGFR as described in Table 2, to as many as seven. Ig-domain information for PDGFR-α and PDGFR-β is provided in Lokker, et al., J. Biol. Chem. 272: 33037-33044 (1997), which is incorporated by reference in its entirety. A binding unit may include sequence before the N-terminal most Ig-domain, may include sequence beyond the C-terminal most Ig-domain, and may include sequence between the Ig-domains as well. Binding units may also comprise variants, e.g., with one or more amino acid substitutions, additions, or deletions of an amino acid residue. Binding units also may comprise chimeras, e.g., combinations of Ig-domains from different receptors. In some embodiments, the first or second polypeptide comprises a receptor fragment comprising at least the first three Ig domains of a receptor tyrosine kinase.

The binding of a binding unit to a particular growth factor ligand refers to the ability to bind at least one natural isoform of at least one target growth factor, especially processed forms that are secreted from cells and circulate in vivo and/or bind heparin moieties. For example, "capable of binding VEGF-A" refers to the ability to bind at least one isoform of VEGF-A under physiological conditions. At least five human VEGF-A isoforms of 121, 145, 165, 189 or 206 amino acids in length (VEGF121-VEGF206), encoded by distinct mRNA splice variants, have been described, all of which are capable of stimulating mitogenesis in endothelial cells. [See generally, Ferrara, *J. Mol. Med.* 77:527-543 (1999).] Two VEGF-B isoforms generated by alternative mRNA splicing exist, VEGF-B186 and VEGF-B167, with the first isoform accounting for about 80% of the total VEGF-B transcripts [Li, X., et al., Growth Factor, 19:49-59 (2001); Grimmond, et al., Genome Res., 6:124-131 (1996);

"Identity" measures the percent of identical matches between the smaller of two or more sequences with gap alignments (if any) addressed by particular a mathematical model of computer program (i.e., "algorithms"). Appropriate algorithms for determining the percent identities of the invention include BLASTP and BLASTN, using the most common and accepted default parameters.

1. VEGFR-1-Derived Binding Units

In some embodiments, a binding unit comprises a polypeptide similar or identical in amino acid sequence to a VEGFR-1 polypeptide or fragment thereof, preferably from the same species as the targeted growth factor(s). Thus, for binding to human growth factors, a binding unit preferably comprises a polypeptide that comprises an amino acid similar or identical to a fragment of SEQ ID NO: 2, wherein the fragment and the polypeptide binds one or more growth factors selected from the group consisting of VEGF-A, VEGF-B, and PlGF. The fragment minimally comprises enough of the VEGFR-1 sequence to bind the ligand, and may comprise the complete receptor. Extracellular domain fragments are preferred. Preferred polypeptides have an amino acid sequence at least 80% identical to a ligand binding fragment thereof. Fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated.

Preferred polypeptides may also be described as having an amino acid sequence encoded by a nucleic acid sequence at least 80% identical to a fragment of SEQ ID NO:1 encoding a ligand binding fragment of VEGFR-1. Nucleic acid fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. A genus of similar polypeptides can alternatively be defined by the ability of encoding polynucleotides to hybridize to the complement of a nucleotide sequence that corresponds to the cDNA sequence encoding the R-1 receptor. For example, a preferred binding unit polypeptide comprises an amino acid sequence that binds one or more R-1 ligands and that is encoded by a nucleotide sequence that hybridizes to the complement of SEQ ID NO: 1 under moderately or highly stringent conditions discussed herein.

Exemplary R1 fragments for use as binding unit polypeptides (or for use as a starting point for designing R-1 analogs) have an amino terminal residue selected from the group consisting of positions 1 to 129 of SEQ ID NO: 2, and a carboxy terminal residue selected from the group consisting of positions 229 to 758 of SEQ ID NO: 2, wherein the VEGFR-1 fragment binds at least one of VEGF-A, VEGF-B, and PlGF.

2. VEGFR-2-Derived Binding Units

In some embodiments, a binding unit comprises a polypeptide similar or identical in amino acid sequence to a VEGFR-2 polypeptide or fragment thereof, preferably from the same species as the targeted growth factor(s). Thus, for binding to human growth factors, a binding unit preferably comprises a polypeptide that comprises an amino acid similar or identical to a fragment of SEQ ID NO: 4, wherein the fragment and the polypeptide binds one or more growth factors selected from the group consisting of VEGF-A, VEGF-C, VEGF-D, or VEGF-E. The fragment minimally comprises enough of the VEGFR-2 sequence to bind the ligand, and may comprise the complete receptor. Extracellular domain fragments are preferred. Preferred polypeptides have an amino acid sequence at least 80% identical to a ligand binding fragment thereof. Fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated.

Preferred polypeptides may also be described as having an amino acid sequence encoded by a nucleic acid sequence at least 80% identical to a fragment of SEQ ID NO:3 encoding a ligand binding fragment of VEGFR-2. Nucleic acid fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. A genus of similar polypeptides can alternatively be defined by the ability of encoding polynucleotides to hybridize to the complement of a nucleotide sequence that corresponds to the cDNA sequence encoding the R-2 receptor. For example, a preferred binding unit polypeptide comprises an amino acid sequence that binds one or more R-2 ligands and that is encoded by a nucleotide sequence that hybridizes to the complement of SEQ ID NO: 3 under moderately or highly stringent conditions discussed herein.

Exemplary R2 fragments for use as binding unit polypeptides (or for use as a starting point for designing R-2 analogs) have an amino terminal residue selected from the group consisting of positions 1 to 118 of SEQ ID NO: 4, and a carboxy terminal residue selected from the group consisting of positions 326 to 764 of SEQ ID NO: 4, wherein VEGFR-2 fragment binds at least one of VEGF-A, VEGF-C, VEGF-D, and VEGF-E. Exemplary R2 fragments for use as binding unit polypeptides (or for use as a starting point for designing R-2 analogs) may alternatively have an amino terminal residue selected from the group consisting of positions 1 to 192 of SEQ ID NO: 4, and a carboxy terminal residue selected from the group consisting of positions 393 to 764 of SEQ ID NO: 4, wherein the VEGFR-2 fragment binds at least one of VEGF-A, VEGF-C, VEGF-D, and VEGF-E. Exemplary R2 fragments for use as binding unit polypeptides (or for use as a starting point for designing R-2 analogs) may also have an amino terminal residue selected from the group consisting of positions 1 to 48 of SEQ ID NO: 4, and a carboxy terminal residue selected from the group consisting of positions 214 to 764 of SEQ ID NO: 4, wherein the VEGFR-2 fragment binds at least one of VEGF-A, VEGF-C, VEGF-D, and VEGF-E.

In some embodiments, a binding unit of the binding construct comprises a fragment of R-2, SEQ ID NO: 4, selected from the group consisting of positions 24-326 (SEQ ID NO: 8), 118-326 (SEQ ID NO: 20), positions 118-220 (SEQ ID NO: 22), positions 118-226 (SEQ ID NO: 24), and positions 118-232 (SEQ ID NO: 26). In some embodiments, a binding unit of the binding construct comprises a fragment of R-2, SEQ ID NO: 4, selected from the group consisting of positions 106-240, positions 112-234, positions 114-220, positions 115-220, positions 116-222, positions 117-220, positions 118-221, positions 118-222, positions 118-223, positions 118-224, and positions 118-228. In some embodiments, a binding unit of the binding construct comprises a fragment of R-2, SEQ ID NO: 4, selected from the group consisting of positions 48-203, and 145-310 and 48-310. Exemplary embodiments are also discussed in Example 1.

3. VEGFR-3-Derived Binding Units

In some embodiments, a binding unit comprises a polypeptide similar or identical in amino acid sequence to a VEGFR-3 polypeptide or fragment thereof, preferably from the same species as the targeted growth factor(s). Thus, for binding to human growth factors, a binding unit preferably comprises a polypeptide that comprises an amino acid similar or identical to a fragment of SEQ ID NO: 6, where the fragment and the polypeptide binds one or more growth factors selected from the group consisting of VEGF-C and VEGF-D. The fragment minimally comprises enough of the VEGFR-3 sequence to bind the ligand, and may comprise the complete receptor. Extracellular domain fragments are preferred. Preferred polypeptides have an amino acid sequence at least 80% identical to a ligand binding fragment thereof. Fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. A genus of similar polypeptides can alternatively be defined by the ability of encoding polynucleotides to hybridize to the complement of a nucleotide sequence that corresponds to the cDNA sequence encoding the R-3 receptor.

Preferred polypeptides may also be described as having an amino acid sequence encoded by a nucleic acid sequence at least 80% identical to a fragment of SEQ ID NO:5 encoding a ligand binding fragment of VEGFR-3. Nucleic acid fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. For example, a preferred binding unit polypeptide comprises an amino acid sequence that binds one or more R-3 ligands and that is encoded by a nucleotide sequence that hybridizes to the complement of SEQ ID NO: 5 under moderately or highly stringent conditions discussed herein.

Exemplary R-3 fragments for use as binding unit polypeptides (or for use as a starting point for designing R-3 analogs) have an amino terminal residue selected from the group consisting of positions 1 to 47 of SEQ ID NO: 6, and a carboxy terminal residue selected from the group consisting of positions 226 to 775 of SEQ ID NO: 6, wherein VEGFR-3 fragment binds at least one of VEGF-C and VEGF-D.

In some embodiments, a binding unit of the binding construct comprises a fragment of R-3, SEQ ID NO: 6, selected from the group consisting of positions 1-226 (SEQ ID NO: 38), positions 1-229 (SEQ ID NO: 36), and positions 1-329 (SEQ ID NO: 44). In some embodiments, a binding unit of the binding construct comprises a fragment of R-3, SEQ ID NO: 6, selected from the group consisting of positions 47-224, positions 47-225, positions 47-226, positions 47-227, positions 47-228, positions 47-229, positions 47-230, positions 47-231, positions 47-232, positions 47-236, positions 47-240, and positions 47-245. In some embodiments, a binding unit of the binding construct comprises a fragment of R-3, SEQ ID NO: 6, selected from the group consisting of positions 47-314, positions 47-210, and positions 47-247. Exemplary embodiments are also discussed in Example 1.

4. Neuropilin-1-Derived Binding Units

In some embodiments, a binding unit comprises a polypeptide similar or identical in amino acid sequence to a neuropilin-1 polypeptide or fragment thereof, preferably from the same species as the targeted growth factor(s). Thus, for binding to human growth factors, a binding unit preferably comprises a polypeptide that comprises an amino acid similar or identical to a fragment of SEQ ID NO: 113, where the fragment and the polypeptide binds one or more growth factors selected from the group consisting of VEGF-A, VEGF-B, VEGF-C, VEGF-E, and PlGF. The fragment minimally comprises enough of the neuropilin-1 sequence to bind the ligand, and may comprise the complete receptor. Extracellular domain fragments are preferred. Preferred polypeptides have an amino acid sequence at least 80% identical to a ligand binding fragment thereof. Fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated.

Preferred polypeptides may also be described as having an amino acid sequence encoded by a nucleic acid sequence at least 80% identical to a fragment of SEQ ID NO:112 encoding a ligand binding fragment of neuropilin-1. Nucleic acid fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. A genus of similar polypeptides can alternatively be defined by the ability of encoding polynucleotides to hybridize to the complement of a nucleotide sequence that corresponds to the cDNA sequence encoding the neuropilin-1 receptor. For example, a preferred binding unit polypeptide comprises an amino acid sequence that binds one or more neuropilin-1 ligands and that is encoded by a nucleotide sequence that hybridizes to the complement of SEQ ID NO: 112 under moderately or highly stringent conditions discussed herein.

Exemplary neuropilin-1 fragments for use as binding unit polypeptides (or for use as a starting point for designing neuropilin-1 analogs) comprise a neuropilin-1 extracellular domain amino acid sequence comprising residues 22-856 of SEQ ID NO: 113, or a portion thereof; wherein the neuropilin-1 fragment and the binding unit bind at least one growth factor selected from the group consisting of VEGF-A, VEGF-B, VEGF-C, VEGF-E, and PlGF.

5. Neuropilin-2-Derived Binding Units

In some embodiments, a binding unit comprises a polypeptide similar or identical in amino acid sequence to a neuropilin-2 polypeptide or fragment thereof, preferably from the same species as the targeted growth factor(s). Thus, for binding to human growth factors, a binding unit preferably comprises a polypeptide that comprises an amino acid similar or identical to a fragment of SEQ ID NO: 115, wherein the fragment and the polypeptide binds one or more growth factors selected from the group consisting of VEGF-A, VEGF-C, and PlGF. The fragment minimally comprises enough of the neuropilin-2 sequence to bind the ligand, and may comprise the complete receptor. Extracellular domain fragments are preferred. Preferred polypeptides have an amino acid sequence at least 80% identical to a ligand binding fragment thereof. Fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated.

Preferred polypeptides may also be described as having an amino acid sequence encoded by a nucleic acid sequence at least 80% identical to a fragment of SEQ ID NO:114 encoding a ligand binding fragment of neuropilin-2. Nucleic acid fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. A genus of similar polypeptides can alternatively be defined by the ability of encoding polynucleotides to hybridize to the complement of a nucleotide sequence that corresponds to the cDNA sequence encoding the neuropilin-2 receptor. For example, a preferred binding unit polypeptide comprises an amino acid sequence that binds one or more neuropilin-2 ligands and that is encoded by a nucleotide sequence that hybridizes to the complement of SEQ ID NO: 114 under moderately or highly stringent conditions discussed herein.

Exemplary neuropilin-2 fragments for use as binding unit polypeptides comprising residues 21-864 of SEQ ID NO: 115, or a portion thereof; wherein the neuropilin-2 fragment and the binding unit bind at least one growth factor selected from the group consisting of VEGF-A, VEGF-C, and PlGF.

Further neuropilin-1 and -2 species, isoforms, soluble fragments, etc., are provided in WO03/029814, U.S. application Ser. Nos. 10/262,538, 10/669,176, and 60/505,607, which are incorporated by reference in their entireties.

6. PDGFR-Alpha-Derived Binding Units

In some embodiments, a binding unit comprises a polypeptide similar or identical in amino acid sequence to a PDGFR-α polypeptide or fragment thereof, preferably from the same species as the targeted growth factor(s). Thus, for binding to human growth factors, a binding unit preferably comprises a polypeptide that comprises an amino acid similar or identical to a fragment of SEQ ID NO: 117, where the fragment and the polypeptide binds one or more growth factors selected from the group consisting of PDGF-A, PDGF-B, and PDGF-C. The fragment minimally comprises enough of the PDGFR-α sequence to bind the ligand, and may comprise the complete receptor. Extracellular domain fragments are preferred. Preferred polypeptides have an amino acid sequence at least 80% identical to a ligand binding fragment thereof. Fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. A genus of similar polypeptides can alternatively be defined by the ability of encoding polynucleotides to hybridize to the complement of a nucleotide sequence that corresponds to the cDNA sequence encoding the R-α receptor.

Preferred polypeptides may also be described as having an amino acid sequence encoded by a nucleic acid sequence at least 80% identical to a fragment of SEQ ID NO:116 encoding a ligand binding fragment of R-α. Nucleic acid fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. For example, a preferred binding unit polypeptide comprises an amino acid sequence that binds one or more R-α ligands and that is encoded by a nucleotide sequence that hybridizes to the complement of SEQ ID NO: 116 under moderately or highly stringent conditions discussed herein.

Exemplary R-α fragments for use as binding unit polypeptides (or for use as a starting point for designing R-α analogs) have an amino terminal residue selected from the group consisting of positions 1 to 123 of SEQ ID NO: 117, and a carboxy terminal residue selected from the group consisting of positions 313 to 524 of SEQ ID NO: 117, wherein the PDGFR-α fragment binds at least one of PDGF-A, PDGF-B, and PDGF-C.

7. PDGFR-Beta-Derived Binding Units

In some embodiments, a binding unit comprises a polypeptide similar or identical in amino acid sequence to a R-β polypeptide or fragment thereof, preferably from the same species as the targeted growth factor(s). Thus, for binding to human growth factors, a binding unit preferably comprises a polypeptide that comprises an amino acid similar or identical to a fragment of SEQ ID NO: 119, where the fragment and the polypeptide binds one or more growth factors selected from the group consisting of PDGF-B and PDGF-D. The fragment minimally comprises enough of the PDGFR-β sequence to bind the ligand, and may comprise the complete receptor. Extracellular domain fragments are preferred. Preferred polypeptides have an amino acid sequence at least 80% identical to a ligand binding fragment thereof. Fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. A genus of similar polypeptides can alternatively be defined by the ability of encoding polynucleotides to hybridize to the complement of a nucleotide sequence that corresponds to the cDNA sequence encoding the R-β receptor.

Preferred polypeptides may also be described as having an amino acid sequence encoded by a nucleic acid sequence at least 80% identical to a fragment of SEQ ID NO:118 encoding a ligand binding fragment of PDGFR-β. Nucleic acid fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. For example, a preferred binding unit polypeptide comprises an amino acid sequence that binds one or more R-β ligands and that is encoded by a nucleotide sequence that hybridizes to the complement of SEQ ID NO: 118 under moderately or highly stringent conditions discussed herein.

Exemplary R-β fragments for use as binding unit polypeptides (or for use as a starting point for designing R-β analogs) have an amino terminal residue selected from the group consisting of positions 1 to 124 of SEQ ID NO: 119, and a carboxy terminal residue selected from the group consisting of positions 314 to 531 of SEQ ID NO: 119, wherein PDGFR-β fragment binds at least one of PDGF-B and PDGF-D.

8. Other Binding Units

Although a binding unit may comprise a polypeptide similar or identical to an extracellular domain fragment of a growth factor receptor tyrosine kinase, other binding units are contemplated as well. In some embodiments, the binding unit is generated using phage display. In some embodiments, the binding unit comprises an antibody. In some embodiments, a binding unit comprises a polypeptide comprising an antibody (antigen binding) fragment, e.g., a domain antibody. Binding units, as well as binding constructs, need not comprise a polypeptide. In some embodiments, the binding construct comprises nucleic acid, e.g., DNA or RNA, such as an aptamer. In some embodiments, the binding construct comprises polysaccharides.

Growth factor binding molecules that have been described in the literature may be used as binding units to construct binding constructs of the inventory including molecules taught by the following: Veikkola, T., et al., *Cancer Res.* 60:203-212 (2000); Davis-Smyth, T., et al., *EMBO J.*, 15(18): 4919-27 (1996), U.S. Pat. Nos. 5,952,199; 6,100, 071; 6,383,486; U.S. Pat. Appl. Nos. 20030092604; Niwa, et al., U.S. Pat. No. 6,348,333; Fairbrother, et al., *Biochemistry*, 37:17754-64 (1998); Starovasnik, M. et al., *J. Mol. Biol.*, 293: 531-44 (1999); Wiesmann, C., et al., *Cell*, 91:695-704 (1997); Fuh, et al., *J. Biol. Chem.*, 273(18): 11197-11204 (1998); Shinkai, A. et al., *J. Biol. Chem.*, 273(47):31283-88 (1998); Lu, et al., *J. Biol. Chem.*, 275(19): 14321-14330 (2000); Lu et al., *J. Immunological Methods*, 230:159-71 (1999); Lu, et al., *J. Biol. Chem.*, 278(44): 43496-43507 (2003); Makkinen, T., et al., *Nature Medicine*, 7(2), 199-205 (2001); Alitalo, et al., WO 02/060950; Karpanen, T., et al., *Cancer Research* 61:1786-90 (2001); Liu, et al., U.S. Pat. Appl. Publ. No. 2003/0064053; Kubo, H., et al., *Blood*, 96(2): 546-553 (2000); Rosen, *Hematol. Oncol. Clin. N. Am.*, 16:1173-1187 (2002); Kaplan, et al., *Growth Factors*, 14:243-256 (1997); Thomas, et al., U.S. Pat. No. 6,375,929; Kendall and Thomas, *PNAS, U.S.A.*, 90:10705-10709 (1993); Kovesdi, U.S. Pat. Appl. Publ. No. 2003/0053989; Daly, et al., U.S. Pat. Appl. Publ. No.: 2004/0014667; and Lokker, et al., J. Biol. Chem. 272: 33037-33044 (1997). These and other documents cited in this application are incorporated in their entireties. Molecules that have not previously been tested for their ability to bind to a particular growth factor may tested according to the assays provided herein. For example, some of the above documents teach a R-2 fragment that binds VEGF-A. That same molecule may be tested for its ability to bind VEGF-C.

Except as otherwise noted, descriptions supplied for receptors, also apply to receptor fragments and such fragments incorporated into binding constructs as described herein.

The growth factor receptors, from which binding units may be derived, include splice variants and naturally-occurring allelic variations. Allelic variants are well known in the art, and represent alternative forms or a nucleic acid sequence that comprise substitution, deletion or addition of one or more nucleotides, but which do not result in any substantial functional alteration of the encoded polypeptide. Standard methods can readily be used to generate such polypeptides including site-directed mutagenesis of polynucleotides, or specific enzymatic cleavage and ligation. Similarly, use of peptidomimetic compounds or compounds in which one or more amino acid residues are replaced by a non-naturally-occurring amino acid or an amino acid analog that retain binding activity is contemplated. Preferably, where amino acid substitution is used, the substitution is conservative, i.e. an amino acid is replaced by one of similar size and with similar charge properties. As used herein, the term "conservative substitution" denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids that can be substituted for one another include asparagine, glutamine, serine and threonine. The term "conservative substitution" also includes the use of a substituted amino acid in place of an unsubstituted amino acid.

Alternatively, conservative amino acids can be grouped as described in Lehninger, (*Biochemistry*, Second Edition; Worth Publishers, Inc. NY, N.Y., pp. 71-77 (1975)) as set out in the following:

Non-polar (hydrophobic)
  A. Aliphatic: A, L, I, V, P,
  B. Aromatic: F, W,
  C. Sulfur-containing: M,
  D. Borderline: G.
Uncharged-polar
  A. Hydroxyl: S, T, Y,
  B. Amides: N, Q,
  C. Sulfhydryl: C,
  D. Borderline: G.
Positively Charged (Basic): K, R, H.
Negatively Charged (Acidic): D, E.

B. Linkers

While binding units may be directly attached to one another (via a peptide, disulfide or other type of covalent bond), the binding constructs of the present invention may further comprise a (one or more) linker that connects together two or more different binding units, e.g., a receptor fragments with another receptor fragment, or even a copy of itself. A linker may also link a binding unit to other substituents described herein. The linker is generally a heterologous protein polypeptide. In some embodiments, the linker comprises a peptide that links the binding units to form a single continuous peptide that can be expressed as a single molecule. Linkers may be chosen such that they are less likely to induce an allergic reaction. Polysaccharides or other moieties also may be used to link binding units to form a binding construct.

More than one linker may be used per binding construct. The linker may be selected for optimal conformational (steric) freedom between the various ligand binding units to allow them to interact with each other if desired, e.g., to form dimers, or to allow them to interact with ligand. The linker may be linear such that consecutive binding units are linked in series, or the linker may serve as a scaffold to which various binding units are attached, e.g., a branched linker. A linker may also have multiple branches, e.g., as disclosed in Tam, J. Immunol. Methods 196:17 (1996). Binding units may be attached to each other or to the linker scaffold via N-terminal amino groups, C-terminal carboxyl groups, side chains, chemically modified groups, side chains, or other means.

Linker peptides may be designed to have sequences that permit desired characteristics. For example, the use of glycyl residues allow for a relatively large degree of conformational freedom, whereas a proline would tend to have the opposite effect. Peptide linkers may be chosen so that they achieve particular secondary and tertiary structures, e.g., alpha helices, beta sheets or beta barrels. Quaternary structure can also be utilized to create linkers that join two binding units together non-covalently. For example, fusing a protein domain with a hydrophobic face to each binding unit may permit the joining of the two binding units via the interaction between the hydrophobic interaction of the two molecules. In some embodiments, the linker may provide for polar interactions. For example, a leucine zipper domain of the proto-oncoproteins Myc and Max, respectively, may be used. Luscher and Larsson, *Ongogene* 18:2955-2966 (1999). In some embodiments, the linker allows for the formation of a salt bridge or disulfide bond. Linkers may comprise non-naturally occurring amino acids, as well as naturally occurring amino acids that are not naturally incorporated into a polypeptide. In some embodiments, the linker comprises a coordination complex between a metal or other ion and various residues from the multiple peptides joined thereby.

Linear peptide linkers of at least one amino acid residue are contemplated. In some embodiments the linker has more than 10,000 residues. In some embodiments the linker has from 1-10,000 residues. In some embodiments, the linker has from 1-1000 residues. In some embodiments, the linker has from 1-100 residues. In some embodiments, the linker has from 1-50 residues. In some embodiments the linker has 1-10 residues. In some embodiments, the linear peptide linker comprises residues with relatively inert side chains. Peptide linker amino acid residues need not be linked entirely or at all via alpha-carboxy and alpha-amino groups. That is, peptides may be linked via side chain groups of various residues.

The linker may affect whether the polypeptide(s) to which it is fused to is able to dimerize to each other or to another polypeptide. The linker serves a number of functions. Native receptor monomers restrained to the roughly two-dimensional plane of the cell membrane enjoy a relatively high local concentration and in the availability of co-receptors (binding units), increasing the probability of finding a partner. Receptors free in solution lacking such advantages may be aided by a linker that increases the effective concentration of the monomers.

In some embodiments, a binding construct may comprise more than one type of linker. Suitable linkers may also comprise the chemical modifications discussed below.

C. Substituents and Other Chemical Modifications

The binding constructs of the invention may be chemically modified with various substituents. Such modifications preferably does not substantially reduce the growth factor binding affinities or specificities of the binding construct. Rather, the chemical modifications impart additional desirable characteristics as discussed herein. Chemical modifications may take a number of different forms such as heterologous peptides, polysaccharides, lipids, radioisotopes, non-standard amino acid resides and nucleic acids, metal chelates, and various toxins.

The receptor fragments, binding constructs, and other peptide molecules of the present invention may be fused to heterologous peptides to confer various properties, e.g., increased solubility, modulation of clearance, targeting to particular cell or tissue types. In some embodiments, the receptor fragment is linked to a Fc domain of IgG or other immunoglobulin. In some embodiments, a receptor fragment is fused to alkaline phosphatase (AP). Methods for making Fc or AP fusion constructs are found in WO 02/060950. By fusing the ligand binding domain of VEGFR-2 or VEGFR-3 (or other receptors) with protein domains that have specific properties (e.g. half life, bioavailability, interaction partners) it is possible to confer these properties to the VEGFR binding domains (e.g., the receptor binding domain could be engineered to have a specific tissue distribution or specific biological half life). In some embodiments, binding construct may include a co-receptor and a VEGFR fragment.

The particular heterologous polypeptide used in a particular construct can influence whether or not a growth factor receptor fragment will dimerize, which in turn may affect ligand binding. Fc fusion all may permit dimers, whereas AP fusions may permit monomers, cited, which along with Ig-domain boundary differences as possible reasons for different results obtained by different groups for receptor fragments binding to ligands. [Lu, et al., *J. Biol. Chem.* 275(19): 14321-14330 (2000).]

For substituents such as an Fc region of human IgG, the fusion can be fused directly to a binding construct or fused through an intervening sequence. For example, a human IgG hinge, CH2 and CH3 region may be fused at either the N-terminus or C-terminus of a binding construct to attach the Fc region. The resulting Fc-fusion construct enables purification via a Protein A affinity column (Pierce, Rockford, Ill.). Peptide and proteins fused to an Fc region can exhibit a substantially greater half-life in vivo than the unfused counterpart. A fusion to an Fc region allows for dimerization/multimerization of the fusion polypeptide. The Fc region may be a naturally occurring Fc region, or may be modified for superior characteristics, e.g., therapeutic qualities, circulation time, reduced aggregation.

Polypeptides can be modified, for instance, by glycosylation, amidation, carboxylation, or phosphorylation, or by the creation of acid addition salts, amides, esters, in particular C-terminal esters, and N-acyl derivatives. The proteins also can be modified to create peptide derivatives by forming covalent or noncovalent complexes with other moieties. Covalently bound complexes can be prepared by linking the chemical moieties to functional groups on the side chains of amino acids comprising the peptides, or at the N- or C-terminus.

Polypeptides can be conjugated to a reporter group, including, but not limited to a radiolabel, a fluorescent label, an enzyme (e.g., that catalyzes a calorimetric or fluorometric reaction), a substrate, a solid matrix, or a carrier (e.g., biotin or avidin). Examples of analogs are described in WO 98/28621 and in Olofsson, et al., *Proc. Nat'l. Acad. Sci. USA*, 95:11709-11714 (1998), U.S. Pat. Nos. 5,512,545, and 5,474,982; U.S. Patent Application Nos. 20020164687 and 20020164710.

Cysteinyl residues most commonly are reacted with haloacetates (and corresponding amines), such as chloroacetic acid or chloroacetamide, to give carboxymethyl or carbocyamidomethyl derivatives. Cysteinyl residues also are derivatized by reaction with bromotrifluoroacetone, α-bromo-β(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, orchloro-7-nitrobenzo-2-oxa-1,3-diazole.

Histidyl residues are derivatized by reaction with diethylprocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylissurea; 2,4 pentanedione; and transaminase catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pK of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using 125I or 131I to prepare labeled proteins for use in radioimmunoassay.

Carboxyl side groups (aspartyl or glutamyl) are selectively modified by reaction with carbodiimides (R1) such as 1-cyclohexyl-3-(2-morpholinyl-(4-ethyl) carbodiimide or 1-ethyl-3 (4 azonia 4,4-dimethylpentyl)carbodiimide. Furthermore, aspartyl and glutamyl residues are converted to asparaginyl and glutaminyl residues by reaction with ammonium ions.

Derivatization with bifunctional agents is useful for cross-linking the binding construct to water-insoluble support matrixes. Such derivation may also provide the linker that may connect adjacent binding elements in a binding construct, or a binding elements to a heterologous peptide, e.g., a Fc fragment. Commonly used crosslinking agents include, e.g., 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiiobis(succinimidylpropioonate), and bifunctional maleimides such as bis-N-maleimido-1,8-octane. Derivatizing agents such as methyl-3-[(p-azidophenyl)dithio]propioimidate yield photoactivatable intermediates that are capable of forming cross links in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440, incorporated herein by reference, are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecule Properties*, W. H. Freeman & Co., San Francisco, pp. 79-86, 1983), acetylation of the N-terminal amine, and, in some instances, amidation of the C-terminal carboxyl groups. Such derivatives are chemically modified polypeptide compositions in which the binding construct polypeptide is linked to a polymer. The polymer selected is typically water soluble so that the protein to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. The polymer may be of any molecular weight, and may be branched or unbranched. Included within the scope of the binding construct polypeptide polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water soluble polymer, some molecules will weigh more, some less, than the stated molecular weight). The average molecular weight of each polymer is between about 5 kDa and about 50 kDa, more preferably between about 12 kDa to about 40 kDa and most preferably between about 20 kDa to about 35 kDa.

Suitable water soluble polymers or mixtures thereof include, but are not limited to, N-linked or O-linked carbohydrates, sugars, phosphates, carbohydrates; sugars; phosphates; polyethylene glycol (PEG) (including the forms of PEG that have been used to derivatize proteins, including mono-(C1-C10) alkoxy- or aryloxy-polyethylene glycol); monomethoxy-polyethylene glycol; dextran (such as low molecular weight dextran, of, for example about 6 kD), cellulose; cellulose; other carbohydrate-based polymers, poly-(N-vinyl pyrrolidone)polyethylene glycol, propylene glycol homopolymers, a polypropylene oxide/ethylene oxide co-polymer, polyoxyethylated polyols (e.g., glycerol) and polyvinyl alcohol. Also encompassed by the present invention are bifunctional crosslinking molecules which may be used to prepare covalently attached multimers.

In general, chemical derivatization may be performed under any suitable condition used to react a protein with an activated polymer molecule. Methods for preparing chemical derivatives of polypeptides will generally comprise the steps of (a) reacting the polypeptide with the activated polymer molecule (such as a reactive ester or aldehyde derivative of the polymer molecule) under conditions whereby the binding construct becomes attached to one or more polymer molecules, and (b) obtaining the reaction product(s). The optimal reaction conditions will be determined based on known parameters and the desired result. For example, the larger the ratio of polymer molecules:protein, the greater the amount of attached polymer molecule. In one embodiment, the binding construct polypeptide derivative may have a single polymer molecule moiety at the amino terminus. (See, e.g., U.S. Pat. No. 5,234,784).

A particularly preferred water-soluble polymer for use herein is polyethylene glycol (PEG). As used herein, polyethylene glycol is meant to encompass any of the forms of PEG that can be used to derivatize other proteins, such as mono-(C1-C10) alkoxy- or aryloxy-polyethylene glycol. PEG is a linear or branched neutral polyether, available in a broad range of molecular weights, and is soluble in water and most organic solvents. PEG is effective at excluding other polymers or peptides when present in water, primarily through its high dynamic chain mobility and hydrophibic nature, thus creating a water shell or hydration sphere when attached to other proteins or polymer surfaces. PEG is nontoxic, non-immunogenic, and approved by the Food and Drug Administration for internal consumption.

Proteins or enzymes when conjugated to PEG have demonstrated bioactivity, non-antigenic properties, and decreased clearance rates when administered in animals. F. M. Veronese et al., Preparation and Properties of Monomethoxypoly(ethylene glycol)-modified Enzymes for Therapeutic Applications, in J. M. Harris ed., *Poly(Ethylene Glycol) Chemistry—Biotechnical and Biomedical Applications,* 127-36, 1992, incorporated herein by reference. These phenomena are due to the exclusion properties of PEG in preventing recognition by the immune system. In addition, PEG has been widely used in surface modification procedures to decrease protein adsorption and improve blood compatibility. S. W. Kim et al., *Ann. N.Y. Acad. Sci.* 516: 116-30 1987; Jacobs et al., *Artif. Organs* 12: 500-501, 1988; Park et al., *J. Poly. Sci, Part A* 29:1725-31, 1991, incorporated herein by reference. Hydrophobic polymer surfaces, such as polyurethanes and polystyrene can be modified by the grafting of PEG (MW 3,400) and employed as non-thrombogenic surfaces. Surface properties (contact angle) can be more consistent with hydrophilic surfaces, due to the hydrating effect of PEG. More importantly, protein (albumin and other plasma proteins) adsorption can be greatly reduced, resulting from the high chain motility, hydration sphere, and protein exclusion properties of PEG.

PEG (MW 3,400) was determined as an optimal size in surface immobilization studies, Park et al., *J. Biomed. Mat. Res.* 26:739-45, 1992, while PEG (MW 5,000) was most beneficial in decreasing protein antigenicity. (F. M. Veronese et al., In J. M. Harris, et al., *Poly(Ethylene Glycol) Chemistry—Biotechnical and Biomedical Applications,* 127-36.)

Methods for preparing pegylated binding construct polypeptides will generally comprise the steps of (a) reacting the polypeptide with polyethylene glycol (such as a reactive ester or aldehyde derivative of PEG) under conditions whereby the binding construct polypeptide becomes attached to one or more PEG groups, and (b) obtaining the reaction product(s). In general, the optimal reaction conditions for the acylation reactions will be determined based on known parameters and the desired result. For example, the larger the ratio of PEG:protein, the greater the percentage of poly-pegylated product. In some embodiments, the binding construct will have a single PEG moiety at the N-terminus. See U.S. Pat. No. 8,234,784, herein incorporated by reference.

Derivatized binding constructs disclosed herein may have additional activities, enhanced or reduced biological activity, or other characteristics, such as increased or decreased half-life, as compared to the non-derivatized molecules.

II. Polynucleotides Encoding Binding Constructs and Expression Systems

The invention comprises not only the binding constructs, binding units, and polypeptides described herein, and uses thereof, but also nucleic acids encoding such molecules, vectors comprising such molecules, and host cells comprising such vectors, and uses thereof. Methods employing any of the constructs, units, polypeptides, nucleic acids, vectors, and hosts cells for the therapeutic uses described herein are all considered aspects of the invention.

A. Nucleic Acids of the Invention

This invention also includes nucleic acid molecules whose sequence encode the polypeptides, binding units, and binding constructs, for use in compositions and methods of the invention. Nucleic acid molecules include those molecules which comprise nucleotide sequences which hybridize under moderately or highly stringent conditions as defined herein with the fully complementary sequence of the nucleic acid molecule of receptor tyrosine kinases described in Table 1A, or of a molecule encoding a polypeptide, which polypeptide comprises the receptor tyrosine kinase amino acids sequences described in Table 1A, or of a nucleic acid fragment as defined herein, or of a nucleic acid fragment encoding a polypeptide as defined herein.

Hybridization probes may be prepared using the sequences provided herein to screen cDNA, genomic or synthetic DNA libraries for related sequences. Regions of the DNA and/or amino acid sequence that exhibit significant identity to known sequences are readily determined using sequence alignment algorithms as described herein, and those regions may be used to design probes for screening.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook, Fritsch & Maniatis, Molecular Cloning: A Laboratory Manual, 2nd Ed., Cold Spring Harbor Laboratory, (Cold Spring Harbor, N.Y. 1989); and Anderson et al., Nucleic Acid Hybridization: a Practical approach, Ch. 4, IRL Press Limited (Oxford, England). Limited, Oxford, England. Other agents may be included in the hybridization and washing buffers for the purpose of reducing non-specific and/or background hybridization. Examples are 0.1% bovine serum albumin, 0.1% polyvinylpyrrolidone, 0.1% sodium pyrophosphate, 0.1% sodium dodecylsulfate (NaDodSO$_4$ or SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, 6.8-7.4; however, at typical ionic strength conditions, the rate of hybridization is nearly independent of pH. See Anderson et al., Nucleic Acid Hybridization: a Practical Approach, Ch. 4, IRL Press Limited (Oxford, England).

Factors affecting the stability of a DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$T_m(°C.)=81.5+16.6(\log [Na^+])+0.41(\% G+C)-600/N-0.72(\% \text{ formamide})$$

where N is the length of the duplex formed, [Na$^+$] is the molar concentration of the sodium ion in the hybridization or washing solution, % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.015 M sodium chloride, 0.0015 M sodium citrate at 50-65° C. or 0.015 M sodium chloride, 0.0015 M sodium citrate, and 20% formamide at 37-50° C. By way of example, a "moderately stringent" condition of 50° C. in 0.015 M sodium ion will allow about a 21% mismatch.

It will be appreciated by those skilled in the art that there is no absolute distinction between "highly" and "moderately" stringent conditions. For example, at 0.015M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl* for oligonucleotide probes up to about 20 nt is given by:

$$Tm=2°\text{ C. per }A-T\text{ base pair}+4°\text{ C. per }G-C\text{ base pair}$$

*The sodium ion concentration in 6× salt sodium citrate (SSC) is 1 M. See Suggs et al., Developmental Biology Using Purified Genes, p. 683, Brown and Fox (eds.) (1981).

High stringency washing conditions for oligonucleotides are usually at a temperature of 0-5° C. below the Tm of the oligonucleotide in 6×SSC, 0.1% SDS.

Differences in the nucleic acid sequence may result in conservative and/or non-conservative modifications of the amino acid sequence relative to the amino acid sequence. The invention is also directed to an isolated and/or purified DNA that corresponds to, or that hybridizes under stringent conditions with, any one of the foregoing DNA sequences.

B. Preparation of DNA Encoding Ligand, Receptor, and Binding Construct Polypeptides A nucleic acid molecule encoding all or part of a polypeptide of the invention such as a binding construct or binding unit of the invention can be made in a variety of ways, including, without limitation, chemical synthesis, cDNA or genomic library screening, expression library screening, and/or PCR amplification of cDNA or genomic DNA. These methods and others useful for isolating such DNA are set forth, for example, by Sambrook, et al., "Molecular Cloning: A Laboratory Manual," Cold Spring Harbor Laboratory Press, Cold Spring Harbor, N.Y. (1989), by Ausubel, et al., eds., "Current Protocols In Molecular Biology," Current Protocols Press (1994), and by Berger and Kimmel, "Methods In Enzymology: Guide To Molecular Cloning Techniques," vol. 152, Academic Press, Inc., San Diego, Calif. (1987). Preferred nucleic acid sequences are mammalian sequences, such as human, rat, and mouse.

Chemical synthesis of nucleic acid molecules can be accomplished using methods well known in the art, such as those set forth by Engels, et al., Angew. Chem. Intl. Ed., 28:716-734 (1989). These methods include, inter alia, the phosphotriester, phosphoramidite and H-phosphonate methods of nucleic acid synthesis. Nucleic acids larger than about 100 nucleotides in length can be synthesized as several fragments, each fragment being up to about 100 nucleotides in length. The fragments can then be ligated together, as described below, to form the full length nucleic acid of interest. A preferred method is polymer-supported synthesis using standard phosphoramidite chemistry.

C. Preparation of a Vector for Expression

The term "vector" refers to a nucleic acid molecule amplification, replication, and/or expression vehicle, often derived from or in the form of a plasmid or viral DNA or RNA system, where the plasmid or viral DNA or RNA is functional in a selected host cell, such as bacterial, yeast, plant, invertebrate, and/or mammalian host cells. The vector may remain independent of host cell genomic DNA or may integrate in whole or in part with the genomic DNA. The vector will contain all necessary elements so as to be functional in any host cell it is compatible with. Such elements are set forth below.

Nucleic acid encoding a polypeptide or fragment thereof has been isolated, it is preferably inserted into an amplification and/or expression vector in order to increase the copy number of the gene and/or to express the encoded polypeptide in a suitable host cell and/or to transform cells in a target organism (to express the polypeptide in vivo). Numerous commercially available vectors are suitable, though "custom made" vectors may be used as well. The vector is selected to be functional in a particular host cell or host tissue (i.e., for replication and/or expression). The polypeptide or fragment thereof may be amplified/expressed in prokaryotic and/or eukaryotic host cells, e.g., yeast, insect (baculovirus systems), plant, and mammalian cells. Selection of the host cell will depend at least in part on whether the polypeptide or fragment thereof is to be glycosylated. If so, yeast, insect, or mammalian host cells are preferable; yeast and mammalian cells will glycosylate the polypeptide if a glycosylation site is present on the amino acid sequence.

Typically, the vectors used in any of the host cells will contain 5' flanking sequence and other regulatory elements such as an enhancer(s), a promoter, an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Optionally, the vector may contain a "tag" sequence, i.e., an oligonucleotide sequence located at the 5' or 3' end of the coding sequence that encodes polyHis (such as hexaHis) or another small immunogenic sequence. This tag will be expressed along with the protein, and can serve as an affinity tag for purification of the polypeptide from the host cell. Optionally, the tag can subsequently be removed from the purified polypeptide by various means such as using a selected peptidase.

The vector/expression construct may optionally contain elements such as a 5' flanking sequence, an origin of replication, a transcription termination sequence, a selectable marker sequence, a ribosome binding site, a signal sequence, and one or more intron sequences. The 5' flanking sequence may be homologous (i.e., from the same species and/or strain as the host cell), heterologous (i.e., from a species other than the host cell species or strain), hybrid (i.e., a combination of 5' flanking sequences from more than one source), synthetic, or it may be the native polypeptide 5' flanking sequence. As such, the source of the 5' flanking sequence may be any unicellular prokaryotic or eukaryotic organism, any vertebrate or invertebrate organism, or any plant, provided that the 5' flanking sequence is functional in, and can be activated by, the host cell machinery.

A transcription termination element is typically located 3' to the end of the polypeptide coding sequence and serves to terminate transcription of the polypeptide. Usually, the transcription termination element in prokaryotic cells is a G-C rich fragment followed by a poly T sequence. Such elements can be cloned from a library, purchased commercially as part of a vector, and readily synthesized.

Selectable marker genes encode proteins necessary for the survival and growth of a host cell in a selective culture medium. Typical selectable marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media.

A ribosome binding element, commonly called the Shine-Dalgarno sequence (prokaryotes) or the Kozak sequence (eukaryotes), is necessary for translation initiation of mRNA. The element is typically located 3' to the promoter and 5' to the coding sequence of the polypeptide to be synthesized. The Shine-Dalgarno sequence is varied but is typically a polypurine (i.e., having a high A-G content). Many Shine-Dalgarno sequences have been identified, each of which can be readily synthesized using methods set forth above.

All of the elements set forth above, as well as others useful in this invention, are well known to the skilled artisan and are described, for example, in Sambrook, et al., "Molecular Cloning: A Laboratory Manual," Cold Spring Harbor Laboratory Press, Cold Spring Harbor, N.Y. (1989) and Berger, et al., eds., "Guide To Molecular Cloning Techniques," Academic Press, Inc., San Diego, Calif. (1987).

For those embodiments of the invention where the recombinant polypeptide is to be secreted, a signal sequence is preferably included to direct secretion from the cell where it is synthesized. Typically, the polynucleotide encoding the signal sequence is positioned at the 5' end of the coding region. Many signal sequences have been identified, and any of them that are functional in a target cell or species may be used in conjunction with the transgene.

In many cases, gene transcription is increased by the presence of one or more introns on the vector. The intron may be naturally-occurring, especially where the transgene is a full length or a fragment of a genomic DNA sequence. The intron may be homologous or heterologous to the transgene and/or to the transgenic mammal into which the gene will be inserted. The position of the intron with respect to the promoter and the transgene is important, as the intron must be transcribed to be effective. A preferred position for an intron is 3' to the transcription start site, and 5' to the polyA transcription termination sequence. For cDNA transgenes, an intron is placed on one side or the other (i.e., 5' or 3') of the transgene coding sequence. Any intron from any source, including any viral, prokaryotic and eukaryotic (plant or animal) organisms, may be used to express the polypeptide, provided that it is compatible with the host cell(s) into which it is inserted. Also included herein are synthetic introns. Optionally, more than one intron may be used in the vector.

Preferred vectors for recombinant expression are those that are compatible with bacterial, insect, and mammalian host cells. Such vectors include, inter alia, pCRII (Invitrogen Company, San Diego, Calif.), pBSII (Stratagene Company, La Jolla, Calif.), and pETL (BlueBacII; Invitrogen).

After the vector has been constructed and a nucleic acid has been inserted into the proper site of the vector, the completed vector may be inserted into a suitable host cell for amplification and/or polypeptide expression. Commonly used include: Prokaryotic cells such as gram negative or gram positive bacteria, i.e., any strain of *E. coli, Bacillus, Streptomyces, Saccharomyces, Salmonella*, and the like; eukaryotic cells such as CHO (Chinese hamster ovary) cells; human kidney 293 cells; COS-7 cells; insect cells such as Sf4, Sf5, Sf9, and Sf21 and High 5 (all from the Invitrogen Company, San Diego, Calif.); plant cells and various yeast cells such as *Saccharomyces* and *Pichia*. Any transformable or transfectable cell or cell line derived from any organism such as bacteria, yeast, fungi, monocot and dicot plants, plant cells, and animals are suitable.

Insertion (also referred to as "transformation" or "transfection") of the vector into the selected host cell may be accomplished using such methods as calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook, et al., supra.

The host cells containing the vector (i.e., transformed or transfected) may be cultured using standard media well known to the skilled artisan. The media will usually contain all nutrients necessary for the growth and survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of polypeptide produced in the host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or binding assays.

D. Purification of Polypeptides

If the polypeptide has been designed to be secreted from the host cells, the majority of polypeptide will likely be found in the cell culture medium. If, however, the polypeptide is not secreted from the host cells, it will be present in the cytoplasm (for eukaryotic, gram positive bacteria, and insect host cells) or in the periplasm (for gram negative bacteria host cells).

For intracellular polypeptides, the host cells are first disrupted mechanically or osmotically to release the cytoplasmic contents into a buffered solution. The polypeptide is then isolated from this solution.

Purification of the polypeptide from solution can be accomplished using a variety of techniques. If the polypeptide has been synthesized such that it contains a tag such as hexahistidine or other small peptide at either its carboxyl or amino terminus, it may essentially be purified in a one-step process by passing the solution through an affinity column where the column matrix has a high affinity for the tag or for the polypeptide directly (i.e., a monoclonal antibody specifically recognizing the polypeptide). For example, polyhistidine binds with great affinity and specificity to nickel, thus an affinity column of nickel (such as the Qiagen nickel columns) can be used for purification of the His-tagged polypeptide. (See, for example, Ausubel, et al., eds., "Current Protocols In Molecular Biology," Section 10.11.8, John Wiley & Sons, New York (1993)).

The strong affinity a ligand for its receptor permits affinity purification of binding constructs, and binding constructs using an affinity matrix comprising a complementary binding partner. Affinity chromatography may be employed, e.g., using either natural binding partners (e.g., a ligand when purifying a binding construct with affinity for the same) or antibodies generated using standard procedures (e.g., immunizing a mouse, rabbit or other animal with an appropriate polypeptide). The peptides of the present invention may be used to generate such antibodies. Known antibodies or antibodies to known growth factor receptors may be employed when they share an epitope with a targeted binding construct.

In addition, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity. Preferred methods for purification include polyhistidine tagging and ion exchange chromatography in combination with preparative isoelectric focusing.

Polypeptide found in the periplasmic space of the bacteria or the cytoplasm of eukaryotic cells, the contents of the periplasm or cytoplasm, including inclusion bodies (bacteria) if the processed polypeptide has formed such complexes, can be extracted from the host cell using any standard technique known to the skilled artisan. For example, the host cells can be lysed to release the contents of the periplasm by French press, homogenization, and/or sonication. The homogenate can then be centrifuged.

If the polypeptide has formed inclusion bodies in the periplasm, the inclusion bodies can often bind to the inner and/or outer cellular membranes and thus will be found primarily in the pellet material after centrifugation. The pellet material can then be treated with a chaotropic agent such as guanidine or urea to release, break apart, and solubilize the inclusion bodies. The solubilized polypeptide can then be analyzed using gel electrophoresis, immunoprecipitation or the like. If it is desired to isolate the polypeptide, isolation may be accomplished using standard methods such as those set forth below and in [Marston, et al., *Meth. Enz.*, 182:264-275 (1990).]

III. Anti-Ligand and Anti-Receptor Therapeutic Compounds

Anti-ligand or anti-receptor therapies as discussed below include, but are not limited to antibody, aptamer, antisense and interference RNA techniques and therapies.

Exemplary anti-VEGFR-3 antibodies and their production are described in U.S. Pat. Nos. 6,107,046 and 6,824,777; U.S. Patent Publication Nos. 2006/0269548 and 2006/0177901; and International Patent Application No. PCT/FI95/00337 (WO 95/33772), all incorporated herein by reference in their entireties.

Exemplary VEGF-D antibodies are described, for example, in International Patent Application Nos. PCT/US97/14696 and PCT/US99/31332; International Publication No.: WO 0037025; U.S. Pat. Nos. 6,383,484, 6,730,489 and 7,097,986; and U.S. Patent Publication Nos. 2006/0177428, 2006/0024302, 2002/0123481, 2005/0282228, 2004/0141917 and 2003/0125537, all incorporated herein by reference.

Exemplary VEGF-C antibodies are described, for example, in International Patent Application Nos. PCT/FI1996/000427 (WO/1997/005250) and PCT/US1998/001973 (WO/1998/033917); and U.S. Patent Publication Nos. 2004/0147726, 2005/0232921, 2005/0192429, 2005/0059117, 2005/0282228, 2003/0176674, and 2006/

0121025, 2006/0030000, and U.S. Pat. No. 6,403,088 all incorporated herein by reference.

U.S. Pat. No. 7,045,133, incorporated herein by reference, describes peptidomimetic inhibitors of VEGF-D/VEGF-C/VEGFR-3.

Exemplary anti-PDGFR antibodies and other inhibitor compounds are described, for example, in U.S. Pat. Nos. 5,418,135; 5,468,468; 5,620,687; 5,932,580; 6,358,954; 6,642,022; and 7,105,305, all incorporated herein by reference.

Exemplary anti-VEGFR antibodies and other inhibitor compounds are described, for example, in U.S. Pat. Nos. 7,056,509; 7,052,693; 6,986,890; 6,897,294; 6,887,468; 6,878,720; 6,344,339; 5,955,311; 5,874,542; and 5,840,301, all incorporated herein by reference.

The following description makes specific reference to the production, testing, and use of particular anti-VEGFR-2 antibodies, as representative of the many receptor and growth factor and growth factor antigens described herein. The methods described may also be readily adapted for the production of other antibodies for use according to the present invention, e.g., anti-growth factor ligand antibodies and anti-receptor antibodies as binding units of the binding constructs. Such antibody-type binding units may themselves the used for practicing methods of the invention, or form one binding unit of a more complex, multivalent binding construct. In some embodiments a binding construct has at least one binding unit that comprising a receptor fragment and at least one binding unit that comprises an antigen binding fragment. Antibodies directed against growth factors and receptors may also be used in combination with the binding constructs of the invention. Exemplary antibodies may be found in U.S. patent application Ser. No. 11/075,400, published as U.S. Patent Publication No. 2005/0282233, and related, co-filed International Patent Application No. PCT/US2005/007742, published as WO 2005/087812; and U.S. Patent Publication Nos. 2006/0177428; 2006/0024302; 2004/0175730; and 2004/0141917; all applications are incorporated by reference in their entireties.

A. Therapeutic Anti-VEGFR-2 Selective VEGF-A Antagonist Antibodies

Polyclonal or monoclonal therapeutic anti-VEGFR-2 antibodies useful in practicing this invention may be prepared in laboratory animals or by recombinant DNA techniques using the following methods. Polyclonal antibodies to the VEGFR-2 molecule or a fragment thereof containing the target amino acid sequence generally are raised in animals by multiple subcutaneous (sc) or intraperitoneal (ip) injections of the VEGFR-2 molecule in combination with an adjuvant such as Freund's adjuvant (complete or incomplete). To enhance immunogenicity, it may be useful to first conjugate the VEGFR-2 molecule or a fragment containing the target amino acid sequence of a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl, or $R^1N=C=NR$, where R and $R^1$ are different alkyl groups. Alternatively, VEGF-2-immunogenic conjugates can be produced recombinantly as fusion proteins.

Animals are immunized against the immunogenic VEGFR-2 conjugates or derivatives (such as a fragment containing the target amino acid sequence) by combining about 1 mg or about 1 microgram of conjugate (for rabbits or mice, respectively) with about 3 volumes of Freund's complete adjuvant and injecting the solution intradermally at multiple sites. Approximately 7 to 14 days later, animals are bled and the serum is assayed for anti-VEGFR-2 titer. Animals are boosted with antigen repeatedly until the titer plateaus. Preferably, the animal is boosted with the same VEGFR-2 molecule or fragment thereof as was used for the initial immunization, but conjugated to a different protein and/or through a different cross-linking agent. In addition, aggregating agents such as alum are used in the injections to enhance the immune response.

Monoclonal antibodies may be prepared by recovering spleen cells from immunized animals and immortalizing the cells in conventional fashion, e.g. by fusion with myeloma cells. The clones are then screened for those expressing the desired antibody. The monoclonal antibody preferably does not cross-react with other VEGFR family members.

Preparation of antibodies using recombinant DNA methods such as the phagemid display method, may be accomplished using commercially available kits, as for example, the Recombinant Phagemid Antibody System available from Pharmacia (Uppsala, Sweden), or the SurfZAP™ phage display system (Stratagene Inc., La Jolla, Calif.).

One may increase the population of anti-VEGFR-2 antibodies that selectively block VEGF-A binding by using a Ig-domain 3 or other fragment as the immunogen, but that is not necessary. After antibodies are generated, they may be tested to ascertain their specific affinities. Competiton studies may be performed that show that the antibody competes for binding to VEGFR-2 with VEGF-A, but not with VEGF-C.

One method comprises incubating VEGFR-2 expressing cells with either labeled-VEGF-A alone, the antibody being tested alone, or with both the VEGF-A and the antibody. A label on the antibody may be employed in addition to that on VEGF-A or instead of that label. The antibody may also be detected using a labeled secondary antibody. The first two groups acting as controls allow one to confirm that both the antibody and the VEGF-A ligand (or optionally VEGF-E) are able to bind to the receptor in the absence of the other. Those cell samples treated with both VEGF-A (or VEGF-E) and an antibody, that reveal binding of the antibody, but not VEGF-A (or VEGF-E) indicate that the antibody should be further tested. As described below, stoichiometric analysis can be used to ascertain that the ligand and antibody are competing for the same molecule.

This further testing may comprise binding studies that reveal that both VEGF-C (or VEGF-D) and the antibody are able to bind the receptor simultaneously. This testing also is designed to determine whether VEGF-C and the antibody are simultaneously binding to a single VEGFR-2 molecule as opposed to binding of VEGF-C and the antibody binding to different VEGFR-2 molecules. Comparative quantitative binding studies may accordingly be used. The VEGFR-2 cells are counted in each sample. VEGFR-2 samples, having been counted, are incubated with either labeled VEGF-C alone or labeled (or unlabeled using a secondary antibody for detection) antibody alone. The degree of binding is measured, quantitated, using suitable imaging procedures, e.g., if radiolabel is employed using a phosphoimager. The average number of VEGFR-2 receptors per cell are calculated by dividing the amount of bound molecules by the total number of cells. Whether the receptors are saturated with molecules may be achieved by repeating the assay with increasing amounts of the labeled molecule(s). The binding assay is repeated again with both ligand and antibody. If the quantification reveals that the number of antibodies and ligands bound is greater than the total number of receptors, then the antibody has the desired characteristics.

The described protocols may also be modified and used to produce antibodies against any of the other antigens identified herein as targets for anti-rejection therapy, including but not limited to VEGFR-3, VEGF-C, VEGF-D, the other VEGF growth factors, the PDGF receptors, and the PDGF growth factors.

Preferably, antibodies for administration to humans, although prepared in a laboratory animal such as a mouse, will be "humanized", or chimeric, i.e. made to be compatible with the human immune system such that a human patient will not develop an immune response to the antibody. Even more preferably, human antibodies which can now be prepared using methods such as those described for example, in Lonberg, et al., *Nature Genetics,* 7:13-21 (1994) are preferred for therapeutic administration to patients. Fully human antibodies are highly preferred.

1. Humanization of Anti-VEGFR-2 Monoclonal Antibodies

Selective binding agents, including monoclonal antibodies, which selectively block VEGF-A without blocking VEGF-C (or VEGF-D) binding may be applied therapeutically. Following are protocols to improve the utility of anti-VEGFR-2 monoclonal antibodies as therapeutics in humans, by "humanizing" the monoclonal antibodies to improve their serum half-life and render them less immunogenic in human hosts (i.e., to prevent human antibody response to non-human anti-VEGFR-2 antibodies). The description also applies to antibodies directed to the other antigens described herein.

The principles of humanization have been described in the literature and are facilitated by the modular arrangement of antibody proteins. To minimize the possibility of binding complement, a humanized antibody of the IgG4 isotype is preferred.

For example, a level of humanization is achieved by generating chimeric antibodies comprising the variable domains of non-human antibody proteins of interest, such as the anti-VEGFR-2 monoclonal antibodies described herein, with the constant domains of human antibody molecules. (See, e.g., Morrison and Oi, *Adv. Immunol.,* 44:65-92 (1989).) The variable domains of VEGFR-2 neutralizing anti-VEGFR-2 antibodies are cloned from the genomic DNA of a B-cell hybridoma or from cDNA generated from mRNA isolated from the hybridoma of interest. The V region gene fragments are linked to exons encoding human antibody constant domains, and the resultant construct is expressed in suitable mammalian host cells (e.g., myeloma or CHO cells).

To achieve an even greater levels of humanization, only those portions of the variable region gene fragments that encode antigen-binding complementarity determining regions ("CDR") of the non-human monoclonal antibody genes are cloned into human antibody sequences. [See, e.g., Jones et al., *Nature,* 321:522-525 (1986); Riechmann et al., *Nature,* 332:323-327 (1988); Verhoeyen et al., *Science,* 239:1534-36 (1988); and Tempest et al., *Bio/Technology,* 9:266-71 (1991).] If necessary, the B-sheet framework of the human antibody surrounding the CDR3 regions also is modified to more closely mirror the three dimensional structure of the antigen-binding domain of the original monoclonal antibody. [(See Kettleborough et al., *Protein Engin.,* 4:773-783 (1991); and Foote et al., *J. Mol. Biol.,* 224:487-499 (1992).)]

In an alternative approach, the surface of a non-human monoclonal antibody of interest is humanized by altering selected surface residues of the non-human antibody, e.g., by site-directed mutagenesis, while retaining all of the interior and contacting residues of the non-human antibody. [See Padlan, *Molecular Immunol.,* 28(4/5):489-98 (1991).]

The foregoing approaches are employed using VEGFR-2-neutralizing anti-VEGFR-2 monoclonal antibodies and the hybridomas that produce them to generate humanized VEGFR-2-neutralizing antibodies useful as therapeutics to treat or palliate conditions wherein VEGFR-2 expression is detrimental and/or activation by VEGF-A. One therapeutic target is selective promotion of lymphangiogenesis while minimizing promotion of angiogenesis.

2. Human VEGFR-2-Neutralizing Antibodies from Phage Display

Human VEGFR-2-neutralizing antibodies are generated by phage display techniques such as those described in Aujame et al., *Human Antibodies,* 8(4):155-168 (1997); Hoogenboom, *TIBTECH,* 15:62-70 (1997); and Rader et al., *Curr. Opin. Biotechnol.,* 8:503-508 (1997), all of which are incorporated by reference. For example, antibody variable regions in the form of Fab fragments or linked single chain Fv fragments are fused to the amino terminus of filamentous phage minor coat protein pIII. Expression of the fusion protein and incorporation thereof into the mature phage coat results in phage particles that present an antibody on their surface and contain the genetic material encoding the antibody. A phage library comprising such constructs is expressed in bacteria, and the library is panned (screened) for VEGFR-2-specific phage-antibodies using labeled or immobilized VEGFR-2 as antigen-probe.

3. Human VEGFR-2-Neutralizing Antibodies from Transgenic Mice

Human VEGFR-2-neutralizing antibodies are generated in transgenic mice essentially as described in Bruggemann and Neuberger, *Immunol. Today,* 17(8):391-97 (1996) and Bruggemann and Taussig, *Curr. Opin. Biotechnol.,* 8:455-58 (1997). Transgenic mice carrying human V-gene segments in germline configuration and that express these transgenes in their lymphoid tissue are immunized with an VEGFR-2 composition using conventional immunization protocols. Hybridomas are generated using B cells from the immunized mice using conventional protocols and screened to identify hybridomas secreting anti-VEGFR-2 human antibodies (e.g., as described above).

4. Bispecific Antibodies

Bispecific antibodies that specifically bind to VEGFR-2 and that specifically bind to other antigens relevant to pathology and/or treatment are produced, isolated, and tested using standard procedures that have been described in the literature. See, e.g., Pluckthun & Pack, *Immunotechnology,* 3:83-105 (1997); Carter et al., *J. Hematotherapy,* 4: 463-470 (1995); Renner & Pfreundschuh, *Immunological Reviews,* 1995, No. 145, pp. 179-209; Pfreundschuh U.S. Pat. No. 5,643,759; Segal et al., *J. Hematotherapy,* 4: 377-382 (1995); Segal et al., *Immunobiology,* 185: 390-402 (1992); and Bolhuis et al., *Cancer Immunol. Immunother.,* 34: 1-8 (1991), all of which are incorporated herein by reference in their entireties. Bispecific antibodies that may be employed in combination with the binding constructs of the invention include those described in U.S. Patent Publication No. 2005/0282233, incorporated herein by reference.

For example, bispecific antibodies (bscAb) are produced by joining two single-chain Fv fragments via a glycine-serine linker using recombinant methods. The V light-chain ($V_L$) and V heavy-chain ($V_H$) domains of two antibodies of interest are isolated using standard PCR methods. The $V_L$ and $V_H$ cDNA's obtained from each hybridoma are then joined to form a single-chain fragment in a two-step fusion PCR. Bispecific fusion proteins are prepared in a similar manner. Bispecific single-chain antibodies and bispecific fusion proteins are antibody substances included within the scope of the present invention.

Antibody fragments that contain the antigen binding, or idiotype, of the molecule may be generated by known techniques. For example, such fragments include, but are not limited to, the F(ab')$_2$ fragment which may be produced by pepsin digestion of the antibody molecule; the Fab' fragments which may be generated by reducing the disulfide bridges of the F(ab')$_2$ fragment, and the two Fab' fragments which may be generated by treating the antibody molecule with papain and a reducing agent.

Chemically constructed bispecific antibodies may be prepared by chemically cross-linking heterologous Fab or F(ab')$_2$ fragments by means of chemicals such as heterobifunctional reagent succinimidyl-3-(2-pyridyldithiol)-propionate (SPDP, Pierce Chemicals, Rockford, Ill.). The Fab and F(ab')$_2$ fragments can be obtained from intact antibody by digesting it with papain or pepsin, respectively (Karpovsky et al., *J. Exp. Med.* 160:1686-701, 1984; Titus et al., *J. Immunol.*, 138:4018-22, 1987).

5. Humanization of Known Anti-VEGFR-2 Antibodies

Existing anti-VEGF-2 antibodies may also be employed in the various methods and compositions of the present invention, and, if not already humanized, may be humanized as discussed herein. Known anti-VEGFR-2 antibodies may be tested for the ability to selectively block VEGF-A binding using the methods discussed herein. Known anti-VEGFR-2 antibodies (anti-KDR antibodies) are taught for example in Lu et al., *J. Immunological Methods,* 230:159-71 (1999); Lu, et al., *J. Biol. Chem.,* 275(19): 14321-14330 (2000); and Lu, et al., *J. Biol. Chem.,* 278(44): 43496-43507 (2003).

6. Domain Antibodies

A domain antibody comprises a functional binding unit of an antibody, and can correspond to the variable regions of either the heavy ($V_H$) or light ($V_L$) chains of antibodies. A domain antibody can have a molecular weight of approximately 13 kDa, or approximately one-tenth of a full antibody. Domain antibodies may be derived from full antibodies such as those described herein.

B. Anti-Receptor and Anti-Ligand Aptamers

Recent advances in the field of combinatorial sciences have identified short polymer sequences with high affinity and specificity to a given target. For example, SELEX technology has been used to identify DNA and RNA aptamers with binding properties that rival mammalian antibodies, the field of immunology has generated and isolated antibodies or antibody fragments which bind to a myriad of compounds and phage display has been utilized to discover new peptide sequences with very favorable binding properties. Based on the success of these molecular evolution techniques, it is certain that molecules can be created which bind to any target molecule. A loop structure is often involved with providing the desired binding attributes as in the case of: aptamers which often utilize hairpin loops created from short regions without complimentary base pairing, naturally derived antibodies that utilize combinatorial arrangement of looped hyper-variable regions and new phage display libraries utilizing cyclic peptides that have shown improved results when compared to linear peptide phage display results. Thus, sufficient evidence has been generated to suggest that high affinity ligands can be created and identified by combinatorial molecular evolution techniques. For the present invention, molecular evolution techniques can be used to isolate binding constructs specific for ligands described herein. For more on aptamers, See generally, Gold, L., Singer, B., He, Y. Y., Brody. E., "Aptamers As Therapeutic And Diagnostic Agents," *J. Biotechnol.* 74:5-13 (2000). Relevant techniques for generating aptamers may be found in U.S. Pat. No. 6,699,843, which is incorporated by reference in its entirety.

In some embodiments, the aptamer may be generated by preparing a library of nucleic acids; contacting the library of nucleic acids with a growth factor, wherein nucleic acids having greater binding affinity for the growth factor (relative to other library nucleic acids) are selected and amplified to yield a mixture of nucleic acids enriched for nucleic acids with relatively higher affinity and specificity for binding to the growth factor. The processes may be repeated, and the selected nucleic acids mutated and rescreened, whereby a growth factor aptamer is be identified. Nucleic acids may be screened to select for molecules that bind to more than growth factor. Binding more than one growth factor can refer to binding more than one growth factor simultaneously or competitively. In some embodiments a binding construct will comprise at least one aptamer, wherein a first binding unit binds VEGF-A and a second binding unit binds VEGF-C. In some embodiments a binding construct will comprise at least one aptamer, wherein a first binding unit binds a VEGF growth factor subfamily member and a second binding unit binds a PDGF subfamily member.

C. Anti-Sense Molecules and Therapy

Another class of inhibitors that may be used in conjunction with the present invention is isolated antisense nucleic acid molecules that can hybridize to, or are complementary to, the nucleic acid molecule, nucleotide sequence, or fragments, analogs or derivatives thereof. Antisense modulation of VEGF-C is described in U.S. Patent Application Publication No. 2003/0232437, the disclosure of which is incorporated herein by reference in its entirety. Antisense modulation of VEGFR-2 is described in U.S. Pat. No. 6,734,017, the disclosure of which is incorporated herein by reference in its entirety.

Antisense and interfering RNA molecules that target any of the growth factors (e.g., VEGF-A, -B, -C, -D; PDGF-A, -B, -C, -D) and growth factor receptors (e.g., VEGFR-1, VEGFR-2, VEGFR-3, PDGFR-alpha, PDGFR-beta) described herein are specifically contemplated for use in methods and products of the invention.

An "antisense" nucleic acid comprises a nucleotide sequence that is complementary to a "sense" nucleic acid encoding a protein (e.g., complementary to the coding strand of a double-stranded cDNA molecule or complementary to an mRNA sequence). In specific embodiments, antisense nucleic acid molecules are provided that comprise a sequence complementary to at least about 10, 25, 50, 100, 250 or 500 nucleotides or an entire receptor or ligand coding strand, or to only a portion thereof. Nucleic acid molecules encoding fragments, homologs, derivatives and analogs of receptor or ligand or antisense nucleic acids complementary to a receptor or ligand nucleic acid sequence are additionally provided.

In one embodiment, an antisense nucleic acid molecule is antisense to a "coding region" of the coding strand of a nucleotide sequence encoding a receptor or ligand protein (or fragments or fragment combination thereof). The term "coding region" refers to the region of the nucleotide sequence comprising codons that are translated into amino acid residues. In another embodiment, the antisense nucleic acid molecule is antisense to a "conceding region" of the coding strand of a nucleotide sequence encoding the receptor or ligand protein. The term "conceding region" refers to 5' and 3' sequences that flank the coding region and that are not translated into amino acids (i.e., also referred to as 5' and 3' untranslated regions).

Given the coding strand sequences encoding the receptor or ligand protein disclosed herein, antisense nucleic acids of the invention can be designed according to the rules of Watson and Crick or Hoogsteen base pairing. The antisense nucleic acid molecule can be complementary to the entire coding region of a ligand or receptor mRNA, but more preferably is an oligonucleotide that is antisense to only a portion of the coding or noncoding region of receptor or ligand mRNA. For example, the antisense oligonucleotide can be complementary to the region surrounding the translation start site of receptor or ligand mRNA. An antisense oligonucleotide can be, for example, about 5, 10, 15, 20, 25, 30, 35, 40, 45, or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally-occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used).

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following section).

The antisense nucleic acid molecules of the invention are typically administered to a subject or generated in situ such that they hybridize with or bind to cellular mRNA and/or genomic DNA encoding a receptor or ligand to thereby inhibit expression of the protein (e.g., by inhibiting transcription and/or translation). The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface (e.g., by linking the antisense nucleic acid molecules to peptides or antibodies that bind to cell surface receptors or antigens). The antisense nucleic acid molecules can also be delivered to cells using the vectors described herein. To achieve sufficient nucleic acid molecules, vector constructs in which the antisense nucleic acid molecule is placed under the control of a strong pol II or pol III promoter are preferred.

In yet another embodiment, the antisense nucleic acid molecule of the invention is an alpha-anomeric nucleic acid molecule. An alpha-anomeric nucleic acid molecule forms specific double-stranded hybrids with complementary RNA in which, contrary to the usual alpha-units, the strands run parallel to each other. See, e.g., Gaultier, et al., *Nucl. Acids Res.*, 15:6625-6641 (1987). The antisense nucleic acid molecule can also comprise a 2'-o-methylribonucleotide (see, e.g., Inoue, et al. *Nucl. Acids Res.*, 15:6131-6148 (1987)) or a chimeric RNA-DNA analogue (see, e.g., Inoue, et al., *FEBS Lett.*, 215:327-330 (1987)).

Production and delivery of antisense molecules are facilitated by providing a vector comprising an anti-sense nucleotide sequence complementary to at least a part of the Receptor or ligand DNA sequence. According to a yet further aspect of the invention such a vector comprising an anti-sense sequence may be used to inhibit, or at least mitigate, Receptor or ligand expression.

Alternatively, nucleic acid sequences which inhibit or interfere with gene expression (e.g., siRNA, shRNA, ribozymes, aptamers) can be used to inhibit or interfere with the activity of RNA or DNA encoding a target protein.

D. Anti-Ligand or Anti-Receptor RNA Interference

Use of RNA Interference to inactivate or modulate receptor or ligand expression is also contemplated by this invention. RNA interference is described in U.S. Patent Appl. Pub. No. 2002/0162126, and Hannon, G., *J. Nature*, 11:418:244-51 (2002). "RNA interference," "post-transcriptional gene silencing," "quelling"—these terms have all been used to describe similar effects that result from the overexpression or misexpression of transgenes, or from the deliberate introduction of double-stranded RNA into cells (reviewed in Fire, A., *Trends Genet* 15:358-363 (1999); Sharp, P. A., *Genes Dev.*, 13:139-141 (1999); Hunter, C., *Curr. Biol.*, 9:R440-R442 (1999); Baulcombe, D. C., *Curr. Biol.* 9:R599-R601 (1999); Vaucheret, et al. *Plant J.* 16:651-659 (1998), all incorporated by reference. RNA interference, commonly referred to as RNAi, offers a way of specifically and potently inactivating a cloned gene. RNA interference of the VEGF family of proteins and receptors is described in U.S. Patent application Publication Nos.: 2006/0217332, 2006/0025370, 2005/0233998, 2005/0222066 and 2005/0171039, the disclosure of which are incorporated herein by reference in their entireties.

Interfering RNA directed to VEGF or VEGFR family members is described in U.S. Patent Publication No. 2006/0217332, incorporated herein by reference.

siRNA (short interfering RNA) technology relates to a process of sequence-specific post-transcriptional gene repression which can occur in eukaryotic cells. In general, this process involves degradation of an mRNA of a particular sequence induced by double-stranded RNA (dsRNA) that is homologous to that sequence. For example, the expression of a long dsRNA corresponding to the sequence of a particular single-stranded mRNA (ss mRNA) will labilize that message, thereby "interfering" with expression of the corresponding gene. Accordingly, any selected gene may be repressed by introducing a dsRNA which corresponds to all or a substantial part of the mRNA for that gene. It appears that when a long dsRNA is expressed, it is initially processed by a ribonuclease III into shorter dsRNA oligonucleotides of as few as 21 to 22 base pairs in length. Accordingly, siRNA may be effected by introduction or expression of relatively short homologous dsRNAs. Indeed the use of relatively short homologous dsRNAs may have certain advantages as discussed below.

Compared to siRNA, shRNA (short hairpin RNA) offers advantages in silencing longevity and delivery options. See, Hannon et al., Nature, 431:371-378, 2004, for review. Vectors that produce shRNAs, which are processed intracellularly into short duplex RNAs having siRNA-like properties have been reported (Brummelkamp et al., Science 296, 550-553, 2000; Paddison et al., Genes Dev. 16, 948-958 (2002). Such vectors provide a renewable source of a gene-silencing reagent that can mediate persistent gene silencing after stable integration of the vector into the host-cell genome. Furthermore, the core silencing 'hairpin' cassette can be readily inserted into retroviral, lentiviral or adenoviral vectors, facilitating delivery of shRNAs into a broad range of cell types (Brummelkamp et al., Cancer Cell 2:243-247, 2002; Dirac, et al., J. Biol. Chem. 278:11731-11734, 2003; Michiels et al., Nat. Biotechnol. 20:1154-1157, 2002; Stegmeie et al., Proc. Natl. Acad. Sci. USA 102: 13212-13217, 2005; Khvorova et al., Cell, 115:209-216 (2003) in any of the innumerable ways that have been devised for delivery of DNA constructs that allow ectopic mRNA expression. These include standard transient transfection, stable transfection and delivery using viruses ranging from retroviruses to adenoviruses. Expression can also be driven by either constitutive or inducible promoter systems (Paddison et al., Methods Mol. Biol. 265:85-100, 2004). Delivery of nucleic acid inhibitors by replicating or replication-deficient vectors is contemplated as an aspect of the invention.

Mammalian cells have at least two pathways that are affected by double-stranded RNA (dsRNA). In the siRNA (sequence-specific) pathway, the initiating dsRNA is first broken into short interfering (si) RNAs, as described above. The siRNAs have sense and antisense strands of about 21 nucleotides that form approximately 19 nucleotide si RNAs with overhangs of two nucleotides at each 3' end. Short interfering RNAs are thought to provide the sequence information that allows a specific messenger RNA to be targeted for degradation. In contrast, the nonspecific pathway is triggered by dsRNA of any sequence, as long as it is at least about 30 base pairs in length.

The nonspecific effects occur because dsRNA activates two enzymes: PKR, which in its active form phosphorylates the translation initiation factor eIF2 to shut down all protein synthesis, and 2',5' oligoadenylate synthetase (2',5'-AS), which synthesizes a molecule that activates RNase L, a nonspecific enzyme that targets all mRNAs. The nonspecific pathway may represent a host response to stress or viral infection, and, in general, the effects of the nonspecific pathway are preferably minimized. Significantly, longer dsRNAs appear to be required to induce the nonspecific pathway and, accordingly, dsRNAs shorter than about 30 bases pairs are preferred to effect gene repression by RNAi (see Hunter et al., 1975, J. Biol. Chem. 250:409-17; Manche et al., 1992, Mol. Cell. Biol. 12:5239-48; Minks et al., 1979, J. Biol. Chem. 254:10180-3; and Elbashir et al., 2001, Nature 411:494-8). siRNA has proven to be an effective means of decreasing gene expression in a variety of cell types including HeLa cells, NIH/3T3 cells, COS cells, 293 cells and BHK-21 cells, and typically decreases expression of a gene to lower levels than that achieved using antisense techniques and, indeed, frequently eliminates expression entirely (see Bass, 2001, Nature 411:428-9). In mammalian cells, siRNAs are effective at concentrations that are several orders of magnitude below the concentrations typically used in antisense experiments (Elbashir et al., 2001, Nature 411:494-8).

The double stranded oligonucleotides used to effect RNAi are preferably less than 30 base pairs in length and, more preferably, comprise about 25, 24, 23, 22, 21, 20, 19, 18 or 17 base pairs of ribonucleic acid. Optionally the dsRNA oligonucleotides may include 3' overhang ends. Exemplary 2-nucleotide 3' overhangs may be composed of ribonucleotide residues of any type and may even be composed of 2'-deoxythymidine resides, which lowers the cost of RNA synthesis and may enhance nuclease resistance of siRNAs in the cell culture medium and within transfected cells (see Elbashi et al., 2001, Nature 411:494-8).

Longer dsRNAs of 50, 75, 100 or even 500 base pairs or more may also be utilized in certain embodiments of the invention. Exemplary concentrations of dsRNAs for effecting RNAi are about 0.05 nM, 0.1 nM, 0.5 nM, 1.0 nM, 1.5 nM, 25 nM or 100 nM, although other concentrations may be utilized depending upon the nature of the cells treated, the gene target and other factors readily discernible to the skilled artisan.

Exemplary dsRNAs may be synthesized chemically or produced in vitro or in vivo using appropriate expression vectors. Exemplary synthetic RNAs include 21 nucleotide RNAs chemically synthesized using methods known in the art. Synthetic oligonucleotides are preferably deprotected and gel-purified using methods known in the art (see e.g. Elbashir et al., 2001, Genes Dev. 15:188-200). Longer RNAs may be transcribed from promoters, such as T7 RNA polymerase promoters, known in the art. A single RNA target, placed in both possible orientations downstream of an in vitro promoter, will transcribe both strands of the target to create a dsRNA oligonucleotide of the desired target sequence. Any of the above RNA species will be designed to include a portion of nucleic acid sequence represented in a target nucleic acid.

The specific sequence utilized in design of the oligonucleotides may be any contiguous sequence of nucleotides contained within the expressed gene message of the target. Programs and algorithms, known in the art, may be used to select appropriate target sequences. In addition, optimal sequences may be selected utilizing programs designed to predict the secondary structure of a specified single stranded nucleic acid sequence and allowing selection of those sequences likely to occur in exposed single stranded regions of a folded mRNA. Methods and compositions for designing appropriate oligonucleotides may be found, for example, in U.S. Pat. No. 6,251,588, the contents of which are incorporated herein by reference.

Although mRNAs are generally thought of as linear molecules containing the information for directing protein synthesis within the sequence of ribonucleotides, most mRNAs have been shown to contain a number of secondary and tertiary structures. Secondary structural elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex three dimensional structure. A number of researchers have measured the binding energies of a large number of RNA duplex structures and have derived a set of rules which can be used to predict the secondary structure of RNA (see e.g. Jaeger et al., 1989, Proc. Natl. Acad. Sci. USA 86:7706; and Turner et al., 1988, Annu. Rev. Biophys. Biophys. Chem. 17:167). The rules are useful in identification of RNA structural elements and, in particular, for identifying single stranded RNA regions which may represent preferred segments of the mRNA to target for siRNA, ribozyme or antisense technologies. Accordingly, preferred segments of the mRNA target can be identified for design of the siRNA mediating dsRNA oligonucleotides as well as for design of appropriate ribozyme and hammerheadribozyme compositions of the invention (see below).

The dsRNA oligonucleotides may be introduced into the cell by transfection with a heterologous target gene using carrier compositions such as liposomes, which are known in the art—e.g. Lipofectamine 2000 (Life Technologies) as described by the manufacturer for adherent cell lines. Transfection of dsRNA oligonucleotides for targeting endogenous genes may be carried out using Oligofectamine (Life Technologies). Transfection efficiency may be checked using fluorescence microscopy for mammalian cell lines after co-transfection of hGFP-encoding pAD3 (Kehlenback et al., 1998, J. Cell Biol. 141:863-74). The effectiveness of the siRNA may be assessed by any of a number of assays following introduction of the dsRNAs. These include Western blot analysis using antibodies which recognize the target gene product following sufficient time for turnover of the endogenous pool after new protein synthesis is repressed, reverse transcriptase polymerase chain reaction and Northern blot analysis to determine the level of existing target mRNA.

Further compositions, methods and applications of siRNA technology are provided in U.S. Pat. Nos. 6,278,039, 5,723, 750 and 5,244,805, which are incorporated herein by reference.

E. Small Molecule Inhibitors

Any chemical substance that can be safely administered as a therapeutic and that can be used to modulate biochemical pathway targets identified herein, such as VEGF-mediated stimulation of VEGF receptors, may be used to practice the invention. Small molecules that inhibit the interaction between VEGF-C and/or VEGFR-3 with VEGFR-3 are specifically contemplated. VEGF-C/VEGF-D inhibitors are disclosed in U.S. Pat. No. 7,045,133, incorporated herein by reference.

The VEGF receptors are receptor tyrosine kinases and intracellular signaling is initiated through receptor phosphorylation. Accordingly, one preferred class of molecules for practice of the invention is tyrosine kinase inhibitors, including those described in and Morin, Oncogene, 19(56):6574-83, 2000, incorporated herein by reference. VEGFR-3 inhibitors are disclosed in U.S. Patent Publication No. 2002-0164667, incorporated herein by reference.

IV. Therapeutic Formulations and Administration

A. Therapeutic Formulations

Binding constructs, or polynucleotides encoding the same, can be used directly to practice materials and methods of the invention, but in preferred embodiments, the compounds are formulated with pharmaceutically acceptable diluents, adjuvants, excipients, or carriers. The phrase "pharmaceutically or pharmacologically acceptable" refers to molecular entities and compositions that do not produce adverse, allergic, or other untoward reactions when administered to an animal or a human, e.g., orally, topically, transdermally, parenterally, by inhalation spray, vaginally, rectally, or by intracranial injection. (The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and/or surgical implantation at a particular site is contemplated as well.) Generally, this will also entail preparing compositions that are essentially free of pyrogens, as well as other impurities that could be harmful to humans or animals. The term "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art.

Therapeutic formulations of the compositions useful for practicing the invention such as polypeptides, polynucleotides, or antibodies may be prepared for storage by mixing the selected composition having the desired degree of purity with optional physiologically pharmaceutically-acceptable carriers, excipients, or stabilizers (*Remington's Pharmaceutical Sciences,* 18th edition, A. R. Gennaro, ed., Mack Publishing Company (1990)) in the form of a lyophilized cake or an aqueous solution. Pharmaceutical compositions may be produced by admixing with one or more suitable carriers or adjuvants such as water, mineral oil, polyethylene glycol, starch, talcum, lactose, thickeners, stabilizers, suspending agents, etc. Such compositions may be in the form of solutions, suspensions, tablets, capsules, creams, salves, ointments, or other conventional forms.

Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The composition to be used for in vivo administration should be sterile. This is readily accomplished by filtration through sterile filtration membranes, prior to or following lyophilization and reconstitution. Therapeutic compositions generally are placed into a container having a sterile access port, for example, an intravenous solution bag or vial having a stopper pierceable by a hypodermic injection needle. The route of administration of the composition is in accord with known methods, e.g. oral, injection or infusion by intravenous, intraperitoneal, intracerebral, intramuscular, intraocular, intraarterial, or intralesional routes, or by sustained release systems or implantation device. Where desired, the compositions may be administered continuously by infusion, bolus injection or by implantation device. The composition for parenteral administration ordinarily will be stored in lyophilized form or in solution.

The pharmaceutical forms suitable for injectable use include sterile aqueous solutions or dispersions and sterile powders for the extemporaneous preparation of sterile injectable solutions or dispersions. In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman, et al., *Biopolymers,* 22: 547-556 (1983)), poly (2-hydroxyethyl-methacrylate) (Langer, et al., *J. Biomed. Mater. Res.,* 15:167-277 (1981) and Langer, *Chem. Tech.,* 12:98-105 (1982)), ethylene vinyl acetate (Langer, et al., supra) or poly-D(−)-3-hydroxybutyric acid (EP 133,988). Sustained-release compositions also may include liposomes, which can be prepared by any of several methods known in the art (e.g., DE 3,218,121; Epstein, et al., *Proc. Natl. Acad. Sci. USA,* 82:3688-3692 (1985); Hwang, et al., *Proc. Natl. Acad. Sci. USA,* 77:4030-4034 (1980); EP 52,322; EP 36,676; EP 88,046; EP 143,949).

An effective amount of the compositions to be employed therapeutically will depend, for example, upon the therapeutic objectives, the route of administration, and the condition of the patient. A therapist can titer the dosage and modify the route of administration to obtain the optimal therapeutic effect. A typical daily dosage may range from about 1 µg/kg to up to 100 mg/kg or more, depending on the factors mentioned above. Typically, a clinician will administer the composition until a dosage is reached that achieves the desired effect. The progress of this therapy is easily monitored by conventional assays designed to evaluate the particular disease state being treated.

B. Kits and Unit Doses

In related variations of the preceding embodiments, a binding construct may be packaged or formulated together with another binding construct or other therapeutic (e.g., an immunosuppressive agent), e.g., in a kit or package or unit dose, to permit co-administration, but these two components are not in admixture. In some embodiments, the two components to the kit/unit dose are packaged with instructions for administering the two compounds to a human subject for treatment of one of the disorders and diseases described herein.

C. Polynucleotide-Based Therapies

The present invention also includes gene therapy materials and methods. Specifically, polypeptides and binding constructions of the invention can be produced at therapeutic levels in vivo by administration of a gene therapy contrast that enters cells and is expressed in vivo to produce the polypeptides or binding constructs. For example, in some embodiments, the vasculature of a cancer cell or cancer cells may be contacted with an expression construct capable of providing a therapeutic peptide or binding constructs of the present invention. Expression of the polypeptide or binding construct causes a therapeutic outcome, for example, inhibition of growth factors and receptors in the vasculature of a tumor, an inhibition of angiogenesis, an inhibition of lymphangiogenesis, an ablation, regression or other inhibition of tumor growth, an induction of apoptosis of the blood or lymphatic vasculature of the tumor or indeed the tumor cells themselves.

For these embodiments, an exemplary expression construct comprises a virus or engineered construct derived from a viral genome. Such vectors and constructs are considered aspect of the invention. The expression construct generally comprises a nucleic acid encoding the gene or binding construct, including any nucleic acid molecule described herein, to be expressed and also additional regulatory regions that will effect the expression of the gene in the cell to which it is administered. Such regulatory regions include for example promoters, enhancers, polyadenylation signals and the like.

DNA may be introduced into a cell using a variety of viral vectors. In such embodiments, expression constructs comprising viral vectors containing the genes of interest may be adenoviral (see, for example, U.S. Pat. No. 5,824,544; U.S. Pat. No. 5,707,618; U.S. Pat. No. 5,693,509; U.S. Pat. No. 5,670,488; U.S. Pat. No. 5,585,362, each incorporated herein by reference), retroviral (see, for example, U.S. Pat. No. 5,888,502; U.S. Pat. No. 5,830,725; U.S. Pat. No. 5,770,414; U.S. Pat. No. 5,686,278; U.S. Pat. No. 4,861,719, each incorporated herein by reference), adeno-associated viral (see, for example, U.S. Pat. No. 5,474,935; U.S. Pat. No. 5,139,941; U.S. Pat. No. 5,622,856; U.S. Pat. No. 5,658,776; U.S. Pat. No. 5,773,289; U.S. Pat. No. 5,789,390; U.S. Pat. No. 5,834,441; U.S. Pat. No. 5,863,541; U.S. Pat. No. 5,851,521; U.S. Pat. No. 5,252,479, each incorporated herein by reference), an adenoviral-adenoassociated viral hybrid (see, for example, U.S. Pat. No. 5,856,152 incorporated herein by reference) or a vaccinia viral or a herpesviral (see, for example, U.S. Pat. No. 5,879,934; U.S. Pat. No. 5,849,571; U.S. Pat. No. 5,830,727; U.S. Pat. No. 5,661,033; U.S. Pat. No. 5,328,688, each incorporated herein by reference) vector. Other vectors described herein may also be employed. Replication-deficient viral vectors are specifically contemplated.

In other embodiments, non-viral delivery is contemplated. These include calcium phosphate precipitation (Graham and Van Der Eb, *Virology,* 52:456-467 (1973); Chen and Okayama, *Mol. Cell Biol.,* 7:2745-2752, (1987); Rippe, et al., *Mol. Cell Biol.,* 10:689-695 (1990)), DEAE-dextran (Gopal, *Mol. Cell Biol.,* 5:1188-1190 (1985)), electroporation (Tur-Kaspa, et al., *Mol. Cell Biol.,* 6:716-718, (1986); Potter, et al., *Proc. Nat. Acad. Sci. USA,* 81:7161-7165, (1984)), direct microinjection (Harland and Weintraub, *J. Cell Biol.,* 101:1094-1099 (1985)), DNA-loaded liposomes (Nicolau and Sene, *Biochim. Biophys. Acta,* 721:185-190 (1982); Fraley, et al., *Proc. Natl. Acad. Sci. USA,* 76:3348-3352 (1979); Felgner, *Sci. Am.,* 276(6):102-6 (1997); Felgner, *Hum. Gene Ther.,* 7(15):1791-3, (1996)), cell sonication (Fechheimer, et al., *Proc. Natl. Acad. Sci. USA,* 84:8463-8467 (1987)), gene bombardment using high velocity microprojectiles (Yang, et al., *Proc. Natl. Acad. Sci. USA,* 87:9568-9572 (1990)), and receptor-mediated transfection (Wu and Wu, *J. Biol. Chem.,* 262:4429-4432 (1987); Wu and Wu, *Biochemistry,* 27:887-892 (1988); Wu and Wu, *Adv. Drug Delivery Rev.,* 12:159-167 (1993)).

In a particular embodiment of the invention, the expression construct (or indeed the peptides discussed above) may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, "In Liver Diseases, Targeted Diagnosis And Therapy Using Specific Receptors And Ligands," Wu, G., Wu, C., ed., New York: Marcel Dekker, pp. 87-104 (1991)). The addition of DNA to cationic liposomes causes a topological transition from liposomes to optically birefringent liquid-crystalline condensed globules (Radler, et al., *Science*, 275(5301):810-4, (1997)). These DNA-lipid complexes are potential non-viral vectors for use in gene therapy and delivery.

Liposome-mediated nucleic acid delivery and expression of foreign DNA in vitro has been very successful. Also contemplated in the present invention are various commercial approaches involving "lipofection" technology. In certain embodiments of the invention, the liposome may be complexed with a hemagglutinating virus (HVJ). This has been shown to facilitate fusion with the cell membrane and promote cell entry of liposome-encapsulated DNA (Kaneda, et al., *Science*, 243:375-378 (1989)). In other embodiments, the liposome may be complexed or employed in conjunction with nuclear nonhistone chromosomal proteins (HMG-1) (Kato, et al., *J. Biol. Chem.*, 266:3361-3364 (1991)). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems that can be employed to deliver a nucleic acid encoding a therapeutic gene into cells include receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu (1993), supra).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu (1987), supra) and transferrin (Wagner, et al., *Proc. Nat'l. Acad Sci. USA*, 87(9):3410-3414 (1990)). Recently, a synthetic neoglycoprotein, which recognizes the same receptor as ASOR, has been used as a gene delivery vehicle (Ferkol, et al., *FASEB. J.*, 7:1081-1091 (1993); Perales, et al., *Proc. Natl. Acad. Sci., USA* 91:4086-4090 (1994)) and epidermal growth factor (EGF) has also been used to deliver genes to squamous carcinoma cells (Myers, EPO 0273085).

In other embodiments, the delivery vehicle may comprise a ligand and a liposome. For example, Nicolau, et al., *Methods Enzymol.*, 149:157-176 (1987) employed lactosylceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a particular cell type by any number of receptor-ligand systems with or without liposomes.

In another embodiment of the invention, the expression construct may simply consist of naked recombinant DNA or plasmids. Transfer of the construct may be performed by any of the methods mentioned above that physically or chemically permeabilize the cell membrane. This is applicable particularly for transfer in vitro, however, it may be applied for in vivo use as well. Dubensky, et al., *Proc. Nat. Acad. Sci. USA*, 81:7529-7533 (1984) successfully injected polyomavirus DNA in the form of $CaPO_4$ precipitates into liver and spleen of adult and newborn mice demonstrating active viral replication and acute infection. Benvenisty and Neshif, *Proc. Nat. Acad. Sci. USA*, 83:9551-9555 (1986) also demonstrated that direct intraperitoneal injection of $CaPO_4$ precipitated plasmids results in expression of the transfected genes.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein, et al., *Nature*, 327:70-73 (1987)). Several devices for accelerating small particles have been developed. One such device relies on a high voltage discharge to generate an electrical current, which in turn provides the motive force (Yang, et al., *Proc. Natl. Acad. Sci USA*, 87:9568-9572 (1990)). The microprojectiles used have consisted of biologically inert substances such as tungsten or gold beads.

Those of skill in the art are well aware of how to apply gene delivery to in vivo and ex vivo situations. For viral vectors, one generally will prepare a viral vector stock. Depending on the kind of virus and the titer attainable, one will deliver $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$ or $1 \times 10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various cell types. For practically any cell, tissue or organ type, systemic delivery is contemplated. In other embodiments, a variety of direct, local and regional approaches may be taken. For example, the cell, tissue or organ may be directly injected with the expression vector or protein.

Promoters for gene therapy for use in this invention include cytomegalovirus (CMV) promoter/enhancer, long terminal repeat (LTR) of retroviruses, keratin 14 promoter, and a myosin heavy chain promoter.

In a different embodiment, ex vivo gene therapy is contemplated. In an ex vivo embodiment, cells from the patient are removed and maintained outside the body for at least some period of time. During this period, a therapy is delivered, after which the cells are reintroduced into the patient; preferably, any tumor cells in the sample have been killed.

The techniques, procedures and methods outlined herein are applicable to any and all of the polypeptides and binding constructs of the present invention.

D. Immunosuppressive and Other Combination Therapies

Any one of the binding constructs of the present invention when used in a method of treating or preventing a disease, e.g., a graft rejection or arteriosclerosis, may be employed alone, or in combination with other agents. In some embodiments, more than one binding construct may be administered. In some embodiments, a binding construct may be administered together with an immuno suppressive protein, antibody, nucleic acid, or chemotherapeutic agent.

Preferably, when used in combination with the endothelial growth factor inhibitor binding constructs of the present invention, the results obtained are synergistic. That is to say, the effectiveness of the combination therapy of a binding construct and the immunosuppressive agent is synergistic, i.e., the effectiveness is greater than the effectiveness expected from the additive individual effects of each. Therefore, the dosage of the immunosuppressive compound can be reduced and thus, the risk of the toxicity problems and other side effects is concomitantly reduced.

Any immunosuppressant therapy that has some efficacy at reducing transplant rejection alone can be used in combination with the inhibitors of the invention, and such combinations are specifically contemplated as combination therapies of the invention.

Corticosteroids are generally considered to be a first-line therapy for acute allograft rejection. Exemplary corticosteroids include prednisone and prednisolone, which are commonly used for prophylaxis against rejection, and methylprednisolone, which is often used for incidences of acute rejection. Dosage of corticosteroids is well developed by those in the field of transplant medicine, and varies depending on whether prescribed as initiation or maintenance therapy, and depending on patient tolerance. It is contemplated that reduced doses of corticosteroids may be used when combined with the inhibitors of the invention. The lower dosing is expected to help reduce known adverse effects of corticosteroids, which include hyperglycemia, diabetes mellitus, edema, hypertension, hyperlipidemia, hypokalemia, hirsutism, GI bleeding, arthralgia, osteoporosis, and psychosis.

A second class of immunosuppressants used with transplant patients, and contemplated for combination of therapy of the invention, is calcineurin inhibitors. Representative members of the class include cyclosporine and tacrolimus. These molecules act as immunosuppressive agents by binding to immunophilin molecules to inhibit calcineurin, and thereby inhibit T cell activation and proliferation. The patient's blood/serum and renal and liver functions are monitored to maintain an effective dose while minimizing toxicity. Combination of cyclosporine with other immunosuppressants is known to cause side-effects and may require dose modulation. The main side effects of CNIs are nephrotoxicity and neurotoxicity.

The mTOR inhibitors (mammalian target of rapamycin) represent a third class of immunosuppressants. The mTOR inhibitors, which include sirolimus and everolimus, inhibit T cell proliferation. Sirolimus has been used extensively in renal transplantation, and can be taken orally. Side effects associated with sirolimus therapy include dyslipidemia, hypertension, thrombocytopenia, anemia, peripheral edema, and tremor.

Antiproliferative agents represent a fourth class of immunosuppressants, and include azathioprine. A common starting dose for adults is 50 mg per day. After 4 to 8 weeks, the dose may be increased. Most adults require 50-150 mg per day. A dose-dependent bone marrow suppression may occur in over half of patients treated with azathioprine, and hepatotoxicity has been reported. Mycophenolic acid is another antiproliferative, which targets inosine monophosphate dehydrogenase (IMPDH), and causes a relatively selective suppression of lymphocyte proliferation. Compared to many of the other immunosuppressants, MPA lacks significant nephrotoxicity. The capsules come in 250 mg and 500 mg and the usual dose for adults is 1-1.5 g (2-6 capsules) twice a day. The dose for children is 15 mg/kg/day.

A fifth class of immunosuppressants used in transplant patients is anti-lymphocyte-depleting antibodies: Induction therapy prior to transplantation and during the first weeks post-transplantation with an antilymphocyte-depleting antibody or an IL-2 receptor (IL-2R) antagonist can provide effective protection against rejection. Polyclonal antilymphocyte-depleting antibodies, ATGAM and Thymoglobulin, sometimes are used after organ transplantation to reduce the risk of acute rejection. These antibodies are directed against T and B lymphocytes, and cause T cell lysis and blockade of B cell activation.

Muromonab C3 is a monoclonal antibody that is sometimes used in the treatment of acute rejection in transplant recipients. It binds to CD3 expressed on T cells and interferes with T cell antigen recognition.

IL-2R antagonists represent yet another class of immunosuppressants. Exemplary members of this class include basiliximab (Simulect) and daclizumab (Zenopax). The act by binding to the CD25 subunit of the IL-2R, to block T cell activation. They are used for prophylaxis, rather than treatment, of acute rejection because during acute rejection, T cells may become activated without the involvement of the CD25 subunit on the IL-2 receptor.

Mercaptopurine (6-MP) belongs to a group of drugs known as antimetabolites. It is used to treat many types of autoimmune diseases. It may interfere with the normal menstrual cycle in women and may stop sperm production in men. The usual adult dose is 2.5 mg/kg/day (100-200 mg). The pediatric dose is 50 mg per day. A maintenance dosage after remission is 1.5-2.5 mg/kg/day.

The foregoing list is not intended to be limiting. Inhibitors of the invention can be co-administered with any immunosuppressive agent to benefit from their complementary effects.

Other exemplary therapies to combine with therapies that target endothelial growth factors and growth factor receptors include those described in International Application No. PCT/EP2004/012406 (WO 2005/049021), incorporated herein by reference in its entirety, relating to a combination of an inhibitor of a mammalian Target of Rapamycin (mTOR), such as rapamycin; and an inhibitor of a Platelet-Derived Growth Factor Receptor (PDGF-R), such as imatinib mesylate.

mTOR inhibitors include, but are not limited to the following drugs:

| Brand Name or Product # | Generic Name | Patent (U.S. Unless Specified) or Reference |
|---|---|---|
| Rapamune ® | rapamycin (sirolimus) | 3,929,992; 5,288,711; 5,516,781 |
| RAD001 (Certican ®) | everolimus; 40-O-(2-hydroxyethyl)-rapamycin | EP663916; U.S. Pat. Appl. 20030170287 |
| CCI-779 | Rapamycin 42-ester with 3-hydroxy-2-(hydroxymethyl)-2-methylpropionic acid | 6,617,333; 5,362,718; 6,277,983 |
| | Tumstatin and related polypeptides | U.S. Pat. Appl. 20030144481 |
| ABT578 | | U.S. Pat. Appl. 20030073737 |
| "rapalogs," e.g., AP23573, AP22594 | | U.S. Pat. Appl. 20030073737; WO01/02441; WO01/14387 |
| AP23841 | | ARIAD Pharmaceuticals |
| TAFA93 | | Isotechnika |

In addition to rapamycin and those derivatives of rapamycin listed in the above table those discussed in U.S. Pat. Appl. No. 20030170287 may also be used. See also WO 94/09010, and WO 96/41807. Rapamycin derivatives may also include without limitation "rapalogs," e.g., as disclosed in WO 98/02441 and WO01/14387; deuterated rapamycin analogs, e.g., as disclosed in U.S. Pat. No. 6,503,921. Derivatives of other mTOR inhibitors are also contemplated.

Exemplary Platelet-Derived Growth Factor Receptor (PDGF-R) inhibitors include the following without limitation:

| Brand Name or Product # | Generic Name | Patent (U.S. Unless Specified) or Reference |
|---|---|---|
| Gleevec | imatinib mesylate (CGP57148B; STI-571) | 5,521,184; Druker, Nature Medicine, 2: 561 (1996) |
| AG1295 | | Kovalenko, Cancer Res 54: 6106 (1994) |
| AG1296 | 6,7-demethoxy-2-phenylquinoxaline | Kovalenko, Cancer Res 54: 6106 (1994) |
| AG1478 | 4(3-chlorophenyamino)-6,7,-dimethoxyquinazoline | Lipson, K., et al., J. Pharmacology and Experimental Therapeutics, 285: 844-852 (1998) |
| Trapidil | triazolopyrimidine | Lotinum et al., Endocrinology, 144: 2000-2007 (2003) |
| | 2-phenylaminopyrimidine class compounds | Buchdunger et al., Cancer Res., 56: 100-1044 (1996) |
| 3744W | | Spacey et al., Bioch. Pharm. 55(3): 261-71, 1998 Feb. 1 |
| Tyrphostin AG1296 | | Kovalenko et al, Cancer Res. 1994 Dec. 1; 54(23) |
| CGP 79787D | | WO00/09098 |
| CGP53'716 | | Buchdunger et al., PNAS 1995 92(7): 2558-62 |
| CGP57'148 | | Buchdunger et al., Cancer Res. 1996 56(1): 100-4 |
| CT52923 | | U.S. Pat. Appl. No. 20030170287; Lokker et al., Cancer Res., 62: 3729-35 (2002). |
| RP-1776 | | U.S. Pat. Appl. No. 20030170287; Toki et al., J Antibiot (Tokyo). 54: 405-14 (2001) |
| GFB-111 | | U.S. Pat. Appl. No. 20030170287; Blaskovich et al., Nat Biotechnol. 18: 1065-70 (2000). |
| | a pyrrolo[3,4-c]-beta-carboline-dione | U.S. Pat. Appl. No. 20030170287; Teller et al., Eur J Med Chem., 35: 413-27 (2000) |
| SU11248 (SU01248) | | Sugen Pharmaceutical; Abrams et al., Mol Cancer Ther. 2: 1011-21 (2003); Mendel et al. Clin Cancer Res. 9: 327-37 (2003). |
| PKC787 | | Novartis |
| PTK787 | | Novartis; U.S. Pat. Appl. No. 20030087934; Wood et al., Cancer Res. 60: 2178-89 (2000). |
| DMBI | | Organon; Zaman, Biochem. Pharmacol. 57: 57 1999 |
| SU101 (LFM, HWA486) | | Sugen; Shawner, Clin. Cancer. Res., 3: 1167 1997 |
| SU0020 (A771726) | | Sugen; Zhang et al., J. Pharm. Biomed. Anal. 28: 701-9 (2002). |
| Comp. 54 | | Parke-Davis; Boschelli, J. Med. Chem. 41: 4365 (1998) |

The above list of PDGF-R inhibitors is not meant to be limiting. Any PDGF-R inhibitor may be employed, including without limitation PDGF-R inhibitors described in U.S. Pat. Nos. 5,932,580, 6,331,555, and 6,358,954; WO 99/28304; WO 00/09098; WO 01/64200. Other inhibitors that may be used include 3-Substituted Indolin-2-ones (e.g., SU5416, SU6668), and derivatives thereof (Sun et al., J. Med. Chem., 41:2588-2603; Sun et al., J. Med. Chem. 43:2655-2663 (2000)); 2-Amino-8H-pyrido[2,3-d]pyrimidines (Boschelli et al., J. Med. Chem. 41:4365-4377 (1998)).

In some embodiments, the PDGF-R inhibitor is a compound described in U.S. Pat. No. 5,521,184, incorporated herein by reference.

In addition to or in substitution for PDGF-R inhibitors, inhibitors of other tyrosine kinases (receptors and other types as well) may also be used in accordance with this invention. Some of these inhibitors may inhibit multiple kinases including, but not limited to, PDGF-Rs. Appropriate TK inhibitors are also taught in WO 99/03854; WO 01/64200; U.S. Pat. No. 5,521,184; WO 00/42042; WO 00/09098; EP 0 564 409 B1; U.S. Pat. No. 5,521,184; WO 97/32604; U.S. Pat. No. 6,610,688; US Patent Appl. Pub. No. 20030194749; Livitzki, A., et al., "Protein Tyrosine Kinase Inhibitors as Novel Therapeutic Agents," Pharmacol. Ther. 82:231-29 (1999). Other classes of compounds may also be employed. For example and without limitation, Leflunomide (U.S. Pat. No. 4,284,786) and/or derivative FK778 may be used. (See, e.g., Savikko Transplantation 2003:76:455 and editorial Williams ibid p 471.)

E. Suitable Transplant Recipients

The present invention is applicable to all cell, tissue, organ fragment, organ, and multi-organ transplant procedures, to inhibit or delay rejection reactions or other undesired side-effects, including arteriosclerosis, that are associated with transplants. Thus, the invention is applicable to any mammal that receives any cell, tissue, organ fragment, organ, or multi-organ transplant.

Exemplary transplants include autografts (transplant or transfer of tissue from an organism to itself, e.g., where donor and recipient are the same organism); isografts (transplants from a donor organism to a genetically identical recipient (e.g., an identical twin or a clone); allografts (transplants from a donor organism to a genetically non-identical organism of the same species); and xenografts (transplants of organs or tissue from one species to another). All of these types of transplants are theoretically possible in humans, although xenografts have thus far been fairly limited (e.g., heart valves), and isograft donors are quite rare. Thus, in the context of transplantation of vital organs or tissues to replace diseased ones, allograft transplants represent the most common class for human therapy. The likelihood of rejection or graft arteriosclerosis increases as the differences between donor and recipient increase.

Exemplary organs that have been transplanted in humans, and for which the methods of the invention are especially applicable, include thoracic organs (e.g., heart, lung); abdominal organs (e.g., liver, kidney, pancreas, small intestine). The invention also is applicable for various tissue and cell transplants, including but not limited to pancreatic islet cells, bone marrow cells, cardiac myocytes, blood vessels or vessel fragments, heart valves, bones, and skin. The invention also is applicable to the emergent fields of transplantation of embryonic stem cells and various pluripotent or multipotent progenitor or precursor cells that have the potential to differentiate into one or more cell types (e.g., hematopoietic progenitor/stem cells, neural progenitor/stem cells, endothelial progenitor cells, and muscle progenitor cells).

F. Transplant Rejection and Monitoring of Transplanted Tissue

After surgery, the transplanted cell, tissue or organ is carefully monitored for any signs that the recipient will reject the new cell, tissue or organ. There are three main types of transplant rejections: (1) hyperacute, (2) acute, and (3) chronic transplant rejections.

Hyperacute rejection is a complement-mediated response in recipients with pre-existing antibodies to the donor (for example, ABO blood type antibodies). Hyperacute rejection occurs within minutes and the transplant must be immediately removed to prevent a severe systemic inflammatory response. Rapid coagulation of the blood occurs. This is a particular risk in kidney transplants, and so a prospective cytotoxic crossmatch is performed prior to kidney transplantation to ensure that antibodies to the donor are not present. For other organs, hyperacute rejection is prevented by transplanting only ABO-compatible grafts. Hyperacute rejection is the likely outcome of xenotransplanted organs.

Acute rejection is generally acknowledged to be mediated by T cell responses to proteins from the donor organ, which differ from those found in the recipient. Unlike antibody-mediated hyperacute rejection, development of T cell responses first occurs several days after a transplant if the patient is not taking immunosuppressant drugs. Since the development of powerful immunosuppressive drugs, such as those discussed above, the incidence of acute rejection has been greatly decreased. However, organ transplant recipients can develop acute rejection episodes months to years after transplantation. Acute rejection episodes can destroy the transplant if it is not recognized and treated appropriately. A single episode is not a cause for grave concern if recognized and treated promptly, and rarely leads to organ failure, but recurrent episodes are associated with chronic rejection of grafts.

The bulk of the immune system response is to the Major Histocompatibility Complex (MHC) proteins. MHC proteins are involved in the presentation of foreign antigens to T cells, and receptors on the surface of the T cell (TCR) are uniquely suited to recognition of proteins of this type. MHC are highly variable between individuals, and therefore the T cells from the donor recognize the foreign MHC with a very high frequency, leading to powerful immune responses that cause rejection of transplanted tissue. Identical twins and cloned tissue are MHC matched, and are therefore not subject to T cell mediated rejection.

The term "chronic rejection" is used when the process is shown to be due to a chronic alloreactive immune response. It can be caused by a member of the Minor Histocompatibility Complex such as the H-Y gene of the male Y chromosome, and usually leads to the need for a new organ after a decade or so.

Cardiac Allograft vasculopathy (CAV), also known as chronic cardiac rejection or transplant coronary artery disease, is the main factor limiting the long term success of heart transplants, and most likely involves both immunological and non-immunological factors (Al-Khaldi et al., Annu. Rev. Med., 57:455-471, 2006, the disclosure of which is incorporated herein by reference). Identified risk factors include older donor and recipient age, ischemia-reperfusion injury, human leukocyte antigen (HLA) mismatch, hypertension, hyperlipidemia, insulin resistance, cytomegalovirus infection, and recurrent rejection (Taylor et al., J. Heart Lung Transplant., 23:796-803, 2004; Valantine et al., Circ., 103: 2144-2152, 2001; Costanzo-Nordin et al., J. Heart. Lung Transplant., 11:S90-103, 1992; Grattan et al., JAMA, 261: 3561-3566, 1989; Kobashigawa et al., J. Heart Lung. Transplant., 14:S221-S226, 1995; and Valantine, H., J. Heart Lung. Transplant., 23:S187-S193, 2004). These risk factors may lead directly or indirectly to endothelial injury with subsequent intimal hyperplasia and vascular smooth muscle proliferation.

Monitoring of heart transplant recipients for the development of allograft rejection includes non-invasive methods such as intramyocardial electrocardiogram (Hetzer et al., Ann Thorac Surg 66:1343, 1998) and echocardiography, radioisotope techniques, magnetic resonance imaging and immunological methods (Kemkes et al., J Heart Lung Transplant 11: S221-31, 1992). The immunological methods include the measurement of serum cytokine levels, particularly IL6 and IL8 (Kimball et al., Transplantation 61: 909-15, 1996), monitoring recipient serum for donor HLA antigens and anti-HLA antibodies (Reed et al., Transplantation 61: 566-72, 1996), and measuring reactivity of alloreactive helper T cells (DeBruyne, Transplantation 56: 722-7, 1993), or cytotoxic T cells in the blood of the recipient (Reader et al. Transplantation 50: 29-33, 1990; Loonen et al., Transplant Int 7:596-598, 1994). Invasive methods include an endomyocardial biopsy, which detects an ongoing immune rejection process that may have already damaged the heart before immunosuppressive intervention has been initiated. Non-invasive methods are associated with the detection of ongoing damage in the heart muscle and thus, may come too late for the preferred goal in improving the care of the transplant recipient: early prevention of the developing rejection episode.

The monitoring methods used in other organ allograft recipients are also directed to detection of damage to the transplanted organ. With respect to kidney allograft recipients, noninvasive methods include the functional indicators of impaired renal activity, such as (a) decreased urine volume, (b) decreased clearance of creatinine and (c) elevated blood urea nitrogen. Monitoring includes detection of lymphocytes in the urine (Salaman, Immunol Lett 29: 139-12, 1991), secretion of neopterin (a pteridine from stimulated macrophages) and interferon-gamma (a cytokine released by activated T cells) (Khoss et al. Child Nephrol Urol 9:46-49, 1988; Grebe et al., Curr Drug Metabol 3:189-202, 2002). The sensitivity of detection of inflammatory products in the urine was further improved by measuring the presence of mRNA for perforin and granzyme B (proteins released from T cells that damage target cells), using the reverse transcriptase-polymerase chain reaction (RT-PCR) for amplification and detection of these molecules (Li et al., N Engl J Med 344: 947-954, 2001).

V. Non-Exclusive Examples of the Invention

The invention may be more readily understood by reference to the following examples, which are given to illustrate the invention and not in any way to limit its scope. The first several examples describe making and testing inhibitor compounds useful to practicing methods of the invention. The second group of examples describe evidence that the antigens are suitable targets for therapy and/or evidence that such therapy is efficacious. These examples primarily make reference to binding constructs that bind particular growth factors of the VEGF subfamily, but they may also be adapted for use of binding constructs that bind other VEGF subfamily members, as well as for binding constructs that bind PDGF subfamily members. Similarly, binding constructs comprising other VEFGR receptor fragments, PDGFR receptor fragments, and neuropilin receptor fragments may also be employed in variations of these examples.

Example 1

VEGFR-2 and VEGFR-3 Fragments that Bind VEGF-A or VEGF-C

To determine the portion of a receptor's extracellular domain (ECD) that was sufficient for ligand binding, fragments of the ECDs of VEGFR-2 (R-2) and VEGFR-3 (R-3)

were used to make various soluble constructs. The constructs included Fc domain human IgG fragments fused to the C-terminus of the receptor fragments. As indicated in Tables 3 and 4, some constructs were made using a heterologous (N-terminal) signal peptide derived from CD33.

Construction of Fragments and Plasmids

R-2 Constructs

To construct the VEGFR-2/IgG expression plasmid, the construct, R-2 A, comprising the first three Ig-domains (D1-3) of VEGFR-2 was amplified by PCR using primers 5'-GCGGATCCTTGCCTAGTGTTTCTCTTGATC-3' (SEQ ID NO: 72), and 5'-CCAGTCACCTGCTCCGGATCTTCATGGACCCTGACAAATG-3' (SEQ ID NO: 73), and cloned into the Signal pIgplus vector (Novagen, Madison, Wis.). The resulting plasmid was digested with BamHI and KpnI, treated with T4 polymerase and back-ligated. To assemble other VEGFR-2/IgG constructs, PCRs were performed using the D1-3 construct as the template, T7 forward primer and the following reverse primers:

```
                                        (SEQ ID NO: 59)
5'-GCTGGATCTTGAACATAGACATAAATG-3'   (R-2 F),, (SEQ ID NO: 60)
5'-CTAGGATCCCCTACAACGACAACTATG-3'   (R-2 B),, (SEQ ID NO: 61)
5'-CTAGGATCCACATCATAAATCCTATAC-3'   (R-2 C),, (SEQ ID NO: 62)
5'-GCATGGTCTCGGATCATGAGAAGACGGACTCAGAAC-3'   (R-2 D),, (SEQ ID NO: 63)
5'-CTAGGATCCTTTTCTCCAACAGATAG-3'   (R-2 E);

forward primer
                                        (SEQ ID NO: 64)
5'-AGCGCTAGCGTTCAAGATTACAGATCTCC-3',
and the following reverse primers:

(SEQ ID NO: 65)
5'-ATGTGTGAGGTTTTGCACAAG-3'   (R-2 G),, (SEQ ID NO: 66)
5'-CTAGGATCCCCTACAACGACAACTATG-3'   (R-2 H),, (SEQ ID NO: 67)
5'-CTAGGATCCACATCATAAATCCTATAC-3'   (R-2 I),, (SEQ ID NO: 68)
5'-GCATGGTCTCGGATCATGAGAAGACGGACTCAGAAC-3'   (R-2 J),, (SEQ ID NO: 69)
5'-CTAGGATCCTTTTCTCCAACAGATAG-3'   (R-2 K),, forward primer
                                        (SEQ ID NO: 70)
5'-AGCGCTAGCTATAGGATTTATGATGTG-3',
and reverse primer (SEQ ID NO: 71)
5'-ATGTGTGAGGTTTTGCACAAG-3'   (R-2 L),.
```

The PCR products were digested with NheI and BstYI (R-2 F and L constructs), NheI and BamHI (R-2 E, and H-K constructs), BamHI (R-2 linker B and C constructs), BamHI and BsaI (R-2 D construct), or NheI and BsmBI (R-2 G construct), and cloned into the Signal pIgplus vector. In order to repair frame-shifts in constructs containing nucleotide sequence coding for domain 1 of VEGFR-2, the vectors were cut with restriction enzyme NotI, blunted with Klenow enzyme, cut with EcoRV and back-ligated.

R-3 Constructs

A series of R-3 constructs with C-termini between Ig domains 2 and 3 of VEGFR-3 (R-3 C through F constructs) was created by PCR using the expression plasmid comprising the R-3 D1-3 transcript (e.g., the R-3 G construct, SEQ ID NO: 43) as template, T7 as forward primer and the following reverse primers:

```
5'-TCAGGATCCGCGAGCTCGTTGCCTG-3',     (SEQ ID NO: 74)

5'-TACAGGATCCCCTGTGATGTGCACCAG-3',   (SEQ ID NO: 75)

5'-TCAGGATCCGCGTGCACCAGGAAGG-3',     (SEQ ID NO: 76)
and

5'-TCAGGATCCGCGAAGGGGTTGGAAAG-3'.    (SEQ ID NO: 77)
```

The Ig homology domain 1 was deleted from the D1-3 expression plasmid (R-3 G construct) by site-directed mutagenesis using primers
5'CCTTGAACATCACGGAGGAGTCACACGTCAGAGACTTTGAGCA GCCATTCATCAACAAGC-3' (SEQ ID NO: 78) and
5'AGCTGCTGGTAGGGGAGAAGGATCCTGAACTGCACCGTGTGG-3' (SEQ ID NO: 79), and excision of the BamH I fragment from the resulting plasmid. That procedure combined with the described truncation primers, for R-3 C through F constructs, allows for the production of the R-3 constructs (e.g., C, D, E, F, J, K, L, and M). The plasmid coding for domains 2 and 3 of VEGFR-3 (R-3 I) was made by transfer of the Sph I fragment from the original expression R-3 D1-3 plasmid into the plasmid encoding only domain 2 of VEGFR-3 (R-3 J). The sequence derived from a particular receptor is listed in Table 2. Expression was performed using standard calcium phosphate-mediated transfection into 293T cells.

The binding assays utilized minimal VEGF-A (SEQ ID NOS: 106 and 107) and VEGF-C(SEQ ID NOS: 108 and 109) fragments with 109 residues each (called VEGF-A 109 and VEGF-C 109). These constructs are not naturally occurring, but are effective for binding assays. Other growth factor constructs, either natural or artificial, may also be used for performing these assays.

Either Tritiated VEGF-A 109 or VEGF-C 109 was used in a given binding experiment. Ligand in solution was precipitated by mixing 175 μl of ligand solution with 100 μl binding mix at 4° C. overnight, with agitation. The ligand solution may be the supernatant of metabolically labeled 293T cells. The binding mixes used for the receptor binding analysis were as follows: for VEGFR-1 binding assays, the binding mix was phosphate buffered saline (PBS) containing 1.5% BSA, 0.06% Tween 20, 3 μg/ml heparin and 400 ng/ml VEGFR-1-Fc fusion protein (100 μl of this binding mix was added to 200 μl of ligand solution). For VEGFR-2 binding assays, the binding mix was 82% conditioned cell supernatant from 293T cells transiently expressing VEGFR-2-Fc fusion protein in mixture with 18% of a PBS solution that contained 5% BSA, 0.2% Tween 20, and 10 μg/ml heparin (250 μl of binding mix was added to 200 μl of ligand solution). For VEGFR-3 binding assays, the binding mix was 82% conditioned cell supernatant from 293T cells transiently expressing VEGFR-3-Fc fusion protein, 18% of PBS containing 5% BSA, 0.2% Tween 20, and 10 μg/ml heparin (250 μl of binding mix was added to 200 μl of ligand solution). To collect precipitated ligand, 50 μl of a 30% protein A sepharose (PAS, Pharmacia) slurry in PBS was added and incubated under agitation for at least 1.5 hr at 4° C. Standard buffer was added to each immunoprecipitation sample and boiled for 5 minutes at 95° C. during which the immunopreciptated proteins become dissociated from the protein A sepharose. After centrifugation, 10 µl of each sample was analyzed on 15% SDS-PAGE under reducing conditions. The gels were dried and exposed for either 12 hours on phosphorimager plates or 4 weeks on X-ray film.

Tables 3 and 4 identify constructs by name, a DNA and deduced amino acid sequence from the sequence listing, the portion of VEGFR-2 (SEQ ID NO: 4) or VEGFR-3 (SEQ ID NO: 6) amino acid sequence that was included in the constructs, whether the constructs expressed, and, if tested, whether constructs bound ligand. The table data is compiled from analysis of PAGE gels. The asterisk adjacent to the "B*" indicates a "spill-over" from the adjacent lane, as the origin of the bands seen in the "B" lane. A failure to express under the particular experimental conditions used in this instance should not be interpreted as a failure to bind. The experiments can be repeated using different receptor fragments, binding constructs, ligands, or combinations thereof.

TABLE 3

| Fc Fusion Constructs | SEQ ID NOS: | SEQ ID NO: 4 | Expression | Binds VEGF-A | Binds VEGF-C |
|---|---|---|---|---|---|
| R-2 A with CD33 Signal Peptide | SEQ ID NOS: 7 and 8 | 24-326 | Yes | Yes | Yes |
| R-2 B with CD33 Signal Peptide | SEQ ID NOS: 9 and 10 | 24-220 | Yes | No | No |
| R-2 C with CD33 Signal Peptide | SEQ ID NOS: 11 and 12 | 24-226 | Yes | No | No |
| R-2 D with CD33 Signal Peptide | SEQ ID NOS: 13 and 14 | 24-232 | Yes | No | No |
| R-2 E with CD33 Signal Peptide | SEQ ID NOS: 15 and 16 | 24-241 | Yes | No | No |
| R-2 F with CD33 Signal Peptide | SEQ ID NOS: 17 and 18 | 24-122 | Yes | No | No |
| R-2 G with CD33 Signal Peptide | SEQ ID NOS: 19 and 20 | 118-326 | Yes | Yes | Yes |
| R-2 H with CD33 Signal Peptide | SEQ ID NOS: 21 and 22 | 118-220 | Yes | No | Yes |
| R-2 I with CD33 Signal Peptide | SEQ ID NOS: 23 and 24 | 118-226 | Yes | No | Weak |
| R-2 J with CD33 Signal Peptide | SEQ ID NOS: 25 and 26 | 118-232 | Yes | No | Very Weak |
| R-2 K with CD33 Signal Peptide | SEQ ID NOS: 27 and 28 | 118-241 | Yes | No | No |
| R-2 L with CD33 Signal Peptide | SEQ ID NOS: 29 and 30 | 220-326 | Yes | No | No |

TABLE 4

VEGFR-3 CONSTRUCTS

| Fc Fusion Constructs | Sequence ID Nos. | SEQ ID NO: 6 | Expression | Binds VEGF-C |
|---|---|---|---|---|
| R-3 A with CD33 Signal Peptide | SEQ ID NOS: 31 and 32 | 138-329 | Yes | — |
| R-3 B with CD33 Signal Peptide | SEQ ID NOS: 33 and 34 | 138-226 | Yes | Yes |
| R-3 C | SEQ ID NOS: 35 and 36 | 1-229 | Yes | Yes |
| R-3 D | SEQ ID NOS: 37 and 38 | 1-226 | Yes | Yes |
| R-3 E | SEQ ID NOS: 39 and 40 | 1-223 | No | — |
| R-3 F | SEQ ID NOS: 41 and 42 | 1-220 | No | — |
| R-3 G | SEQ ID NOS: 43 and 44 | 1-329 | Yes | Yes |
| R-3 H | SEQ ID NOS: 45 and 46 | 1-134 | Yes | No |
| R-3 I | SEQ ID NOS: 47 and 48 | 1-39, 132-329 | Yes | No |
| R-3 J | SEQ ID NOS: 49 and 50 | 1-39, 132-247 | Yes | No |
| R-3 K | SEQ ID NOS: 51 and 52 | 1-39, 132-229 | Yes | No |
| R-3 L | SEQ ID NOS: 53 and 54 | 1-39, 132-226 | Yes | — |
| R-3 M | SEQ ID NOS: 55 and 56 | 1-39, 132-223 | No | — |
| R-3 N | SEQ ID NOS: 57 and 58 | 1-40, 226-329 | — | — |

The results of these assays demonstrate that novel receptor fragments are capable of binding ligands that the receptor as a whole may bind. In addition to providing a clearer picture as to what regions of the ECD are necessary for ligand binding, the binding data identifies receptor fragments useful as therapeutics.

The present data show that the R-2 H fragment of R-2 of approximately 100 residues and spanning D2 of R-2 is sufficient for VEGF-C binding. For R-3, a larger fragment is required for VEGF-C binding, e.g., the R-3 D construct in table 4, which spans D1-2 of R-3.

Three-dimensional modeling based on the structure of VEGFR-1 complexed with VEGF-A was used to predict that a groove in VEGF-C might accommodate the region between Ig-like domains 2 and 3 of VEGFR-3 (Flt4). WO 01/62942. The present data shows for the first time that sequence intermediate between the second and third Ig domains of R-3 is important for ligand binding.

For R-1 and R-2, the first Ig-domain has been described as inhibitory for VEGF-A binding. Lu, et al., *J. Biol. Chem.*, 275(19): 14321-14330 (2000); Shinkai, A. et al., *J. Biol. Chem.*, 273(47):31283-88 (1998). For VEGF-C binding, the present data show that the inhibitory role of the first Ig-domain appears to apply to R-2 fragments, but not R-3 fragments.

The data also provides novel information regarding R-2 fragments and VEGF-A binding. Conflicting reports exist for constructs comprising the second and third Ig-domains of R-2 and VEGF-A binding. Fuh, et al., *J. Biol. Chem.*, 273(18): 11197-11204 (1998); Niwa, et al., U.S. Pat. No. 6,348,333; Shinkai, A. et al., *J. Biol. Chem.*, 273(47):31283-88 (1998). Fuh reported that only domains 2 and 3 were needed. Niwa taught that only 1 and 2 were needed. Shinkai stressed the importance of domain 4 of R-2. The issue is further confused because different reports have defined the boundaries of the Ig-domains in different ways, i.e., different start and stop points, a practice that has been recognized as potentially affecting whether fragments bind ligands, and with what degree of affinity. Shinkai, A. et al., *J. Biol. Chem.*, 273(47):31283-88 (1998).

Example 2

Ligand Binding Assays Involving Binding Constructs with More than One Binding Element The assays as performed in Example 1 are repeated, substituting a binding construct with multiple binding units. For example, one employs a binding construct comprising a binding unit that binds VEGF-A and a binding unit that binds VEGF-C. One looks for the ability of such a binding construct to bind both VEGF-A and VEGF-C. This information may be obtained by using different radio- or other labels, e.g., fluorescent labels for fluorescence resonance energy transfer (FRET), on each type of ligand or use of labels on the binding construct and or ligands, to determine whether a given binding construct molecules are binding a molecule of VEGF-A and VEGF-C. Constructs that are shown to bind more than one growth factor ligand, as well as those described in Example 1 and elsewhere herein, have an indication for anti-neoplastic therapies where multiple growth factors contribute to neoplastic cell growth.

Example 3

Chimeric VEGFR Binding Constructs which Bind Multiple Ligands

As stated above, constructs that bind more than one growth factor ligand have an indication as anti-neoplastic therapies where multiple growth factors contribute to neoplastic cell growth. In order to determine the efficacy of a binding construct designed to bind more than one growth factor, two chimeric binding constructs were generated and their ability of each to bind to two growth factors was measured.

The binding constructs were designed as immunoblobulin fusion proteins as described above. To construct chimeric VEGF receptor/hIgG1Fc fusion proteins, the pIgPlus vector was used to build a construct comprising the first immunoglobulin-like domain of VEGFR-3 and the second and third Ig-like domains of VEGFR-2. The construct is designated R-3D1-R2D2+3/hIgG1Fc. To clone the R-3D1-R2D2+3/hIgG1Fc construct, PCR was performed with CMV forward primer (18782, 5' TACTTGGCAGTACATCTACGTATT-AGTCATCGC-3') (SEQ ID NO: 122) and reverse primer v360 (5'-CGGAGATCTGTAGTCTTGCACGTACACG-TAGGAGCTGGC-3') (SEQ ID NO: 123) using pIgPlus-hVEGFR-3D1-3-IgG1Fc as a template. The PCR-product was cut with SnaBI and BglII. The 718 bp D1-R2D2+3/hIgG1Fc insert was ligated into the SnaBI- and partially BglII-cut vector pIgPlus-hVEGFR-2D1-3-IgG1Fc described above. The presence and sequence of the correct insert was confirmed by sequencing a representative isolated hVEGFR-3D1-R2D2+3/hIgG1Fc clone (clone #2). (SEQ ID NO: 124 and SEQ ID NO: 125).

In addition to the above chimeric construct, a chimeric VEGF receptor/hIgG1Fc fusion protein was constructed having the first Ig-like domain of VEGFR-3, the second Ig-like domain of VEGFR-2 and the third Ig-like domain of VEGFR-1. The construct is designated R-3D1-R2D2-R1D3/hIgG1Fc.

To clone the pIgPlus-hVEGFR-3D1-R2D2-R1D3/hIgG1Fc construct, PCR was performed using pIgPlushVEGFR-3D1-R2D2+3/hIgG1Fc as a template and the T7 forward and reverse primer v362 (5'-TACAATTGAGGA-CAAGCGTATGTCCACGAAGTAGTTTAACTGGAC-GAGGC GTGCTTATTTGCACATCATAAATCCTATACC-3') (SEQ ID NO: 126). The PCR-product was cut with HindIII and MfeI/MunI. The 787 bp VEGFR-3D1-R2D2+3/hIgG1Fc insert was ligated into the HindIII- and partially MfeI-cut vector pIgPlus-hVEGFR-1D1-3-IgG1Fc. The presence and sequence of the correct chimeric insert was confirmed by sequencing the a representative hVEGFR-3D1-R2D2-R1D3/hIgG1Fc clone (clone #6) (SEQ ID NO: 127 and SEQ ID NO: 128).

Expression of Chimeric VEGFR/hIgG1Fc Fusions:

For expression analysis, the two new chimeric VEGF receptors and control constructs expressing R-1D1-3/hIgG1Fc, R-2D1-3/hIgG1Fc, R-3D1-3/hIgG1Fc, mature VEGF-C and VEGF-$A_{165}$ were transiently transfected into 293T cells using JetPEI (QBioGene/MP Biomedicals, Irvine, Calif.). Metabolic labeling with $^{35}$S-methionine and $^{35}$S-cysteine was carried out at 48 hours post-transfection and labeling maintained for 24 hours. The serum-free conditioned medium was then immunoprecipitated using Protein A sepharose and either: a) specific antiserum against human mature VEGF-C; b) goat polyclonal antibody against human VEGF-A (R&D systems, Minneapolis, Minn.); or, c) serum-free medium of 293T cells taken 48 to 72 hours post-transient transfection with VEGF receptor/hIgG1Fc proteins (control proteins, R-1D1-3, R-2D1-3, R-3D1-3; chimeric proteins, R-3D1-R2D2+3 and R-3D1-R2D2-R1D3).

The immunoprecipitated fractions were analyzed on 17% SDS-PAGE and the dried gels were exposed for 12 hours on phosphoimager plates or 36 hours on X-ray films. Expression analysis demonstrated that the chimeric receptor fusion proteins exhibited high expression levels in transfected 293 T cells.

Analysis of Binding Properties of Chimeric VEGF Receptor/hIgG1Fc Fusions:

Ligand binding analysis was performed as described for the VEGF-C/VEGF-A hybrid growth factors in Example 1. Briefly, the unlabeled conditioned medium of transiently transfected 293T cells expressing the chimeric VEGFR/IgG1Fc fusion proteins was used to precipitate the $^{35}$S metabolically labeled mature VEGF-C, full-length VEGF-C, and VEGF-$A_{165}$. SDS-PAGE of ligands immunoprecipitated with chimeric and control VEGFR/IgFc showed that the R-3D1-R2D2-R1D3/Ig chimeric protein strongly bound both VEGF-A and VEGF-C, as predicted based on the VEGFR2 and R1 immunoglobulin domains. In one experiment, the chimeric construct R-3D1-R2D2+3/Ig exhibited binding to VEGF-C and not VEGF-A. A second experiment with the R-3D1-R2D2+3/Ig construct showed only weak binding to VEGF-A.

These results demonstrate that the ligand binding constructs generated herein are useful in developing compositions that bind multiple growth factors involved in numerous cell activities. These constructs provide promising therapy for diseases such as cancer and other proliferative diseases wherein multiple growth factors mediate the condition or disease state.

Example 4

Assay for Neutralization of Growth Factor Activity

The following protocol provides an assay to determine whether a binding construct neutralizes one or more PDGF/VEGF growth factors by preventing the growth factor(s) from stimulating phosphorylation of its receptor.

Cells such as NIH 3T3 cells are transformed or transfected with a cDNA encoding a PDGFR/VEGFR receptor, such as VEGFR-3, and cultured under conditions where the encoded receptor is expressed on the surface of the cells. Transfected cells are cultured with either 1) plain growth medium; 2) growth medium supplemented with 50 ng/ml of one or more ligands for the recombinant receptor, such as fully processed VEGF-C and/or VEGF-D, which are ligands for VEGFR-3; 3) growth medium supplemented with 50 ng/ml of growth factor that does not bind the recombinant receptor (e.g., VEGF-A in the case of VEGFR-3), to serve as a control; or any of (1), (2), or (3) that is first pre-incubated with varying concentrations of a binding construct to be tested.

After culturing with the culture mediums described above in the presence or absence of the binding construct, the cells are lysed, immunoprecipitated using anti-receptor (e.g., anti-VEGFR-3) antiserum, and analyzed by Western blotting using anti-phosphotyrosine antibodies. Cells stimulated with the appropriate growth factor ligand (VEGF-C/D) stimulate VEGFR-3 autophosphorylation, which is detected with the anti-phosphotyrosine antibodies. Binding constructs that reduce or eliminate the ligand-mediated stimulation of receptor phosphorylation (e.g., in a dose-dependent manner) are considered neutralizing binding constructs.

Example 5

EPO Chimera Survival/Proliferation Blocking Assay

A binding construct is tested for the ability to block the binding of the growth factor(s) to their receptors, using bioassays of receptor binding and cross-linking. These assays involve the use of Ba/F3 pre-B cells which have been transfected with plasmid constructs encoding chimeric receptors consisting of the extracellular domain of growth factor receptors and the cytoplasmic domain of the erythropoietin receptor (Stacker, S A. et al., J. Biol. Chem. 274:34884-34892, 1999; Achen, M G. et al., Eur. J. Biochem. 267:2505-2515, 2000). These cells are routinely passaged in interleukin-3 (IL-3) and will die in the absence of IL-3. However, if signaling is induced from the cytoplasmic domain of the chimeric receptors, these cells survive and proliferate in the absence of IL-3. Such signaling is induced by ligands which bind and cross-link the extracellular domains of the chimeric receptors. Therefore binding of a growth factor ligand to the extracellular domains of the chimeric receptors causes the cells to survive and proliferate in the absence of IL-3. Addition of binding constructs that block the binding of growth factor to the extracellular domains will cause cell death in the absence of IL-3. An alternative Ba/F3 cell line which expresses a chimeric receptor containing the extracellular domain of the Tie2 receptor (that does not bind VEGF family members) is not induced by the relevant growth factors to proliferate and is used, in the presence of IL-3, as a control to test for non-specific effects of potential inhibitors.

In an exemplary assay, a binding construct that can bind VEGF-A and VEGF-C is tested. Samples of purified VEGF-A and VEGF-C are incubated with varying amounts of the binding construct for one hour at 4° C. in PBS before dilution of the mixtures 1:10 with IL-3-deficient cell culture medium. Ba/F3 cell lines expressing receptor(s) capable of binding the growth factors are then incubated in the media for 48 hours at 37° C. To measure DNA synthesis in the cells, 1 μCi of 3H-thymidine is added and the cells are incubated for 4 hours prior to harvesting. Incorporated 3H-thymidine is measured using a cell harvester (Tomtec®) and beta counting. The ability of the binding construct to block growth factor-mediated cell growth and survival (as measured by DNA synthesis) is analyzed relative to the control Tie2 cell line in the presence of IL-3. Growth inhibition in the experimental group relative to the control group demonstrates that the binding construct blocks cell growth, presumably by blocking the binding and cross-linking of receptors by growth factor ligands at the cell surface.

Example 6

Effect of Binding Constructs on BCE Migration

Solutions containing growth factors pre-incubated alone or with varying concentrations of a binding construct are placed in wells made in collagen gel and used to stimulate the migration of bovine capillary endothelial (BCE) cells in the gel as follows. A further control comprising neither growth factor ligand nor binding construct may also be employed, as may a control with just binding construct. Binding constructs that cause a decrease in migration (relative to when growth factor alone is employed) have an indication as therapeutics to prevent or retard angiogenesis.

BCE cells (Folkman et al., Proc. Natl. Acad. Sci. (USA), 76:5217-5221 (1979)) are cultured as described in Pertovaara et al., J. Biol. Chem., 269:6271-74 (1994). These or other cells employed may be transformed with growth factor receptor if not already expressed. For testing of VEGF-A/VEGF-C binding constructs, cells would be transformed with both VEGFR-2 and/or VEGFR-3. The collagen gels are prepared by mixing type I collagen stock solution (5 mg/ml in 1 mM HCl) with an equal volume of 2×MEM and 2 volumes of MEM containing 10% newborn calf serum to give a final collagen concentration of 1.25 mg/ml. The tissue culture plates (5 cm diameter) are coated with about 1 mm thick layer of the solution, which is allowed to polymerize at 37° C. BCE cells were seeded on top of this layer. For the migration assays, the cells are allowed to attach inside a plastic ring (1 cm diameter) placed on top of the first collagen layer. After 30 minutes, the ring is removed and unattached cells are rinsed away. A second layer of collagen and a layer of growth medium (5% newborn calf serum (NCS)), solidified by 0.75% low melting point agar (FMC BioProducts, Rockland, Me.), are added. A well (3 mm diameter) is punched through all the layers on both sides of the cell spot at a distance of 4 mm, and the sample or control solutions are pipetted daily into the wells. Photomicrographs of the cells migrating out from the spot edge are taken after six days through an Olympus CK 2 inverted microscope equipped with phase-contrast optics. The migrating cells are counted after nuclear staining with the fluorescent dye bisbenzimide (1 mg/ml, Hoechst 33258, Sigma).

The number of cells migrating at different distances from the original area of attachment towards wells containing sample solutions are determined 6 days after addition of the media. The number of cells migrating out from the original ring of attachment is counted in five adjacent 0.5 mm×0.5 mm squares using a microscope ocular lens grid and 10× magnification with a fluorescence microscope. Cells migrating further than 0.5 mm are counted in a similar way by moving the grid in 0.5 mm steps. The experiments are carried out twice with similar results. Daily addition of 1 ng of FGF2 into the wells may be employed as a positive control for cell migration.

Example 7

Suppression of VEGFR-3 Signalling Pathway Improves Allograft Survival

Experiments described herein elucidate the role of lymphatic vessels and their principal growth signalling pathway, VEGF-C/VEGFR-3, in experimental cardiac allograft alloimmunity and arteriosclerosis. We found functional lymphatic vessels in rat cardiac allografts that co-expressed LYVE-1, Prox-1, VEGFR-3 and chemokine CCL21, and were active in transferring antigen presenting cells (APC). Chronic rejection enhanced the number of graft-infiltrating VEGF-C$^+$ inflammatory cells, and induced myocardial lymphangiogenesis. Lymphatic EC almost exclusively originated from donor-derived cells. Systemic VEGFR-3 inhibition with VEGFR-3-Ig gene delivery reduced allograft CCL21 production, alloimmune activation, and improved cardiac allograft survival of recipients receiving suboptimal cyclosporine A immunosuppression. In a mouse chronic rejection model, treatment with neutralizing VEGFR-3 antibodies reduced allograft CCL21 production, inflammation and arteriosclerosis. Collectively, our results indicate interplay of inflammation and lymphangiogenesis in cardiac allografts. Moreover, VEGFR-3 inhibition reduced APC trafficking possibly through direct DC-mediated and indirect CCL21 mediated effects. VEGFR-3 inhibition may thus be used as a novel non-T cell-targeted induction therapy to regulate alloimmune activation after solid organ transplantation.

Methods

Experimental Design

The effect of heart transplantation on the expression of lymphatic endothelial markers and lymphatic growth factors was investigated using a rat heterotopic heart transplantation model comparing non-transplanted hearts, acutely and chronically-rejecting cardiac allografts, and syngenic controls. Marker gene transgenic mice were used to determine the origin of VEGFR-3$^+$ lymphatic EC in chronically-rejecting mouse cardiac allografts. The functional role of VEGFR-3 singalling in alloimmune responses was investigated by perfusing rat cardiac allograft recipients intrapotally with an adenovirally expressed soluble VEGFR-3 receptor extracellular domain (Ad.VEGFR-3-Ig) that traps VEGFR-3 ligands. Neutralizing monoclonal VEGFR-3 antibodies (VEGFR-3 mAb) were used to confirm the effect of VEGFR-3 inhibition on lymphangiogenesis and inflammation-driven arteriosclerosis in chronically-rejecting mouse cardiac allografts. Permission for animal experimentation was obtained from the State Provincial Office of Southern Finland. The mice and rats received care in compliance with the "Guide for the Care and Use of Laboratory Animals" prepared by the National Academy of Sciences and published by the National Academy Press (ISBN 0-309-05377-3, revised 1996).

Rat and Mouse Heterotopic Heart Transplantation Model

Specific pathogen-free inbred male Dark Agouti (DA, RT1av1) and Wistar Furth (WF, RT1u) rats (Scanbur, Sollentuna, Sweden) weighing 250-300 g and 2-3 months of age were used. Heterotopic cardiac allografts were transplanted in abdominal position between fully MHC-mismatched strains. The donor heart was perfused through the inferior vena cava with 1 ml of +4° C. 0.9% NaCl with 500 IU heparin. The inferior and superior vena cava, and pulmonary veins were ligated. The ascending aorta and pulmonary artery were excised distally, and the donor heart was removed and kept in +4° C. PBS. The allograft aorta and pulmonary artery were then anastomozed to the abdominal aorta and vena cava inferior of the recipient. In the acute rejection model, no immunosuppression was used and the syngrafts (DA→DA) and allografts (DA→WF) were harvested at 5 days. In the chronic rejection model, the recipients received cyclosporine A (CsA, Novartis Basel, Switzerland) 2 mg/kg/d for the first week and 1 mg/kg/d thereafter, and the grafts were harvested at 8 weeks. CsA was dissolved in Intralipid (100 mg/ml, Fresenius Kabi, Bad Homburg, Germany) and was administered subcutaneously.

In the mouse model, specific pathogen-free inbred male BALB/c (B/c, H-2d) and C57BL/6J (B6, H-2b) mice (Harlan) weighing 25-30 g and 2-3 months of age were used. The recipients received FK506 (intramuscular formulation, Astellas Pharma, Tokyo, Japan) subcutaneously 3.0 mg/kg/d for the first week and 1.5 mg/kg/d thereafter as background immunosuppression, and the allografts were harvested at 8 weeks for histological and immunohistochemical analysis. This immunosuppression was chosen after preliminary studies with different FK506 dosing, as the current administration resulted in prolonged allograft survival and development of CAV.

Origin of Allograft Lymphatic EC

Transgenic marker gene mice that express LacZ under VEGFR-3 promoter (VEGFR-3/LacZ) were used to investigate the origin of allograft VEGFR-3 lymphatic EC. To investigate recipient-derived VEGFR-3 expression in the transplanted heart, Balb/c hearts were transplanted to VEGFR-3/LacZ recipients using the mouse chronic rejection heart transplant model. Replacement of allograft lymphatic EC with bone marrow (BM)-derived cells was investigated using C57 mice that had received a BM transplant from GFP-expressing syngenic mice (GFP-BM) as Balb cardiac allograft recipients using the mouse chronic rejection heterotopic heart transplant model (n=3). Allografts were harvested at 8 weeks. Samples were first incubated in 2% paraformaldehyde for 30 min, then in 20% sucrose overnight, embedded in TissueTek and snap-frozen in liquid nitrogen.

Effect of VEGFR-3 Inhibition on Alloimmune Responses in Rat Cardiac Allografts

To investigate the role of VEGFR-3 ligand inhibition in rat cardiac allografts, recipients were perfused in the beginning of the operation intraportally with adenoviral vectors ($1 \times 10^9$ pfu in 1 ml) encoding control vector (Ad.LacZ or Ad.GFP) or soluble VEGFR-3 receptor (Ad.VEGFR-3-Ig). The recipients received CsA 1.0 mg/kg/d as background immunosuppression. The recipient livers and the transplanted allografts were harvested on day 5 (ad.GFP. n=7; ad.VEGFR-3-Ig n=7) to investigate the efficiency of adenoviral gene transfer, and alloimmune activation in the allograft. The effect of intraportal ad.VEGFR3-Ig perfusion on cardiac allograft survival (ad.LacZ, n=10; ad.VEGFR-3-Ig, n=10) was investigated by harvesting allografts at 8 weeks or if the graft function deteriorated. Hepatocyte GFP expression was detected immunohistochemically.

ELISA

ELISA (Quantikine-R&D Systems) was used to detect the presence of VEGFR-3-Ig in rat serum collected at day 5 postransplantation, confirming the functionality of the adenoviral gene transfer in our system.

Effect of VEGFR-3 Inhibition in Chronically-Rejecting Mouse Cardiac Allografts

To investigate the functional role of VEGFR-3, mouse cardiac allograft recipients were treated with 800 μg of rat IgG (n=7; Sigma-Aldrich, St. Louise, Mo.) or rat anti-mouse VEGFR-3 neutralizing antibody (n=8; mF4-31C1, ImClone, New York, N.Y.). Antibodies were administered intraperitoneally every third day for four weeks, starting immediately after operation.

Histology

Cardiac transplant arteriosclerosis was determined by two independent observers in blinded manner from paraformaldehyde-fixed paraffin sections stained with hematoxylin-eosin and Resorcin fuchsin for internal elastic lamina using computer-assisted image processing (Axiovision 4.4, Carl Zeiss, Oberkochen, Germany) and measuring the area surrounded by the internal elastic lamina and vessel lumen. Arterial occlusion percentage was determined as the ratio of neointimal area and internal elastic lamina area.

Immunohistochemistry

Cryostat sections were stained using peroxidase ABC method (Vectastain Elite ABC Kit; Vector Laboratories, Burlingame, Calif.) and the reaction was revealed by 3-amino-9-ethylcarbazole (AEC, Vectastain). Immunofluorescence double stainings were performed using a sequential approach and Alexa Fluor 488 (green) and Alexa Fluor 568 (red), (Promega, Madison, Wis.) secondary antibodies. Antibodies and dilutions used were CD4 (5 μg/ml, 22021D), CD8 (5 μg/ml, 22071D), ED1 (5 μg/ml, 22451D), CD11β (5 μg/ml, 553308) and IL-2Rα (5 μg/ml, 22090D) from BDPharmingen, San Diego, Calif.; Ki67 (1:2000, NCL-Ki67p) from Novocastra Laboratories Ltd, New Castle, UK; rabbit anti-mouse affinity purified LYVE-1 (1:1000 with TSA amplification) and Anti-mouse CCL-21/6Ckine Antibody (1:200) from Professor Kari Alitalo; VEGF-C (0.5 μg/ml, ab9546) and anti-GFP (1:200, ab 290) from Abcam, Cambridge, UK; mouse anti-rat OX-62 (10 μg/ml, MCA1029G), RECA-1 (50 μg/ml, MCA970) and major histocompatibility complex (MHC) class II (10 μg/ml, MCA46R) from Serotec, Oxford, UK; VEGFR-3 (200 μg/ml, AF743) from R&D Systems, Minneapolis, Minn.; PROX-1 (0.01 mg/ml, DP 3501P) from Acris Antibodies, Hiddenhausen, Germany. All analyses were performed in a blinded manner by two independent observers.

Analysis of the Immunohistochemical Stainings

Graft-infiltrating inflammatory cells and LYVE-1$^+$, VEGFR-3$^+$ or CCL-21$^+$ lymphatic vessels with clear lumen were counted from four random fields from each quadrant of the section's parenchyme with 40× magnification and are given as the mean number of positive cells or vessels per mm2. Lymphatic vessels were also counted from the epicardium of the section and the amount of vessels are given as the mean number of positive vessels per mm$^2$.

RNA Isolation and Reverse Transcription

Total RNA was extracted using RNeasy Mini Kit (Qiagen, Hilden, Germany) (n=4-6 per group). Reverse transcription of mRNA was carried out from 100 ng total RNA in a final volume of 20 μl, using 200 U M-MLV reverse transcriptase (Sigma-Aldrich), with 20 U recombinant RNasin ribonuclease inhibitor (Promega), 0.5 mM dNTPs (Sigma-Aldrich), and 2.5 μm random nonamers (Sigma-Aldrich). After RT, 40 μl of nuclease-free water was added to each cDNA and 3 μl of each sample was used in each subsequent PCR reaction.

Real-Time PCR

External standards were used to generate a standard curve for each gene of interest. The templates of these standards consisted of PCR fragments generated with the same primers as used in real-time PCR. The DNA concentrations were determined by spectrophotometry (Eppendorf, Hamburg, Germany), followed by calculation of the PCR fragment concentrations. For each standard curve, 10-fold serial dilutions were made starting from $10^7$ PCR fragments. The number of copies of the gene of interest was calculated from the corresponding standard curve using LightCycler software (Roche, Basel, Switzerland).

Real-time RT-PCR reactions were carried out in a LightCycler using LightCycler FastStart DNA MasterPLUS SYBR Green I mix (Roche), primer concentrations of 0.4 µM, and a cDNA amount corresponding to 5 ng total RNA in a reaction volume of 10 µl. A typical protocol included a 10-min denaturation step at +95° C. followed by 35 cycles with a +95° C. denaturation step for 10 sec, annealing at +59° C. for 10 sec, and extension at +72° C. depending on the length of the product (1 sec for 25 bp). Measurement of the PCR product was performed at the end of each extension period. Amplification specificity was checked using melting curve analysis. Results are given in relation to 18S rRNA molecule numbers.

The following primers for rat IL-2 (Gene Bank accession no. NM_053836), IL-4 (acc. No. NM_201270), IL-6 (acc. No. NM_012589), IL-10 (acc. No. NM_012854), TNF-α (acc. No. NM_012675), IFN-γ (acc. No. NM_138880), CCL-21 (acc. No. NM_011124) and FOXP-3 (acc. No. XM_228771) were used:

```
IL-2 fwd
                              (SEQ ID NO:129)
5'-CTGAGAGGGATCGATAATTACAAGA-3';

bwd
                              (SEQ ID NO: 130)
5'-ATTGGCACTCAAATTTGTTTTCAG-3';

IL-4 fwd
                              (SEQ ID NO:131)
5'-ATGTTTGTACCAGACGTCCTTACG-3';

bwd
                              (SEQ ID NO: 132)
5'-TGCGAAGCACCCTGGAA-3';

IL-6 fwd
                              (SEQ ID NO:133)
5'-CCCAACTTCCAATGCTCTCCTAATG-3';

bwd
                              (SEQ ID NO: 134)
5'-GCACACTAGGTTTGCCGAGTAGACC-3';

IL-10 fwd
                              (SEQ ID NO: 135)
5'-TAAGGGTTACTTGGGTTGCC-3';

bwd
                              (SEQ ID NO: 136)
5'-TATCCAGAGGGTCTTCAGC-3';

TNF-α fwd
                              (SEQ ID NO:137)
5'-CTGTGCCTCAGCCTCTTCTCATTC-3';

bwd
                              (SEQ ID NO: 138)
5'-TTGGGAACTTCTCCTCCTTGTTGG-3';

IFN-γ fwd
                              (SEQ ID NO: 139)
5'-GAGGTGAACAACCCACAGA-3';

bwd
                              (SEQ ID NO: 140)
5'-TATTGGCACACTCTCTACCC-3';

CCL-21 fwd
                              (SEQ ID NO: 141)
5'-CCCTGGACCCAAGGCAGT-3';

bwd
                              (SEQ ID NO: 142)
5'-AGGCTTAGAGTGCTTCCGGG-3';
and FOXP-3 fwd
                              (SEQ ID NO: 143)
5'-GCTTGTTTGCTGTGCGGAGAC-3';

bwd
                              (SEQ ID NO: 144)
5'-GTTTCTGAAGTAGGCGAACAT-3'.
```

Flow Cytometry

The cardiac allograft spleens were harvested at 5 days after the transplantation to RPMI-1640 medium. The tissue was homogenized with a scalpel and $1 \times 10^6$ spleen cells were incubated with FITC- or PE-conjugated antibodies for 15 minutes at room temperature. The cells were then washed twice with PBS and analyzed with a FACScan (Becton Dickinson) flow cytometer. Antibodies used were CD45-FITC (MCA43FT, Serotec), CD68-RPE (MCA341PE, Serotec), OX62-RPE (MCA1029PE, Serotec). IgG1-FITC (MCA43FT, Serotec) and IgG-RPE (MCAl209PE) were used as negative isotype controls.

Statistics

All data are given as mean±SEM and analyzed by parametric Student T test, or by log-rank test (graft survival) using SPSS for Windows version 11.5.1 (SPSS inc., Chicago, Ill.). $P<0.05$ was regarded as statistically significant.

Results

Chronic Alloimmune Stimulus Induces Myocardial Lymphangiogenesis in Cardiac Allografts As lymphatic growth is often seen during inflammation, we evaluated whether acute or chronic rejection induces lymphangiogenesis in rat cardiac allografts by using lymphatic endothelium-specific hyaluronan acid receptor-1 (LYVE-1). In the acute rejection model, fully MHC-mismatched rat heterotopic cardiac allograft recipients were non-immunosuppressed, and allografts developed an intense acute rejection at 5 days. In the chronic rejection model, allograft recipients received suboptimal cyclosporine A (CsA) immunosuppression, and allografts showed chronic rejection with moderate allograft inflammation, myocardial fibrosis, and arteriosclerosis at 8 weeks. We found small and large LYVE-1⁺ vessel structures in the myocardium of normal non-transplanted and transplanted hearts. These vessels opened to larger epicardial collecting LYVE-1+ lymphatic vessels. In normal hearts and syngeneic controls, LYVE-1⁺ lymphatic vessel density was two times higher in the epicardial area than in the myocardium. Chronic rejection doubled the myocardial LYVE-1⁺ lymphatic vessel density, suggesting active lymphangiogenesis during chronic allograft inflammation. Acute rejection decreased the epicardial lymphatic vessel density, possibly indicating lymphatic vessel destruction during intense inflammation.

Immunofluorescence double stainings of chronically-rejecting cardiac allografts demonstrated the expression of lymphatic endothelial cell transcription factor Prox-1 in the nucleus of the LYVE-1⁺ cells, confirming the lymphatic phenotype. This was further supported by the observation that LYVE-1 and rat vascular endothelial cell antigen-1 (RECA-1) were not expressed in same vessels, suggesting that these are markers of lymphatic and vascular EC in the rat, respectively. The proliferation marker Ki67 was infrequently found in LYVE-1$^+$ EC, whereas several Ki67$^+$ LYVE-1$^-$ allograft-infiltrating mononuclear cells were detected outside LYVE-1$^+$ lymphatic vessels. CD4$^+$ and CD8$^+$ T lymphocytes were mainly detected outside the LYVE-1$^+$ lymphatic vessels. In contrast, ED1$^+$ macrophages and OX-62$^+$ DC were found both outside and inside the LYVE-1$^+$ vascular structures, indicating that the lymphatic vessels in cardiac allografts are functional in transferring APC.

Macrophages and CD4+ Lymphocytes are the Major Source of VEGF-C in Chronically-Rejecting Cardiac Allografts Our finding that chronic alloimune stimulus induces lymphangiogenesis in cardiac allografts prompted us to investigate the expression of a potent lymphangiogenic cytokine VEGF-C in transplanted hearts. VEGF-C was mainly expressed in graft-infiltrating mononuclear cells. The density of VEGF-C$^+$ cells was similar in non-transplanted hearts, acutely rejecting cardiac allografts, and syngenic controls, whereas myocardial VEGF-C$^+$ density was two times higher in cardiac allografts undergoing chronic rejection. Immunofluorescense double stainings showed that a subset of ED1$^+$ macrophages and CD4$^+$ lymphocytes were VEGF-C positive, whereas CD8$^+$ lymphocytes did not show VEGF-C immunoreactivity. These findings indicate that during chronic cardiac allograft rejection, macrophages and CD4$^+$ T lymphocytes are the major source for lymphangiogenic VEGF-C.

VEGFR-3 is Expressed in Lymphatic Endothelium and a Subset of Dendritic Cells in Cardiac Allografts We determined the expression of VEGFR-3—the receptor for VEGF-C—in transplanted rat hearts. VEGFR-3 immunoreactivity was detected in lymphatic-like vessels of non-transplanted and transplanted hearts. Mononuclear cells were encountered inside the VEGFR-3$^+$ vessels of cardiac allografts. Immunohistochemical staining of consecutive sections showed that VEGFR-3 and CCL21 expression was localized in the same lymphatic EC of chronically rejecting allografts. The density of VEGFR-3$^+$ vessels was generally lower in the myocardium than in the epicardial area. Myocardial VEGFR-3$^+$ vessel density was three times higher in chronically-rejecting cardiac allografts than in syngenic controls.

Immunofluorescence double stainings of chronically-rejecting cardiac allografts showed that endothelial VEGFR-3 immunoreactivity co-localized with LYVE-1 expression, although not all LYVE-1$^+$ vessels expressed VEGFR-3. In addition to the lymphatic VEGFR-3 expression, we also detected lower VEGFR-3 immunoreactivity in occasional allograft-infiltrating mononuclear cells. The majority of these VEGFR-3$^+$ cells were identified as OX-62$^+$ DC, whereas very few ED1$^+$ macrophages, and no CD4$^+$ or CD8$^+$ cells expressed VEGFR-3. ED1$^+$ macrophages were often encountered inside the VEGFR-3$^+$ lymphatic vessels. Collectively, these findings indicate that VEGFR-3 is expressed in lymphatic vessels and subset of DC in cardiac allografts.

Cardiac Allograft VEGFR-3+ Lymphatic Vessels but not Spleen Mariginal Zone VEGFR-3+ Vessels Produce CCL21

Distinct molecular properties of lymphatic endothelial cells, such as production of CCL21 chemokine (Kriehuber et al., J. Exp. Med., 194:797-808, 2001), are essential in the specialized function of lymphatic vessels in transferring APCs to secondary lymphoid organs. This prompted us to investigate whether CCL21 is produced by cardiac allograft lymphatic vessels. Immunohistochemical staining of consecutive sections showed that VEGFR-3 and CCL21 were expressed in the same lymphatic vessels of chronically-rejecting allografts. In contrast, VEGFR-3 and CCL21 expression did not co-localize in normal spleen or in the spleen of cardiac allograft recipients. Results indicated that VEGFR-3 was expressed in the endothelium of vessel-like structures around spleen T cell zones, whereas CCL21 expression localized to white pulp stromal cells and to the central arterioles. The finding that allograft VEGFR-3+ lymphatic vessels produce CCL21 suggests that lymphatic endothelial cell-derived chemokine-mediated signals are present at the exit of APCs from cardiac allografts similarly as in corneal allografts (Jin et al., Mol. Vis., 13:626-634, 2007). In contrast, the VEGFR-3+ vessels in the spleen (presumably capillaries or venous sinuses of the marginal zone) did not produce CCL21 but may be involved in leukocyte trafficking through non-CCL21-mediated mechanisms.

The Majority of VEGFR-3+ Lymphatic EC in Chronically-Rejecting Mouse Cardiac Allografts are Donor-Derived Recent evidence suggests that BM-derived and non-BM-derived VEGFR-3$^+$ cells contribute to lymphangiogenesis (Kerjaschki et al., (2006), "Lymphatic endothelial progenitor cells contribute to de novo lymphangiogenesis in human renal transplants," Nat. Med. 12: 230-234; and Maruyama et al., (2005), "Inflammation-induced lymphangiogenesis in the cornea arises from CD11b-positive macrophages," J. Clin. Invest., 115: 2363-2372). As we found active lymphangiogenesis in chronically-rejecting cardiac allografts, we next used marker gene mice as cardiac allograft recipients to determine the origin of VEGFR-3$^+$ lymphatic EC. First, C57/bl mice that had received BM transplantation from GFP mice (GFP-BM) were used as heart transplant recipients allowing the detection of BM-derived cells in cardiac allografts. The recipients were treated with suboptimal FK506 immunosuppression to prevent severe acute rejection, and the cardiac allografts were harvested eight weeks after the transplantation. Immunofluorescence double stainings showed that BM-derived GFP cells localized mainly around VEGFR-3$^+$ lymphatic vessels. Less than 4% of the BM-derived GFP cells co-localized with VEGFR-3$^+$ lymphatic EC.

As some of these GFP cells may actually be BM-derived inflammatory cells migrating to the VEGFR-3$^+$ lymphatic vessels, Balb/c hearts were next transplanted to mice that express LacZ under VEGFR-3 promoter (VEGFR-3/LacZ, C57/bl background, n=3), to allow the direct detection of recipient-derived VEGFR-3$^+$ lymphatic cells in the allografts. The x-gal staining revealed epicardial lymphatic endothelial VEGFR-3 expression in the VEGFR-3/LacZ recipient's own heart. In contrast, no recipient-derived VEGFR-3$^+$ lymphatic EC were encountered in the myocardium of wild type cardiac allografts transplanted to VEGFR-3/LacZ recipients. These results indicate that the replacement of cardiac allograft VEGFR-3$^+$ lymphatic EC with recipient BM-derived, or non-BM-derived cells is rare in this chronic rejection heterotopic heart transplantation model.

VEGFR-3 Inhibition Improves Cardiac Allograft Survival

We next determined the effect of VEGFR-3 inhibition on alloimmune response by injecting suboptimally immunosuppressed rat cardiac allograft recipients intraportally with adenovirus vector encoding the soluble form of VEGFR-3

(Ad.VEGFR-3-Ig, VEGF-C/D-trap). Hepatocyte GFP expression was seen in Ad.GFP-perfused recipients, but not in Ad.VEGFR-3-Ig-perfused recipients. See FIGS. 1A and 1B. Also, the serum levels of VEGFR-3-Ig were elevated in the Ad.VEGFR-3-Ig-perfused animals 5 days after transplantation (FIG. 1C), and remained elevated for at least 21 days, confirming the functionality of the adenoviral gene transfer.

Next, we investigated the effect of VEGFR-3 inhibition on the survival of fully MHC-mismatched rat cardiac allografts. In non-immunosuppressed cardiac allograft recipients, intraportal Ad.VEGFR-3-Ig-perfusion increased allograft survival from 4.9 to 6.0 days ($p<0.05$, $n=7$ per group). Intraportal Ad.VEGFR-3-Ig-perfusion in cardiac allograft recipients receiving suboptimal dose of CsA significantly improved allograft survival. See FIG. 1D. Our results thus suggest that VEGFR-3 inhibition together with CsA background immunosuppression markedly prolongs long-term allograft survival while it only has a marginal effect as sole treatment in a fully MHC-mismatched model.

VEGFR-3 Inhibition Decreases Cardiac Intragraft CCL21 Production, Alloimmune Activation and Effector Cell Recruitment To clarify the underlying mechanisms behind the beneficial effect on allograft survival, we used the same experimental setting (Ad.VEGFR-3 perfusion and suboptimal CsA immunosuppression) and harvested the allografts 5 days after transplantation. Ad.VEGFR-3-Ig-perfusion decreased the density of, graft infiltrating CD8+ T cells, and alloimmune activation in the form of IL-2R$\alpha^+$ and MHC class II expression. In contrast, no changes in graft infiltrating ED1$^+$ macrophages, allograft CD4$^+$ cells or OX-62$^+$ DC s or the density of LYVE-1$^+$ vessels were observed.

Real time RT-PCR showed that intraportal Ad.VEGFR-3-Ig perfusion resulted in a two-fold decrease in allograft CCL21 mRNA expression. No significant changes were observed in IL-6, Foxp3, INF-$\gamma$, IL-10, TNF-$\alpha$, Nf$\kappa\beta$, lymphotoxin (LT)-$\alpha$ or LT-$\beta$ mRNA levels. Together, these findings indicate that VEGFR-3 inhibition decreases alloimmune activation and infiltration of effector cells in cardiac allografts together with a decrease in intragraft CCL21 production.

VEGFR-3 Inhibition Decreases Dendritic Cell Recruitment to Spleen

We next investigated whether the reduction of alloimmune response with VEGFR-3 inhibition after heart transplantation was associated with impaired APC recruitment to recipient secondary lymphoid organs using FACS analysis from peripheral blood and spleen leukocytes. Ad.VEGFR-3-Ig perfusion decreased the proportion of OX-62$^+$ DC, and ED1$^+$ cells (p=NS) of spleen CD45$^+$ leukocytes. The proportion of OX-62$^+$ cells of peripheral blood leukocytes was $12.7\pm2.5\%$ in Ad.GFP group and $15.7\pm4.2\%$ in Ad.VEGFR-3 group. This indicates that the decrease in spleen DC was due to impaired APC homing to the spleen rather than impaired APC mobilization from the BM. Results further indicated that VEGFR-3-Ig increased the proportion of VEGFR-3+ leukocytes in peripheral blood possibly due to a trapping effect. VEGFR-3-Ig did not change the proportion of OX-62+ DC in peripheral blood but decreased the recruitment of OX-62+ DC to the recipient spleen. These results indicate that VEGFR-3 regulates APC traffic to secondary lymphoid organs.

VEGFR-3 Inhibition Regulates Chemokine Balance Between Allograft and Secondary Lymphoid Organs RT-PCR analysis of a subpopulation (n=3) revealed that VEGFR-3 inhibition was associated with over two-fold increase in spleen mRNA levels of CCL21, IL-10, and Foxp3. Spleen VEGFR-3 immunoreactivity was mainly detected in lymphatic-like vessel structures surrounding the T cell zones, whereas CCL21 immunoreactivity was mainly detected in the T cell zones and the central arterioles, and did not co-localize with VEGFR-3$^+$ vessels. In cardiac allografts on the other hand, CCL21 was mainly expressed in VEGFR-3$^+$ lymphatic-like vessels. These observations, together with the unexpected CCL21 response after VEGFR-3 inhibition, may indicate that CCL21 is differentially regulated in peripheral tissues and secondary lymphatic tissue.

We performed real time RT-PCR analysis of the recipient spleen 5 days after heart transplantation to investigate whether VEGFR-3-Ig decreased CCL21 production in the spleen similarly as in the allograft. In contrast to the results in the transplanted heart, treatment with VEGFR-3-Ig actually resulted in 1.5 times higher CCL21 mRNA levels in the spleen. We also observed that VEGFR-3-Ig markedly increased the ratio of spleen-to-allograft CCL21 mRNA from 9:1 to 23:1. The differential effect of VEGFR-3 inhibition on allograft and spleen CCL21 mRNA production may be explained by the finding that cardiac allograft VEGFR-3+ lymphatic vessels produced CCL21 whereas VEGFR-3 and CCL21 were not produced by the same cells in the spleen. Further RT-PCR analysis of the spleen revealed that VEGFR-3 inhibition resulted in a significant increase in Treg transcription factor Foxp3. This is interesting in the light of recent reports that CCL21 plays a vital role in homing, localization and function of Tregs (Schneider et al., J. Exp. Med., 204:735-745, 2007; Kocks et al., J. Exp. Med., 204:723-734, 2007). In addition, VEGFR-3 inhibition did not significantly alter spleen mRNA levels of IL-10 (Hori et al., Science, 299:1057-1061, 2003), IL-6, IFN-$\gamma$, TNF-$\alpha$, NF-$\kappa$B, LT-$\alpha$, and LT-$\beta$ at 5 days after transplantation. These results suggest that VEGFR-3 inhibition regulates chemokine balance between allograft and secondary lymphoid organs in favour of attenuated immune response.

VEGFR-3 Neutralizing Monoclonal Antibody Decreases Inflammation and Inflammation-Driven Arteriosclerosis in Chronically-Rejecting Mouse Cardiac Allografts We wanted to confirm the results of VEGFR-3 inhibition with neutralizing antibodies against VEGFR-3 in another chronic rejection heart transplantation model. Mouse cardiac allograft recipients received suboptimal FK506 immunosuppression to prevent intense acute rejection and to allow the development of chronic rejection at 8 weeks. In addition, the recipients were treated either with rat IgG or rat anti-mouse neutralizing antibodies (VEGFR-3 mAb, ImClone) against VEGFR-3 for one month. At two months, the effect of VEGFR-3 inhibition reduced the density of VEGFR-3$^+$ and CCL-21$^+$ lymphatic vessels in the allograft. In addition, VEGFR-3 inhibition reduced the density of CD4$^+$ lymphocytes, CD8$^+$ lymphocytes, and CD11b$^+$ myelomonocytic cells. Interestingly, treatment with VEGFR-3 mAb significantly decreased the mean arterial occlusion compared to the control group. Our results thus show that early treatment with neutralizing VEGFR-3 antibody decreases allograft CCL21 production, inflammation, and arteriosclerosis in chronically-rejecting mouse cardiac allografts.

Finally, because lymphoid neogenesis (i.e., organization of chronic inflammatory infiltrates into functional ectopic germinal centers or tertiary lymphoid organs (TLOs)), has been linked with the formation of chronic rejection (Thaunat et al., Proc. Natl. Acad. Sci. USA, 102:14723-14728, 2005; Baddoura et al., Am. J. Transplant, 5:510-516, 2005; Nasr et al., Am. J. Transplant., 7:1071-1079, 2007), we investigated the presence of TLOs in our chronically-rejecting cardiac allografts. Immunohistochemical stainings revealed a characteristic pattern of peripheral node adressin-positive high endothelial venules, and discrete B and T cell accumulation only in one allograft in the control group (FIG. 10, A-C). This implies that lymphoid neogenesis is not a critical phenomenon at least in the two month end-point of our chronic rejection model, and the effect of VEGFR-3 inhibition on TLO formation thus cannot be evaluated in this model within this timeframe.

Analysis

The lymphatic network is adapted at both structural and molecular level to transfer leukocytes out of tissues. The thin-walled lymphatic capillaries provide easy access for interstitial cells and fluid, whereas the smooth muscle coverage and valves of the collecting lymphatic vessels provide unilateral movement towards secondary lymphoid organs. Lymphatic EC have distinct molecular properties that reflect their function and have been utilized for the detection of lymphatic vessels. These cells express podoplanin, hyaluronan receptor LYVE-1, VEGFR-3 and inflammatory cytokine CCL21 that are not found in vascular EC. The identification of signals that regulate lymphatic growth—most importantly VEGF-C/VEGFR-3—has greatly improved our knowledge of lymphatic vessels in both physiological and pathological situations.

Effective transfer of APC from transplanted organs to secondary lymphoid organs is critical for the priming of alloreactive T cells and the development of alloimmune responses that may be detrimental for the heart transplant recipient. In the current study, we found that chronic cardiac allograft rejection increased myocardial lymphatic vessel density. The capillary lymphatics in cardiac allografts opened to epicardial collecting lymphatic vessels, and expressed the lymphatic transcription factor Prox-1, LYVE-1, VEGFR-3, and CCL21. In addition, APC such as macrophages and DC were often encountered inside these vessels, indicating vessel functionality. Active lymphangiogenesis is seen in human kidney transplants with nodular inflammatory infiltrates (Kerjaschki et al., (2004), "Lymphatic neoangiogenesis in human kidney transplants is associated with immunologically active lymphocytic infiltrates," J. Am. Soc. Nephrol., 15: 603-612) and in other inflammatory conditions. As the observed lymphangiogenesis in chronically-rejecting allografts in this study was accompanied with an increase in VEGF-C-producing macrophages and CD4+ lymphocytes, our results suggest interplay of chronic inflammation, VEGF-C/VEGFR-3 signalling, and lymphangiogenesis in cardiac allografts.

Lymphatic EC in the transplanted heart may originate from recipient BM cells, from recipient non-BM cells or from donor cells. Recently, it was shown that recipient-derived lymphatic endothelial progenitor cells—possibly in the form of macrophages—participate in lymphangiogenesis of human kidney allografts (Kerjaschki et al., (2006), "Lymphatic endothelial progenitor cells contribute to de novo lymphangiogenesis in human renal transplants," Nat. Med. 12: 230-234). Also, macrophages may directly trans-differentiate to lymphatic EC in the inflamed cornea (Maruyama et al., (2005), "Inflammation-induced lymphangiogenesis in the cornea arises from CD11b-positive macrophages," J. Clin. Invest. 115: 2363-2372), and may provide cytokines for the expansion of resident lymphatics (Kerjaschki, D. (2005), "The crucial role of macrophages in lymphangiogenesis," J. Clin. Invest. 115: 2316-2319). Here, we used marker gene mice as cardiac allograft recipients and found that recipient-derived cells contribute only minimally to the formation of VEGFR-3+ lymphatic vessels in the heterotopically transplanted hearts. As Kerjascki et al found that about 13% of Prox-1+ lymphatic vessels in rejected and nephrectomized kidney transplants originated from the recipient, it is possible that the involvement of recipient-derived lymphatic progenitors is dependent on the severity of allograft injury. Paralleling this hypothesis, the degree of allograft injury may determine whether allograft vascular EC originate from the recipient—as in aortic transplantation—or from the donor—as in cardiac allografts (Hillebrands et al., (2001), "Origin of neointimal endothelium and alpha-actin-positive smooth muscle cells in transplant arteriosclerosis", J. Clin. Invest., 107: 1411-1422). Also, the actual effect of lymphatic endothelium chimerism of transplanted organs on alloimmune responses remains unknown.

Chen et al (2004) have recently reported that VEGFR-3 inhibition impairs DC migration to draining LN and improves the survival of cornea transplants. These effects were possibly mediated through direct inhibition of VEGFR-3+DC migration independent of lymphangiogenic effects. However, the functional role of VEGFR-3 after solid organ transplantation has been unclear. Here, systemic VEGFR-3 inhibition using adenoviruses encoding soluble VEGFR-3-Ig that traps VEGFR-3 ligands decreased DC migration to spleen, alloimmune activation and improved the long term survival of cardiac allografts. Similarly, treatment with neutralizing VEGFR-3 antibodies decreased allograft inflammation and development of inflammation-driven arteriosclerosis in the chronically rejecting mice cardiac allografts. As we found VEGFR-3$^+$ DC in cardiac allografts, it is possible that VEGFR-3 inhibition had direct effects on DC migration in the current study similar to the findings in the corneal transplantation model (18).

In addition to the direct effects on VEGFR-3+ DC, our results suggest that VEGFR-3 inhibition also had lymphatic EC- and chemokine-mediated effects. Specifically, both VEGFR-3 and CCL21, a chemokine for CCR7+ APC, were co-expressed in allograft lymphatic EC, and VEGFR-3 inhibition decreased allograft CCL21 production. Our results thus indicate that VEGFR-3 in allograft lymphatic EC may regulate the production of CCL21, that may in turn facilitate the movement of APC from the allograft to secondary lymphoid tissue and subsequent alloimmune activation. Surprisingly, in contrast to the allograft, VEGFR-3 inhibition increased CCL21 production in the spleen. VEGFR-3 was mainly expressed around the spleen T cell zones whereas the central arterioles and stromal cells of the T cell zones were the main source of CCL21 in the spleen. Therefore, the regulation of CCL21 production may be different in the heart and the spleen due to the differential pattern of VEGFR-3 and CCL21 expression.

In experimental studies, the survival of cardiac allografts is modestly increased in CCR7-deficient recipients as well as in CCL21-deficient recipients (Forster et al., (1999), "CCR7 coordinates the primary immune response by establishing functional microenvironments in secondary lymphoid organs," Cell, 99: 23-33; and Colvin et al., (2005), "CXCL9 antagonism further extends prolonged cardiac allograft survival in CCL19/CCL21-deficient mice," Am. J. Transplant., 5: 2104-2113). Collectively, these studies show an important but not critical role of CCL21/CCR7-signalling in alloimmune reactions.

In the present study, VEGFR-3 inhibition that resulted in decreased CCL21 production did not completely prevent alloimmune responses in recipients receiving suboptimal dose of CsA. Therefore, VEGFR-3 inhibition alone may not completely prevent alloimmune responses in transplant recipients. For optimal results VEGFR-3 inhibition can be used as induction or adjuvant therapy in the prevention and treatment of acute rejection, in addition to (in combination with) conventional T-cell-targeted immunosuppression. Combination therapy targeting other VEGFR's or PDGFR's or their cognate growth factors also is contemplated. Interestingly, VEGFR-3 inhibition resulted in over two-fold increase in spleen Foxp3 and IL-10 mRNA production. Therefore, VEGFR-3 inhibition may also have beneficial effects on Treg, but further studies are needed to clarify the effect of VEGFR-3 signalling on Tregs.

In conclusion, these results indicate that VEGF-C/VEGFR-3 signalling has important effects on proximal events in cardiac allograft alloimmunity and inflammation-driven arteriosclerosis, possibly through regulating lymphatic endothelial cell CCL21 production and leukocyte trafficking and through direct effects on VEGFR-3+ DC. As an important safety aspect, adult lymphatic vessels are fairly resistant to VEGFR-3 inhibition, suggesting that this treatment in transplant recipients would also primarily inhibit lymphangiogenesis and the functionality of lymphatic vessels in contrast to regression of the existing lymphatic network. Therefore, VEGFR-3 inhibition could be used as a non-T cell-targeted induction therapy to regulate alloimmune activation after solid organ transplantation.

Example 8

VEGFR-1 and -2 Regulate Inflammation, Myocardial Angiogenesis and Arteriosclerosis in Chronically Rejecting Cardiac Allografts/R1

We investigated how the two vascular endothelial growth factor receptors VEGFR-1 and VEGFR-2 regulate inflammation and angiogenesis in chronically rejecting cardiac allografts. As described below in detail, chronic rejection in mouse cardiac allografts induced primitive myocardial, adventitial, and intimal angiogenesis with endothelial expression of CD31, stem cell marker c-kit, and VEGFR-2. Experiments using marker gene mice or rats as cardiac allograft recipients revealed that replacement of cardiac allograft endothelial cells with recipient bone-marrow- or non-bone-marrow-derived cells was rare and restricted only to sites with severe injury. Targeting VEGFR-1 with neutralizing antibodies in mice reduced allograft CD11b+ myelomonocyte infiltration and allograft arteriosclerosis. VEGFR-2 inhibition prevented myocardial c-kit+ and CD31+ angiogenesis in the allograft, and decreased allograft inflammation and arteriosclerosis. These results indicate an interplay of inflammation, primitive donor-derived myocardial angiogenesis, and arteriosclerosis in transplanted hearts, and further indicate that targeting VEGFR-1 and -2 with inhibitors differentially regulate these pathological reparative processes.

Materials and Methods

Experimental Design

Mouse chronic rejection heart transplantation model and immunohistochemical stainings were used to identify angiogenesis and progenitor cells in allografts. Marker gene mice and rats, and strain-specific major histocompatibility complex (MHC) class I antibodies, were used to determine whether allograft EC originate from the donor, or from the recipient. Neutralizing antibodies were used to investigate the functional role of VEGFR-1 and VEGFR-2 on mouse cardiac allograft angiogenesis, inflammation, and arteriosclerosis.

Mouse Chronic Rejection Heterotopic Heart Transplantation Model

Heterotopic cardiac allografts were transplanted in abdominal position from Balb (B/c, H-$2^d$) to C57 (B6, H-$2^b$) mice (Harlan, Horst, The Netherlands). The recipients received sub-optimal FK506 immunosuppression (i.m. formulation, Astellas Pharma, Tokyo, Japan) and the allografts were harvested at 8 weeks.

Origin of Allograft Endothelial Cells

Tie1/LacZ rats32 were used as allograft recipients (n=4) or donors (n=14, with or without immunosuppression) to investigate Tie1 expression, and the origin of Tie1-positive EC in transplanted hearts. Contribution of BM-derived cells in allograft angiogenesis was investigated using recipient mice with green fluorescent protein-expressing BM cells (GFP-BM, n=3). See Rajantie et al., "Adult bone marrow-derived cells recruited during angiogenesis comprise precursors for periendothelial vascular mural cells," Blood, (2004); 104: 2084-2086.

VEGFR-1 and VEGFR-2 Inhibition

Cardiac allograft recipients were treated with 800 μg of rat IgG (n=8; Sigma-Aldrich, St. Louis, Mo.), anti-VEGFR-1 antibody (n=9; MF1, ImClone, New York, N.Y.), anti-VEGFR-2 antibody (n=9; DC101, ImClone) or their combination (n=10) every third day for 10 doses, starting immediately after the transplantation.

Histology and Immunohistochemistry

Arterial occlusion percentage was determined using morphometry. Immunohistochemical stainings were performed using peroxidase ABC method or Alexa Fluor 488 (green) and 568 (red, Promega, Madison, Wis.) secondary antibodies.

Analysis of Immunohistochemical Stainings

Allograft parenchymal inflammatory cells and c-kit+ capillaries were counted from 16 random sections, and are summarized as the mean density of positive cells or vessels. CD31 and α-SMA immunofluorescense stainings were analyzed with Axioplan 2 microscope and Axiovision 4.2 analysis software (Carl Zeiss, Oberkochen, Germany) using a semiautomated script.

Real Time RT-PCR

Total RNA was extracted using RNeasy Mini Kit (Qiagen, Hilden, Germany) (n=4-6 per group). RT-PCR reactions were carried out using LightCycler (Roche, Basel, Switzerland) and the results are given in relation to 18S rRNA molecule numbers.

Statistical Analysis

Data are mean±SEM and analyzed by parametric ANOVA with Dunnett's correction to compare the treatment groups to the control group. Linear regression analysis was applied to evaluate relation of c-kit+ cells to CD11b+ cells and to cardiac allograft vasculopathy (CAV). P<0.05 was regarded as statistically significant.

Results

Chronic Rejection Induces Primitive Myocardial Angiogenesis in Cardiac Allografts We detected only occasional stem cell marker c-kit immunoreactive cells in cross-sections of non-transplanted mouse hearts. In contrast, numerous myocardial capillary-like c-kit+ cells and c-kit+ vein EC were observed in chronically-rejecting cardiac allografts harvested 2 months after the transplant operation. In allografts with severe arteriosclerotic changes, c-kit+ cells were also found in the adventitia and intima of coronary arteries.

Allograft myocardial c-kit+ cells were nearly all positive for endothelial marker CD31, and co-expressed VEGFR-2. The majority of c-kit+ capillaries did not express proliferation marker Ki67, but some c-kit+ cells with nuclear Ki67 immunoreactivity were also detected.

In contrast to the preferential expression of VEGFR-2 in the endothelium, VEGFR-1 was mainly expressed in allograft α-SMA+ SMC. In peripheral blood, over 50% of VEGFR-1+ cells coexpressed the myelomonocyte marker CD11b.

No specific immunoreactivity with IgG control was observed.

A positive correlation was verified between the density of c-kit+ capillaries in the myocardium and the number of allograft-infiltrating CD11b+ myelomonocytic inflammatory cells, as well as with the incidence of arteriosclerotic changes and the mean occlusion of allograft arteries. These results indicate that chronic rejection in transplanted hearts induces myocardial, adventitial and intimal angiogenesis with endothelial expression of primitive markers c-kit and VEGFR-2.

Endothelial Replacement with Recipient-Derived Cells is Rare in Cardiac Allografts Because recipient-derived circulating EPC could differentiate to EC in the transplanted heart, we determined the origin of cardiac allograft EC by using marker gene rats (Tie1/LacZ) or mice (GFP-BM) as allograft recipients.

When Tie1/LacZ allografts were transplanted to wild type (WT) recipients, areas with abundant X-gal reactivity in venous and arterial allograft endothelium was detected, indicating Tie1 expression in the donor EC.

Next, WT cardiac allografts were transplanted to Tie1/LacZ recipients to detect recipient-derived EC in the transplanted hearts. Only few donor-derived X-gal+ EC, localizing to severely fibrotic areas, were seen in cross-sections in a total of 14 WT cardiac allografts.

Additionally, GFP-BM mice were used as cardiac allograft recipients, allowing the detection of BM-derived cells in the allografts. The majority of allograft-infiltrating CD11b+ myelomonocytic cells expressed GFP. Although GFP+ cells often surrounded allograft blood vessels, no co-localization with allograft CD31+ or c-kit+ capillaries was detected.

Donor- and recipient-specific MHC class I antibodies were used to identify the source of EC in allograft arteriosclerotic arteries. Numerous recipient MHC class I+ cells were found around occluded arteries, whereas only few positive cells were detected in the intima. In contrast, abundant donor MHC Class I immunoreactivity was found in the neointima. The contribution of recipient-derived SMC to neointimal formation was not assessed, as MHC Class I expression was low in SMC34.

VEGFR-2 Inhibition Normalizes C-kit+ and CD31+ Capillary Density in Chronically Rejecting Cardiac Allografts To investigate the functional role of VEGFR-1 and -2, chronically rejecting mouse cardiac allograft recipients with suboptimal FK506 immunosuppression were treated with rat IgG (n=8); or with antibodies against VEGFR-1 (MF1, n=9), antibodies against VEGFR-2 (DC101, n=9), or both antibodies against VEGFR-1 and R-2 (n=10) for thirty days. Two months after heart transplantation, the antibodies targeting VEGFR-2 reduced the density of myocardial c-kit+ capillaries and CD31+ capillaries in the allograft to the level found in non-transplanted mouse hearts. VEGFR-1 inhibition also resulted in a smaller decrease in c-kit+ capillary density ($p$=NS with Dunnett's correction, $p<0.05$ with LSD correction). VEGFR-1 or -2 inhibition did not change the density of SMC coated vessels (α-SMA+), indicating that VEGFR-2 inhibition specifically regulated angiogenesis at microvascular level.

VEGFR-1 and -2 Inhibition Reduces Inflammation in Chronically Rejecting Cardiac Allografts Immunohistochemical analysis showed that targeting VEGFR-1, VEGFR-2, or both profoundly reduced the density of allograft-infiltrating CD11b+ myelomonocytic cells. VEGFR-2 inhibition also resulted in a similar reduction in CD8+ and CD4+ lymphocyte density in the allograft (for the combination group: $p$=NS with Dunnett's correction and $p<0.05$ with LSD correction).

VEGFR-1 and -2 Inhibition Reduces Arteriosclerosis in Chronically Rejecting Cardiac Allografts Morphometrical analysis of allograft arteries revealed that targeting VEGFR-1, VEGFR-2, or both decreased the incidence of allograft arteries with intimal changes from about 55% in the IgG control mice to under 40% in the mice receiving anti-VEGFR-1 ($p<0.05$), anti-VEGFR-2 ($p<0.05$), or both ($p<0.01$). A similar result was also obtained on the mean occlusion of allograft arteries (about 18% arterial occlusion in the IgG controls, compared to about 7% in the anti-VEGFR-1 mice ($p<0.01$), about 11% in the anti-VEGFR-2 mice ($p<0.05$), and about 10% in the mice receiving both antibodies ($p<0.05$). These results indicate that both VEGFR-1 and -2 are involved in events leading to CAV.

Effect of VEGFR-1 and -2 Inhibition on Allograft Cytokine mRNA Levels

Finally, we used real time RT-PCR to determine the mRNA levels of inflammatory cytokines IFN-inducible protein-10 (IP-10) and monocyte chemotactic protein-1 (MCP-1) that are potentially regulated by VEGF in cardiac allografts, and the mRNA levels of stem cell factor (SCF) that is the ligand for c-kit. The analysis revealed that VEGFR-2 inhibition decreased allograft IP-10 mRNA by approximately 50% alone, and by 75% in combination with VEGFR-1 inhibition, and MCP-1 mRNA by 50%. In contrast, allograft TNF-α and SCF mRNA levels were similar in the control and treatment groups. These results indicate that the VEGFR-2 inhibition regulated at least in part the T cell and monocyte recruitment by decreasing IP-10 and MCP-1 production, respectively. Also, the effect of VEGFR-2-inhibition on c-kit+ capillaries was not associated with changes in SCF production.

Analysis

Angiogenesis is a prominent feature in the intima and adventitia of cardiac allograft coronary arteries and it may be a driving force for the development of CAV. The results of these experiments demonstrate that, in addition to intimal and adventitial angiogenesis, chronic rejection induces the expression of primitive markers c-kit and VEGFR-2 in allograft myocardial capillaries. As the density of myocardial c-kit+ capillaries correlated with the severity of cardiac allograft inflammation and arteriosclerosis, alloimmune and ischemic stimuli may be important regulators of the myocardial angiogenesis we observed. This primitive ckit+ angiogenic response probably represents a repair process that, interestingly, in light of the present VEGF intervention results, may in fact aggravate inflammation and arteriosclerosis in transplanted hearts. Importantly, there may be a balance between early capillary formation and later destruction of allograft capillaries as seen in skin transplants. (See Moulton et al., "Angiogenesis in the huPBL-SCID model of human transplant rejection," Transplantation, (1999); 67:1626-1631.)

In experiments using marker gene animals and donor- or recipient-specific antibodies, we found only few recipient-derived EC in the transplanted hearts and they were restricted to severely fibrotic areas. These observations suggest that recipient-derived circulating cells do not differentiate into allograft EC unless the injury to the allograft extensive. Although this notion argues against direct involvement of recipient-derived EPC in allograft angiogenesis, these circulating cells may have important paracrine effects. Our results on the origin and c-kit+ phenotype of allograft EC further indicates that donor-derived progenitor cells—such as resident cardiac stem cells or adventitial stem cells—directly participate in allograft angiogenesis. Alternatively, the hypoxic and inflammatory signals related to the transplantation may have induced dedifferentiation of allograft EC to a more primitive phenotype. Interestingly, EPC-derived soluble factors such as VEGF, VEGF-B, stromal cell derived factor-1, and insulin-like growth factor-1, and also hepatocyte growth factor may regulate the functions of c-kit+ cardiac progenitor cells, and the present results suggest important role for VEGFR-2.

VEGF is perhaps the most important angiogenic cytokine and it also has many proinflammatory properties. The present findings support the theory of regulatory role of VEGF in the pathogenesis of alloimmune responses and CAV in transplanted hearts, and shed light to the mechanisms, and the two VEGFR involved. In transplanted hearts VEGFR-2 inhibition reduced myocardial angiogenesis to the level seen in normal hearts, consistent with the important angiogenic role for VEGFR-2. In addition, targeting VEGFR-2 decreased inflammatory cell infiltration, and production of IP-10 and MCP-1 in the allograft, similarly to previous reports with anti-VEGF therapies. (See, e.g., Reinders et al., "Proinflammatory functions of vascular endothelial growth factor in alloimmunity," J. Clin. Invest., (2003); 112:1655-1665.) Our results thus suggest that VEGFR-2 in cardiac allografts functions mainly at the endothelial level and regulates both pathological capillary angiogenesis and inflammation. Involvement of VEGFR-2 in cardiac inflammation may be a more general phenomenon, as the receptor participates in cardiac dysfunction during sepsis, and also in vascular permeability following myocardial infarction.

In contrast to VEGFR-2, VEGFR-1 was primarily found in allograft SMC and in peripheral blood myelomonocytic cells. As VEGFR-1 directly regulates SMC during arterial injury, VEGFR-1 inhibition in the current study may have directly decreased SMC recruitment to the intima. VEGFR-1 inhibition also profoundly reduced myelomonocyte recruitment to the allograft, consistent with its role in monocytes and inflammatory diseases. Although VEGFR-2 inhibition prominently decreased the density of myocardial c-kit+ cells, VEGFR-1 inhibition had a similar but more subtle effect. This indicates that also VEGFR-1 may in part regulate the capillary angiogenesis, and possibly involves cross-talk with VEGFR-2, or in-direct inflammation-mediated effects. The reason why combined VEGFR-1 and -2 inhibition did not have a beneficial additive effect may be explained by the moderate injury in the current experimental setting. Supporting this, our unpublished trachea transplantation findings show additive beneficial effect after severe but not after moderate tracheal injury. (See also Sho et al., "Function of the Vascular Endothelial Growth Factor Receptors Flt-1 and Flk-1/KDR in the Alloimmune Response In Vivo," Transplantation, (2005); 80: 717-722.)

In summary, these experiments demonstrated that chronic rejection in cardiac allografts induced donor-derived capillary angiogenesis. Also, selective VEGFR-inhibition prevented allograft angiogenesis and had beneficial effects on inflammation and arteriosclerosis. These results indicate therapeutic applications for anti-VEGF strategies during pathological angiogenesis and inflammation in transplanted hearts.

Example 9

Combination Therapy Targeting Receptors of Multiple Growth Factors

The data in Examples 7 and 8 implicate VEGFR-1, VEGFR-2, and VEGFR-3 (and the growth factor ligands of these receptors) in chronic allograft rejection, particularly with reference to the model system used: cardiac transplants.

The experiments of Examples 7 and 8 are modified in that new combinations of inhibitors of growth factors and/or growth factor receptors are employed, and the protective effects of the combinations are evaluated. Evidence exists that the PDGF receptors and PDGF ligands may have a role in allograft disease. See, e.g., Nykänen et al., "Angiogenic Growth Factors in Cardiac Allograft Rejection," Transplantation, (2006); 82: S22-S24, incorporated herein by reference. It is expected that combinations of inhibitors that are directed to receptors of distinct growth factor ligands (and/or directed to distinct growth factors themselves) will have additive or synergistic effects. All combinations described herein are specifically contemplated, including but not limited to the following:

(a) inhibitor of VEGFR-3 interaction with its ligands (VEGF-C or D), in combination with one or more inhibitors of VEGFR-1 and its ligands, or inhibitors of VEGFR-2 and its ligands, or both;

(b) inhibitor of VEGFR-3 interaction with its ligands, in combination with one or more inhibitors of PDGFR-alpha and its ligands, or PDGFR-beta and its ligands, or both;

(c) inhibitor of VEGFR-3 interaction with its ligands in combination with both (i) inhibitor of VEGFR-1 and its ligands, or inhibitor of VEGFR-2 and its ligands; and (ii) inhibitor of PDGFR-alpha and its ligands, or PDGFR-beta and its ligands;

(d) inhibitors of VEGFR-3, VEGFR-2, VEGFR-1, PDGFR-alpha, and PDGFR-beta with their respective ligands;

(e) inhibitors of VEGFR-1 or VEGFR-2 in combination with inhibitors of PDGFR-alpha or PDGFR-beta, and their respective ligands.

The inhibition of multiple receptors or ligands can be achieved with multivalent inhibitor substances described herein; small molecule non-specific inhibitors (e.g., tyrosine kinase inhibitors); or with co-administration of multiple, selective inhibitors, such as those described herein. The inhibition can be directed to inhibit ligand/receptor interaction; or to inhibit expression of the ligands or receptors; or to inhibit downstream signaling, for example. A composition comprising an inhibitor can be administered, or a composition comprising a pro-drug that is metabolized into an inhibitor can be administered; or a polynucleotide that encodes an inhibitor can be administered in a manner that achieves expression of the encoded inhibitor in the recipient organism.

Example 10

Inhibition of Rejection of Other Organ Grafts and in Other Species

The experiments described in Examples 7-9 are repeated in rodent models for all other organ transplants, including kidney, liver, lung, pancreas, intestine, and esophagus; to demonstrate that therapy directed to these molecular targets for intervention is effective with respect to recipients of other organ transplants.

The experiments described in Examples 7-9, or in the preceding paragraph, are repeated in larger mammals (e.g., felines, canines, porcines, equines, bovines, primates) to demonstrate efficacy in other species that may be considered more representative of humans, as a prerequisite to proving efficacy in human clinical trials.

The foregoing description and examples have been set forth merely to illustrate the invention and are not intended to be limiting. Because modifications of the disclosed embodiments incorporating the spirit and substance of the invention may occur to persons skilled in the art, the invention should be construed to include everything within the scope of the appended claims and equivalents thereof. The patents, patent application publications and other publications (e.g., Journal articles, and web/Internet materials) referenced herein are incorporated in their entirety.

Although the applicant(s) invented the full scope of the claims appended hereto, the claims are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

The patents, patent application publications and other publications (e.g., Journal articles) referenced herein are incorporated in their entirety.

What is claimed is:

1. A method for inhibiting rejection of a vascularized tissue or vascularized organ transplant, or for inhibiting arteriosclerosis in a human allograft transplant recipient, comprising: administering to a human allograft transplant recipient a composition that comprises an endothelial growth factor inhibitor in an amount effective to inhibit rejection, or inhibit arteriosclerosis,
   wherein the endothelial growth factor inhibitor comprises a compound that inhibits stimulation of human VEGFR-3 by VEGF-C or inhibits stimulation of human VEGFR-3 by VEGF-D, and
   wherein the compound comprises a soluble human VEGFR-3 polypeptide.

2. The method of claim 1, wherein the composition further comprises a pharmaceutically acceptable carrier, and
   wherein the composition is administered intravenously, intramuscularly, intraperitoneally, or perorally.

3. The method of claim 1, where the transplant is a vascularized tissue transplant.

4. The method of claim 1, wherein the transplant comprises a vascularized organ, or comprises an organ fragment capable of performing functions of the organ or capable of regenerating into the organ.

5. The method of claim 1, wherein the transplant comprises an organ selected from the group consisting of a heart, a lung, a liver, and a kidney.

6. The method of claim 1, wherein the composition is administered locally to the transplanted vascularized tissue or vascularized organ in the human allograft transplant recipient.

7. The method of claim 1, wherein the composition is administered systemically to the human allograft transplant recipient.

8. The method of claim 1, further comprising administering the composition to the organ or the organ donor before the transplant.

9. The method of claim 1, further comprising repeated administration of the composition to the human allograft transplant recipient.

10. The method of claim 1, wherein the composition is administered to the human allograft transplant recipient perioperatively, relative to the transplant operation.

11. The method of claim 1, wherein the composition is administered to the human allograft transplant recipient post-operatively, relative to the transplant operation.

12. The method of claim 1, comprising:
   screening the human allograft transplant recipient for symptoms of an acute rejection reaction; and
   administering the composition to the human allograft transplant recipient upon detection of symptoms of acute rejection, in an amount effective to inhibit the rejection.

13. The method of claim 1, wherein the polypeptide comprises a human VEGFR-3 extracellular domain polypeptide that binds VEGF-C or VEGF-D.

14. The method of claim 1, wherein the soluble VEGFR-3 polypeptide comprises the VEGFR-3 extracellular domain, or a fragment thereof sufficient to bind VEGF-C or VEGF-D and wherein the fragment consists of amino acid 138-226 of SEQ ID NO: 6.

15. The method of claim 1, wherein the soluble VEGFR-3 polypeptide comprises the first and second immunoglobulin-like domains of the VEGFR-3.

16. The method of claim 1, wherein the soluble VEGFR-3 polypeptide comprises the first, second, and third immunoglobulin-like domains of the VEGFR-3.

17. The method of claim 1, wherein the soluble VEGFR-3 polypeptide is fused to an immunoglobulin constant domain.

18. The method of claim 1, further comprising administering an immunosuppressive agent to the human allograft transplant recipient, wherein the immunosuppressive agent comprises at least one compound selected from the group consisting of: Tacrolimus, Mycophenolic acid, Prednisone, cyclosporine, Azathioprine, Basiliximab, Daclizumab, Muromonab-CD3, Mycophenolate Mofetil, Sirolimus, Methylprednisolone, Thymoglobulin, Rapamycin, and Interleukin-2 Receptor Antagonist.

19. The method of claim 18, further comprising administering an antibiotic or antifungal agent to the human allograft transplant recipient.

20. The method of claim 18, further comprising administering to a human donor organism a composition that comprises an endothelial growth factor inhibitor, prior to harvesting a vascularized tissue, or vascularized organ for transplantation into the human allograft transplant recipient.

21. The method of claim 1, further comprising administering an antibiotic or antifungal agent to the human allograft transplant recipient.

22. The method of claim 1, further comprising administering to a human donor organism a composition that comprises an endothelial growth factor inhibitor, prior to harvesting a vascularized tissue or vascularized organ for transplantation into the human allograft transplant recipient.

23. The method of claim 1, further comprising contacting a vascularized tissue or vascularized organ with a composition that comprises an endothelial growth factor inhibitor, prior to transplanting the vascularized tissue or vascularized organ into the human allograft transplant recipient.

24. A method for inhibiting rejection of a vascularized tissue or vascularized organ transplant, or for inhibiting arteriosclerosis in a human allograft transplant recipient, comprising: administering to a human allograft transplant recipient a composition that comprises an endothelial growth factor inhibitor in an amount effective to inhibit rejection, or inhibit arteriosclerosis,
    wherein the endothelial growth factor inhibitor comprises a compound that inhibits stimulation of human VEGFR-3 by VEGF-C or inhibits stimulation of human VEGFR-3 by VEGF-D, and
    wherein the compound comprises an amino acid sequence at least 95% identical to amino acids 138-226 of SEQ ID NO: 6, and that binds VEGF-C or VEGF-D.

25. The method of claim 24, wherein the inhibitor comprises an amino acid sequence at least 95% identical to amino acids 47-224 of SEQ ID NO: 6.

26. The method of claim 24, wherein the inhibitor comprises an amino acid sequence at least 95% identical to amino acids 47-314 of SEQ ID NO: 6.

27. The method of claim 24, wherein the inhibitor comprises an amino acid sequence at least 95% identical to amino acids 24-775 of SEQ ID NO: 6 or fragments thereof that bind VEGF-C.

28. A method for inhibiting rejection of a transplanted organ, or fragment thereof, the organ selected from the group consisting of a heart, a kidney, a lung, a liver, an intestine, a pancreas, skin, and bone, the method comprising:
    administering to a human transplant recipient a composition that comprises an endothelial growth factor inhibitor in an amount effective to inhibit rejection,
    wherein the endothelial growth factor inhibitor comprises a compound that inhibits stimulation of human VEGFR-3 by VEGF-C or inhibits stimulation of human VEGFR-3 by VEGF-D, and
    wherein the compound comprises a soluble human VEGFR-3 polypeptide.

29. The method of claim 1, wherein the composition is administered to the recipient for 1-90 days post-operatively, relative to the transplant operation.

30. The method of claim 1, wherein the composition is administered to the recipient for 1-60 days post-operatively, relative to the transplant operation.

31. The method of claim 1, wherein the composition is administered to the recipient for 1-30 days post-operatively, relative to the transplant operation.

32. The method of claim 1, wherein the composition is administered to the recipient for 1-15 days post-operatively, relative to the transplant operation.

33. The method of claim 1, further comprising administering to the recipient a composition that comprises at least one growth factor inhibitor selected from the group consisting of:
    inhibitors of VEGFR-1;
    inhibitors of VEGFR-2;
    inhibitors of PDGFR-alpha; and
    inhibitors of PDGFR-beta;
    wherein the combination of inhibitors are administered in amounts effective to inhibit rejection, or inhibit arteriosclerosis.

34. The method of claim 27, wherein the composition is administered to the recipient for 1-90 days post-operatively, relative to the transplant operation.

35. The method of claim 27, wherein the composition is administered to the recipient for 1-60 days post-operatively, relative to the transplant operation.

36. The method of claim 27, wherein the composition is administered to the recipient for 1-30 days post-operatively, relative to the transplant operation.

37. The method of claim 27, wherein the composition is administered to the recipient for 1-15 days post-operatively, relative to the transplant operation.

38. The method of claim 27, further comprising administering to the recipient a composition that comprises at least one growth factor inhibitor selected from the group consisting of:
    inhibitors of VEGFR-1;
    inhibitors of VEGFR-2;
    inhibitors of PDGFR-alpha; and
    inhibitors of PDGFR-beta;
    wherein the combination of inhibitors are administered in amounts effective to inhibit rejection, or inhibit arteriosclerosis.

* * * * *